(12) United States Patent
Hoelder et al.

(10) Patent No.: US 9,409,907 B2
(45) Date of Patent: Aug. 9, 2016

(54) INHIBITOR COMPOUNDS

(71) Applicant: Cancer Research Technology Limited, London (GB)

(72) Inventors: Swen Hoelder, London (GB); Julian Blagg, London (GB); Savade Solanki, London (GB); Hannah Woodward, London (GB); Sebastien Naud, London (GB); Vassilios Bavetsias, London (GB); Peter Sheldrake, London (GB); Paolo Innocenti, London (GB); Kwai-Ming J. Cheung, London (GB); Butrus Atrash, London (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 14/426,549

(22) PCT Filed: Sep. 9, 2013

(86) PCT No.: PCT/GB2013/052360
§ 371 (c)(1),
(2) Date: Mar. 6, 2015

(87) PCT Pub. No.: WO2014/037750
PCT Pub. Date: Mar. 13, 2014

(65) Prior Publication Data
US 2015/0239884 A1     Aug. 27, 2015

(30) Foreign Application Priority Data

Sep. 7, 2012   (GB) .................... 1216017.2

(51) Int. Cl.
| | | |
|---|---|---|
| *A01N 43/90* | (2006.01) | |
| *A61K 31/519* | (2006.01) | |
| *C07D 471/00* | (2006.01) | |
| *C07D 487/00* | (2006.01) | |
| *C07D 471/04* | (2006.01) | |
| *C07D 401/14* | (2006.01) | |
| *C07D 413/14* | (2006.01) | |
| *C07D 401/04* | (2006.01) | |
| *C07D 405/04* | (2006.01) | |
| *C07D 519/00* | (2006.01) | |

(52) U.S. Cl.
CPC ............ *C07D 471/04* (2013.01); *C07D 401/04* (2013.01); *C07D 401/14* (2013.01); *C07D 405/04* (2013.01); *C07D 413/14* (2013.01); *C07D 519/00* (2013.01)

(58) Field of Classification Search
None
See application file for complete search history.

(56) References Cited

U.S. PATENT DOCUMENTS

| 2,697,710 | A | 12/1954 | Hitchings et al. |
|---|---|---|---|
| 3,021,332 | A | 2/1962 | Hitchings et al. |
| 2003/0073668 | A1 | 4/2003 | Booth et al. |
| 2003/0105115 | A1 | 6/2003 | Metcalf et al. |
| 2004/0092521 | A1 | 5/2004 | Altenbach et al. |
| 2005/0256118 | A1 | 11/2005 | Altenbach et al. |
| 2005/0272728 | A1 | 12/2005 | Altenbach et al. |
| 2011/0257196 | A1 | 10/2011 | Lu et al. |
| 2015/0031672 | A1 | 1/2015 | Ren et al. |

FOREIGN PATENT DOCUMENTS

| WO | WO-9615128 A2 | 5/1996 |
|---|---|---|
| WO | WO-01/55147 A1 | 8/2001 |
| WO | WO-02090360 A1 | 11/2002 |
| WO | WO-03/051366 A2 | 6/2003 |
| WO | WO-03074530 A1 | 9/2003 |
| WO | WO-2004/043458 A1 | 5/2004 |
| WO | WO-2004065378 A1 | 8/2004 |
| WO | WO-2007/000240 A1 | 1/2007 |
| WO | WO-2007/125405 A2 | 11/2007 |
| WO | WO-2007/140222 A2 | 12/2007 |
| WO | WO-2008/135232 A1 | 11/2008 |
| WO | WO-2009/032694 A1 | 3/2009 |
| WO | WO-2009/103966 A1 | 8/2009 |
| WO | WO-2010/007374 A1 | 1/2010 |
| WO | WO-2010/129816 A2 | 11/2010 |

(Continued)

OTHER PUBLICATIONS

Balog et al., "Novel fluorescent isoquinoline derivatives obtained via Buchwald-Hartwig coupling of isoquinolin-3-amines", *Arkivoc*, vol. 5, 109-119 (2012).

(Continued)

*Primary Examiner* — Jeffrey H Murray
(74) *Attorney, Agent, or Firm* — Foley Hoag LLP; David P. Halstead

(57) ABSTRACT

The present invention relates to compounds of formula I

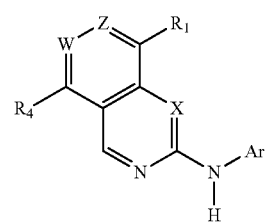

wherein $R_1$, $R_4$, Ar, W, X and Z are all as defined herein. The compounds of the present invention are known to inhibit the spindle checkpoint function of Monospindle 1 (Mps1—also known as TTK) kinases either directly or indirectly via interaction with the Mps1 kinase itself. In particular, the present invention relates to the use of these compounds as therapeutic agents for the treatment and/or prevention of proliferative diseases, such as cancer. The present invention also relates to processes for the preparation of these compounds, and to pharmaceutical compositions comprising them.

2 Claims, No Drawings

(56) References Cited

FOREIGN PATENT DOCUMENTS

| WO | WO-2012/013557 A2 | 2/2012 |
|---|---|---|
| WO | WO-2012/028756 A1 | 3/2012 |
| WO | WO-2012/064973 A2 | 5/2012 |
| WO | WO-2012/080284 A2 | 6/2012 |
| WO | WO-2012/088438 A1 | 6/2012 |
| WO | WO-2012/092471 A2 | 7/2012 |
| WO | WO-2012/101032 A1 | 8/2012 |
| WO | WO-2014/037750 A1 | 3/2014 |

OTHER PUBLICATIONS

Bathini et al., "2-Aminoquinazoline inhibitors of cyclin-dependent kinases", *Bioorg. Med. Chem. Lett.* vol. 15(17), 3881-3885 (2005).

Cabarello et al., "2D Autocorrelation, CoMFA, and CoMSIA modeling of protein tyrosine kinases' inhibition by substituted pyrido[2,3-d]pyrimidine derivatives", *Bioorg. Med. Chem.*, vol. 16(2), 810-821 (2008).

Database PubChem Compounds [Online] Dec. 1, 2012, Database accession No. CID 70113665, abstract.

Database PubChem Compounds [Online] Jul. 13, 2005, Database accession No. CID 2000835, abstract.

Database PubChem Compounds [Online] Jul. 13, 2005, Database accession No. CID 2004801, abstract.

Database PubChem Compounds [Online] Jul. 9, 2005, Database accession No. CID 940974, abstract.

Database PubChem Compounds [Online] Jul. 9, 2005, Database accession No. CID 945107, abstract.

Database PubChem Compounds [Online] Jul. 9, 2005, Database accession No. CID 945815, abstract.

Database PubChem Compounds [Online] NCBI; Dec. 1, 2012 Database accession No. CID 69975764, abstract.

Database PubChem Compounds [Online] NCBI; Sep. 13, 2005, Database accession No. CID 4000352, abstract.

Database Registry [Online] Chemical Abstracts Service, Columbus, Ohio, US; Jan. 19, 2004, Database accession No. 639005-15-5, abstract.

Database PubChem Compounds [Online] Jul. 13, 2005, Database accession No. CID 2019230, abstract.

Lainchbury et al., "Discovery of 3-Alkoxyamino-5-(pyridin-2-ylamino)pyrazine-2-carbonitriles as Selective, Orally Bioavailable CHK1 Inhibitors", *J. Med. Chem.*, vol. 55(22), 10229-10240 (2012).

Ranjitkar et al., "Affinity-Based Probes Based on Type II Kinase Inhibitors", *J. Am. Chem. Soc.* vol. 134(16), 19017-19025 (2012).

Thompson et al., "Synthesis and Structure—Activity Relationships of 7-Substituted 3-(2,6-Dichlorophenyl)-1,6-naphthyridin-2(1H)-ones as Selective Inhibitors of pp60", *J. Med. Chem. Lett.*, vol. 43(16), 3134-3147 (2000).

Trumpp-Kallmeyer et al., "Development of a Binding Model to Protein Tyrosine Kinases for Substituted Pyrido[2,3-d]pyrimidine Inhibitors", *J. Med. Chem.*, vol. 41(11), 1752-1763 (1998).

Walton et al., "The Preclinical Pharmacology and Therapeutic Activity of the Novel CHK1 Inhibitor SAR-020106", *Molecular Cancer Therapeutics*, vol. 9, 89 (2010).

Reader et al., "Structure-Guided Evolution of Potent and Selective CHK1 Inhibitors through Scaffold Morphing," Journal of Medicinal Chemistry, vol. 54(24), 8328-8342 (2011).

Proisy et al., "Rapid synthesis of 3-aminoisoquinoline-5-sulfonamides using the Buchwald-Hartwig reaction," Synthesis, vol. 4, 561-566 (2009).

Scifinder Search Report, pp. 1-104, Aug. 20, 2012.

INHIBITOR COMPOUNDS

RELATED APPLICATIONS

This application is the U.S. National Stage of International Patent Application No. PCT/GB2013/052360, filed Sep. 9, 2013, which claims the benefit of priority to Great Britain Patent Application serial number 1216017.2, filed Sep. 7, 2012.

INTRODUCTION

The present invention relates to compounds that inhibit the spindle checkpoint function of monopolar spindle 1 (Mps1— also known as TTK) kinases, either directly or indirectly via interaction with the Mps1 kinase itself. In particular, the present invention relates to compounds for use as therapeutic agents for the treatment and/or prevention of proliferative diseases, such as cancer. The present invention also relates to processes for the preparation of these compounds, and to pharmaceutical compositions comprising them.

BACKGROUND OF THE INVENTION

Cancer is caused by uncontrolled and unregulated cellular proliferation. Precisely what causes a cell to become malignant and proliferate in an uncontrolled and unregulated manner has been the focus of intense research over recent decades. This research has led to the targeting of surveillance mechanisms, such as those responsible for regulating the cell cycle, with anticancer agents. For example, published patent application WO 2009/103966 (CANCER RESEARCH TECHNOLOGY LIMITED) relates to the inhibition of checkpoint kinase 1 (CHK1) kinase function, with bicyclylaryl-arylamine compounds, in the treatment of cancer.

The main role of the cell cycle is to enable error-free DNA replication, chromosome segregation and cytokinesis. Surveillance mechanisms, the so-called checkpoint pathways, monitor passage through mitosis at several stages. One of the best characterised is the spindle assembly checkpoint that prevents anaphase onset until the appropriate tension and attachment across kinetochores is achieved (HARDWICK KG, 1998, "The spindle checkpoint", *Trends Genet* 14, 1-4). The majority of proteins involved in the checkpoint exert their functions through protein binding interactions with the involvement of only a small number of kinases (MUSACCHIO A et al, 2007, "The spindle-assembly checkpoint in space and time", *Nature Reviews, Molecular and Cell Biology*, 8, 379-393). A mitotic checkpoint complex (MCC) that contains three checkpoint proteins (Mad2, BubR1/Mad3, Bub3) and the APC/C co-factor, CDC20, concentrates at the kinetochores and acts as a spindle checkpoint effector. Other core proteins required to amplify the checkpoint signal include Mad1 and the kinases Bub1, Mps1 (also known as TTK) and Aurora-B (MUSACCHIO, referenced above).

One of the first components of the spindle assembly checkpoint signal, identified by a genetic screen in budding yeast, was dubbed Mps1 (monopolar spindle 1) for the monopolar spindles produced by Mps1 mutant cells (WEISS E, 1996, "The *Saccharomyces cerevisiae* spindle pole body duplication gene MPS1 is part of a mitotic checkpoint", *J Cell Biol* 132, 111-123), however, it still remains one of the least studied checkpoint components in higher eukaryotes. Subsequently, the Mps1 gene was shown to encode an essential dual-specificity kinase (LAUZE et al, 1995, "Yeast spindle pole body duplication gene MPS1 encodes an essential dual specificity protein kinase", *EMBO J* 14, 1655-1663 and also POCH et al, 1994, "RPK1, an essential yeast protein kinase involved in the regulation of the onset of mitosis, shows homology to mammalian dual-specificity kinases", *Mol Gen Genet* 243, 641-653) conserved from yeast to humans (MILLS et al, 1992, "Expression of TTK, a novel human protein kinase, is associated with cell proliferation", *J Biol Chem* 267, 16000-16006). Mps1 activity peaks at the $G_2/M$ transition and is enhanced upon activation of the spindle checkpoint with nocodazole (STUCKE et al, 2002, "Human Mps1 kinase is required for the spindle assembly checkpoint but not for centrosome duplication", *EMBO J* 21, 1723-1732 and also LIU et al, 2003, "Human MPS1 kinase is required for mitotic arrest induced by the loss of CENP-E from kinetochores", *Mol Biol Cell* 14, 1638-1651). The autophosphorylation of Mps1 at Thr676 in the activation loop has been identified and is essential for Mps1 function (MATTISON et al, 2007, "Mps1 activation loop autophosphorylation enhances kinase activity", *J Biol Chem* 282, 30553-30561).

Given the importance of Mps1 in spindle checkpoint activation, the development of Mps1 inhibitors would be an asset, not only as a tool to further investigate its cell cycle-related functions, but also as a form of anticancer treatment. The first generation inhibitors of Mps1 have been described. Cincreasin, caused chromosome mis-segregation and death in yeast cells (DORER et al, 2005, "A small-molecule inhibitor of Mps1 blocks the spindle-checkpoint response to a lack of tension on mitotic chromosomes", *Curr Biol* 15, 1070-1076) and SP600125, a JNK (c-Jun amino-terminal kinase) inhibitor, also disrupts spindle checkpoint function in a JNK-independent manner via the inhibition of Mps1 (SCHMIDT et al, 2005, "Ablation of the spindle assembly checkpoint by a compound targeting Mps1", *EMBO Rep* 6, 866-872). Recently, three small molecule inhibitors of Mps1 were identified (KWIATOWSKI et al, 2010, "Small-molecule kinase inhibitors provide insight into Mps1 cell cycle function", *Nat Chem Biol* 6, 359-368; HEWITT et al, 2010, "Sustained Mps1 activity is required in mitosis to recruit 0-Mad2 to the Mad1-C-Mad2 core complex", *J Cell Biol* 190, 25-34; and SANTAGUIDA et al, 2010, "Dissecting the role of MPS1 in chromosome biorientation and the spindle checkpoint through the small molecule inhibitor reversine", *J Cell Biol* 190, 73-87). Chemical inhibition of Mps1 induced premature mitotic exit, gross aneuploidy and death to human cancer cell lines (KWIATOWSKI, above). Mps1 inhibitors AZ3146 and reversine, severely impaired recruitment of Mad1, Mad2 and CENP-E to kinetochores (HEWITT, and SANTAGUIDA, above).

Dysregulation of the mitotic checkpoint is recognised as a feature of the malignant transformation process. Mitotic checkpoint dysfunction in tumors provides an opportunity for developing a therapeutic strategy using small molecules. This is based on the proposition that pharmacologic disruption of an already compromised mitotic checkpoint may selectively sensitize tumors. This observation has led to the hypothesis that inhibition of Mps1 may be of therapeutic benefit.

SUMMARY OF THE INVENTION

In one aspect, the present invention provides a compound, or a pharmaceutically acceptable salt or solvate thereof, as defined herein.

In another aspect, the present invention provides a pharmaceutical composition which comprises a compound as defined herein, or a pharmaceutically acceptable salt or solvate thereof, and one or more pharmaceutically acceptable excipients.

In another aspect, the present invention provides a compound as defined herein, or a pharmaceutically acceptable salt or solvate thereof, or a pharmaceutical composition as defined herein for use in therapy.

In another aspect, the present invention provides a compound as defined herein, or a pharmaceutically acceptable salt or solvate thereof, or a pharmaceutical composition as defined herein, for use in the treatment of a proliferative condition.

In another aspect, the present invention provides a compound as defined herein, or a pharmaceutically acceptable salt or solvate thereof, or a pharmaceutical composition as defined herein, for use in the treatment of cancer. In a particular embodiment, the cancer is a human cancer.

In another aspect, the present invention provides a compound as defined herein, or a pharmaceutically acceptable salt or solvate thereof, or a pharmaceutical composition as defined herein, for use in the production of a Mps1 kinase inhibitory effect.

In another aspect, the present invention provides the use of a compound as defined herein, or a pharmaceutically acceptable salt or solvate thereof, in the manufacture of a medicament for use in the treatment of a proliferative condition.

In another aspect, the present invention provides the use of a compound as defined herein, or a pharmaceutically acceptable salt or solvate thereof, in the manufacture of a medicament for use in the treatment of cancer. Suitably, the medicament is for use in the treatment of human cancers.

In another aspect, the present invention provides the use of a compound as defined herein, or a pharmaceutically acceptable salt or solvate thereof, in the manufacture of a medicament for use in the production of an Mps1 kinase inhibitory effect.

In another aspect, the present invention provides a method of inhibiting Mps1 kinase in vitro or in vivo, said method comprising contacting a cell with an effective amount of a compound as defined herein, or a pharmaceutically acceptable salt or solvate thereof.

In another aspect, the present invention provides a method of inhibiting cell proliferation in vitro or in vivo, said method comprising contacting a cell with an effective amount of a compound as defined herein, or a pharmaceutically acceptable salt or solvate thereof.

In another aspect, the present invention provides a method of treating a proliferative disorder in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating cancer in a patient in need of such treatment, said method comprising administering to said patient a therapeutically effective amount of a compound as defined herein, or a pharmaceutically acceptable salt or solvate thereof, or a pharmaceutical composition as defined herein.

The present invention further provides a method of synthesising a compound as defined herein, or a pharmaceutically acceptable salt or solvate thereof.

In another aspect, the present invention provides a compound as defined herein, or a pharmaceutically acceptable salt or solvate thereof, obtainable by, or obtained by, or directly obtained by a method of synthesis as defined herein.

In another aspect, the present invention provides novel intermediates defined herein which are suitable for use in any one of the synthetic methods set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicycle[2.2.2]octane, bicycle[2.1.1]hexane, bicycle[1.1.1]pentane and bicyclo[2.2.1]heptyl.

The term "(1-8C)heteroalkyl" refers to an alkyl chain comprising 1-8 carbon atoms which additionally comprises one, two or three heteroatoms present within the alkyl chain which are selected from the group consisting of N, O, or S.

The term "halo" refers to fluoro, chloro, bromo and iodo.

The term "fluoroalkyl" is used herein to refer to an alkyl group in which one or more hydrogen atoms have been replaced by fluorine atoms. Examples of fluoroalkyl groups include —$CHF_2$, —$CH_2CF_3$, or perfluoroalkyl groups such as —$CF_3$ or —$CF_2CF_3$.

The term "fluoroakoxy" is used herein to refer to an alkoxy group in which one or more hydrogen atoms have been replaced by fluorine atoms. Examples of fluoroalkoxy groups include —$OCHF_2$, —$OCH_2CF_3$, or perfluoroalkoxy groups such as —$OCF_3$ or —$OCF_2CF_3$.

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

By "spiro bi-cyclic ring systems" we mean that the two ring systems share one common spiro carbon atom, i.e. the heterocyclic ring is linked to a further carbocyclic or heterocyclic ring through a single common spiro carbon atom. Examples of spiro ring systems include 6-azaspiro[3.4]octane, 2-oxa-6-azaspiro[3.4]octane, 2-azaspiro[3.3]heptanes, 2-oxa-6-azaspiro[3.3]heptanes, 7-oxa-2-azaspiro[3.5]nonane, 6-oxa-2-azaspiro[3.4]octane, 2-oxa-7-azaspiro[3.5]nonane and 2-oxa-6-azaspiro[3.5]nonane.

"Heterocyclyl(m-nC)alkyl" means a heterocyclyl group covalently attached to a (m-nC)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:

a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a 5- or 6-membered ring containing 1, 2 or 3 ring heteroatoms;
e) a pyrazole ring fused to a 5- or 6-membered ring containing 1 or 2 ring heteroatoms;
f) a pyrazine ring fused to a 5- or 6-membered ring containing 1 or 2 ring heteroatoms;
g) an imidazole ring fused to a 5- or 6-membered ring containing 1 or 2 ring heteroatoms;
h) an oxazole ring fused to a 5- or 6-membered ring containing 1 or 2 ring heteroatoms;

i) an isoxazole ring fused to a 5- or 6-membered ring containing 1 or 2 ring heteroatoms;
j) a thiazole ring fused to a 5- or 6-membered ring containing 1 or 2 ring heteroatoms;
k) an isothiazole ring fused to a 5- or 6-membered ring containing 1 or 2 ring heteroatoms;
l) a thiophene ring fused to a 5- or 6-membered ring containing 1, 2 or 3 ring heteroatoms;
m) a furan ring fused to a 5- or 6-membered ring containing 1, 2 or 3 ring heteroatoms;
n) a cyclohexyl ring fused to a 5- or 6-membered heteroaromatic ring containing 1, 2 or 3 ring heteroatoms; and
o) a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(m-nC)alkyl" means a heteroaryl group covalently attached to a (m-nC)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species.

Examples of aryl groups include, but are not limited to, phenyl, biphenyl, naphthyl and the like. In particular embodiment, an aryl is phenyl.

The term "aryl(m-nC)alkyl" means an aryl group covalently attached to a (m-nC)alkylene group, both of which are defined herein. Examples of aryl-(m-nC)alkyl groups include benzyl, phenylethyl, and the like.

This specification also makes use of several composite terms to describe groups comprising more than one functionality. Such terms will be understood by a person skilled in the art. For example heterocyclyl(m-nC)alkyl comprises (m-nC) alkyl substituted by heterocyclyl.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In one aspect, the present invention provides a compound of formula I shown below:

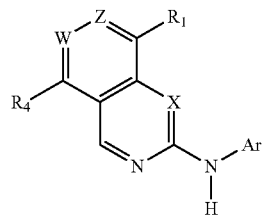

wherein:
W is N or C—$R_3$;
X is CH or N;
Z is N or C—H;
$R_1$ is selected from chloro, (1-6C)alkyl, (1-8C)heteroalkyl, aryl, aryl(1-2C)alkyl, heteroaryl, heteroaryl(1-2C)alkyl, heterocyclyl, heterocyclyl(1-2C)alkyl, (3-8C)cycloalkyl, (3-8C)cycloalkyl(1-2C)alkyl, $NR_7R_8$, $OR_9$, $C(O)R_9$, $C(O)OR_9$, $OC(O)R_9$, $N(R_{10})OR_9$, $N(R_{10})C(O)OR_9$, $C(O)N(R_{10})R_9$, $N(R_{10})C(O)R_9$, $S(O)_pR_9$ (where p is 0, 1 or 2), $SO_2N(R_{10})R_9$, $N(R_{10})SO_2R_9$, $N(R_{10})SOR_9$ or $SON(R_{10})R_9$;

and wherein $R_1$ is optionally substituted by one or more substituent groups selected from fluoro, chloro, trifluoromethyl, trifluoromethoxy, cyano, nitro, hydroxy, amino, carboxy, carbamoyl, sulphamoyl, (1-4C)alkyl, (1-4C)alkoxy, $S(O)_qCH_3$ (where q is 0, 1 or 2), methylamino or dimethylamino, aryl, aryl(1-2C)alkyl, heteroaryl, heteroaryl(1-2C) alkyl, heterocyclyl, heterocyclyl(1-2C)alkyl, (3-8C)cycloalkyl, or (3-8C)cycloalkyl(1-2C)alkyl, and wherein any (1-4C)alkyl, (1-4C)alkoxy, aryl, heteroaryl, heterocyclyl, or (3-8C)cycloalkyl moiety present within a substituent group on $R_1$ is optionally further substituted by fluoro, chloro, trifluoromethyl, trifluoromethoxy, cyano, nitro, hydroxy, amino, carboxy, carbamoyl, sulphamoyl, (1-4C)alkyl, $NR_aR_b$, $OR_a$, $C(O)R_a$, $C(O)OR_a$, $OC(O)R_a$, $N(R_b)OR_a$, $C(O)N(R_b)R_a$, $N(R_b)C(O)R_a$, $S(O)_pR_a$ (where p is 0, 1 or 2), $SO_2N(R_b)R_a$, or $N(R_b)SO_2R_a$, wherein $R_a$ and $R_b$ are each independently selected from H or (1-4C)alkyl;

$R_3$ is hydrogen, (1-4C)alkyl, (3-6C)cycloalkyl, halo, $CF_3$, CN and (1-4C)alkoxy;

$R_4$ is hydrogen, (1-3C)alkyl, (1-3C)alkoxy, fluoro, chloro or $CF_3$;

Ar has the formula:

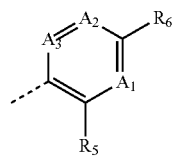

wherein:
(i) all of $A_1$, $A_2$ and $A_3$ are CH;
(ii) one of $A_1$, $A_2$ and $A_3$ is N and the others are CH; or
(iii) two of $A_1$, $A_2$ and $A_3$ are N and the other is CH;
$R_5$ is selected from hydrogen, cyano, (1-3C)alkyl, (1-3C) fluoroalkyl, (1-3C)alkoxy, (1-3C)fluoroalkoxy, halo, (1-3C)alkanoyl, $C(O)NR_{15}R_{16}$ or $S(O)_2NR_{15}R_{16}$, and wherein $R_{15}$ and $R_{16}$ are each independently selected from H or (1-3C) alkyl, and wherein any alkyl or alkoxy moities present within a $R_5$ substituent group are optionally further substituted by hydroxy or methoxy;

$R_6$ is selected from halo, trifluoromethyl, trifluoromethoxy, cyano, nitro, hydroxy, amino, carboxy, carbamoyl, sulphamoyl, ureido, (1-6C)alkyl, (2-6C)alkenyl, (2-6C)alkynyl, or $R_6$ is a group of the formula:

-L$^1$-L$^2$-R$_{17}$ wherein
L$^1$ is absent or a linker group of the formula —[CR$_{18}$R$_{19}$]$_n$— in which n is an integer selected from 1, 2, 3 or 4, and $R_{18}$ and $R_{19}$ are each independently selected from hydrogen or (1-2C) alkyl;
L$^2$ is absent or is selected from O, S, SO, SO$_2$, N(R$_{20}$), C(O), C(O)O, OC(O), CH(OR$_{20}$), C(O)N(R$_{20}$), N(R$_{20}$)C(O), N(R$_{20}$)C(O)N(R$_{21}$), S(O)$_2$N(R$_{20}$), or N(R$_{21}$)SO$_2$, wherein $R_{20}$ and $R_{21}$ are each independently selected from hydrogen or (1-2C)alkyl; and
$R_{17}$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C) alkyl, heterocyclyl, heterocyclyl-(1-4C)alkyl,
and wherein $R_{17}$ is optionally further substituted by one or more substituent groups independently selected from oxo, halo, cyano, nitro, hydroxy, NR$_{22}$R$_{23}$, (1-4C)alkoxy, (1-4C) alkyl, (3-8C)cycloalkyl, (3-8C)cycloalkyl-(1-3C)alkyl, (1-5C)alkanoyl, (1-5C)alkylsulphonyl, heterocyclyl, heterocyclyl-(1-2C)alkyl, heteroaryl, heteroaryl-(1-2C)alkyl, CONR$_{22}$R$_{23}$, and SO$_2$NR$_{22}$R$_{23}$, wherein $R_{22}$ and $R_{23}$ are each independently selected from hydrogen, (1-4C)alkyl or (3-6C) cycloalkyl or (3-6C)cycloalkyl(1-2C)alkyl;
and wherein when said substituent group comprises an alkyl, cycloalkyl, heterocyclyl or heteroaryl moiety then said moiety is optionally further substituted by hydroxy, fluoro, chloro, cyano, CF$_3$, OCF$_3$, (1-2C)alkyl, (1-2C)alkoxy, SO$_2$ (1-2C)alkyl or NR$_e$R$_f$ (where $R_e$ and $R_f$ are each independently selected from hydrogen, (1-3C)alkyl, (3-6C)cycloalkyl, or (3-6C)cycloalkyl(1-2C)alkyl);
or $R_{17}$ is a group having the formula:

-L$^3$-L$^4$-R$_{24}$

L$^3$ is absent or a linker group of the formula —[CR$_{25}$R$_{26}$]$_n$— in which n is an integer selected from 1, 2, 3 or 4, and $R_{25}$ and $R_{26}$ are each independently selected from hydrogen or (1-2C) alkyl;
L$^4$ is absent or is selected from O, S, SO, SO$_2$, N(R$_{27}$), C(O), C(O)O, OC(O), CH(OR$_{27}$), C(O)N(R$_{27}$), N(R$_{27}$)C(O), N(R$_{27}$)C(O)N(R$_{28}$), S(O)$_2$N(R$_{27}$), or N(R$_{28}$)SO$_2$, wherein $R_{27}$ and $R_{28}$ are each independently selected from hydrogen or (1-2C)alkyl; and
$R_{24}$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C) alkyl, heterocyclyl, heterocyclyl-(1-4C)alkyl;
$R_8$ and $R_9$ are each independently selected from hydrogen, (1-6C)alkyl, (1-6C)alkoxy, (3-9C)cycloalkyl, (3-9C)cycloalkyl-(1-2C)alkyl, aryl, aryl-(1-2C)alkyl, heterocyclyl, heterocyclyl-(1-2C)alkyl, heteroaryl, heteroaryl-(1-2C) alkyl, and wherein $R_8$ and $R_9$ are optionally further substituted by one or more substituents selected from hydroxy, fluoro, chloro, cyano, CF$_3$, OCF$_3$ (1-2C)alkyl or (1-2C) alkoxy;
$R_7$ and $R_{10}$ are independently selected from hydrogen, (1-6C) alkyl, (3-6C)cycloalkyl, (3-6C)cycloalkyl-(1-2C)alkyl, and wherein $R_7$ and $R_{10}$ are optionally further substituted by one or more substituents selected from hydroxy, fluoro, chloro, cyano, CF$_3$, OCF$_3$, (1-2C)alkyl or (1-2C)alkoxy;
subject to the proviso that:
X is only N when Z is N;
W is only N when X and Z are both N; and
$R_6$ is not methoxy when $R_1$ is S(O)$_2$R$_9$ and $R_9$ is heterocyclyl;
or a pharmaceutically acceptable salt or solvate thereof.

In another aspect, the present invention provides a compound of formula I wherein:
W, X, Z, $R_3$, $R_4$, $R_7$, $R_8$, $R_9$ and $R_{10}$ are each as defined above;
$R_1$ is selected from chloro, (1-6C)alkyl, (1-8C)heteroalkyl, aryl, aryl(1-2C)alkyl, heteroaryl, heteroaryl(1-2C)alkyl, heterocyclyl, heterocyclyl(1-2C)alkyl, (3-8C)cycloalkyl, (3-8C) cycloalkyl(1-2C)alkyl, NR$_7$R$_8$, OR$_9$, C(O)R$_9$, C(O)OR$_9$, OC(O)R$_9$, N(R$_{10}$)OR$_9$, N(R$_{10}$)C(O)OR$_9$, C(O)N(R$_{10}$)R$_9$, N(R$_{10}$)C(O)R$_9$, S(O)$_p$R$_9$ (where p is 0, 1 or 2), SO$_2$N(R$_{10}$)R$_9$ or N(R$_{10}$)SO$_2$R$_9$;
and wherein $R_1$ is optionally substituted by one or more substituent groups selected from fluoro, chloro, trifluoromethyl, trifluoromethoxy, cyano, nitro, hydroxy, amino, carboxy, carbamoyl, sulphamoyl, (1-4C)alkyl, (1-4C)alkoxy, S(O)$_q$CH$_3$ (where q is 0, 1 or 2), methylamino or dimethylamino, aryl, aryl(1-2C)alkyl, heteroaryl, heteroaryl(1-2C) alkyl, heterocyclyl, heterocyclyl(1-2C)alkyl, (3-8C)cycloalkyl, or (3-8C)cycloalkyl(1-2C)alkyl,
and wherein any (1-4C)alkyl, (1-4C)alkoxy, aryl, heteroaryl, heterocyclyl, or (3-8C)cycloalkyl moiety present within a substituent group on $R_1$ is optionally further substituted by fluoro, chloro, trifluoromethyl, trifluoromethoxy, cyano, nitro, hydroxy, amino, carboxy, carbamoyl, sulphamoyl, (1-4C)alkyl, NR$_a$R$_b$, OR$_a$, C(O)R$_a$, C(O)OR$_a$, OC(O)R$_a$, N(R$_b$)OR$_a$, C(O)N(R$_b$)R$_a$, N(R$_b$)C(O)R$_a$, S(O)$_p$R$_a$ (where p is 0, 1 or 2), SO$_2$N(R$_b$)R$_a$, or N(R$_b$)SO$_2$R$_a$, wherein $R_a$ and $R_b$ are each independently selected from H or (1-4C)alkyl;
Ar has the formula:

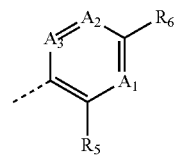

wherein:
$A_1$, $A_2$, $A_3$, $R_6$ are as defined above;
(i) of $A_1$, $A_2$ and $A_3$ is N and the others are CH; or
(ii) two of $A_1$, $A_2$ and $A_3$ are N and the other is CH;
$R_5$ is selected from hydrogen, cyano, (1-3C)alkyl, (1-3C) perfluoroalkyl, (1-3C)alkoxy, (1-3C)fluoroalkoxy, halo, (1-3C)alkanoyl, C(O)NR$_{15}$R$_{16}$ or S(O)$_2$NR$_{15}$R$_{16}$, and wherein $R_{15}$ and $R_{16}$ are each independently selected from H or (1-3C)alkyl,
and wherein any alkyl or alkoxy moities present within a $R_5$ substituent group are optionally further substituted by hydroxy or methoxy;
$R_6$ is selected from halo, trifluoromethyl, trifluoromethoxy, cyano, nitro, hydroxy, amino, carboxy, carbamoyl, sulphamoyl, ureido, (1-6C)alkyl, (2-6C)alkenyl, (2-6C)alkynyl, or $R_6$ is a group of the formula:

-L$_1$-L$_2$-R$_{17}$ wherein
L$^1$ is absent or a linker group of the formula —[CR$_{18}$R$_{19}$]$_n$— in which n is an integer selected from 1, 2, 3 or 4, and $R_{18}$ and $R_{19}$ are each independently selected from hydrogen or (1-2C) alkyl;
L$^2$ is absent or is selected from O, S, SO, SO$_2$, N(R$_{20}$), C(O), C(O)O, OC(O), CH(OR$_{20}$), C(O)N(R$_{20}$), N(R$_{20}$)C(O), N(R$_{20}$)C(O)N(R$_{21}$), S(O)$_2$N(R$_{20}$), or N(R$_{21}$)SO$_2$, wherein $R_{20}$ and $R_{21}$ are each independently selected from hydrogen or (1-2C)alkyl; and $R_{17}$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, heterocyclyl-(1-4C)alkyl, and wherein $R_{17}$ is optionally further substituted by one or more substituent groups independently selected from oxo, halo, cyano, nitro, hydroxy, $NR_{22}R_{23}$, (1-4C)alkoxy, (1-4C)alkyl, (3-8C)cycloalkyl, (3-8C)cycloalkyl-(1-3C)alkyl, (1-5C)alkanoyl, (1-5C)alkylsulphonyl, heterocyclyl, heterocyclyl-(1-2C)alkyl, heteroaryl, heteroaryl-(1-2C)alkyl, $CONR_{22}R_{23}$, and $SO_2NR_{22}R_{23}$ wherein $R_{22}$ and $R_{23}$ are each independently selected from hydrogen, (1-4C)alkyl or (3-6C)cycloalkyl or (3-6C)cycloalkyl(1-2C)alkyl;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$(1-2C)alkyl or $NR_eR_f$ (where $R_e$ and $R_f$ are each independently selected from hydrogen, (1-3C)alkyl, (3-6C)cycloalkyl, or (3-6C)cycloalkyl(1-2C)alkyl);

subject to the proviso that:

X is only N when Z is N;

W is only N when X and Z are both N; and $R_6$ is not methoxy when $R_1$ is $S(O)_2R_9$ and $R_9$ is heterocyclyl;

or a pharmaceutically acceptable salt or solvate thereof.

Suitably, $R_6$ is not methoxy when $R_1$ is $S(O)_2R_9$.

Suitably, $R_6$ is not methoxy when $R_1$ is $S(O)_pR_9$ (where p is 0, 1 or 2).

In an embodiment, $R_1$ is not $S(O)_pR_9$ (where p is 0, 1 or 2).

Particular compounds of the invention include, for example, compounds of the formula I, or pharmaceutically acceptable salts or solvates thereof, wherein, unless otherwise stated, each of X, W, Z, $R_1$, $R_3$, $R_4$, Ar, $R_5$, $R_6$, $R_7$, $R_8$, $R_9$, $R_{10}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_a$, $R_b$, $R_e$ and $R_f$ has any of the meanings defined hereinbefore or in any one of paragraphs (1) to (63) hereinafter:—

(1) X is CH;

(2) X and Z are both N;

(3) Z is N;

(4) Z is C—H;

(5) $R_1$ is selected from (1-6C)alkyl, (1-8C)heteroalkyl, phenyl, phenyl(1-2C)alkyl, 5 or 6 membered heteroaryl, 5 or 6 membered heteroaryl(1-2C)alkyl, 3 to 9 membered heterocyclyl, 3 to 9 membered heterocyclyl(1-2C)alkyl, (3-6C)cycloalkyl, (3-6C)cycloalkyl(1-2C)alkyl, $NR_7R_8$, $OR_9$, $C(O)R_9$, $C(O)OR_9$, $OC(O)R_9$, $N(R_{10})OR_9$, $N(R_{10})C(O)OR_9$, $C(O)N(R_{10})R_9$, $N(R_{10})C(O)R_9$, $S(O)_pR_9$ (where p is 0, 1 or 2), $SO_2N(R_{10})R_9$, $N(R_{10})SO_2R_9$, $N(R_{10})SOR_9$ or $SON(R_{10})R_9$;

and wherein $R_1$ is optionally substituted by one or more substituent groups selected from fluoro, chloro, trifluoromethyl, trifluoromethoxy, cyano, hydroxy, amino, carboxy, carbamoyl, sulphamoyl, (1-4C)alkyl, (1-4C)alkoxy, $S(O)_qCH_3$ (where q is 0, 1 or 2), methylamino or dimethylamino, phenyl, phenyl(1-2C)alkyl, 5 or 6 membered heteroaryl, 5 or 6 membered heteroaryl(1-2C)alkyl, 3 to 6 membered heterocyclyl, 3 to 6 membered heterocyclyl(1-2C)alkyl, (3-6C)cycloalkyl, or (3-6C)cycloalkyl(1-2C)alkyl, and wherein any (1-4C)alkyl, (1-4C)alkoxy, phenyl, heteroaryl, heterocyclyl, or (3-6C)cycloalkyl moiety present within a substituent group on $R_1$ is optionally further substituted by fluoro, chloro, trifluoromethyl, trifluoromethoxy, cyano, nitro, hydroxy, amino, carboxy, carbamoyl, sulphamoyl, (1-4C)alkyl, $NR_aR_b$, $OR_a$, $C(O)R_a$, $C(O)OR_a$, $OC(O)R_a$, $N(R_b)OR_a$, $C(O)N(R_b)R_a$, $N(R_b)C(O)R_a$, $S(O)_pR_a$ (where p is 0, 1 or 2), $SO_2N(R_b)R_a$, or $N(R_b)SO_2R_a$, wherein $R_a$ and $R_b$ are each independently selected from H or (1-4C)alkyl;

(6) $R_1$ is selected from (1-6C)alkyl, phenyl, phenyl(1-2C)alkyl, 5 or 6 membered heteroaryl, 5 or 6 membered heteroaryl(1-2C)alkyl, 3 to 9 membered heterocyclyl, 3 to 9 membered heterocyclyl(1-2C)alkyl, (3-6C)cycloalkyl, (3-6C)cycloalkyl(1-2C)alkyl, $NR_7R_8$, $OR_9$, $C(O)R_9$, $C(O)OR_9$, $OC(O)R_9$, $N(R_{10})OR_9$, $N(R_{10})C(O)OR_9$, $C(O)N(R_{10})R_9$, $N(R_{10})C(O)R_9$, $S(O)_pR_9$ (where p is 0, 1 or 2), $SO_2N(R_{10})R_9$, $N(R_{10})SOR_9$ or $N(R_{10})SO_2R_9$;

and wherein $R_1$ is optionally substituted by one or more substituent groups selected from fluoro, chloro, trifluoromethyl, trifluoromethoxy, cyano, hydroxy, amino, carbamoyl, sulphamoyl, (1-4C)alkyl, (1-4C)alkoxy, $S(O)_qCH_3$ (where q is 0, 1 or 2), methylamino or dimethylamino, 5 or 6 membered heteroaryl, 5 or 6 membered heteroaryl(1-2C)alkyl, 3 to 6 membered heterocyclyl, 3 to 6 membered heterocyclyl(1-2C)alkyl, (3-6C)cycloalkyl, or (3-6C)cycloalkyl(1-2C)alkyl, and wherein any (1-4C)alkyl, (1-4C)alkoxy, heteroaryl, heterocyclyl, or (3-6C)cycloalkyl moiety present within a substituent group on $R_1$ is optionally further substituted by fluoro, chloro, trifluoromethyl, trifluoromethoxy, cyano, hydroxy, amino, carboxy, carbamoyl, sulphamoyl, (1-4C)alkyl, $NR_aR_b$, $OR_a$, $C(O)R_a$, $C(O)OR_a$, $OC(O)R_a$, $N(R_b)OR_a$, $C(O)N(R_b)R_a$, $N(R_b)C(O)R_a$, $S(O)_pR_a$ (where p is 0, 1 or 2), $SO_2N(R_b)R_a$, or $N(R_b)SO_2R_a$, wherein $R_a$ and $R_b$ are each independently selected from H or (1-4C)alkyl;

(7) $R_1$ is selected from (1-6C)alkyl, phenyl, phenyl(1-2C)alkyl, 5 or 6 membered heteroaryl, 5 or 6 membered heteroaryl(1-2C)alkyl, 3 to 9 membered heterocyclyl, 3 to 9 membered heterocyclyl(1-2C)alkyl, (3-6C)cycloalkyl, (3-6C)cycloalkyl(1-2C)alkyl, $NR_7R_8$, $OR_9$, $C(O)R_9$, $C(O)OR_9$, $OC(O)R_9$, $N(R_{10})OR_9$, $N(R_{10})C(O)OR_9$, $C(O)N(R_{10})R_9$, $N(R_{10})C(O)R_9$, $S(O)_pR_9$ (where p is 0, 1 or 2), $SO_2N(R_{10})R_9$, $N(R_{10})SOR_9$ or $N(R_{10})SO_2R_9$;

and wherein $R_1$ is optionally substituted by one or more substituent groups selected from fluoro, chloro, trifluoromethyl, trifluoromethoxy, cyano, hydroxy, amino, carbamoyl, sulphamoyl, (1-4C)alkyl, (1-4C)alkoxy, $S(O)_pCH_3$ (where q is 0, 1 or 2), methylamino or dimethylamino, 5 or 6 membered heteroaryl, or 3 to 6 membered heterocyclyl, and wherein any (1-4C)alkyl, (1-4C)alkoxy, heteroaryl, or heterocyclyl moiety present within a substituent group on $R_1$ is optionally further substituted by fluoro, chloro, trifluoromethyl, trifluoromethoxy, cyano, hydroxy, amino, carboxy, carbamoyl, sulphamoyl, (1-4C)alkyl, $NR_aR_b$, $OR_a$, $C(O)R_a$, $C(O)OR_a$, $OC(O)R_a$, $N(R_b)OR_a$, $C(O)N(R_b)R_a$, $N(R_b)C(O)R_a$, $S(O)_pR_a$ (where p is 0, 1 or 2), $SO_2N(R_b)R_a$, or $N(R_b)SO_2R_a$, wherein $R_a$ and $R_b$ are each independently selected from H or (1-4C)alkyl; (8) $R_1$ is selected from (1-6C)alkyl, phenyl, phenyl(1-2C)alkyl, 5 or 6 membered heteroaryl, 5 or 6 membered heteroaryl(1-2C)alkyl, 3 to 9 membered heterocyclyl, 3 to 9 membered heterocyclyl(1-2C)alkyl, (3-6C)cycloalkyl, (3-6C)cycloalkyl(1-2C)alkyl, $NR_7R_8$, $OR_9$, $C(O)R_9$, $C(O)OR_9$, $OC(O)R_9$, $N(R_{10})OR_9$, $N(R_{10})C(O)OR_9$, $C(O)N(R_{10})R_9$, $N(R_{10})C(O)R_9$, $S(O)_pR_9$ (where p is 0, 1 or 2), $SO_2N(R_{10})R_9$, $N(R_{10})SOR_9$ or $N(R_{10})SO_2R_9$;

and wherein $R_1$ is optionally substituted by one or more substituent groups selected from fluoro, chloro, trifluoromethyl, trifluoromethoxy, cyano, hydroxy, amino, carbamoyl, sulphamoyl, (1-4C)alkyl, (1-4C)alkoxy, $S(O)_pCH_3$ (where q is 0, 1 or 2), methylamino or dimethylamino, 5 or 6 membered heteroaryl, or 4 to 6 membered heterocyclyl, and wherein any (1-4C)alkyl, (1-4C)alkoxy, heteroaryl, or heterocyclyl moiety present within a substituent group on $R_1$ is optionally further substituted by fluoro, chloro, trifluoromethyl, trifluoromethoxy, cyano, hydroxy, amino, carbamoyl, sulphamoyl, (1-4C)alkyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_pR_a$ (where p is 0, 1 or 2), $SO_2N(R_b)R_a$, or $N(R_b)SO_2R_a$, wherein $R_a$ and $R_b$ are each independently selected from H or (1-4C)alkyl;

(9) $R_1$ is selected from phenyl, 5 or 6 membered heteroaryl, 3 to 9 membered heterocyclyl, 3 to 9 membered heterocyclyl(1-2C)alkyl, (3-6C)cycloalkyl, $NR_7R_8$, $OR_9$, $C(O)R_9$, $C(O)OR_9$, $OC(O)R_9$, $N(R_{10})OR_9$, $C(O)N(R_{10})R_9$, $N(R_{10})C(O)R_9$, $S(O)_pR_9$ (where p is 0, 1 or 2), $SO_2N(R_{10})R_9$, $N(R_{10})SOR_9$ or $N(R_{10})SO_2R_9$;

and wherein $R_1$ is optionally substituted by one or more substituent groups selected from fluoro, chloro, trifluoromethyl, trifluoromethoxy, cyano, hydroxy, amino, (1-4C)alkyl, (1-4C)alkoxy, $S(O)_qCH_3$ (where q is 0, 1 or 2), methylamino or dimethylamino, or 4 to 6 membered heterocyclyl, and wherein any (1-4C)alkyl or heterocyclyl moiety present within a substituent group on $R_1$ is optionally further substituted by fluoro, chloro, trifluoromethyl, trifluoromethoxy, cyano, hydroxy, amino, carbamoyl, sulphamoyl, (1-4C)alkyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_pR_a$ (where p is 0, 1 or 2), $SO_2N(R_b)R_a$, or $N(R_b)SO_2R_a$, wherein $R_a$ and $R_b$ are each independently selected from H or (1-4C)alkyl;

(10) $R_1$ is selected from phenyl, 5 or 6 membered heteroaryl, 3 to 9 membered heterocyclyl, 3 to 9 membered heterocyclyl(1-2C)alkyl, (3-6C)cycloalkyl, $NR_7R_8$, $OR_9$, $N(R_{10})OR_9$, $C(O)N(R_{10})R_9$, $N(R_{10})C(O)R_9$, $S(O)_pR_9$ (where p is 0, 1 or 2), $SO_2N(R_{10})R_9$, $N(R_{10})SOR_9$ or $N(R_{10})SO_2R_9$;

and wherein $R_1$ is optionally substituted by one or more substituent groups selected from fluoro, chloro, trifluoromethyl, trifluoromethoxy, cyano, hydroxy, amino, (1-4C)alkyl, (1-4C)alkoxy, $S(O)_qCH_3$ (where q is 0, 1 or 2), methylamino or dimethylamino, or 4 to 6 membered heterocyclyl, and wherein any (1-4C)alkyl, heteroaryl, or heterocyclyl moiety present within a substituent group on $R_1$ is optionally further substituted by fluoro, chloro, trifluoromethyl, trifluoromethoxy, cyano, hydroxy, amino, carbamoyl, sulphamoyl, (1-4C)alkyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_pR_a$ (where p is 0, 1 or 2), $SO_2N(R_b)R_a$, or $N(R_b)SO_2R_a$, wherein $R_a$ and $R_b$ are each independently selected from H or (1-4C)alkyl;

(11) $R_1$ is selected from phenyl, 5 or 6 membered heteroaryl, 3 to 9 membered heterocyclyl, 3 to 9 membered heterocyclyl(1-2C)alkyl, (3-6C)cycloalkyl, $NR_7R_8$, $OR_9$, $N(R_{10})OR_9$, $N(R_{10})SO_2R_9$, $N(R_{10})SOR_9$ or $S(O)_pR_9$ (where p is 0, 1 or 2);

and wherein $R_1$ is optionally substituted by one or more substituent groups selected from fluoro, chloro, trifluoromethyl, trifluoromethoxy, cyano, hydroxy, amino, (1-4C)alkyl, (1-4C)alkoxy, $S(O)_qCH_3$ (where q is 0, 1 or 2), methylamino or dimethylamino, or 4 to 6 membered heterocyclyl, and wherein any (1-4C)alkyl, heteroaryl, or heterocyclyl moiety present within a substituent group on $R_1$ is optionally further substituted by fluoro, chloro, trifluoromethyl, trifluoromethoxy, cyano, hydroxy, amino, carbamoyl, sulphamoyl, (1-4C)alkyl, $NR_aR_b$, $OR_a$, $C(O)R_a$, $C(O)OR_a$, $OC(O)R_a$, $C(O)N(R_b)R_a$, $N(R_b)C(O)R_a$, $S(O)_pR_a$ (where p is 0, 1 or 2), $SO_2N(R_b)R_a$, or $N(R_b)SO_2R_a$, wherein $R_a$ and $R_b$ are each independently selected from H or (1-4C)alkyl;

(12) $R_1$ is selected from phenyl, 5 or 6 membered heteroaryl, 3 to 9 membered heterocyclyl, 3 to 9 membered heterocyclyl(1-2C)alkyl, (3-6C)cycloalkyl, $NR_7R_8$, $OR_9$, $N(R_{10})OR_9$, $N(R_{10})SO_2R_9$, $N(R_{10})SOR_9$ or $S(O)_pR_9$ (where p is 0);

and wherein $R_1$ is optionally substituted by one or more substituent groups selected from fluoro, chloro, trifluoromethyl, trifluoromethoxy, cyano, hydroxy, amino, carboxy, carbamoyl, sulphamoyl, (1-4C)alkyl, (1-4C)alkoxy, $S(O)_pCH_3$ (where q is 0, 1 or 2), methylamino or dimethylamino, phenyl, phenyl(1-2C)alkyl, 5 or 6 membered heteroaryl, 5 or 6 membered heteroaryl(1-2C)alkyl, 3 to 6 membered heterocyclyl, 3 to 6 membered heterocyclyl(1-2C)alkyl, (3-6C)cycloalkyl, or (3-6C)cycloalkyl(1-2C)alkyl, and wherein any (1-4C)alkyl, (1-4C)alkoxy, aryl, heteroaryl, heterocyclyl, or (3-6C)cycloalkyl moiety present within a substituent group on $R_1$ is optionally further substituted by fluoro, chloro, trifluoromethyl, trifluoromethoxy, cyano, nitro, hydroxy, amino, carboxy, carbamoyl, sulphamoyl, (1-4C)alkyl, $NR_aR_b$, $OR_a$, $C(O)R_a$, $C(O)OR_a$, $OC(O)R_a$, $N(R_b)OR_a$, $C(O)N(R_b)R_a$, $N(R_b)C(O)R_a$, $S(O)_pR_a$ (where p is 0, 1 or 2), $SO_2N(R_b)R_a$, or $N(R_b)SO_2R_a$, wherein $R_a$ and $R_b$ are each independently selected from H or (1-4C)alkyl;

(13) $R_1$ is selected from phenyl, 5 or 6 membered heteroaryl, 3 to 9 membered heterocyclyl, 3 to 9 membered heterocyclyl(1-2C)alkyl, (3-6C)cycloalkyl, $NR_7R_8$, $N(R_{10})OR_9$, $N(R_{10})SO_2R_9$, $N(R_{10})SOR_9$ or $OR_9$;

and wherein $R_1$ is optionally substituted by one or more substituent groups selected from fluoro, chloro, trifluoromethyl, trifluoromethoxy, cyano, hydroxy, amino, carboxy, carbamoyl, sulphamoyl, (1-4C)alkyl, (1-4C)alkoxy, $S(O)_pCH_3$ (where q is 0, 1 or 2), methylamino or dimethylamino, phenyl, 5 or 6 membered heteroaryl, 3 to 6 membered heterocyclyl, or (3-6C)cycloalkyl, and wherein any (1-4C)alkyl, (1-4C)alkoxy, phenyl, heteroaryl, heterocyclyl, or (3-6C)cycloalkyl group present within a substituent group on $R_1$ is optionally further substituted by fluoro, chloro, trifluoromethyl, trifluoromethoxy, cyano, nitro, hydroxy, amino, carboxy, carbamoyl, sulphamoyl, (1-4C)alkyl, $NR_aR_b$, $OR_a$, $C(O)R_a$, $C(O)OR_a$, $OC(O)R_a$, $N(R_b)OR_a$, $C(O)N(R_b)R_a$, $N(R_b)C(O)R_a$, $S(O)_pR_a$ (where p is 0, 1 or 2), $SO_2N(R_b)R_a$, or $N(R_b)SO_2R_a$, wherein $R_a$ and $R_b$ are each independently selected from H or (1-4C)alkyl;

(14) $R_1$ is selected from phenyl, 5 or 6 membered heteroaryl, 3 to 9 membered heterocyclyl, 3 to 9 membered heterocyclyl(1-2C)alkyl, (4-6C)cycloalkyl, $N(R_{10})OR_9$, $N(R_{10})SO_2R_9$, $N(R_{10})SOR_9$ or $NR_7R_8$;

and wherein $R_1$ is optionally substituted by one or more substituent groups selected from fluoro, chloro, trifluoromethyl, trifluoromethoxy, cyano, hydroxy, amino, carboxy, carbamoyl, sulphamoyl, (1-4C)alkyl, (1-4C)alkoxy, $S(O)_qCH_3$ (where q is 0, 1 or 2), methylamino or dimethylamino, phenyl, 5 or 6 membered heteroaryl, 3 to 6 membered heterocyclyl, or (3-6C)cycloalkyl, and wherein any (1-4C)alkyl, (1-4C)alkoxy, phenyl, heteroaryl, heterocyclyl, or (3-6C)cycloalkyl group present within a substituent group on $R_1$ is optionally further substituted by fluoro, chloro, trifluoromethyl, trifluoromethoxy, cyano, nitro, hydroxy, amino, carboxy, carbamoyl, sulphamoyl, (1-4C)alkyl, $NR_aR_b$, $OR_a$, $C(O)R_a$, $C(O)OR_a$, $OC(O)R_a$, $N(R_b)OR_a$, $C(O)N(R_b)R_a$, $N(R_b)C(O)R_a$, $S(O)_pR_a$ (where p is 0, 1 or 2), $SO_2N(R_b)R_a$, or $N(R_b)SO_2R_a$, wherein $R_a$ and $R_b$ are each independently selected from H or (1-4C)alkyl;

(15) $R_1$ is selected from phenyl, 5 or 6 membered heteroaryl, 3 to 9 membered heterocyclyl, 3 to 9 membered heterocyclyl(1-2C)alkyl, $N(R_{10})OR_9$, $N(R_{10})SO_2R_9$, $N(R_{10})SOR_9$ or $NR_7R_8$;

and wherein $R_1$ is optionally substituted by one or more substituent groups selected from fluoro, chloro, trifluoromethyl, trifluoromethoxy, cyano, hydroxy, amino, carboxy, carbamoyl, sulphamoyl, (1-4C)alkyl, (1-4C)alkoxy, $S(O)_qCH_3$ (where q is 0, 1 or 2), methylamino or dimethylamino, phenyl, 5 or 6 membered heteroaryl, 3 to 6 membered heterocyclyl, or (3-6C)cycloalkyl, and wherein any (1-4C)alkyl, (1-4C)alkoxy, phenyl, heteroaryl, heterocyclyl, or (3-6C)cycloalkyl group present within a substituent group on $R_1$ is optionally further substituted by fluoro, chloro, trifluoromethyl, trifluoromethoxy, cyano, nitro, hydroxy, amino, carboxy, carbamoyl, sulphamoyl, (1-4C)alkyl, $NR_aR_b$, $OR_a$, $C(O)R_a$, $C(O)OR_a$, $OC(O)R_a$, $N(R_b)OR_a$, $C(O)N(R_b)R_a$, $N(R_b)C(O)R_a$, $S(O)_pR_a$ (where p is 0, 1 or 2), $SO_2N(R_b)R_a$, or $N(R_b)SO_2R_a$, wherein $R_a$ and $R_b$ are each independently selected from H or (1-4C)alkyl;
(16) $R_1$ is a 3 to 9 membered nitrogen-linked heterocyclyl or $NR_7R_8$;
and wherein 3 to 9 membered nitrogen-linked heterocyclyl is optionally substituted by one or more substituent groups selected from fluoro, chloro, trifluoromethyl, trifluoromethoxy, cyano, hydroxy, amino, carboxy, carbamoyl, sulphamoyl, (1-4C)alkyl, (1-4C)alkoxy, $S(O)_qCH_3$ (where q is 0, 1 or 2), methylamino, dimethylamino, phenyl, 5 or 6 membered heteroaryl, 3 to 6 membered heterocyclyl, or (3-6C)cycloalkyl;
$R_7$ is hydrogen; and
$R_8$ is (1-6C)alkyl or a 3 to 9 membered heterocyclyl, each of which is optionally substituted by one or more substituents selected from hydroxyl, fluoro, chloro, cyano, $CF_3$, $OCF_3$, (1-2C)alkyl or (1-2C)alkoxy;
(17) $R_1$ is a 3 to 9 membered nitrogen-linked monocyclic, bicyclic, or spiro bicyclic heterocyclyl or $NR_7R_8$;
and wherein 3 to 9 membered nitrogen-linked heterocyclyl is optionally substituted by one or more substituent groups selected from fluoro, chloro, trifluoromethyl, trifluoromethoxy, cyano, hydroxy, amino, carboxy, carbamoyl, sulphamoyl, (1-4C)alkyl, (1-4C)alkoxy, $S(O)_qCH_3$ (where q is 0, 1 or 2), methylamino or dimethylamino;
$R_7$ is hydrogen; and
$R_8$ is (1-6C)alkyl or a 3 to 9 membered heterocyclyl, each of which is optionally substituted by one or more substituents selected from hydroxyl, fluoro, chloro, cyano, $CF_3$, $OCF_3$, (1-2C)alkyl or (1-2C)alkoxy;
(18) $R_3$ is hydrogen, (1-2C)alkyl, or (3-6C)cycloalkyl;
(19) $R_3$ is hydrogen or (1-2C)alkyl;
(20) $R_3$ is hydrogen or methyl;
(21) $R_3$ is hydrogen;
(22) $R_3$ is methyl;
(23) $R_3$ is (3-6C)cycloalkyl;
(24) $R_4$ is hydrogen, (1-2C)alkyl, (1-2C)alkoxy, fluoro, chloro or $CF_3$;
(25) $R_4$ is chloro, methoxy and ethyl;
(26) $R_4$ is hydrogen or methyl;
(27) $R_4$ is hydrogen;
(28) $R_4$ is methyl;
(29) Ar has the formula:

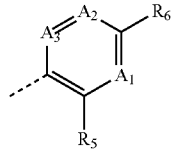

wherein:
(i) all of $A_1$, $A_2$ and $A_3$ are CH; or
(ii) one of $A_1$, $A_2$ and $A_3$ is N and the others are CH;
and $R_5$ and $R_6$ each have any one of the definitions set out herein;

(30) Ar has the formula:

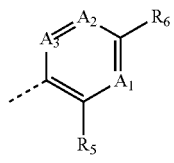

wherein:
(i) all of $A_1$, $A_2$ and $A_3$ are CH; or
(ii) $A_3$ is CH and $A_1$ or $A_2$ are selected from N or CH;
and $R_5$ and $R_6$ each have any one of the definitions set out herein;
(31) Ar has the formula:

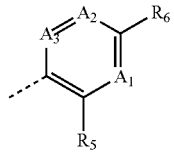

wherein:
(i) all of $A_1$, $A_2$ and $A_3$ are CH; or
(ii) $A_3$ is CH and one of $A_1$ or $A_2$ is N and the other is CH;
and $R_5$ and $R_6$ each have any one of the definitions set out herein;
(32) Ar has the formula:

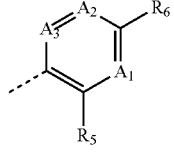

wherein:
(i) all of $A_1$, $A_2$ and $A_3$ are CH; or
(ii) $A_2$ and $A_3$ are both CH and $A_1$ is N;
and $R_5$ and $R_6$ each have any one of the definitions set out herein;
(33) Ar has the formula:

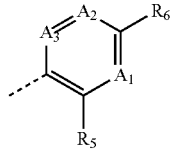

wherein:
all of $A_1$, $A_2$ and $A_3$ are CH; or
and $R_5$ and $R_6$ each have any one of the definitions set out herein;
(34) $R_5$ is hydrogen, cyano, (1-3C)alkyl, (1-3C)perfluoroalkyl, (1-3C)alkoxy, (1-3C) fluoroalkoxy, and halo, and wherein any alkyl or alkoxy moities present within a $R_5$ substituent group are optionally further substituted by hydroxy or methoxy;

(35) $R_5$ is hydrogen, (1-3C)alkyl, (1-3C)alkoxy, (1-3C) fluoroalkoxy and halo, and wherein any alkyl or alkoxy moieties present within a $R_5$ substituent group are optionally further substituted by methoxy;

(36) $R_5$ is (1-2C)alkyl, $CF_3$, (1-2C)alkoxy, —$OCF_2H$, —$OCF_3$ or Cl;

(37) $R_5$ is (1-2C)alkoxy or Cl;

(38) $R_5$ is $OCH_3$;

(39) $R_5$ is Cl;

(40) $R_6$ is halogeno, trifluoromethyl, trifluoromethoxy, cyano, hydroxy, amino, carboxy, carbamoyl, sulphamoyl, or $R_6$ is a group of the formula:

$$-L^1-L^2-R_{17}$$

wherein $L^1$ is absent or a linker group of the formula —$[CR_{18}R_{19}]_n$— in which n is an integer selected from 1 or 2, and $R_{18}$ and $R_{19}$ are each independently selected from hydrogen or methyl;

$L^2$ is absent or is selected from O, S, SO, $SO_2$, $N(R_{20})$, C(O), C(O)O, OC(O), $CH(OR_{20})$, $C(O)N(R_{20})$, $N(R_{20})C(O)$, $N(R_{20})C(O)N(R_{21})$, $S(O)_2N(R_{20})$, or $N(R_{20})SO_2$, wherein $R_{20}$ and $R_{21}$ are each independently selected from hydrogen or (1-2C)alkyl; and $R_{17}$ is (1-6C)alkyl, aryl, (3-6C)cycloalkyl, 5 or 6 membered heteroaryl, or 3 to 8 membered heterocyclyl, and wherein $R_{17}$ is optionally further substituted by one or more substituent groups independently selected from oxo, halo, cyano, nitro, hydroxy, $NR_{22}R_{23}$, (1-4C)alkoxy, (1-4C)alkyl, (3-8C)cycloalkyl, (3-8C)cycloalkyl-(1-3C)alkyl, (1-5C)alkanoyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, $CONR_{22}R_{23}$, and $SO_2NR_{22}R_{23}$; wherein $R_{22}$ and $R_{23}$ are each independently selected from hydrogen, (1-4C)alkyl or (3-6C)cycloalkyl or (3-6C)cycloalkyl(1-2C)alkyl; or $R_{22}$ and $R_{23}$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$(1-2C)alkyl or $NR_eR_f$ (where $R_e$ and $R_f$ are each independently selected from hydrogen, (1-3C)alkyl, (3-6C)cycloalkyl, or (3-6C)cycloalkyl(1-2C)alkyl);

or $R_{17}$ is a group having the formula:

$$-L^3-L^4-R_{24}$$

$L^3$ is absent or a linker group of the formula —$[CR_{25}R_{26}]_n$— in which n is an integer selected from 1, 2, 3 or 4, and $R_{25}$ and $R_{26}$ are each independently selected from hydrogen or (1-2C)alkyl;

$L^4$ is absent or is selected from O, S, SO, $SO_2$, $N(R_{27})$, C(O), C(O)O, OC(O), $CH(OR_{27})$, $C(O)N(R_{27})$, $N(R_{27})C(O)$, $N(R_{27})C(O)N(R_{28})$, $S(O)_2N(R_{27})$, or $N(R_{28})SO_2$, wherein $R_{27}$ and $R_{28}$ are each independently selected from hydrogen or (1-2C)alkyl; and $R_{24}$ is (1-6C)alkyl, aryl, aryl-(1-6C)alkyl, (3-6C)cycloalkyl, (3-6C)cycloalkyl-(1-4C)alkyl, heteroaryl, heteroaryl-(1-4C)alkyl, heterocyclyl, heterocyclyl-(1-4C)alkyl;

(41) $R_6$ is halogeno, trifluoromethyl, trifluoromethoxy, cyano, hydroxy, amino, carboxy, carbamoyl, sulphamoyl, or $R_6$ is a group of the formula:

$$-L^1-L^2-R_{17}$$

wherein $L^1$ is absent or a linker group of the formula —$[CR_{18}R_{19}]_n$— in which n is an integer selected from 1 or 2, and $R_{18}$ and $R_{10}$ are both hydrogen;

$L^2$ is absent or is selected from O, S, SO, $SO_2$, $N(R_{20})$, C(O), C(O)O, OC(O), $CH(OR_{20})$, $C(O)N(R_{20})$, $N(R_{20})C(O)$, $N(R_{20})C(O)N(R_{21})$, $S(O)_2N(R_{20})$, or $N(R_{20})SO_2$, wherein $R_{20}$ and $R_{21}$ are each independently selected from hydrogen or (1-2C)alkyl; and $R_{17}$ is (1-6C)alkyl, aryl, (3-6C)cycloalkyl, 5 or 6 membered heteroaryl, or 3 to 8 membered heterocyclyl, and wherein $R_{17}$ is optionally further substituted by one or more substituent groups independently selected from oxo, halo, cyano, hydroxy, $NR_{22}R_{23}$, (1-4C)alkoxy, (1-4C)alkyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, $CONR_{22}R_{23}$, and $SO_2NR_{22}R_{23}$, wherein $R_{22}$ and $R_{23}$ are each independently selected from hydrogen, (1-4C)alkyl or (3-6C)cycloalkyl or (3-6C)cycloalkyl(1-2C)alkyl; or $R_{22}$ and $R_{23}$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$ (1-2C)alkyl or $NR_eR_f$ (where $R_e$ and $R_f$ are each independently selected from hydrogen or (1-2C)alkyl);

or $R_{17}$ is a group having the formula:

$$-L^3-L^4-R_{24}$$

$L^3$ is absent or a linker group of the formula —$[CR_{25}R_{26}]_n$— in which n is an integer selected from 1 or 2, and $R_{25}$ and $R_{26}$ are each hydrogen;

$L^4$ is absent or is selected from O, S, SO, $SO_2$, $N(R_{27})$, C(O), C(O)O, OC(O), $CH(OR_{27})$, $C(O)N(R_{27})$, $N(R_{27})C(O)$, $N(R_{27})C(O)N(R_{28})$, $S(O)_2N(R_{27})$, or $N(R_{28})SO_2$, wherein $R_{27}$ and $R_{28}$ are each independently selected from hydrogen or (1-2C)alkyl; and $R_{24}$ is (1-2C)alkyl, aryl, aryl-(1-6C)alkyl, (3-6C)cycloalkyl, 5 or 6 membered heteroaryl, 3 to 8 membered heterocyclyl;

(42) $R_6$ is a group of the formula:

$$-L^1-L^2-R_{17}$$

wherein $L^1$ is absent or a linker group of the formula —$[CR_{18}R_{19}]_n$— in which n is an integer selected from 1 or 2, and $R_{18}$ and $R_{10}$ are both hydrogen;

$L^2$ is absent or is selected from O, S, SO, $SO_2$, $N(R_{20})$, C(O), C(O)O, OC(O), $CH(OR_{20})$, $C(O)N(R_{20})$, $N(R_{20})C(O)$, $N(R_{20})C(O)N(R_{21})$, $S(O)_2N(R_{20})$, or $N(R_{20})SO_2$, wherein $R_{20}$ and $R_{21}$ are each independently selected from hydrogen or (1-2C)alkyl; and $R_{17}$ is (1-6C)alkyl, aryl, (3-6C)cycloalkyl, 5 or 6 membered heteroaryl, or 3 to 8 membered heterocyclyl, and wherein $R_{17}$ is optionally further substituted by one or more substituent groups independently selected from oxo, halo, cyano, hydroxy, $NR_{22}R_{23}$, (1-4C)alkoxy, (1-4C)alkyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, $CONR_{22}R_{23}$, and $SO_2NR_{22}R_{23}$, wherein $R_{22}$ and $R_{23}$ are each independently selected from hydrogen, (1-4C)alkyl or (3-6C)cycloalkyl or (3-6C)cycloalkyl(1-2C)alkyl; or $R_{22}$ and $R_{23}$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$(1-2C)alkyl or $NR_eR_f$ (where $R_e$ and $R_f$ are each independently selected from hydrogen or (1-2C)alkyl);

or $R_{17}$ is a group having the formula:

$$-L^3-L^4-R_{24}$$

$L^3$ is absent or a linker group of the formula $—[CR_{25}R_{26}]_n—$ in which n is an integer selected from 1 or 2, and $R_{25}$ and $R_{26}$ are each hydrogen;

$L^4$ is absent or is selected from O, S, SO, $SO_2$, $N(R_{27})$, C(O), C(O)O, OC(O), $CH(OR_{27})$, $C(O)N(R_{27})$, $N(R_{27})C(O)$, $N(R_{27})C(O)N(R_{28})$, $S(O)_2N(R_{27})$, or $N(R_{28})SO_2$, wherein $R_{27}$ and $R_{28}$ are each independently selected from hydrogen or (1-2C)alkyl; and $R_{24}$ is (1-2C)alkyl, aryl, (3-6C)cycloalkyl, 5 or 6 membered heteroaryl, 3 to 8 membered heterocyclyl;

(43) $R_6$ is a group of the formula:

$$-L^1-L^2-R_{17}$$

wherein $L^1$ is absent or a linker group of the formula $—[CR_{18}R_{19}]_n—$ in which n is an integer selected from 1 or 2, and $R_{18}$ and $R_{19}$ are both hydrogen;

$L^2$ is absent or is selected from O, S, SO, $SO_2$, $N(R_{20})$, C(O), C(O)O, OC(O), $CH(OR_{20})$, $C(O)N(R_{20})$, $N(R_{20})C(O)$, $N(R_{20})C(O)N(R_{21})$, $S(O)_2N(R_{20})$, or $N(R_{20})SO_2$, wherein $R_{20}$ and $R_{21}$ are each independently selected from hydrogen or (1-2C)alkyl; and $R_{17}$ is (1-6C)alkyl, aryl, (3-6C)cycloalkyl, 5 or 6 membered heteroaryl, or 3 to 8 membered heterocyclyl, and wherein $R_{17}$ is optionally further substituted by one or more substituent groups independently selected from oxo, halo, cyano, hydroxy, $NR_{22}R_{23}$, (1-4C)alkoxy, (1-4C)alkyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, $CONR_{22}R_{23}$, and $SO_2NR_{22}R_{23}$, wherein $R_{22}$ and $R_{23}$ are each independently selected from hydrogen, (1-4C)alkyl or (3-6C)cycloalkyl or (3-6C)cycloalkyl(1-2C)alkyl; or $R_{22}$ and $R_{23}$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$(1-2C)alkyl or $NR_eR_f$ (where $R_e$ and $R_f$ are each independently selected from hydrogen or (1-2C)alkyl);

or $R_{17}$ is a group having the formula:

$$-L^3-L^4-R_{24}$$

$L^3$ is absent;
$L^4$ is absent or is selected from O, S, SO, $SO_2$, $N(R_{27})$, C(O), C(O)O, OC(O), $CH(OR_{27})$, $C(O)N(R_{27})$, $N(R_{27})C(O)$, $N(R_{27})C(O)N(R_{28})$, $S(O)_2N(R_{27})$, or $N(R_{28})SO_2$, wherein $R_{27}$ and $R_{28}$ are each independently selected from hydrogen or (1-2C)alkyl; and $R_{24}$ is (1-2C)alkyl, aryl, (3-6C)cycloalkyl, 5 or 6 membered heteroaryl, 3 to 8 membered heterocyclyl;

(44) $R_6$ is a group of the formula:

$$-L^1-L^2-R_{17}$$

wherein
$L^1$ is absent;
$L^2$ is absent or is selected from O, S, SO, $SO_2$, $N(R_{20})$, C(O), C(O)O, OC(O), $CH(OR_{20})$, $C(O)N(R_{20})$, $N(R_{20})C(O)$, $S(O)_2N(R_{20})$, or $N(R_{20})SO_2$, wherein $R_{20}$ is selected from hydrogen or (1-2C)alkyl; and $R_{17}$ is (1-6C)alkyl, aryl, (3-6C)cycloalkyl, 5 or 6 membered heteroaryl, or 3 to 8 membered heterocyclyl, and wherein $R_{17}$ is optionally further substituted by one or more substituent groups independently selected from oxo, halo, cyano, hydroxy, $NR_{22}R_{23}$, (1-4C)alkoxy, (1-4C)alkyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, $CONR_{22}R_{23}$, and $SO_2NR_{22}R_{23}$, wherein $R_{22}$ and $R_{23}$ are each independently selected from hydrogen or (1-4C)alkyl;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$(1-2C)alkyl or $NR_eR_f$ (where $R_e$ and $R_f$ are each independently selected from hydrogen or (1-2C)alkyl);

or $R_{17}$ is a group having the formula:

$$-L^3-L^4-R_{24}$$

$L^3$ is absent;
$L^4$ is absent or is selected from O, S, SO, $SO_2$, $N(R_{27})$, C(O), C(O)O, OC(O), $CH(OR_{27})$, $C(O)N(R_{27})$, $N(R_{27})C(O)$, $N(R_{27})C(O)N(R_{28})$, $S(O)_2N(R_{27})$, or $N(R_{28})SO_2$, wherein $R_{27}$ and $R_{28}$ are each independently selected from hydrogen or (1-2C)alkyl; and $R_{24}$ is aryl, (3-6C)cycloalkyl, 5 or 6 membered heteroaryl, 3 to 8 membered heterocyclyl;

(45) $R_6$ is a group of the formula:

$$-L^1-L^2-R_{17}$$

wherein
$L^1$ is absent;
$L^2$ is absent or is selected from O, S, SO, $SO_2$, $N(R_{20})$, C(O), C(O)O, OC(O), $CH(OR_{20})$, $C(O)N(R_{20})$, $N(R_{20})C(O)$, $S(O)_2N(R_{20})$, or $N(R_{20})SO_2$, wherein $R_{20}$ is selected from hydrogen or (1-2C)alkyl; and $R_{17}$ is (1-6C)alkyl, phenyl, (3-6C)cycloalkyl, 5 or 6 membered heteroaryl, or 3 to 6 membered heterocyclyl, and wherein $R_{17}$ is optionally further substituted by one or more substituent groups independently selected from oxo, halo, cyano, hydroxy, $NR_{22}R_{23}$, (1-4C)alkoxy, (1-4C)alkyl, (1-4C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, $CONR_{22}R_{23}$, and $SO_2NR_{22}R_{23}$, wherein $R_{22}$ and $R_{23}$ are each independently selected from hydrogen or (1-2C)alkyl;

and wherein when said substituent group comprises an alkyl, cycloalkyl, heterocyclyl or heteroaryl moiety then said moiety is optionally further substituted by hydroxy, fluoro, chloro, cyano, $CF_3$, $OCF_3$, (1-2C)alkyl, (1-2C)alkoxy, $SO_2$(1-2C)alkyl or $NR_eR_f$ (where $R_e$ and $R_f$ are each independently selected from hydrogen or methyl);

or $R_{17}$ is a group having the formula:

$$-L^3-L^4-R_{24}$$

$L^3$ is absent;
$L^4$ is absent or is selected from O, S, SO, $SO_2$, $N(R_{27})$, C(O), C(O)O, OC(O), $CH(OR_{27})$, $C(O)N(R_{27})$, $N(R_{27})C(O)$, $N(R_{27})C(O)N(R_{28})$, $S(O)_2N(R_{27})$, or $N(R_{28})SO_2$, wherein $R_{27}$ and $R_{28}$ are each independently selected from hydrogen or (1-2C)alkyl; and $R_{24}$ is 3 to 8 membered heterocyclyl;

(46) $R_6$ is halogeno, trifluoromethyl, trifluoromethoxy, cyano, hydroxy, amino, carboxy, carbamoyl, sulphamoyl, or $R_6$ is a group of the formula:

$$-L^1-L^2-R_{17}$$

wherein $L^1$ is absent or a linker group of the formula $—[CR_{18}R_{19}]_n—$ in which n is an integer selected from 1 or 2, and $R_{15}$ and $R_{19}$ are each independently selected from hydrogen or methyl;

$L^2$ is absent or is selected from O, S, SO, SO$_2$, N(R$_{20}$), C(O), C(O)O, OC(O), CH(OR$_{20}$), C(O)N(R$_{20}$), N(R$_{20}$)C(O), N(R$_{20}$)C(O)N(R$_{21}$), S(O)$_2$N(R$_{20}$), or N(R$_{20}$)SO$_2$, wherein R$_{20}$ and R$_{21}$ are each independently selected from hydrogen or (1-2C)alkyl; and R$_{17}$ is (1-6C)alkyl, aryl, (3-6C)cycloalkyl, 5 or 6 membered heteroaryl, or 3 to 8 membered heterocyclyl, and wherein R$_{17}$ is optionally further substituted by one or more substituent groups independently selected from oxo, halo, cyano, nitro, hydroxy, NR$_{22}$R$_{23}$, (1-4C)alkoxy, (1-4C)alkyl, (3-8C)cycloalkyl, (3-8C)cycloalkyl-(1-3C)alkyl, (1-5C)alkanoyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, CONR$_{22}$R$_{23}$, and SO$_2$NR$_{22}$R$_{23}$; wherein R$_{22}$ and R$_{23}$ are each independently selected from hydrogen, (1-4C)alkyl or (3-6C)cycloalkyl or (3-6C)cycloalkyl(1-2C)alkyl; or R$_{22}$ and R$_{23}$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, CF$_3$, OCF$_3$, (1-2C)alkyl, (1-2C)alkoxy, SO$_2$(1-2C)alkyl or NR$_e$R$_f$ (where R$_e$ and R$_f$ are each independently selected from hydrogen, (1-3C)alkyl, (3-6C)cycloalkyl, or (3-6C)cycloalkyl(1-2C)alkyl);

(47) R$_6$ is halogeno, trifluoromethyl, trifluoromethoxy, cyano, hydroxy, amino, carboxy, carbamoyl, sulphamoyl, or R$_6$ is a group of the formula:

-L$^1$-L$^2$-R$_{17}$ wherein

L$^1$ is absent or a linker group of the formula —[CR$_{18}$R$_{19}$]$_n$— in which n is an integer selected from 1 or 2, and R$_{18}$ and R$_{19}$ are both hydrogen;

L$^2$ is absent or is selected from O, S, SO, SO$_2$, N(R$_{20}$), C(O), C(O)O, OC(O), CH(OR$_{20}$), C(O)N(R$_{20}$), N(R$_{20}$)C(O), N(R$_{20}$)C(O)N(R$_{21}$), S(O)$_2$N(R$_{20}$), or N(R$_{20}$)SO$_2$, wherein R$_{20}$ and R$_{21}$ are each independently selected from hydrogen or (1-2C)alkyl; and R$_{17}$ is (1-6C)alkyl, aryl, (3-6C)cycloalkyl, 5 or 6 membered heteroaryl, or 3 to 8 membered heterocyclyl, and wherein R$_{17}$ is optionally further substituted by one or more substituent groups independently selected from oxo, halo, cyano, hydroxy, NR$_{22}$R$_{23}$, (1-4C)alkoxy, (1-4C)alkyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, CONR$_{22}$R$_{23}$, and SO$_2$NR$_{22}$R$_{23}$, wherein R$_{22}$ and R$_{23}$ are each independently selected from hydrogen, (1-4C)alkyl or (3-6C)cycloalkyl or (3-6C)cycloalkyl(1-2C)alkyl; or R$_{22}$ and R$_{23}$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, CF$_3$, OCF$_3$, (1-2C)alkyl, (1-2C)alkoxy, SO$_2$(1-2C)alkyl or NR$_e$R$_f$ (where R$_e$ and R$_f$ are each independently selected from hydrogen or (1-2C)alkyl); (48) R$_6$ is a group of the formula:

-L$^1$-L$^2$-R$_{17}$ wherein

L$^1$ is absent or a linker group of the formula —[CR$_{18}$R$_{19}$]$_n$— in which n is an integer selected from 1 or 2, and R$_{18}$ and R$_{19}$ are both hydrogen;

L$^2$ is absent or is selected from O, S, SO, SO$_2$, N(R$_{20}$), C(O), C(O)O, OC(O), CH(OR$_{20}$), C(O)N(R$_{20}$), N(R$_{20}$)C(O), N(R$_{20}$)C(O)N(R$_{21}$), S(O)$_2$N(R$_{20}$), or N(R$_{20}$)SO$_2$, wherein R$_{20}$ and R$_{21}$ are each independently selected from hydrogen or (1-2C)alkyl; and R$_{17}$ is (1-6C)alkyl, aryl, (3-6C)cycloalkyl, 5 or 6 membered heteroaryl, or 3 to 8 membered heterocyclyl, and wherein R$_{17}$ is optionally further substituted by one or more substituent groups independently selected from oxo, halo, cyano, hydroxy, NR$_{22}$R$_{23}$, (1-4C)alkoxy, (1-4C)alkyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, CONR$_{22}$R$_{23}$, and SO$_2$NR$_{22}$R$_{23}$, wherein R$_{22}$ and R$_{23}$ are each independently selected from hydrogen, (1-4C)alkyl or (3-6C)cycloalkyl or (3-6C)cycloalkyl(1-2C)alkyl; or R$_{22}$ and R$_{23}$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, CF$_3$, OCF$_3$, (1-2C)alkyl, (1-2C)alkoxy, SO$_2$(1-2C)alkyl or NR$_e$R$_f$ (where R$_e$ and R$_f$ are each independently selected from hydrogen or (1-2C)alkyl); (49) R$_6$ is a group of the formula:

-L$^1$-L$^2$-R$_{17}$ wherein

L$^1$ is absent or a linker group of the formula —[CR$_{18}$R$_{19}$]$_n$— in which n is an integer selected from 1 or 2, and R$_{18}$ and R$_{19}$ are both hydrogen;

L$^2$ is absent or is selected from O, S, SO, SO$_2$, N(R$_{20}$), C(O), C(O)O, OC(O), CH(OR$_{20}$), C(O)N(R$_{20}$), N(R$_{20}$)C(O), N(R$_{20}$)C(O)N(R$_{21}$), S(O)$_2$N(R$_{20}$), or N(R$_{20}$)SO$_2$, wherein R$_{20}$ and R$_{21}$ are each independently selected from hydrogen or (1-2C)alkyl; and R$_{17}$ is (1-6C)alkyl, aryl, (3-6C)cycloalkyl, 5 or 6 membered heteroaryl, or 3 to 8 membered heterocyclyl, and wherein R$_{17}$ is optionally further substituted by one or more substituent groups independently selected from oxo, halo, cyano, hydroxy, NR$_{22}$R$_{23}$, (1-4C)alkoxy, (1-4C)alkyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, CONR$_{22}$R$_{23}$, and SO$_2$NR$_{22}$R$_{23}$, wherein R$_{22}$ and R$_{23}$ are each independently selected from hydrogen, (1-4C)alkyl or (3-6C)cycloalkyl or (3-6C)cycloalkyl(1-2C)alkyl; or R$_{22}$ and R$_{23}$ can be linked such that, together with the nitrogen atom to which they are attached, they form a 4-6 membered heterocyclic ring;

and wherein when said substituent group comprises an alkyl, cycloalkyl, heterocyclyl or heteroaryl moiety then said moiety is optionally further substituted by hydroxy, fluoro, chloro, cyano, CF$_3$, OCF$_3$, (1-2C)alkyl, (1-2C)alkoxy, SO$_2$(1-2C)alkyl or NR$_e$R$_f$ (where R$_e$ and R$_f$ are each independently selected from hydrogen or (1-2C)alkyl);

(50) R$_6$ is a group of the formula:

-L$^1$-L$^2$-R$_{17}$ wherein

L$^1$ is absent;

L$^2$ is absent or is selected from O, S, SO, SO$_2$, N(R$_{20}$), C(O), C(O)O, OC(O), CH(OR$_{20}$), C(O)N(R$_{20}$), N(R$_{20}$)C(O), S(O)$_2$N(R$_{20}$), or N(R$_{20}$)SO$_2$, wherein R$_{20}$ is selected from hydrogen or (1-2C)alkyl; and R$_{17}$ is (1-6C)alkyl, aryl, (3-6C)cycloalkyl, 5 or 6 membered heteroaryl, or 3 to 8 membered heterocyclyl, and wherein R$_{17}$ is optionally further substituted by one or more substituent groups independently selected from oxo, halo, cyano, hydroxy, NR$_{22}$R$_{23}$, (1-4C)alkoxy, (1-4C)alkyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, CONR$_{22}$R$_{23}$, and SO$_2$NR$_{22}$R$_{23}$, wherein R$_{22}$ and R$_{23}$ are each independently selected from hydrogen or (1-4C)alkyl;

and wherein when said substituent group comprises an alkyl, cycloalkyl, heterocyclyl or heteroaryl moiety then said moiety is optionally further substituted by hydroxy, fluoro, chloro, cyano, CF$_3$, OCF$_3$, (1-2C)alkyl, (1-2C)alkoxy, SO$_2$(1-2C)alkyl or NR$_e$R$_f$ (where R$_e$ and R$_f$ are each independently selected from hydrogen or (1-2C)alkyl);

(51) R$_6$ is a group of the formula:

wherein
L$^1$ is absent;
L$^2$ is absent or is selected from O, S, SO, SO$_2$, N(R$_{20}$), C(O), C(O)O, OC(O), CH(OR$_{20}$), C(O)N(R$_{20}$), N(R$_{20}$)C(O), S(O)$_2$N(R$_{20}$), or N(R$_{20}$)SO$_2$, wherein R$_{20}$ is selected from hydrogen or (1-2C)alkyl;
R$_{17}$ is (1-6C)alkyl, phenyl, (3-6C)cycloalkyl, 5 or 6 membered heteroaryl, or 3 to 6 membered heterocyclyl, and wherein R$_{17}$ is optionally further substituted by one or more substituent groups independently selected from oxo, halo, cyano, hydroxy, NR$_{22}$R$_{23}$, (1-4C)alkoxy, (1-4C)alkyl, (1-4C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, CONR$_{22}$R$_{23}$, and SO$_2$NR$_{22}$R$_{23}$, wherein R$_{22}$ and R$_{23}$ are each independently selected from hydrogen or (1-2C)alkyl; and and wherein when said substituent group comprises an alkyl, cycloalkyl, heterocyclyl or heteroaryl moiety then said moiety is optionally further substituted by hydroxy, fluoro, chloro, cyano, CF$_3$, OCF$_3$, (1-2C)alkyl, (1-2C)alkoxy, SO$_2$(1-2C)alkyl or NR$_e$R$_f$ (where R$_e$ and R$_f$ are each independently selected from hydrogen or methyl);

(52) R$_6$ is a group of the formula:

wherein
L$^1$ is absent;
L$^2$ is absent; and
R$_{17}$ is a 5 or 6 membered heteroaryl comprising 1, 2 or 3 nitrogen atoms, and wherein R$_{17}$ is optionally further substituted by one or more substituent groups independently selected from halo, cyano, hydroxy, NR$_{22}$R$_{23}$, (1-4C)alkoxy, (1-4C)alkyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, CONR$_{22}$R$_{23}$, and SO$_2$NR$_{22}$R$_{23}$, wherein R$_{22}$ and R$_{23}$ are each independently selected from hydrogen or (1-4C)alkyl;

(53) R$_6$ is a group of the formula:

wherein
L$^1$ is absent;
L$^2$ is absent; and
R$_{17}$ is a 5 membered heteroaryl comprising 1, 2 or 3 nitrogen atoms;

and wherein R$_{17}$ is optionally further substituted by one or more substituent groups independently selected from halo, cyano, hydroxy, NR$_{22}$R$_{23}$, (1-4C)alkoxy, (1-4C)alkyl, (1-5C)alkylsulphonyl, 3 to 6 membered heterocyclyl, 3 to 6 membered heterocyclyl-(1-2C)alkyl, 5 or 6 membered heteroaryl, 5 or 6 membered heteroaryl-(1-2C)alkyl, CONR$_{22}$R$_{23}$, and SO$_2$NR$_{22}$R$_{23}$, wherein R$_{22}$ and R$_{23}$ are each independently selected from hydrogen or (1-4C)alkyl;

(54) R$_8$ and R$_9$ are each independently selected from hydrogen, (1-6C)alkyl, (3-9C)cycloalkyl, (3-6C)cycloalkyl-(1-2C)alkyl, phenyl, 3 to 9 membered heterocyclyl, 3 to 9 membered heterocyclyl-(1-2C)alkyl, 5 or 6 membered heteroaryl, 5 or 6 membered heteroaryl-(1-2C)alkyl, and wherein R$_8$ and R$_9$ are optionally further substituted by one or more substituents selected from hydroxy, fluoro, chloro, cyano, CF$_3$, OCF$_3$, (1-2C)alkyl or (1-2C)alkoxy;

(55) R$_8$ and R$_9$ are each independently selected from hydrogen, (1-6C)alkyl, (3-6C)cycloalkyl, (3-6C)cycloalkyl-(1-2C)alkyl, 3 to 6 membered heterocyclyl, 3 to 6 membered heterocyclyl-(1-2C)alkyl, and wherein R$_8$ and R$_9$ are optionally further substituted by one or more substituents selected from hydroxy, fluoro, chloro, cyano, CF$_3$, OCF$_3$, methyl or methoxy;

(56) R$_7$ and R$_{10}$ are independently selected from hydrogen, (1-4C)alkyl, (3-6C)cycloalkyl, (3-6C)cycloalkyl-(1-2C)alkyl;

(57) R$_7$ and R$_{10}$ are independently selected from hydrogen or (1-4C)alkyl;

(58) R$_7$ and R$_{10}$ are independently selected from hydrogen or (1-2C)alkyl;

(59) R$_7$ and R$_{10}$ are independently selected from hydrogen or methyl;

(60) R$_7$ and R$_{10}$ are hydrogen;

(61) W is N;

(62) W is C—R$_3$;

(63) W is C—CH$_3$.

As stated above, X can only be N when Z is N and W may only be N when X and Z are both N. Accordingly, the compounds of formula I may have one of the structures Ia, Ib, Ic or Id shown below:

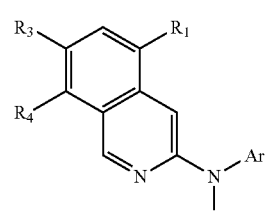

Ia

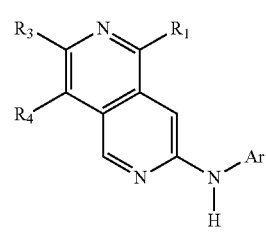

Ib

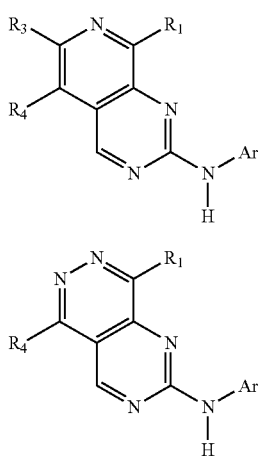

or a pharmaceutically acceptable salt or solvate thereof.

Suitably, the compounds of formula I have one or the structures Ib, Ic or Id above, or a pharmaceutically acceptable salt or solvate thereof.

In an embodiment, the compound of the invention is a compound of formula Ia above, wherein $R_1$, $R_3$, $R_4$ and Ar each have any one of the definitions set out herein, or a pharmaceutically acceptable salt or solvate thereof.

In an embodiment, the compound of the invention is a compound of formula Ib, wherein $R_1$, $R_3$, $R_4$ and Ar each have any one of the definitions set out herein, or a pharmaceutically acceptable salt or solvate thereof.

In an embodiment, the compound of the invention is a compound of formula Ic, wherein $R_1$, $R_3$, $R_4$ and Ar each have any one of the definitions set out herein, or a pharmaceutically acceptable salt or solvate thereof.

In an embodiment, the compound of the invention is a compound of formula Id, wherein $R_1$, $R_4$ and Ar each have any one of the definitions set out herein, or a pharmaceutically acceptable salt or solvate thereof.

Suitably, the compounds of formula I have the structural formula Ia or Ic, especially structural formula Ic, or a pharmaceutically acceptable salt or solvate thereof.

Suitably, $R_1$ is as defined in any one of paragraphs (5) to (17) above.

Suitably, $R_3$ is as defined in any one of paragraphs (18) to (23) above.

Suitably, $R_4$ is as defined in any one of paragraphs (24) to (28) above.

Suitably, Ar is as defined in any one of paragraphs (29) to (33) above.

Suitably, $R_5$ is as defined in any one of paragraphs (34) to (39) above.

Suitably, $R_6$ is as defined in any one of paragraphs (40) to (53) above.

Suitably, $R_8$ and $R_9$ are as defined in any one of paragraphs (54) to (55) above.

Suitably, $R_7$ and $R_{10}$ are as defined in any one of paragraphs (56) to (60) above.

Suitably, W is as defined in any one of paragraphs (61) to (63) above.

In an embodiment, the compound is a compound of formula I, Ia, Ib or Ic as defined herein wherein $R_3$ is H and $R_1$, $R_4$, and Ar each have any one of the definitions set out herein, or a pharmaceutically acceptable salt or solvate thereof.

In an embodiment, the compound is a compound of formula I, Ia, Ib, Ic or Id as defined herein wherein $R_4$ is H and $R_1$, $R_3$, and Ar each have any one of the definitions set out herein, or a pharmaceutically acceptable salt or solvate thereof.

In an embodiment, the compound is a compound of formula I, Ia, Ib or Ic as defined herein wherein $R_3$ and $R_4$ are H, and $R_1$ and Ar each have any one of the definitions set out herein, or a pharmaceutically acceptable salt or solvate thereof.

In an embodiment, the compound is a compound of formula Ia, Ib, Ic or Id as defined herein wherein $A_3$ is CH and $R_1$, $R_3$, $R_4$, $R_5$, $R_6$, $A_1$ and $A_2$ each have any one of the definitions set out herein, or a pharmaceutically acceptable salt or solvate thereof.

In an embodiment, the compound is a compound of formula Ia, Ib, Ic or Id as defined herein wherein $A_3$ is CH; $R_3$ and $R_4$ are both H; and $R_1$, $R_5$, $R_6$, $A_1$ and $A_2$ each have any one of the definitions set out herein, or a pharmaceutically acceptable salt or solvate thereof.

In an embodiment, the compound is a compound of formula Ia, Ib, Ic or Id as defined herein wherein
$A_3$ is CH;
$R_3$ and $R_4$ are both H;
$R_1$ is as defined in any one of paragraphs (5) to (15) above;
$R_5$ is as defined in any one of paragraphs (30) to (35) above;
$R_6$ is as defined in any one of paragraphs (36) to (44) above;
both of $A_1$ and $A_2$ are CH or one of $A_1$ and $A_2$ is CH and the other is N;
or a pharmaceutically acceptable salt or solvate thereof.

In an embodiment, the compound is a compound of formula Ia, Ib, Ic or Id as defined herein wherein
$A_3$ is CH;
$R_3$ and $R_4$ are both H;
$R_2$ is as defined in any one of paragraphs (10) to (16) above;
$R_5$ is as defined in any one of paragraphs (32) to (35) above;
$R_6$ is as defined in any one of paragraphs (36) to (44) above;
both of $A_1$ and $A_2$ are CH or one of $A_1$ and $A_2$ is CH and the other is N;
or a pharmaceutically acceptable salt or solvate thereof.

In an embodiment, the compound is a compound of formula I, Ia, Ib, Ic or Id as defined herein wherein Ar is as defined in either paragraph (28) or (29) above, and $R_1$, $R_3$ and $R_4$ each have any one of the definitions set out herein, or a pharmaceutically acceptable salt or solvate thereof.

In an embodiment, the compound is a compound of formula I, Ib, Ic or Id as defined herein wherein Ar is as defined in either paragraph (28) or (29) above, and $R_1$, $R_3$ and $R_4$ each have any one of the definitions set out herein, or a pharmaceutically acceptable salt or solvate thereof.

In an embodiment, the compound is a compound of formula I, Ia, Ib, Ic or Id as defined herein in which Ar has the formula:

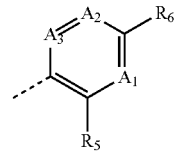

wherein:
(i) all of $A_1$, $A_2$ and $A_3$ are CH; or
(ii) $A_2$ and $A_3$ are both CH and $A_1$ is N;
$R_5$ is methoxy or chloro; and
$R_1$, $R_3$, $R_4$ and $R_6$ each have any one of the definitions set out herein;
or a pharmaceutically acceptable salt or solvate thereof.

In an embodiment, the compound is a compound of formula I, Ia, Ib, Ic or Id (especially formula Ic) as defined herein before in which Ar has the formula:

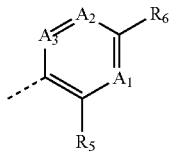

wherein:
(i) all of $A_1$, $A_2$ and $A_3$ are CH; or
(ii) $A_3$ is CH and one of $A_1$ or $A_2$ is N;
$R_5$ is (1-2C)alkoxy, $OCF_3$, or $OCHF_2$;
$R_3$ is hydrogen or methyl;
$R_4$ is hydrogen;
$R_1$ is as defined in any one of paragraphs (16) or (17) above; and
$R_6$ is as defined in any one of paragraphs (52) or (53) above;
or a pharmaceutically acceptable salt or solvate thereof.

In an embodiment, the compound is a compound of formula I, Ia, Ib, Ic or Id (especially formula Ic) as defined herein before in which Ar has the formula:

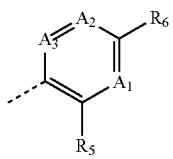

wherein:
all of $A_1$, $A_2$ and $A_3$ are CH;
$R_5$ is (1-2C)alkoxy or $OCHF_2$;
$R_3$ is hydrogen or methyl;
$R_4$ is hydrogen;
$R_1$ is as defined in paragraph (16) or (17) above; and
$R_6$ is as defined in any one of paragraphs (52) or (53) above;
or a pharmaceutically acceptable salt or solvate thereof.

Particular compounds of the present invention include any one of the compounds exemplified in the present application, or a pharmaceutically acceptable salt or solvate thereof, and, in particular, any one of the following:
5-(furan-2-yl)-N-(4-methoxyphenyl)isoquinolin-3-amine;
N-(4-methoxyphenyl)-5-(1-methyl-1H-pyrazol-4-yl)isoquinolin-3-amine;
N-(2-methoxy-4-((1-methylpiperidin-4-yl)oxy)phenyl)-5-(1-methyl-1H-pyrazol-4-yl)isoquinolin-3-amine;
N-(2,4-dimethoxyphenyl)-5-(1-methyl-1H-pyrazol-4-yl)isoquinolin-3-amine;
3-chloro-N,N-dimethyl-4-((5-(1-methyl-1H-pyrazol-4-yl)isoquinolin-3-yl)amino)benzamide;
3-methoxy-N,N-dimethyl-4-((5-(1-methyl-1H-pyrazol-4-yl)isoquinolin-3-yl)amino)benzamide;
(3-methoxy-4-((5-(1-methyl-1H-pyrazol-4-yl)isoquinolin-3-yl)amino)phenyl)(3-methoxyazetidin-1-yl)methanone;
N-(2-chloro-4-(1-methyl-1H-pyrazol-4-yl)phenyl)-5-(1-methyl-1H-pyrazol-4-yl)isoquinolin-3-amine;
(3-chloro-4-((5-(1-methyl-1H-pyrazol-4-yl)isoquinolin-3-yl)amino)phenyl)(3-methoxyazetidin-1-yl)methanone;
(3-methoxy-4-((5-(pyridin-3-yl)isoquinolin-3-yl)amino)phenyl)(3-methoxyazetidin-1-yl)methanone;
N-(4-(3,5-dimethylisoxazol-4-yl)-2-methoxyphenyl)-5-(1-methyl-1H-pyrazol-4-yl)isoquinolin-3-amine;
(3-methoxy-4-((8-(1-methyl-1H-pyrazol-4H)pyrido[3,4-d]pyrimidin-2-yl)amino)phenyl)(3-methoxyazetidin-1-yl)methanone;
N-(2-methoxy-4-(1-methyl-1H-pyrazol-4-yl)phenyl)-8-(1-methyl-1H-pyrazol-4-yl)pyrido[3,4-d]pyrimidin-2-amine;
N-(2-chloro-4-(1-methyl-1H-pyrazol-4-yl)phenyl)-8-(1-methyl-1H-pyrazol-4-yl)pyrido[3,4-d]pyrimidin-2-amine;
N-(2-chloro-4-(1-methyl-1H-imidazol-5-yl)phenyl)-5-(1-methyl-1H-pyrazol-4-yl)isoquinolin-3-amine;
N-(2-methoxy-4-(1-methyl-1H-pyrazol-4-yl)phenyl)-5-(1-methyl-1H-pyrazol-4-yl)isoquinolin-3-amine;
(3-methoxy-4-((5-(pyrimidin-5-yl)isoquinolin-3-yl)amino)phenyl)(3-methoxyazetidin-1-yl)methanone;
N-(2-methoxy-4-(1-methyl-1H-imidazol-5-yl)phenyl)-5-(1-methyl-1H-pyrazol-4-yl)isoquinolin-3-amine;
(4-((5-(1,5-dimethyl-1H-pyrazol-4-yl)isoquinolin-3-yl)amino)-3-methoxyphenyl)(3-methoxyazetidin-1-yl)methanone;
(3-methoxy-4-((5-(1-methyl-1H-pyrazol-3-yl)isoquinolin-3-yl)amino)phenyl)(3-methoxyazetidin-1-yl)methanone;
N-(2-chloro-4-(1,2-dimethyl-1H-imidazol-5-yl)phenyl)-5-(1-methyl-1H-pyrazol-4-yl)isoquinolin-3-amine;
N-(4-(1,2-dimethyl-1H-imidazol-5-yl)-2-methoxyphenyl)-5-(1-methyl-1H-pyrazol-4-yl)isoquinolin-3-amine;
N-(2-methoxy-4-(1-methyl-1H-pyrazol-4-yl)phenyl)-8-phenylpyrido[3,4-d]pyrimidin-2-amine;
8-cyclopropyl-N-(2-methoxy-4-(1-methyl-1H-pyrazol-4-yl)phenyl)pyrido[3,4-d]pyrimidin-2-amine;
N-(2-methoxy-5-methyl-4-(1-methyl-1H-pyrazol-4-yl)phenyl)-8-(1-methyl-1H-pyrazol-4-yl)pyrido[3,4-d]pyrimidin-2-amine;
(3-methoxy-4-((5-(1-methyl-1H-pyrazol-5-yl)isoquinolin-3-yl)amino)phenyl)(3-methoxyazetidin-1-yl)methanone;
(4-((5-(1,3-dimethyl-1H-pyrazol-4-yl)isoquinolin-3-yl)amino)-3-methoxyphenyl)(3-methoxyazetidin-1-yl)methanone;
(4-((5-(1-isopropyl-1H-pyrazol-4-yl)isoquinolin-3-yl)amino)-3-methoxyphenyl)(3-methoxyazetidin-1-yl)methanone;
4-((5-(1-methyl-1H-pyrazol-4-yl)isoquinolin-3-yl)amino)-N-(1-methylpiperidin-4-yl)-3-(trifluoromethoxy)benzamide;
(4-((5-(3,5-dimethylisoxazol-4-yl)isoquinolin-3-yl)amino)-3-methoxyphenyl)(3-methoxyazetidin-1-yl)methanone;
(3-methoxy-4-((5-(1-methyl-1H-imidazol-5-yl)isoquinolin-3-yl)amino)phenyl)(3-methoxyazetidin-1-yl)methanone;
N-(2-methoxy-4-(1-methyl-1H-pyrazol-4-yl)phenyl)-8-(pyrrolidin-1-yl)pyrido[3,4-d]pyrimidin-2-amine;
N-(4-(1,2-dimethyl-1H-imidazol-5-yl)-2-methoxyphenyl)-8-(1-methyl-1H-pyrazol-4-yl)pyrido[3,4-d]pyrimidin-2-amine;
tert-butyl 4-(4-(3-((2-methoxy-4-(3-methoxyazetidine-1-carbonyl)phenyl)amino)isoquinolin-5-yl)-1H-pyrazol-1-yl)piperidine-1-carboxylate;
(3-methoxy-4-((5-(1-(piperidin-4-yl)-1H-pyrazol-4-yl)isoquinolin-3-yl)amino)phenyl)(3-methoxyazetidin-1-yl)methanone;
(3-methoxy-4-((5-(1-(1-methylpiperidin-4-yl)-1H-pyrazol-4-yl)isoquinolin-3-yl)amino)phenyl)(3-methoxyazetidin-1-yl)methanone;
(3-methoxy-4-((5-(1-(2-methoxyethyl)-1H-pyrazol-4-yl)isoquinolin-3-yl)amino)phenyl)(3-methoxyazetidin-1-yl)methanone;

N8,N8-diethyl-N2-(2-methoxy-4-(1-methyl-1H-pyrazol-4-yl)phenyl)pyrido[3,4-d]pyrimidine-2,8-diamine;
N8-cyclopentyl-N2-(2-methoxy-4-(1-methyl-1H-pyrazol-4-yl)phenyl)pyrido[3,4-d]pyrimidine-2,8-diamine;
(4-((5-(1-(2-(dimethylamino)ethyl)-1H-pyrazol-4-yl)isoquinolin-3-yl)amino)-3-methoxyphenyl)(3-methoxyazetidin-1-yl)methanone;
N-(2-methoxy-4-(1-methyl-1H-pyrazol-4-yl)phenyl)-5-(1-methyl-1H-pyrazol-4-yl)-2,6-naphthyridin-3-amine;
N-(2-methoxy-4-(1-methyl-1H-pyrazol-4-yl)phenyl)-8-(piperidin-1-yl)pyrido[3,4-d]pyrimidin-2-amine;
N8-cyclohexyl-N2-(2-methoxy-4-(1-methyl-1H-pyrazol-4-yl)phenyl)pyrido[3,4-d]pyrimidine-2,8-diamine;
N-(2-methoxy-4-(1-methyl-1H-pyrazol-4-yl)phenyl)-8-(3-methylpyrrolidin-1-yl)pyrido[3,4-d]pyrimidin-2-amine;
8-(3,3-difluoropyrrolidin-1-yl)-N-(2-methoxy-4-(1-methyl-1H-pyrazol-4-yl)phenyl)pyrido[3,4-d]pyrimidin-2-amine;
N-(4-(1,2-dimethyl-1H-imidazol-5-yl)-2-methoxyphenyl)-5-(1-methyl-1H-pyrazol-4-yl)-2,6-naphthyridin-3-amine;
N8-(cyclopropylmethyl)-N2-(2-methoxy-4-(1-methyl-1H-pyrazol-4-yl)phenyl)pyrido[3,4-d]pyrimidine-2,8-diamine;
8-(1-methyl-1H-pyrazol-4-yl)-N-(2-methyl-4-(1-methyl-1H-pyrazol-4-yl)phenyl)pyrido[3,4-d]pyrimidin-2-amine;
N8-cyclopentyl-N2-(2-methoxy-4-(1-methyl-1H-pyrazol-4-yl)phenyl)-N8-methylpyrido[3,4-d]pyrimidine-2,8-diamine;
N-(2-ethoxy-4-(1-methyl-1H-pyrazol-4-yl)phenyl)-8-(1-methyl-1H-pyrazol-4-yl)pyrido[3,4-d]pyrimidin-2-amine;
N-(2-isopropoxy-4-(1-methyl-1H-pyrazol-4-yl)phenyl)-8-(1-methyl-1H-pyrazol-4-yl)pyrido[3,4-d]pyrimidin-2-amine;
N-(2-(2-methoxyethoxy)-4-(1-methyl-1H-pyrazol-4-yl)phenyl)-8-(1-methyl-1H-pyrazol-4-yl)pyrido[3,4-d]pyrimidin-2-amine;
N8-isopentyl-N2-(2-methoxy-4-(1-methyl-1H-pyrazol-4-yl)phenyl)pyrido[3,4-d]pyrimidine-2,8-diamine;
N-(2-methoxy-4-(1-methyl-1H-pyrazol-4-yl)phenyl)-8-morpholinopyrido[3,4-d]pyrimidin-2-amine;
N-(2-methoxy-4-(1-methyl-1H-pyrazol-4-yl)phenyl)-8-(4-methylpiperazin-1-yl)pyrido[3,4-d]pyrimidin-2-amine;
8-(3,3-difluoroazetidin-1-yl)-N-(2-methoxy-4-(1-methyl-1H-pyrazol-4-yl)phenyl)pyrido[3,4-d]pyrimidin-2-amine;
N-(2-methoxy-4-(1-methyl-1H-pyrazol-4-yl)phenyl)-8-(2-methylpyrrolidin-1-yl)pyrido[3,4-d]pyrimidin-2-amine;
N8-isobutyl-N2-(2-methoxy-4-(1-methyl-1H-pyrazol-4-yl)phenyl)pyrido[3,4-d]pyrimidine-2,8-diamine;
8-(cyclohexylthio)-N-(2-methoxy-4-(1-methyl-1H-pyrazol-4-yl)phenyl)pyrido[3,4-d]pyrimidin-2-amine;
N-(2-methoxy-4-(1-methyl-1H-pyrazol-4-yl)phenyl)-8-(6-azaspiro[3.4]octan-6-yl)pyrido[3,4-d]pyrimidin-2-amine;
N8-cyclohexyl-N2-(2-methoxy-4-(1-(2-(4-methylpiperazin-1-yl)ethyl)-1H-pyrazol-4-yl)phenyl)pyrido[3,4-d]pyrimidine-2,8-diamine;
8-(1-ethyl-1H-pyrazol-4-yl)-N-(2-methoxy-4-(1-methyl-1H-pyrazol-4-yl)phenyl)pyrido[3,4-d]pyrimidin-2-amine;
8-(1-isopropyl-1H-pyrazol-4-yl)-N-(2-methoxy-4-(1-methyl-1H-pyrazol-4-yl)phenyl)pyrido[3,4-d]pyrimidin-2-amine;
N-(2-methoxy-4-(1-methyl-1H-pyrazol-4-yl)phenyl)-8-(3-methoxyazetidin-1-yl)pyrido[3,4-d]pyrimidin-2-amine;
N1-(cyclopropylmethyl)-N7-(2-methoxy-4-(1-methyl-1H-pyrazol-4-yl)phenyl)-2,6-naphthyridine-1,7-diamine;
N1-cyclohexyl-N7-(2-methoxy-4-(1-methyl-1H-pyrazol-4-yl)phenyl)-2,6-naphthyridine-1,7-diamine;
N8-cyclohexyl-N2-(4-(1-(2-(dimethylamino)ethyl)-1H-pyrazol-4-yl)-2-methoxyphenyl)pyrido[3,4-d]pyrimidine-2,8-diamine;
N2-(2-methoxy-4-(1-methyl-1H-pyrazol-4-yl)phenyl)-N8-neopentylpyrido[3,4-d]pyrimidine-2,8-diamine;
N2-(2-methoxy-4-(1-methyl-1H-pyrazol-4-yl)phenyl)-N8-(tetrahydro-2H-pyran-4-yl)pyrido[3,4-d]pyrimidine-2,8-diamine;
N8-(cyclopropylmethyl)-N2-(2-methyl-4-(1-methyl-1H-pyrazol-4-yl)phenyl)pyrido[3,4-d]pyrimidine-2,8-diamine;
N8-cyclohexyl-N2-(2-methyl-4-(1-methyl-1H-pyrazol-4-yl)phenyl)pyrido[3,4-d]pyrimidine-2,8-diamine;
N8-(cyclopropylmethyl)-N2-(2-ethoxy-4-(1-methyl-1H-pyrazol-4-yl)phenyl)pyrido[3,4-d]pyrimidine-2,8-diamine;
N8-(cyclohexylmethyl)-N2-(2-methoxy-4-(1-methyl-1H-pyrazol-4-yl)phenyl)pyrido[3,4-d]pyrimidine-2,8-diamine;
2-(4-(4-((8-(cyclohexylamino)pyrido[3,4-d]pyrimidin-2-yl)amino)-3-methoxyphenyl)-1H-pyrazol-1-yl)ethanol;
8-(cyclopropylmethoxy)-N-(2-methoxy-4-(1-methyl-1H-pyrazol-4-yl)phenyl)pyrido[3,4-d]pyrimidin-2-amine;
1-((2-((2-methoxy-4-(1-methyl-1H-pyrazol-4-yl)phenyl)amino)pyrido[3,4-d]pyrimidin-8-yl)amino)-2-methylpropan-2-ol;
N2-(2-methoxy-4-(1-methyl-1H-pyrazol-4-yl)phenyl)-N8-(oxetan-3-ylmethyl)pyrido[3,4-d]pyrimidine-2,8-diamine;
N8-(3,3-dimethylbutan-2-yl)-N2-(2-methoxy-4-(1-methyl-1H-pyrazol-4-yl)phenyl)pyrido[3,4-d]pyrimidine-2,8-diamine;
3-((2-((2-methoxy-4-(1-methyl-1H-pyrazol-4-yl)phenyl)amino)pyrido[3,4-d]pyrimidin-8-yl)amino)-2,2-dimethylpropan-1-ol;
N2-(2-ethoxy-4-(1-methyl-1H-pyrazol-4-yl)phenyl)-N8-(tetrahydro-2H-pyran-4-yl)pyrido[3,4-d]pyrimidine-2,8-diamine;
N2-(2-methoxy-6-morpholinopyridin-3-yl)-N8-neopentylpyrido[3,4-d]pyrimidine-2,8-diamine;
N2-(2-methoxy-6-(methylsulfonyl)pyridin-3-yl)-N8-neopentylpyrido[3,4-d]pyrimidine-2,8-diamine;
N2-(2-methoxy-4-(1-methyl-1H-imidazol-5-yl)phenyl)-N8-neopentylpyrido[3,4-d]pyrimidine-2,8-diamine;
N2-(4-(1,3-dimethyl-1H-pyrazol-4-yl)-2-methoxyphenyl)-N8-neopentylpyrido[3,4-d]pyrimidine-2,8-diamine;
N8-(1-cyclopropylethyl)-N2-(2-methoxy-4-(1-methyl-1H-pyrazol-4-yl)phenyl)pyrido[3,4-d]pyrimidine-2,8-diamine;
2-(4-(3-methoxy-4-((8-((tetrahydro-2H-pyran-4-yl)amino)pyrido[3,4-d]pyrimidin-2-yl)amino)phenyl)-1H-pyrazol-1-yl)ethanol;
N2-(4-(1,5-dimethyl-1H-pyrazol-4-yl)-2-methoxyphenyl)-N8-neopentylpyrido[3,4-d]pyrimidine-2,8-diamine;
(R)—N8-(3,3-dimethylbutan-2-yl)-N2-(2-methoxy-4-(1-methyl-1H-pyrazol-4-yl)phenyl)pyrido[3,4-d]pyrimidine-2,8-diamine;
(S)—N8-(3,3-dimethylbutan-2-yl)-N2-(2-methoxy-4-(1-methyl-1H-pyrazol-4-yl)phenyl)pyrido[3,4-d]pyrimidine-2,8-diamine;
N2-(2-methoxy-4-(1-methyl-1H-pyrazol-4-yl)phenyl)-N8-(tetrahydrofuran-3-yl)pyrido[3,4-d]pyrimidine-2,8-diamine;

N2-(2-methoxy-4-(1-methyl-1H-pyrazol-4-yl)phenyl)-N8-((tetrahydrofuran-3-yl)methyl)pyrido[3,4-d]pyrimidine-2,8-diamine;

1-(2-((2-methoxy-4-(1-methyl-1H-pyrazol-4-yl)phenyl)amino)pyrido[3,4-d]pyrimidin-8-yl)pyrrolidin-3-ol;

N2-(2-methoxy-4-(1-methyl-1H-pyrazol-4-yl)phenyl)-N8-methyl-N8-(tetrahydro-2H-pyran-4-yl)pyrido[3,4-d]pyrimidine-2,8-diamine;

N8-(tert-butyl)-N2-(2-methoxy-4-(1-methyl-1H-pyrazol-4-yl)phenyl)pyrido[3,4-d]pyrimidine-2,8-diamine;

N2-(2-methoxy-4-(1-methyl-1H-pyrazol-4-yl)phenyl)-N8-(1-methylcyclohexyl)pyrido[3,4-d]pyrimidine-2,8-diamine;

8-(1-(2,2-difluoroethyl)-1H-pyrazol-4-yl)-N-(2-methoxy-4-(1-methyl-1H-pyrazol-4-yl)phenyl)pyrido[3,4-d]pyrimidin-2-amine;

N2-(4-(1,2-dimethyl-1H-imidazol-5-yl)-2-methoxyphenyl)-N8-neopentylpyrido[3,4-d]pyrimidine-2,8-diamine;

N2-(2-methoxy-4-(1-methyl-1H-pyrazol-4-yl)phenyl)-6-methyl-N8-neopentylpyrido[3,4-d]pyrimidine-2,8-diamine;

N2-(2-methoxy-4-morpholinophenyl)-N8-neopentylpyrido[3,4-d]pyrimidine-2,8-diamine;

N8-(2,2-difluoropropyl)-N2-(2-methoxy-4-(1-methyl-1H-pyrazol-4-yl)phenyl)pyrido[3,4-d]pyrimidine-2,8-diamine;

N8-(3-methoxy-2,2-dimethylpropyl)-N2-(2-methoxy-4-(1-methyl-1H-pyrazol-4-yl)phenyl)pyrido[3,4-d]pyrimidine-2,8-diamine;

N8-(2-methoxy-2-methylpropyl)-N2-(2-methoxy-4-(1-methyl-1H-pyrazol-4-yl)phenyl)pyrido[3,4-d]pyrimidine-2,8-diamine;

N2-(2-methoxy-4-(1-methyl-1H-pyrazol-4-yl)phenyl)-N8-(2,2,2-trifluoroethyl)pyrido[3,4-d]pyrimidine-2,8-diamine;

N-(2-methoxy-4-(1-methyl-1H-pyrazol-4-yl)phenyl)-8-(2-oxa-6-azaspiro[3.4]octan-6-yl)pyrido[3,4-d]pyrimidin-2-amine;

1-(((2-((2-methoxy-4-(1-methyl-1H-pyrazol-4-yl)phenyl)amino)pyrido[3,4-d]pyrimidin-8-yl)amino)methyl)cyclobutanol;

8-chloro-N-(2-methoxy-4-(1-methyl-1H-pyrazol-4-yl)phenyl)pyrido[3,4-d]pyrimidin-2-amine;

N2-(2-ethyl-4-(1-methyl-1H-pyrazol-4-yl)phenyl)-N8-neopentylpyrido[3,4-d]pyrimidine-2,8-diamine;

N2-(4-(1-methyl-1H-pyrazol-4-yl)-2-(trifluoromethoxy)phenyl)-N8-neopentylpyrido[3,4-d]pyrimidine-2,8-diamine;

N2-(2-methoxy-4-(1-methyl-1H-pyrazol-4-yl)phenyl)-N8-methylpyrido[3,4-d]pyrimidine-2,8-diamine;

N2-(2-methoxy-4-(1-methyl-1H-pyrazol-4-yl)phenyl)-N8,N8-dimethylpyrido[3,4-d]pyrimidine-2,8-diamine;

N-(2-((2-methoxy-4-(1-methyl-1H-pyrazol-4-yl)phenyl)amino)pyrido[3,4-d]pyrimidin-8-yl)-2-methylpropane-2-sulfinamide;

N2-(2-methoxy-4-(4-morpholinopiperidin-1-yl)phenyl)-N8-neopentylpyrido[3,4-d]pyrimidine-2,8-diamine;

N2-(2-methoxy-4-(1-methyl-1H-pyrazol-4-yl)phenyl)-N8-((3-methyloxetan-3-yl)methyl)pyrido[3,4-d]pyrimidine-2,8-diamine;

N2-(2-methoxy-4-(piperidin-1-yl)phenyl)-N8-neopentylpyrido[3,4-d]pyrimidine-2,8-diamine;

N-(2-((2-methoxy-4-(1-methyl-1H-pyrazol-4-yl)phenyl)amino)pyrido[3,4-d]pyrimidin-8-yl)-2-methylpropane-2-sulfonamide;

N2-(2-methoxy-4-(1-methyl-1H-pyrazol-4-yl)phenyl)-N8-(oxetan-3-yl)pyrido[3,4-d]pyrimidine-2,8-diamine;

(1-(3-methoxy-4-((8-(neopentylamino)pyrido[3,4-d]pyrimidin-2-yl)amino)phenyl)piperidin-4-yl)(morpholino)methanone;

N2-(2-methoxy-4-(4-methylpiperazin-1-yl)phenyl)-N8-neopentylpyrido[3,4-d]pyrimidine-2,8-diamine;

1-(((2-((2-methoxy-4-(1-methyl-1H-pyrazol-4-yl)phenyl)amino)pyrido[3,4-d]pyrimidin-8-yl)amino)methyl)cyclopropanol;

N2-(2-methoxy-4-(1-methyl-1H-pyrazol-4-yl)phenyl)-N8-(1-methylpiperidin-4-yl)pyrido[3,4-d]pyrimidine-2,8-diamine;

2-((2-((2-methoxy-4-(1-methyl-1H-pyrazol-4-yl)phenyl)amino)pyrido[3,4-d]pyrimidin-8-yl)amino)-2-methylpropan-1-ol;

N-(2-methoxy-4-(1-methyl-1H-pyrazol-4-yl)phenyl)-8-(2-oxa-6-azaspiro[3.3]heptan-6-yl)pyrido[3,4-d]pyrimidin-2-amine;

N2-(2-methoxy-4-(1-methyl-1H-pyrazol-4-yl)phenyl)-N8-(oxetan-2-ylmethyl)pyrido[3,4-d]pyrimidine-2,8-diamine;

N2-(2-chloro-4-morpholinophenyl)-N8-neopentylpyrido[3,4-d]pyrimidine-2,8-diamine N2-(2-methoxy-4-(4-methyl-4H-1,2,4-triazol-3-yl)phenyl)-N8-neopentylpyrido[3,4-d]pyrimidine-2,8-diamine;

N2-(2-methoxy-4-(4-(methylsulfonyl)piperazin-1-yl)phenyl)-N8-neopentylpyrido[3,4-d]pyrimidine-2,8-diamine;

N2-(2-methoxy-4-(1-methyl-1H-pyrazol-4-yl)phenyl)-N8-((3-methyltetrahydrofuran-3-yl)methyl)pyrido[3,4-d]pyrimidine-2,8-diamine;

N-(4-(1,5-dimethyl-1H-pyrazol-4-yl)-2-methoxyphenyl)-8-(2-oxa-6-azaspiro[3.4]octan-6-yl)pyrido[3,4-d]pyrimidin-2-amine;

N2-(4-(1,5-dimethyl-1H-pyrazol-4-yl)-2-methoxyphenyl)-N8-((3-methyloxetan-3-yl)methyl)pyrido[3,4-d]pyrimidine-2,8-diamine;

N2-(4-(1,5-dimethyl-1H-pyrazol-4-yl)-2-methoxyphenyl)-N8-(2-methoxy-2-methylpropyl)pyrido[3,4-d]pyrimidine-2,8-diamine;

N2-(4-(1,2-dimethyl-1H-imidazol-5-yl)-2-methoxyphenyl)-N8-(2-methoxy-2-methylpropyl)-6-methylpyrido[3,4-d]pyrimidine-2,8-diamine;

N2-(4-(1,2-dimethyl-1H-imidazol-5-yl)-2-methoxyphenyl)-6-methyl-N8-neopentylpyrido[3,4-d]pyrimidine-2,8-diamine;

N2-(2-methoxy-4-(4-methyl-4H-1,2,4-triazol-3-yl)phenyl)-6-methyl-N8-neopentylpyrido[3,4-d]pyrimidine-2,8-diamine;

N-(2-ethoxy-4-(1-methyl-1H-pyrazol-4-yl)phenyl)-8-(2-oxa-6-azaspiro[3.4]octan-6-yl)pyrido[3,4-d]pyrimidin-2-amine;

2-((2-((2-methoxy-4-(1-methyl-1H-pyrazol-4-yl)phenyl)amino)pyrido[3,4-d]pyrimidin-8-yl)amino)ethanol;

N2-(2-methoxy-4-(1-methyl-1H-pyrazol-4-yl)phenyl)-N8-(2-methoxyethyl)pyrido[3,4-d]pyrimidine-2,8-diamine;

1-((2-((2-methoxy-4-(1-methyl-1H-pyrazol-4-yl)phenyl)amino)pyrido[3,4-d]pyrimidin-8-yl)amino)propan-2-ol;

2-((2-((2-methoxy-4-(1-methyl-1H-pyrazol-4-yl)phenyl)amino)pyrido[3,4-d]pyrimidin-8-yl)amino)propan-1-ol;

N2-(4-(1,5-dimethyl-1H-pyrazol-4-yl)-2-methoxyphenyl)-N8-((3-methyltetrahydrofuran-3-yl)methyl)pyrido[3,4-d]pyrimidine-2,8-diamine;

4-(2-((2-methoxy-4-(1-methyl-1H-pyrazol-4-yl)phenyl)amino)pyrido[3,4-d]pyrimidin-8-yl)thiomorpholine 1,1-dioxide;

N-(2-methoxy-4-(1-methyl-1H-pyrazol-4-yl)phenyl)-8-(7-oxa-2-azaspiro[3.5]nonan-2-yl)pyrido[3,4-d]pyrimidin-2-amine;

N2-(2-methoxy-4-(1-methyl-1H-pyrazol-4-yl)phenyl)-5-methyl-N8-neopentylpyrido[3,4-d]pyrimidine-2,8-diamine;

N-(2-methoxy-4-(1-methyl-1H-pyrazol-4-yl)phenyl)-8-(6-oxa-2-azaspiro[3.4]octan-2-yl)pyrido[3,4-d]pyrimidin-2-amine;

1-(2-((2-methoxy-4-(1-methyl-1H-pyrazol-4-yl)phenyl)amino)pyrido[3,4-d]pyrimidin-8-yl)azetidine-3-carbonitrile;

N-(2-methoxy-4-(1-methyl-1H-pyrazol-4-yl)phenyl)-8-(2-oxa-7-azaspiro[4.4]nonan-7-yl)pyrido[3,4-d]pyrimidin-2-amine;

N-(2-methoxy-4-(1-methyl-1H-pyrazol-4-yl)phenyl)-8-(2-oxa-6-azaspiro[3.5]nonan-6-yl)pyrido[3,4-d]pyrimidin-2-amine;

N8-((3-fluorooxetan-3-yl)methyl)-N2-(2-methoxy-4-(1-methyl-1H-pyrazol-4-yl)phenyl)pyrido[3,4-d]pyrimidine-2,8-diamine;

N-(4-chloro-2-methoxyphenyl)-8-(2-oxa-6-azaspiro[3.4]octan-6H)pyrido[3,4-d]pyrimidin-2-amine;

N-(2,4-dichlorophenyl)-8-(2-oxa-6-azaspiro[3.4]octan-6-yl)pyrido[3,4-d]pyrimidin-2-amine;

4-((8-(2-oxa-6-azaspiro[3.4]octan-6-yl)pyrido[3,4-d]pyrimidin-2-yl)amino)-3-methoxybenzonitrile;

N-(2-chloro-4-(methylsulfonyl)phenyl)-8-(2-oxa-6-azaspiro[3.4]octan-6-yl)pyrido[3,4-d]pyrimidin-2-amine;

N-(2-chloro-4-(pyrimidin-5-yl)phenyl)-8-(2-oxa-6-azaspiro[3.4]octan-6-yl)pyrido[3,4-d]pyrimidin-2-amine;

N-(2-chloro-4-(5-methyl-1,3,4-oxadiazol-2-yl)phenyl)-8-(2-oxa-6-azaspiro[3.4]octan-6-yl)pyrido[3,4-d]pyrimidin-2-amine;

N8-(2-methoxy-2-methylpropyl)-N2-(2-methoxy-4-(4-methyl-4H-1,2,4-triazol-3-yl)phenyl)-6-methylpyrido[3,4-d]pyrimidine-2,8-diamine;

6-cyclopropyl-N-(2-methoxy-4-(1-methyl-1H-pyrazol-4-yl)phenyl)-8-(2-oxa-6-azaspiro[3.4]octan-6-yl)pyrido[3,4-d]pyrimidin-2-amine;

2-((2-((2-methoxy-4-(1-methyl-1H-pyrazol-4-yl)phenyl)amino)pyrido[3,4-d]pyrimidin-8-yl)amino)propane-1,3-diol;

3-methoxy-2-((2-((2-methoxy-4-(1-methyl-1H-pyrazol-4-yl)phenyl)amino)pyrido[3,4-d]pyrimidin-8-yl)amino)propan-1-ol;

(3-(((2-((2-methoxy-4-(1-methyl-1H-pyrazol-4-yl)phenyl)amino)pyrido[3,4-d]pyrimidin-8-yl)amino)methyl)oxetan-3-yl)methanol;

(S)—N2-(2-methoxy-4-(1-methyl-1H-pyrazol-4-yl)phenyl)-N8-((3-methyltetrahydrofuran-3-yl)methyl)pyrido[3,4-d]pyrimidine-2,8-diamine;

(R)—N2-(2-methoxy-4-(1-methyl-1H-pyrazol-4-yl)phenyl)-N8-((3-methyltetrahydrofuran-3-yl)methyl)pyrido[3,4-d]pyrimidine-2,8-diamine;

N-(4-chloro-2-fluorophenyl)-8-(2-oxa-6-azaspiro[3.4]octan-6-yl)pyrido[3,4-d]pyrimidin-2-amine;

4-((8-(2-oxa-6-azaspiro[3.4]octan-6-yl)pyrido[3,4-d]pyrimidin-2-yl)amino)-3-chlorobenzonitrile;

N2-(2-methoxy-4-(1-(2-methoxyethyl)-2-methyl-1H-imidazol-5-yl)phenyl)-6-methyl-N8-neopentylpyrido[3,4-d]pyrimidine-2,8-diamine;

N2-(2-ethoxy-4-(4-methyl-4H-1,2,4-triazol-3-yl)phenyl)-6-methyl-N8-neopentylpyrido[3,4-d]pyrimidine-2,8-diamine;

N2-(2-methoxy-4-(4-(methylsulfonyl)piperazin-1-yl)phenyl)-6-methyl-N8-neopentylpyrido[3,4-d]pyrimidine-2,8-diamine;

N-(2-methoxy-4-(1-methyl-1H-pyrazol-4-yl)phenyl)-8-(pyridin-4H)pyrido[3,4-d]pyrimidin-2-amine;

N8-(2-methoxy-2-methylpropyl)-N2-(2-methoxy-4-(4-methyl-4H-1,2,4-triazol-3-yl)phenyl)-5-methylpyrido[3,4-d]pyrimidine-2,8-diamine;

N2-(2-methoxy-4-(4-methyl-4H-1,2,4-triazol-3-yl)phenyl)-5-methyl-N8-neopentylpyrido[3,4-d]pyrimidine-2,8-diamine;

N-(2-methoxy-4-(1-methyl-1H-pyrazol-4-yl)phenyl)-8-(2-methylmorpholino)pyrido[3,4-d]pyrimidin-2-amine;

(4-(3-methoxy-4-((8-((2-methoxy-2-methylpropyl)amino)pyrido[3,4-d]pyrimidin-2-yl)amino)phenyl)-1-methyl-1H-pyrazol-5-yl)methanol;

(4-(3-methoxy-4-((8-(((3-methyltetrahydrofuran-3-yl)methyl)amino)pyrido[3,4-d]pyrimidin-2-yl)amino)phenyl)-1-methyl-1H-pyrazol-5-yl)methanol;

N8-(2-methoxy-2-methylpropyl)-N2-(2-methoxy-4-(1-(2-methoxyethyl)-2-methyl-1H-imidazol-5-yl)phenyl)pyrido[3,4-d]pyrimidine-2,8-diamine;

N2-(2-methoxy-4-(1-(2-methoxyethyl)-2-methyl-1H-imidazol-5-yl)phenyl)-N8-((3-methyltetrahydrofuran-3-yl)methyl)pyrido[3,4-d]pyrimidine-2,8-diamine;

N2-(2-ethoxy-4-(4-methyl-4H-1,2,4-triazol-3-yl)phenyl)-N8-(2-methoxy-2-methylpropyl)pyrido[3,4-d]pyrimidine-2,8-diamine;

N2-(2-ethoxy-4-(4-methyl-4H-1,2,4-triazol-3-yl)phenyl)-N8-((3-methyltetrahydrofuran-3-yl)methyl)pyrido[3,4-d]pyrimidine-2,8-diamine;

8-(3,6-dihydro-2H-pyran-4-yl)-N-(2-methoxy-4-(1-methyl-1H-pyrazol-4-yl)phenyl)pyrido[3,4-d]pyrimidin-2-amine;

N8-(2-methoxy-2-methylpropyl)-N2-(2-methoxy-6-(1-methyl-1H-tetrazol-5-yl)pyridin-3-yl)pyrido[3,4-d]pyrimidine-2,8-diamine;

N2-(6-(1,2-dimethyl-1H-imidazol-5-yl)-2-methoxypyridin-3-yl)-N8-(2-methoxy-2-methylpropyl)pyrido[3,4-d]pyrimidine-2,8-diamine;

N8-(2-methoxy-2-methylpropyl)-N2-(2-methoxy-4-(1-methyl-1H-tetrazol-5-yl)phenyl)pyrido[3,4-d]pyrimidine-2,8-diamine;

N-(2-methoxy-4-(1-methyl-1H-pyrazol-4-yl)phenyl)-8-(pyrimidin-5-yl)pyrido[3,4-d]pyrimidin-2-amine;

N2-(2-methoxy-4-(1-methyl-1H-pyrazol-4-yl)phenyl)-N8-(1-(tetrahydrofuran-3-yl)ethyl)pyrido[3,4-d]pyrimidine-2,8-diamine;

N2-(4-(1,3-dimethyl-1H-pyrazol-4-yl)-2-methoxyphenyl)-N8-(2-methoxy-2-methylpropyl)pyrido[3,4-d]pyrimidine-2,8-diamine;

N2-(4-(1,3-dimethyl-1H-pyrazol-4-yl)-2-methoxyphenyl)-N8-((3-methyltetrahydrofuran-3-yl)methyl)pyrido[3,4-d]pyrimidine-2,8-diamine;

N-(2-methoxy-4-(1-methyl-1H-pyrazol-4-yl)phenyl)-8-(4-methoxypiperidin-1-yl)pyrido[3,4-d]pyrimidin-2-amine;

1-(2-((2-methoxy-4-(1-methyl-1H-pyrazol-4-yl)phenyl)amino)pyrido[3,4-d]pyrimidin-8-yl)piperidine-4-carbonitrile;

N-(2-methoxy-4-(1-methyl-1H-pyrazol-4-yl)phenyl)-8-(4-(methylsulfonyl)piperazin-1-yl)pyrido[3,4-d]pyrimidin-2-amine;

N2-(4-(1,3-dimethyl-1H-pyrazol-4-yl)-2-methoxyphenyl)-N8-(2-methoxy-2-methylpropyl)-6-methylpyrido[3,4-d]pyrimidine-2,8-diamine;

N-(2-ethoxy-4-(4-methyl-4H-1,2,4-triazol-3-yl)phenyl)-6-methyl-8-(6-oxa-2-azaspiro[3.4]octan-2-yl)pyrido[3,4-d]pyrimidin-2-amine;

N2-(6-(1,3-dimethyl-1H-pyrazol-4-yl)-2-methoxypyridin-3-yl)-N8-(2-methoxy-2-methylpropyl)pyrido[3,4-d]pyrimidine-2,8-diamine;

N2-(6-(1,5-dimethyl-1H-pyrazol-4-yl)-2-methoxypyridin-3-yl)-N8-(2-methoxy-2-methylpropyl)pyrido[3,4-d]pyrimidine-2,8-diamine;

N8-(2-methoxy-2-methylpropyl)-N2-(2-methoxy-6-(1-methyl-1H-1,2,3-triazol-5H)pyridin-3H)pyrido[3,4-d]pyrimidine-2,8-diamine;

N8-(2-methoxy-2-methylpropyl)-N2-(2-methoxy-6-(2-methyl-2H-1,2,3-triazol-4H)pyridin-3H)pyrido[3,4-d]pyrimidine-2,8-diamine;

(3-methoxy-4-((8-((2-methoxy-2-methylpropyl)amino)pyrido[3,4-d]pyrimidin-2-yl)amino)phenyl)(3-methoxyazetidin-1-yl)methanone;

3-methoxy-4-((8-((2-methoxy-2-methylpropyl)amino)pyrido[3,4-d]pyrimidin-2-yl)amino)-N,N-dimethylbenzamide;

(3-methoxy-4-((8-((2-methoxy-2-methylpropyl)amino)pyrido[3,4-d]pyrimidin-2-yl)amino)phenyl)(4-methylpiperazin-1-yl)methanone;

(1-(2-((2-methoxy-4-(1-methyl-1H-pyrazol-4-yl)phenyl)amino)pyrido[3,4-d]pyrimidin-8-yl)pyrrolidin-3-yl)methanol;

(1-(2-((2-methoxy-4-(1-methyl-1H-pyrazol-4-yl)phenyl)amino)pyrido[3,4-d]pyrimidin-8-yl)piperidin-3-yl)methanol;

(4-(2-((2-methoxy-4-(1-methyl-1H-pyrazol-4-yl)phenyl)amino)pyrido[3,4-d]pyrimidin-8-yl)morpholin-2-yl)methanol;

N2-(2-(difluoromethoxy)-4-(1-methyl-1H-pyrazol-4-yl)phenyl)-N8-(2-methoxy-2-methylpropyl)pyrido[3,4-d]pyrimidine-2,8-diamine;

N2-(2-(difluoromethoxy)-4-fluorophenyl)-N8-(2-methoxy-2-methylpropyl)pyrido[3,4-d]pyrimidine-2,8-diamine;

N2-(4-(1-ethyl-1H-pyrazol-4-yl)-2-methoxyphenyl)-N8-(2-methoxy-2-methylpropyl)pyrido[3,4-d]pyrimidine-2,8-diamine;

(3-methoxy-4-((8-(neopentylamino)pyrido[3,4-d]pyrimidin-2-yl)amino)phenyl)(3-methoxyazetidin-1-yl)methanone;

N2-(2-methoxy-4-(tetrahydro-2H-pyran-4-yl)phenyl)-N8-((3-methyltetrahydrofuran-3-yl)methyl)pyrido[3,4-d]pyrimidine-2,8-diamine;

N2-(4-chloro-2-(difluoromethoxy)phenyl)-N8-(2-methoxy-2-methylpropyl)pyrido[3,4-d]pyrimidine-2,8-diamine;

N2-(2-methoxy-4-(4-methyl-4H-1,2,4-triazol-3-yl)phenyl)-5-methyl-N8-((3-methyloxetan-3H)methyl)pyrido[3,4-d]pyrimidine-2,8-diamine;

N2-(2-methoxy-4-(4-methyl-4H-1,2,4-triazol-3-yl)phenyl)-5-methyl-N8-((3-methyltetrahydrofuran-3-yl)methyl)pyrido[3,4-d]pyrimidine-2,8-diamine;

N-(2-methoxy-4-(4-methyl-4H-1,2,4-triazol-3-yl)phenyl)-5-methyl-8-(6-oxa-2-azaspiro[3.4]octan-2H)pyrido[3,4-d]pyrimidin-2-amine;

N8-(2-methoxy-2-methylpropyl)-N2-(2-methoxy-4-(1-methyl-1H-1,2,4-triazol-3-yl)phenyl)-6-methylpyrido[3,4-d]pyrimidine-2,8-diamine;

N2-(2-(difluoromethoxy)-4-(1-methyl-1H-pyrazol-4-yl)phenyl)-N8-(2-methoxy-2-methylpropyl)-6-methylpyrido[3,4-d]pyrimidine-2,8-diamine;

(4-(3-methoxy-4-((8-((2-methoxy-2-methylpropyl)amino)-6-methylpyrido[3,4-d]pyrimidin-2-yl)amino)phenyl)-1-methyl-1H-pyrazol-5-yl)methanol;

or a pharmaceutically acceptable salt or solvate thereof.

The various functional groups and substituents making up the compounds of the present invention are typically chosen such that the molecular weight of the compound does not exceed 1000. More usually, the molecular weight of the compound will be less than 750, for example less than 700, or less than 650, or less than 600, or less than 550. More preferably, the molecular weight is less than 525 and, for example, is 500 or less.

Suitable or preferred features of any compounds of the present invention may also be suitable features of any other aspect.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess Mps1 kinase inhibitory activity.

The present invention also encompasses compounds of the invention as defined herein which comprise one or more isotopic substitutions. For example, H may be in any isotopic form, including $^1H$, $^2H(D)$, and $^3H$ (T); C may be in any isotopic form, including $^{12}C$, $^{13}C$, and $^{14}C$; and O may be in any isotopic form, including $^{16}O$ and $^{18}O$; and the like.

It is also to be understood that certain compounds of the invention may exist in solvated as well as unsolvated forms such as, for example, hydrated forms. It is to be understood that the invention encompasses all such solvated forms that possess Mps1 kinase inhibitory activity.

It is also to be understood that certain compounds of the invention may exhibit polymorphism, and that the invention encompasses all such forms that possess Mps1 kinase inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

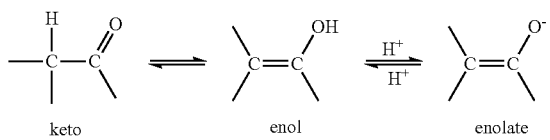

Compounds of the invention containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of the invention may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the invention and in-vivo cleavable amide derivatives that may be formed at a carboxy group or an amino group in a compound of the invention.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenyl-methyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula I that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$ alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula I that possesses a carboxy group is, for example, an in vivo cleavable amide thereof, for example an amide formed with an amine such as ammonia, a $C_{1-4}$alkylamine such as methylamine, a $(C_{1-4}alkyl)_2$ amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

It shall also be appreciated that compounds of formula I may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

Synthesis

In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3.OEt_2$. A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

In a particular aspect, the present invention provides a method of synthesising a compound of the formula I, or a pharmaceutically acceptable salt or solvate thereof, the method comprising:

a) reacting a compound of formula A:

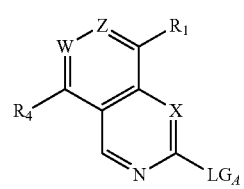

Formula A wherein W, X, Z, $R_1$ and $R_4$ each have any one of the meanings as defined hereinbefore, and $LG_A$ is a suitable leaving group;

with a compound of formula B:

 

H₂N—Ar   Formula B wherein Ar is as defined herein; and b) optionally thereafter, and if necessary:

i) removing any protecting groups present;

ii) converting the compound formula I into another compound of formula I; and/or iii) forming a pharmaceutically acceptable salt or solvate thereof.

$LG_A$ may be any suitable leaving group. Suitably $LG_A$ is a halogen or any other suitable leaving group (e.g. trifluoromethylsulphonate etc.). Suitably $LG_A$ may be chlorine, bromine or trifluoromethylsulphonate.

Suitably the coupling reaction between compound A and compound B takes place in the presence of a suitable solvent. Any suitable solvent or solvent mixture may be used for this reaction. A person skilled in the art will know how to select suitable solvents or solvent mixtures for use in these reactions. Examples of suitable solvents include DMA, 1,4-dioxane, toluene, DMF, tBuOH, THF and $H_2O$.

A person skilled in the art will be able to select appropriate reaction conditions to use in order to facilitate this reaction. Suitably, the reaction is carried out in anhydrous conditions and in the presence of an inert atmosphere, such as argon or nitrogen. The reaction may also be carried out an elevated temperature, such as, for example, within the range of 80 to 160° C. or, more suitably 100 to 160° C. (depending on the solvent utilised), for a suitable time period of, for example, 2 hours to 7 days, or more suitably 2 to 10 hours either thermally or under microwave irradiation.

Suitably the coupling reaction between compound A and compound B takes place in the presence of a catalyst, suitably a palladium-derived catalyst, such as Pd or $Pd_2(dba)_3$ or by using an acid catalysis, such as trifluoroacetic acid.

Suitably the coupling reaction between compound A and compound B takes place in the presence of an organophosphorus compound, suitably an organophosphorus compound which serves as a suitable ligand to the catalyst. The organophosphorus compound may suitably be a phosphine-derivative, such as Xantphos.

Suitably the coupling reaction between compound A and compound B takes place in the presence of a base, for example a metal carbonate, such as cesium carbonate, or metal hydrides, such as sodium hydride.

The compound of formula A can be prepared by processes known in the art, and suitably by the processes described herein with reference to the examples.

The compound of formula B can be prepared by processes known in the art, and suitably by the processes described herein with reference to the examples.

A racemic compound of formula I may be separated using suitable chiral separation chromatography to furnish the desired enantiomers.

In another aspect, the present invention provides a method of synthesising a compound of the formula I, or a pharmaceutically acceptable salt or solvate thereof, the method comprising:

a) reacting a compound of formula C:

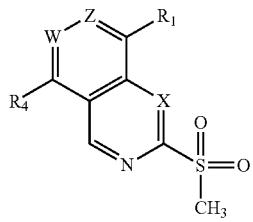 

Formula C wherein W, X, Z, $R_1$ and $R_4$ each have any one of the meanings as defined hereinbefore; with a compound of formula B as defined hereinbefore, or a compound of formula D:

 

HC(O)HN—Ar   Formula D wherein Ar is as defined herein; and b) optionally thereafter, and if necessary:

i) removing any protecting groups present;

ii) converting the compound formula I into another compound of formula I; and/or iii) forming a pharmaceutically acceptable salt or solvate thereof.

Suitably the coupling reaction between compound C and compound B or D takes place in the presence of a suitable solvent. Any suitable solvent or solvent mixture may be used for this reaction. A person skilled in the art will know how to select suitable solvents or solvent mixtures for use in these reactions. Examples of suitable solvents include THF, TFE (1,2,3-trifluoroethanol) or DMF.

A person skilled in the art will be able to select appropriate reaction conditions to use in order to facilitate this reaction. Suitably, the reaction is carried out in anhydrous conditions and in the presence of an inert atmosphere, such as argon or nitrogen. The reaction may also be carried out an elevated temperature, such as, for example, within the range of 30 to 170° C. or, more suitably 30 to 50° C. for compounds of formula D and 120 to 170 50° C. for compounds of formula B (depending on the solvent utilised), for a suitable time period of, for example, 2 hours to 7 days, or more suitably 2 to 10 hours either thermally or under microwave irradiation.

Suitably the coupling reaction between compound C and compounds B or D takes place in the presence of a catalyst, suitably a palladium-derived catalyst, such as Pd or $Pd_2(dba)_3$ or by using an acid catalysis, such as trifluoroacetic acid.

Suitably the coupling reaction between compound C and compounds B or D takes place in the presence of an organophosphorus compound, suitably an organophosphorus compound which serves as a suitable ligand to the catalyst. The organophosphorus compound may suitably be a phosphine-derivative, such as Xantphos.

Suitably the coupling reaction between compound C and compounds B or D takes place in the presence of a base, for example a metal carbonate, such as cesium carbonate, or metal hydrides, such as sodium hydride.

The compound of formula C can be prepared by processes known in the art, and suitably by the processes described herein with reference to the examples.

The compound of formula D can be prepared by processes known in the art, and suitably by the processes described herein with reference to the examples.

In another aspect, the present invention provides a method of synthesising a compound of the formula I, or a pharmaceutically acceptable salt or solvate thereof, the method comprising:

a) reacting a compound of formula E:

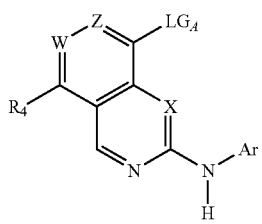

Formula E wherein W, X, Z, Ar and $R_4$ each have any one of the meanings as defined hereinbefore, and $LG_A$ is a suitable leaving group as hereinbefore defined;
with a compound of formula F:

Formula F or $R_1BX_2$, wherein $R_1$ is as defined herein, and $BX_2$ represents boronic acids (e.g. $B(OH)_2$), tetrafluoroborates (e.g. $R_1BF_3$), or pinacol esters;
or $R_1SH$, wherein $R_1$ is as defined herein, and
b) optionally thereafter, and if necessary:
i) removing any protecting groups present;
ii) converting the compound formula I into another compound of formula I; and/or
iii) forming a pharmaceutically acceptable salt or solvate thereof.

As described above, $LG_A$ may be any suitable leaving group. Suitably $LG_A$ is a halogen or any other suitable leaving group (e.g. trifluoromethylsulphonate etc.). Suitably $LG_A$ may be chlorine or bromine.

Suitably the coupling reaction between compound E and compound F takes place in the presence of a suitable solvent. Any suitable solvent or solvent mixture may be used for this reaction. A person skilled in the art will know how to select suitable solvents or solvent mixtures for use in these reactions. Examples of suitable solvents include dioxane, DMA, NMP, THF, or TFE.

A person skilled in the art will be able to select appropriate reaction conditions to use in order to facilitate this reaction. Suitably, the reaction is carried out in anhydrous conditions and in the presence of an inert atmosphere, such as argon or nitrogen. The reaction may also be carried out an elevated temperature, such as, for example, within the range of 100 to 140° C. (depending on the solvent utilised), for a suitable time period of, for example, 2 hours to 7 days, or more suitably 2 to 10 hours either thermally or under microwave irradiation.

Suitably the coupling reaction between compound E and compound F takes place in the presence of a catalyst, suitably a palladium-derived catalyst, such as Pd or $Pd_2(dba)_3$, $Pd(PPh_3)_4$ or $Pd(dppf)Cl_2$ or by using an acid catalysis, such as trifluoroacetic acid.

Suitably the coupling reaction between compound E and compound F takes place in the presence of an organophosphorus compound, suitably an organophosphorus compound which serves as a suitable ligand to the catalyst. The organophosphorus compound may suitably be a phosphine-derivative, such as Xantphos or DavePhos.

Suitably the coupling reaction between compound E and compound F takes place in the presence of a base, for example a metal carbonate, such as cesium carbonate, or metal hydrides, such as sodium hydride.

The compound of formula E can be prepared by processes known in the art and/or by the processes described herein with reference to the examples.

The compound of formula F can be prepared by processes known in the art, and/or by the processes described herein with reference to the examples.

The resultant compound of formula I can be isolated and purified using techniques well known in the art.

The processes defined herein may further comprise the step of subjecting the compound of formula I to a salt exchange, particularly in situations where the compound of formula I is formed as a mixture of different salt forms. The salt exchange suitably comprises immobilising the compound of formula I on a suitable solid support or resin, and eluting the compounds with an appropriate acid to yield a single salt of the compound of formula I.

In a further aspect of the invention, there is provided a compound of formula I obtainable by any one of the processes defined herein.

In a further aspect of the invention, there is provided a compound of formula I obtained by any one of the processes defined herein.

In a further aspect of the invention, there is provided a compound of formula I directly obtained by any one of the processes defined herein.

By way of example, particular synthetic schemes by which compounds of the invention can be prepared are shown below in Schemes 1 to 12:

Scheme 1:

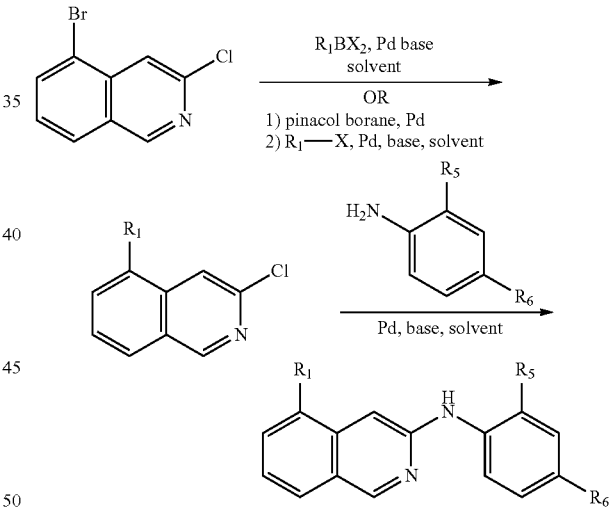

Scheme 2:

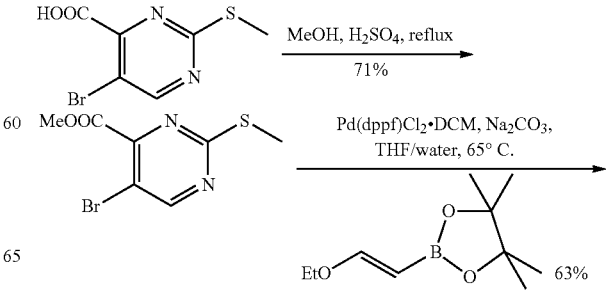

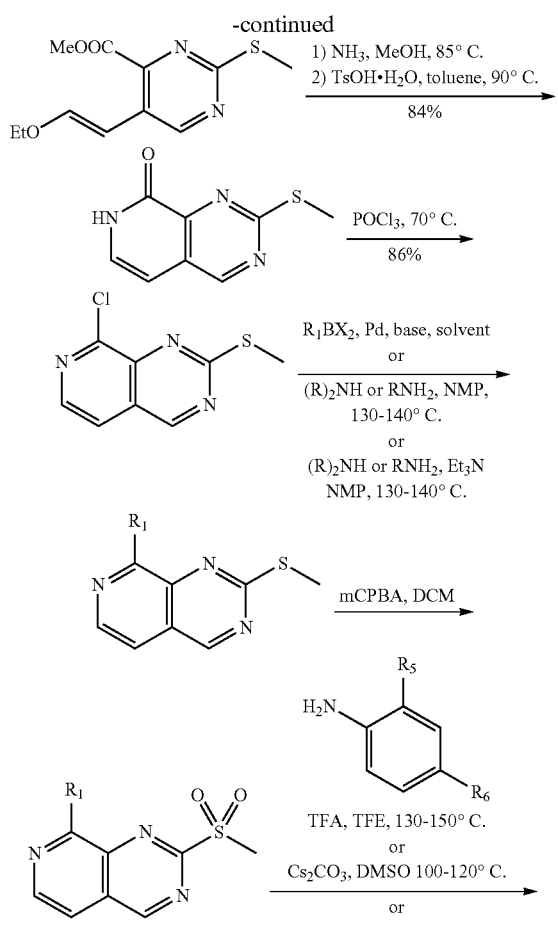
Scheme 3:
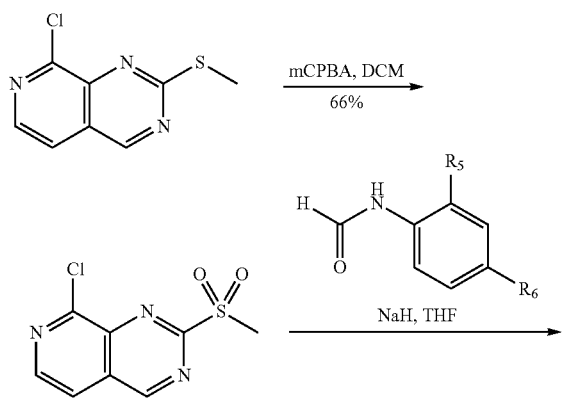
Scheme 4:
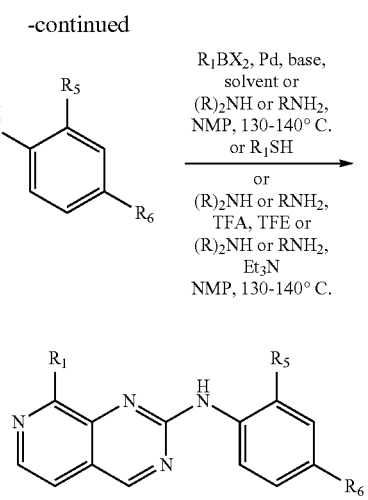

-continued
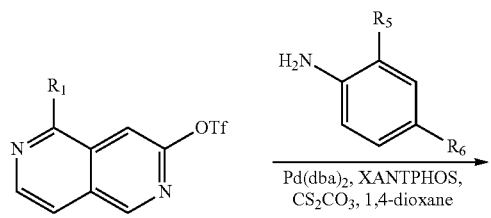
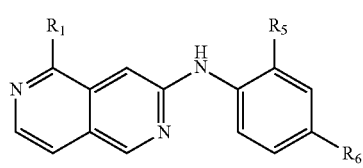
Scheme 5:
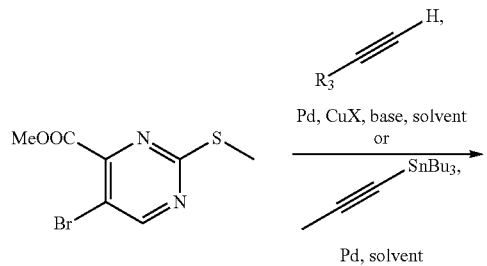
-continued
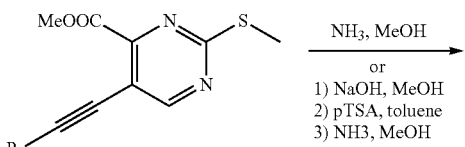
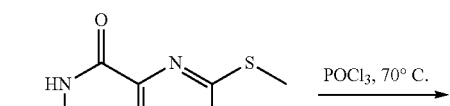
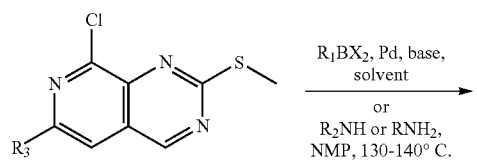
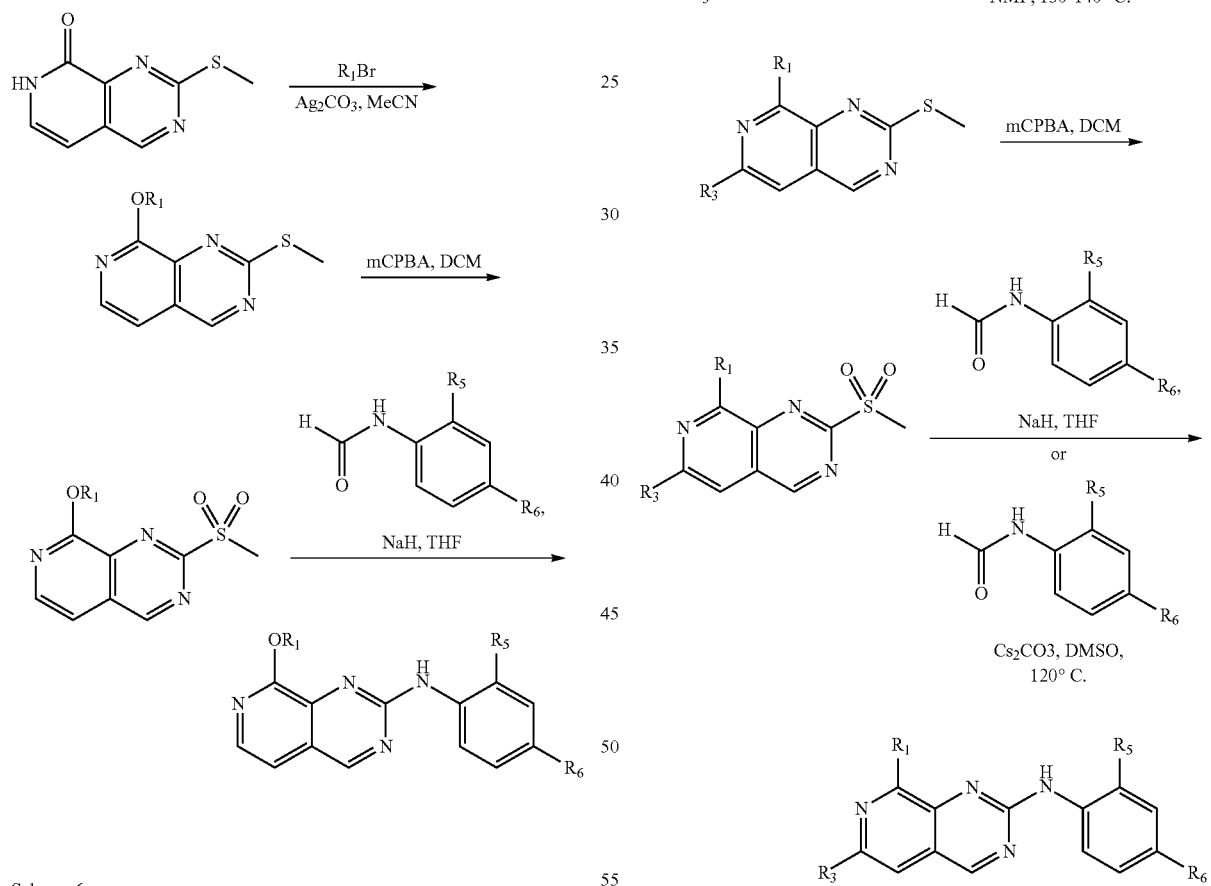
Scheme 7:
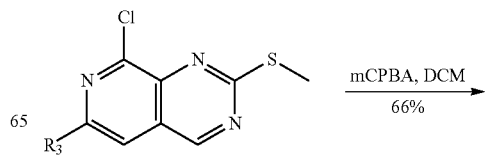

49
-continued
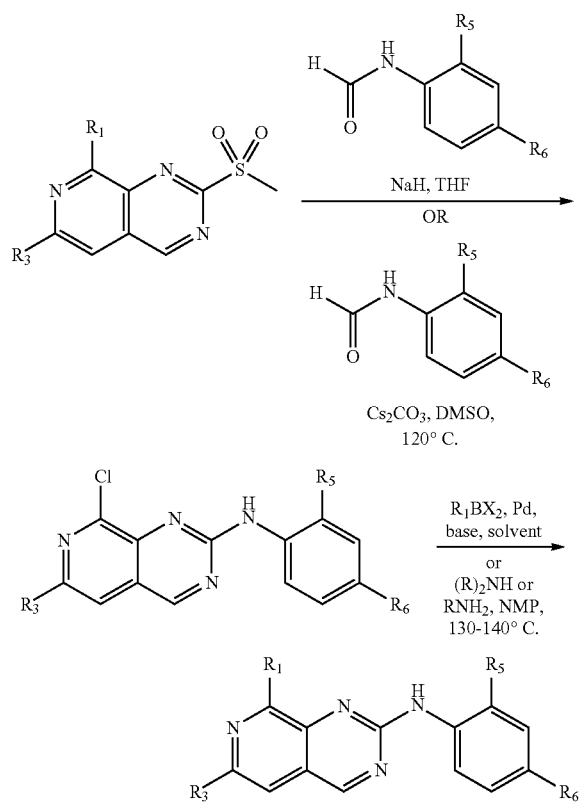
Scheme 8:
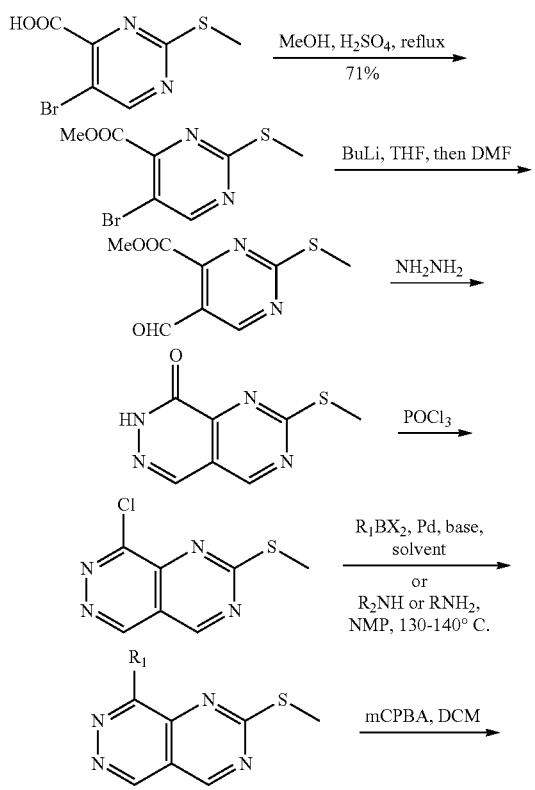
50
-continued
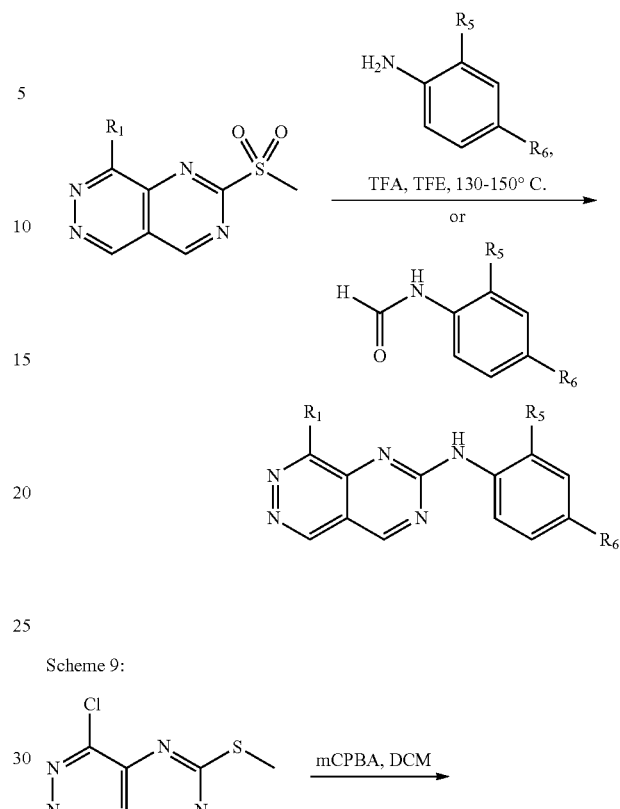
Scheme 9:
Scheme 10:
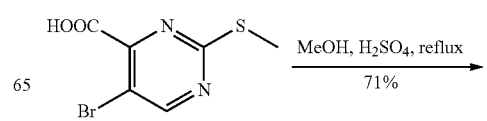

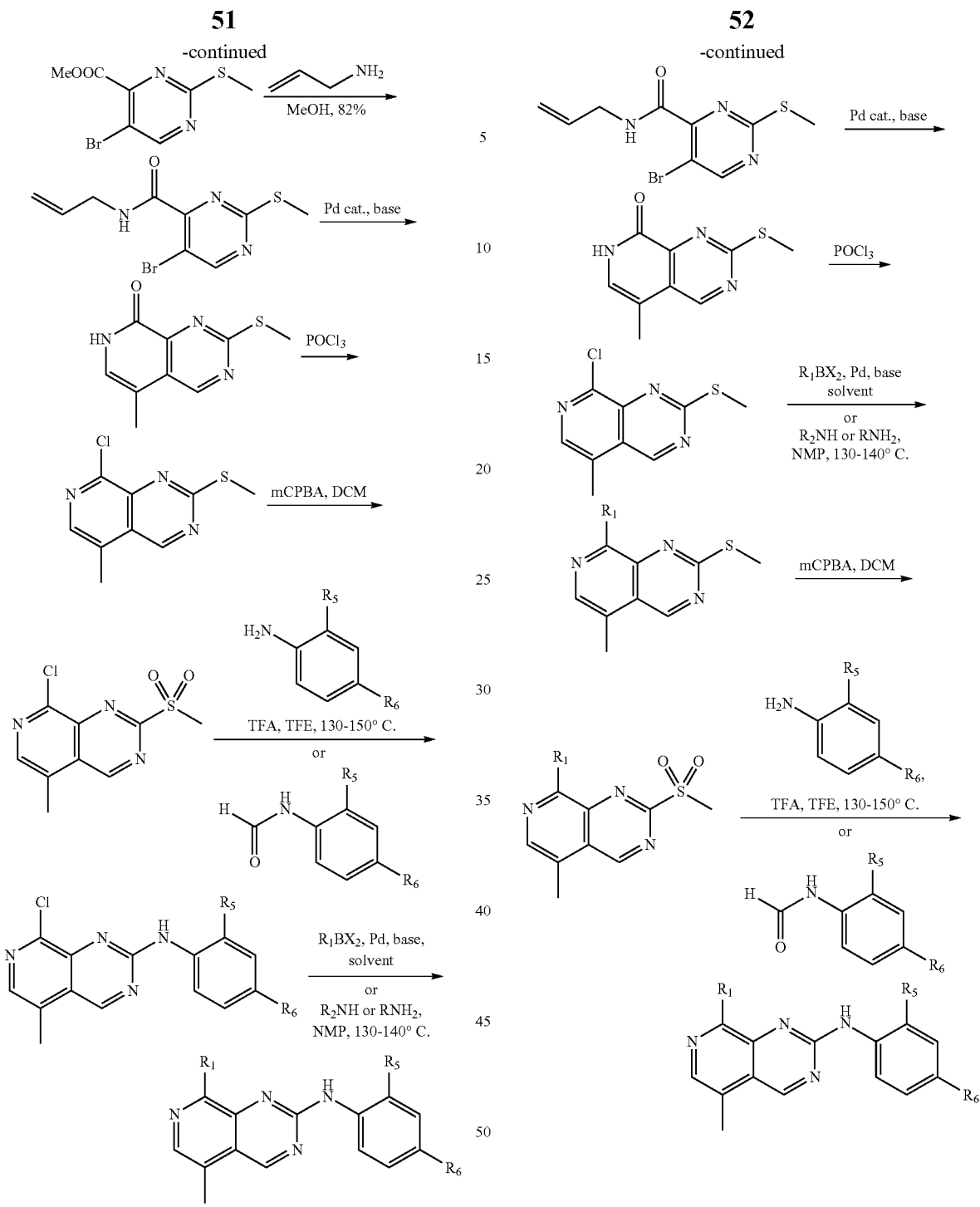
Scheme 11:
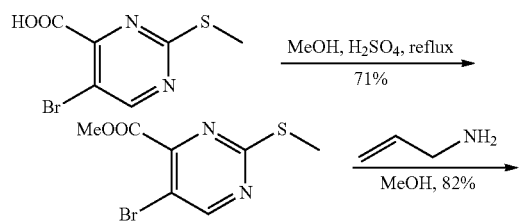
Scheme 12:
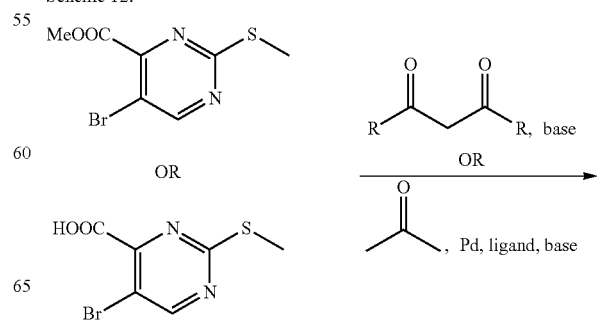

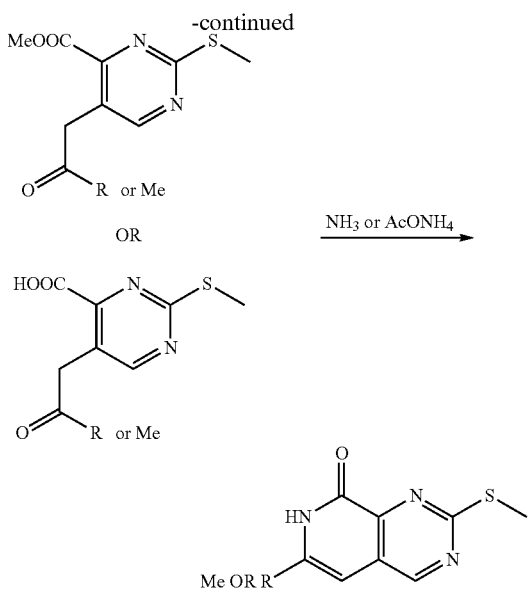

The product of Scheme 12 is then reacted to form a compound of formula I using the last two steps of previous Scheme 11.

In schemes 1 to 9, $R_1$ is suitably aryl or heteroaryl, but may also be alkyl or alkenyl. BX2 represents boronic acids $(B(OH)_2)$, tetrafluoroborates $(R1BF_3^-)$, or pinacol esters, e.g.

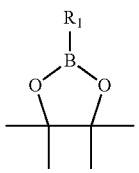

Biological Activity

The following biological assays may be used to measure the pharmacological effects of the compounds of the present invention.

Measurement of Inhibition of MPS1 Kinase

The enzyme reaction (total volume 10 µl) was carried out in black 384-well low volume plates containing full length MPS1 (12.5 nM or 3 nM), fluorescent labelled peptide [known as H236, which has the sequence: 5FAM-DHTG-FLTEYVATR-CONH$_2$] (5 µM), ATP(10 µM), either DMSO (1% v/v) or the test compound (in the range 0.25 nM-100 µM in 1% DMSO) and assay buffer (50 mM HEPES (pH 7.0), 0.02% NaN$_3$, 0.01% BSA, 0.1 mM Orthovandate, 10 µM MgCl$_2$, 1 µM DTT, Roche protease inhibitor). The reaction was carried out for 60 min at room temperature and stopped by the addition of buffer (10 µl) containing 20 mM EDTA, 0.05% (v/v) Brij-35, in 0.1M HEPES-buffered saline (Free acid, Sigma, UK). The plate was read on a Caliper EZ reader II (Caliper Life Sciences).

The reader provides a Software package ('Reviewer') which converts the peak heights into % conversion by measuring both product and substrate peak and also allows selection of control well which represent 0% and 100% inhibition, respectively. The % inhibition of the compounds is calculated relative to the means of selected control wells. IC$_{50}$s are determined by testing the compounds at a range of concentrations from 0.25 nM-100 µM. The % inhibitions at each concentration are then fitted to a 4 parameter logistic fit:

$$y=(a+((b-a)/(1+((c/x^{\wedge}d))))$$

where a=asym min, b=asym max, c=IC$_{50}$ and d=hill coefficient

In general, activity possessed by compounds of the formula I, may be demonstrated in the inhibition assay by an IC$_{50}$ value of less than 15 µM. Suitably compounds have an IC$_{50}$ value of less than 10 µM, suitably less than 1 µM, suitably less than 0.1 µM, and suitably less than 0.01 µM (i.e. less than 10 nM).

The activities of compounds of the invention in the above assay are shown in the accompanying example section.

Pharmaceutical Compositions

According to a further aspect of the invention there is provided a pharmaceutical composition which comprises a compound of the invention as defined hereinbefore, or a pharmaceutically acceptable salt or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of proliferative disease is an amount sufficient to symptomatically relieve in a warm-blooded animal, particularly a human the symptoms of infection, to slow the progression of infection, or to reduce in patients with symptoms of infection the risk of getting worse.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

In one aspect, the present invention provides a compound of Formula I, or a pharmaceutically acceptable salt or solvate thereof, or a pharmaceutical composition as defined herein for use in therapy.

The compounds of the invention are capable of inhibiting Mps1 kinase activity. Thus, in another aspect, the present invention provides a method of inhibiting Mps1 kinase activity in a cell, the method comprising administering to said cell compound of formula I as defined herein, or a pharmaceutically acceptable salt or solvate thereof.

In a further aspect, the present invention provides a method of inhibiting Mps1 kinase in vitro or in vivo, said method comprising contacting a cell with an effective amount of a compound, or a pharmaceutically acceptable salt or solvate thereof, as defined herein.

In another aspect, the present invention provides a method of inhibiting Mps1 kinase activity in a human or animal subject in need of such inhibition, the method comprising administering to said subject an effective amount of a compound of formula I as defined herein, or a pharmaceutically acceptable salt or solvate thereof.

In another aspect, the present invention provides a compound of formula I as defined herein, or a pharmaceutically acceptable salt or solvate thereof for use in the treatment of disease or condition associated with Mps1 kinase activity.

In another aspect, the present invention provides the use of a compound of formula I as defined herein, or a pharmaceutically acceptable salt or solvate thereof, in the manufacture of a medicament for use in the treatment of disease or condition associated with Mps1 kinase activity.

In yet another aspect, the present invention provides a method of treating a proliferative disorder in a human or animal subject, the method comprising administering to said subject a therapeutically acceptable amount of a compound of formula I as defined herein, or a pharmaceutically acceptable salt or solvate thereof.

In yet another aspect, the present invention provides a compound of formula I as defined herein, or a pharmaceutically acceptable salt or solvate thereof, for use in the treatment of a proliferative disorder.

In yet another aspect, the present invention provides the use of a compound of formula I as defined herein, or a pharmaceutically acceptable salt or solvate thereof, in the manufacture of a medicament for use in the treatment of a proliferative disorder.

The term "proliferative disorder" are used interchangeably herein and pertain to an unwanted or uncontrolled cellular proliferation of excessive or abnormal cells which is undesired, such as, neoplastic or hyperplasticgrowth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

The anti-proliferative effects of the compounds of the present invention have particular application in the treatment of human cancers by virtue of their Mps1 kinase inhibitory properties.

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

Therefore, in another aspect, the present invention provides a compound, or a pharmaceutically acceptable salt or solvate thereof, or a pharmaceutical composition as defined herein for use in the treatment of cancer.

In yet another aspect, the present invention provides the use of a compound, or a pharmaceutically acceptable salt or solvate thereof, as defined herein in the manufacture of a medicament for use in the treatment of cancer.

In yet another aspect, the present invention provides a method of treating cancer in a patient in need of such treatment, said method comprising administering to said patient a therapeutically effective amount of a compound, or a pharmaceutically acceptable salt or solvate thereof, or a pharmaceutical composition as defined herein.

The invention further provides a method of treatment of the human or animal body, the method comprising administering to a subject in need of treatment a therapeutically-effective amount of an active compound, preferably in the form of a pharmaceutical composition.

Routes of Administration

The compounds of the invention or pharmaceutical composition comprising the active compound may be administered to a subject by any convenient route of administration, whether systemically/peripherally or topically (ie. at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); anti-tumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and another anti-tumour agent.

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and any one of the anti-tumour agents listed under (i)-(ix) above.

In a further aspect of the invention there is provided a compound of the invention or a pharmaceutically acceptable salt or solvate thereof, in combination with an anti-tumour agent selected from one listed under (i)-(ix) herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt or solvate thereof in combination with an anti-tumour agent selected from one listed under (i)-(ix) herein above, in association with a pharmaceutically acceptable diluent or carrier.

EXAMPLES

Commercially available starting materials, reagents and dry solvents were used as supplied. Flash column chromatography was performed using Merck silica gel 60 (0.025-0.04 mm). Column chromatography was also performed on a FlashMaster personal unit using isolute Flash silica columns or a Biotage SP1 purification system using Merck or Biotage Flash silica cartridges. Preparative TLC was performed on Analtech or Merck plates. Ion exchange chromatography was performed using acidic Isolute Flash SCX-II columns, Isolute Si-carbonate columns or basic isolute Flash NH$_2$ columns.

Where a preparative HPLC method is used, the following conditions apply:
Grad15mins20mIsLipo:
Reagents:
HPLC grade solvents, formic acid, or alternative eluent modifiers were purchased from Sigma Aldrich (Poole, UK) unless otherwise stated.
Instrumentation:
450 uL standard injections (with needle rinse) of the sample, at 10 mg/mL concentration in MeOH, were made onto a Phenomenex Gemini column (10 μm, 250×21.2 mm, C18, Phenomenex, Torrance, USA)

Chromatographic separation at room temperature was carried out using Gilson GX-281 Liquid Handler system combined with a Gilson 322 HPLC pump (Gilson, Middleton, USA) over a 15 minute gradient elution from 40:60 to 100:0 methanol:water (both modified with 0.1% formic acid) at a flow rate of 20 mL/min.

UV-Vis spectra were acquired at 254 nm on a Gilson 156 UV-Vis detector (Gilson, Middleton, USA).

Collection was triggered by UV signal, and collected using a Gilson GX-281 Liquid Handler system (Gilson, Middleton, USA).

Raw data was processed using Gilson Trilution Software.
Where an LCMS method is used, the following conditions apply:
LCT Method:
LC/MS analysis was also performed on a Waters Alliance 2795 Separations Module and Waters 2487 dual wavelength absorbance detector coupled to a Waters/Micromass LCt time of flight mass spectrometer with ESI source. Analytical separation was carried out at 30° C. either on a Merck Chromolith SpeedROD column (RP-18e, 50×4.6 mm) using a flow rate of 2 mL/min in a 4 minute gradient elution with detection at 254 nm or on a Merck Purospher STAR column (RP-18e, 30×4 mm) using a flow rate of 1.5 mL/min in a 4 minute gradient elution with detection at 254 nm. The mobile phase was a mixture of methanol (solvent A) and water (solvent B) both containing formic acid at 0.1%. Gradient elution was as follows: 1:9 (A/B) to 9:1 (A/B) over 2.25 min, 9:1 (A/B) for 0.75 min, and then reversion back to 1:9 (A/B) over 0.3 min, finally 1:9 (A/B) for 0.2 min Where an LCMS/HRMS method is used, the following conditions apply:
Agilent ToF Method:
LC/MS and HRMS analysis was performed on an Agilent 1200 series HPLC and diode array detector coupled to a 6210 time of flight mass spectrometer with dual multimode APCl/ESI source.

Analytical separation was carried out at 30° C. on a Merck Purospher STAR column (RP-18e, 30×4 mm) using a flow rate of 1.5 mL/min in a 4 minute gradient elution with detection at 254 nm. The mobile phase was a mixture of methanol (solvent A) and water containing formic acid at 0.1% (solvent B). Gradient elution was as follows: 1:9 (A/B) to 9:1 (A/B) over 2.5 min, 9:1 (A/B) for 1 min, and then reversion back to 1:9 (A/B) over 0.3 min, finally 1:9 (A/B) for 0.2 min.

The references used for HRMS analysis were: caffeine [M+H]$^+$ 195.087652; hexakis (2,2-difluroethoxy)phosphazene [M+H]$^+$ 622.02896; and hexakis(1H,1H,3H-tetrafluoropentoxy)phosphazene [M+H]$^+$ 922.009798.

Routine LCMS was performed using the LCT method whereas HRMS data were recored using the Agilent ToF method.

Example 1

(4-((5-(1-(2-(Dimethylamino)ethyl)-1H-pyrazol-4-yl)isoquinolin-3-yl)amino)-3-methoxyphenyl)(3-methoxyazetidin-1-yl)methanone

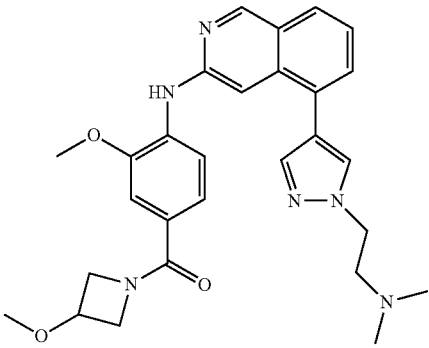

Method 1

A suspension of 2-(4-(3-chloroisoquinolin-5-yl)-1H-pyrazol-1-yl)-N,N-dimethylethanamine (Preparation 1, 10 mg, 0.033 mmol), (4-amino-3-methoxyphenyl)(3-methoxyazetidin-1-yl)methanone (Preparation 28, 15.7 mg, 0.066 mmol), xantphos (11.5 mg, 0.02 mmol), Pd$_2$(dba)$_3$ (3 mg, 0.003 mmol) and Cs$_2$CO$_3$ (87 mg, 0.27 mmol) in toluene/DMF (3/1 mL) was stirred at 160° C. under microwave irradiation for 2 hours. The reaction mixture was filtered, diluted with NaCl solution and extracted with EtOAc. The organic layer was purified by SCX-2 column eluting with 2M NH$_3$/MeOH and concentrated in vacuo. The residue was purified by Biotage silica gel column chromatography eluting with 0-4% MeOH in EtOAc followed by preparative HPLC to afford the title compound (5 mg, 30%).

$^1$H NMR (500 MHz, CDCl$_3$): δ 9.07 (d, J=0.8 Hz, 1H), 8.06 (d, J=8.3 Hz, 1H), 7.90 (s, 1H), 7.84 (dt, J=8.1, 1.0 Hz, 1H), 7.81 (d, J=0.8 Hz, 1H), 7.61-7.55 (m, 2H), 7.52 (d, J=1.1 Hz, 1H), 7.38 (dd, J=8.2, 7.0 Hz, 1H), 7.34 (d, J=1.9 Hz, 1H), 7.27-7.20 (m, 1H), 4.68 (t, J=6.4 Hz, 2H), 4.55-4.35 (m, 2H), 4.31-4.25 (m, 2H), 4.15-4.05 (m, 1H), 3.98 (s, 3H), 3.42 (t, J=6.4 Hz, 2H), 3.35 (s, 3H), 2.60 (s, 6H).

LCMS (ESI) Rt=1.92 minutes MS m/z 501 [M+H]$^+$
MPS1 IC50 (μM): 0.061

The following Examples were prepared according to Method 1 (Example 1) above using the appropriate chloroisoquinoline and the appropriate aniline as described. The crude reaction residues were purified as above or according to one of the following methods:

Method A: Biotage silica gel column chromatography eluting with between 0-6% MeOH/EtOAc.
Method B: Biotage silica gel column chromatography eluting with EtOAc.
Method C: Biotage silica gel column chromatography eluting with 0-12% MeOH/EtOAc.
Method D: Biotage silica gel column chromatography eluting with 60% EtOAc/cyclohexane followed by preparative HPLC.
Method E: Biotage silica gel column chromatography eluting with 0-30% MeOH/EtOAc followed by preparative HPLC.

Method F: Biotage silica gel column chromatography eluting with 60-100% EtOAc/cyclohexane.

Method G: Biotage silica gel column chromatography eluting with 40% EtOAc/cyclohexane.

| Example No | Name/Structure | Data | MPS1 IC50 (μM) |
|---|---|---|---|
| 2 | (3-Methoxy-4-((5-(1-(2-methoxyethyl)-1H-pyrazol-4-yl)isoquinolin-3-yl)amino)phenyl)(3-methoxyazetidin-1-yl)methanone 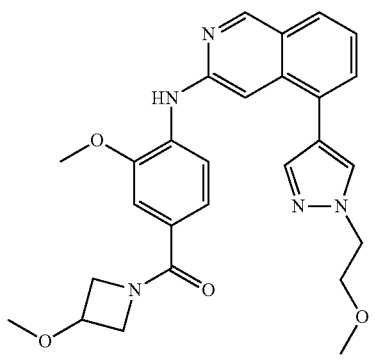 | $^1$H NMR (500 MHz, CDCl$_3$): δ 9.06 (d, J = 0.9 Hz, 1H), 8.06 (d, J = 8.3 Hz, 1H), 7.82 (dt, J = 8.3, 1.1 Hz, 1H), 7.79 (d, J = 0.8 Hz, 1H), 7.75 (d, J = 0.9 Hz, 1H), 7.57 (dd, J = 7.1, 1.2 Hz, 1H), 7.51 (d, J = 1.1 Hz, 1H), 7.40-7.32 (m, 3H), 7.21 (dd, J = 8.4, 1.9 Hz, 1H), 4.55-4.35 (m, 2H), 4.42 (t, J = 5.2 Hz, 2H), 4.30-4.24 (m, 2H), 4.15-4.05 (m, 1H), 3.98 (s, 3H), 3.85 (t, J = 5.2 Hz, 2H), 3.39 (s, 3H), 3.34 (s, 3H). LCMS (ESI) Rt = 2.57 minutes MS m/z 488 [M + H]$^+$ Using 3-chloro-5-(1-(2-methoxyethyl)-1H-pyrazol-4-yl)isoquinoline (Preparation 2) and purification method A. | 0.014 |
| 3 | tert-Butyl 4-(4-(3-((2-methoxy-4-(3-methoxyazetidine-1-carbonyl)phenyl)amino)isoquinolin-5-yl)-1H-pyrazol-1-yl)piperidine-1-carboxylate 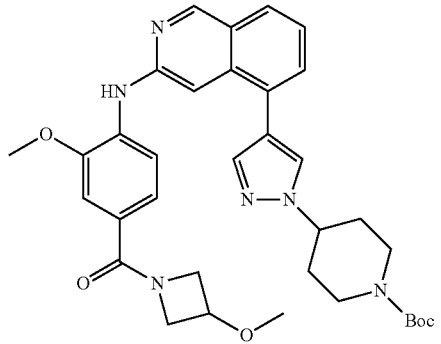 | $^1$H NMR (500 MHz, CDCl$_3$): δ 9.06 (d, J = 0.9 Hz, 1H), 8.05 (d, J = 8.3 Hz, 1H), 7.82 (dt, J = 8.2, 1.0 Hz, 1H), 7.79 (d, J = 0.8 Hz, 1H), 7.66 (d, J = 0.8 Hz, 1H), 7.53 (dd, J = 7.1, 1.2 Hz, 1H), 7.46 (d, J = 1.1 Hz, 1H), 7.40-7.32 (m, 3H), 7.19 (dd, J = 8.4, 1.8 Hz, 1H), 4.55-4.20 (m, 7H), 4.14-4.02 (m, 1H), 3.97 (s, 3H), 3.33 (s, 3H), 3.00-2.90 (m, 2H), 2.26-2.20 (m, 2H), 2.06-1.97 (m, 2H), 1.49 (s, 9H). LCMS (ESI) Rt = 3.00 minutes MS m/z 613 [M + H]$^+$ Using tert-butyl 4-(4-(3-chloroisoquinolin-5-yl)-1H-pyrazol-1-yl)piperidine-1-carboxylate (Preparation 5) at 140° C. and purification method B. | 0.125 |
| 4 | (3-Methoxy-4-((5-(1-methyl-1H-imidazol-5-yl)isoquinolin-3-yl)amino)phenyl)(3-methoxyazetidin-1-yl)methanone 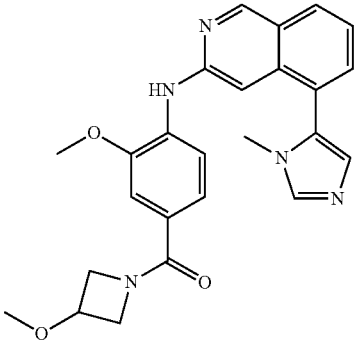 | $^1$H NMR (500 MHz, CDCl$_3$): δ 9.10 (d, J = 1.0 Hz, 1H), 8.08 (d, J = 8.4 Hz, 1H), 7.95 (dt, J = 8.3, 1.1 Hz, 1H), 7.69 (s, 1H), 7.54 (dd, J = 7.1, 1.3 Hz, 1H), 7.43 (dd, J = 8.2, 7.0 Hz, 1H), 7.39-7.32 (m, 2H), 7.24-7.15 (m, 2H), 6.99 (d, J = 1.0 Hz, 1H), 4.51-4.35 (m, 2H), 4.30-4.20 (m, 2H), 4.20-4.10 (m, 1H), 3.97 (s, 3H), 3.48 (s, 3H), 3.34 (s, 3H). LCMS (ESI) Rt = 1.73 minutes MS m/z 444 [M + H]$^+$ Using 3-chloro-5-(1-methyl-1H-imidazol-5-yl)isoquinoline (Preparation 4) and purification method C. | 0.112 |

-continued

| Example No | Name/Structure | Data | MPS1 IC50 (μM) |
|---|---|---|---|
| 5 | (4-((5-(3,5-Dimethylisoxazol-4-yl)isoquinolin-3-yl)amino)-3-methoxyphenyl)(3-methoxyazetidin-1-yl)methanone | $^1$H NMR (500 MHz, CDCl$_3$): δ 9.10 (d, J = 0.9 Hz, 1H), 8.07 (d, J = 8.3 Hz, 1H), 7.94 (ddd, J = 6.9, 2.6, 0.9 Hz, 1H), 7.48-7.38 (m, 2H), 7.36 (d, J = 2.0 Hz, 2H), 7.19 (dd, J = 8.4, 1.8 Hz, 1H), 6.85 (t, J = 1.0 Hz, 1H), 4.55-4.35 (m, 2H), 4.30-4.25 (m, 2H), 4.15-4.05 (m, 1H), 3.98 (s, 3H), 3.35 (s, 3H), 2.30 (s, 3H), 2.14 (s, 3H). LCMS (ESI) Rt = 2.65 minutes MS m/z 459 [M + H]$^+$ Using 4-(3-chloroisoquinolin-5-yl)-3,5-dimethylisoxazole (Preparation 6) at 140° C. and purification method D. | 0.261 |
| 6 | 4-((5-(1-Methyl-1H-pyrazol-4-yl)isoquinolin-3-yl)amino)-N-(1-methylpiperidin-4-yl)-3-(trifluoromethoxy)benzamide | $^1$H NMR (500 MHz, CDCl$_3$): δ 9.09 (s, 1H), 8.02 (d, J = 8.5 Hz, 1H), 7.92-7.82 (m, 2H), 7.80-7.72 (m, 2H), 7.66-7.51 (m, 3H), 7.44 (t, J = 7.6 Hz, 1H), 7.15-7.05 (m, 2H), 4.30-4.20 (m, 1H), 4.04 (s, 3H), 3.74-3.53 (m, 4H), 2.82-2.70 (m, 4H), 2.30-2.10 (m, 2H), 1.35-1.22 (m, 1H). LCMS (ESI) Rt = 2.08 minutes MS m/z 525 [M + H]$^+$ Using 3-chloro-5-(1-methyl-1H-pyrazol-4-yl)isoquinoline (Preparation 7) and 4-amino-N-(1-methylpiperidin-4-yl)-3-(trifluoromethoxy)benzamide (Preparation 26) at 140° C. and purification method E. | 0.293 |
| 7 | 4-((5-(1-Isopropyl-1H-pyrazol-4-yl)isoquinolin-3-yl)amino)-3-methoxyphenyl)(3-methoxyazetidin-1-yl)methanone | $^1$H NMR (500 MHz, CDCl$_3$) δ 9.06 (d, J = 0.9 Hz, 1H), 8.00 (d, J = 8.4 Hz, 1H), 7.82 (dt, J = 8.2, 1.1 Hz, 1H), 7.78 (d, J = 0.8 Hz, 1H), 7.68 (d, J = 0.8 Hz, 1H), 7.56 (dd, J = 7.0, 1.2 Hz, 1H), 7.53 (t, J = 0.9 Hz, 1H), 7.41-7.32 (m, 3H), 7.19 (dd, J = 8.4, 1.8 Hz, 1H), 4.63 (septet, J = 6.7 Hz, 1H), 4.52-4.35 (m, 2H), 4.30-4.22 (m, 2H), 4.14-4.06 (m, 1H), 3.98 (s, 3H), 3.34 (s, 3H), 1.62 (d, J = 6.7 Hz, 6H). LCMS (ESI) Rt = 2.73 minutes MS m/z 472 [M + H]$^+$ Using 3-chloro-5-(1-isopropyl-1H-pyrazol-4-yl)isoquinoline (Preparation 8) at 140° C. and purification method A. | 0.011 |

-continued

| Example No | Name/Structure | Data | MPS1 IC50 (μM) |
|---|---|---|---|
| 8 | 4-((5-(1,3-Dimethyl-1H-pyrazol-4-yl)isoquinolin-3-yl)amino)-3-methoxyphenyl)(3-methoxyazetidin-1-yl)methanone 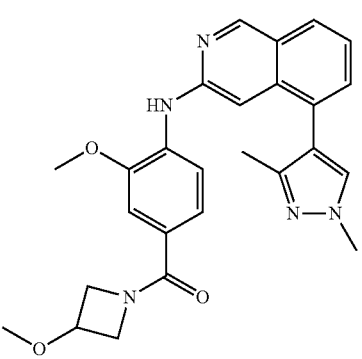 | $^1$H NMR (500 MHz, CDCl$_3$): δ 9.07 (d, J = 0.9 Hz, 1H), 8.07 (d, J = 8.4 Hz, 1H), 7.85 (dt, J = 8.2, 1.1 Hz, 1H), 7.46 (dd, J = 7.0, 1.3 Hz, 1H), 7.42 (s, 1H), 7.38 (dd, J = 8.2, 7.0 Hz, 1H), 7.35-7.29 (m, 2H), 7.18 (dd, J = 8.4, 1.8 Hz, 1H), 7.16 (d, J = 1.0 Hz, 1H), 4.52-4.35 (m, 2H), 4.28-4.22 (m, 2H), 4.15-4.07 (m, 1H), 3.97 (s, 3H), 3.96 (s, 3H), 3.33 (s, 3H), 2.20 (s, 3H). LCMS (ESI) Rt = 2.62 minutes MS m/z 458 [M + H]$^+$ Using 3-chloro-5-(1,3-dimethyl-1H-pyrazol-4-yl)isoquinoline (Preparation 9) at 140° C. and purification method A. | 0.027 |
| 9 | (3-Methoxy-4-((5-(1-methyl-1H-pyrazol-5-yl)isoquinolin-3-yl)amino)phenyl)(3-methoxyazetidin-1-yl)methanone 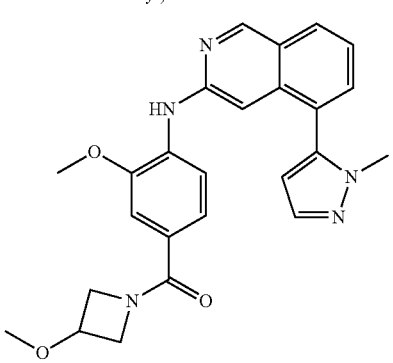 | $^1$H NMR (500 MHz, CDCl$_3$): δ 9.10 (d, J = 0.9 Hz, 1H), 8.06 (d, J = 8.4 Hz, 1H), 7.97 (dt, J = 8.3, 1.1 Hz, 1H), 7.68 (d, J = 1.8 Hz, 1H), 7.55 (dd, J = 7.0, 1.2 Hz, 1H), 7.43 (dd, J = 8.2, 7.0 Hz, 1H), 7.39-7.32 (m, 2H), 7.18 (dd, J = 8.4, 1.8 Hz, 1H), 6.92 (t, J = 0.9 Hz, 1H), 6.42 (d, J = 1.9 Hz, 1H), 4.54-4.35 (m, 2H), 4.31-4.20 (m, 2H), 4.15-4.05 (m, 1H), 3.97 (s, 3H), 3.72 (s, 3H), 3.34 (s, 3H). LCMS (ESI) Rt = 2.60 minutes MS m/z 444 [M + H]$^+$ Using 3-chloro-5-(1-methyl-1H-pyrazol-5-yl)isoquinoline (Preparation 10) at 140° C. and purification method A. | 0.022 |
| 10 | N-(4-(1,2-dimethyl-1H-imidazol-5-yl)-2-methoxyphenyl)-5-(1-methyl-1H-pyrazol-4-yl)isoquinolin-3-amine 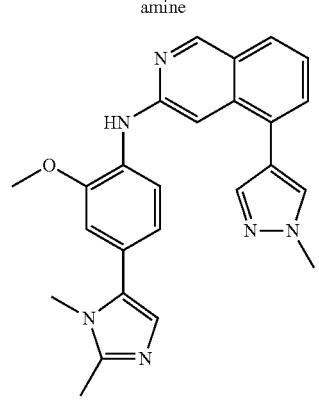 | $^1$H NMR (500 MHz, CDCl$_3$): δ 9.05 (d, J = 0.9 Hz, 1H), 8.01 (d, J = 8.2 Hz, 1H), 7.82 (dt, J = 8.2, 1.1 Hz, 1H), 7.76 (d, J = 0.8 Hz, 1H), 7.63-7.61 (m, 1H), 7.53 (dd, J = 7.0, 1.2 Hz, 1H), 7.49 (t, J = 0.9 Hz, 1H), 7.38-7.32 (m, 1H), 7.22 (s, 1H), 7.00-6.93 (m, 2H), 6.89 (d, J = 1.9 Hz, 1H), 4.03 (s, 3H), 3.95 (s, 3H), 3.56 (s, 3H), 2.49 (s, 3H). LCMS (ESI) Rt = 2.00 minutes MS m/z 425 [M + H]$^+$ Using 3-chloro-5-(1-methyl-1H-pyrazol-4-yl)isoquinoline (Preparation 7) and 4-(1,2-dimethyl-1H-imidazol-5-yl)-2-methoxyaniline (Preparation 18) and purification method A. | 0.006 |

| Example No | Name/Structure | Data | MPS1 IC50 (μM) |
|---|---|---|---|
| 11 | N-(2-chloro-4-(1,2-dimethyl-1H-imidazol-5-yl)phenyl)-5-(1-methyl-1H-pyrazol-4-yl)isoquinolin-3-amine | $^1$H NMR (500 MHz, CDCl$_3$): δ 9.07 (d, J = 0.9 Hz, 1H), 8.01 (d, J = 8.5 Hz, 1H), 7.85 (dt, J = 8.3, 1.1 Hz, 1H), 7.75 (d, J = 0.8 Hz, 1H), 7.64-7.59 (m, 1H), 7.56 (dd, J = 7.1, 1.2 Hz, 1H), 7.50 (d, J = 1.0 Hz, 1H), 7.45-7.37 (m, 2H), 7.26-7.21 (m, 1H), 7.06 (s, 1H), 6.96 (s, 1H), 4.03 (s, 3H), 3.55 (s, 3H), 2.47 (s, 3H). LCMS (ESI) Rt = 1.95 minutes MS m/z 429 [M + H]$^+$ Using 3-chloro-5-(1-methyl-1H-pyrazol-4-yl)isoquinoline (Preparation 7) and 2-chloro-4-(1,2-dimethyl-1H-imidazol-5-yl)aniline (Preparation 23) at 140° C. | 0.006 |
| 12 | (3-Methoxy-4-((5-(1-methyl-1H-pyrazol-3-yl)isoquinolin-3-yl)amino)phenyl)(3-methoxyazetidin-1-yl)methanone | $^1$H NMR (500 MHz, CDCl$_3$): δ 9.05 (d, J = 0.9 Hz, 1H), 8.25 (t, J = 0.9 Hz, 1H), 8.05 (d, J = 8.4 Hz, 1H), 7.86 (dt, J = 8.2, 1.1 Hz, 1H), 7.81 (dd, J = 7.1, 1.2 Hz, 1H), 7.51 (d, J = 2.2 Hz, 1H), 7.45-7.39 (m, 2H), 7.32 (d, J = 1.8 Hz, 1H), 7.26-7.21 (m, 1H), 6.59 (d, J = 2.2 Hz, 1H), 4.52-4.35 (m, 2H), 4.32-4.22 (m, 2H), 4.15-4.08 (m, 1H), 4.06 (s, 3H), 3.97 (s, 3H), 3.34 (s, 3H). LCMS (ESI) Rt = 2.58 minutes MS m/z 444 [M + H]$^+$ Using 3-chloro-5-(1-methyl-1H-pyrazol-3-yl)isoquinoline (Preparation 11) at 140° C. and purification method A. | 0.026 |
| 13 | (4-((5-(1,5-Dimethyl-1H-pyrazol-4-yl)isoquinolin-3-yl)amino)-3-methoxyphenyl)(3-methoxyazetidin-1-yl)methanone | $^1$H NMR (500 MHz, CDCl$_3$): δ 9.05 (d, J = 0.9 Hz, 1H), 8.05 (d, J = 8.4 Hz, 1H), 7.83 (dt, J = 8.0, 1.2 Hz, 1H), 7.58 (s, 1H), 7.45-7.35 (m, 2H), 7.35-7.30 (m, 2H), 7.21 (t, J = 0.9 Hz, 1H), 7.18 (dd, J = 8.4, 1.8 Hz, 1H), 4.52-4.34 (m, 2H), 4.28-4.22 (m, 2H), 4.15-4.04 (m, 1H), 3.95 (s, 3H), 3.91 (s, 3H), 3.32 (s, 3H), 2.21 (s, 3H). LCMS (ESI) Rt = 2.60 minutes MS m/z 458 [M + H]$^+$ Using 3-chloro-5-(1,5-dimethyl-1H-pyrazol-4-yl)isoquinoline (Preparation 12) at 140° C. and purification method A. | 0.012 |

| Example No | Name/Structure | Data | MPS1 IC50 (μM) |
|---|---|---|---|
| 14 | N-(2-methoxy-4-(1-methyl-1H-imidazol-5-yl)phenyl)-5-(1-methyl-1H-pyrazol-4-yl)isoquinolin-3-amine | $^1$H NMR (500 MHz, CDCl$_3$): δ 9.05 (d, J = 0.9 Hz, 1H), 8.03 (d, J = 8.2 Hz, 1H), 7.82 (dt, J = 8.3, 1.1 Hz, 1H), 7.77 (d, J = 0.8 Hz, 1H), 7.61 (d, J = 0.8 Hz, 1H), 7.56 (s, 1H), 7.53 (dd, J = 7.1, 1.2 Hz, 1H), 7.49 (t, J = 0.9 Hz, 1H), 7.35 (dd, J = 8.2, 7.0 Hz, 1H), 7.23 (s, 1H), 7.09 (d, J = 1.2 Hz, 1H), 7.00 (dd, J = 8.2, 1.8 Hz, 1H), 6.92 (d, J = 1.9 Hz, 1H), 4.03 (s, 3H), 3.96 (s, 3H), 3.70 (s, 3H). LCMS (ESI) Rt = 1.92 minutes MS m/z 411 [M + H]$^+$ Using 3-chloro-5-(1-methyl-1H-pyrazol-4-yl)isoquinoline (Preparation 7) and 2-methoxy-4-(1-methyl-1H-imidazol-5-yl)aniline (Preparation 17) at 140° C. and purification method A. | 0.007 |
| 15 | (3-Methoxy-4-((5-(pyrimidin-5-yl)isoquinolin-3-yl)amino)phenyl)(3-methoxyazetidin-1-yl)methanone | $^1$H NMR (500 MHz, CDCl$_3$): δ 9.33 (s, 1H), 9.13 (d, J = 1.0 Hz, 1H), 8.93 (s, 2H), 8.05 (d, J = 8.3 Hz, 1H), 7.99 (dt, J = 8.3, 1.1 Hz, 1H), 7.55 (dd, J = 7.0, 1.3 Hz, 1H), 7.47 (dd, J = 8.2, 6.9 Hz, 1H), 7.38-7.32 (m, 2H), 7.18 (dd, J = 8.4, 1.9 Hz, 1H), 7.06 (t, J = 1.1 Hz, 1H), 4.52-4.35 (m, 2H), 4.31-4.22 (m, 2H), 4.15-4.03 (m, 1H), 3.97 (s, 3H), 3.34 (s, 3H). LCMS (ESI) Rt = 2.47 minutes MS m/z 442 [M + H]$^+$ Using 3-chloro-5-(pyrimidin-5-yl)isoquinoline (Preparation 13) at 140° C. and purification method A. | 0.098 |
| 16 | N-(2-methoxy-4-(1-methyl-1H-pyrazol-4-yl)phenyl)-5-(1-methyl-1H-pyrazol-4-yl)isoquinolin-3-amine | $^1$H NMR (500 MHz, CDCl$_3$): δ 9.02 (d, J = 0.9 Hz, 1H), 7.83 (d, J = 8.2 Hz, 1H), 7.78 (dt, J = 8.2, 1.1 Hz, 1H), 7.76 (d, J = 0.8 Hz, 1H), 7.74 (d, J = 0.8 Hz, 1H), 7.59 (d, J = 0.8 Hz, 2H), 7.50 (dd, J = 7.1, 1.2 Hz, 1H), 7.47 (t, J = 1.0 Hz, 1H), 7.31 (dd, J = 8.2, 7.0 Hz, 1H), 7.12-7.06 (m, 2H), 7.01 (d, J = 1.9 Hz, 1H), 4.01 (s, 3H), 3.96 (s, 3H), 3.95 (s, 3H). LCMS (ESI) Rt = 2.57 minutes MS m/z 411 [M + H]$^+$ Using 3-chloro-5-(1-methyl-1H-pyrazol-4-yl)isoquinoline (Preparation 7) and 2-methoxy-4-(1-methyl-1H-pyrazol-4-yl)aniline (Preparation 19) at 140° C. and purification method F. | 0.071 |

-continued

| Example No | Name/Structure | Data | MPS1 IC50 (μM) |
|---|---|---|---|
| 17 | N-(2-chloro-4-(1-methyl-1H-imidazol-5-yl)phenyl)-5-(1-methyl-1H-pyrazol-4-yl)isoquinolin-3-amine 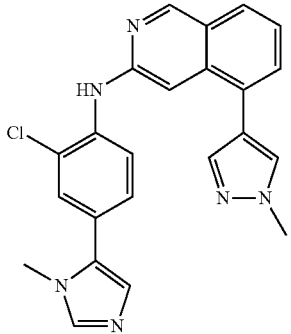 | $^1$H NMR (500 MHz, CDCl$_3$): δ 9.08 (d, J = 0.9 Hz, 1H), 8.04 (d, J = 8.5 Hz, 1H), 7.86 (dt, J = 8.2, 1.1 Hz, 1H), 7.75 (d, J = 0.8 Hz, 1H), 7.62 (s, 1H), 7.57 (dd, J = 7.0, 1.2 Hz, 1H), 7.53 (s, 1H), 7.51 (t, J = 1.0 Hz, 1H), 7.45 (d, J = 2.1 Hz, 1H), 7.42 (dd, J = 8.2, 7.0 Hz, 1H), 7.29 7.26 (m, 1H), 7.10 (s, 1H), 7.05 (s, 1H), 4.04 (s, 3H), 3.70 (s, 3H). LCMS (ESI) Rt = 1.94 minutes MS m/z 415 [M + H]$^+$ Using 3-chloro-5-(1-methyl-1H-pyrazol-4-yl)isoquinoline (Preparation 7) and 2-chloro-4-(1-methyl-1H-imidazol-5-yl)aniline (Preparation 20) at 140° C. and purification method A. | 0.051 |
| 18 | N-(4-(3,5-dimethylisoxazol-4-yl)-2-methoxyphenyl)-5-(1-methyl-1H-pyrazol-4-yl)isoquinolin-3-amine 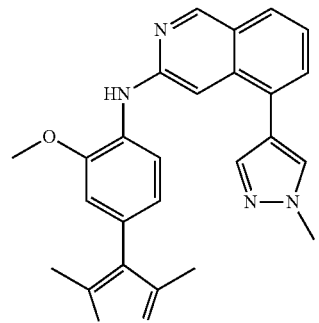 | $^1$H NMR (500 MHz, CDCl$_3$): δ 9.04 (d, J = 0.9 Hz, 1H), 8.03 (d, J = 8.2 Hz, 1H), 7.81 (dt, J = 8.2, 1.1 Hz, 1H), 7.76 (d, J = 0.8 Hz, 1H), 7.61 (d, J = 0.9 Hz, 1H), 7.52 (dd, J = 7.1, 1.2 Hz, 1H), 7.49 (t, J = 0.9 Hz, 1H), 7.34 (dd, J = 8.2, 7.0 Hz, 1H), 7.18 (s, 1H), 6.87 (dd, J = 8.2, 1.9 Hz, 1H), 6.78 (d, J = 1.9 Hz, 1H), 4.03 (s, 3H), 3.94 (s, 3H), 2.44 (s, 3H), 2.31 (s, 3H). LCMS (ESI) Rt = 2.78 minutes MS m/z 426 [M + H]$^+$ Using 3-chloro-5-(1-methyl-1H-pyrazol-4-yl)isoquinoline (Preparation 7) and 4-(3,5-dimethylisoxazol-4-yl)-2-methoxyaniline (Preparation 22) at 140° C. and purification method G. | 0.095 |

Example 19

(3-Methoxy-4-((5-(1-(1-methylpiperidin-4-yl)-1H-pyrazol-4-yl)isoquinolin-3-yl)amino)phenyl)(3-methoxyazetidin-1-yl)methanone

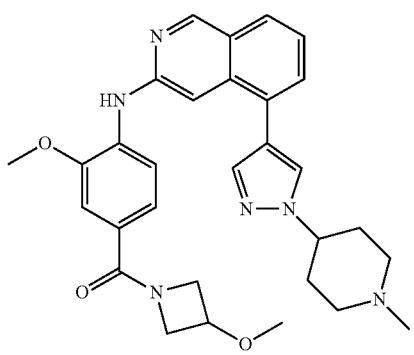

To a solution of (3-methoxy-4-((5-(1-(piperidin-4-yl)-1H-pyrazol-4-yl)isoquinolin-3-yl)amino)phenyl)(3-methoxyazetidin-1H)methanone (Example 20, 18 mg, 0.035 mmol) in DCM/MeOH (4/2 mL) was added acetic acid (2.5 uL, 0.044 mmol) and aqueous formaldehyde solution (38% w/w, 6.0 uL, 0.073 mmol) followed by sodium triacetoxyborohydride (11.2 mg, 0.053 mmol). The reaction mixture was stirred at room temperature for 1 hour. Solvents were removed and the residue was purified by SCX-2 column, eluting with 2M NH$_3$/MeOH to afford the title compound as yellow oil (17 mg, 92%).

$^1$H NMR (500 MHz, CDCl$_3$): δ 9.05 (d, J=0.9 Hz, 1H), 8.01 (d, J=8.3 Hz, 1H), 7.82 (dt, J=8.3, 1.1 Hz, 1H), 7.78 (d, J=0.8 Hz, 1H), 7.69 (d, J=0.8 Hz, 1H), 7.54 (dd, J=7.1, 1.2 Hz, 1H), 7.49 (t, J=1.0 Hz, 1H), 7.40-7.32 (m, 3H), 7.20 (dd, J=8.4, 1.9 Hz, 1H), 4.47-4.35 (m, 2H), 4.30-4.20 (m, 2H), 4.17-4.03 (m, 1H), 3.97 (s, 3H), 3.33 (s, 3H), 3.07-3.00 (m, 2H), 2.37 (s, 3H), 2.34-2.09 (m, 7H).

LCMS (ESI) Rt=1.97 minutes MS m/z 527 [M+H]$^+$

MPS1 IC50 (μM): 0.031

Example 20

(3-Methoxy-4-((5-(1-(piperidin-4-yl)-1H-pyrazol-4-yl)isoquinolin-3-yl)amino)phenyl)(3-methoxyazetidin-1-yl)methanone

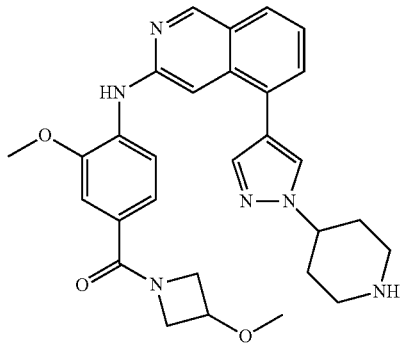 [SMILES: COc1cc(C(=O)N2CC(OC)C2)ccc1Nc1cc2c(-c3cnn(C4CCNCC4)c3)cccc2cn1]

To a solution of tert-butyl 4-(4-(3-((2-methoxy-4-(3-methoxyazetidine-1-carbonyl)phenyl)-amino)isoquinolin-5-yl)-1H-pyrazol-1-yl)piperidine-1-carboxylate (Example 3, 23 mg, 0.038 mmol) in DCM (8 mL) at 0° C. was added TFA (0.5 mL). The reaction was stirred at room temperature for 16 hours. The solvents were removed in vacuo and the residue was purified by SCX-2 column eluting with 2M NH₃/MeOH to afford the title compound as yellow oil (19 mg, 98%).

¹H NMR (500 MHz, CDCl₃): δ 9.05 (d, J=0.9 Hz, 1H), 8.00 (d, J=8.3 Hz, 1H), 7.81 (d, J=8.1 Hz, 1H), 7.77 (s, 1H), 7.69 (s, 1H), 7.54 (dd, J=7.1, 1.3 Hz, 1H), 7.50 (s, 1H), 7.40-7.30 (m, 3H), 7.20 (dd, J=8.3, 1.9 Hz, 1H), 4.55-4.35 (m, 2H), 4.35-4.30 (m, 1H), 4.29-4.20 (m, 2H), 4.15-4.05 (m, 1H), 3.96 (s, 3H), 3.33 (s, 3H), 3.32-3.27 (m, 2H), 2.87-2.78 (m, 2H), 2.30-2.22 (m, 2H), 2.04-1.92 (m, 2H).

LCMS (ESI) Rt=1.97 minutes MS m/z 513 [M+H]⁺
MPS1 IC50 (µM): 0.020

Example 21

(3-Methoxy-4-((5-(pyridin-3-yl)isoquinolin-3-yl)amino)phenyl)(3-methoxyazetidin-1-yl)methanone

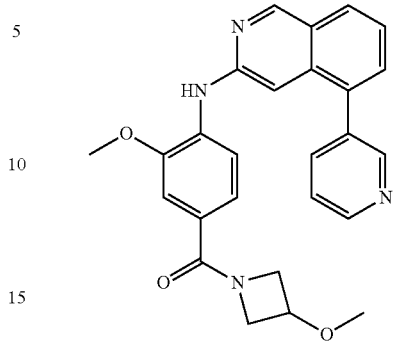

Method 2

A suspension of 3-chloro-5-(pyridin-3-yl)isoquinoline (Preparation 14, 33 mg, 0.14 mmol), (4-amino-3-methoxyphenyl)(3-methoxyazetidin-1-yl)methanone (Preparation 28, 32.5 mg, 0.14 mmol), xantphos (55.5 mg, 0.10 mmol), Pd(OAc)₂ (18.5 mg, 0.08 mmol) and Cs₂CO₃ (366 mg, 1.12 mmol) in toluene/DMF (3/1 mL) was stirred at 120° C. under microwave irradiation for 2 hours. The reaction mixture was filtered, diluted with NaCl solution and extracted with EtOAc. The organic layer was purified by SCX-2 column eluting with 2M NH₃/MeOH and concentrated in vacuo. The residue was purified by Biotage silica gel column chromatography eluting with 0-4% MeOH/EtOAc to afford the title compound as yellow oil (13 mg, 22%).

¹H NMR (500 MHz, CDCl₃): δ 9.12 (d, J=0.9 Hz, 1H), 8.79 (dd, J=2.4, 0.9 Hz, 1H), 8.73 (dd, J=4.9, 1.6 Hz, 1H), 8.02 (d, J=8.3 Hz, 1H), 7.95 (dt, J=8.2, 1.1 Hz, 1H), 7.84 (ddd, J=7.7, 2.2, 1.6 Hz, 1H), 7.55 (dd, J=7.1, 1.2 Hz, 1H), 7.51-7.42 (m, 2H), 7.33 (d, J=2.2 Hz, 2H), 7.20-7.14 (m, 2H), 4.53-4.35 (m, 2H), 4.31-4.24 (m, 2H), 4.16-4.02 (m, 1H), 3.96 (s, 3H), 3.35 (s, 3H).

LCMS (ESI) Rt=2.49 minutes MS m/z 441 [M+H]⁺
MPS1 IC50 (µM): 0.030

The following Examples were prepared according to Method 2 (Example 21) above using 3-chloro-5-(1-methyl-1H-pyrazol-4-yl)isoquinoline (Preparation 7) and the appropriate aniline as described for 1-2 hours. The crude reaction residues were purified as above or according to one of the following methods:

Method A: Biotage silica gel column chromatography eluting with 60% EtOAc/cyclohexane.

| Example No | Name/Structure | Data | MPS1 IC50 (µM) |
|---|---|---|---|
| 22 | (3-Chloro-4-((5-(1-methyl-1H-pyrazol-4-yl)isoquinolin-3-yl)amino)phenyl)(3-methoxyazetidin-1-yl)methanone | ¹H NMR (500 MHz, CDCl₃): δ 9.08 (d, J = 0.9 Hz, 1H), 8.06 (d, J = 8.0 Hz, 1H), 7.85 (dd, J = 4.9, 1.6 Hz, 1H), 7.75 (d, J = 8.3 Hz, 1H), 7.73 (d, J = 1.1 Hz, 1H), 7.62 (s, 1H), 7.57 (dd, J = 7.1, 1.2 Hz, 1H), 7.54-7.51 (m, 2H), 7.45-7.41 (m, 1H), 7.18 (s, 1H), 4.53-4.35 (m, 2H), 4.31-4.24 (m, 2H), 4.16-4.02 (m, 1H), 4.03 (s, 3H), 3.33 (s, 3H). LCMS (ESI) Rt = 2.60 minutes 448 [M + H]⁺ Using (4-amino-3-chlorophenyl)(3-methoxyazetidin-1-yl)methanone (Preparation 27). | 0.100 |

| Example No | Name/Structure | Data | MPS1 IC50 (μM) |
|---|---|---|---|
| 23 | N-(2-chloro-4-(1-methyl-1H-pyrazol-4-yl)phenyl)-5-(1-methyl-1H-pyrazol-4-yl)isoquinolin-3-amine | $^1$H NMR (500 MHz, MeOD): δ 8.97 (d, J = 0.9 Hz, 1H), 7.95 (d, J = 0.9 Hz, 1H), 7.89 (d, J = 0.8 Hz, 1H), 7.87 (dt, J = 8.3, 1.1 Hz, 1H), 7.81 (d, J = 0.8 Hz, 1H), 7.74 (d, J = 0.8 Hz, 1H), 7.71 (d, J = 8.4 Hz, 1H), 7.66 (d, J = 2.0 Hz, 1H), 7.59 (dd, J = 7.1, 1.2 Hz, 1H), 7.46 (dd, J = 8.4, 2.1 Hz, 1H), 7.40 (t, J = 0.9 Hz, 1H), 7.38 (dd, J = 8.2, 7.1 Hz, 1H), 3.97 (s, 3H), 3.93 (s, 3H). LCMS (ESI) Rt = 2.73 minutes MS m/z 415 [M + H]$^+$ Using 2-chloro-4-(1-methyl-1H-pyrazol-4-yl)aniline (Preparation 21). | 0.225 |
| 24 | (3-Methoxy-4-((5-(1-methyl-1H-pyrazol-4-yl)isoquinolin-3-yl)amino)phenyl)(3-methoxyazetidin-1-yl)methanone | $^1$H NMR (500 MHz, MeOD): δ 8.97 (d, J = 1.0 Hz, 1H), 7.99 (d, J = 8.4 Hz, 1H), 7.90 (d, J = 0.8 Hz, 1H), 7.83 (dt, J = 8.4, 1.1 Hz, 1H), 7.75 (d, J = 0.9 Hz, 1H), 7.57 (dd, J = 7.1, 1.2 Hz, 1H), 7.54 (t, J = 0.9 Hz, 1H), 7.36 (dd, J = 8.2, 7.1 Hz, 1H), 7.28 (d, J = 1.9 Hz, 1H), 7.21 (dd, J = 8.4, 1.9 Hz, 1H), 4.62-4.50 (m, 1H), 4.38-4.30 (m, 1H), 4.340-4.22 (m, 2H), 4.03-3.95 (m, 1H + 3H), 3.94 (s, 3H). LCMS (ESI) Rt = 2.57 minutes MS m/z 444 [M + H]$^+$ Using (4-amino-3-methoxyphenyl)(3-methoxyazetidin-1-yl)methanone (Preparation 28). | 0.020 |
| 25 | 3-Methoxy-N,N-dimethyl-4-((5-(1-methyl-1H-pyrazol-4-yl)isoquinolin-3-yl)amino)benzamide | $^1$H NMR (500 MHz, MeOD): δ 9.02 (d, J = 0.9 Hz, 1H), 7.98 (d, J = 8.2 Hz, 1H), 7.95 (d, J = 0.8 Hz, 1H), 7.88 (dt, J = 8.3, 1.1 Hz, 1H), 7.78 (d, J = 0.8 Hz, 1H), 7.61 (dd, J = 7.1, 1.2 Hz, 1H), 7.56 (t, J = 1.0 Hz, 1H), 7.39 (dd, J = 8.2, 7.0 Hz, 1H), 7.12 (d, J = 1.8 Hz, 1H), 7.07 (dd, J = 8.3, 1.8 Hz, 1H), 4.02 (s, 3H), 3.97 (s, 3H), 3.13 (s, 6H). LCMS (ESI) Rt = 2.57 minutes MS m/z 402 [M + H]$^+$ Using 4-amino-3-methoxy-N,N-dimethylbenzamide (Preparation 24) and purification method A. | 0.028 |

| Example No | Name/Structure | Data | MPS1 IC50 (μM) |
|---|---|---|---|
| 26 | 3-Chloro-N,N-dimethyl-4-((5-(1-methyl-1H-pyrazol-4-yl)isoquinolin-3-yl)amino)benzamide 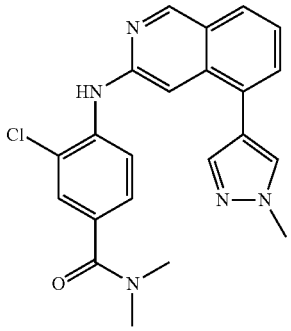 | ¹H NMR (500 MHz, MeOD): δ 9.06 (s, 1H), 8.00-7.95 (m, 2H), 7.94 (dt, J = 8.3, 1.1 Hz, 1H), 7.80 (d, J = 0.8 Hz, 1H), 7.66 (dd, J = 7.1, 1.2 Hz, 1H), 7.64-7.61 (m, 1H), 7.57 (d, J = 2.0 Hz, 1H), 7.46 (dd, J = 8.2, 7.1 Hz, 1H), 7.37 (dd, J = 8.5, 2.0 Hz, 1H), 4.02 (s, 3H), 3.12 (s, 6H). LCMS (ESI) Rt = 2.58 minutes MS m/z 406 [M + H]⁺ Using 4-amino-3-chloro-N,N-dimethylbenzamide (Preparation 25) and purification method A. | 0.078 |

Example 27

5-(Furan-2-yl)-N-(4-methoxyphenyl)isoquinolin-3-amine

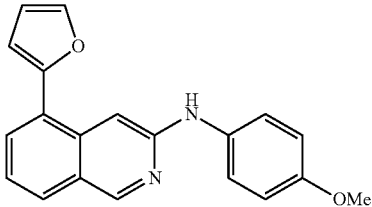 [SMILES: COc1ccc(Nc2cc3c(-c4ccco4)cccc3cn2)cc1]

Method 3

3-Chloro-5-(furan-2-yl)isoquinoline (Preparation 15, 41 mg, 0.18 mmol), 4-methoxyaniline (29 mg, 0.23 mmol), caesium carbonate (204 mg, 0.63 mmol), 2-di-tert-butylphosphino-2',4',6'-triisopropylbiphenyl (30 mg, 0.071 mmol), tris(dibenzylideneacetone)dipalladium(O) (16 mg, 0.018 mmol) and ᵗBuOH (3% H₂O) (1 mL) were mixed and the mixture heated at 80° C. under microwave irradiation for 3 hours. The reaction mixture was concentrated onto silica gel in vacuo and purified by silica gel column chromatography eluting with 0-100% EtOAc in cyclohexane to afford the title compound (10 mg, 18%).

¹H NMR (500 MHz, CDCl₃): δ 8.95 (s, 1H), 7.84-7.75 (m, 2H), 7.61 (s, 1H), 7.57 (s, 1H), 7.58-7.25 (m, 3H), 7.17-6.90 (m, 2H), 6.77-6.60 (m, 2H), 6.54 (dd, J=3.3, 1.8 Hz, 1H), 3.85 (s, 3H).

LCMS m/z 317 [M+H]⁺ HRMS (ESI) m/z calcd for C₂₀H₁₇N₂O₂[M+H]⁺ 317.1285. found 317.1282.

MPS1 IC50 (μM): 3.657

Example 28

N-(4-Methoxyphenyl)-5-(1-methyl-1H-pyrazol-4-yl)isoquinolin-3-amine

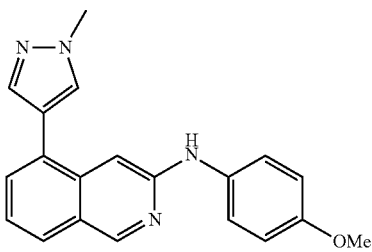 [SMILES: COc1ccc(Nc2cc3c(-c4cnn(C)c4)cccc3cn2)cc1]

The title compound was prepared according to Method 3 (Example 27) using 4-methoxyaniline and 3-Chloro-5-(1-methyl-1H-pyrazol-4-yl)isoquinoline (Preparation 7).

¹H NMR (500 MHz, CDCl₃): δ 8.95 (s, 1H), 7.75 (d, J=8.2 Hz, 1H), 7.68 (s, 1H), 7.52 (s, 1H), 7.50-7.46 (m, 1H), 7.31-7.21 (m, 3H), 7.03-6.89 (m, 2H), 6.48 (s, 1H), 3.98 (s, 3H), 3.83 (s, 3H).

LCMS m/z 331 [M+H]⁺ HRMS (ESI) m/z calcd for C₂₀H₁₉N₄O [M+H]⁺ 331.1553. found 331.1546.

MPS1 IC50 (μM): 0.666

Example 29

N-(2-Methoxy-4-((1-methylpiperidin-4-yl)oxy)phenyl)-5-(1-methyl-1H-pyrazol-4-yl)isoquinolin-3-amine

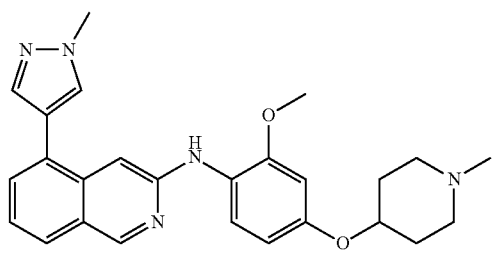 [SMILES: COc1cc(OC2CCN(C)CC2)ccc1Nc1cc2c(-c3cnn(C)c3)cccc2cn1]

The title compound was prepared according to Method 3 (Example 27) using 3-Chloro-5-(1-methyl-1H-pyrazol-4-yl)isoquinoline (Preparation 7) and 2-methoxy-4-(1-methylpiperidin-4-yloxy)aniline at 100° C. for 3 hours. The reaction mixture was concentrated onto silica gel in vacuo and purified by silica gel column chromatography eluting with 0-100% EtOAc in cyclohexane followed by 0-10% MeOH in CH₂Cl₂ and finally eluting with 10% 1M NH₃/MeOH in DCM to afford the title compound (5 mg, 5%).

¹H NMR (500 MHz, MeOD): δ 8.86 (s, 1H), 7.77 (m, 2H), 7.65 (s, 1H), 7.49 (dt, J=7.6, 3.8 Hz, 1H), 7.41 (t, J=7.8 Hz, 1H), 7.26 (dd, J=8.1, 7.1 Hz, 1H), 7.17 (s, 1H), 6.66 (d, J=2.6 Hz, 1H), 6.56 (dd, J=8.7, 2.6 Hz, 1H), 4.40 (br s, 1H), 3.95 (s, 3H), 3.82 (s, 3H), 2.77 (br s, 2H), 2.43 (br s, 2H), 2.35 (s, 3H), 2.04 (br s, 2H), 1.83 (br s, 2H).

LCMS m/z 444 [M+H]⁺ HRMS (ESI) m/z calcd for C₂₆H₃₀N₅O₂ [M+H]⁺ 444.2394. found 444.2388.

MPS1 IC50 (μM): 0.017

Example 30

N-(2,4-Dimethoxyphenyl)-5-(1-methyl-1H-pyrazol-4-yl)isoquinolin-3-amine

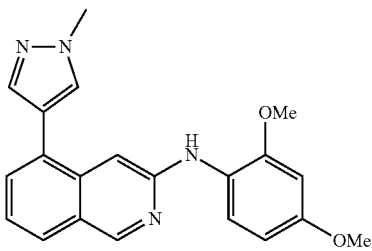 [SMILES: COc1ccc(Nc2cc3c(-c4cnn(C)c4)cccc3cn2)c(OC)c1]

The title compound was prepared according to Method 3 (Example 27) using 3-Chloro-5-(1-methyl-1H-pyrazol-4-yl)isoquinoline (Preparation 7) and 2,4-dimethoxyaniline at 80° C. for 1.5 hours followed by 100° C. for 1.5 hours. The reaction mixture was concentrated onto silica gel in vacuo and purified by silica gel column chromatography eluting with 0-100% EtOAc in cyclohexane to afford the title compound (22 mg, 27%).

$^1$H NMR (50 MHz, CDCl$_3$): δ 8.96 (s, 1H), 7.78-7.69 (m, 2H), 7.61 (d, J=8.6 Hz, 1H), 7.54 (s, 1H), 7.47 (dd, J=7.0, 1.0 Hz, 1H), 7.33-7.23 (m, 2H), 6.73 (s, 1H), 6.58-6.49 (m, 2H), 3.99 (s, 3H), 3.85 (s, 3H), 3.83 (s, 3H).

LCMS m/z 61 [M+H]$^+$ HRMS (ESI) m/z calcd for C$_{21}$H$_{21}$N$_4$O$_2$ [M+H]$^+$ 361.1659. found 361.1661.

MPS1 IC5 (W): 0.074

Example 31

(3-methoxy-4-((8-(1-methyl-1H-pyrazol-4-yl)pyrido[3,4-d]pyrimidin-2-yl)amino)phenyl)(3-methoxyazetidin-1-yl)methanone

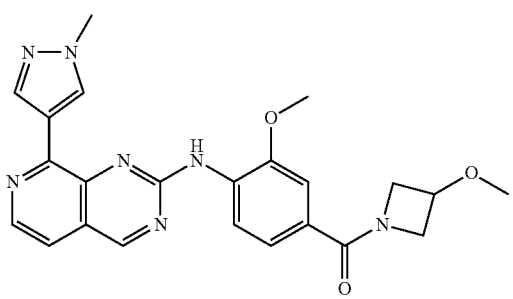 [SMILES: COc1cc(C(=O)N2CC(OC)C2)ccc1Nc1ncc2ccnc(-c3cnn(C)c3)c2n1]

A solution of (4-amino-3-methoxyphenyl)(3-methoxyazetidin-1-yl)methanone (Preparation 28, 56 mg, 0.237 mmol), TFA (46 μL, 0.601 mmol) and 8-(1-methyl-1H-pyrazol-4-yl)-2-(methylsulfonyl)pyrido[3,4-d]pyrimidine (Preparation 35, 35 mg, 0.121 mmol) in 2,2,2-trifluoroethanol (0.6 mL) was heated to reflux for 5 hours and then to 80° C. for 18 hours. The reaction was diluted with EtOAc, quenched with aqueous saturated NaHCO$_3$ and the aqueous layer extracted with EtOAc. The combined organic layers were washed with water, brine, dried, concentrated in vacuo and purified by silica gel column chromatography eluting with 0 to 100% EtOAc in cyclohexane followed by a second chromatography eluting with 0 to 10% MeOH in EtOAc to afford the title compound (11 mg, 20%). $^1$H $^1$HNMR (500 MHz, DMSO-d$_6$): δ 9.43 (s, 1H), 9.17 (s, 1H), 8.64 (s, 1H), 8.40 (d, J=5.2 Hz, 1H), 8.28 (s, 1H), 8.05 (d, J=8.1 Hz, 1H), 7.62 (d, J=5.2 Hz, 1H), 7.42-7.28 (m, 2H), 4.56 (s, 1H), 4.33-4.20 (m, 3H), 3.89-3.87 (m, 7H), 3.25 (s, 3H).

HRMS (ESI) MS m/z calcd for C$_{23}$H$_{24}$N$_7$O$_3$ [M+H]$^+$ 446.1935. found 446.1925.

MPS1 IC50 (μM):—no data

Example 32

N-(2-methoxy-4-(1-methyl-1H-pyrazol-4-yl)phenyl)-8-(1-methyl-1H-pyrazol-4-yl)pyrido[3,4-d]pyrimidin-2-amine

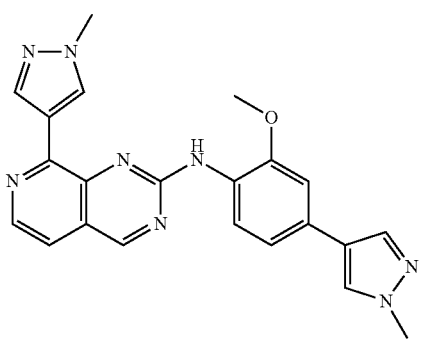 [SMILES: COc1cc(-c2cnn(C)c2)ccc1Nc1ncc2ccnc(-c3cnn(C)c3)c2n1]

Method 4

A solution of 2-methoxy-4-(1-methyl-1H-pyrazol-4-yl)aniline (Preparation 19, 42 mg, 0.207 mmol) TFA (45 μL, 0.588 mmol) and 8-(1-methyl-1H-pyrazol-4-yl)-2-(methylsulfonyl)pyrido[3,4-d]pyrimidine (Preparation 35, 31 mg, 0.107 mmol) in 2,2,2-trifluoroethanol (0.6 mL) was heated to 130° C. under microwave irradiation for 1 hour 30 minutes. The reaction was diluted with EtOAc and quenched with aqueous saturated NaHCO$_3$. The aqueous layer was extracted with EtOAc and the combined organic layers were washed with water, brine, dried, concentrated in vacuo and purified by silica gel column chromatography eluting with 0 to 10% MeOH in EtOAc to give the title compound (21 mg, 48%).

$^1$H NMR (500 MHz, DMSO-d$_6$): δ 9.35 (s, 1H), 9.08 (s, 1H), 8.53 (s, 1H), 8.33 (d, J=5.3 Hz, 1H), 8.25-8.19 (m, 2H), 7.96 (d, J=0.9 Hz, 1H), 7.72 (d, J=8.1 Hz, 1H), 7.56 (d, J=5.3 Hz, 1H), 7.36 (d, J=1.9 Hz, 1H), 7.28 (dd, J=8.0, 1.9 Hz, 1H), 3.89 (s, 3H), 3.85 (s, 3H), 3.74 (s, 3H).

HRMS (ESI) MS m/z calcd for C$_{22}$H$_{22}$N$_8$O [M+H]$^+$ 413.1833. found 413.1823.

MPS1 IC50 (μM): 0.008

The following Examples were prepared according to Method 4 (Example 32) above using the appropriate pyridopyrimidine and the appropriate aniline as described. The crude reaction residues were purified as above or according to one of the following methods:

Method A: Biotage silica gel column chromatography eluting with 0-40% EtOAc in DCM followed by 0-60% EtOAc in cyclohexane.
Method B: Biotage silica gel column chromatography eluting with 0-60% or 0-70% EtOAc in cyclohexane.
Method C: Biotage silica gel column chromatography eluting with 0-100% EtOAc in cyclohexane.
Method D: Biotage silica gel column chromatography eluting with 0-70% EtOAc in cyclohexane followed by a second chromatography eluting with 0-2% MeOH in DCM followed by preparative HPLC eluting with 10° A, to 90% MeOH in H$_2$O (0.1% formic acid).
Method E: Biotage silica gel column chromatography eluting with 0-5% MeOH in DCM.

| Example No | Name/Structure | Data | MPS1 IC50 (μM) |
|---|---|---|---|
| 33 | N-(2-chloro-4-(1-methyl-1H-pyrazol-4-yl)phenyl)-8-(1-methyl-1H-pyrazol-4-yl)pyrido[3,4-d]pyrimidin-2-amine | $^1$H NMR (500 MHz, DMSO-d$_6$): δ 9.69 (s, 1H), 9.40 (s, 1H), 8.39-8.32 (m, 2H), 8.29 (s, 1H), 8.16 (s, 1H), 8.01 (d, J = 0.8 Hz, 1H), 7.90 (d, J = 1.9 Hz, 1H), 7.73-7.64 (m, 2H), 7.59 (d, J = 5.3 Hz, 1H), 3.89 (s, 3H), 3.66 (s, 3H). HRMS (ESI) MS m/z calcd for C$_{21}$H$_{18}$ClN$_8$ [M + H]$^+$ 417.1337, found 417.1327. Using 2-chloro-4-(1-methyl-1H-pyrazol-4-yl)aniline (Preparation 21) for 2 hours. | — |
| 34 | N-(2-methoxy-4-(1-methyl-1H-pyrazol-4-yl)phenyl)-8-phenyl)pyrido[3,4-d]pyrimidin-2-amine | $^1$H NMR (500 MHz, DMSO-d$_6$): δ 9.48 (s, 1H), 8.65 (s, 1H), 8.57 (d, J = 5.2 Hz, 1H), 8.26-8.16 (m, 4H), 7.92 (s, 1H), 7.82 (d, J = 5.2 Hz, 1H), 7.57-7.44 (m, 3H), 7.27 (d, J = 1.9 Hz, 1H), 7.10 (d, J = 8.2 Hz, 1H), 3.93 (s, 3H), 3.89 (s, 3H). HRMS (ESI) MS m/z calcd for C24H21N6O [M + H]$^+$ 409.1771, found 409.1763. Using 2-(methylsulfonyl)-8-phenylpyrido[3,4-d]pyrimidine (Preparation 36) and method A. | 0.014 |
| 35 | 8-cyclopropyl-N-(2-methoxy-4-(1-methyl-1H-pyrazol-4-yl)phenyl)pyrido[3,4-d]pyrimidin-2-amine | $^1$H NMR (500 MHz, DMSO-d$_6$): δ 9.40 (s, 1H), 8.54 (s, 1H), 8.41 (d, J = 8.3 Hz, 1H), 8.28 (d, J = 5.3 Hz, 1H), 8.17 (d, J = 0.9 Hz, 1H), 7.90 (d, J = 0.8 Hz, 1H), 7.56 (d, J = 5.3 Hz, 1H), 7.30 (d, J = 1.8 Hz, 1H), 7.25 (dd, J = 8.2, 1.8 Hz, 1H), 3.96 (s, 3H), 3.88 (s, 3H), 3.28-3.19 (m, 1H), 1.16-1.08 (m, 4H). HRMS (ESI) MS m/z calcd for C$_{21}$H$_{21}$N$_6$O [M + H]$^+$ 373.1771, found 373.1773. Using 8-cyclopropyl-2-(methylsulfonyl)pyrido[3,4-d]pyrimidine (Preparation 38) and purification method B. | 0.096 |

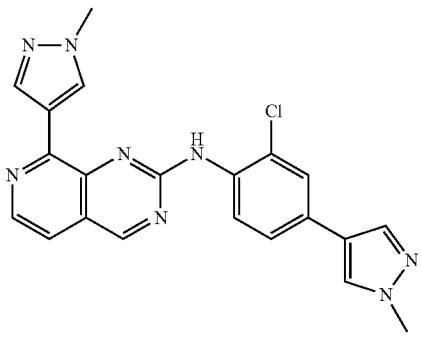

| Example No | Name/Structure | Data | MPS1 IC50 (μM) |
|---|---|---|---|
| 36 | N-(2-methoxy-5-methyl-4-(1-methyl-1H-pyrazol-4-yl)phenyl)-8-(1-methyl-1H-pyrazol-4-yl)pyrido[3,4-d]pyrimidin-2-amine 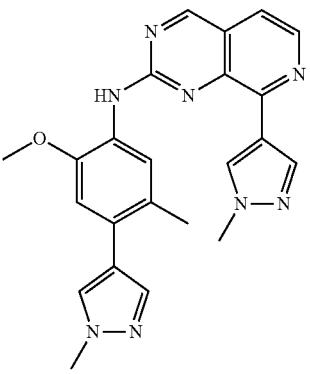 | $^1$H NMR (500 MHz, CDCl$_3$): δ 9.16 (s, 1H), 8.67 (s, 1H), 8.60 (s, 1H), 8.55 (s, 1H), 8.46 (d, J = 5.0 Hz, 1H), 7.90 (br s, 1H), 7.67 (s, 1H), 7.52 (s, 1H), 7.38 (d, J = 5.0 Hz, 1H), 6.94 (s, 1H), 4.01 (s, 3H), 3.98 (s, 3H), 3.96 (s, 3H), 2.45 (s, 3H). HRMS (ESI) MS m/z calcd for C$_{23}$H$_{22}$N$_8$O [M + H]$^+$ 427.1989, found 427.1980; LCMS (ESI) Rt = 2.65 minutes 427 [M + H]$^+$ Using 2-methoxy-5-methyl-4-(1-methyl-1H-pyrazol-4-yhaniline (Preparation 40) at 130 ° C. for 4.5 hours and purification method E. | 0.100 |
| 37 | N-(2-methoxy-4-(1-methyl-1H-pyrazol-4-yl)phenyl)-8-(pyrrolidin-1-yl)pyrido[3,4-d]pyrimidin-2-amine 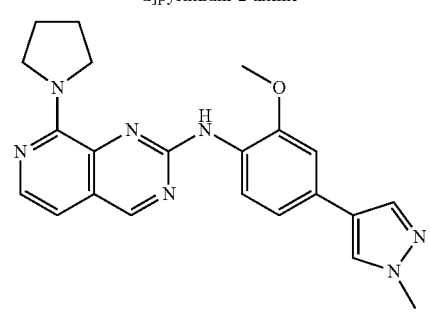 | $^1$H NMR (500 MHz, DMSO-d$_6$): δ 9.12 (s, 1H), 8.37 (s, 1H), 8.14 (s, 1H), 7.88 (d, J = 0.9 Hz, 1H), 7.87-7.79 (m, 2H), 7.24 (d, J = 1.9 Hz, 1H), 7.17 (dd, J = 8.2, 1.9 Hz, 1H), 6.86 (d, J = 5.4 Hz, 1H), 3.89 (s, 3H), 3.87 (s, 3H), 3.84-3.76 (m, 4H), 1.91-1.81 (m, 4H). HRMS (ESI) MS m/z calcd for C22H24N7O [M + H]$^+$ 402.2037, found 402.2040. Using 2-(methylsulfonyl)-8-(pyrrolidin-1-yl)pyrido[3,4-d]pyrimidine (Preparation 41) at 180° C. with an extra aliquot of TFA (50 uL) for a further 2 hours and purification method C. | 0.008 |
| 38 | N$^8$,N$^8$-diethyl-N2-(2-methoxy-4-(1-methyl-1H-pyrazol-4-yl)phenyl)pyrido[3,4-d]pyrimidine-2,8-amine 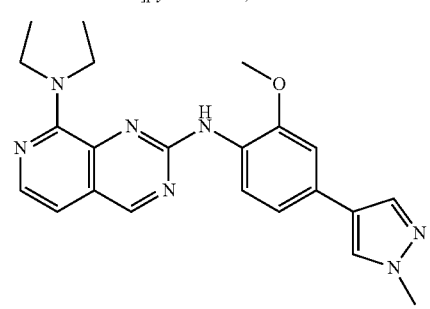 | $^1$H NMR (500 MHz, DMSO-d$_6$): δ 9.13 (s, 1H), 8.51 (s, 1H), 8.16 (s, 1H), 7.89 (d, J = 0.9 Hz, 1H), 7.84 (d, J = 5.3 Hz, 1H), 7.68 (d, J = 8.1 Hz, 1H), 7.25 (d, J = 1.9 Hz, 1H), 7.17 (dd, J = 8.1, 1.9 Hz, 1H), 6.91 (d, J = 5.3 Hz, 1H), 3.87 (s, 3H), 3.85 (s, 3H), 3.78 (q, J = 6.9 Hz, 4H), 1.02 (t, J = 6.9 Hz, 6H). HRMS (ESI) MS m/z calcd for C22H26N7O [M + H]$^+$ 404.2193, found 404.2191. Using N,N-diethyl-2-(methylsulfonyl)pyrido[3,4-d]pyrimidin-8-amine (Preparation 42) at 170° C. for 4 hours followed by method D. | 0.069 |

| Example No | Name/Structure | Data | MPS1 IC50 (μM) |
|---|---|---|---|
| 39 | N8-cyclopentyl-N2-(2-methoxy-4-(1-methyl-1H-pyrazol-4-yl)phenyl)pyrido[3,4-d]pyrimidin-2,8-amine | $^1$H NMR (500 MHz, DMSO-d$_6$): δ 9.16 (s, 1H), 8.48 (s, 1H), 8.16 (s, 1H), 8.11 (d, J = 8.3 Hz, 1H), 7.89 (d, J = 0.9 Hz, 1H), 7.78 (d, J = 5.7 Hz, 1H), 7.27 (d, J = 1.9 Hz, 1H), 7.19 (dd, J = 8.2, 1.9 Hz, 1H), 6.85 (d, J = 5.7 Hz, 1H), 6.58 (d, J = 7.4 Hz, 1H), 4.39 (h, J = 6.8 Hz, 1H), 3.92 (s, 3H), 3.87 (s, 3H), 2.09-1.97 (m, 1H), 1.80-1.68 (m, 2H), 1.68-1.49 (m, 4H). HRMS (ESI) MS m/z calcd for C23H26N7O [M + H]$^+$ 416.2193, found 416.2182. Using N-cyclopentyl-2-(methylsulfonyl)pyrido[3,4-d]pyrimidin-8-amine (Preparation 43) at 170° C. for 4 hours followed by method B. | 0.007 |

Example 40

N-(4-(1,2-dimethyl-1H-imidazol-5-yl)-2-methoxyphenyl)-8-(1-methyl-1H-pyrazol-4-yl)pyrido[3,4-d]pyrimidin-2-amine

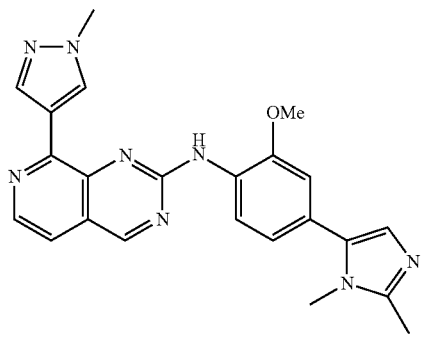 [SMILES: COc1cc(-c2cnc(C)n2C)ccc1Nc1ncc2ccnc(-c3cnn(C)c3)c2n1]

A solution of N-(4-(1,2-dimethyl-1H-imidazol-5-yl)-2-methoxyphenyl)formamide (Preparation 55, 37 mg, 0.151 mmol) in THF (1 mL) was treated with sodium hydride (10 mg, 0.250 mmol) at 0° C. After stirring for 20 minutes at room temperature, the mixture was cooled to 0° C. and 8-(1-methyl-1H-pyrazol-4-yl)-2-(methylsulfonyl)pyrido[3,4-d]pyrimidine (Preparation 35, 50 mg, 0.173 mmol) was added. The reaction was allowed to reach room temperature and stirred for 18 hours. Aqueous NaOH (2M, 0.5 mL) and MeOH (0.5 mL) were added and the resulting mixture stirred at room temperature for 1 hour. The volatiles were removed under reduced pressure and the residue was partitioned between EtOAc and water. The aqueous layer was extracted with EtOAc and the combined organic layers were washed with water, brine, dried and evaporated. The residue was purified by silica gel column chromatography eluting with 0 to 10% MeOH in EtOAc to give the title compound (9 mg, 14%).

$^1$H NMR (500 MHz, DMSO-d$_6$): δ 9.39 (s, 1H), 9.12 (s, 1H), 8.63 (s, 1H), 8.36 (d, J=5.3 Hz, 1H), 8.25 (s, 1H), 7.94 (d, J=8.1 Hz, 1H), 7.59 (d, J=5.2 Hz, 1H), 7.17 (s, 1H), 7.13 (d, J=8.4 Hz, 1H), 6.97 (s, 1H), 3.86 (s, 3H), 3.82 (s, 3H), 3.62 (s, 3H), 2.38 (s, 3H).

HRMS (ESI) MS m/z calcd for C$_{23}$H$_{23}$N$_8$O [M+H]$^+$ 427.1989. found 427.1991.

MPS1 IC50 (μM): 0.004

Example 41

N$^8$-cyclohexyl-N2-(2-methoxy-4-(1-(2-(4-methylpiperazin-1-yl)ethyl)-1H-pyrazol-4-yl)phenyl)pyrido[3,4-d]pyrimidine-2,8-diamine

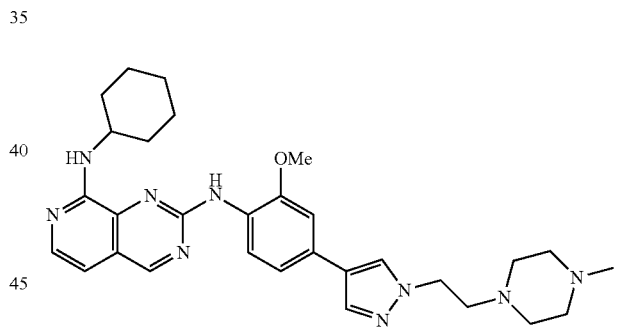

The title compound was prepared according to Example 40 above using N-(2-methoxy-4-(1-(2-(4-methylpiperazin-1-yl)ethyl)-1H-pyrazol-4-yl)phenyl)formamide (Preparation 61) and N-cyclohexyl-2-(methylsulfonyl)pyrido[3,4-d]pyrimidin-8-amine (Preparation 44). The residue was purified by silica gel column chromatography eluting with 0 to 15% MeOH in DCM to give the title compound (51 mg, 48%).

$^1$H NMR (500 MHz, DMSO-d$_6$): δ 9.16 (s, 1H), 8.50 (s, 1H), 8.19 (s, 1H), 8.11 (d, J=8.2 Hz, 1H), 7.90 (s, 1H), 7.77 (d, J=5.7 Hz, 1H), 7.27 (d, J=2.0 Hz, 1H), 7.19 (dd, J=8.3, 1.9 Hz, 1H), 6.85 (d, J=5.6 Hz, 1H), 6.51 (d, J=8.0 Hz, 1H), 4.22 (t, J=6.7 Hz, 2H), 3.99 (br s, 1H), 3.93 (s, 3H), 2.74 (t, J=6.7 Hz, 2H), 2.45 (br s, 4H), 2.34 (br s, 4H), 2.16 (s, 3H), 1.99 (br s, 2H), 1.72 (br s, 2H), 1.60 (s, 1H), 1.45-1.34 (d, 4H), 1.29 (br s, 1H).

HRMS (ESI) MS m/z calcd for C$_{30}$H$_{40}$N$_9$O [M+H]$^+$ 542.3350. found 542.3320.

MPS1 IC50 (μM): 0.003

Example 42

N8-cyclohexyl-N2-(4-(1-(2-(dimethylamino)ethyl)-1H-pyrazol-4-yl)-2-methoxyphenyl)pyrido[3,4-d]pyrimidine-2,8-diamine

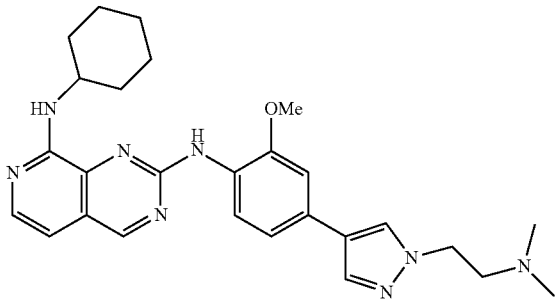 [SMILES: COc1cc(-c2cnn(CCN(C)C)c2)ccc1Nc1ncc2ccnc(NC3CCCCC3)c2n1]

The title compound was prepared according to Example 40 using N-(4-(1-(2-(dimethylamino)ethyl)-1H-pyrazol-4-yl)-2-methoxyphenyl)formamide (Preparation 64) and N-cyclohexyl-2-(methylsulfonyl)pyrido[3,4-d]pyrimidin-8-amine (Preparation 44). The residue was purified by silica gel column chromatography eluting with 0 to 10% MeOH in DCM to give the title compound (26 mg, 25%).

$^1$H NMR (500 MHz, DMSO-d$_6$): δ 9.17 (s, 1H), 8.51 (s, 1H), 8.21 (d, J=0.9 Hz, 1H), 8.12 (d, J=8.2 Hz, 1H), 7.91 (d, J=0.8 Hz, 1H), 7.78 (d, J=5.7 Hz, 1H), 7.28 (d, J=1.9 Hz, 1H), 7.21 (dd, J=8.2, 1.9 Hz, 1H), 6.86 (d, J=5.7 Hz, 1H), 6.52 (d, J=8.1 Hz, 1H), 4.22 (t, J=6.6 Hz, 2H), 4.05-3.96 (m, 1H), 3.94 (s, 3H), 2.70 (t, J=6.5 Hz, 2H), 2.20 (s, 6H), 2.07-1.96 (m, 2H), 1.78-1.69 (m, 2H), 1.62 (br d, J=12.3 Hz, 1H), 1.48-1.34 (m, 4H), 1.34-1.23 (m, 1H).

HRMS (ESI) MS m/z calcd for C$_{27}$H$_{36}$N$_8$O [M+H]$^+$ 487.2928. found 487.2921.

MPS1 IC50 (μM): 0.003

Example 43

2-(4-(4-((8-(cyclohexylamino)pyrido[3,4-d]pyrimidin-2-yl)amino)-3-methoxyphenyl)-1H-pyrazol-1-yl)ethanol

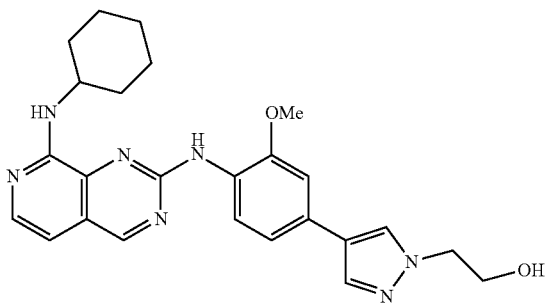 [SMILES: COc1cc(-c2cnn(CCO)c2)ccc1Nc1ncc2ccnc(NC3CCCCC3)c2n1]

A solution of N-(4-(1-(2-(tert-butyldiphenylsilyloxy)ethyl)-1H-pyrazol-4-yl)-2-methoxyphenyl)formamide (Preparation 67, 124 mg, 0.248 mmol) in THF (1.5 mL) was treated with sodium hydride (14 mg, 0.350 mmol) at 0° C. After stirring for 25 minutes at room temperature, the mixture was cooled to 0° C. and N-cyclohexyl-2-(methylsulfonyl)pyrido[3,4-d]pyrimidin-8-amine (Preparation 44, 79 mg, 0.258 mmol) was added. The reaction was allowed to reach room temperature and stirred for 18 hours. Aqueous NaOH (2M, 1 mL) and MeOH (1 mL) were added and the resulting mixture stirred for 1 hour. The volatiles were removed under reduced pressure and the residue was partitioned between EtOAc and water. The aqueous layer was extracted with EtOAc and the combined organic layers were washed with water, brine, dried and evaporated. The residue was purified by silica gel column chromatography eluting with 0 to 30% EtOAc in cyclohexane to give the silyl ether (53 mg, 31%).

A solution of silyl ether (30 mg, 0.043 mmol) in THF (0.4 mL) was treated with TBAF (1M in THF, 100 μl, 0.100 mmol) at room temperature for 2 hours. The volatiles were removed under reduced pressure and the residue was adsorbed on silica. The residue was purified by silica gel column chromatography eluting with 0 to 100% EtOAc in cyclohexane to give the title compound (12 mg, 60%).

$^1$H NMR (500 MHz, DMSO-d$_6$): δ 9.17 (s, 1H), 8.50 (s, 1H), 8.18 (s, 1H), 8.12 (d, J=8.2 Hz, 1H), 7.92 (s, 1H), 7.78 (d, J=5.6 Hz, 1H), 7.29 (d, J=1.9 Hz, 1H), 7.22 (dd, J=8.2, 1.9 Hz, 1H), 6.86 (d, J=5.7 Hz, 1H), 6.52 (d, J=8.2 Hz, 1H), 4.95 (t, J=5.2 Hz, 1H), 4.17 (t, J=5.7 Hz, 2H), 4.07-3.96 (m, 1H), 3.83-3.76 (m, 2H), 2.05-1.96 (m, 2H), 1.79-1.69 (m, 2H), 1.62 (br d, J=12.6 Hz, 1H), 1.45-1.33 (m, 4H), 1.30-1.22 (m, 1H).

HRMS (ESI) MS m/z calcd for C$_{26}$H$_{30}$N$_7$O$_2$ [M+H]$^+$ 460.2455. found 460.2454.

MPS1 IC50 (μM): 0.014

Example 44

2-(4-(3-methoxy-4-((8-((tetrahydro-2H-pyran-4-yl)amino)pyrido[3,4-d]pyrimidin-2-yl)amino)phenyl)-1H-pyrazol-1-yl)ethanol

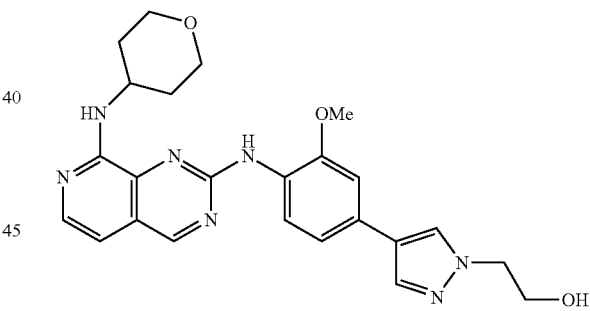

The title compound was prepared according to Example 43 using N-(4-(1-(2-(tert-butyldiphenylsilyloxy)ethyl)-1H-pyrazol-4-yl)-2-methoxyphenyl)formamide (Preparation 67) and 2-(methylsulfonyl)-N-(tetrahydro-2H-pyran-4-yl)pyrido[3,4-d]pyrimidin-8-amine (Preparation 45). The intermediate silyl ether was purified using silica gel column chromatography eluting with 0 to 55% EtOAc in cyclohexane and the title compound was purified using silica gel column chromatography eluting with 0 to 5% MeOH in EtOAc (6 mg, 85%).

$^1$H NMR (500 MHz, CDCl$_3$): δ 9.00 (s, 1H), 8.51 (d, J=8.3 Hz, 1H), 7.98 (s, 1H), 7.89 (d, J=5.7 Hz, 1H), 7.84 (s, 1H), 7.74 (s, 1H), 7.19 (dd, J=8.3, 1.8 Hz, 1H), 7.06 (d, J=1.9 Hz, 1H), 6.79 (d, J=5.7 Hz, 1H), 6.40 (br s, 1H), 4.42-4.30 (m, 3H), 4.12-4.04 (m, 4H), 4.02 (s, 3H), 3.73-3.62 (m, 2H), 3.05 (br s, 1H), 2.20 (br d, J=12.6 Hz, 2H), 1.80-1.66 (m, 2H).

HRMS (ESI) MS m/z calcd for C$_{24}$H$_{28}$N$_7$O$_3$ [M+H]$^+$ 462.2248. found 462.2239.

MPS1 IC50 (μM): 0.003

Example 45

N²-(2-methoxy-6-morpholinopyridin-3-yl)-N8-neopentylpyrido[3,4-d]pyrimidine-2,8-diamine

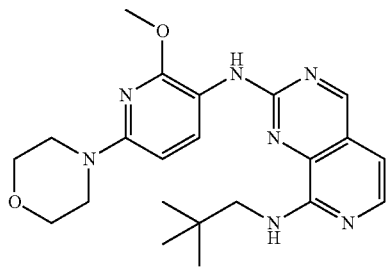 [SMILES: COc1nc(N2CCOCC2)ccc1Nc1ncc2ccnc(NCC(C)(C)C)c2n1]

The title compound was prepared according to Example 40 using N-(2-methoxy-6-morpholinopyridin-3-yl)formamide (Preparation 71) and 2-(methylsulfonyl)-N-neopentylpyrido[3,4-d]pyrimidin-8-amine (Preparation 47). The residue was purified by silica gel column chromatography eluting with 0-5% MeOH EtOAc followed by a second chromatography eluting with 50-100% EtOAc in cyclohexane. The residue was dissolved in EtOAc and washed with HCl (0.5 M, 10 mL), dried (MgSO₄) and concentrated in vacuo. The residue was further purified by passage through a SCX-2 cartridge eluting with 100% MeOH—1 M NH₃ in MeOH, to afford the title compound (10 mg, 14%).

¹H NMR (500 MHz, CDCl₃): δ 8.93 (s, 1H), 8.52 (d, J=8.5 Hz, 1H), 7.85 (d, J=6.0 Hz, 1H), 7.48 (br s, 1H), 6.72 (d, J=6.0 Hz, 1H), 6.53 (br s, 1H), 6.22 (d, J=8.5 Hz, 1H), 4.01 (s, 3H), 3.88 (app t, J=5.0 Hz, 4H), 3.46 (t, J=5.0 Hz, 4H), 3.44 (d, J=6.0 Hz, 2H), 1.10 (s, 9H).

HRMS (ESI) MS m/z calcd for $C_{22}H_{29}N_7O_2$ [M+H]⁺ 424.2455. found 424.2446; LCMS (ESI) Rt=2.18 minutes MS m/z 424.07 [M+H]⁺.

MPS1 IC50 (μM): 0.013

Example 46

N2-(2-methoxy-6-(methylsulfonyl)pyridin-3-yl)-N8-neopentylpyrido[3,4-d]pyrimidine-2,8-diamine

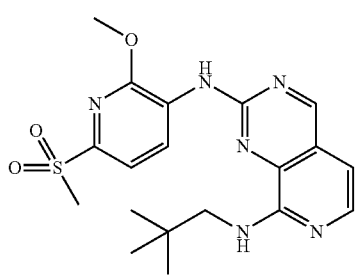 [SMILES: COc1nc(S(C)(=O)=O)ccc1Nc1ncc2ccnc(NCC(C)(C)C)c2n1]

The title compound was prepared according to Example 40 using N-(2-methoxy-6-(methylsulfonyl)pyridin-3-yl)formamide (Preparation 73) and 2-(methylsulfonyl)-N-neopentylpyrido[3,4-d]pyrimidin-8-amine (Preparation 47). The residue was purified by silica gel column chromatography eluting with 50-100% EtOAc in cyclohexane. The residue was dissolved in EtOAc and washed with HCl (0.5 M, 10 mL), dried (MgSO₄) and concentrated in vacuo. The residue was triturated with DCM and dried under vacuum to give the title compound (3 mg, 6%).

¹H NMR (500 MHz, CDCl₃): δ 9.09 (s, 1H), 9.01 (d, J=8.0 Hz, 1H), 8.14 (br s, 1H), 7.99 (d, J=5.5 Hz, 1H), 7.79 (d, J=8.0 Hz, 1H), 6.81 (d, J=5.5 Hz, 1H), 6.48 (br t, J=6.5 Hz, 1H), 4.20 (s, 3H), 3.49 (d, J=6.5 Hz, 2H), 3.23 (s, 3H), 1.12 (s, 9H).

HRMS (ESI) MS m/z calcd for $C_{19}H_{24}N_6O_3S$ [M+H]⁺ 417.1703. found 417.1699; LCMS (ESI) Rt=2.02 minutes MS m/z 416.99 [M+H]⁺.

MPS1 IC50 (μM): 0.017

Example 47

N2-(2-methoxy-4-(1-methyl-1H-imidazol-5-yl)phenyl)-N8-neopentylpyrido[3,4-d]pyrimidine-2,8-diamine

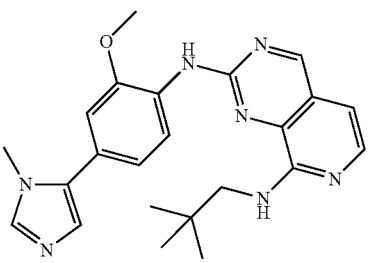 [SMILES: COc1cc(-c2cncn2C)ccc1Nc1ncc2ccnc(NCC(C)(C)C)c2n1]

The title compound was prepared according to Example 40 using N-(2-methoxy-4-(1-methyl-1H-imidazol-5-yl)phenyl)formamide (Preparation 74) and 2-(methylsulfonyl)-N-neopentylpyrido[3,4-d]pyrimidin-8-amine (Preparation 47). The residue was purified by silica gel column chromatography eluting with 0-20% MeOH in EtOAc followed by a second chromatography eluting with 0-10% MeOH in EtOAc to give the title compound (7.5 mg, 38%).

¹H NMR (500 MHz, CDCl₃): δ 9.01 (s, 1H), 8.68 (d, J=8 Hz, 1H), 8.06 (s, 1H), 7.91 (d, J=6.0 Hz, 1H), 7.68 (s, 1H), 7.15 (s, 1H), 7.03 (dd, J=8.0, 1.5 Hz, 1H), 6.97 (d, J=1.5 Hz, 1H), 6.76 (d, J=6.0 Hz, 1H), 6.63 (br t, J=6.5 Hz, 1H), 4.00 (s, 3H), 3.72 (s, 3H), 3.49 (d, J=6.5 Hz, 2H), 1.12 (s, 9H).

HRMS (ESI) MS m/z calcd for $C_{23}H_{27}N_7O$ [M+H]⁺ 418.2360. found 418.2341; LCMS (ESI) Rt=1.45 minutes MS m/z 418.12 [M+H]+.

MPS1 IC50 (μM): 0.002

Example 48

N2-(4-(1,3-dimethyl-1H-pyrazol-4-yl)-2-methoxyphenyl)-N8-neopentylpyrido[3,4-d]pyrimidine-2,8-diamine

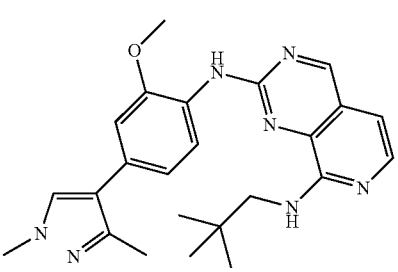 [SMILES: CN/C=C(\C(C)=N)c1ccc(Nc2ncc3ccnc(NCC(C)(C)C)c3n2)c(OC)c1]

The title compound was prepared according to Example 40 using N-(4-(1,3-dimethyl-1H-pyrazol-4-yl)-2-methoxyphenyl)formamide (Preparation 76) and 2-(methylsulfonyl)-N-neopentylpyrido[3,4-d]pyrimidin-8-amine (Preparation 47). The residue was purified by silica gel column chromatography eluting with 50-100% EtOAc in cyclohexane to give the title compound (4 mg, 21%).

$^1$H NMR (500 MHz, CDCl$_3$): δ 8.98 (s, 1H), 8.60 (d, J=8.5 Hz, 1H), 7.97 (br s, 1H), 7.89 (d, J=6.0 Hz, 1H), 7.45 (s, 1H), 7.03 (dd, J=8.5, 2.0 Hz, 1H), 6.97 (d, J=2.0 Hz, 1H), 6.74 (d, J=6.0 Hz, 1H), 6.63 (br t, J=6.5 Hz, 1H), 3.99 (s, 3H), 3.91 (s, 3H), 3.47 (d, J=6.5 Hz, 2H), 2.43 (s, 3H), 1.12 (s, 9H).

HRMS (ESI) MS m/z calcd for C$_{24}$H$_{23}$N$_7$O [M+H]$^+$ 432.2506. found 432.2502; LCMS (ESI) Rt=2.37 minutes MS m/z 432.09 [M+H]$^+$.

MPS1 IC50 (μM): 0.005

Example 49

N2-(4-(1,5-dimethyl-1H-pyrazol-4-yl)-2-methoxyphenyl)-N8-neopentylpyrido[3,4-d]pyrimidine-2,8-diamine

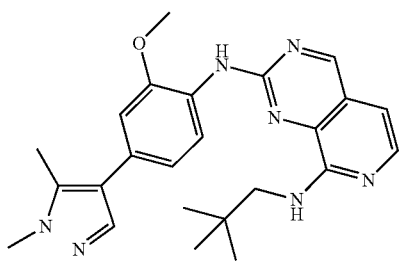 [SMILES: CN/C(C)=C(\C=N)c1ccc(Nc2ncc3ccnc(NCC(C)(C)C)c3n2)c(OC)c1]

The title compound was prepared according to Example 40 using N-(4-(1,5-dimethy-1H-pyrazol-4-yl)-2-methoxyphenyl)formamide (Preparation 77) and 2-(methylsulfonyl)-N-neopentylpyrido[3,4-d]pyrimidin-8-amine (Preparation 47). The residue was purified by silica gel column chromatography eluting with 50-100% EtOAc in cyclohexane followed by a second chromatography eluting with, 50-90% EtOAc in cyclohexane. The residue was passed through a SCX-2 cartridge eluting with 100% MeOH-1M NH$_3$ in MeOH to give the title compound (5 mg, 8%).

$^1$H NMR (500 MHz, CDCl$_3$): δ 9.02 (s, 1H), 8.51 (br s, 1H), 8.05 (m, 1H), 7.84 (m, 1H), 7.58 (s, 1H), 6.99 (dd, J=8.0, 1.5 Hz, 1H), 6.96 (d, J=1.5 Hz, 1H), 6.80 (br s, 1H), 3.99 (s, 3H), 3.88 (s, 3H), 3.64 (br s, 2H), 2.42 (s, 3H), 1.14 (s, 9H).

HRMS (ESI) MS m/z calcd for C$_{24}$H$_{29}$N$_7$O [M+H]$^+$ 432.2506. found 432.2504; LCMS (ESI) Rt=2.33 minutes MS m/z 432.10 [M+H]$^+$.

MPS1 IC50 (μM): 0.005

Example 50

N2-(4-(1,2-dimethyl-1H-imidazol-5-yl)-2-methoxyphenyl)-N8-neopentylpyrido[3,4-d]pyrimidine-2,8-diamine

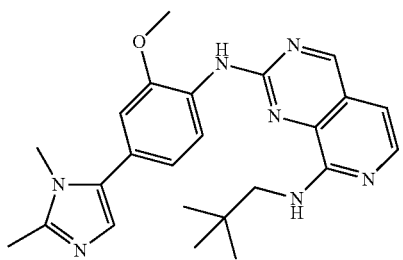 [SMILES: COc1cc(-c2cnc(C)n2C)ccc1Nc1ncc2ccnc(NCC(C)(C)C)c2n1]

The title compound was prepared according to Example 40 using N-(4-(1,2-dimethyl-1H-imidazol-5-yl)-2-methoxyphenyl)formamide (Preparation 55) and 2-(methylsulfonyl)-N-neopentylpyrido[3,4-d]pyrimidin-8-amine (Preparation 47). The residue was purified by silica gel column chromatography eluting with 0-10% MeOH in EtOAc. The residue was purified by passage through a SCX-2 cartridge eluting with 100% MeOH-1M NH$_3$ in MeOH. The residue was diluted with DCM (30 mL) and washed with 0.1M HCl (30 mL), dried (MgSO$_4$) and concentrated in vacuo. The residue was further purified by SCX-2 cartridge eluting with 100% MeOH-1M NH$_3$ in MeOH followed by silica gel column chromatography eluting with 0-7% MeOH in EtOAc to give the title compound (5.5 mg, 21%).

$^1$H NMR (500 MHz, CDCl$_3$): δ 9.04 (s, 1H), 8.76 (d, J=8.0 Hz, 1H), 8.12 (s, 1H), 7.94 (d, J=6.0 Hz, 1H), 7.21 (s, 1H), 6.99 (dd, J=8.0, 2.0 Hz, 1H), 6.91 (d, J=2.0 Hz, 1H), 6.79 (d, J=6.0 Hz, 1H), 6.58 (br s, 1H), 4.02 (s, 3H), 3.67 (s, 3H), 3.50 (d, J=6.0 Hz, 2H), 2.82 (s, 3H), 1.12 (s, 9H).

HRMS (ESI) MS m/z calcd for C$_{24}$H$_{29}$N$_7$O [M+H]$^+$ 432.2506. found 432.2504; LCMS (ESI) Rt=1.49 minutes MS m/z 432.37 [M+H]$^+$.

MPS1 IC50 (μM): 0.007

Example 51

N$^2$-(2-methoxy-4-(1-methyl-1H-pyrazol-4-yl)phenyl)-6-methyl-N8-neopentylpyrido[3,4-d]pyrimidine-2,8-diamine

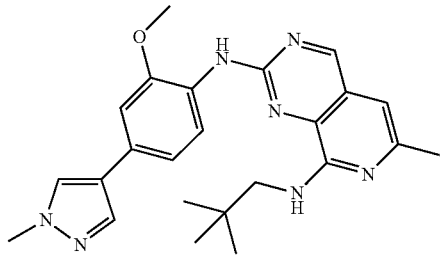

To a cooled (0° C.) suspension of N-(2-methoxy-4-(1-methyl-1H-pyrazol-4-yl)phenyl)formamide (Preparation 56, 8.5 mg, 0.037 mmol) in THF (1 mL) was added NaH (60% dispersion in oil, 2.4 mg, 0.059 mmol). The reaction mixture was stirred at room temperature for 10 minutes. The reaction mixture was cooled to 0° C. and 6-methyl-2-(methysulfonyl)-N-neopentylpyrido[3,4-d]pyrimidin-8-amine (Preparation 54, 12.5 mg, 0.040 mmol) in THF (1 mL) was added. The reaction mixture was stirred for 5 hours, whilst slowly warming to room temperature. The reaction mixture was concentrated in vacuo. The residue was partitioned between EtOAc (30 mL) and water (30 mL). The aqueous layer was re-extracted with EtOAc and DCM (25 mL). The combined organic layers were washed with water (25 mL) and brine (25 mL), dried (MgSO$_4$) and concentrated in vacuo. The residue was purified by silica gel column chromatography eluting with 50-100% EtOAc in cyclohexane. The residue was purified by passage through a SCX-2 cartridge eluting with 100% MeOH-1M NH$_3$ in MeOH to give the title compound (5.0 mg, 32%).

$^1$H NMR (500 MHz, MeOD): δ 8.98 (s, 1H), 8.42 (d, J=8.5 Hz, 1H), 7.97 (s, 1H), 7.83 (s, 1H), 7.23 (d, J=2.0 Hz, 1H), 7.15 (dd, J=8.5, 2.0 Hz, 1H), 6.68 (s, 1H), 4.02 (s, 3H), 3.95 (s, 3H), 3.44 (s, 2H), 2.43 (s, 3H), 1.10 (s, 9H).

HRMS (ESI) MS m/z calcd for $C_{24}H_{29}N_7O$ [M+H]$^+$ 432.2506. found 432.2505; LCMS (ESI) Rt=2.32 minutes MS m/z 432.36 [M+H]$^+$.

MPS1 IC50 (μM): 0.029

Example 52

N2-(2-methoxy-4-morpholinophenyl)-N8-neopentyprido[3,4-d]pyrimidine-2,8-diamine

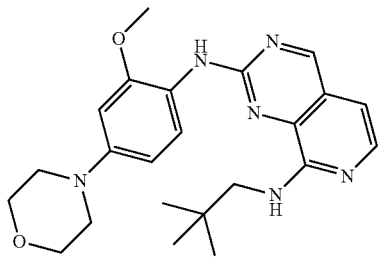 [SMILES: COc1cc(N2CCOCC2)ccc1Nc1ncc2ccnc(NCC(C)(C)C)c2n1]

The title compound was prepared according to Example 40 using N-(2-methoxy-4-morpholinophenyl)formamide (Preparation 80) and 2-(methylsulfonyl)-N-neopentylpyrido[3,4-d]pyrimidin-8-amine (Preparation 47). The residue was purified by silica gel column chromatography eluting with 50-100% EtOAc in hexane to give the title compound (55.5 mg, 77%).

$^1$H NMR (500 MHz, MeOD): δ 9.01 (s, 1H), 8.11 (d, J=9.0 Hz, 1H), 7.66 (d, J=6.0 Hz, 1H), 6.81 (d, J=6.0 Hz, 1H), 6.73 (d, J=2.5 Hz, 1H), 6.58 (dd, J=9.0, 2.5 Hz, 1H), 3.93 (s, 3H), 3.88-3.86 (m, 4H), 3.37 (s, 2H), 3.17-3.15 (m, 4H), 1.06 (s, 9H).

HRMS (ESI) MS m/z calcd for $C_{23}H_{30}N_6O_2$ [M+H]$^+$ 423.2503. found 423.2498; LCMS (ESI) Rt=2.07 minutes MS m/z 423.36 [M+H]$^+$.

MPS1 IC50 (μM): 0.008

Example 53

8-(cyclopropylmethoxy)-N-(2-methoxy-4-(1-methyl-1H-pyrazol-4-yl)phenyl)pyrido[3,4-d]pyrimidin-2-amine

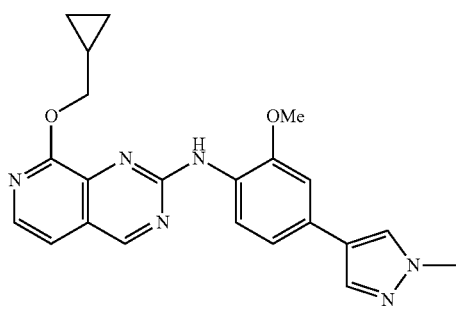 [SMILES: COc1cc(-c2cnn(C)c2)ccc1Nc1ncc2ccnc(OCC3CC3)c2n1]

The title compound was prepared according to Example 40 using N-(2-methoxy-4-(1-methyl-1H-pyrazol-4-yl)phenyl)formamide (Preparation 56) and 8-(cyclopropylmethoxy)-2-(methylsulfonyl)pyrido[3,4-d]pyrimidine (Preparation 69). The residue was purified by silica gel column chromatography eluting with 0 to 75% EtOAc in cyclohexane to give the title compound (27 mg, 52%).

$^1$H NMR (500 MHz, DMSO): δ 9.31 (s, 1H), 8.61 (s, 1H), 8.39 (s, 1H), 8.17 (d, J=0.8 Hz, 1H), 7.94-7.84 (m, 2H), 7.35 (d, J=5.6 Hz, 1H), 7.28 (d, J=1.8 Hz, 1H), 7.19 (dd, J=8.3, 1.8 Hz, 1H), 4.33 (d, J=6.9 Hz, 2H), 3.94 (s, 3H), 3.88 (s, 3H), 1.45-1.33 (m, 1H), 0.68-0.59 (m, 2H), 0.49-0.39 (m, 2H).

HRMS (ESI) MS m/z calcd for $C_{22}H_{23}N_6O_2$ [M+H]$^+$ 403.1877. found 403.1871.

MPS1 IC50 (μM): 0.098

Example 54

N-(2-methoxy-4-(1-methyl-1H-pyrazol-4-yl)phenyl)-8-(piperidin-1-yl)pyrido[3,4-d]pyrimidin-2-amine

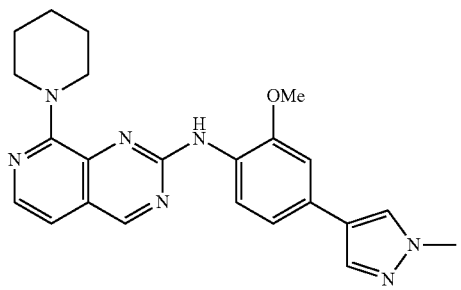 [SMILES: COc1cc(-c2cnn(C)c2)ccc1Nc1ncc2ccnc(N3CCCCC3)c2n1]

Method 5

A mixture of 8-chloro-N-(2-methoxy-4-(1-methyl-1H-pyrazol-4-yl)phenyl)pyrido[3,4-d]pyrimidin-2-amine (Example 94, 27 mg, 0.074 mmol) and piperidine (100 μL, 1.010 mmol) in N-methyl-2-pyrrolidinone (0.7 mL) was stirred at 120° C. for 2 hours in a closed cap vial. The reaction was quenched with saturated aqueous NaHCO$_3$ and extracted with EtOAc. The combined organic layers were washed with water and brine, dried and concentrated. The residue was purified by silica gel column chromatography eluting with 0 to 80% EtOAc in cyclohexane to give the title compound (24 mg, 77%).

$^1$H NMR (500 MHz, DMSO-d$_6$): δ 9.25 (s, 1H), 8.44 (s, 1H), 8.25 (d, J=8.2 Hz, 1H), 8.18 (d, J=0.9 Hz, 1H), 7.97 (d, J=5.3 Hz, 1H), 7.91 (d, J=0.8 Hz, 1H), 7.28 (d, J=1.8 Hz, 1H), 7.20 (dd, J=8.2, 1.8 Hz, 1H), 7.16 (d, J=5.3 Hz, 1H), 3.93 (s, 3H), 3.88 (s, 3H), 3.77-3.69 (m, 4H), 1.76-1.57 (m, 6H).

HRMS (ESI) MS/z calcd for $C_{23}H_{26}N_7O$ [M+H]$^+$ 416.2193. found 416.2190.

MPS1 IC50 (μM):—no data

The following Examples were prepared according to Method 5 (Example 54) above using 8-chloro-N-(2-methoxy-4-(1-methyl-1H-pyrazol-4-yl)phenyl)pyrido[3,4-d]pyrimidin-2-amine (Example 94) and the appropriate amine as described. Where the amine hydrochloride was used, triethylamine (190 uL, 0.373 mmol) was also added to the reaction. The crude reaction residues were purified as above or according to one of the following methods:

Method A: Silica gel column chromatography eluting with 0-5% or 0-10% MeOH in DCM.

Method B: Silica gel column chromatography eluting with 0-5% MeOH in EtOAc.

Method C: Silica gel column chromatography eluting with 0-70% EtOAc in cyclohexane followed by reverse phase preparative HPLC eluting with 10-90% MeOH in water (0.1% formic acid).

| Example No | Name/Structure | Data | MPS1 IC50 (μM) |
|---|---|---|---|
| 55 | N8-cyclohexyl-N2-(2-methoxy-4-(1-methyl-1H-pyrazol-4-yl)phenyl)pyrido[3,4-d]pyrimidine-2,8-diamine | $^1$H NMR (500 MHz, DMSO-d$_6$): δ 9.16 (s, 1H), 8.51 (s, 1H), 8.17 (s, 1H), 8.11 (d, J = 8.3 Hz, 1H), 7.90 (d, J = 0.9 Hz, 1H), 7.78 (d, J = 5.7 Hz, 1H), 7.28 (d, J = 1.9 Hz, 1H), 7.21 (dd, J = 8.2, 1.9 Hz, 1H), 6.86 (d, J = 5.7 Hz, 1H), 6.52 (d, J = 8.1 Hz, 1H), 3.99 (br s, 1H), 3.93 (s, 3H), 3.88 (s, 3H), 2.04-1.94 (m, 2H), 1.79-1.69 (m, 2H), 1.65-1.59 (m, 1H), 1.45-1.34 (m, 4H), 1.33-1.23 (m, 1H). HRMS (ESI) MS m/z calcd for C$_{24}$H$_{28}$N$_7$O [M + H]$^+$ 430.2350, found 430.2347. Using cyclohexylamine at 130° C. for 6 hours. | 0.009 |
| 56 | N-(2-methoxy-4-(1-methyl-1H-pyrazol-4-yl)phenyl)-8-(3-methylpyrrolidin-1-yl)pyrido[3,4-d]pyrimidin-2-amine | $^1$H NMR (500 MHz, DMSO-d$_6$): δ 9.12 (s, 1H), 8.44 (s, 1H), 8.15 (d, J = 0.5 Hz, 1H), 7.88 (d, J = 0.8 Hz, 1H), 7.81 (d, J = 5.4 Hz, 1H), 7.78 (d, J = 8.2 Hz, 1H), 7.25 (d, J = 1.9 Hz, 1H), 7.16 (dd, J = 8.1, 1.8 Hz, 1H), 6.85 (d, J = 5.4 Hz, 1H), 4.15-4.00 (m, 1H), 3.88 (s, 3H), 3.89-3.83 (m, 4H), 3.71 (q, J = 10.9, 9.6 Hz, 1H), 3.37-3.30 (m, 1H), 2.26-2.15 (m, 1H), 2.05-1.94 (m, 1H), 1.54-1.38 (m, 1H), 1.03 (d, J = 6.6 Hz, 3H). HRMS (ESI) MS m/z calcd for C$_{23}$H$_{26}$N$_7$O [M + H]$^+$ 416.2193, found 416.2201. Using 3-methylpyrrolidine hydrochloride | 0.010 |
| 57 | 8-(3,3-difluoropyrroldin-1-yl)-N-(2-methoxy-4-(1-methyl-1H-pyrazol-4-yl)phenyl)pyrido[3,4-d]pyrimidin-2-amine | $^1$H NMR (500 MHz, DMSO-d$_6$): δ 9.19 (s, 1H), 8.71 (s, 1H), 8.15 (d, J = 1.0 Hz, 1H), 7.92-7.85 (m, 2H), 7.67 (d, J = 8.1 Hz, 1H), 7.26 (d, J = 1.9 Hz, 1H), 7.16 (dd, J = 8.2, 1.8 Hz, 1H), 7.03 (d, J = 5.5 Hz, 1H), 4.23 (t, J = 13.7 Hz, 2H), 3.95 (t, J = 7.3 Hz, 2H), 3.88 (s, 3H), 3.87 (s, 3H), 2.43 (tt, J = 14.3, 7.4 Hz, 2H). $^{19}$F NMR (471 MHz, DMSO-d$_6$): δ −100.17 (s). HRMS (ESI) MS m/z calcd for C$_{22}$H$_{22}$F$_2$N$_7$O [M + H]$^+$ 438.1848, found 438.1839. Using 3,3-difluoropyrrolidine hydrochloride for 5 hours. | 0.012 |
| 58 | N8-(cyclopropylmethyl)-N2-(2-methoxy-4-(1-methyl-1H-pyrazol-4-yl)phenyl)pyrido[3,4-d]pyrimidine-2,8-diamine | $^1$H NMR (500 MHz, DMSO-d$_6$): δ 9.17 (s, 1H), 8.43 (s, 1H), 8.20 (d, J = 8.2 Hz, 1H), 8.15 (s, 1H), 7.88 (d, J = 0.8 Hz, 1H), 7.77 (d, J = 5.6 Hz, 1H), 7.27 (d, J = 1.9 Hz, 1H), 7.21 (dd, J = 8.3, 1.8 Hz, 1H), 6.90 (t, J = 5.7 Hz, 1H), 6.85 (d, J = 5.7 Hz, 1H), 3.93 (s, 3H), 3.87 (s, 3H), 3.41-3.35 (m, 2H), 1.26-1.14 (m, 1H), 0.54-0.43 (m, 2H), 0.35-0.26 (m, 2H). HRMS (ESI) MS m/z calcd for C$_{22}$H$_{24}$N$_7$O [M + H]$^+$ 402.2037, found 402.2030 Using cyclopropylmethanamine at 130° C. for 7 hours | 0.006 |

-continued

| Example No | Name/Structure | Data | MPS1 IC50 (μM) |
|---|---|---|---|
| 59 | N8-cyclopentyl-N2-(2-methoxy-4-(1-methyl-1H-pyrazol-4-yl)phenyl)-N8-methylpyrido[3,4-d]pyrimidine-2,8-diamine | $^1$H NMR (500 MHz, DMSO-d$_6$): δ 9.18 (s, 1H), 8.49 (s, 1H), 8.16 (s, 1H), 7.92-7.85 (m, 3H), 7.26 (d, J = 1.9 Hz, 1H), 7.17 (dd, J = 8.0, 1.9 Hz, 1H), 7.02 (d, J = 5.3 Hz, 1H), 5.47-5.36 (m, 1H), 3.88 (s, 3H), 3.87 (s, 3H), 3.00 (s, 3H), 1.73-1.64 (m, 2H), 1.62-1.55 (m, 4H), 1.46-1.37 (m, 2H). HRMS (ESI) MS m/z calcd for C$_{24}$H$_{28}$N$_7$O [M + H]$^+$ 430.2350, found 430.2360 Using N-methylcyclopentanamine at 130° C. for 12 hours. | 0.045 |
| 60 | N8-isopentyl-N2-(2-methoxy-4-(1-methyl-1H-pyrazol-4-yl)phenyl)pyrido[3,4-d]pyrimidine-2,8-diamine | $^1$H NMR (500 MHz, DMSO-d$_6$): δ 9.17 (s, 1H), 8.40 (s, 1H), 8.23 (d, J = 8.3 Hz, 1H), 8.15 (d, J = 0.8 Hz, 1H), 7.89 (d, J = 0.8 Hz, 1H), 7.79 (d, J = 5.6 Hz, 1H), 7.27 (d, J = 1.9 Hz, 1H), 7.20 (dd, J = 8.2, 1.9 Hz, 1H), 6.89-6.79 (m, 2H), 3.94 (s, 3H), 3.88 (s, 3H), 3.54 (ddd, J = 8.4, 7.2, 5.9 Hz, 2H), 1.74-1.64 (m, 1H), 1.58-1.50 (m, 2H), 0.95 (d, J = 6.6 Hz, 6H). HRMS (ESI) MS m/z calcd for C$_{23}$H$_{28}$N$_7$O [M + H]$^+$ 418.2350, found 418.2355. Using 3-methylbutan-1-amine for 3 hours. | 0.021 |
| 61 | N-(2-methoxy-4-(1-methyl-1H-pyrazol-4-yl)phenyl)-8-morpholinopyrido[3,4-d]pyrimidin-2-amine | $^1$H NMR (500 MHz, DMSO-d$_6$): δ 9.27 (s, 1H), 8.59 (s, 1H), 8.20 (s, 1H), 8.04 (d, J = 8.2 Hz, 1H), 7.98 (d, J = 5.4 Hz, 1H), 7.93 (d, J = 0.9 Hz, 1H), 7.28 (d, J = 1.8 Hz, 1H), 7.25-7.20 (m, 2H), 3.91 (s, 3H), 3.88 (s, 3H), 3.79-3.67 (m, 8H). HRMS (ESI) MS m/z calcd for C$_{22}$H$_{24}$N$_7$O$_2$ [M + H]$^+$ 418.1986, found 418.1983. Using morpholine for 3 hours. | 0.003 |
| 62 | N-(2-methoxy-4-(1-methyl-1H-pyrazol-4-yl)phenyl)-8-(4-methylpiperazin-1-yl)pyrido[3,4-d]pyrimidin-2-amine | $^1$H NMR (500 MHz, DMSO-d$_6$): δ 9.26 (s, 1H), 8.53 (s, 1H), 8.17 (s, 1H), 8.11 (d, J = 8.2 Hz, 1H), 7.96 (d, J = 5.4 Hz, 1H), 7.91 (s, 1H), 7.28 (d, J = 2.0 Hz, 1H), 7.23-7.14 (m, 2H), 3.92 (s, 3H), 3.89 (s, 3H), 3.77 (br s, 4H), 2.50 (br s, 4H), 2.26 (s, 3H). HRMS (ESI) MS m/z calcd for C$_{23}$H$_{27}$N$_8$O [M + H]$^+$ 431.2302, found 431.2295 Using 1-methylpiperazine at 130° C. for 6 hours and purified using method A. | 0.009 |

| Example No | Name/Structure | Data | MPS1 IC50 (μM) |
|---|---|---|---|
| 63 | 8-(3,3-difluoroazetidin-1-yl)-N-(2-methoxy-4-(1-methyl-1H-pyrazol-4-yl)phenyl)pyrido[3,4-d]pyrimidin-2-amine 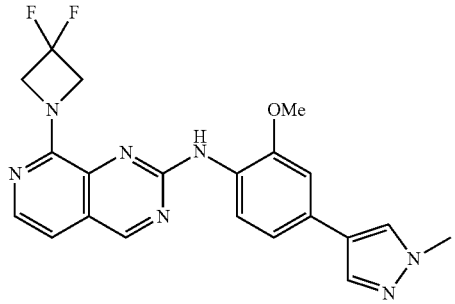 [SMILES: COc1cc(-c2cnn(C)c2)ccc1Nc1ncc2ccnc(N3CC(F)(F)C3)c2n1] | $^1$H NMR (500 MHz, DMSO-d$_6$): δ 9.25 (s, 1H), 8.68 (s, 1H), 8.19 (d, J = 0.9 Hz, 1H), 7.92 (s, 1H), 7.90 (d, J = 5.5 Hz, 1H), 7.80 (d, J = 8.2 Hz, 1H), 7.29 (d, J = 1.9 Hz, 1H), 7.22 (dd, J = 8.1, 1.9 Hz, 1H), 7.14 (d, J = 5.5 Hz, 1H), 4.68-4.57 (m, 4H), 3.89 (s, 3H), 3.88 (s, 3H).<br>$^{19}$F NMR (471 MHz, DMSO-d$_6$): δ −99.23 (s).<br>HRMS (ESI) MS m/z calcd for C$_{21}$H$_{20}$F$_2$N$_7$O [M + H]$^+$ 424.1692, found 424.1681.<br>Using 3,3-difluoroazetidine hydrochloride at 130° C. for 4 hours. | 0.025 |
| 64 | N-(2-methoxy-4-(1-methyl-1H-pyrazol-4-yl)phenyl)-8-(2-methylpyrroldin-1-yl)pyrido[3,4-d]pyrimidin-2-amine 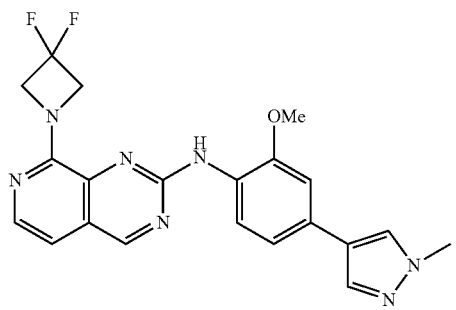 | $^1$H NMR (500 MHz, DMSO-d$_6$): δ 9.12 (s, 1H), 8.44 (s, 1H), 8.15 (s, 1H), 7.89 (d, J = 0.9 Hz, 1H), 7.83 (d, J = 5.4 Hz, 1H), 7.75 (d, J = 8.1 Hz, 1H), 7.24 (d, J = 1.9 Hz, 1H), 7.17 (dd, J = 8.2, 1.8 Hz, 1H), 6.87 (d, J = 5.4 Hz, 1H), 4.90-4.76 (m, 1H), 4.03-3.93 (m, 1H), 3.87 (s, 6H), 3.80-3.70 (m, 1H), 2.05-1.97 (m, 1H), 1.96-1.87 (m, 1H), 1.83-1.72 (m, 1H), 1.63-1.52 (m, 1H), 1.03 (d, J = 6.1 Hz, 3H).<br>HRMS (ESI) MS m/z calcd for C$_{23}$H$_{26}$N$_7$O [M + H]$^+$ 416.2193, found 416.2180.<br>Using 2-methylpyrrolidine at 130° C. for 5 hours. | 0.006 |
| 65 | N8-isobutyl-N2-(2-methoxy-4-(1-methyl-1H-pyrazol-4-yl)phenyl)pyrido[3,4-d]pyrimidine-2,8-diamine 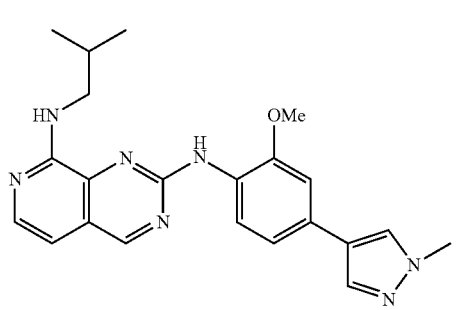 [SMILES: COc1cc(-c2cnn(C)c2)ccc1Nc1ncc2ccnc(NCC(C)C)c2n1] | $^1$H NMR (500 MHz, DMSO-d$_6$): δ 9.16 (s, 1H), 8.43 (s, 1H), 8.19 (d, J = 8.3 Hz, 1H), 8.15 (d, J = 0.8 Hz, 1H), 7.88 (d, J = 0.8 Hz, 1H), 7.77 (d, J = 5.7 Hz, 1H), 7.27 (d, J = 1.9 Hz, 1H), 7.18 (dd, J = 8.2, 1.9 Hz, 1H), 6.85 (dd, J = 9.3, 5.8 Hz, 2H), 3.93 (s, 3H), 3.87 (s, 3H), 3.39-3.28 (m, 2H), 1.99 (dp, J = 13.5, 6.7 Hz, 1H), 0.95 (d, J = 6.7 Hz, 6H).<br>HRMS (ESI) MS m/z calcd for C$_{22}$H$_{26}$N$_7$O [M + H]$^+$ 404.2193, found 404.2177.<br>Using 2-methylpropan-1-amine at 130° C. for 5 hours. | 0.008 |

| Example No | Name/Structure | Data | MPS1 IC50 (μM) |
|---|---|---|---|
| 66 | N-(2-methoxy-4-(1-methyl-1H-pyrazol-4-yl)phenyl)-8-(6-azaspiro[3.4]octan-6-yl)pyrido[3,4-d]pyrimidin-2-amine | $^1$H NMR (500 MHz, DMSO-d$_6$): δ 9.10 (s, 1H), 8.47 (s, 1H), 8.14 (s, 1H), 7.87 (s, 1H), 7.78 (d, J = 5.4 Hz, 1H), 7.74 (d, J = 8.1 Hz, 1H), 7.27 (d, J = 1.8 Hz, 1H), 7.17 (dd, J = 8.1, 1.8 Hz, 1H), 6.83 (d, J = 5.4 Hz, 1H), 3.88 (s, 3H), 3.87 (s, 3H), 3.82 (s, 2H), 3.74-3.68 (m, 2H), 1.92-1.81 (m, 8H). HRMS (ESI) MS m/z calcd for C$_{25}$H$_{28}$N$_7$O [M + H]$^+$ 442.2350, found 442.2326 Using 6-azaspiro[3,4]octane at 130° C. for 4 hours. | 0.008 |
| 67 | N-(2-methoxy-4-(1-methyl-1H-pyrazol-4-yl)phenyl)-8-(3-methoxyazetidin-1-yl)pyrido[3,4-d]pyrimidin-2-amine | $^1$H NMR (500 MHz, DMSO-d$_6$): δ 9.17 (s, 1H), 8.51 (s, 1H), 8.17 (s, 1H), 7.90 (d, J = 0.9 Hz, 1H), 7.85 (d, J = 8.2 Hz, 1H), 7.82 (d, J = 5.5 Hz, 1H), 7.27 (d, J = 1.8 Hz, 1H), 7.19 (dd, J = 8.2, 1.8 Hz, 1H), 6.96 (d, J = 5.5 Hz, 1H), 4.48-4.39 (m, 2H), 4.32-4.22 (m, 1H), 4.12-4.02 (m, 2H), 3.90 (s, 3H), 3.88 (s, 3H), 3.22 (s, 3H). HRMS (ESI) MS m/z calcd for C$_{22}$H$_{24}$N$_7$O$_2$ [M + H]$^+$ 418.1986, found 418.1966. Using 3-methoxyazetidine hydrochloride at 130° C. for 5 hours and purification method B. | 0.010 |
| 68 | N8-cyclohexyl-N2-(4-(1-(2-(dimethylamino)ethyl)-1H-pyrazol-4-yl)-2-methoxyphenyl)pyrido[3,4-d]pyrimidine-2,8-diamine | $^1$H NMR (500 MHz, DMSO-d$_6$): δ 9.17 (s, 1H), 8.56 (s, 1H), 8.21-8.07 (m, 2H), 7.88 (d, J = 0.8 Hz, 1H), 7.76 (d, J = 5.6 Hz, 1H), 7.28 (d, J = 1.8 Hz, 1H), 7.15 (dd, J = 8.3, 1.8 Hz, 1H), 6.85 (d, J = 5.7 Hz, 1H), 6.65 (t, J = 6.2 Hz, 1H), 3.93 (s, 3H), 3.88 (s, 3H), 3.38 (d, J = 6.2 Hz, 2H), 0.99 (s, 9H). HRMS (ESI) MS m/z calcd for C$_{23}$H$_{28}$N$_7$O [M + H]$^+$ 418.2350, found 418.2352. Using 2,2-dimethylpropan-1-amine at 130° C. for 5 hours. | 0.008 |

| Example No | Name/Structure | Data | MPS1 IC50 (μM) |
|---|---|---|---|
| 69 | N2-(2-methoxy-4-(1-methyl-1H-pyrazol-4-yl)phenyl)-N8-(tetrahydro-2H-pyran-4-yl)pyrido[3,4-d]pyrimidine-2,8-diamine<br>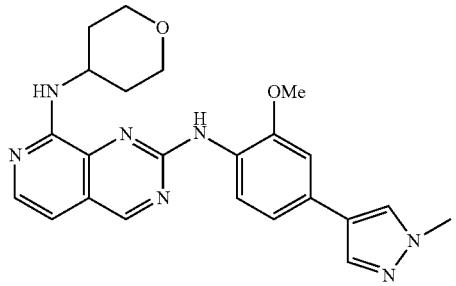 [SMILES: COc1cc(-c2cnn(C)c2)ccc1Nc1ncc2ccnc(NC3CCOCC3)c2n1] | $^1$H NMR (500 MHz, DMSO-d$_6$): δ 9.19 (s, 1H), 8.49 (s, 1H), 8.23-8.09 (m, 2H), 7.90 (d, J = 0.8 Hz, 1H), 7.79 (d, J = 5.6 Hz, 1H), 7.28 (d, J = 1.9 Hz, 1H), 7.22 (dd, J = 8.3, 1.8 Hz, 1H), 6.89 (d, J = 5.7 Hz, 1H), 6.64 (d, J = 7.9 Hz, 1H), 4.29-4.16 (m, 1H), 3.96-3.84 (m, 8H), 3.49 (td, J = 11.5, 2.2 Hz, 2H), 1.98 (br d, J = 14.0 Hz, 2H), 1.70-1.57 (m, 2H). HRMS (ESI) MS m/z calcd for C$_{23}$H$_{26}$N$_7$O$_2$ [M + H]$^+$ 432.2142, found 432.2135. Using tetrahydro-2H-pyran-4-amine at 135° C. for 6 hours and purification method B. | 0.003 |
| 70 | N8-(cyclohexylmethyl)-N2-(2-methoxy-4-(1-methyl-1H-pyrazol-4-yl)phenyl)pyrido[3,4-d]pyrimidine-2,8-diamine<br>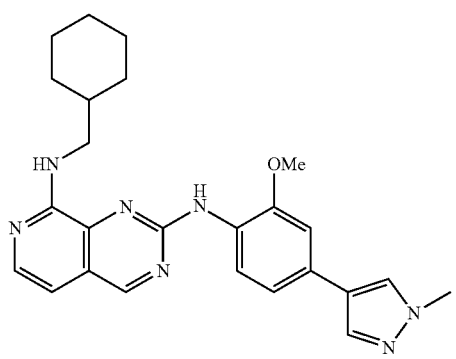 [SMILES: COc1cc(-c2cnn(C)c2)ccc1Nc1ncc2ccnc(NCC3CCCCC3)c2n1] | $^1$H NMR (500 MHz, DMSO-d$_6$): δ 9.17 (s, 1H), 8.45 (s, 1H), 8.18 (d, J = 8.2 Hz, 1H), 8.15 (s, 1H), 7.88 (s, 1H), 7.77 (d, J = 5.7 Hz, 1H), 7.28 (d, J = 1.8 Hz, 1H), 7.18 (dd, J = 8.3, 1.8 Hz, 1H), 6.89-6.79 (m, 2H), 3.94 (s, 3H), 3.88 (s, 3H), 3.38 (t, J = 6.4 Hz, 2H), 1.82-1.60 (m, 7H), 1.29-1.12 (m, 2H), 1.08-0.96 (m, 2H). HRMS (ESI) MS m/z calcd for C$_{25}$H$_{30}$N$_7$O [M + H]$^+$ 444.2506, found 444.2497. Using cyclohexylmethanamine at 130° C. for 8 hours. | 0.061 |
| 71 | 1-((2-((2-methoxy-4-(1-methyl-1H-pyrazol-4-yl)phenyl)amino)pyrido[3,4-d]pyrimidin-8-yl)amino)-2-methylpropan-2-ol<br>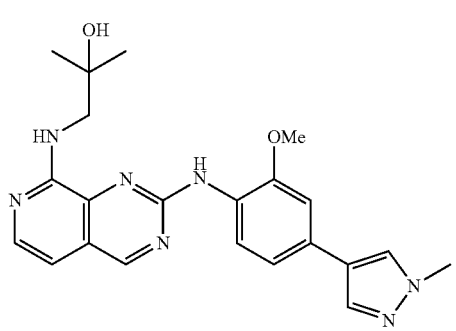 [SMILES: COc1cc(-c2cnn(C)c2)ccc1Nc1ncc2ccnc(NCC(C)(C)O)c2n1] | $^1$H NMR (500 MHz, DMSO-d$_6$): δ 9.18 (s, 1H), 8.52 (s, 1H), 8.19 (d, J = 8.2 Hz, 1H), 8.15 (s, 1H), 7.88 (d, J = 0.8 Hz, 1H), 7.76 (d, J = 5.7 Hz, 1H), 7.27 (d, J = 1.9 Hz, 1H), 7.17 (dd, J = 8.2, 1.8 Hz, 1H), 6.90 (t, J = 5.6 Hz, 1H), 6.87 (d, J = 5.7 Hz, 1H), 4.89 (br s, 1H), 3.94 (s, 3H), 3.88 (s, 3H), 3.48 (d, J = 5.6 Hz, 2H), 1.20 (s, 6H). HRMS (ESI) MS m/z calcd for C$_{22}$H$_{26}$N$_7$O$_2$ [M + H]$^+$ 420.2142, found 420.2138. Using 1-amino-2-methylpropan-2-ol at 130° C. for 8 hours and purification method B. | 0.006 |

| Example No | Name/Structure | Data | MPS1 IC50 (µM) |
|---|---|---|---|
| 72 | N2-(2-methoxy-4-(1-methyl-1H-pyrazol-4-yl)phenyl)-N8-(oxetan-3-ylmethyl)pyrido[3,4-d]pyrimidine-2,8-diamine 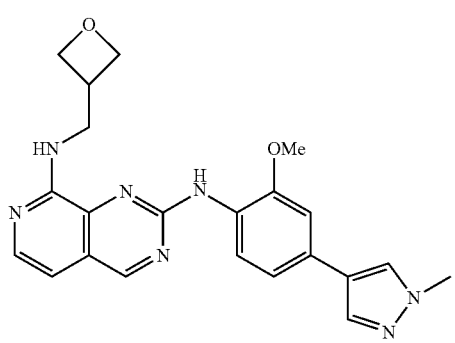 [SMILES: COc1cc(-c2cnn(C)c2)ccc1Nc1ncc2ccnc(NCC3COC3)c2n1] | $^1$H NMR (500 MHz, DMSO-d$_6$): δ 9.16 (s, 1H), 8.40 (s, 1H), 8.15 (s, 1H), 7.96 (d, J = 8.2 Hz, 1H), 7.89 (d, J = 0.9 Hz, 1H), 7.82 (d, J = 5.5 Hz, 1H), 7.25 (d, J = 1.9 Hz, 1H), 7.18 (dd, J = 8.2, 1.9 Hz, 1H), 6.92 (d, J = 5.5 Hz, 1H), 4.78 (t, J = 5.2 Hz, 1H), 4.33 (br s, 2H), 4.06 (br s, 2H), 3.91 (s, 3H), 3.88 (s, 3H), 3.58 (t, J = 5.7 Hz, 2H), 2.84-2.73 (m, 1H). HRMS (ESI MS m/z calcd for C$_{22}$H$_{24}$N$_7$O$_2$ [M + H]$^+$ 418.1986, found 418.1986. Using oxetan-3-yl-methanamine at 130° C. for 8 hours and purification method B. | 0.005 |
| 73 | N8-(3,3-dimethylbutan-2-yl)-N2-(2-methoxy-4-(1-methyl-1H-pyrazol-4-yl)phenyl)pyrido[3,4-d]pyrimidine-2,8-diamine 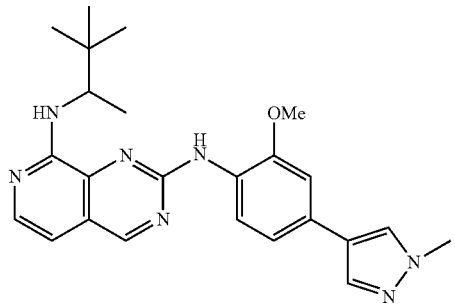 [SMILES: COc1cc(-c2cnn(C)c2)ccc1Nc1ncc2ccnc(NC(C)C(C)(C)C)c2n1] | $^1$H NMR (500 MHz, DMSO-d$_6$): δ 9.17 (s, 1H), 8.62 (s, 1H), 8.17 (s, 1H), 8.07 (d, J = 8.2 Hz, 1H), 7.89 (s, 1H), 7.76 (d, J = 5.6 Hz, 1H), 7.29 (d, J = 1.9 Hz, 1H), 7.15 (dd, J = 8.2, 1.9 Hz, 1H), 6.85 (d, J = 5.7 Hz, 1H), 6.44 (d, J = 9.4 Hz, 1H), 4.18-4.04 (m, 1H), 3.93 (s, 3H), 3.88 (s, 3H), 1.14 (d, J = 6.6 Hz, 3H), 0.99 (s, 9H). HRMS (ESI) MS m/z calcd for C$_{24}$H$_{30}$N$_7$O [M + H]$^+$ 432.2506, found 432.2503. Using 3,3-dimethylbutan-2-amine at 140° C. for 18 hours. | 0.012 |
| 74 | 3-((2-((2-methoxy-4-(1-methyl-1H-pyrazol-4-yl)phenyl)amino)pyrido[3,4-d]pyrimidin-8-yl)amino)-2,2-dimethylpropan-1-ol 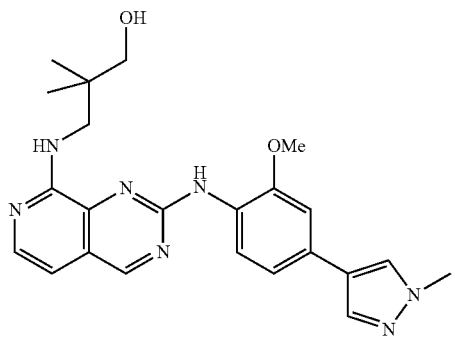 [SMILES: COc1cc(-c2cnn(C)c2)ccc1Nc1ncc2ccnc(NCC(C)(C)CO)c2n1] | $^1$H NMR (500 MHz, DMSO-d$_6$): δ 9.18 (s, 1H), 8.40 (s, 1H), 8.33 (d, J = 8.3 Hz, 1H), 8.13 (s, 1H), 7.88 (d, J = 0.8 Hz, 1H), 7.76 (d, J = 5.7 Hz, 1H), 7.27 (d, J = 1.9 Hz, 1H), 7.24-7.16 (m, 2H), 6.86 (d, J = 5.7 Hz, 1H), 5.14 (t, J = 5.5 Hz, 1H), 3.95 (s, 3H), 3.89 (s, 3H), 3.45 (d, J = 5.9 Hz, 2H), 3.30 (d, J = 5.5 Hz, 2H), 0.94 (s, 6H). HRMS (ESI) MS m/z calcd for C$_{23}$H$_{28}$N$_7$O$_2$ [M + H]$^+$ 434.2299, found 434.2296. Using 3-amino-2,2-dimethylpropan-1-ol at 130° C. for 4 hours. | 0.004 |

| Example No | Name/Structure | Data | MPS1 IC50 (μM) |
|---|---|---|---|
| 75 | N8-(1-cyclopropylethyl)-N2-(2-methoxy-4-(1-methyl-1H-pyrazol-4-yl)phenyl)pyrido[3,4-d]pyrimidine-2,8-diamine | ¹H NMR (500 MHz, CDCl₃): δ 8.98 (s, 1H), 8.55 (d, J = 8.3 Hz, 1H), 7.97 (s, 1H), 7.87 (d, J = 5.8 Hz, 1H), 7.79 (s, 1H), 7.64 (s, 1H), 7.17 (dd, J = 8.3, 1.8 Hz, 1H), 7.06 (d, J = 1.8 Hz, 1H), 6.74 (d, J = 5.9 Hz, 1H), 6.50 (br d, J = 7.8 Hz, 1H), 4.02 (s, 3H), 3.99 (s, 3H), 3.91-3.81 (m, 1H), 1.42 (d, J = 6.5 Hz, 3H), 1.18-1.08 (m, 1H), 0.67-0.54 (m, 2H), 0.53-0.45 (m, 1H), 0.43-0.36 (m, 1H). HRMS (ESI) MS m/z calcd for C₂₃H₂₆N₇O [M + H]⁺ 416.2193, found 416.2189. Using 1-cyclopropylethanamine at 130° C. for 8 hours and purification method C. | 0.004 |
| 76 | (R)-N8-(3,3-dimethylbutan-2-yl)-N2-(2-methoxy-4-(1-methyl-1H-pyrazol-4-yl)phenyl)pyrido[3,4-d]pyrimidine-2,8-diamine | ¹H NMR (500 MHz, DMSO-d₆): δ 9.16 (s, 1H), 8.61 (s, 1H), 8.16 (d, J = 0.9 Hz, 1H), 8.07 (d, J = 8.3 Hz, 1H), 7.89 (d, J = 0.8 Hz, 1H), 7.76 (d, J = 5.6 Hz, 1H), 7.28 (d, J = 1.9 Hz, 1H), 7.15 (dd, J = 8.2, 1.8 Hz, 1H), 6.84 (d, J = 5.7 Hz, 1H), 6.44 (d, J = 9.5 Hz, 1H), 4.16-4.06 (m, 1H), 3.92 (s, 3H), 3.88 (s, 3H), 1.14 (d, J = 6.7 Hz, 3H), 0.98 (s, 9H). HRMS (ESI) MS m/z calcd for C₂₄H₃₀N₇O [M + H]⁺ 432.2506, found 432.2504. Using (R)-3,3-dimethylbutan-2-amine at 140° C. for 18 hours. | 0.009 |
| 77 | (S)-N8-(3,3-dimethylbutan-2-yl)-N2-(2-methoxy-4-(1-methyl-1H-pyrazol-4-yl)phenyl)pyrido[3,4-d]pyrimidine-2,8-diamine | ¹H NMR (500 MHz, DMSO-d₆): δ 9.16 (s, 1H), 8.61 (s, 1H), 8.16 (d, J = 0.9 Hz, 1H), 8.07 (d, J = 8.3 Hz, 1H), 7.89 (d, J = 0.8 Hz, 1H), 7.76 (d, J = 5.6 Hz, 1H), 7.28 (d, J = 1.9 Hz, 1H), 7.15 (dd, J = 8.2, 1.8 Hz, 1H), 6.84 (d, J = 5.7 Hz, 1H), 6.44 (d, J = 9.5 Hz, 1H), 4.16-4.06 (m, 1H), 3.92 (s, 3H), 3.88 (s, 3H), 1.14 (d, J = 6.7 Hz, 3H), 0.98 (s, 9H). HRMS (ESI) MS m/z calcd for C₂₄H₃₀N₇O [M + H]⁺ 432.2506, found 432.2503. Using (S)-3,3-dimethylbutan-2-amine at 140° C. for 18 hours. | 0.005 |
| 78 | N2-(2-methoxy-4-(1-methyl-1H-pyrazol-4-yl)phenyl)-N8-(tetrahydrofuran-3-yl)pyrido[3,4-d]pyrimidine-2,8-diamine | ¹H NMR (500 MHz, DMSO-d₆): δ 9.20 (s, 1H), 8.51 (s, 1H), 8.16 (s, 1H), 8.14 (d, J = 8.3 Hz, 1H), 7.90 (d, J = 0.8 Hz, 1H), 7.81 (d, J = 5.7 Hz, 1H), 7.27 (d, J = 1.9 Hz, 1H), 7.21 (dd, J = 8.2, 1.9 Hz, 1H), 6.93 (d, J = 5.7 Hz, 1H), 6.78 (br d, J = 6.8 Hz, 1H), 4.68-4.58 (m, 1H), 3.98-3.85 (m, 8H), 3.82-3.75 (m, 1H), 3.68 (dd, J = 8.9, 3.9 Hz, 1H), 2.36-2.25 (m, 1H), 2.03-1.93 (m, 1H). HRMS (ESI) MS m/z calcd for C₂₂H₂₄N₇O₂ [M + H]⁺ 418.1986, found 418.1983. Using tetrahydrofuran-3-amine at 140° C. for 24 hours and purification method B. | 0.008 |

| Example No | Name/Structure | Data | MPS1 IC50 (μM) |
|---|---|---|---|
| 79 | N2-(2-methoxy-4-(1-methyl-1H-pyrazol-4-yl)phenyl)-N8-((tetrahydrofuran-3-yl)methyl)pyrido[3,4-d]pyrimidine-2,8-diamine | $^1$H NMR (500 MHz, DMSO-d$_6$): δ 9.24-9.15 (m, 1H), 8.38 (s, 1H), 8.27 (d, J = 8.2 Hz, 1H), 8.15 (d, J = 0.9 Hz, 1H), 7.89 (d, J = 0.8 Hz, 1H), 7.80 (d, J = 5.6 Hz, 1H), 7.27 (d, J = 1.9 Hz, 1H), 7.21 (dd, J = 8.3, 1.8 Hz, 1H), 7.08 (t, J = 5.8 Hz, 1H), 6.88 (d, J = 5.7 Hz, 1H), 3.95 (s, 3H), 3.88 (s, 3H), 3.81 (td, J = 8.1, 5.6 Hz, 1H), 3.73 (dd, J= 8.5, 7.0 Hz, 1H), 3.65 (td, J = 7.9, 6.7 Hz, 1H), 3.58 (dd, J = 8.5, 5.1 Hz, 1H), 3.53 (ddd, J = 7.1, 5.9, 1.6 Hz, 2H), 2.74-2.64 (m, 1H), 2.05-1.95 (m, 1H), 1.68 (dddd, J = 12.2, 7.9, 6.8, 5.6 Hz, 1H). HRMS (ESI) MS m/z calcd for C$_{23}$H$_{26}$N$_7$O$_2$ [M + H]$^+$ 432.2142, found 432.2137. Using (tetrahydrofuran-3-yl)methanamine at 135° C. for 18 hours and purification method B. | 0.005 |
| 80 | 1-(2-(2-methoxy-4-(1-methyl-1H-pyrazol-4-yl)phenylamino)pyrido[3,4-d]pyrimidin-8-yl)pyrrolidin-3-ol | $^1$H NMR (500 MHz, DMSO-d$_6$): δ 9.14 (s, 1H), 8.39 (s, 1H), 8.15 (d, J = 0.9 Hz, 1H), 7.89 (d, J = 0.8 Hz, 1H), 7.87 (d, J = 8.2 Hz, 1H), 7.83 (d, J = 5.4 Hz, 1H), 7.25 (d, J = 1.9 Hz, 1H), 7.18 (dd, J = 8.2, 1.9 Hz, 1H), 6.87 (d, J = 5.4 Hz, 1H), 4.87 (d, J = 3.4 Hz, 1H), 4.32 (br s, 1H), 3.96-3.83 (m, 9H), 3.78 (d, J = 12.5 Hz, 1H), 1.97-1.88 (m, 1H), 1.87-1.80 (m, 1H). HRMS (ESI) MS m/z calcd for C$_{22}$H$_{24}$N$_7$O$_2$ [M + H]$^+$ 418.1986, found 418.1982. Using pyrrolidin-3-ol at 135° C. for 7 hours and purification method A. | 0.006 |
| 81 | N2-(2-methoxy-4-(1-methyl-1H-pyrazol-4-yl)phenyl)-N8-methyl-N8-(tetrahydro-2H-pyran-4-yl)pyrido[3,4-d]pyrimidine-2,8-diamine | $^1$H NMR (500 MHz, DMSO-d$_6$): δ 9.21 (s, 1H), 8.54 (s, 1H), 8.17 (d, J = 0.8 Hz, 1H), 7.97-7.84 (m, 3H), 7.27 (d, J = 1.9 Hz, 1H), 7.15 (dd, J = 8.2, 1.8 Hz, 1H), 7.08 (d, J = 5.3 Hz, 1H), 4.95 (tt, J = 11.7, 3.9 Hz, 1H), 3.89 (s, 3H), 3.88 (s, 3H), 3.78 (dd, J = 11.1, 4.2 Hz, 2H), 3.13-3.04 (m, 2H), 3.01 (s, 3H), 1.81 (qd, J = 12.1, 4.5 Hz, 2H), 1.61-1.52 (m, 2H). HRMS (ESI) MS m/z calcd for C$_{24}$H$_{28}$N$_7$O$_2$ [M + H]$^+$ 446.2299, found 446.2295. Using N-methyltetrahydro-2H-pyran-4-amine 135° C. for 17 hours and purification method A. | 0.033 |
| 82 | N8-tert-butyl-N2-(2-methoxy-4-(1-methyl-1H-pyrazol-4-yl)phenyl)pyrido[3,4-d]pyrimidine-2,8-diamine | $^1$H NMR (500 MHz, DMSO-d$_6$): δ 9.15 (s, 1H), 8.57 (s, 1H), 8.17 (d, J = 1.0 Hz, 1H), 8.06 (d, J = 8.2 Hz, 1H), 7.90 (d, J = 0.8 Hz, 1H), 7.79 (d, J = 5.7 Hz, 1H), 7.28 (d, J = 1.9 Hz, 1H), 7.20 (dd, J = 8.3, 1.9 Hz, 1H), 6.85 (d, J = 5.7 Hz, 1H), 6.48 (s, 1H), 3.93 (s, 3H), 3.88 (s, 3H), 1.52 (s, 9H). HRMS (ESI) MS m/z calcd for C$_{22}$H$_{26}$N$_7$O [M + H]$^+$ 404.2193, found 404.2191 Using 2-methylpropan-2-amine at 140° C. for 7 days. | 0.025 |

| Example No | Name/Structure | Data | MPS1 IC50 (μM) |
|---|---|---|---|
| 83 | N2-(2-methoxy-4-(1-methyl-1H-pyrazol-4-yl)phenyl)-N8-(1-methylcyclohexyl)pyrido[3,4-d]pyrimidine-2,8-diamine | $^1$H NMR (500 MHz, DMSO-d$_6$): δ 9.15 (s, 1H), 8.61 (s, 1H), 8.17 (d, J = 0.8 Hz, 1H), 8.06 (d, J = 8.2 Hz, 1H), 7.90 (d, J = 0.8 Hz, 1H), 7.75 (d, J = 5.7 Hz, 1H), 7.29 (d, J = 1.9 Hz, 1H), 7.16 (dd, J = 8.2, 1.8 Hz, 1H), 6.84 (d, J = 5.7 Hz, 1H), 6.48 (s, 1H), 3.92 (s, 3H), 3.88 (s, 3H), 2.34-2.24 (m, 2H), 1.62-1.37 (m, 9H), 1.32-1.19 (m, 2H). HRMS (ESI) MS m/z calcd for C$_{25}$H$_{30}$N$_7$O [M + H]$^+$ 444.2506, found 444.2521. Using 1-methylcyclohexanamine hydrochloride at 130° C. for 7 days and purification method C. | 0.019 |
| 84 | N8-(2,2-difluoropropyl)-N2-(2-methoxy-4-(1-methyl-1H-pyrazol-4-yl)phenyl)pyrido[3,4-d]pyrimidine-2,8-diamine | $^1$H NMR (500 MHz, DMSO-d$_6$): δ 9.21 (s, 1H), 8.52 (s, 1H), 8.21-8.12 (m, 2H), 7.88 (d, J = 0.9 Hz, 1H), 7.81 (d, J = 5.6 Hz, 1H), 7.27 (d, J = 1.9 Hz, 1H), 7.18 (dd, J = 8.2, 1.9 Hz, 1H), 7.00 (t, J = 6.3 Hz, 1H), 6.97 (d, J = 5.6 Hz, 1H), 4.05 (td, J = 14.2, 6.6 Hz, 2H), 3.92 (s, 3H), 3.87 (s, 3H), 1.66 (t, J = 19.0 Hz, 3H). $^{19}$F NMR (471 MHz, DMSO-d$_6$):δ −94.22 (s). HRMS (ESI) MS m/z calcd for C$_{21}$H$_{22}$F$_2$N$_7$O [M + H]$^+$ 426.1848, found 426.1842. Using 2,2-difluoropropan-1-amine hydrochloride at 140° C. for 24 hours. | 0.014 |
| 85 | N8-(3-methoxy-2,2-dimethylpropyl)-N2-(2-methoxy-4-(1-methyl-1H-pyrazol-4-yl)phenyl)pyrido[3,4-d]pyrimidine-2,8-diamine | $^1$H NMR (500 MHz, DMSO-d$_6$): δ 9.16 (s, 1H), 8.50 (s, 1H), 8.17-8.11 (m, 2H), 7.87 (d, J = 0.8 Hz, 1H), 7.76 (d, J = 5.7 Hz, 1H), 7.28 (d, J = 1.9 Hz, 1H), 7.16 (dd, J = 8.2, 1.9 Hz, 1H), 6.84 (d, J = 5.6 Hz, 2H), 3.93 (s, 3H), 3.87 (s, 3H), 3.45 (d, J = 5.9 Hz, 2H), 3.22 (s, 3H), 3.20 (s, 2H), 0.95 (s, 6H). HRMS (ESI) MS m/z calcd for C$_{24}$H$_{30}$N$_7$O$_2$ [M + H]$^+$ 448.2455, found 448.2451. Using 3-methoxy-2,2-dimethylpropan-1-amine hydrochloride for 2 hours. | 0.024 |
| 86 | N8-(2-methoxy-2-methylpropyl)-N2-(2-methoxy-4-(1-methyl-1H-pyrazol-4-yl)phenyl)pyrido[3,4-d]pyrimidine-2,8-diamine | $^1$H NMR (500 MHz, DMSO-d$_6$): δ 9.18 (s, 1H), 8.57 (s, 1H), 8.17 (d, J = 0.9 Hz, 1H), 8.12 (d, J = 8.2 Hz, 1H), 7.89 (d, J = 0.8 Hz, 1H), 7.77 (d, J = 5.6 Hz, 1H), 7.29 (d, J = 1.9 Hz, 1H), 7.15 (dd, J = 8.2, 1.9 Hz, 1H), 6.88 (d, J = 5.7 Hz, 1H), 6.67 (t, J = 5.5 Hz, 1H), 3.93 (s, 3H), 3.88 (s, 3H), 3.55 (d, J = 5.5 Hz, 2H), 3.22 (s, 3H), 1.19 (s, 6H). HRMS (ESI) MS m/z calcd for C$_{23}$H$_{28}$N$_7$O$_2$ [M + H]$^+$ 434.2299, found 434.2296. Using 2-methoxy-2-methylpropan-1-amine for 24 hours. | 0.005 |

| Example No | Name/Structure | Data | MPS1 IC50 (μM) |
|---|---|---|---|
| 87 | N2-(2-methoxy-4-(1-methyl-1H-pyrazol-4-yl)phenyl)-N8-(2,2,2-trifluoroethyl)pyrido[3,4-d]pyrimidine-2,8-diamine 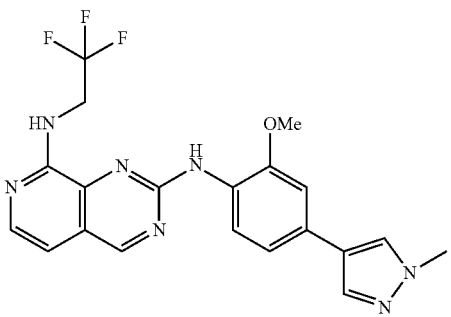 [SMILES: COc1cc(-c2cnn(C)c2)ccc1Nc1ncc2ccnc(NCC(F)(F)F)c2n1] | $^1$H NMR (500 MHz, DMSO-d$_6$): δ 9.24 (s, 1H), 8.46 (s, 1H), 8.24 (d, J = 8.2 Hz, 1H), 8.15 (s, 1H), 7.88 (d, J = 0.9 Hz, 1H), 7.85 (d, J = 5.6 Hz, 1H), 7.33 (t, J = 6.6 Hz, 1H), 7.27 (d, J = 1.9 Hz, 1H), 7.20 (dd, J = 8.2, 1.9 Hz, 1H), 7.04 (d, J = 5.7 Hz, 1H), 4.48-4.32 (m, 2H), 3.93 (s, 3H), 3.87 (s, 3H). $^{19}$F NMR (471 MHz, DMSO-d$_6$): δ −70.33 (s). HRMS (ESI) MS m/z calcd for C$_{20}$H$_{19}$F$_3$N$_7$O [M + H]$^+$ 430.1598, found 430.1593. Using 2,2,2-trifluoroethanamine, trifluoroacetic acid and 2,2,2-trifluoroethanol instead of N-methyl-2-pyrrolidinone at 130° C. for 6 hours. | 0.075 |
| 88 | N-(2-methoxy-4-(1-methyl-1H-pyrazol-4-yl)phenyl)-8-(2-oxa-6-azaspiro[3.4]oxtan-6-yl)pyrido[3,4-d]pyrimidin-2-amine 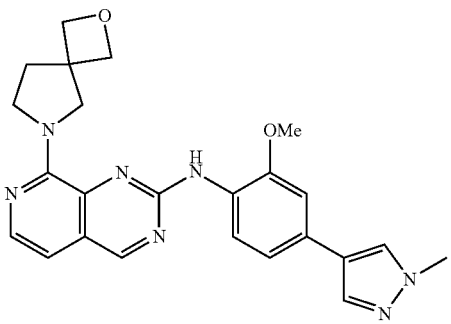 [SMILES: COc1cc(-c2cnn(C)c2)ccc1Nc1ncc2ccnc(N3CCC4(COC4)C3)c2n1] | $^1$H NMR (500 MHz, DMSO-d$_6$): δ 9.13 (s, 1H), 8.53 (s, 1H), 8.14 (s, 1H), 7.87 (s, 1H), 7.81 (d, J = 5.5 Hz, 1H), 7.74 (d, J = 8.1 Hz, 1H), 7.26 (d, J = 2.0 Hz, 1H), 7.19 (d, J = 7.9 Hz, 1H), 6.88 (d, J = 5.4 Hz, 1H), 4.48 (s, 4H), 4.08 (s, 2H), 3.89 (s, 3H), 3.87 (s, 3H), 3.77-3.66 (m, 2H), 2.18-2.07 (m, 2H). HRMS (ESI) MS m/z calcd for C$_{24}$H$_{26}$N$_7$O$_2$ [M + H]$^+$ 444.2142, found 444.2137. Using (2-oxa-6-azaspiro[3,4]octan-6-amine at 130° C. for 4 hours and purification method B. | 0.003 |
| 89 | 1-((2-(2-methoxy-4-(1-methyl-1H-pyrazol-4-yl)phenylamino)pyrido[3,4-d]pyrimidin-8-ylamino)methyl)cyclobutanol 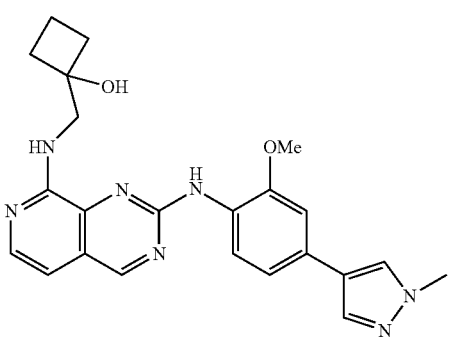 [SMILES: COc1cc(-c2cnn(C)c2)ccc1Nc1ncc2ccnc(NCC3(O)CCC3)c2n1] | $^1$H NMR (500 MHz, DMSO-d$_6$): δ 9.16 (s, 1H), 8.51 (s, 1H), 8.21-8.06 (m, 2H), 7.87 (d, J = 0.8 Hz, 1H), 7.76 (d, J = 5.7 Hz, 1H), 7.26 (d, J = 1.9 Hz, 1H), 7.16 (dd, J = 8.2, 1.9 Hz, 1H), 6.92-6.74 (m, 2H), 5.60 (s, 1H), 3.92 (s, 3H), 3.87 (s, 3H), 3.62 (d, J = 5.4 Hz, 2H), 2.05-1.98 (m, 4H), 1.70-1.62 (m, 1H), 1.59-1.48 (m, 1H). HRMS (ESI) MS m/z calcd for C$_{23}$H$_{26}$N$_7$O$_2$ [M + H]$^+$ 432.2142, found 432.2161. Using 1-(aminomethyl)cyclobutanol at 130° C. for 4 hours and purification method B. | 0.007 |

Example 90

8-(cyclohexylthio)-N-(2-methoxy-4-(1-methyl-1H-pyrazol-4-yl)phenyl)pyrido[3,4-d]pyrimidin-2-amine

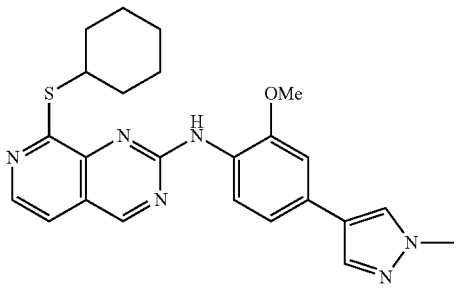 [SMILES: COc1cc(-c2cnn(C)c2)ccc1Nc1ncc2ccnc(SC3CCCCC3)c2n1]

A mixture of 8-chloro-N-(2-methoxy-4-(1-methyl-1H-pyrazol-4-yl)phenyl)pyrido[3,4-d]pyrimidin-2-amine (Example 94, 26 mg, 0.071 mmol) and potassium carbonate (15 mg, 0.109 mmol) in DMF (0.35 mL) was treated with cyclohexanethiol (12 µL, 0.098 mmol) and stirred at room temperature for 4 days. An additional batch of potassium carbonate (10 mg, 0.07 mmol) and thiol (12 µL, 0.098 mmol) were added and the mixture stirred at 50° C. for 18 hours. The reaction was quenched with brine and extracted with EtOAc. The combined organic layers were washed with water and brine, dried and concentrated. The residue was purified by silica gel column chromatography eluting with 0 to 80% EtOAc in cyclohexane to give the title compound (30 mg, 94%).

$^1$H NMR (500 MHz, DMSO-$d_6$): δ 9.35 (s, 1H), 8.55 (br s, 1H), 8.29 (d, J=5.4 Hz, 1H), 8.20 (d, J=0.9 Hz, 1H), 7.93 (d, J=0.8 Hz, 1H), 7.48 (d, J=5.4 Hz, 1H), 7.29 (d, J=1.9 Hz, 1H), 7.26 (dd, J=8.2, 1.9 Hz, 1H), 3.96 (br s, 4H), 3.87 (s, 3H), 2.17-2.05 (m, 2H), 1.82-1.72 (m, 2H), 1.69-1.59 (m, 1H), 1.59-1.40 (m, 4H), 1.39-1.28 (m, 1H).

HRMS (ESI) MS m/z calcd for $C_{24}H_{27}N_6OS$ [M+H]$^+$ 447.1962. found 447.1948.

MPS1 IC50 (µM): 0.234

Example 91

8-(1-ethyl-1H-pyrazol-4-yl)-N-(2-methoxy-4-(1-methyl-1H-pyrazol-4-yl)phenyl)pyrido[3,4-d]pyrimidin-2-amine

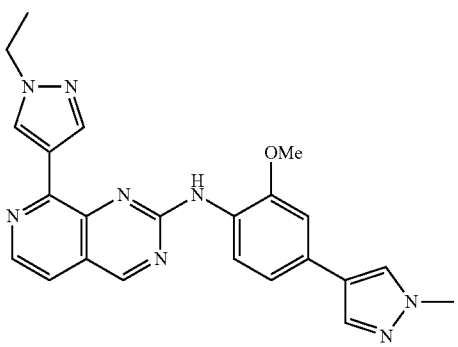 [SMILES: CCn1cc(-c2nccc3cnc(Nc4ccc(-c5cnn(C)c5)cc4OC)nc23)cn1]

A solution of 8-chloro-N-(2-methoxy-4-(1-methyl-1H-pyrazol-4-yl)phenyl)pyrido[3,4-d]pyrimidin-2-amine (Example 94, 35 mg, 0.095 mmol), 1-ethyl-4-(4,4,5,5-tetramethyl-1,3,2-dioxaborolan-2-yl)-1H-pyrazole (32 mg, 0.144 mmol) and Pd(dppf)Cl$_2$.DCM (8 mg, 9.79 µmol) was dissolved in THF (0.6 mL) and 2M sodium carbonate in water (0.2 mL) and heated to 65° C. for 18 hours. The mixture was diluted with DCM and quenched with saturated aqueous NaHCO$_3$. The aqueous layer was extracted with DCM three times. The combined organic layers were dried and concentrated. The residue was purified by silica gel column chromatography eluting with 0 to 5% MeOH in EtOAc to give the title compound (28 mg, 68%).

$^1$H NMR (500 MHz, DMSO-$d_6$): δ 9.35 (s, 1H), 9.10 (s, 1H), 8.50 (s, 1H), 8.33 (d, J=5.2 Hz, 1H), 8.23 (s, 1H), 8.21 (s, 1H), 7.96 (d, J=0.9 Hz, 1H), 7.67 (d, J=8.1 Hz, 1H), 7.56 (d, J=5.3 Hz, 1H), 7.37 (d, J=1.9 Hz, 1H), 7.28 (dd, J=8.0, 1.9 Hz, 1H), 3.99 (q, J=7.1 Hz, 2H), 3.90 (s, 3H), 3.84 (s, 3H), 1.22 (t, J=7.2 Hz, 3H).

HRMS (ESI) MS m/z calcd for $C_{23}H_{23}N_8O$ [M+H]$^+$ 427.1989. found 427.1967.

MPS1 IC50 (µM): 0.010

Example 92

8-(1-isopropyl-1H-pyrazol-4-yl)-N-(2-methoxy-4-(1-methyl-1H-pyrazol-4-yl)phenyl)pyrido[3,4-d]pyrimidin-2-amine

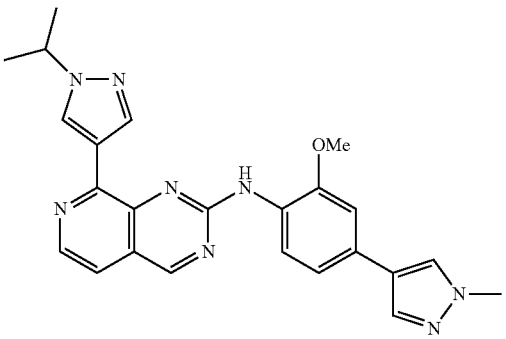 [SMILES: COc1cc(-c2cnn(C)c2)ccc1Nc1ncc2ccnc(-c3cnn(C(C)C)c3)c2n1]

The title compound was prepared according to the method described for Example 91 using 1-isopropyl-4-(4,4,5,5-tetramethyl-1,3,2-dioxaborolan-2-yl)-1H-pyrazole. After heating to 65° C. for 18 hours, an additional batch of catalyst (8 mg, 9.79 µmol) and boronic ester (17 mg, 0.07) were added, and the mixture heated to 65° C. for 3 hours.

$^1$H NMR (500 MHz, DMSO-$d_6$): δ 9.36 (s, 1H), 9.10 (s, 1H), 8.50 (br s, 1H), 8.34 (d, J=5.2 Hz, 1H), 8.23 (s, 2H), 7.96 (d, J=0.9 Hz, 1H), 7.67 (d, J=8.1 Hz, 1H), 7.57 (d, J=5.3 Hz, 1H), 7.38 (d, J=1.9 Hz, 1H), 7.27 (dd, J=8.2, 1.9 Hz, 1H), 4.37-4.25 (m, 1H), 3.91 (s, 3H), 3.84 (s, 3H), 1.29 (d, J=6.7 Hz, 6H).

HRMS (ESI) MS m/z calcd for $C_{24}H_{26}N_8O$ [M+H]$^+$ 441.2146. found 441.2122.

MPS1 IC50 (µM): 0.014

Example 93

8-(1-(2,2-difluoroethyl)-1H-pyrazol-4-yl)-N-(2-methoxy-4-(1-methyl-1H-pyrazol-4-yl)phenyl)pyrido[3,4-d]pyrimidin-2-amine

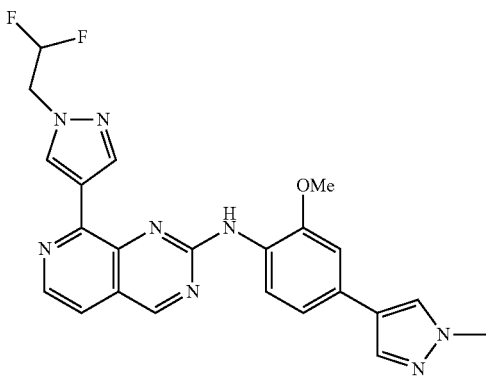 [SMILES: COc1cc(-c2cnn(C)c2)ccc1Nc1ncc2ccnc(-c3cnn(CC(F)F)c3)c2n1]

The title compound was prepared according to the method described for Example 91 using 1-(2,2-difluoroethyl)-4-(4,4,5,5-tetramethyl-1,3,2-dioxaborolan-2-yl)-1H-pyrazole (Preparation 112). The residue was purified by silica gel column chromatography eluting with 0 to 80% EtOAc in cyclohexane to give the title compound (18 mg, 41%).

$^1$H NMR (500 MHz, DMSO-d$_6$): δ 9.39 (s, 1H), 9.10 (s, 1H), 8.63 (s, 1H), 8.44-8.32 (m, 2H), 8.21 (d, J=0.9 Hz, 1H), 7.94 (d, J=0.8 Hz, 1H), 7.73 (d, J=8.1 Hz, 1H), 7.62 (d, J=5.2 Hz, 1H), 7.36 (d, J=1.8 Hz, 1H), 7.27 (dd, J=8.0, 1.8 Hz, 1H), 6.50-6.18 (m, 1H), 4.50 (t, J=14.2 Hz, 2H), 3.90 (s, 3H), 3.86 (s, 3H). $^{19}$F NMR (471 MHz, DMSO) δ −122.71 (d, J=54.8 Hz).

HRMS (ESI) MS m/z calcd for $C_{23}H_{21}F_2N_8O$ [M+H]$^+$ 463.1801. found 463.1808.

MPS1 IC50 (μM): 0.010

Example 94

8-chloro-N-(2-methoxy-4-(1-methyl-1H-pyrazol-4-yl)phenyl)pyrido[3,4-d]pyrimidin-2-amine

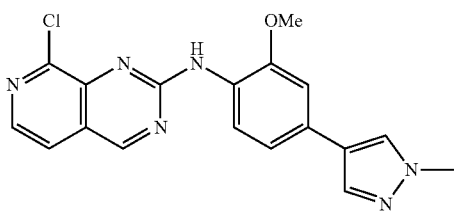 [SMILES: COc1cc(-c2cnn(C)c2)ccc1Nc1ncc2ccnc(Cl)c2n1]

A solution of N-(2-methoxy-4-(1-methyl-1H-pyrazol-4-yl)phenyl)formamide (Preparation 56, 24 mg, 0.104 mmol) in THF (1 mL) was treated with sodium hydride (7 mg, 0.175 mmol) at 0° C. After stirring for 20 minutes at room temperature the mixture was cooled to 0° C. and 8-chloro-2-(methylsulfonyl)pyrido[3,4-d]pyrimidine (Preparation 97, 33 mg, 0.135 mmol) was added. The reaction was allowed to reach room temperature and stirred for 18 hours. Aqueous NaOH (2M, 0.5 mL) and MeOH (0.5 mL) were added and the resulting mixture stirred for 1 hour. The volatiles were removed under reduced pressure and the residue was partitioned between EtOAc and water. The aqueous layer was extracted with EtOAc and the combined organic layers were washed with water, brine, dried and concentrated. The residue was purified by silica gel column chromatography eluting with 0 to 80% EtOAc in cyclohexane to give the title compound (30 mg, 79%).

$^1$H NMR (500 MHz, DMSO): δ 9.47 (s, 1H), 8.84 (s, 1H), 8.51 (br s, 1H), 8.25 (d, J=5.2 Hz, 1H), 8.18 (s, 1H), 7.92 (s, 1H), 7.86 (d, J=5.2 Hz, 1H), 7.30 (d, J=1.9 Hz, 1H), 7.26 (dd, J=8.3, 1.9 Hz, 1H), 3.95 (s, 3H), 3.87 (s, 3H).

LCMS (ESI) Rt=2.81 minutes MS m/z 367 [M+H]$^+$

MPS1 IC50 (μM): 0.164

Example 95

8-(1-methyl-1H-pyrazol-4-yl)-N-(2-methyl-4-(1-methyl-1H-pyrazol-4-yl)phenyl)pyrido[3,4-d]pyrimidin-2-amine

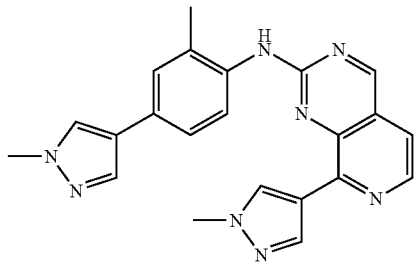 [SMILES: Cc1cc(-c2cnn(C)c2)ccc1Nc1ncc2ccnc(-c3cnn(C)c3)c2n1]

To a solution of 8-chloro-N-(2-methyl-4-(1-methyl-1H-pyrazol-4-yl)phenyl)pyrido[3,4-d]pyrimidin-2-amine (Preparation 113, 12 mg, 0.034 mmol) in 1,4-dioxane (2 mL) and water (1 mL) was added 1-methylpyrazole-4-boronic acid pinacol ester (14 mg, 0.068 mmol), cesium carbonate (17 mg, 0.051 mmol) and Pd(PPh$_3$)$_4$ (2 mg, 1.71 umol). The reaction mixture was heated to 100° C. under microwave irradiation for 30 minutes. The reaction mixture was diluted with EtOAc (20 mL) and water (20 mL). The organic layer was washed with water (20 mL) and brine (20 mL), dried (MgSO$_4$) and concentrated in vacuo. The residue was purified by silica gel column chromatography eluting with 0-15% MeOH in EtOAc to give the title compound (7 mg, 52%).

$^1$H NMR (500 MHz, CDCl$_3$): δ 9.16 (s, 1H), 8.43 (d, J=5.5 Hz, 1H), 8.40 (d, J=5.5 Hz, 2H), 7.86 (d, J=8.0 Hz, 1H), 7.82 (s, 1H), 7.67 (s, 1H), 7.50-7.45 (m, 2H), 7.36 (d, J=5.5 Hz, 1H), 7.05 (br s, 1H), 4.00 (s, 3H), 3.77 (s, 3H), 2.39 (s, 3H).

HRMS (ESI) MS m/z calcd for $C_{22}H_{20}N_8$ [M+H]$^+$ 397.1884. found 397.1878.

LCMS (ESI) Rt=2.37 minutes MS m/z 397.05 [M+H]$^+$

MPS1 IC50 (μM): 0.021

Example 96

N-(2-ethoxy-4-(1-methyl-1H-pyrazol-4-yl)phenyl)-8-(1-methyl-1H-pyrazol-4-yl)pyrido[3,4-d]pyrimidin-2-amine

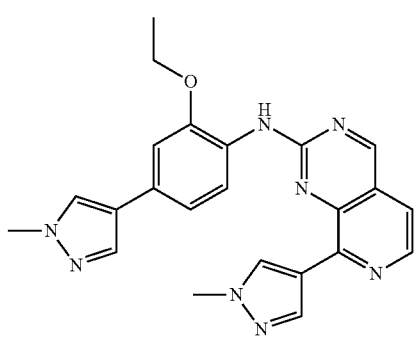 [SMILES: CCOc1cc(-c2cnn(C)c2)ccc1Nc1ncc2ccnc(-c3cnn(C)c3)c2n1]

The title compound was prepared according to the method described for Example 95 using 8-chloro-N-(2-ethoxy-4-(1-methyl-1H-pyrazol-4-yl)phenyl)pyrido[3,4-d]pyrimidin-2-amine (Preparation 114) and 1-Methylpyrazole-4-boronic acid pinacol ester.

¹H NMR (500 MHz, CDCl₃): δ 9.16 (s, 1H), 8.72 (s, 1H), 8.60 (d, J=8.0 Hz, 1H), 8.54 (s, 1H), 8.45 (d, J=5.5 Hz, 1H), 7.90 (br s, 1H), 7.77 (d, J=0.5 Hz, 1H), 7.63 (s, 1H), 7.38 (d, J=5.5 Hz, 1H), 7.17 (dd, J=8.0, 2.0 Hz, 1H), 7.07 (m, 1H), 4.23 (q, J=7.0 Hz, 2H), 3.99 (s, 3H), 3.98 (s, 3H), 1.54 (t, J=7.0 Hz, 3H).

HRMS (ESI) MS m/z calcd for C₂₃H₂₂N₈O [M+H]⁺ 427.1989. found 427.1984.

LCMS (ESI) RT=2.66 minutes MS m/z 427.03 [M+H]⁺

MPS1 IC50 (μM): 0.008

Example 97

N-(2-isopropoxy-4-(1-methyl-1H-pyrazol-4-yl)phenyl)-8-(1-methyl-1H-pyrazol-4-yl)pyrido[3,4-d]pyrimidin-2-amine

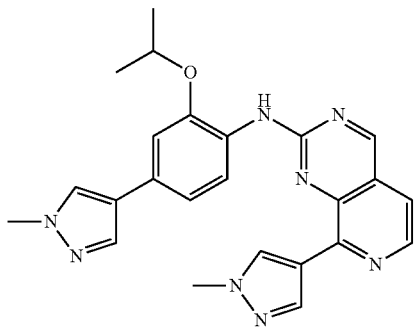 [SMILES: CC(C)Oc1cc(-c2cnn(C)c2)ccc1Nc1ncc2ccnc(-c3cnn(C)c3)c2n1]

The title compound was prepared according to the method described for Example 95 using 8-chloro-N-(2-isopropoxy-4-(1-methyl-1H-pyrazol-4-yl)phenyl)pyrido[3,4-d]pyrimidin-2-amine (Preparation 115) and 1-methylpyrazole-4-boronic acid pinacol ester.

¹H NMR (500 MHz, CDCl₃): δ 9.16 (s, 1H), 8.73 (s, 1H), 8.63 (d, J=9.0 Hz, 1H), 8.54 (s, 1H), 8.45 (d, J=5.5 Hz, 1H), 7.92 (br s, 1H), 7.76 (d, J=0.5 Hz, 1H), 7.63 (s, 1H), 7.38 (d, J=5.5 Hz, 1H), 7.16 (dd, J=9.0, 2.0 Hz, 1H), 7.09 (d, J=2.0 Hz, 1H), 4.74 (quin, J=6.0 Hz, 1H), 4.00 (s, 3H), 3.99 (s, 3H), 1.47 (s, 3H), 1.46 (s, 3H).

HRMS (ESI) MS m/z calcd for C₂₄H₂₄N₈O [M+H]⁺ 441.2146. found 441.2139.

LCMS (ESI) Rt=2.75 minutes MS m/z 441.05 [M+H]⁺

MPS1 IC50 (μM): 0.049

Example 98

N-(2-(2-methoxyethoxy)-4-(1-methyl-1H-pyrazol-4-yl)phenyl)-8-(1-methyl-1H-pyrazol-4-yl)pyrido[3,4-d]pyrimidin-2-amine

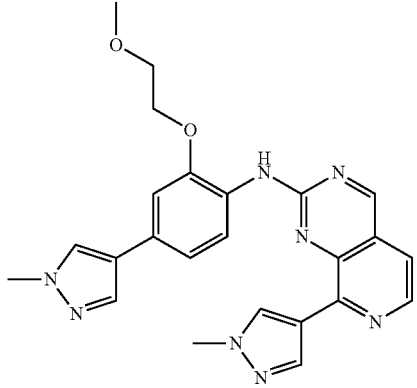 [SMILES: COCCOc1cc(-c2cnn(C)c2)ccc1Nc1ncc2ccnc(-c3cnn(C)c3)c2n1]

The title compound was prepared according to the method described for Example 95 using 8-chloro-N-(2-(2-methoxyethoxy)-4-(1-methyl-1H-pyrazol-4-yl)phenyl)pyrido[3,4-d]pyrimidin-2-amine (Preparation 116) and 1-methylpyrazole-4-boronic acid pinacol ester.

¹H NMR (500 MHz, CDCl₃): δ 9.16 (s, 1H), 8.71 (s, 1H), 8.59 (d, J=8.5 Hz, 1H), 8.53 (s, 1H), 8.45 (d, J=5.5 Hz, 1H), 8.10 (br s, 1H), 7.77 (d, J=0.5 Hz, 1H), 7.63 (s, 1H), 7.38 (d, J=5.5 Hz, 1H), 7.21 (dd, J=8.0, 2.0 Hz, 1H), 7.14 (d, J=2.0 Hz, 1H), 4.32-4.30 (m, 2H), 3.99 (s, 6H), 3.84-3.82 (m, 2H), 3.51 (s, 3H).

HRMS (ESI) MS m/z calcd for C₂₃H₂₄N₈O₂ [M+H]⁺ 457.2095. found 457.2089.

LCMS (ESI) Rt=2.45 minutes MS m/z 457.02 [M+H]⁺

MPS1 IC50 (μM): 0.146

Example 99

N8-(cyclopropylmethyl)-N2-(2-methyl-4-(1-methyl-1H-pyrazol-4-yl)phenyl)pyrido[3,4-d]pyrimidine-2,8-diamine

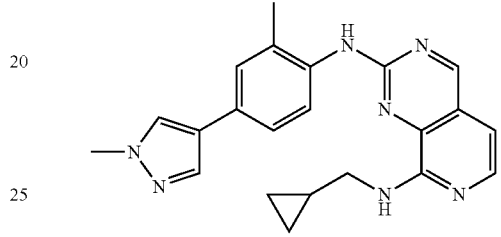

To a solution of 8-chloro-N-(2-methyl-4-(1-methyl-1H-pyrazol-4-yl)phenyl)pyrido[3,4-d]pyrimidin-2-amine (Preparation 113, 40 mg, 0.114 mmol) in NMP (3 mL) was added cyclopropanemethylamine (0.1 ml, 1.140 mmol). The reaction mixture was heated to 120° C. for 18 hours. The reaction mixture was diluted with aqueous saturated NaHCO₃ (20 mL) and EtOAc (2×20 mL). The combined organic layers were washed with water (30 mL) and brine (30 mL), dried (MgSO₄) and concentrated in vacuo. The residue was purified by silica gel column chromatography eluting with 0-5% MeOH in EtOAc to give the title compound (4.2 mg, 10%).

¹H NMR (500 MHz, CDCl₃): δ 8.96 (s, 1H), 8.11 (d, J=9.0 Hz, 1H), 7.88 (d, J=5.5 Hz, 1H), 7.62 (s, 1H), 7.41-7.38 (m, 2H), 7.06 (br s, 1H), 6.74 (d, J=5.5 Hz, 1H), 6.51 (br t, J=5.5 Hz, 2H), 3.98 (s, 3H), 3.45 (dd, J=7.0, 5.5 Hz, 2H), 2.40 (s, 3H), 1.21 (m, 1H), 0.60 (ddd, J=8.0, 5.5, 5.0 Hz, 2H), 0.37-0.34 (m, 2H).

HRMS (ESI) MS m/z calcd for C₂₂H₂₃N₇ [M+H]⁺ 386.2088. found 386.2083.

LCMS (ESI) Rt=1.81 minutes MS m/z 386.10 [M+H]⁺

MPS1 IC50 (μM): 0.008

Example 100

N8-cyclohexyl-N2-(2-methyl-4-(1-methyl-1H-pyrazol-4-yl)phenyl)pyrido[3,4-d]pyrimidine-2,8-diamine

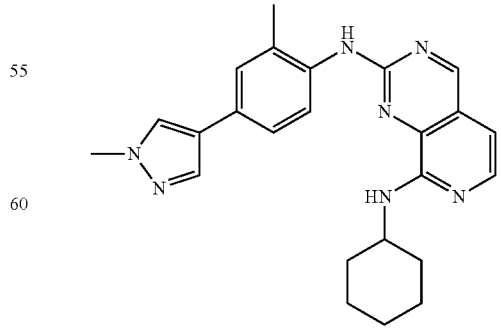

The title compound was prepared according to the method described for Example 99 using cyclohexylamine.

$^1$H NMR (500 MHz, CDCl$_3$): δ 8.95 (s, 1H), 8.12 (d, J=8.5 Hz, 1H), 7.88 (d, J=6.0 Hz, 1H), 7.79 (s, 1H), 7.63 (s, 1H), 7.40-7.38 (m, 2H), 7.04 (br s, 1H), 6.72 (d, J=5.0 Hz, 1H), 6.40 (br d, J=8.5 Hz, 1H), 3.98 (s, 3H), 2.41 (s, 3H), 2.23 (m, 1H), 2.14-2.09 (m, 2H), 1.81-1.77 (m, 2H), 1.71-1.62 (m, 2H), 1.46-1.28 (m, 4H).

HRMS (ESI) MS m/z calcd for C$_{24}$H$_{27}$N$_7$ [M+H]$^+$ 414.2401. found 414.2398.

LCMS (ESI) Rt=2.03 minutes MS m/z 414.08 [M+H]$^+$

MPS1 IC50 (μM): no data

Example 101

N8-(cyclopropylmethyl)-N2-(2-ethoxy-4-(1-methyl-1H-pyrazol-4-yl)phenyl)pyrido[3,4-d]pyrimidine-2,8-diamine

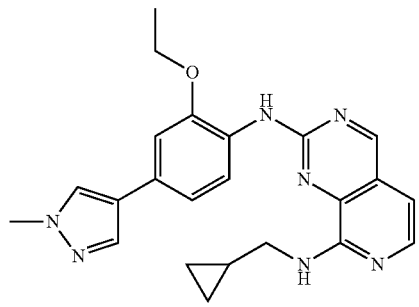 [SMILES: CCOc1cc(-c2cnn(C)c2)ccc1Nc1ncc2ccnc(NCC3CC3)c2n1]

The title compound was prepared according to the method described for Example 99 using 8-chloro-N-(2-ethoxy-4-(1-methyl-1H-pyrazol-4-yl)phenyl)pyrido[3,4-d]pyrimidin-2-amine (Preparation 114) and cyclopropanemethylamine for 5 hours. The residue was further purified by passage through a SCX-2 cartridge eluting with 100% MeOH—0.5 M NH$_3$ in MeOH to give the title compound (2.6 mg, 5%).

$^1$H NMR (500 MHz, CDCl$_3$): δ 8.99 (s, 1H), 8.57 (d, J=8.5 Hz, 1H), 7.99 (br s, 1H), 7.90 (d, J=6.0 Hz, 1H), 7.77 (s, 1H), 7.62 (s, 1H), 7.15 (dd, J=8.5, 2.0 Hz, 1H), 7.04 (d, J=2.0 Hz, 1H), 6.77 (d, J=6.0 Hz, 1H), 6.58 (br s, 1H), 4.23 (q, J=7.0 Hz, 2H), 3.98 (s, 3H), 3.50 (t, J=6.0 Hz, 2H), 1.56 (t, J=7.0 Hz, 3H), 1.27 (m, 1H), 0.65 (ddd, J=8.0, 5.0, 4.0 Hz, 2H), 0.40 (app q, J=5.0 Hz, 2H).

HRMS (ESI) MS m/z calcd for C$_{23}$H$_{25}$N$_7$O [M+H]$^+$ 416.2193. found 416.2185.

LCMS (ESI) Rt=2.13 minutes MS m/z 416.08 [M+H]$^+$

MPS1 IC50 (μM): 0.049

Example 102

N2-(2-ethoxy-4-(1-methyl-1H-pyrazol-4-yl)phenyl)-N8-(tetrahydro-2H-pyran-4-yl)pyrido[3,4-d]pyrimidine-2,8-diamine

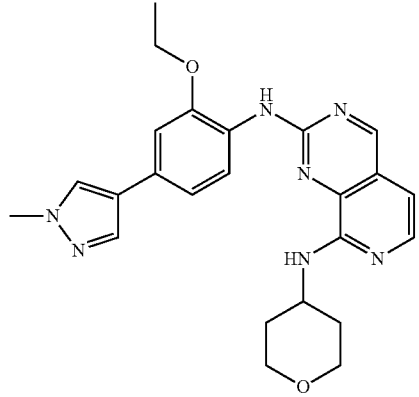 [SMILES: CCOc1cc(-c2cnn(C)c2)ccc1Nc1ncc2ccnc(NC3CCOCC3)c2n1]

The title compound was prepared according to the method described for Example 99 using 8-chloro-N-(2-ethoxy-4-(1-methyl-1H-pyrazol-4-yl)phenyl)pyrido[3,4-d]pyrimidin-2-amine (Preparation 114) and 4-aminotetrahydropyran. The residue was further purified by passage through a SCX-2 cartridge eluting with 100% MeOH—1M NH$_3$ in MeOH to give the title compound (3 mg, 9%).

$^1$H NMR (500 MHz, CDCl$_3$): δ 8.99 (s, 1H), 8.51 (d, J=8.0 Hz, 1H), 7.98 (br s, 1H), 7.89 (d, J=5.5 Hz, 1H), 7.77 (d, J=0.5 Hz, 1H), 7.64 (s, 1H), 7.16 (dd, J=8.0, 2.0 Hz, 1H), 7.05 (d, J=2.0 Hz, 1H), 6.78 (d, J=5.5 Hz, 1H), 6.40 (br d, J=8.0 Hz, 1H), 4.37 (br s, 1H), 4.24 (q, J=7.0 Hz, 2H), 4.08 (dt, J=11.0, 3.0 Hz, 2H), 3.99 (s, 3H), 3.68 (td, J=11.0, 2.0 Hz, 2H), 2.21-2.17 (m, 2H), 1.76-1.67 (m, 3H), 1.56 (t, J=7.0 Hz, 3H).

HRMS (ESI) MS m/z calcd for C$_{24}$H$_{27}$N$_7$O$_2$ [M+H]$^+$ 446.2299. found 446.2299.

LCMS (ESI) Rt=2.16 minutes MS m/z 446.01 [M+H]$^+$

MPS1 IC50 (μM): 0.010

Example 103

N-(2-methoxy-4-(1-methyl-1H-pyrazol-4-yl)phenyl)-5-(1-methyl-1H-pyrazol-4-yl)-2,6-naphthyridin-3-amine

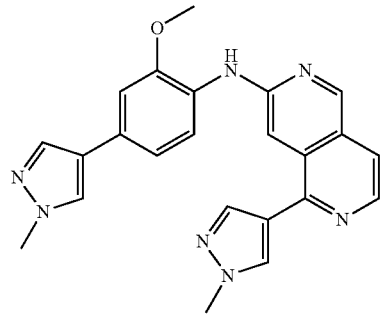 [SMILES: COc1cc(-c2cnn(C)c2)ccc1Nc1cc2c(-c3cnn(C)c3)nccc2cn1]

Method 6

To a solution of 5-(1-methyl-1H-pyrazol-4-yl)-2,6-naphthyridin-3-yl trifluoromethanesulfonate (Preparation 90, 7 mg, 0.020 mmol) in 1,4-dioxane (1.5 ml) was added 2-methoxy-4-(1-methyl-1H-pyrazol-4-yl)aniline (Preparation 19, 5 mg, 0.023 mmol), cesium carbonate (9 mg, 0.028 mmol), xantphos (0.51 mg, 0.879 umol) and Pd(dba)$_2$ (1 mg, 1.1739 umol). The reaction mixture was heated to 100° C. for 1 hr. The reaction mixture was filtered through Celite® and concentrated in vacuo. The residue was purified by silica gel column chromatography eluting with 50-100% EtOAc in cyclohexane followed by 10% MeOH in EtOAc. The residue was passed through a SCX-2 cartridge eluting with 100% MeOH followed by 1M NH$_3$ in MeOH, to give the title compound (2.2 mg, 27%).

$^1$H NMR (500 MHz, CDCl$_3$): δ 9.05 (d, J=5.5 Hz, 1H), 8.40 (d, J=5.5 Hz, 1H), 8.03 (s, 1H), 7.96 (s, 1H), 7.82 (d, J=8.0 Hz, 1H), 7.76 (d, J=1.0 Hz, 1H), 7.63-7.62 (m, 2H), 7.51 (dd, J=5.5, 1.0 Hz, 1H), 7.17 (br s, 1H), 7.15 (dd, J=8.0, 2.0 Hz, 1H), 7.05 (d, J=2.0 Hz, 1H), 4.03 (s, 3H), 3.98 (d, J=1.0 Hz, 6H).

HRMS (ESI) MS m/z calcd for C$_{23}$H$_{21}$N$_7$O [M+H]$^+$ 412.1880. found 412.1876; LCMS (ESI) Rt=2.30 minutes MS m/z 412.07 [M+H]$^+$.

MPS1 IC50 (μM): 0.012

Example 104

N-(4-(1,2-dimethyl-1H-imidazol-5-yl)-2-methoxyphenyl)-5-(1-methyl-1H-pyrazol-4-yl)-2,6-naphthyridin-3-amine

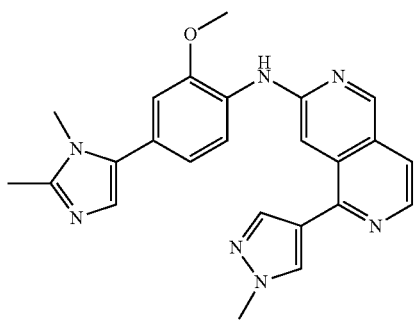 [SMILES: COc1cc(-c2cnc(C)n2C)ccc1Nc1cc2c(-c3cnn(C)c3)nccc2cn1]

The title compound was prepared according to Method 6 (Example 103) using 4-(1,2-dimethyl-1H-imidazol-5-yl)-2-methoxyaniline (Preparation 18) for 18 hours. The residue was purified using silica gel column chromatography eluting with 0-20% MeOH in EtOAc.

$^1$H NMR (500 MHz, CDCl$_3$): δ 9.09 (s, 1H), 8.43 (d, J=5.5 Hz, 1H), 8.04 (s, 1H), 8.00 (d, J=8.0 Hz, 1H), 7.97 (s, 1H), 7.66 (s, 1H), 7.54 (dd, J=5.5, 1.0 Hz, 1H), 7.01 (dd, J=8.0, 2.0 Hz, 1H), 6.97 (s, 1H), 6.94 (d, J=2.0 Hz, 1H), 4.04 (s, 3H), 3.97 (s, 3H), 3.58 (s, 3H), 2.48 (s, 3H).

HRMS (ESI) MS m/z calcd for C$_{24}$H$_{23}$N$_7$O [M+H]$^+$ 426.2037. found 426.2029; LCMS (ESI) Rt=1.62 minutes MS m/z 426.05 [M+H]$^+$.

MPS1 IC50 (μM): 0.007

Example 105

N1-cyclohexyl-N7-(2-methoxy-4-(1-methyl-1H-pyrazol-4-yl)phenyl)-2,6-naphthyridine-1,7-diamine

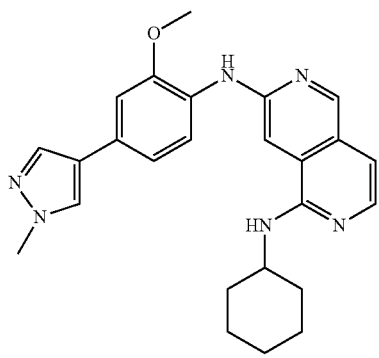 [SMILES: COc1cc(-c2cnn(C)c2)ccc1Nc1cc2c(NC3CCCCC3)nccc2cn1]

The title compound was prepared according to Method 6 (Example 103) using 5-(cyclohexylamino)-2,6-naphthyridin-3-yl trifluoromethanesulfonate (Preparation 93) and 2-methoxy-4-(1-methyl-1H-pyrazol-4-yl)aniline (Preparation 19) for 18 hours. The residue was purified using silica gel column chromatography eluting with 0-10% MeOH in DCM.

$^1$H NMR (500 MHz, CDCl$_3$): δ 8.83 (s, 1H), 7.91 (d, J=8.5 Hz, 1H), 7.87 (d, J=6.0 Hz, 1H), 7.71 (s, 1H), 7.62 (s, 1H), 7.14 (dd, J=8.5, 2.0 Hz, 1H), 7.06-7.04 (m, 2H), 6.98 (s, 1H), 6.88 (d, J=6.0 Hz, 1H), 4.86 (m, 1H), 3.97 (s, 6H), 2.19-2.14 (m, 4H), 1.82-1.77 (m, 3H), 1.74-1.67 (m, 3H).

HRMS (ESI) MS m/z calcd for C$_{25}$H$_{28}$N$_6$O [M+H]$^+$ 429.2397. found 429.2394; LCMS (ESI) Rt=2.02 minutes MS m/z 429.07 [M+H]$^+$.

MPS1 IC50 (μM): 0.056

Example 106

N1-(cyclopropylmethyl)-N7-(2-methoxy-4-(1-methyl-1H-pyrazol-4-yl)phenyl)-2,6-naphthyridine-1,7-diamine

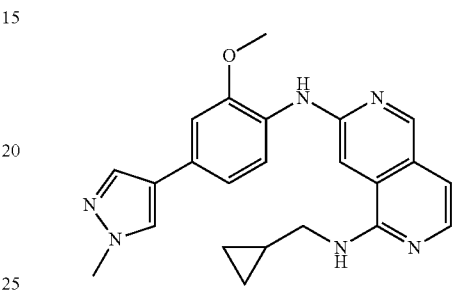

The title compound was prepared according to Method 6 (Example 103) using 5-((cyclopropylmethyl)amino)-2,6-naphthyridin-3-yl trifluoromethanesulfonate (Preparation 96) and 2-methoxy-4-(1-methyl-1H-pyrazol-4-yl)aniline (Preparation 19) for 3 hours. The residue was purified using silica gel column chromatography eluting with 0-10% MeOH in DCM.

$^1$H NMR (500 MHz, CDCl$_3$): δ 8.85 (s, 1H), 7.93 (d, J=8.0 Hz, 1H), 7.87 (d, J=5.5 Hz, 1H), 7.62 (s, 1H), 7.14 (dd, J=8.0, 2.0 Hz, 1H), 7.08 (br s, 1H), 7.06 (dd, J=5.5, 2.0 Hz, 1H), 6.93 (t, J=5.5 Hz, 1H), 5.13 (m, 1H), 3.98 (s, 6H), 3.46-3.42 (m, 2H), 1.24-1.18 (m, 2H), 0.63-0.59 (m, 2H).

HRMS (ESI) MS m/z calcd for C$_{23}$H$_{24}$N$_6$O [M+H]$^+$ 401.2084. found 401.2077; LCMS (ESI) Rt=1.89 minutes MS m/z 401.06 [M+H]$^+$.

MPS1 IC50 (μM): 0.082

Example 107

N-(2-(2-methoxy-4-(1-methyl-1H-pyrazol-4-yl)phenylamino)pyrido[3,4-d]pyrimidin-8-yl)-2-methylpropane-2-sulfonamide

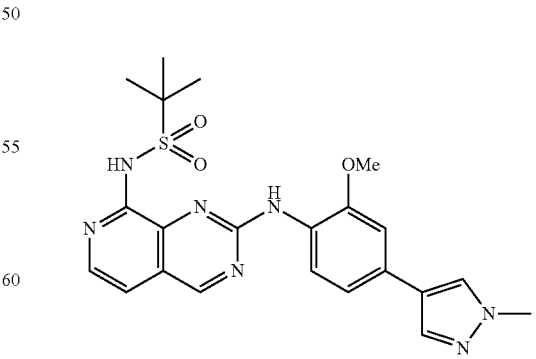

A mixture of 8-chloro-N-(2-methoxy-4-(1-methyl-1H-pyrazol-4-yl)phenyl)pyrido[3,4-d]pyrimidin-2-amine (Example 94, 27 mg, 0.074 mmol), tell-butylsulfonamide (13 mg, 0.095 mmol), tris(dibenzylideneacetone)dipalladium(O) (2 mg, 2.183 µmol), cesium carbonate (34 mg, 0.104 mmol) and DavePhos (3 mg, 7.61 µmol) in 1,4-dioxane (0.7 mL) (degassed) was stirred at 100° C. for 18 hours. The reaction was quenched with water and extracted with EtOAc. The combined organic layers were washed with brine, dried and concentrated in vacuo The residue was purified by silica gel column chromatography eluting with 0 to 90% EtOAc in cyclohexane to give the title compound (29 mg, 85%).

$^1$H NMR (500 MHz, DMSO-$d_6$): δ 11.97 (s, 1H), 9.17 (s, 1H), 8.84 (br. s, 1H), 8.50 (s, 1H), 8.16 (s, 1H), 7.88 (s, 1H), 7.36 (d, J=7.0 Hz, 1H), 7.27 (d, J=1.9 Hz, 1H), 7.06 (dd, J=8.4, 1.8 Hz, 1H), 6.89 (d, J=6.9 Hz, 1H), 3.96 (s, 3H), 3.88 (s, 3H), 1.48 (s, 9H).

HRMS (ESI) MS m/z calcd for $C_{22}H_{26}N_7O_3S$ [M+H]$^+$ 468.1812. found 468.1808.

MPS1 IC50 (µM): 0.039

The following Examples were prepared according to Method 5 (Example 54) above using 8-chloro-N-(2-methoxy-4-(1-methyl-1H-pyrazol-4-yl)phenyl)pyrido[3,4-d]pyrimidin-2-amine (Example 94) and the appropriate amine as described. The crude reaction residues were purified as above or according to one of the following methods:

Method A: Silica gel column chromatography eluting with 0-5% or 0-10% MeOH in DCM.
Method B: Silica gel column chromatography eluting with 0-5% MeOH in EtOAc.
Method C: Silica gel column chromatography eluting with 0-70% EtOAc in cyclohexane followed by reverse phase preparative HPLC eluting with 10-90% MeOH in water (0.1% formic acid).
Method D: Silica gel column chromatography eluting with 0-100% EtOAc in cyclohexane followed by a second chromatography eluting with either 0-5% or 0-20% MeOH in either DCM or EtOAc.
Method E: Silica gel column chromatography eluting with between 0-20% MeOH in DCM.
Method F: Elution through an SCX-2 column followed by silica gel column chromatography eluting with 0-5% MeOH in EtOAc.
Method G: Elution through an SCX-2 column followed by silica gel column chromatography eluting with 0-5% MeOH/ aq NH$_3$ (10/1) in DCM.
Method I: Elution through an SCX-2 column using 1M followed by 7M methanolic ammonia followed by trituration with MeOH.
Method J: Elution through an SCX-2 column followed by silica gel column chromatography eluting with 0-10% EtOH in DCM.
Method K: Trituration with ether.
Method L: Elution through an SCX column using 50% MeOH in chloroform followed by 50% chloroform in 7N NH$_3$/MeOH.

| Example No | Name/Structure | Data | MPS1 IC50 (µM) |
|---|---|---|---|
| 108 | N$^2$-(2-methoxy-4-(1-methyl-1H-pyrazol-4-yl)phenyl)-N$^8$,N$^8$-dimethylpyrido[3,4-d]pyrimidine-2,8-diamine | $^1$H NMR (500 MHz, DMSO-$d_6$): δ 9.21 (s, 1H), 8.47 (s, 1H), 8.20-8.13 (m, 1H), 8.05 (d, J = 8.2 Hz, 1H), 7.91 (d, J = 5.4Hz, 1H), 7.90 (d, J = 0.8 Hz, 1H), 7.27 (d, J = 1.8 Hz, 1H), 7.22 (dd, J = 8.2, 1.9 Hz, 1H), 7.05 (d, J = 5.4 Hz, 1H), 3.91 (s, 3H), 3.88 (s, 3H), 3.27 (s, 6H). HRMS (ESI) MS m/z calcd for $C_{20}H_{22}N_7O$ [M + H]$^+$ 376.1880, found 376.1876. Using 2M dimethylamine in THF at 100° C. for 5 hours. | 0.016 |
| 109 | N$^2$-(2-methoxy-4-(1-methyl-1H-pyrazol-4-yl)phenyl)-N$^8$-((3-methyloxetan-3-yl)methyl)pyrido(3,4-d]pyrimidine-2,8-diamine | $^1$H NMR (500 MHz, DMSO-$d_6$): δ 9.15 (s, 1H), 8.38 (s, 1H), 8.15 (d, J = 0.8 Hz, 1H), 7.96 (d, J = 8.2 Hz, 1H), 7.88 (d, J = 0.8 Hz, 1H), 7.81 (d, J = 5.5 Hz, 1H), 7.25 (d, J = 1.8 Hz, 1H), 7.16 (dd, J = 8.2, 1.9 Hz, 1H), 6.90 (d, J = 5.5 Hz, 1H), 4.90 (t, J = 5.3 Hz, 1H), 4.17 (br. s, 2H), 3.97-3.80 (m, 8H), 3.43 (d, J = 5.3 Hz, 2H), 1.25 (s, 3H). HRMS (ESI) MS m/z calcd for $C_{23}H_{26}N_7O_2$ [M + H]$^+$ 432.2142, found 432.2137. Using (3-methyloxetan-3-yl)methanamine at 130° for 8 hours and purification method B. | 0.002 |

| Example No | Name/Structure | Data | MPS1 IC50 (μM) |
|---|---|---|---|
| 110 | N²-(2-methoxy-4-(1-methyl-1H-pyrazol-4-yl)phenyl)-N⁸-methylpyrido[3,4-d]pyrimidine-2,8-diamine | $^1$H NMR (500 MHz, DMSO-d$_6$): δ 9.18 (s, 1H), 8.37 (d, J = 8.3 Hz, 1H), 8.30 (s, 1H), 8.14 (d, J = 0.9 Hz, 1H), 7.88 (d, J = 0.8 Hz, 1H), 7.82 (d, J = 5.6 Hz, 1H), 7.27 (d, J = 1.9 Hz, 1H), 7.23 (dd, J = 8.3, 1.9 Hz, 1H), 7.06-6.99 (m, 1H), 6.86 (d, J = 5.6 Hz, 1H), 3.95 (s, 3H), 3.88 (s, 3H), 3.03 (d, J = 4.8 Hz, 3H). HRMS (ESI) MS m/z calcd for C$_{19}$H$_{20}$N$_7$O [M + H]⁺ 362.1724, found 362.1746. Using 2M methylamine in THF at 100° C. for 10 hours. | 0.017 |
| 111 | N²-(2-methoxy-4-(1-methyl-1H-pyrazol-4-yl)phenyl)-N⁸-(oxetan-3-yl)pyrido[3,4-d]pyrimidine-2,8-diamine | $^1$H NMR (500 MHz, DMSO): δ 8.78 (s, 1H), 8.30 (d, J = 8.3 Hz, 1H), 8.24 (s, 1H), 8.14 (s, 1H), 7.88 (s, 1H), 7.24 (d, J = 1.9 Hz, 1H), 7.18 (dd, J = 8.4, 1.9 Hz, 1H), 7.10 (d, J = 7.0 Hz, 1H), 5.99 (d, J = 7.0 Hz, 1H), 4.82 (br. s, 1H), 4.31-4.19 (m, 1H), 4.11 (t, J = 11.0 Hz, 1H), 3.99-3.91 (m, 4H), 3.87 (s, 3H), 3.64-3.55 (m, 1H), 3.48-3.40 (m, 1H). HRMS (ESI) m/z calcd for C$_{21}$H$_{22}$N$_7$O$_2$ [M + H]⁺ 404.1829, found 404.1827. Using oxetan-3-amine at 130° C. for 3 hours and purification method D. | >1 |
| 112 | 1-((2-(2-methoxy-4-(1-methyl-1H-pyrazol-4-yl)phenylamino)pyrido[3,4-d]pyrimidin-8-ylamino)methyl)cyclopropanol | $^1$H NMR (500 MHz, DMSO-d$_6$): δ 9.18 (s, 1H), 8.51 (s, 1H), 8.23-8.09 (m, 2H), 7.88 (d, J = 0.8 Hz, 1H), 7.76 (d, J = 5.7 Hz, 1H), 7.28 (d, J = 1.9 Hz, 1H), 7.18 (dd, J = 8.2, 1.9 Hz, 1H), 6.96 (t, J = 5.5 Hz, 1H), 6.88 (d, J = 5.7 Hz, 1H), 5.67 (s, 1H), 3.94 (s, 3H), 3.88 (s, 3H), 3.63 (d, J = 5.4 Hz, 2H), 0.68-0.63 (m, 2H), 0.62-0.58 (m, 2H). HRMS (ESI) MS m/z calcd for C$_{22}$H$_{24}$N$_7$O$_2$ [M + H]⁺ 418.1986, found 418.1995. Using 1-(aminomethyl)cyclopropanol at 130° C. for 6 hours. | 0.005 |
| 113 | N²-(2-methoxy-4-(1-methyl-1H-pyrazol-4-yl)phenyl)-N⁸-(1-methylpiperidin-4-yl)pyrido[3,4-d]pyrimidine-2,8-diamine | $^1$H NMR (500 MHz, DMSO-d$_6$): δ 9.18 (s, 1H), 8.51 (s, 1H), 8.17 (s, 1H), 8.13 (d, J = 8.2 Hz, 1H), 7.90 (d, J = 0.8 Hz, 1H), 7.79 (d, J = 5.7 Hz, 1H), 7.28 (d, J = 1.9 Hz, 1H), 7.21 (dd, J = 8.3, 1.8 Hz, 1H), 6.88 (d, J = 5.7 Hz, 1H), 6.60 (br. d, J = 7.5 Hz, 1H), 4.03 (br. s, 1H), 3.93 (s, 3H), 3.88 (s, 3H), 2.82 (br. s, 2H), 2.30 (br. s, 5H), 2.08-1.95 (br. m. 2H), 1.76-1.57 (br. m, 2H). HRMS (ESI) MS m/z calcd for C$_{24}$H$_{29}$N$_8$O [M + H]⁺ 445.2459, found 445.2458. Using 1-methylpiperidin-4-amine at 130° C. for 10 hours and purification method E. | 0.009 |

| Example No | Name/Structure | Data | MPS1 IC50 (μM) |
|---|---|---|---|
| 114 | 2-(2-(2-methoxy-4-(1-methyl-1H-pyrazol-4-yl)phenylamino)pyrido[3,4-d]pyrimidin-8-ylamino-2-methylpropan-1-ol | ¹H NMR (500 MHz, DMSO-d₆): δ 9.16 (s, 1H), 8.47 (s, 1H), 8.23 (d, J = 8.2 Hz, 1H), 8.15 (s, 1H), 7.88 (d, J = 0.8 Hz, 1H), 7.77 (d, J = 5.7 Hz, 1H), 7.27 (d, J = 1.9 Hz, 1H), 7.21 (dd, J = 8.2, 1.9 Hz, 1H), 6.91 (s, 1H), 6.87 (d, J = 5.7 Hz, 1H), 5.38 (t, J = 5.1 Hz, 1H), 3.94 (s, 3H), 3.88 (s, 3H), 3.59 (d, J = 5.1 Hz, 2H), 1.46 (s, 6H). HRMS (ESI) MS m/z calcd for $C_{22}H_{26}N_7O_2$ [M + H]⁺ 420.2142, found 420.2146. Using 2-amino-2-methylpropan-1-ol neat at 130° C. for 36 hours. | 0.017 |
| 115 | N-(2-methoxy-4-(1-methyl-1H-pyrazol-4-yl)phenyl)-8-(2-oxa-6-azaspiro[3.3]heptan-6-yl)pyrido[3,4-d]pyrimidin-2-amine | ¹H NMR (500 MHz, DMSO-d₆): δ 9.18 (s, 1H), 8.45 (s, 1H), 8.18 (d, J = 0.9 Hz, 1H), 7.99 (d, J = 8.1 Hz, 1H), 7.92 (d, J = 0.8 Hz, 1H), 7.84 (d, J = 5.5 Hz, 1H), 7.33-7.18 (m, 2H), 6.97 (d, J = 5.4 Hz, 1H), 4.73 (s, 4H), 4.46 (s, 4H), 3.92 (s, 3H), 3.89 (s, 3H). HRMS (ESI) MS m/z calcd for $C_{23}H_{24}N_7O_2$ [M + H]⁺ 430.1986, found 430.1990. Using 2-oxa-6-azaspiro[3.3]heptane oxalate and triethylamine at 130° for 6 hours and purification method B. | 0.003 |
| 116 | N²-(2-methoxy-4-(1-methyl-1H-pyrazol-4-yl)phenyl)-N8-(oxetan-2-ylmethyl)pyrido[3,4-d]pyrimidine-2,8-diamine | ¹H NMR (500 MHz, DMSO-d₆): δ 9.20 (s, 1H), 8.49 (s, 1H), 8.18 (d, J = 8.2 Hz, 1H), 8.16 (d, J = 0.9 Hz, 1H), 7.89 (d, J = 0.8 Hz, 1H), 7.79 (d, J = 5.6 Hz, 1H), 7.27 (d, J = 1.9 Hz, 1H), 7.18 (dd, J = 8.2, 1.9 Hz, 1H), 7.01 (t, J = 5.9 Hz, 1H), 6.91 (d, J = 5.6 Hz, 1H), 5.01 (ddd, J = 12.2, 7.1, 5.2 Hz, 1H), 4.56 (ddd, J = 8.5, 7.3, 5.8 Hz, 1H), 4.46 (dt, J = 9.1, 5.9 Hz, 1H), 3.93 (s, 3H), 3.88 (s, 3H), 3.87-3.78 (m, 1H), 3.71 (dt, J = 13.9, 5.0 Hz, 1H), 2.68-2.60 (m, 1H), 2.49-2.43 (m, 1H). HRMS (ESI) MS m/z calcd for $C_{22}H_{24}N_7O_2$ [M + H]⁺ 418.1986, found 418.1990. Using oxetan-2-ylmethanamine at 130° C. for 11 hours and purification method B. | 0.008 |

| Example No | Name/Structure | Data | MPS1 IC50 (μM) |
|---|---|---|---|
| 117 | N²-(2-methoxy-4-(1-methyl-1H-pyrazol-4-yl)phenyl)-N⁸-((3-methyltetrahydrofuran-3-yl)methyl)pyrido[3,4-d]pyrimidine-2,8-diamine 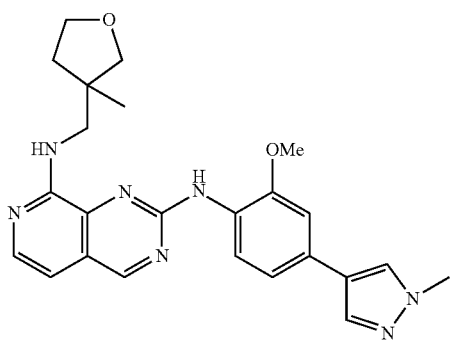 [SMILES: COc1cc(-c2cnn(C)c2)ccc1Nc1ncc2ccnc(NCC3(C)CCOC3)c2n1] | $^1$H NMR (500 MHz, DMSO-d$_6$): δ 9.18 (d, J = 0.9 Hz, 1H), 8.48 (s, 1H), 8.22 (d, J = 8.3 Hz, 1H), 8.15 (s, 1H), 7.88 (d, J = 0.8 Hz, 1H), 7.78 (d, J = 5.6 Hz, 1H), 7.28 (d, J = 1.8 Hz, 1H), 7.17 (dd, J = 8.2, 1.8 Hz, 1H), 6.88 (dd, J = 5.6, 0.9 Hz, 2H), 3.94 (s, 3H), 3.88 (s, 3H), 3.87-3.83 (m, 1H), 3.78 (td, J = 8.3, 6.8 Hz, 1H), 3.70 (d, J = 8.5 Hz, 1H), 3.63-3.52 (m, 2H), 3.34 (s, 1H), 1.92 (ddd, J = 12.5, 8.3, 6.8 Hz, 1H), 1.65 (ddd, J = 12.2, 8.1, 5.6 Hz, 1H), 1.16 (s, 3H). HRMS (ESI) MS m/z calcd for C$_{24}$H$_{28}$N$_7$O$_2$ [M + H]$^+$ 446.2299, found 446.2321. Using (3-methyltetrahydrofuran-3-yl)methanamine at 135° C. for 16 hours. | 0.003 |
| 118 | 4-(2-((2-methoxy-4-(1-methyl-1H-pyrazol-4-yl)phenyl)amino)pyrido[3,4-d]pyrimidin-8-yl)thiomorpholine 1,1-dioxide 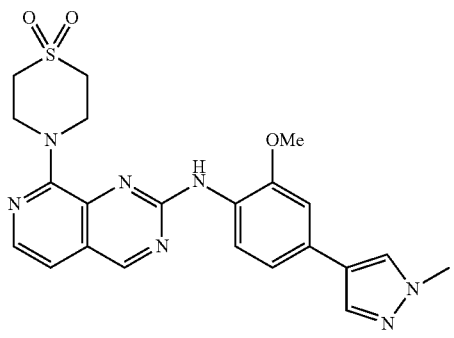 [SMILES: COc1cc(-c2cnn(C)c2)ccc1Nc1ncc2ccnc(N3CCS(=O)(=O)CC3)c2n1] | $^1$H NMR (500 MHz, DMSO-d$_6$): δ 9.29 (s, 1H), 8.76 (s, 1H), 8.19 (d, J = 0.9 Hz, 1H), 7.98 (d, J = 5.4 Hz, 1H), 7.92 (d, J = 0.8 Hz, 1H), 7.84 (d, J = 8.1 Hz, 1H), 7.30 (d, J = 1.8 Hz, 1H), 7.27 (d, J = 5.4 Hz, 1H), 7.25 (dd, J = 8.1, 1.9 Hz, 1H), 4.31 (s, 4H), 3.89 (s, 6H), 3.17 (s, 4H). HRMS (ESI) MS m/z calcd for C$_{22}$H$_{24}$N$_7$O$_3$S [M + H]$^+$ 466.1656, found 466.1647. Using thiomorpholine 1,1-dioxide at 135° C. for 18 hours. | 0.011 |
| 119 | N-(2-methoxy-4-(1-methyl-1H-pyrazol-4-yl)phenyl)-8-(7-oxa-2-azaspiro[3.5]nonan-2-yl)pyrido[3,4-d]pyrimidin-2-amine 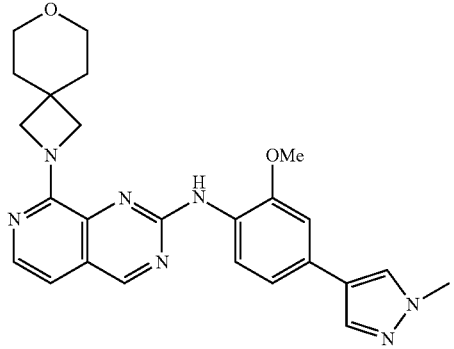 [SMILES: COc1cc(-c2cnn(C)c2)ccc1Nc1ncc2ccnc(N3CC4(CCOCC4)C3)c2n1] | $^1$H NMR (500 MHz, DMSO-d$_6$): δ 9.15 (s, 1H), 8.52 (s, 1H), 8.15 (s, 1H), 7.88 (d, J = 0.8 Hz, 1H), 7.82 (d, J = 8.2 Hz, 1H), 7.79 (d, J = 5.5 Hz, 1H), 7.26 (d, J = 1.8 Hz, 1H), 7.17 (dd, J = 8.2, 1.8 Hz, 1H), 6.91 (d, J = 5.5 Hz, 1H), 4.01 (s, 4H), 3.89 (d, J = 2.0 Hz, 6H), 3.50 (s, 4H), 1.72 (t, J = 5.1 Hz, 4H). HRMS (ESI) MS m/z calcd for C$_{25}$H$_{28}$N$_7$O$_2$ [M + H]$^+$ 458.2299, found 458.2289. Using N-methyl-2-pyrrolidinone at 135° C. for 3 hours and purification method D. | 0.003 |

| Example No | Name/Structure | Data | MPS1 IC50 (μM) |
|---|---|---|---|
| 120 | N-(2-methoxy-4-(1-methyl-1H-pyrazol-4-yl)phenyl)-8-(6-oxa-2-azaspiro[3.4]octan-2-yl)pyrido[3,4-d]pyrimidin-2-amine 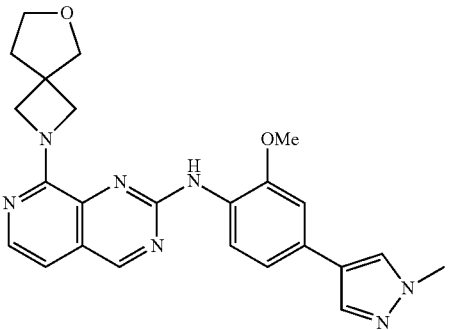 [SMILES: COc1cc(-c2cnn(C)c2)ccc1Nc1ncc2ccnc(N3CC4(CCOC4)C3)c2n1] | $^1$H NMR (500 MHz, DMSO-d$_6$): δ 9.17 (s, 1H), 8.48 (s, 1H), 8.15 (d, J = 0.9 Hz, 1H), 7.91-7.86 (m, 2H), 7.83 (d, J = 5.5 Hz, 1H), 7.25 (d, J = 1.8 Hz, 1H), 7.17 (dd, J = 8.2, 1.8 Hz, 1H), 6.96 (d, J = 5.5 Hz, 1H), 4.25 (s, 4H), 3.90 (s, 3H), 3.88 (s, 3H), 3.81 (s, 2H), 3.71 (t, J = 6.9 Hz, 2H), 2.14 (t, J = 6.9 Hz, 2H). HRMS (ESI) MS m/z calcd for C$_{24}$H$_{26}$N$_7$O$_2$ [M + H]$^+$ 444.2142, found 444.2127. Using 6-oxa-2-azaspiro[3.4]octane oxalate and triethylamine at 135° C. for 2 hours and purification method D. | 0.003 |
| 121 | 1-(2-(2-methoxy-4-(1-methyl-1H-pyrazol-4-yl)phenylamino)pyrido[3,4-d]pyrimidin-8-yl)azetidine-3-carbonitrile 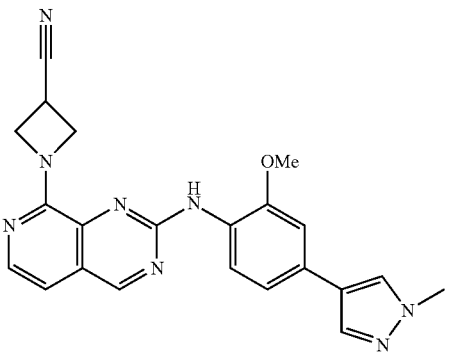 [SMILES: COc1cc(-c2cnn(C)c2)ccc1Nc1ncc2ccnc(N3CC(C#N)C3)c2n1] | $^1$H NMR (500 MHz, DMSO-d$_6$): δ 9.21 (s, 1H), 8.61 (s, 1H), 8.16 (d, J = 0.8 Hz, 1H), 7.89 (s, 1H), 7.87 (d, J = 5.5 Hz, 1H), 7.82 (d, J = 8.2 Hz, 1H), 7.27 (d, J = 1.9 Hz, 1H), 7.20 (dd, J = 8.2, 1.8 Hz, 1H), 7.07 (d, J = 5.5 Hz, 1H), 4.54 (t, J = 8.8 Hz, 2H), 4.42-4.32 (m, 2H), 3.90 (s, 3H), 3.89-3.84 (m, 4H). HRMS (ESI) MS m/z calcd for C$_{22}$H$_{21}$N$_8$O [M + H]$^+$ 413.1833, found 413.1817. Using azetidine-3-carbonitrile hydrochloride and triethylamine at 135° C. for 8 hours. | 0.008 |
| 122 | N-(2-methoxy-4-(1-methyl-1H-pyrazol-4-yl)phenyl)-8-(2-oxa-7-azaspiro[4.4]nonan-7-yl)pyrido[3,4-d]pyrimidin-2-amine 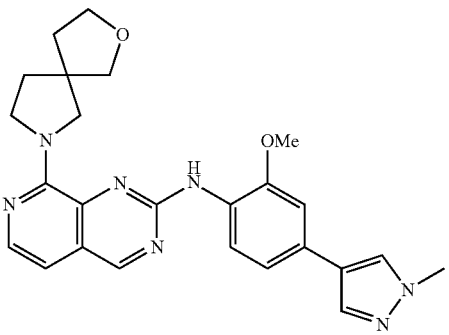 [SMILES: COc1cc(-c2cnn(C)c2)ccc1Nc1ncc2ccnc(N3CCC4(CCOC4)C3)c2n1] | $^1$H NMR (500 MHz, DMSO-d$_6$): δ 9.12 (s, 1H), 8.51 (s, 1H), 8.14 (d, J = 0.8 Hz, 1H), 7.88 (d, J = 0.8 Hz, 1H), 7.81 (d, J = 5.4 Hz, 1H), 7.72 (d, J = 8.1 Hz, 1H), 7.25 (d, J = 1.9 Hz, 1H), 7.16 (dd, J = 8.1, 1.8 Hz, 1H), 6.88 (d, J = 5.4 Hz, 1H), 3.88 (s, 3H), 3.87 (s, 3H), 3.86-3.66 (m, 6H), 3.58-3.46 (m, 2H), 1.88-1.78 (m, 4H). HRMS (ESI) MS m/z calcd for C$_{25}$H$_{28}$N$_7$O$_2$ [M + H]$^+$ 458.2299, found 458.2292. Using 2-oxa-7-azaspiro[4.4]nonane at 135° C. for 2 hours. | 0.003 |

-continued

| Example No | Name/Structure | Data | MPS1 IC50 (μM) |
|---|---|---|---|
| 123 | N-(2-methoxy-4-(1-methyl-1H-pyrazol-4-yl)phenyl)-8-(2-oxa-6-azaspiro[3.5]nonan-6-yl)pyrido[3,4-d]pyrimidin-2-amine | $^1$H NMR (500 MHz, MeOD): δ 9.17 (s, 1H), 8.44 (d, J = 8.1 Hz, 1H), 8.05-7.94 (m, 1H), 7.87 (s, 1H), 7.24 (s, 1H), 7.19 (d, J = 5.4 Hz, 1H), 7.19-7.12 (m, 1H), 6.98 (s, 1H), 4.09-3.99 (m, 5H), 3.99-3.91 (m, 5H), 3.87-3.77 (m, 2H), 2.84 (t, J = 7.4 Hz, 1H), 2.59 (t, J = 7.4 Hz, 1H), 2.06-1.94 (m, 2H), 1.90-1.78 (m, 2H). HRMS (ESI) MS m/z calcd for $C_{25}H_{28}N_7O_2$ [M + H]$^+$ 458.2299, found 458.2299. Using 2-oxa-6-azaspiro[3.5]nonane at 135° C. for 24 hours. | 0.011 |
| 124 | $N^8$-((3-fluorooxetan-3-yl)methyl)-$N^2$-(2-methoxy-4-(1-methyl-1H-pyrazol-4-yl)phenyl)pyrido[3,4-d]pyrimidine-2,8-diamine | $^1$H NMR (500 MHz, MeOD): δ 9.22 (s, 1H), 8.21 (d, J = 8.3 Hz, 1H), 8.02 (s, 1H), 7.87 (d, J = 0.9 Hz, 1H), 7.49 (d, J = 7.1 Hz, 1H), 7.30-7.24 (m, 2H), 7.20 (d, J = 7.1 Hz, 1H), 4.01 (s, 2H), 3.97 (s, 2H), 3.62 (s, 6H), 3.44-3.20 (m, 2H). HRMS (ESI) MS m/z calcd for $C_{22}H_{23}FN_7O_2$ [M + H]$^+$ 436.1892, found 436.1887. Using (3-fluorooxetan-3-yl)methanamine and TFA in 2,2,2-trifluoroethanol at 130° C. for 7 hours and purification method E. | >1 |
| 125 | Racemic $N^2$-(2-methoxy-4-(1-methyl-1H-pyrazol-4-yl)phenyl)-$N^8$-(1-(tetrahydrofuran-3-yl)ethyl)pyrido[3,4-d]pyrimidine-2,8-diamine | $^1$H NMR (500 MHz, DMSO-d$_6$): δ 9.18 (s, 1H), 8.49 (s, 1H), 8.44 (s, 1H), 8.16 (dd, J = 33.1, 8.3 Hz, 1Ha), 8.16 (d, J = 6.4 Hz, 1Hb), 7.89 (dd, J = 7.2, 0.8 Hz, 1H), 7.78 (dd, J = 5.6, 4.7 Hz, 1H), 7.28 (dd, J = 3.6, 1.8 Hz, 1H), 7.20 (d, J = 8.3 Hz, 1H), 6.87 (dd, J = 5.7, 1.4 Hz, 1H), 6.68 (dd, J = 23.9, 8.6 Hz, 1H), 4.30-4.18 (m, 1H), 3.94 (s, 3Ha), 3.93 (s, 3Hb), 3.88 (s, 3H), 3.86-3.71 (m, 2H), 3.70-3.59 (m, 1H), 3.51-3.43 (m, 1H), 2.60-2.53 (m, 1H), 2.07-1.95 (m, 1H), 1.69 (ddd, J = 19.6, 12.2, 7.6 Hz, 1H), 1.25 (d, J = 6.5 Hz, 3Ha), 1.22 (d, J = 6.5 Hz, 3Hb). HRMS (ESI) MS m/z calcd for $C_{24}H_{28}N_7O_2$ [M + H]$^+$ 446.2299, found 446.2288. Using racemic 1-(tetrahydrofuran-3-yl)ethanamine at 135° C. for 24 hours. | 0.003 |
| 126 | 2-(2-(2-Methoxy-4-(1-methyl-1H-pyrazol-4-yl)phenylamino)pyrido[3,4-d]pyrimidin-8-ylamino)ethanol | $^1$H NMR (500 MHz, CD$_3$OD): δ 8.92 (s, 1H), 8.34 (d, J = 8.3 Hz, 1H), 7.86 (d, J = 0.8 Hz, 1H), 7.78 (d, J = 0.8 Hz, 1H), 7.66 (d, J = 5.8 Hz, 1H), 7.12 (dd, J = 8.3, 1.9 Hz, 1H), 7.07 (d, J = 1.9 Hz, 1H), 6.76 (d, J = 5.8 Hz, 1H), 3.94 (s, 3H), 3.92 (s, 3H), 3.87 (dd, J = 5.8, 4.9 Hz, 2H), 3.67 (dd, J = 5.8, 4.9 Hz, 2H). HRMS (ESI) MS m/z calcd for $C_{20}H_{22}N_7O_2$ [M + H]$^+$ 392.1819, found: 392.1819. Using ethanolamine at 130° C. for 5 hours and purification method F. | 0.011 |

-continued

| Example No | Name/Structure | Data | MPS1 IC50 (μM) |
|---|---|---|---|
| 127 | N²-(2-Methoxy-4-(1-methyl-1H-pyrazol-4-yl)phenyl)-N⁸-(2-methoxyethyl)pyrido[3,4-d]pyrimidine-2,8-diamine | ¹H NMR (500 MHz, CD₃OD): δ 8.98 (d, J = 1.7 Hz, 1H). 8.33 (d, J = 8.1 Hz, 1H), 7.91 (s, 1H), 7.80 (s, 1H), 7.70 (d, J = 5.7 Hz, 1H), 7.13 (m, 2H), 6.81 (d, J = 5.7 Hz, 1H), 3.98 (s, 3H), 3.94 (s, 3H), 3.71 (s, 4H), 3.49 (s, 3H). HRMS (ESI) MS m/z calcd for C₂₁H₂₄N₇O₂ [M + H]⁺ 406.1986, found: 406.1979. Using 2-methoxyethylamine at 130° C. for 5 hours and purification method F. | 0.008 |
| 128 | Racemic 1-(2-(2-Methoxy-4-(1-methyl-1H-pyrazol-4-yl)phenylamino)pyrido[3,4-d]pyrimidin-8-ylamino)propan-2-ol | ¹H NMR (500 MHz, CD₃OD):δ 8.98 (s, 1H), 8.41 (d, J = 8.3 Hz, 1H), 7.91 (s, 1H), 7.81 (s, 1H), 7.69 (d, J = 5.7 Hz, 1H), 7.18 (d, J = 8.3 Hz, 1H), 7.13 (s, 1H), 6.80 (d, J = 5.7 Hz, 1H), 4.04-4.14 (m, 1H), 3.98 (s, 3H), 3.94 (s, 3H), 3.70 (dd, J = 13.5, 3.6 Hz, 1H), 3.37 (dd, J = 13.5, 7.6 Hz, 1H), 1.31 (d, J = 6.2 Hz, 3H). HRMS (ESI) MS m/z calcd for C₂₁H₂₄N₇O₂ [M + H]⁺ 406.1986, found 406.1978. Using Racemic 1-aminopropan-2-ol at 130° C. for 5 hours and purification method F. | 0.008 |
| 129 | Racemic 2-(2-(2-Methoxy-4-(1-methyl-1H-pyrazol-4-yl)phenylamino)pyrido[3,4-d]pyrimidin-8-ylamino)propan-1-ol | ¹H NMR (500 MHz, CD₃OD): δ 8.92 (s, 1H), 8.32 (d, J = 8.3 Hz, 1H), 7.86 (d, J = 0.8 Hz, 1H), 7.77 (d, J = 0.8 Hz, 1H), 7.66 (d, J = 5.8 Hz, 1H), 7.11 (dd, J = 8.3, 1.9 Hz, 1H), 7.07 (d, J = 1.9 Hz, 1H), 6.75 (d, J = 5.8 Hz, 1H), 4.22 (qt, J = 6.6, 4.5 Hz, 1H), 3.94 (s, 3H), 3.91 (s, 3H), 3.78 (dd, J = 10.9, 4.5 Hz, 1H), 3.72 (dd, J = 10.9, 4.5 Hz, 1H), 1.37 (d, J = 6.6 Hz, 3H), HRMS (ESI) MS m/z calcd for C₂₁H₂₄N₇O₂ [M + H]⁺ 406.1986, found 406.1976. Using DL-alaninol and triethylamine at 130° C. for 1.5 hours. | 0.007 |
| 130 | 2-(2-(2-Methoxy-4-(1-methyl-1H-pyrazol-4-yl)phenylamino)pyrido[3,4-d]pyrimidin-8-ylamino)propane-1,3-diol | ¹H NMR (500 MHz, CD₃OD): δ 9.07 (s, 1H), 8.49 (d, J = 8.3 Hz, 1H), 7.96 (d, J = 0.8 Hz, 1H), 7.84 (d, J = 0.8 Hz, 1H), 7.75 (d, J = 5.8 Hz, 1H), 7.23 (dd, J = 8.3, 1.9 Hz, 1H), 7.21 (d, J = 1.9 Hz, 1H), 6.89 (d, J = 5.8 Hz, 1H), 4.20 (quin, J = 5.2 Hz, 1H), 4.02 (s, 3H), 3.95 (s, 3H), 3.89 (dd, J = 11.0, 5.2 Hz, 2H), 3.83 (dd, J = 11.0, 5.2 Hz, 2H). HRMS (ESI) MS m/z calcd for C₂₁H₂₄N₇O₃ [M + H]⁺ 422.1935, found 422.1929 Using 2-aminopropane-1,3-diol and triethylamine in DMA at 130° C. for 4 hours and purification method G. | 0.004 |

| Example No | Name/Structure | Data | MPS1 IC50 (μM) |
|---|---|---|---|
| 131 | 3-Methoxy-2-(2-(2-methoxy-4-(1-methyl-1H-pyrazol-4-yl)phenylamino)pyrido[3,4-d]pyrimidin-8-ylamino)propan-1-ol<br>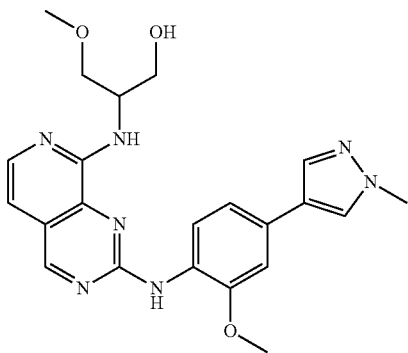 [SMILES: COCC(CO)Nc1nccc2cnc(Nc3ccc(-c4cnn(C)c4)cc3OC)nc12] | ¹H NMR (500 MHz, CD₃OD): δ 9.04 (s, 1H), 8.40 (d, J = 8.8 Hz, 1H), 7.94 (d, J = 0.8 Hz, 1H), 7.82 (d, J = 0.8 Hz, 1H), 7.74 (d, J = 5.8 Hz, 1H), 7.17-7.20 (m, 2H), 6.86 (d, J = 5.8 Hz, 1H), 4.31 (tt, J = 5.6, 4.4 Hz, 1H), 4.01 (s, 3H), 3.95 (s, 3H), 3.88 (dd, J = 10.9, 4.4 Hz, 1H), 3.75-3.81 (m, 2H), 3.66 (dd, J = 9.4, 5.6 Hz, 1H), 3.48 (s, 3H). HRMS (ESI) MS m/z calcd for C₂₂H₂₆N₇O₃ [M + H]⁺ 436.2092, found 436.2085. Using 2-amino-3-methoxypropan-1-ol and triethylamine at 130° C. for 5 hours followed by purification method F. | 0.004 |
| 132 | (3-((2-(2-Methoxy-4-(1-methyl-1H-pyrazol-4-yl)phenylamino)pyrido[3,4-d]pyrimidin-8-ylamino)methyl)oxetan-3-yl)methanol<br>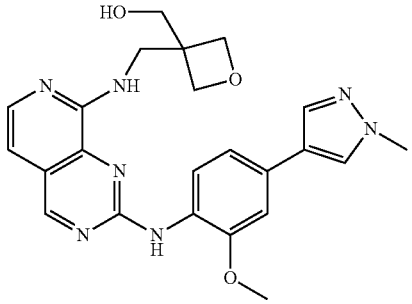 [SMILES: COc1cc(-c2cnn(C)c2)ccc1Nc1ncc2ccnc(NCC3(CO)COC3)c2n1] | ¹H NMR (500 MHz, DMSO-d₆): δ 8.75 (s, 1H), 8.43 (d, J = 8.2 Hz, 1H), 8.16 (s, 1H), 8.14 (s, 1H), 7.88 (s, 1H), 7.24 (d, J = 2.0 Hz, 1H), 7.18 (dd, J = 8.2, 2.0 Hz, 1H), 6.83 (d, J = 7.3 Hz, 1H), 6.08 (d, J = 7.3 Hz, 1H), 4.75 (m, 2H), 3.94 (s, 3H), 3.87 (s, 3H), 3.68 (s, 2H), 3.40 (s, 2H), 3.34 (s, 4H). HRMS (ESI) MS m/z calcd for C₂₃H₂₆N₇O₃ [M + H]⁺ 448.2092, found 448.2086. Using (3-(aminomethyl)oxetan-3-yl)methanol at 130° C. for 3 hours and purification method I. | >1 |
| 133 | (1-(2-(2-Methoxy-4-(1-methyl-1H-pyrazol-4-yl)phenylamino)pyrido[3,4-d]pyrimidin-8-yl)pyrrolidin-3-yl)methanol<br>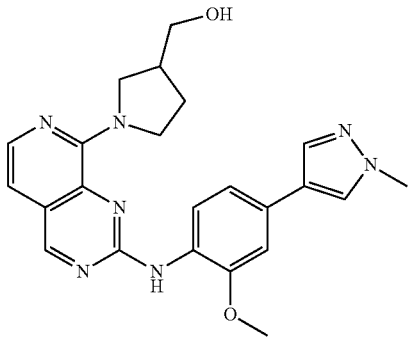 [SMILES: COc1cc(-c2cnn(C)c2)ccc1Nc1ncc2ccnc(N3CCC(CO)C3)c2n1] | ¹H NMR (500 MHz, CDCl₃): δ 8.94 (s, 1H), 8.29 (d, J = 8.3 Hz, 1H), 7.94 (d, J = 5.5 Hz, 1H), 7.76 (d, J = 0.8 Hz, 1H), 7.73 (s, 1H), 7.61 (d, J = 0.8 Hz, 1H), 7.12 (dd, J = 8.3, 1.9 Hz, 1H), 7.00 (d, J = 1.9 Hz, 1H), 6.75 (d, J = 5.5 Hz, 1H), 4.21 (dd, J = 11.7, 7.4 Hz, 1H), 4.14 (ddd, J = 11.9, 7.9, 4.2 Hz, 1H), 3.98-4.05 (m, 1H), 3.97 (s, 3H), 3.97 (s, 3H), 3.89 (dd, J = 11.7, 7.4 Hz, 1H), 3.76 (d, J = 6.7 Hz, 2H), 2.52-2.63 (m, 1H), 2.16 (dtd, J = 11.8, 7.0, 4.2 Hz, 1H), 1.97 (br s, 1H), 1.82 (dq, J = 11.8, 7.9 Hz, 1H). HRMS (ESI) MS m/z calcd for C₂₃H₂₆N₇O₂ [M + H]⁺ 432.2142, found 432.2150. Using pyrrolidin-3-ylmethanol and triethylamine at 130° C. for 4.5 hours and purification method J. | 0.003 |

| Example No | Name/Structure | Data | MPS1 IC50 (μM) |
|---|---|---|---|
| 134 | (1-(2-(2-Methoxy-4-(1-methyl-1H-pyrazol-4-yl)phenylamino)pyrido[3,4-d]pyrimidin-8-yl)piperidin-3-yl)methanol 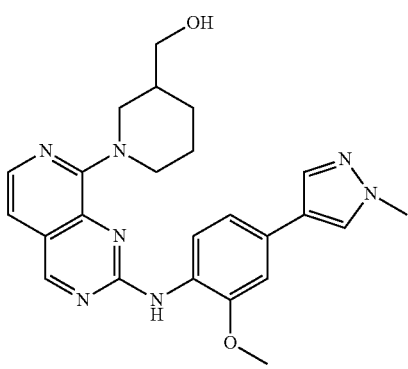 [SMILES: COc1cc(-c2cnn(C)c2)ccc1Nc1ncc2ccnc(N3CCCC(CO)C3)c2n1] | $^1$H NMR (500 MHz, CDCl$_3$): δ 9.04 (s, 1H), 8.65 (d, J = 8.3 Hz, 1H), 8.01 (s, 1H), 8.00 (d, J = 5.5 Hz, 1H), 7.79 (d, J = 0.8 Hz, 1H), 7.65 (d, J = 0.8 Hz, 1H), 7.19 (dd, J = 8.3, 1.9 Hz, 1H), 7.03 (d, J = 1.9 Hz, 1H), 6.97 (d, J = 5.5 Hz, 1H), 4.12-4.21 (m, 1H), 3.97-4.09 (m, 2H), 4.00 (s, 3H), 3.98 (s, 3H), 3.56-3.71 (m, 3H), 3.61 (br s, 1H), 2.14-2.23 (m, 1H), 2.00 (ddt, J = 12.4, 8.2, 4.4 Hz, 1H), 1.65-1.88 (m, 2H), 1.43-1.52 (m, 1H). HRMS (ESI) MS m/z calcd for C$_{24}$H$_{28}$N$_7$O$_2$ [M + H]$^+$ 446.2299, found 446.2303. Using piperidin-3-ylmethanol and triethylamine at 130° C. for 4.5 hours and purification method J. | 0.004 |
| 135 | (4-(2-(2-Methoxy-4-(1-methyl-1H-pyrazol-4-yl)phenylamino)pyrido[3,4-d]pyrimidin-8-yl)morpholin-2-yl)methanol 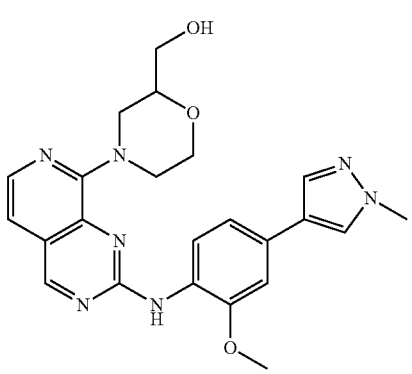 [SMILES: COc1cc(-c2cnn(C)c2)ccc1Nc1ncc2ccnc(N3CCOC(CO)C3)c2n1] | $^1$H NMR (500 MHz, CDCl$_3$): δ 9.07 (s, 1H), 8.61 (d, J = 8.2 Hz, 1H), 8.07 (d, J = 5.4 Hz, 1H), 8.04 (s, 1H), 7.79 (d, J = 0.8 Hz, 1H), 7.68 (d, J = 0.8 Hz, 1H), 7.19 (dd, J = 8.2, 1.8 Hz, 1H), 7.08 (d, J = 5.4 Hz, 1H), 7.05 (d, J = 1.8 Hz, 1H), 4.56-4.65 (m, 2H), 4.17 (ddd, J = 11.4, 3.4, 1.7 Hz, 1H), 4.06-4.13 (m, 2H), 4.01 (s, 3H), 3.98 (s, 3H), 3.67-3.81 (m, 2H), 3.22 (ddd, J = 12.8, 11.4, 3.4 Hz, 1H), 2.96 (dd, J = 12.5, 10.4 Hz, 1H), 2.20 (d, J = 6.5Hz, 1H). HRMS (ESI) MS m/z calcd for C$_{23}$H$_{26}$N$_7$O$_3$ [M + H]$^+$ 448.2092. found 448.2098. Using morpholin-2-ylmethanol and triethylamine at 130° C. for 4.5 hours and purification method J. | 0.004 |
| 136 | 6-Cyclopropyl-N-(2-methoxy-4-(1-methyl-1H-pyrazol-4-yl)phenyl)-8-(2-oxa-6-azaspiro[3.4]octan-6-yl)pyrido[3,4-d]pyrimidin-2-amine 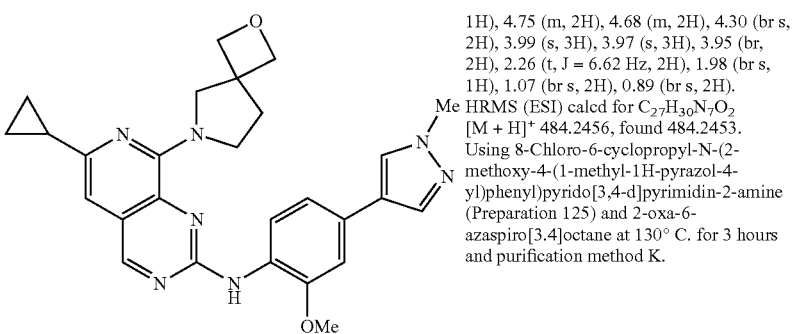 | $^1$H NMR (500 MHz, CDCl$_3$): δ 8.90 (s, 1H), 8.29 (br d, J = 7.25 Hz, 1H), 7.76 (s, 1H), 7.66 (s, 1H), 7.62 (s, 1H), 7.12 (dd, J = 1,89, 8.20 Hz, 1H), 7.03 (s, 1H), 6.70 (s, 1H), 4.75 (m, 2H), 4.68 (m, 2H), 4.30 (br s, 2H), 3.99 (s, 3H), 3.97 (s, 3H), 3.95 (br, 2H), 2.26 (t, J = 6.62 Hz, 2H), 1.98 (br s, 1H), 1.07 (br s, 2H), 0.89 (br s, 2H). HRMS (ESI) calcd for C$_{27}$H$_{30}$N$_7$O$_2$ [M + H]$^+$ 484.2456, found 484.2453. Using 8-Chloro-6-cyclopropyl-N-(2-methoxy-4-(1-methyl-1H-pyrazol-4-yl)phenyl)pyrido[3,4-d]pyrimidin-2-amine (Preparation 125) and 2-oxa-6-azaspiro[3.4]octane at 130° C. for 3 hours and purification method K. | 0.093 |

| Example No | Name/Structure | Data | MPS1 IC50 (μM) |
|---|---|---|---|
| 137 | Racemic N-(2-Mthoxy-4-(1-methyl-1H-pyrazol-4-yl)phenyl)-8-(2-methylmorpholino)pyrido[3,4-d]pyrimidin-2-amine 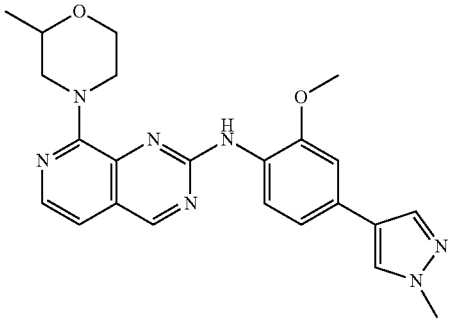 [SMILES: COc1cc(-c2cnn(C)c2)ccc1Nc1ncc2ccnc(N3CCOC(C)C3)c2n1] | $^1$H NMR (500 MHz, CDCl$_3$): δ 9.06 (s, 1H), 8.6 (d, J = 8.3 Hz, 1H), 8.07 (d J = 5.5 Hz, 1H), 8.04 (s, 1H), 7.77 (s, 1H), 7.63 (s, 1H), 7.13 (dd, J = 8.3, 1.8 Hz, 1H), 7.05 (d, J = 5.4 Hz, 1H), 7.04 (d, J = 1.8 Hz, 1H), 4.59 (d, J = 12 Hz, 2H), 4.16-4.1 (m, 3H), 4 (s, 3H), 3.98 (s, 3H), 3.18-3.16 (m, 1H), 2.81-2.79 (m, 1H), 1.26 (d, J = 6.3 Hz, 3H). HRMS (ESI) calcd for C$_{23}$H$_{25}$N$_7$NaO$_2$ [M + H]$^+$ 454.1962, found 454.1956. Using racemic 2-methylmorpholine hydrochloride with triethylamine at 135° C. for 18 hours and purification method B. | 0.007 |
| 138 | N-(2-Methoxy-4-(1-methyl-1H-pyrazol-4-yl)phenyl)-8-(4-methoxypiperidin-1-yl)pyrido[3,4-d]pyrimidin-2-amine 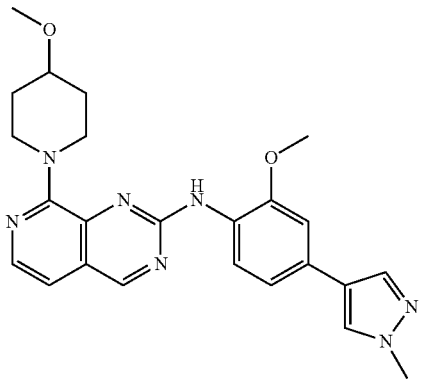 [SMILES: COc1cc(-c2cnn(C)c2)ccc1Nc1ncc2ccnc(N3CCC(OC)CC3)c2n1] | $^1$H NMR (500 MHz, CDCl$_3$); δ 9.04 (s, 1H), 8.06 (s, 1H), 8.05 (d, J = 5.4 Hz, 1H), 7.77 (s, 1H), 7.64 (s, 1H), 7.17 (dd, J = 8.3, 1.8 Hz, 1H), 7.03 (d, J = 1.8 Hz, 1H), 7.01 (d, J = 5.4 Hz, 1H), 4.44-4.42 (m, 2H), 4 (s, 3H), 3.98 (s, 3H), 3.52-3.5 (m, 1H), 3.46 (s, 3H), 3.39-3.41 (m, 2H), 2.2-2.18 (m, 2H), 1.92-1.9 (m, 2H). HRMS (ESI) calcd for C$_{24}$H$_{28}$N$_7$O$_2$ [M + H]$^+$ 446.2299, found 446.229. Using 4-methoxypiperidine hydrochloride with triethylamine at 135° C. for 18 hours and purification method L. | 0.008 |
| 139 | N-(2-Methoxy-4-(1-methyl-1H-pyrazol-4-yl)phenyl)-8-(4-(methylsulfonyl)piperazin-1-yl)pyrido[3,4-d]pyrimidin-2-amine 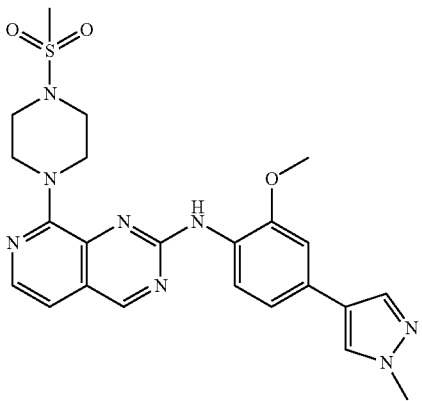 [SMILES: COc1cc(-c2cnn(C)c2)ccc1Nc1ncc2ccnc(N3CCN(S(C)(=O)=O)CC3)c2n1] | $^1$H NMR (500 MHz, CDCl$_3$): δ 9.08 (s, 1H), 8.48 (d, J = 7.1 Hz, 1H), 8.06 (d, J = 5.4 Hz, 1H), 1H), 7.99 (s, 1H), 7.77 (s, 1H), 7.65 (s, 1H), 7.09 (dd, J = 5.4, 1.8 Hz, 2H), 7.05 (d, J = 1.8 Hz, 1H), 4.08 (br, s, 2H), 4 (s, 3H). 3.98 (s, 3H), 3.51 (t, J = 5 Hz, 2H), 2.86 (s, 3H), 2.39-2.37 (m, 1H), 2.06-2.04 (m, 1H), 1.61 (br s, 2H). HRMS (ESI) calcd for C$_{23}$H$_{27}$N$_8$O$_3$S [M + H]$^+$ 495.1921, found 495.1914. Using 1-(methylsulfonyl)piperazine at 135° C. for 18 hours and purification method L. | 0.006 |

| Example No | Name/Structure | Data | MPS1 IC50 (μM) |
|---|---|---|---|
| 140 | 1-(2-(2-Methoxy-4-(1-methyl-1H-pyrazol-4-yl)phenylamino)pyrido[3,4-d]pyrimidin-8-yl)piperidine-4-carbonitrile 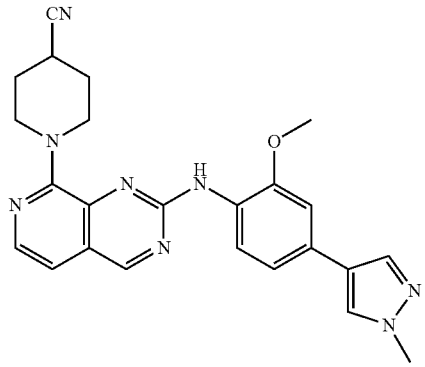 [SMILES: COc1cc(-c2cnn(C)c2)ccc1Nc1ncc2ccnc(N3CCC(C#N)CC3)c2n1] | $^1$H NMR (500 MHz, CDCl$_3$): δ 9.05 (s, 1H), 8.59 (d, J = 8.3 Hz, 1H), 8.05 (d, J = 5.5 Hz, 1H), 8.04 (s, 1H), 7.78 (s, 1H), 7.66 (s, 1H), 7.14 (dd, J = 8.3, 1.8 Hz, 1H), 7.06 (d, J = 5.4 Hz, 1H), 7.04 (d, J = 1.8 Hz, 1H), 4.27-4.24 (m, 2H), 4 (s, 3H), 3.98 (s, 3H), 3.67 (br, s, 2H), 2.95- 2.93 (m, 1H), 2.23-2.17 (m, 4H). HRMS (ESI) calcd for C$_{24}$H$_{25}$N$_8$O [M + H]$^+$ 441.2146, found 441.2138. Using 4-cyanopiperidine at 135° C. for 18 hours and purification method L. | 0.004 |

Examples 141 and 142

(S)—N$^2$-(2-methoxy-4-(1-methyl-1H-pyrazol-4-yl)phenyl)-N$^3$-((3-methyltetrahydrofuran-3-yl)methyl)pyrido[3,4-d]pyrimidine-2,8-diamine and (R)—N$^2$-(2-methoxy-4-(1-methyl-1-pyrazol-4-yl)phenyl)-N$^3$-((3-methyltetrahydrofuran-3-yl)methyl)pyrido[3,4-d]pyrimidine-2,8-diamine The title compounds were separated by Preparative HPLC (chiralpak IA 90/10 MeCN/IPA (0.1% diethylamine)) from racemic N2-(2-methoxy-4-(1-methyl-1H-pyrazol-4-yl)phenyl)-N8-((3-methyltetrahydrofuran-3-yl)methyl)pyrido[3,4-d]pyrimidine-2,8-diamine (Example 117).

Example 141

(S)—N$^2$-(2-methoxy-4-(1-methyl-1H-pyrazol-4-yl)phenyl)-N$^3$-((3-methyltetrahydrofuran-3-yl)methyl)pyrido[3,4-d]pyrimidine-2,8-diamine LCMS (ESI) Rt=2.35 minutes MS m/z 446 [M+H]$^+$, 99% ee

MPS1 IC50 (μM): 0.003

Example 142

(R)—N$^2$-(2-methoxy-4-(1-methyl-1H-pyrazol-4-yl)phenyl)-N$^3$-((3-methyltetrahydrofuran-3-yl)methyl)pyrido[3,4-d]pyrimidine-2,8-diamine LCMS (ESI) Rt=2.36 minutes MS m/z 446 [M+H]$^+$, 97% ee

MPS1 IC50 (μM): 0.003

Example 143

(±)-N-(2-(2-methoxy-4-(1-methyl-1H-pyrazol-4-yl)phenylamino)pyrido[3,4-d]pyrimidin-8-yl)-2-methylpropane-2-sulfinamide

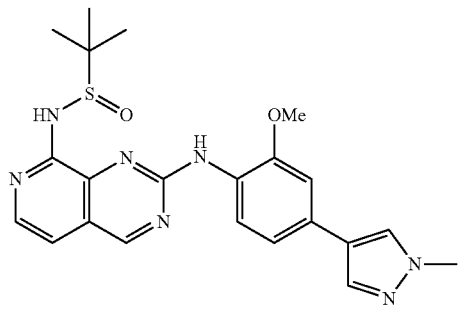 [SMILES: COc1cc(-c2cnn(C)c2)ccc1Nc1ncc2ccnc(NS(=O)C(C)(C)C)c2n1]

A mixture of 8-chloro-N-(2-methoxy-4-(1-methyl-1H-pyrazol-4-yl)phenyl)pyrido[3,4-d]pyrimidin-2-amine (Example 94, 27 mg, 0.074 mmol), (±)-2-methyl-2-propanesulfinamide (12 mg, 0.099 mmol), palladium(II) acetate (1 mg, 4.44 μmol), cesium carbonate (48 mg, 0.147 mmol) and Xantphos (5 mg, 8.64 μmol) in 1,4-dioxane (0.7 mL) (degassed) was stirred at 100° C. for 18 hours. The reaction was quenched with water and extracted with EtOAc. The combined organic layers were washed with brine, dried and concentrated in vacuo. The residue was purified by silica gel column chromatography eluting with 0 to 90% EtOAc in cyclohexane to give the title compound (14 mg, 42%).

$^1$H NMR (500 MHz, DMSO-d$_6$): δ 9.35 (s, 1H), 9.01 (s, 1H), 8.19 (d, J=1.0 Hz, 1H), 8.08 (s, 1H), 7.98 (d, J=5.6 Hz, 1H), 7.95-7.91 (m, 2H), 7.36 (d, J=5.6 Hz, 1H), 7.30 (d, J=1.9 Hz, 1H), 7.17 (dd, J=8.2, 1.8 Hz, 1H), 3.90 (s, 3H), 3.89 (s, 3H), 1.27 (s, 9H).

HRMS (ESI) MS m/z calcd for C$_{22}$H$_{26}$N$_7$O$_2$S [M+H]$^+$ 452.1863. found 452.1856.

MPS1 IC50 (μM): 0.005

Example 144

8-(3,6-Dihydro-2H-pyran-4-yl)-N-(2-methoxy-4-(1-methyl-1H-pyrazol-4-yl)phenyl)pyrido[3,4-d]pyrimidin-2-amine

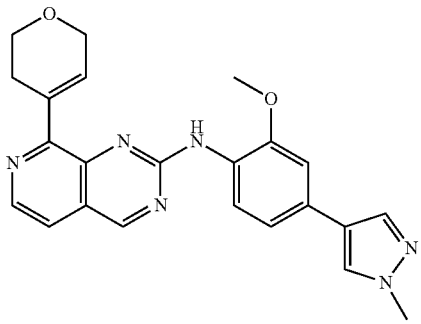 [SMILES: COc1cc(-c2cnn(C)c2)ccc1Nc1ncc2ccnc(C3=CCOCC3)c2n1]

The title compound was prepared according to the method described for Example 91 using 8-chloro-N-(2-methoxy-4-(1-methyl-1H-pyrazol-4-yl)phenyl)pyrido[3,4-d]pyrimidin-2-amine (Example 94) and 2-(3,6-dihydro-2H-pyran-4-yl)-4,4,5,5-tetramethyl-1,3,2-dioxaborolane.

$^1$H NMR (500 MHz, CDCl$_3$): δ 9.14 (s, 1H), 8.8 (d, J=8.3 Hz, 1H), 8.46 (d, J=5.3 Hz, 1H), 8.07 (s, 1H), 7.77 (s, 1H), 7.64 (s, 1H), 7.42 (d, J=5.3, 1H), 7.17-7.13 (m, 2H), 7.03 (d, J=1.8 Hz, 1H), 4.53 (q, J=2.7 Hz, 2H), 4.07 (t, J=5.4 Hz, 2H), 4 (s, 3H), 3.98 (s, 3H), 2.9-2.88 (m, 2H).

HRMS (ESI) calcd for C$_{23}$H$_{23}$N$_6$O$_2$ [M+H]$^+$ 415.1877. found 415.1875.

MPS1 IC50 (μM): 0.005

The following Examples were prepared according to Method 5 (Example 54) above using 8-chloro-N-(4-(1,5-dimethyl-1H-pyrazol-4-yl)-2-methoxyphenyl)pyrido[3,4-d]pyrimidin-2-amine (Preparation 117) and the appropriate amine as described. The crude reaction residues were purified as described or according to one of the following methods:

Method A: Silica gel column chromatography eluting with 0-5% MeOH in DCM or EtOAc.

Method B: Silica gel column chromatography eluting with 0-90% EtOAc in cyclohexanes.

| Example No | Name/Structure | Data | MPS1 IC50 (μM) |
|---|---|---|---|
| 145 | N-(4-(1,5-dimethyl-1H-pyrazol-4-yl)-2-methoxyphenyl)-8-(2-oxa-6-azaspiro[3.4]octan-6-yl)pyrido[3,4-d]pyrimidin-2-amine | $^1$H NMR (500 MHz, DMSO-D6): δ 9.15 (d, J = 0.9 Hz, 1H), 8.56 (s, 1H), 7.86-7.76 (m, 2H), 7.61 (s, 1H), 7.07 (d, J = 1.9 Hz, 1H), 7.02 (dd, J = 8.1, 1.8 Hz, 1H), 6.90 (d, J = 5.5 Hz, 1H), 4.49 (s, 4H), 4.12 (s, 2H), 3.88 (s, 3H), 3.80 (s, 3H), 3.73 (t, J = 6.9 Hz, 2H), 2.42 (s, 3H), 2.14 (t, J = 6.9 Hz, 2H). HRMS (ESI) MS m/z calcd for C$_{25}$H$_{28}$N$_7$O$_2$ [M + H]$^+$ 458.2299, found 458.229. Using 2-oxa-6-azaspiro[3.4]octane at 130° C. for 7 hours and purification method A. | 0.002 |
| 146 | N$^2$-(4-(1,5-dimethyl-1H-pyrazol-4-yl)-2-methoxyphenyl)-N$^8$-((3-methyloxetan-3-yl)methyl)pyrido[3,4-d]pyrimidine-2,8-diamine | $^1$H NMR (500 MHz, DMSO-d$_6$): δ 9.15 (s, 1H), 8.47 (s, 1H), 7.92 (d, J = 8.2 Hz, 1H), 7.80 (d, J = 5.5 Hz, 1H), 7.59 (s, 1H), 7.03 (d, J = 1.9 Hz, 1H), 6.97 (dd, J = 8.2, 1.9 Hz, 1H), 6.90 (d, J = 5.6 Hz, 1H), 4.89 (t, J = 5.3 Hz, 1H), 4.35 (br s, J = 5.7 Hz, 1H), 4.15 (br. s, 2H), 3.88 (br. s, 4H), 3.80 (s, 3H), 3.41 (d, J = 5.3 Hz, 2H), 2.40 (s, 3H), 1.23 (s, 3H). HRMS (ESI) MS m/z calcd for C$_{24}$H$_{28}$N$_7$O$_2$ [M + H]$^+$ 446.2299, found 446.2284. Using (3-methyloxetan-3-yl)methanamine at 130° C. for 8 hours and purification method A. | 0.004 |

-continued

| Example No | Name/Structure | Data | MPS1 IC50 (μM) |
|---|---|---|---|
| 147 | N²-(4-(1,5-dimethyl-1H-pyrazol-4-yl)-2-methoxyphenyl)-N⁸-(2-methoxy-2-methylpropyl)pyrido[3,4-d]pyrimidine-2,8-diamine | ¹H NMR (500 MHz, DMSO-d₆): δ 9.19 (s, 1H), 8.59 (s, 1H), 8.18 (d, J = 8.2 Hz, 1H), 7.78 (d, J = 5.6 Hz, 1H), 7.61 (s, 1H), 7.08 (d, J = 1.9 Hz, 1H), 6.98 (dd, J = 8.2, 1.9 Hz, 1H), 6.88 (d, J = 5.7 Hz, 1H), 6.67 (t, J = 5.5 Hz, 1H), 3.92 (s, 3H), 3.80 (s, 3H), 3.56 (d, J = 5.5 Hz, 2H), 3.21 (s, 3H), 2.41 (s, 3H), 1.19 (s, 6H). HRMS (ESI) MS m/z calcd for C₂₄H₃₀N₇O₂ [M + H]⁺ 448.2455, found 448.2447. Using 2-methoxy-2-methylpropan-1-amine at 130° C. and purification method B. | 0.002 |
| 148 | N²-(4-(1,5-dimethyl-1H-pyrazol-4-yl)-2-methoxyphenyl)-N⁸-((3-methyltetrahydrofuran-3-yl)methyl)pyrido[3,4-d]pyrimidine-2,8-diamine | ¹H NMR (500 MHz, DMSO-d₆): δ 9.19 (s, 1H), 8.53 (s, 1H), 8.26 (d, J = 8.2 Hz, 1H), 7.78 (d, J = 5.6 Hz, 1H), 7.60 (s, 1H), 7.07 (d, J = 1.9 Hz, 1H), 7.00 (dd, J = 8.2, 1.9 Hz, 1H), 6.88 (d, J = 5.7 Hz, 2H), 3.92 (s, 3H), 3.86 (td, J = 8.3, 5.6 Hz, 1H), 3.80 (s, 3H), 3.77 (td, J = 8.3, 6.9 Hz, 1H), 3.70 (d, J = 8.4 Hz, 1H), 3.57 (qd, J = 13.1, 6.0 Hz, 2H), 3.36 (d, J = 8.5 Hz, 1H), 2.41 (s, 3H), 1.92 (ddd, J = 12.2, 8.3, 6.8 Hz, 1H), 1.65 (ddd, J = 12.2, 8.1, 5.5 Hz, 1H), 1.15 (s, 3H). HRMS (ESI) MS m/z calcd for C₂₅H₃₀N₇O₂ [M + H]⁺ 460.2455, found 460.2445. Using (3-methyltetrahydrofuran-3-yl)methanamine at 135° C. for 24 hours and purification method B. | 0.003 |

Example 149

N²-(2-methoxy-4-(1-methyl-1H-pyrazol-4-yl)phenyl)-5-methyl-N³-neopentylpyrido[3,4-d]pyrimidine-2,8-diamine

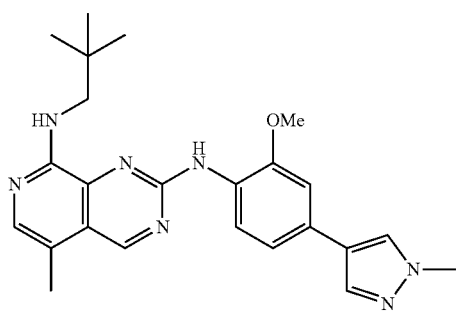 [SMILES: COc1cc(-c2cnn(C)c2)ccc1Nc1ncc2c(C)cnc(NCC(C)(C)C)c2n1]

A solution of N-(2-methoxy-4-(1-methyl-1H-pyrazol-4-yl)phenyl)formamide (Preparation 56, 35 mg, 0.151 mmol) in THF (1 mL) was treated with sodium hydride (60% w/w, 8 mg, 0.200 mmol) at 0° C. After stirring for 20 minutes at room temperature the mixture was cooled to 0° C. and 8-chloro-5-methyl-2-(methylsulfonyl)pyrido[3,4-d]pyrimidine (Preparation 184, 42 mg, 0.163 mmol) in THF (2 mL) was added. The reaction was allowed to reach room temperature and stirred for 18 hours. A solution of aqueous 2M NaOH (1 mL) and MeOH (1 mL) were added and the resulting mixture stirred at room temperature for 1 hour before concentrating in vacuo. The residue was partitioned between DCM and water. The aqueous layer was extracted with DCM and the combined organic layers were dried and concentrated in vacuo. The residue was purified by silica gel column chromatography eluting with 0 to 75% EtOAc in cyclohexanes to afford the intermediate that was combined with 2,2-dimethylpropan-1-amine (110 μl, 0.934 mmol) in N-methyl-2-pyrrolidinone (0.7 mL) and stirred at 130° C. for 13 hours. An additional batch of 2,2-dimethylpropan-1-amine (55 μl, 0.47 mmol) was added and the mixture heated to 130° C. for 18 hours. The reaction was quenched with saturated aqueous NaHCO₃ and extracted with EtOAc. The combined organic layers were washed with water and brine, dried and concentrated in vacuo. The residue was purified by preparative HPLC (40% to 100% MeOH in H₂O (0.1% formic acid)) to give the title compound (20 mg, 50%).

¹H NMR (500 MHz, DMSO-d₆): δ 9.26 (s, 1H), 8.56 (s, 1H), 8.19-8.10 (m, 2H), 7.88 (d, J=0.9 Hz, 1H), 7.55 (d, J=1.3 Hz, 1H), 7.28 (d, J=1.9 Hz, 1H), 7.14 (dd, J=8.3, 1.8 Hz, 1H), 6.52 (t, J=6.2 Hz, 1H), 3.93 (s, 3H), 3.88 (s, 3H), 3.35 (s, 2H), 2.38 (d, J=1.2 Hz, 3H), 0.98 (s, 9H).

HRMS (ESI) MS m/z calcd for C₂₄H₃₀N₇O [M+H]⁺ 432.2506. found 432.2497.

MPS1 IC50 (μM): 0.034

The following Examples were prepared according to Method 5 (Example 54) above using the appropriate chloro-pyrido[3,4-d]pyrimidine and the appropriate amine as described. The crude reaction residues were purified as described or according to one of the following methods:
Method A: Silica gel column chromatography eluting with 0-10% MeOH in DCM or EtOAc.
Method B: Silica gel column chromatography eluting with 0-90% EtOAc in cyclohexanes.
Method C: Silica gel column chromatography eluting with 0-40% EtOAc in cyclohexanes.
Method D: Silica gel column chromatography eluting with 0-10% MeOH in EtOAc followed by elution through an SCX-2 cartridge using 1M $NH_3$ in MeOH.
Method E: Elution through an SCX-2 column using 1M $NH_3$ in MeOH.
Method F: Silica gel column chromatography eluting with 0-10% MeOH in DCM followed by elution through an SCX-2 cartridge using 1M $NH_3$ in MeOH followed by silica gel column chromatography eluting with 0-20% MeOH in EtOAc.

| Example No | Name/Structure | Data | MPS1 IC50 (μM) |
|---|---|---|---|
| 150 | $N^8$-(2-methoxy-2-methylpropyl)-$N^2$-(2-methoxy-4-(4-methyl-4H-1,2,4-triazol-3-yl)phenyl)-5-methylpyrido[3,4-d]pyrimidine-2,8-diamine 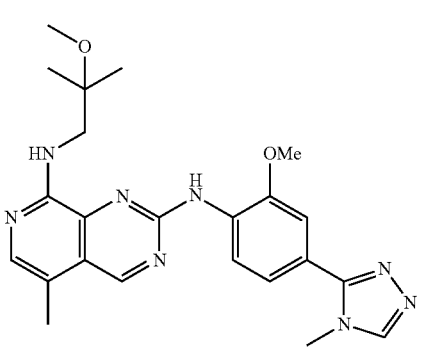 [SMILES: COc1cc(-c2nncn2C)ccc1Nc1ncc2c(C)cnc(NCC(C)(C)OC)c2n1] | $^1$H NMR (500 MHz, DMSO-d6): δ 9.34 (s, 1H), 8.74 (s, 1H), 8.58 (s, 1H), 8.44 (d, J = 8.3 Hz, 1H), 7.62 (d, J = 1.2 Hz, 1H), 7.44 (d, J = 1.9 Hz, 1H), 7.34 (dd, J = 8.3, 1.9 Hz, 1H), 6.60 (t, J = 5.5 Hz, 1H), 3.98 (s, 3H), 3.80 (s, 3H), 3.54 (d, J = 5.5 Hz, 2H), 3.21 (s, 3H), 2.41 (s, 3H), 1.19 (s, 6H). HRMS (ESI) MS m/z calcd for $C_{23}H_{29}N_8O_2$ [M + H]$^+$ 449.2408, found 449.2408. Using 8-chloro-N-(2-methoxy-4-(4-methyl-4H-1,2,4-triazol-3-yl)phenyl)-5-methylpyrido[3,4-d]pyrimidin-2-amine (Preparation 118) and 2-methoxy-2-methylpropan-1-amine at 135° C. for 18 hours and purification method A. | 0.003 |
| 151 | $N^2$-(2-methoxy-4-(4-methyl-4H-1,2,4-triazol-3-yl)phenyl)-5-methyl-$N^8$-neopentylpyrido[3,4-d]pyrimidine-2,8-diamine 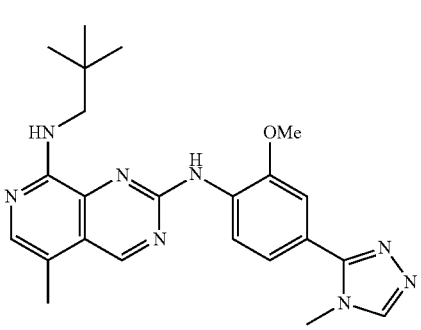 [SMILES: COc1cc(-c2nncn2C)ccc1Nc1ncc2c(C)cnc(NCC(C)(C)C)c2n1] | $^1$H NMR (500 MHz, DMSO-$d_6$): δ 9.33 (s, 1H), 8.74 (s, 1H), 8.58 (s, 1H), 8.46 (d, J = 8.3 Hz, 1H), 7.60 (d, J = 1.3 Hz, 1H), 7.43 (d, J = 1.9 Hz, 1H), 7.34 (dd, J = 8.3, 1.9 Hz, 1H), 6.61 (br. s, 1H), 3.97 (s, 3H), 3.79 (s, 3H), 3.37 (d, J = 6.2 Hz, 2H), 2.40 (d, J = 1.1 Hz, 3H), 0.98 (s, 9H). HRMS (ESI) MS m/z calcd for $C_{23}H_{29}N_8O$ [M + H]$^+$ 433.2459, found 433.2446. Using 8-chloro-N-(2-methoxy-4-(4-methyl-4H-1,2,4-triazol-3-yl)phenyl)-5-methylpyrido[3,4-d]pyrimidin-2-amine (Preparation 118) and 2,2-dimethylpropan-1-amine at 135° C. for 18 hours and purification method A. | 0.002 |
| 152 | $N^2$-(4-(1-ethyl-1H-pyrazol-4-yl)-2-methoxyphenyl)-$N^8$-(2-methoxy-2-methylpropyl)pyrido[3,4-d]pyrimidine-2,8-diamine 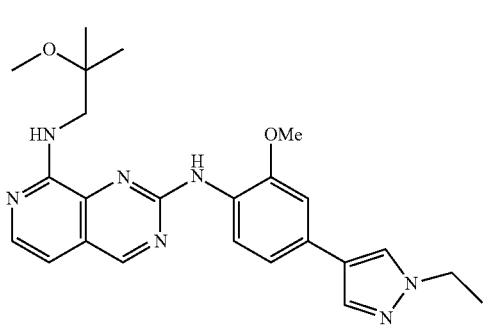 [SMILES: CCn1cc(-c2ccc(Nc3ncc4ccnc(NCC(C)(C)OC)c4n3)c(OC)c2)cn1] | $^1$H NMR (500 MHz, DMSO-$d_6$): δ 9.18 (s, 1H), 8.57 (s, 1H), 8.22 (d, J = 0.8 Hz, 1H), 8.12 (d, J = 8.2 Hz, 1H), 7.90 (d, J = 0.8 Hz, 1H), 7.77 (d, J = 5.7 Hz, 1H), 7.30 (d, J = 1.9 Hz, 1H), 7.17 (dd, J =8.2, 1.9 Hz, 1H), 6.88 (d, J = 5.7 Hz, 1 H), 6.67 (t, J = 5.5 Hz, 1H), 4.17 (q, J = 7.3 Hz, 2H), 3.94 (s, 3H), 3.56 (d, J = 5.6 Hz, 2H), 3.22 (s, 3H), 1.43 (t, J = 7.3 Hz, 3H), 1.20 (s, 6H). HRMS (ESI) MS m/z calcd for $C_{24}H_{30}N_7O_2$ [M + H]$^+$ 448.2455, found 448.2461. Using 8-chloro-N-(4-(1-ethyl-1H-pyrazol-4-yl)-2-methoxyphenyl)pyrido[3,4-d]pyrimidin-2-amine (Preparation 119) and 2-methoxy-2-methylpropan-1-amine at 130° C. for 18 hours and purification method B. | 0.007 |

| Example No | Name/Structure | Data | MPS1 IC50 (μM) |
|---|---|---|---|
| 153 | (3-methoxy-4-(8-(neopentylamino)pyrido[3,4-d]pyrimidin-2-ylamino)phenyl)(3-methoxyazetidin-1-yl)methanone 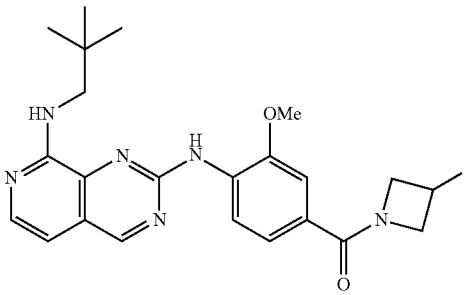 | $^1$H NMR (500 MHz, DMSO-d$_6$): δ 9.24 (s, 1H), 8.69 (s, 1H), 8.41 (d, J = 8.3 Hz, 1H), 7.81 (d, J = 5.7 Hz, 1H), 7.30 (d, J = 1.8 Hz, 1H), 7.26 (dd, J = 8.3, 1.8 Hz, 1H), 6.89 (d, J = 5.7 Hz, 1H), 6.74 (t, J = 6.2 Hz, 1H), 4.51 (br. s, 1H), 4.33-4.21 (br. m, 2H), 4.18 (br. s, 1H), 3.94 (s, 3H), 3.86 (br. s, 1H), 3.40 (d, J = 6.4 Hz, 2H), 3.24 (s, 3H), 0.99 (s, 9H). HRMS (ESI) MS m/z calcd for C$_{24}$H$_{31}$N$_6$O$_3$ [M + H]$^+$ 451.2452, found 451.2458. Using (4-(8-chloropyrido[3,4-d]pyrimidin-2-ylamino)-3-methoxyphenyl)(3-methoxyazetidin-1-yl)methanone (Preparation 120) and 2,2-dimethylpropan-1-amine at 130° C. for 18 hours and purification method B. | 0.004 |
| 154 | N$^2$-(2-methoxy-4-(tetrahydro-2H-pyran-4-yl)phenyl)-N$^8$-((3-methyltetrahydrofuran-3-yl)methyl)pyrido[3,4-d]pyrimidine-2,8-diamine 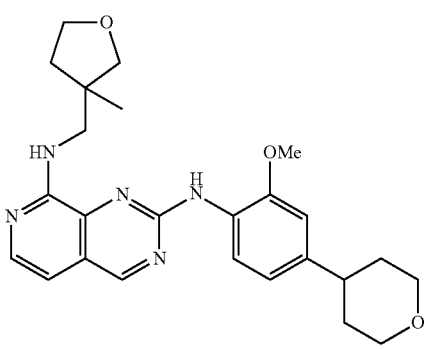 [SMILES: COc1cc(C2CCOCC2)ccc1Nc1ncc2ccnc(NCC3(C)CCOC3)c2n1] | $^1$H NMR (500 MHz, DMSO-d$_6$): δ 9.17 (s, 1H), 8.47 (s, 1H), 8.12 (d, J = 8.2 Hz, 1H), 7.76 (d, J = 5.7 Hz, 1H), 6.99 (d, J = 1.9 Hz, 1H), 6.87 (d, J = 5.8 Hz, 2H), 6.83 (t, J = 6.1 Hz, 1H), 4.02-3.91 (m, 2H), 3.88 (s, 3H), 3.85 (td, J = 8.5, 5.8 Hz, 1H), 3.77 (td, J = 8.3, 6.8 Hz, 1H), 3.68 (d, J = 8.5 Hz, 1H), 3.61-3.51 (m, 2H), 3.49-3.42 (m, 2H), 3.38-3.30 (m, 1H), 2.84-2.73 (m, 1H), 1.90 (ddd, J = 12.3, 8.3, 6.8 Hz, 1H), 1.77-1.69 (m, 4H), 1.65 (ddd, J = 12.2, 8.1, 5.7 Hz, 1H), 1.15 (s, 3H). HRMS (ESI) MS m/z calcd for C$_{25}$H$_{31}$N$_5$NaO$_3$ [M + Na]$^+$ 472.2319, found 472.2315. Using 8-chloro-N-(2-methoxy-4-(tetrahydro-2H-pyran-4-yl)phenyl)pyrido[3,4-d]pyrimidin-2-amine (Preparation 123) and (3-methyltetrahydrofuran-3-yl)methanamine at 130° C. for 18 hours and purification method C. | 0.007 |
| 155 | N$^2$-(2-methoxy-4-(4-methyl-4H-1,2,4-triazol-3-yl)phenyl)-5-methyl-N$^8$-((3-methyloxetan-3-yl)methyl)pyrido[3,4-d]pyrimidine-2,8-diamine 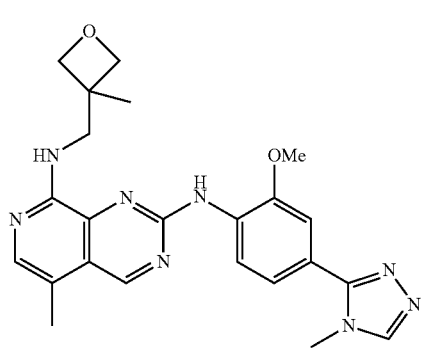 [SMILES: COc1cc(-c2nncn2C)ccc1Nc1ncc2c(C)cnc(NCC3(C)COC3)c2n1] | $^1$H NMR (500 MHz, DMSO-d$_6$): δ 9.32 (s, 1H), 8.68 (br. s, 1H), 8.58 (s, 1H), 8.19 (br. d, J = 8.1 Hz, 1H), 7.64 (br. s, 1H), 7.40 (d, J = 1.8 Hz, 1H), 7.36 (dd, J = 8.2, 1.8 Hz, 1H), 4.90 (br. t, J = 5.3 Hz, 1H), 4.16 (br. d, J = 8.7 Hz, 2H), 3.94 (s, 3H), 3.89 (br. s, 2H), 3.79 (s, 3H), 3.42 (d, J = 5.0 Hz, 2H), 2.40 (d, J = 1.1 Hz, 3H), 1.24 (s, 3H). HRMS (ESI) MS m/z calcd for C$_{23}$H$_{27}$N$_8$O$_2$ [M + H]$^+$ 447.2251, found 447.2250. Using 8-chloro-N-(2-methoxy-4-(4-methyl-4H-1,2,4-triazol-3-yl)phenyl)-5-methylpyrido[3,4-d]pyrimidin-2-amine (Preparation 118) and (3-methyloxetan-3-yl)methanamine at 130° C. for 36 hours and purification method A. | 0.004 |

-continued

| Example No | Name/Structure | Data | MPS1 IC50 (μM) |
|---|---|---|---|
| 156 | N²-(2-methoxy-4-(4-methyl-4H-1,2,4-triazol-3-yl)phenyl)-5-methyl-N⁸-((3-methyltetrahydrofuran-3-yl)methyl) pyrido[3,4-d]pyrimidine-2,8-diamine<br>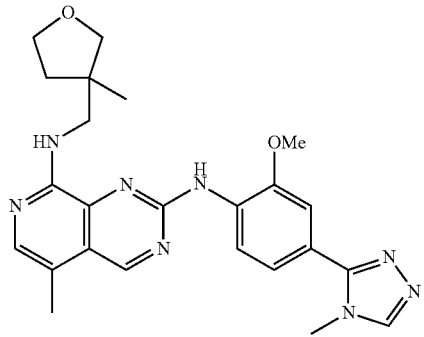 [SMILES: COc1cc(-c2nncn2C)ccc1Nc1ncc2c(C)cnc(NCC3(C)CCOC3)c2n1] | ¹H NMR (500 MHz, DMSO-d$_6$): δ 9.34 (d, J = 0.9 Hz, 1H), 8.67 (s, 1H), 8.58 (s, 1H), 8.53 (d, J = 8.3 Hz, 1H), 7.61 (d, J = 1.7 Hz, 1H), 7.43 (d, J = 1.9 Hz, 1H), 7.37 (dd, J = 8.3, 1.8 Hz, 1H), 6.88 (br. s, 1H), 3.98 (s, 3H), 3.86 (td, J = 8.4, 5.5 Hz, 1H), 3.80 (s, 3H), 3.76 (td, J = 8.4, 7.0 Hz, 1H), 3.72 (d, J = 8.5 Hz, 1H), 3.59 (dd, J = 13.1, 6.5 Hz, 1H), 3.52 (dd, J = 13.1, 5.6 Hz, 1H), 3.36 (d, J = 8.5 Hz, 1H), 2.40 (s, 3H), 1.93 (ddd, J = 12.3, 8.3, 6.9 Hz, 1H), 1.65 (ddd, J = 12.3, 8.1, 5.5 Hz, 1H), 1.15 (s, 3H). HRMS (ESI) MS m/z calcd for C$_{24}$H$_{29}$N$_8$O$_2$ [M + H]⁺ 461.2408, found 461.2411. Using 8-chloro-N-(2-methoxy-4-(4-methyl-4H-1,2,4-triazol-3-yl)phenyl)-5-methylpyrido[3,4-d]pyrimidin-2-amine (Preparation 118) and (3-methyltetrahydrofuran-3-yl)methanamine at 130° C. for 36 hours and purification method A. | 0.005 |
| 157 | N-(2-methoxy-4-(4-methyl-4H-1,2,4-triazol-3-yl)phenyl)-5-methyl-8-(6-oxa-2-azaspiro[3.4]octan-2-yl) pyrido[3,4-d]pyrimidin-2-amine<br>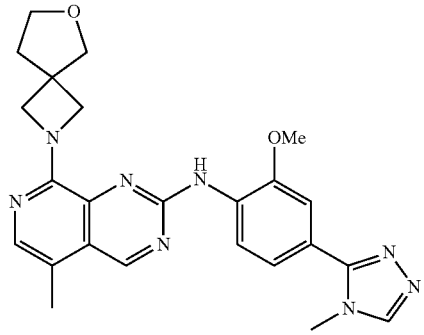 [SMILES: COc1cc(-c2nncn2C)ccc1Nc1ncc2c(C)cnc(N3CC4(CCOC4)C3)c2n1] | ¹H NMR (500 MHz, DMSO-d$_6$): δ 9.34 (s, 1H), 8.70 (br. s, 1H), 8.58 (s, 1H), 8.17 (d, J = 8.2 Hz, 1H), 7.69 (s, 1H), 7.41 (d, J = 1.9 Hz, 1H), 7.38 (dd, J = 8.2, 1.9 Hz, 1H), 4.25 (s, 4H), 3.94 (s, 3H), 3.81 (s, 2H), 3.79 (s, 3H), 3.71 (t, J = 6.9 Hz, 2H), 2.42 (d, J = 1.1 Hz, 3H), 2.14 (t, J = 6.9 Hz, 2H). HRMS (ESI) MS m/z calcd for C$_{24}$H$_{27}$N$_8$O$_2$ [M + H]⁺ 459.2251, found 459.2247. Using 8-chloro-N-(2-methoxy-4-(4-methyl-4H-1,2,4-triazol-3-yl)phenyl)-5-methylpyrido[3,4-d]pyrimidin-2-amine (Preparation 118) and 6-oxa-2-azaspiro[3.4]octane oxalate and triethylamine at 130° C. for 36 hours and purification method A. | 0.006 |
| 158 | N2-(4-1,2-dimethyl-1H-imidazol-5-yl)-2-methoxyphenyl)-N8-(2-methoxy-2-methylpropyl)-6-methylpyrido[3,4-d]pyrimidine-2,8-diamine<br>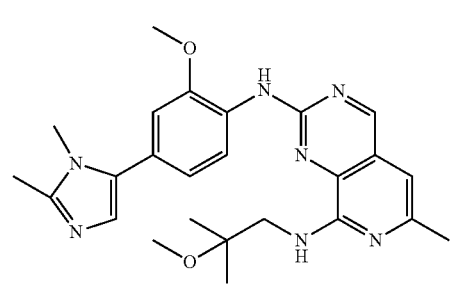 | ¹H NMR (500 MHz, MeOD): δ 9.03 (s, 1H), 8.63 (d, J = 8.5 Hz, 1H), 7.09 (d, J = 2.0 Hz, 1H), 7.06 (dd, J = 8.5 and 2.0 Hz, 1H), 6.89 (s, 1H), 6.72 (d, J = 1.0 Hz, 1H), 4.02 (s, 3H), 3.65 (s, 2H), 3.63 (s, 3H), 3.35 (s, 3H), 2.45 (s, 3H), 2.44 (d, J = 1.0 Hz, 3H), 1.32 (s, 6H). HRMS (ESI) calcd for C$_{25}$H$_{32}$N$_7$O$_2$ [M + H]⁺ 462.2612, found 462.2605. Using 8-chloro-N-(4-(1,2-dimethyl-1H-imidazol-5-yl)-2-methoxyphenyl)-6-methylpyrido[3,4-d]pyrimidin-2-amine (Preparation 121) and 2-methoxy-2-methylpropylamine at 135° C. for 24 hours and purification method D. | 0.003 |

| Example No | Name/Structure | Data | MPS1 IC50 (µM) |
|---|---|---|---|
| 159 | N-(2-ethoxy-4-(1-methyl-1H-pyrazol-4-yl)phenyl)-8-(2-oxa-6-azaspiro[3.4]octan-6-yl)pyrdio[3,4-d]pyrimidin-2-amine | $^1$H NMR (500 MHz, MeOD): δ 9.06 (s, 1H), 7.99-7.97 (m, 2H), 7.84 (app s, 1H), 7.80 (d, J = 6.0 Hz, 1H), 7.24-7.22 (m, 2H), 6.89 (d, J = 6.0 Hz, 1H), 4.66 (q, J = 7.0 Hz, 4H), 4.29 (br s, 2H), 4.23 (q, J = 7.0 Hz, 2H), 3.95 (s, 3H), 3.86 (t, J = 7.0 Hz, 2H), 2.25 (t, J = 7.0 Hz, 2H), 1.46 (t, J = 7.0 Hz, 3H). HRMS (ESI) calcd for $C_{25}H_{28}N_7O_2$ [M + H]$^+$ 458.2299, found 458.2294. Using 8-chloro-N-(2-ethoxy-4-(1-methyl-1H-pyrazol-4-yl)phenyl)pyrido[3,4-d]pyrimidin-2-amine (Preparation 122) and 2-oxa-6-azaspiro[3,4]octane with triethylamine and purification method E. | 0.005 |
| 160 | N-(2-ethoxy-4-(4-methyl-4H-1,2,4-triazol-3-yl)phenyl)-6-methyl-8-(6-oxa-2-azaspiro[3.4]octan-2-yl)pyrido[3,4-d]pyrimidin-2-amine | $^1$H NMR (500 Mhz, Acetone-d6): δ 9.11 (s, 1H), 8.62 (d, J = 8.5 Hz, 1H), 8.36 (s, 1H), 8.06 (br s, 1H), 7.43 (s, 1H), 7.42 (dd, J = 8.5, 2.0 Hz, 1H), 6.83 (s, 1H), 4.46 (br s, 4H), 4.33 (q, J = 7.0 Hz, 2H), 3.93 (s, 2H), 3.90 (s, 3H), 3.82 (t, J = 7.0 Hz, 2H), 2.41 (s, 3H), 2.27 (t, J = 7.0 Hz, 2H), 1.54 (t, J = 7.0 Hz, 3H). HRMS (ESI) calcd for $C_{25}H_{29}N_8O_2$ [M + H]$^+$ 473.2408, found 473.2409. Using 8-chloro-N-(2-ethoxy-4-(4-methyl-4H-1,2,4-triazol-3-yl)phenyl)-6-methylpyrido[3,4-d]pyrimidin-2-amine (Preparation 124) and 6-oxa-2-azaspiro[3,4]octane with triethylamine and purification method F. | 0.003 |

Example 161

$N^3$-(2-Methoxy-2-methylpropyl)-$N^2$-(2-methoxy-6-(1-methyl-1H-tetrazol-5-yl)pyridin-3-yl)pyrido[3,4-d]pyrimidine-2,8-diamine

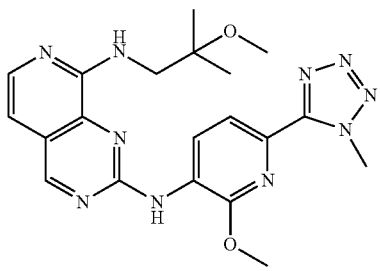

Method 7

Sodium hydride (3.4 mg, 0.086 mmol) was added to a suspension of N-(2-methoxy-6-(1-methyl-1H-tetrazol-5-yl)pyridin-3-yl)formamide (Preparation 126, 20 mg, 0.086 mmol) in DMF (815 µL) at 0° C. After stirring for 20 minutes at room temperature, the solution was cooled to 0° C. and N-(2-methoxy-2-methylpropyl)-2-(methylsulfonyl)pyrido[3,4-d]pyrimidin-8-amine (Preparation 173, 29.2 mg, 0.094 mmol) was added. The reaction was then stirred for 18 hours at room temperature. 2M aqueous NaOH (0.25 mL) and MeOH (0.25 mL) were added and the reaction mixture was stirred at room temperature for 1 hour. The reaction mixture was then concentrated in vacuo and the residue partitioned between DCM and water. The aqueous layer was extracted with DCM and the combined organic layers were washed with brine, dried ($Na_2SO_4$) and concentrated in vacuo. The residue was purified using Biotage silica gel column chromatography eluting with DCM/EtOAc (80/20 to 67/33) followed by elution through an SCX-2 column using a mixture of DCM and 1 M ammonia in MeOH to afford the title product as a yellow solid (22 mg, 59%).

$^1$H NMR (500 MHz, CDCl$_3$): δ 9.05 (s, 1H), 9.04 (d, J=8.2 Hz, 1H), 8.09-8.12 (m, 2H), 7.95 (d, J=5.7 Hz, 1H), 6.78-6.82 (m, 2H), 4.55 (s, 3H), 4.18 (s, 3H), 3.66 (d, J=5.2 Hz, 2H), 3.39 (s, 3H), 1.34 (s, 6H).

HRMS (ESI) calcd for $C_{20}H_{25}N_{10}O_2$ [M+H]$^+$, 437.2156. Found: 437.2154.

MPS1 IC50 (µM): 0.031

The following Examples were prepared according to Method 7 (Example 161) above using the appropriate pyrido[3,4-d]pyrimidine and the formamide as described in either DMF or THF. The crude reaction residues were purified as described or according to one of the following methods:

Method A: Silica gel column chromatography eluting with 0-5% EtOH in DCM followed by preparative HPLC eluting with water/MeOH (90/10 to 0/100, containing 0.1% formic acid).

Method B: Preparative HPLC eluting with water/MeOH (60/40 to 0/100, containing 0.1% formic acid) followed by Biotage silica gel column chromatography eluting with 1:1 DCM:EtOAc followed by 3-5% EtOH in DCM.

Method C: Preparative HPLC eluting with water/MeOH (60/40 to 0/100, containing 0.1% formic acid).

Method D: Silica gel column chromatography eluting with 50-100% EtOAc in cyclohexanes followed by elution through an SCX column using 1M $NH_3$ in MeOH followed by silica gel column chromatography eluting with 0-10% MeOH in DCM or 0-40% EtOAc in cyclohexanes.

Method E: Silica gel column chromatography eluting with 0-15% MeOH in EtOAc followed by elution through an SCX column using 0.7M $NH_3$ in MeOH.

Method F: Silica gel column chromatography eluting with 0-80% EtOAc in cyclohexanes followed by elution through an SCX column using 0.7M $NH_3$ in MeOH.

Method G: Reverse phase chromatography eluting with 0-50% MeCN in water followed by silica gel column chromatography eluting with 0-20% EtOAc in cyclohexanes or 0-10% MeOH in DCM.

Method H: Silica gel column chromatography eluting with 20-60% EtOAc in cyclohexanes followed by reverse phase chromatography eluting with 0-75% MeCN in water.

Method I: Silica gel column chromatography eluting with 20-100% EtOAc in cyclohexanes

| Example No | Name/Structure | Data | MPS1 IC50 (μM) |
|---|---|---|---|
| 162 | $N^2$-(6-(1,2-Dimethyl-1H-imidazol-5-yl)-2-methoxypyridin-3-yl)-$N^8$-(2-methoxy-2-methylpropyl)pyrido[3,4-d]pyrimidine-2,8-diamine 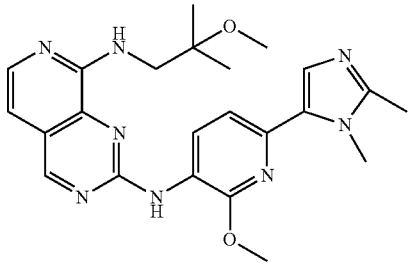 [SMILES: COc1nc(-c2cnc(C)n2C)ccc1Nc1ncc2ccnc(NCC(C)(C)OC)c2n1] | $^1$H NMR (500 MHz, CDCl$_3$): δ 9.00 (s, 1H), 8.84 (d, J = 8.1 Hz, 1H), 7.90-7.93 (m, 2H), 7.25 (s, 1H), 7.23 (d, J = 8.1 Hz, 1H), 6.81 (t, J = 5.3 Hz, 1H), 6.77 (d, J = 5.7 Hz, 1H), 4.11 (s, 3H), 3.93 (s, 3H), 3.66 (d, J = 5.3 Hz, 2H), 3.38 (s, 3H), 2.48 (s, 3H), 1.34 (s, 3H). HRMS (ESI) calcd for $C_{23}H_{29}N_8O_2$ [M + H]$^+$ 449.2408, found 449.2399. Using N-(6-(1,2-dimethyl-1H-imidazol-5-yl)-2-methoxypyridin-3-yl)formamide (Preparation 130) and N-(2-methoxy-2-methylpropyl)-2-(methylsulfonyl)pyrido[3,4-d]pyrimidin-8-amine (Preparation 173) and purification method A | 0.003 |
| 163 | $N^8$-(2-Methoxy-2-methylpropyl)-$N^2$-(2-methoxy-4-(1-methyl-1H-tetrazol-5-yl)phenyl)pyrido[3,4-d]pyrimidine-2,8-diamine 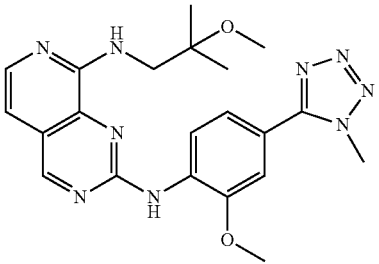 [SMILES: COc1cc(-c2nnnn2C)ccc1Nc1ncc2ccnc(NCC(C)(C)OC)c2n1] | $^1$H NMR (500 MHz, CDCl3): δ 9.05 (s, 1H), 8.89 (d, J = 8.4 Hz, 1H), 8.24 (s, 1H), 7.94 (d, J = 5.7 Hz, 1H), 7.46 (d, J = 1.9 Hz, 1H), 7.36 (dd, J = 8.4, 1.9 Hz, 1H), 6.84 (t, J = 5.1 Hz, 1H), 6.80 (d, J = 5.7 Hz, 1H), 4.25 (s, 3H), 4.07 (s, 3H), 3.68 (d, J = 5.1 Hz, 2H), 3.36 (s, 3H), 1.34 (s, 6H). HRMS (ESI) calcd for $C_{21}H_{26}N_9O_2$ [M + H]$^+$ 436.2204, found 436.2195. Using N-(2-methoxy-4-(1-methyl-1H-tetrazol-5-yl)phenyl)formamide (Preparation 131) and N-(2-methoxy-2-methylpropyl)-2-(methylsulfonyl)pyrido[3,4-d]pyrimidin-8-amine (Preparation 173). | 0.002 |
| 164 | $N^2$-(6-(1,3-Dimethyl-1H-pyrazol-4-yl)-2-methoxypyridin-3-yl)-$N^8$-(2-methoxy-2-methylpropyl)pyrido[3,4-d]pyrimidine-2,8-diamine 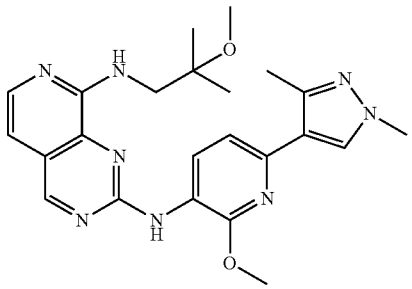 [SMILES: COc1nc(-c2cn(C)nc2C)ccc1Nc1ncc2ccnc(NCC(C)(C)OC)c2n1] | $^1$H NMR (500 MHz, CDCl$_3$): δ 8.99 (s, 1H), 8.80 (d, J = 8.1 Hz, 1H), 7.89-7.91 (m, 2H), 7.75 (s, 1H), 7.10 (d, J = 8.1 Hz, 1H), 6.81 (t, J = 5.2 Hz, 1H), 6.77 (d, J = 5.7 Hz, 1H), 4.13 (s, 3H), 3.91 (s, 3H), 3.67 (d, J = 5.2 Hz, 2H), 3.37 (s, 3H), 2.59 (s, 3H), 1.33 (s, 6H). HRMS (ESI) calcd for $C_{23}H_{29}N_8O_2$ [M + H]$^+$ 449.2408, found 449.2408. Using N-(6-(1,3-dimethyl-1H-pyrazol-4-yl)-2-methoxypyridin-3-yl)formamide (Preparation 132) and and N-(2-methoxy-2-(methylsulfonyl)pyrido[3,4-d]pyrimidin-8-amine (Preparation 173) and purification method B. | 0.003 |

| Example No | Name/Structure | Data | MPS1 IC50 (μM) |
|---|---|---|---|
| 165 | N²-(6-(1,5-dimethyl-1H-pyrazol-4-yl)-2-methoxypyridin-3-yl)-N⁸-(2-methoxy-2-methylpropyl)pyrido[3,4-d]pyrimidine-2,8-diamine | ¹H NMR (500 MHz, CDCl₃): δ 8.98 (s, 1H), 8.79 (d, J = 8.1 Hz, 1H), 7.87-7.90 (m, 2H), 7.80 (s, 1H), 7.14 (d, J = 8.1 Hz, 1H), 6.81 (t, J = 5.2 Hz, 1H), 6.75 (d, J = 5.7 Hz, 1H), 4.12 (s, 3H), 3.87 (s, 3H), 3.67 (d, J = 5.2 Hz, 2H), 3.38 (s, 3H), 2.68 (s, 3H), 1.34 (s, 6H). HRMS (ESI) calcd for C₂₃H₂₉N₈O₂ [M + H]⁺ 449.2408, found 449.2404. Using N-(6-(1,5-dimethyl-1H-pyrazol-4-yl)-2-methoxypyridin-3-yl)formamide (Preparation 133) and N-(2-methoxy-2-methylpropyl)-2-(methylsulfonyl)pyrido[3,4-d]pyrimidin-8-amine (Preparation 173) and purification method C. | 0.003 |
| 166 | N⁸-(2-Methoxy-2-methylpropyl)-N²-(2-methoxy-6-(1-methyl-1H-1,2,3-triazol-5-yl)pyridin-3-yl)pyrido[3,4-d]pyrimidine-2,8-diamine | ¹H NMR (500 MHz, CDCl₃): δ 9.05 (s, 1H), 8.94 (d, J = 8.1 Hz, 1H), 8.02 (s, 1H), 7.96 (s, 1H), 7.94 (d, J = 5.7 Hz, 1H), 7.34 (d, J = 8.1 Hz, 1H), 7.34 (d, J = 8.1 Hz, 1H), 6.80 (m, 2H), 4.47 (s, 3H), 4.16 (s, 3H), 3.68 (d, J = 5.2 Hz, 2H), 3.38 (s, 3H), 1.35 (s, 6H). HRMS (ESI) calcd for C₂₁H₂₆N₉O₂ [M + H]⁺ 436.2204, found 436.2210. Using N-(2-methoxy-6-(1-methyl-1H-1,2,3-triazol-5-yl)pyridin-3-yl)formamide (Preparation 134) and N-(2-methoxy-2-methylpropyl)-2-(methylsulfonyl)pyrido[3,4-d]pyrimidin-8-amine (Preparation 173) and purification method C. | 0.003 |
| 167 | N⁸-(2-Methoxy-2-methylpropyl)-N²-(2-methoxy-6-(2-methyl-2H-1,2,3-triazol-4-yl)pyridin-3-yl)pyrido[3,4-d]pyrimidine-2,8-diamine | ¹H NMR (500 MHz, CDCl₃): δ 9.01 (s, 1H), 8.88 (d, J = 8.1 Hz, 1H), 8.06 (s, 1H), 8.01 (s, 1H), 7.92 (d, J = 5.7 Hz, 1H), 7.60 (d, J = 8.1 Hz, 1H), 6.82 (t, J = 5.2 Hz, 1H), 6.78 (d, J = 5.7 Hz, 1H),4.28 (s, 3H), 4.18 (s, 3H), 3.67 (d, J = 5.2 Hz, 2H), 3.39 (s, 3H), 1.35 (s, 3H). HRMS (ESI) calcd for C₂₁H₂₆N₉O₂ [M + H]⁺ 436.2204, found 436.2209. Using N-(2-methoxy-6-(2-methyl-2H-1,2,3-triazol-4-yl)pyridin-3-yl)formamide (Preparation 135) and N-(2-methoxy-2-methylpropyl)-2-(methylsulfonyl)pyrido[3,4-d]pyrimidin-8-amine (Preparation 173) and purification method C. | 0.023 |
| 168 | N2-(2-ethyl-4-(1-methyl-1H-pyrazol-4-yl)phenyl)-N8-neopentylpyrido[3,4-d]pyrimidine-2,8-diamine | ¹H NMR (500 MHz, MeOD): δ 9.04 (s, 1H), 7.97 (s, 1H), 7.82 (s, 1H), 7.62-7.59 (m, 2H), 7.52 (d, J = 2.0 Hz, 1H), 7.43 (dd, J = 8.5, 2.0 Hz, 1H), 6.85 (br d, J = 7.0 Hz, 1H), 3.96 (3H, s), 3.29 (2H, s), 2.75 (q, J = 7.5 Hz, 2H), 1.25 (t, J = 7.5 Hz, 3H), 0.97 (9H, s). HRMS (ESI) calcd for C₂₄H₃₀N₇ [M + H]⁺ 416.2557, found 416.2540. Using N-(2-ethyl-4-(1-methyl-1H-pyrazol-4-yl)phenyl)formamide (Preparation 136) and-(methylsulfonyl)-N-neopentylpyrido[3,4-d]pyrimidin-8-amine (Preparation 47) and purification method D. | 0.027 |

| Example No | Name/Structure | Data | MPS1 IC50 (μM) |
|---|---|---|---|
| 169 | N2-(4-(1-methyl-1H-pyrazol-4-yl)-2-(trifluoromethoxy)phenyl)-N8-neopentylpyrido[3,4-d]pyrimidine-2,8-diamine 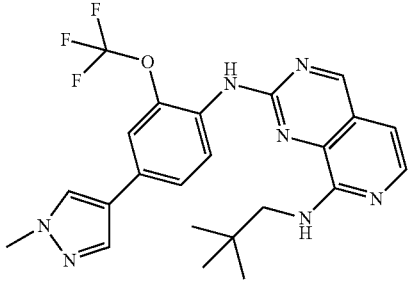 [SMILES: Cn1cc(-c2ccc(Nc3ncc4ccnc(NCC(C)(C)C)c4n3)c(OC(F)(F)F)c2)cn1] | $^1$H NMR (500 MHz, MeOD): δ 9.20 (s, 1H), 8.21 (d, J = 8.5 Hz, 1H), 8.03 (s, 1H), 7.85 (d, J = 0.5 Hz, 1H), 7.72 (d, J = 6.0 Hz, 1H), 7.57 (dd, J = 8.5, 2.0 Hz, 1H), 7.56 (app s, 1H), 6.86 (d, J = 6.0 Hz, 1H), 3.96 (s, 3H), 3.37 (s, 2H), 1.04 (s, 9H). HRMS (ESI) calcd for $C_{23}H_{25}F_3N_7O$ [M + H]$^+$ 472.2067, found 472.2054. Using N-(4-(1-methyl-1H-pyrazol-4-yl)-2-(trifluoromethoxy)phenyl)formamide (Preparation 137) and 2-(methylsulfonyl)-N-neopentylpyrido[3,4-d]pyrimidin-8-amine (Preparation 47) and purification method D. | 0.048 |
| 170 | N2-(2-methoxy-4-(4-morpholinopiperidin-1-yl)phenyl)-N8-neopentylpyrido[3,4-d]pyrimidine-2,8-diamine 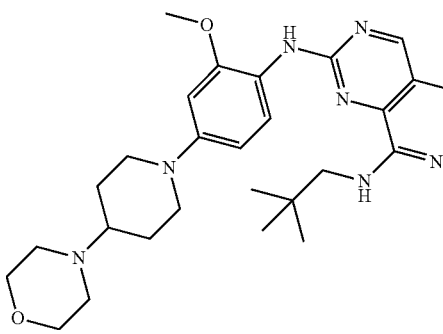 | $^1$H NMR (500 MHz, MeOD): δ 9.02 (s, 1H), 8.11 (d, J = 8.5 Hz, 1H), 7.66 (d, J = 6.0 Hz, 1H), 6.83 (d, J = 6.0 Hz, 1H), 6.76 (d, J = 2.0 Hz, 1H), 6.61 (dd, J = 8.5, 2.5 Hz, 1H), 3.93 (s, 3H), 3.83-3.76 (m, 6H), 3.38 (s, 2H), 2.94-2.84 (m, 4H), 2.77 (dt, J = 12.0, 1.5 Hz, 3H), 2.14 (br d, J = 12.0 Hz, 2H), 1.78-1.70 (m, 2H), 1.07 (s, 9H). HRMS (ESI) calcd for $C_{28}H_{40}N_7O_2$ [M + H]$^+$ 506.3238, found 506.3232. Using N-(2-methoxy-4-(4-morpholinopiperidin-1-yl)phenyl)formamide (Preparation 138) and 2-(methylsulfonyl)-N-neopentylpyrido[3,4-d]pyrimidin-8-amine (Preparation 47) and purification method E. | 0.004 |
| 171 | N2-(2-methoxy-4-(piperidin-1-yl)phenyl)-N8-neopentylpyrido[3,4-d]pyrimidine-2,8-diamine 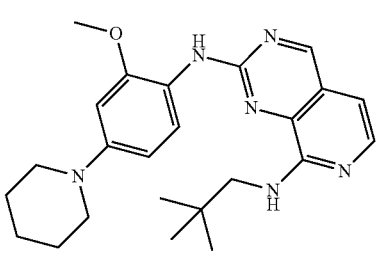 [SMILES: COc1cc(N2CCCCC2)ccc1Nc1ncc2ccnc(NCC(C)(C)C)c2n1] | $^1$H NMR (500 MHz, MeOD): δ 9.02 (s, 1H), 8.09 (d, J = 9.0 Hz, 1H), 7.65 (d, J = 6.0 Hz, 1H), 6.83 (d, J = 6.0 Hz, 1H), 6.75 (d, J = 2.5 Hz, 1H), 6.61 (dd, J = 9.0, 2.5 Hz, 1H), 3.92 (s, 3H), 3.37 (s, 2H), 3.15 (app t, J = 5.0 Hz, 4H), 1.77 (app quin, J = 5.0 Hz, 4H), 1.65-1.61 (m, 2H), 1.07 (s, 9H). HRMS (ESI) calcd for $C_{24}H_{33}N_6O$ [M + H]$^+$ 421.271, found 421.2722. Using N-(2-methoxy-4-(piperidin-1-yl)phenyl)formamide (Preparation 139) and 2-(methylsulfonyl)-N-neopentylpyrido[3,4-d]pyrimidin-8-amine (Preparation 47) and purification method F. | 0.065 |

-continued

| Example No | Name/Structure | Data | MPS1 IC50 (μM) |
|---|---|---|---|
| 172 | (1-(3-methoxy-4-((8-(neopentylamino)pyrido[3,4-d]pyrimidin-2-yl)amino)phenyl)piperidin-4-yl)(morpholino)methanone | ¹H NMR (500 MHz, MeOD): δ 9.01 (s, 1H), 8.11 (d, J = 8.5 Hz, 1H), 7.66 (d, J = 5.5 Hz, 1H), 6.82 (d, J = 5.5 Hz, 1H), 6.75 (d, J = 2.5 Hz, 1H), 6.61 (dd, J = 8.5, 2.5 Hz, 1H), 3.93 (s, 3H), 3.73-3.65 (m, 8H), 3.63-3.60 (m, 2H), 3.37 (s, 2H), 2.83-2.78 (m, 3H), 1.95-1.90 (m, 2H), 1.87-1.84 (m, 2H), 1.07 (s, 9H). HRMS (ESI) calcd for $C_{29}H_{40}N_7O_3$ [M + H]⁺ 534.3187, found 534.3182. Using N-(2-methoxy-4-(4-(morpholine-4-carbonyl)piperidin-1-yl)phenyl)formamide (Preparation 140) and 2-(methylsulfonyl)-N-neopentylpyrido[3,4-d]pyrimidin-8-amine (Preparation 47) and purification method E. | 0.012 |
| 173 | N2-(2-methoxy-4-(4-methylpiperazin-1-yl)phenyl)-N8-neopentylpyrido[3,4-d]pyrimidine-2,8-diamine | ¹H NMR (500 MHz, MeOD): 9.01 (s, 1H), 8.11 (d, J = 8.5 Hz, 1H), 7.66 (d, J = 6.0 Hz, 1H), 6.81 (d, J = 6.0 Hz, 1H), 6.73 (d, J = 2.5 Hz, 1H), 6.58 (dd, J = 8.5, 2.5 Hz, 1H), 3.93 (s, 3H), 3.37 (br s, 2H), 3.22 (app t, J = 5.5 Hz, 4H), 2.67 (app t, J = 5.5 Hz, 4H), 2.38 (s, 3H), 1.07 (s, 9H). HRMS (ESI) calcd for $C_{24}H_{34}N_7O$ [M + H]⁺ 436.2819, found 436.2815. Using N-(2-methoxy-4-(4-methylpiperazin-1-yl)phenyl)formamide (Preparation 141) and 2-(methylsulfonyl)-N-neopentylpyrido[3,4-d]pyrimidin-8-amine (Preparation 47) and purification method G. | 0.004 |
| 174 | N2-(2-chloro-4-morpholinophenyl)-N8-neopentylpyrido[3,4-d]pyrimidine-2,8-diamine | ¹H NMR (500 MHz, MeOD): δ 9.03 (s, 1H), 7.81 (d, J = 9.5 Hz, 1H), 7.66 (d, J = 6.0 Hz, 1H), 7.11 (d, J = 3.0 Hz, 1H), 6.98 (dd, J = 9.5, 3.0 Hz, 1H), 6.82 (d, J = 6.0 Hz, 1H), 3.86 (app t, J = 5.0 Hz, 4H), 3.33 (s, 2H), 3.17 (app t, J = 5.0 Hz, 4H), 1.01 (s, 9H). HRMS (ESI) calcd for $C_{22}H_{28}ClN_6O$ [M + H]⁺ 427.2008, found 427.2001. Using N-(2-chloro-4-morpholinophenyl)formamide (Preparation 142) and 2-(methylsulfonyl)-N-neopentylpyrido[3,4-d]pyrimidin-8-amine (Preparation 47) and purification method H. | 0.010 |
| 175 | N2-(2-methoxy-4-(4-methyl-4H-1,2,4-triazol-3-yl)phenyl)-N8-neopentylpyrido[3,4-d]pyrimidine-2,8-diamine | ¹H NMR (500 MHz, MeOD): δ 9.15 (s, 1H), 8.74 (d, J = 8.5 Hz, 1H), 8.57 (s, 1H), 7.77 (d, J = 6.0 Hz, 1H), 7.43 (d, J = 1.5 Hz, 1H), 7.35 (dd, J = 8.5, 1.5 Hz, 1H), 6.90 (d, J = 6.0 Hz, 1H), 4.07 (s, 3H), 3.87 (s, 3H), 3.44 (s, 2H), 1.10 (s, 9H). HRMS (ESI) calcd for $C_{22}H_{27}N_8O$ [M + H]⁺ 419.2302, found 419.2288. Using N-(2-methoxy-4-(4-methyl-4H-1,2,4-triazol-3-yl)phenyl)formamide (Preparation 221) and 2-(methylsulfonyl)-N-neopentylpyrido[3,4-d]pyrimidin-8-amine (Preparation 47) and purification method G. | 0.002 |

| Example No | Name/Structure | Data | MPS1 IC50 (μM) |
|---|---|---|---|
| 176 | N2-(2-methoxy-4-(4-(methylsulfonyl)piperazin-1-yl)phenyl)-N8-neopentylpyrido[3,4-d]pyrimidine-2,8-diamine 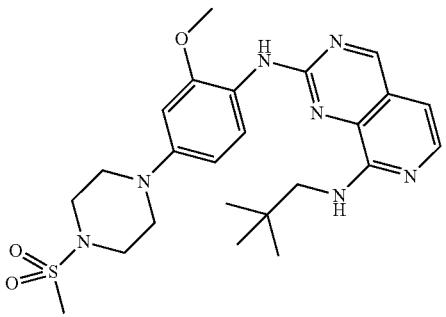 [SMILES: COc1cc(N2CCN(S(C)(=O)=O)CC2)ccc1Nc1ncc2ccnc(NCC(C)(C)C)c2n1] | $^1$H NMR (500 MHz, MeOD): 9.02 (s, 1H), 8.14 (d, J = 9.0 Hz, 1H), 7.67 (d, J = 6.0 Hz, 1H), 6.82 (d, J = 6.0 Hz, 1H), 6.77 (d, J = 2.5 Hz, 1H), 6.61 (dd, J = 9.0, 2.5 Hz, 1H), 3.94 (s, 3H), 3.42-3.40 (m, 4H), 3.37 (s, 2H), 3.29-3.27 (m, 4H), 2.92 (s, 3H), 1.07 (s, 9H). HRMS (ESI) calcd for $C_{24}H_{34}N_7O_3S$ [M + H]$^+$ 500.2438, found 500.2423. Using N-(2-methoxy-4-(4-(methylsulfonyl)piperazin-l-yl)phenyl)formamide (Preparation 143) and 2-(methylsulfonyl)-N-neopentylpyrido[3,4-d]pyrimidin-8-amine (Preparation 47) and purification method I. | 0.003 |
| 177 | N2-(4-(1,2-dimethyl-1H-imidazol-5-yl)-2-methoxyphenyl)-6-methyl-N8-neopentylpyrido[3,4-d]pyrimidine-2,8-diamine 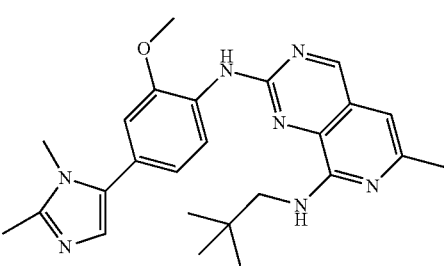 | $^1$H NMR (500 MHz, MeOD): δ 9.02 (s, 1H), 8.57 (d, J = 8.5 Hz, 1H), 7.09 (d, J = 2.0 Hz, 1H), 7.02 (dd, J = 8.5 and 2.0 Hz, 1H), 6.88 (s, 1H), 6.70 (d, J = 1.0 Hz, 1H), 4.02 (s, 3H), 3.61 (s, 3H), 3.45 (s, 2H), 2.45 (s, 3H), 2.44 (d, J = 1.0 Hz, 3H), 1.09 (s, 9H) HRMS (ESI) calcd for $C_{25}H_{32}N_7O$ [M + H]$^+$ 446.2663, found 446.2648. Using N-(4-(1,2-dimethyl-1H-imidazol-5-yl)-2-methoxyphenyl)formamide (Preparation 55) and 6-methyl-2-(methysulfonyl)-N-neopentylpyrido[3,4-d]pyrimidin-8-amine (Preparation 54) and purification method E. | 0.005 |
| 178 | N-(4-Chloro-2-methoxyphenyl)-8-(2-oxa-6-azaspiro[3.4]octan-6-yl)pyrido[3,4-d]pyrimidin-2-amine 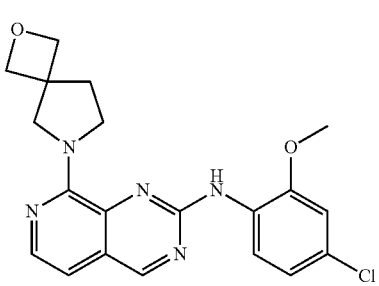 [SMILES: COc1cc(Cl)ccc1Nc1ncc2ccnc(N3CCC4(COC4)C3)c2n1] | $^1$H NMR (500 MHz, CDCl$_3$): δ 8.99 (s, 1H), 8.22 (d, J = 8.5 Hz, 1H), 7.96 (d, J = 5.6 Hz, 1H), 7.66 (s, 1H), 6.99 (dd, J = 8.6, 2.2 Hz, 1H), 6.94 (d, J = 2.3 Hz, 1H), 6.81 (d, J = 5.5 Hz, 1H), 4.73 (d, J = 6.4 Hz, 2H), 4.69 (d, J = 6.1 Hz, 2H), 4.3 (s, 2H), 4 (t, J = 6.8 Hz, 2H), 3.95 (s, 3H), 2.31 (t, J = 6.9 Hz, 2H). HRMS (ESI) calcd for $C_{20}H_{21}ClN_5O_2$ [M + H]$^+$ 398.1378, found 398.1375. Using N-(4-chloro-2-methoxyphenyl)formamide and 6-(2-(methylsulfonyl)pyrido[3,4-d]pyrimidin-8-yl)-2-oxa-6-azaspiro[3.4]octane (Preparation 220) and purification method F. | 0.024 |

Example 179

N2-(2-methoxy-4-(4-methyl-4H-1,2,4-triazol-3-yl) phenyl)-6-methyl-N8-neopentylpyrido[3,4-d]pyrimidine-2,8-diamine

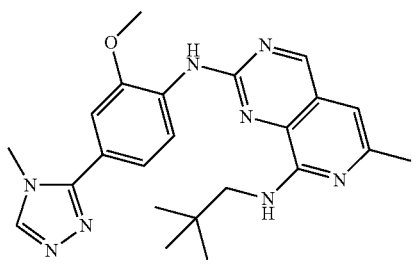

Method 8

To a solution of 6-methyl-2-(methysulfonyl)-N-neopentylpyrido[3,4-d]pyrimidin-8-amine (Preparation 54, 40 mg, 0.130 mmol) in DMSO (7 mL) was added N-(2-methoxy-4-(4-methyl-4H-1,2,4-triazol-3-yl)phenyl)formamide (Preparation 221, 36 mg, 0.156 mmol) and $Cs_2CO_3$ (85 mg, 0.259 mmol). The reaction mixture was heated to 100° C. for 18 hours. The reaction mixture was cooled to room temperature and diluted with EtOAc (40 mL) and water (40 mL). The aqueous layer was re-extracted with DCM (40 mL). The combined organic layer was washed with brine (40 mL), dried ($MgSO_4$) and concentrated in vacuo. The residue was purified by elution through an SCX-2 column using 1M $NH_3$ in MeOH to afford the title compound (6.7 mg, 48%).

$^1$H NMR (500 MHz, MeOD): δ 9.05 (s, 1H), 8.75 (d, J=8.5 Hz, 1H), 8.56 (s, 1H), 7.42 (d, J=2.0 Hz, 1H), 7.34 (dd, J=8.5, 2.0 Hz, 1H), 6.71 (d, J=1.0 Hz, 1H), 4.07 (s, 3H), 3.87 (s, 3H), 3.48 (s, 2H), 2.44 (app s, 3H), 1.10 (s, 9H).

HRMS (ESI) calcd for $C_{23}H_{29}N_8O$ [M+H]$^+$ 433.2459. found 433.2447.

MPS1 IC50 (μM): 0.002

The following Examples were prepared according to Method 8 (Example 179) above using the appropriate pyrido[3,4-d]pyrimidine and the formamide or aniline as described. The crude reaction residues were purified as described or according to one of the following methods, and where necessary the residue was eluted though an SCX-2 column using 1M or 7M $NH_3$ in MeOH.

Method A: Silica gel column chromatography eluting with 0-10% MeOH in EtOAc.

Method B: Silica gel column chromatography eluting with 0-10% MeOH in DCM.

Method C: Silica gel column chromatography eluting with 0-10% MeOH in DCM followed by reverse phase chromatography eluting with MeOH/water.

Method D: Preparative TLC eluting with 3% MeOH in EtOAc/DCM 1/1 or 6% MeOH in EtOAc.

Method E: Elution through an SCX-2 column using 50% MeOH in chloroform followed by 50% chloroform in 7N $NH_3$/MeOH.

| Example No | Name/Structure | Data | MPS1 IC50 (μM) |
|---|---|---|---|
| 180 | N8-(2-methoxy-2-methylpropyl)-N2-(2-methoxy-4-(4-methyl-4H-1,2,4-triazol-3-yl)phenyl)-6-methylpyrido[3,4-d]pyrimidine-2,8-diamine | $^1$H NMR (500 MHz, acetone-d6): δ 9.11 (s, 1H), 8.81 (d, J = 8.5 Hz, 1H), 8.38 (s, 1H), 8.21 (br s, 1H), 7.48 (d, J = 2.0 Hz, 1H), 7.43 (dd, J = 8.5, 2.0 Hz, 1H), 6.81 (br s, 1H), 6.75 (d, J = 0.5 Hz, 1H), 4.11 (s, 3H), 3.92 (s, 3H), 3.66 (d, J = 5.0 Hz, 2H), 3.36 (s, 3H), 2.42 (d, J = 0.5 Hz, 3H), 1.30 (s, 6H). HRMS (ESI) calcd for $C_{23}H_{29}N_8O_2$ [M + H]$^+$ 449.2408, found 449.2404. Using N-(2-methoxy-2-methylpropyl)-6-methyl-2-(methylsulfonyl)pyrido[3,4-d]pyrimidin-8-amine (Preparation 172) and N-(2-methoxy-4-(4-methyl-4H-1,2,4-triazol-3-yl)phenyl)formamide (Preparation 221) at 120° C. for 18 hours. | 0.003 |
| 181 | N2-(2-methoxy-4-(1-(2-methoxyethyl)-2-methyl-1H-imidazol-5-yl)phenyl)-6-methyl-N8-neopentylpyrido[3,4-d]pyrimidine-2,8-diamine | $^1$H NMR (500 MHz, MeOD): δ 9.02 (s, 1H), 8.57 (d, J = 8.5 Hz, 1H), 7.17 (d, J = 2.0 Hz, 1H), 7.04 (dd, J = 8.5, 2.0 Hz, 1H), 6.86 (s, 1H), 6.70 (d, J = 0.5 Hz, 1H), 4.21 (t, J = 5.5 Hz, 2H), 4.01 (s, 3H), 3.52 (t, J = 5.5 Hz, 2H), 3.45 (s, 2H), 3.25 (s, 3H), 2.48 (s, 3H), 2.44 (d, J = 0.5 Hz, 3H), 1.09 (s, 9H). HRMS (ESI) calcd for $C_{27}H_{38}N_7O_2$ [M + H]$^+$ 490.2925, found 490.2921. Using 6-methyl-2-(methysulfonyl)-N-neopentylpyrido[3,4-d]pyrimidin-8-amine (Preparation 54) and N-(2-methoxy-4-(1-(2-methoxyethyl)-2-methyl-1H-imidazol-5-yl)phenyl)formamide (Preparation 144) at 120° C. for 18 hours and purification method A. | 0.0194 |

| Example No | Name/Structure | Data | MPS1 IC50 (μM) |
|---|---|---|---|
| 182 | N2-(2-ethoxy-4-(4-methyl-4H-1,2,4-triazol-3-yl)phenyl)-6-methyl-N8-neopentylpyrido[3,4-d]pyrimidine-2,8-diamine 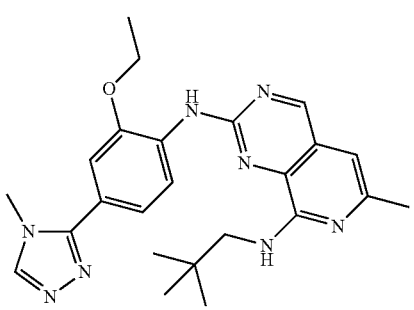 | $^1$H NMR (500 MHz, Acetone-d6): δ 9.11 (s, 1H), 8.80 (d, J = 8.5 Hz, 1H), 8.37 (s, 1H), 8.21 (br s, 1H), 7.46 (d, J = 2.0 Hz, 1H), 7.40 (dd, J = 8.5, 2.0 Hz, 1H), 6.74 (d, J = 0.5 Hz, 1H), 4.35 (q, J = 7.0 Hz, 2H), 3.90 (s, 3H), 3.51 (s, 2H), 2.41 (d, J = 0.5 Hz, 3H), 1.55 (t, J = 7.0 Hz, 3H), 1.08 (s, 9H). HRMS (ESI) calcd for $C_{24}H_{31}N_8O$ [M + H]$^+$ 447.2615, found 447.2629. Using 6-methyl-2-(methylsulfonyl)-N-neopentylpyrido[3,4-d]pyrimidin-8-amine (Preparation 54) and N-(2-ethoxy-4-(4-methyl-4H-1,2,4-triazol-3-yl)phenyl)formamide (Preparation 150) at 120° C. for 18 hours and purification method B. | 0.003 |
| 183 | N2-(2-methoxy-4-(4-(methylsulfonyl)piperazin-1-yl)phenyl)-6-methyl-N8-neopentylpyrido[3,4-d]pyrimidine-2,8-diamine 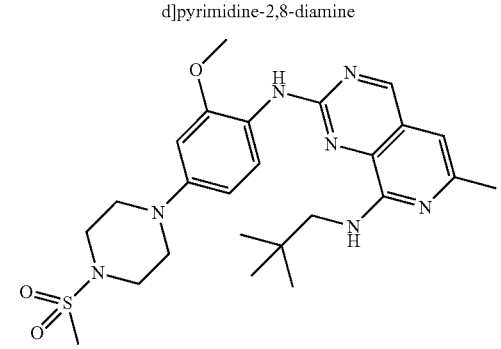 | $^1$H NMR (500 MHz, MeOD): δ 8.92 (s, 1H), 8.18 (d, J = 8.5 Hz, 1H), 6.76 (d, J = 2.5 Hz, 1H), 6.64 (s, 1H), 6.60 (dd, J = 8.5, 2.5 Hz, 1H), 3.94 (s, 3H), 3.41-3.40 (m, 4H), 3.39 (s, 2H), 3.28-3.26 (m, 4H), 2.91 (s, 3H), 2.41 (s, 3H), 1.07 (s, 9H). HRMS (ESI) calcd for $C_{25}H_{36}N_7O_3S$ [M + H]$^+$ 514.2595, found 514.2613. Using 6-methyl-2-(methylsulfonyl)-N-neopentylpyrido[3,4-d]pyrimidin-8-amine (Preparation 54) and N-(2-methoxy-4-(4-(methylsulfonyl)piperazin-1-yl)phenyl)formamide (Preparation 143) at 120° C. for 18 hours and purification method B. | 0.016 |
| 184 | (4-(3-methoxy-4-((8-((2-methoxy-2-methylpropyl)amino)pyrido[3,4-d]pyrimidin-2-yl)amino)phenyl)-1-methyl-1H-pyrazol-5-yl)methanol 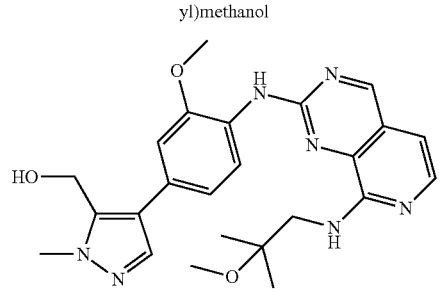 | $^1$H NMR (500 MHz, MeOD): δ 9.10 (s, 1H), 8.53 (d, J = 8.5 Hz, 1H), 7.75 (d, J = 6.0 Hz, 1H), 7.64 (s, 1H), 7.21 (d, J = 2.0 Hz, 1H), 7.15 (dd, J = 8.5, 2.0 Hz, 1H), 6.89 (d, J = 6.0 Hz, 1H), 4.76 (s, 2H), 4.03 (s, 3H), 4.00 (s, 3H), 3.60 (s, 2H), 3.37 (s, 3H), 1.33 (s, 6H). HRMS (ESI) calcd for $C_{24}H_{30}N_7O_3$ [M + H]$^+$ 465.2433, found 465.2426. Using N-(2-Methoxy-2-methylpropyl)-2-(methylsulfonyl)pyrido[3,4-d]pyrimidin-8-amine (Preparation 173) and (4-(4-formamido-3-methoxyphenyl)-1-methyl-1H-pyrazol-5-yl)methyl formate (Preparation 145) at 120° C. for 18 hours and purification method B. | 0.002 |

| Example No | Name/Structure | Data | MPS1 IC50 (μM) |
|---|---|---|---|
| 185 | (4-(3-methoxy-4-((8-(((3-methyltetrahydrofuran-3-yl)methyl)amino)pyrido[3,4-d]pyrimidin-2-yl)amino)phenyl)-1-methyl-1H-pyrazol-5-yl)methanol | $^1$H NMR (500 MHz, MeOD): δ 9.10 (s, 1H), 8.51 (d, J = 8.5 Hz, 1H), 7.75 (d, J = 6.0 Hz, 1H), 7.64 (s, 1H), 7.21 (d, J = 2.0 Hz, 1H), 7.15 (dd, J = 8.5, 2.0 Hz, 1H), 6.89 (d, J = 6.0 Hz, 1H), 4.75 (s, 2H), 4.01 (s, 3H), 4.00 (s, 3H), 3.96-3.86 (m, 3H), 3.65 (d, J = 13.0 Hz, 1H), 3.58 (d, J = 13.0 Hz, 1H), 3.53 (d, J = 8.5 Hz, 3H), 2.06 (m, 1H), 1.83 (m, 1H), 1.29 (s, 3H).<br>HRMS (ESI) calcd for $C_{25}H_{30}N_7O_3$ [M + H]$^+$ 476.2405, found 476.2398.<br>Using 2-(methylsulfonyl)-N-((3-methyltetrahydrofuran-3-yl)methyl)pyrido[3,4-d]pyrimidin-8-amine (Preparation 174) and (4-(4-formamido-3-methoxyphenyl)-1-methyl-1H-pyrazol-5-yl)methyl formate (Preparation 145) and at 120° C. for 18 hours and purification method B. | 0.001 |
| 186 | N8-(2-methoxy-2-methylpropyl)-N2-(2-methoxy-4-(1-(2-methoxyethyl)-2-methyl-1H-imidazol-5-yl)phenyl)pyrido[3,4-d]pyrimidine-2,8-diamine | $^1$H NMR (500 MHz, MeOD): δ 9.12 (s, 1H), 8.60 (d, J = 8.5 Hz, 1H), 7.77 (d, J = 6.0 Hz, 1H), 7.19 (d, J = 2.0 Hz, 1H), 7.09 (dd, J = 8.5, 2.0 Hz, 1H), 6.90 (d, J = 6.0 Hz, 1H), 6.89 (s, 1H), 4.23 (t, J = 5.5 Hz, 2H), 4.02 (s, 3H), 3.60 (s, 2H), 3.53 (t, J = 5.5 Hz, 2H), 3.35 (s, 3H), 3.26 (s, 3H), 2.49 (s, 3H), 1.32 (s, 6H).<br>HRMS (ESI) calcd for $C_{26}H_{34}N_7O_3$ [M + H]$^+$ 492.2718, found 492.2714.<br>Using N-(2-methoxy-2-methylpropyl)-2-(methylsulfonyl)pyrido[3,4-d]pyrimidin-8-amine (Preparation 173) and N-(2-methoxy-4-(1-(2-methoxyethyl)-2-methyl-1H-imidazol-5-yl)phenyl)formamide (Preparation 144) at 120° C. for 18 hours and purification method B. | 0.004 |
| 187 | N2-(2-methoxy-4-(1-(2-methoxyethyl)-2-methyl-1H-imidazol-5-yl)phenyl)-N8-((3-methyltetrahydrofuran-3-yl)methyl)pyrido[3,4-d]pyrimidine-2,8-diamine | $^1$H NMR (500 MHz, MeOD): δ 9.11 (s, 1H), 8.62 (d, J = 8.5 Hz, 1H), 7.77 (d, J = 6.0 Hz, 1H), 7.17 (d, J = 2.0 Hz, 1H), 7.10 (dd, J = 8.5, 2.0 Hz, 1H), 6.90 (s, 1H), 6.89 (s, 1H), 4.23 (t, J = 5.5 Hz, 2H), 4.05 (td, J = 8.5, 5.5 Hz, 1H), 4.01 (s, 3H), 3.91-3.87 (m, 3H), 3.66 (d, J = 13.0 Hz, 1H), 3.57 (d, J = 13.0 Hz, 1H), 3.53 (t, J = 5.5 Hz, 2H), 3.26 (s, 3H), 2.49 (s, 3H), 2.06 (m, 1H), 1.83 (m, 1H), 1.29 (s, 3H).<br>HRMS (ESI) calcd for $C_{27}H_{34}N_7O_3$ [M + H]$^+$ 504.2718, found 504.2717.<br>Using 2-(methylsulfonyl)-N-((3-methyltetrahydrofuran-3-yl)methyl)pyrido[3,4-d]pyrimidin-8-amine (Preparation 174) and N-(2-methoxy-4-(1-(2-methoxyethyl)-2-methyl-1H-imidazol-5-yl)phenyl)formamide (Preparation 144) at 120° C. for 18 hours and purification method A. | 0.002 |

| Example No | Name/Structure | Data | MPS1 IC50 (μM) |
|---|---|---|---|
| 188 | N2-(2-ethoxy-4-(4-methyl-4H-1,2,4-triazol-3-yl)phenyl)-N8-(2-methoxy-2-methylpropyl)pyrido[3,4-d]pyrimidine-2,8-diamine 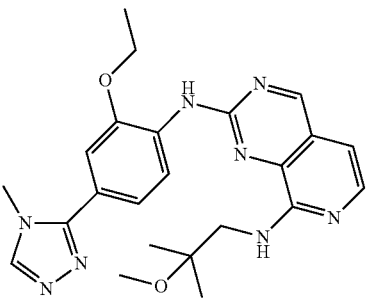 | $^1$H NMR (500 MHz, MeOD): δ 9.16 (s, 1H), 8.78 (d, J = 8.0 Hz, 1H), 8.56 (s, 1H), 7.80 (d, J = 5.5 Hz, 1H), 7.41 (d, J = 1.5 Hz, 1H), 7.38 (dd, J = 8.0, 1.5 Hz, 1H), 6.93 (d, J = 5.5 Hz, 1H), 4.32 (q, J = 7.0 Hz, 2H), 3.88 (s, 3H), 3.62 (s, 2H), 3.37 (s, 3H), 1.57 (t, J = 7.0 Hz, 3H), 1.33 (s, 6H). HRMS (ESI) calcd for $C_{23}H_{29}N_8O_2$ [M + H]$^+$ 449.2408, found 449.2392. Using N-(2-methoxy-2-methylpropyl)-2-(methylsulfonyl)pyrido[3,4-d]pyrimidin-8-amine (Preparation 173) and N-(2-ethoxy-4-(4-methyl-4H-1,2,4-triazol-3-yl)phenyl)formamide (Preparation 150) at 120° C. for 18 hours and purification method B. | 0.002 |
| 189 | N2-(2-ethoxy-4-(4-methyl-4H-1,2,4-triazol-3-yl)phenyl)-N8-((3-methyltetrahydrofuran-3-yl)methyl)pyrido[3,4-d]pyrimidine-2,8-diamine 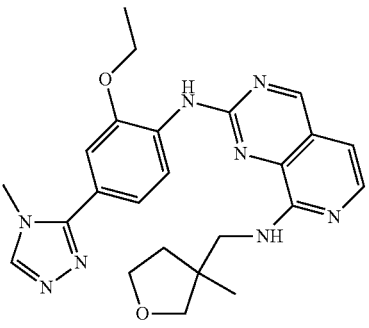 | $^1$H NMR (500 MHz, MeOD): δ 9.15 (s, 1H), 8.81 (d, J = 9.0 Hz, 1H), 8.56 (s, 1H), 7.81 (d, J = 6.0 Hz, 1H), 7.41-7.39 (m, 2H), 6.93 (d, J = 6.0 Hz, 1H), 4.31 (q, J = 7.0 Hz, 2H), 4.07 (td, J = 8.5, 6.0 Hz, 1H), 3.91 (t, J = 9.0 Hz, 2H), 3.87 (s, 3H), 3.69 (d, J = 13.0 Hz, 1H), 3.58 (d, J = 13.0 Hz, 1H), 3.52 (d, J = 9.0 Hz, 1H), 2.07 (m, 1H), 1.84 (m, 1H), 1.56 (t, J = 7.0 Hz, 3H), 1.29 (s, 3H). HRMS (ESI) calcd for $C_{24}H_{29}N_8O_2$ [M + H]$^+$ 461.2408, found 461.2404. Using 2-(methylsulfonyl)-N-((3-methyltetrahydrofuran-3-yl)methyl)pyrido[3,4-d]pyrimidin-8-amine (Preparation 174) and N-(2-ethoxy-4-(4-methyl-4H-1,2,4-triazol-3-yl)phenyl)formamide (Preparation 150) at 120° C. for 18 hours and purification method B. | 0.001 |
| 190 | N2-(4-(1,3-dimethyl-1H-pyrazol-4-yl)-2-methoxyphenyl)-N8-(2-methoxy-2-methylpropyl)pyrido[3,4-d]pyrimidine-2,8-diamine 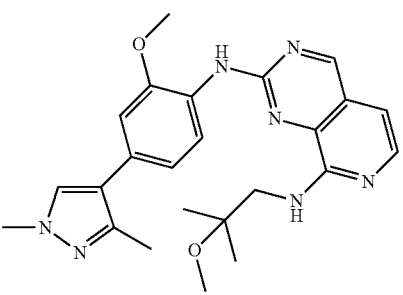 | $^1$H NMR (500 MHz, MeOD): δ 9.09 (s, 1H), 8.50 (d, J = 8.0 Hz, 1H), 7.75-7.74 (m, 2H), 7.10-7.07 (m, 2H), 6.89 (d, J = 6.0 Hz, 1H), 4.01 (s, 3H), 3.88 (s, 3H), 3.60 (s, 2H), 3.36 (s, 3H), 2.41 (s, 3H), 1.33 (s, 6H). HRMS (ESI) calcd for $C_{24}H_{30}N_7O_2$ [M + H]$^+$ 448.2455, found 448.2459. Using N-(2-methoxy-2-methylpropyl)-2-(methylsulfonyl)pyrido[3,4-d]pyrimidin-8-amine (Preparation 173) and N-(4-(1,3-dimethyl-1H-pyrazol-4-yl)-2-methoxyphenyl)formamide (Preparation 76) at 120° C. for 18 hours and purification method B. | 0.003 |

| Example No | Name/Structure | Data | MPS1 IC50 (μM) |
|---|---|---|---|
| 191 | N2-(4-(1,3-dimethyl-1H-pyrazol-4-yl)-2-methoxyphenyl)-N8-((3-methyltetrahydrofuran-3-yl)methyl)pyrido[3,4-d]pyrimidine-2,8-diamine 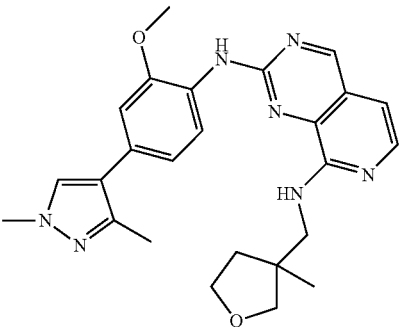 | $^1$H NMR (500 MHz, MeOD): δ 9.07 (s, 1H), 8.48 (d, J = 8.5 Hz, 1H), 7.74 (d, J = 5.5 Hz, 1H), 7.73 (s, 1H), 7.09 (dd, J = 8.5, 2.0 Hz, 1H), 7.08 (s, 1H), 6.88 (d, J = 5.5 Hz, 1H), 4.04 (td, J = 8.0, 5.5, 1H), 3.99 (s, 3H), 3.91 (td, J = 8.0, 7.5, 1H), 3.88 (s, 3H), 3.87 (d, J = 8.5 Hz, 1H, 3.60 (q, J = 13.0 Hz, 2H), 3.52 (d, J = 8.5 Hz, 1H), 2.40 (s, 3H), 2.05 (m, 1H), 1.82 (m, 1H), 1.28 (s, 3H). HRMS (ESI) calcd for $C_{25}H_{30}N_7O_2$ [M + H]$^+$ 460.2455, found 460.2450. Using 2-(methylsulfonyl)-N-((3-methyltetrahydrofuran-3-yl)methyl)pyrido[3,4-d]pyrimidin-8-amine (Preparation 174) and N-(4-(1,3-dimethyl-1H-pyrazol-4-yl)-2-methoxyphenyl)formamide (Preparation 76) at 120° C. for 18 hours and purification method B. | 0.002 |
| 192 | N2-(4-(1,3-dimethyl-1H-pyrazol-4-yl)-2-methoxyphenyl)-N8-(2-methoxy-2-methylpropyl)-6-methylpyrido[3,4-d]pyrimidine-2,8-diamine 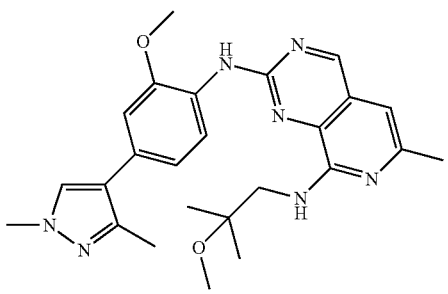 | $^1$H NMR (500 MHz, MeOD): δ 8.98 (s, 1H), 8.52 (d, J = 8.0 Hz, 1H), 7.73 (s, 1H), 7.08-7.06 (m, 2H), 6.70 (d, J = 0.5 Hz, 1H), 4.01 (s, 3H), 3.88 (s, 3H), 3.64 (s, 2H), 3.36 (s, 3H), 2.44 (d, J = 0.5 Hz, 3H), 2.40 (s, 3H), 1.32 (s, 6H). HRMS (ESI) calcd for $C_{25}H_{32}N_7O_2$ [M + H]$^+$ 462.2612, found 462.2613. Using N-(2-methoxy-2-methylpropyl)-6-methyl-2-(methylsulfonyl)pyrido[3,4-d]pyrimidin-8-amine (Preparation 172) and N-(4-(1,3-dimethyl-1H-pyrazol-4-yl)-2-methoxyphenyl)formamide (Preparation 76) at 120° C. for 18 hours and purification method B. | 0.005 |
| 193 | (3-methoxy-4-((8-((2-methoxy-2-methylpropyl)amino)pyrido[3,4-d]pyrimidin-2-yl)amino)phenyl)(3-methoxyazetidin-1-yl)methanone 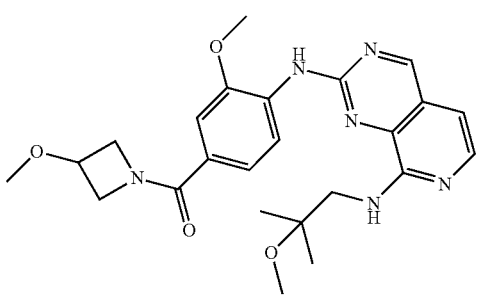 | $^1$H NMR (500 MHz, MeOD): δ 9.15 (s, 1H), 8.66 (d, J = 8.0 Hz, 1H), 7.79 (d, J = 6.5 Hz, 1H), 7.38 (d, J = 2.0 Hz, 1H), 7.35 (dd, J = 8.0, 2.0 Hz, 1H), 6.92 (d, J = 6.5 Hz, 1H), 4.62 (br m, 1H), 4.38 (m, 1H), 4.35-4.28 (m, 3H), 4.04 (s, 3H), 3.61 (s, 2H), 3.37 (s, 3H), 3.35 (s, 3H), 1.33 (s, 6H). HRMS (ESI) calcd for $C_{24}H_{31}N_6O_4$ [M + H]$^+$ 467.2401, found 467.2397. Using N-(2-methoxy-2-methylpropyl)-2-(methylsulfonyl)pyrido[3,4-d]pyrimidin-8-amine (Preparation 173) and N-(2-methoxy-4-(3-methoxyazetidine-1-carbonyl)phenyl)formamide (Preparation 129) at 120° C. for 18 hours and purification method B. | 0.004 |

| Example No | Name/Structure | Data | MPS1 IC50 (µM) |
|---|---|---|---|
| 194 | (3-methoxy-4-((8-((2-methoxy-2-methylpropyl)amino)pyrido[3,4-d]pyrimidin-2-yl)amino)-N,N-dimethylbenzamide | $^1$H NMR (500 MHz, MeOD): δ 9.14 (s, 1H), 8.63 (d, J = 8.5 Hz, 1H), 7.78 (d, J = 6.0 Hz, 1H), 7.17 (d, J = 2.0 Hz, 1H), 7.13 (dd, J = 8.5, 2.0 Hz, 1H), 6.91 (d, J = 6.0 Hz, 1H), 4.03 (s, 3H), 3.61 (s, 2H), 3.36 (s, 3H), 3.13 (s, 6H), 1.32 (s, 6H). HRMS (ESI) calcd for $C_{22}H_{29}N_6O_3$ [M + H]$^+$ 425.2296, found 425.2289. Using N-(2-methoxy-2-methylpropyl)-2-(methylsulfonyl)pyrido[3,4-d]pyrimidin-8-amine (Preparation 173) and 4-formamido-3-methoxy-N,N-dimethylbenzamide (Preparation 146) at 120° C. for 18 hours and purification method B. | 0.011 |
| 195 | (3-methoxy-4-((8-((2-methoxy-2-methylpropyl)amino)pyrido[3,4-d]pyrimidin-2-yl)amino)phenyl)(4-methylpiperazin-1-yl)methanone | $^1$H NMR (500 MHz, MeOD): δ 9.13 (s, 1H), 8.63 (d, J = 8.5 Hz, 1H), 7.78 (d, J = 6.0 Hz, 1H), 7.16 (d, J = 2.0 Hz, 1H), 7.12 (dd, J = 8.5, 2.0 Hz, 1H), 6.91 (d, J = 6.0 Hz, 1H), 4.03 (s, 3H), 3.72 (br s, 4H), 3.60 (s, 2H), 3.36 (s, 3H), 2.54 (br s, 4H), 2.38 (s, 3H), 1.32 (s, 6H). HRMS (ESI) calcd for $C_{25}H_{34}N_7O_3$ [M + H]$^+$ 480.2718, found 480.2711. Using N-(2-methoxy-2-methylpropyl)-2-(methylsulfonyl)pyrido[3,4-d]pyrimidin-8-amine (Preparation 173) and N-(2-methoxy-4-(4-methylpiperazine-1-carbonyl)phenyl)formamide (Preparation 147) at 120° C. for 18 hours and purification method B. | 0.008 |
| 196 | N8-(2-methoxy-2-methylpropyl)-N2-(2-methoxy-4-(1-methyl-1H-1,2,4-triazol-5-yl)phenyl)-6-methylpyrido[3,4-d]pyrimidine-2,8-diamine | $^1$H NMR (500 MHz, MeOD): δ 9.06 (s, 1H), 8.79 (d, J = 8.5 Hz, 1H), 8.01 (s, 1H), 7.43 (d, J = 1.5 Hz, 1H), 7.40 (dd, J = 8.5, 1.5 Hz, 1H), 6.74 (d, J = 1.0 Hz, 1H), 4.08 (s, 3H), 4.07 (s, 3H), 3.66 (s, 2H), 3.37 (s, 3H), 2.45 (d, J = 1.0 Hz, 3H), 1.33 (s, 6H). HRMS (ESI) calcd for $C_{23}H_{29}N_8O_2$ [M + H]$^+$ 449.2408, found 449.2391. Using N-(2-methoxy-2-methylpropyl)-6-methyl-2-(methylsulfonyl)pyrido[3,4-d]pyrimidin-8-amine (Preparation 172) and N-(2-methoxy-4-(1-methyl-1H-1,2,4-triazol-5-yl)phenyl)formamide (Preparation 127) at 120° C. for 18 hours. | 0.020 |

| Example No | Name/Structure | Data | MPS1 IC50 (μM) |
|---|---|---|---|
| 197 | N2-(2-(difluoromethoxy)-4-(1-methyl-1H-pyrazol-4-yl)phenyl)-N8-(2-methoxy-2-methylpropyl)-6-methylpyrido[3,4-d]pyrimidine-2,8-diamine 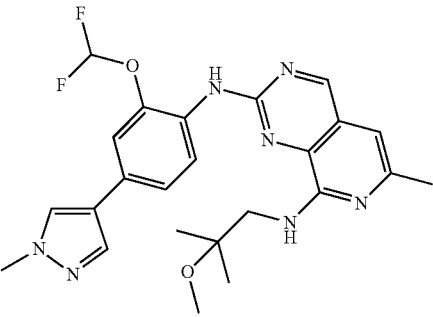 | $^1$H NMR (500 MHz, MeOD): δ 9.01 (s, 1H), 8.41 (d, J = 8.5 Hz, 1H), 8.00 (s, 1H), 7.83 (s, 1H), 7.48 (dd, J = 8.5, 2.0 Hz, 1H), 7.45 (m, 1H), 6.71 (d, J = 0.5 Hz, 1H), 3.97 (d, J = 4.0 Hz, 1H), 3.95 (s, 3H), 3.62 (s, 2H), 3.34 (s, 3H), 2.44 (d, J = 0.5 Hz, 3H), 1.30 (s, 6H).<br>HRMS (ESI) calcd for $C_{24}H_{28}F_2N_7O_2$ [M + H]$^+$ 484.2267, found 484.2246.<br>Using N-(2-methoxy-2-methylpropyl)-6-methyl-2-(methylsulfonyl)pyrido[3,4-d]pyrimidin-8-amine (Preparation 172) and N-(2-(difluoromethoxy)-4-(1-methyl-1H-pyrazol-4-yl)phenyl)formamide (Preparation 149) at 120° C. for 18 hours and purification method B. | 0.034 |
| 198 | (4-(3-methoxy-4-((8-((2-methoxy-2-methylpropyl)amino)-6-methylpyrido[3,4-d]pyrimidin-2-yl)amino)phenyl)-1-methyl-1H-pyrazol-5-yl)methanol 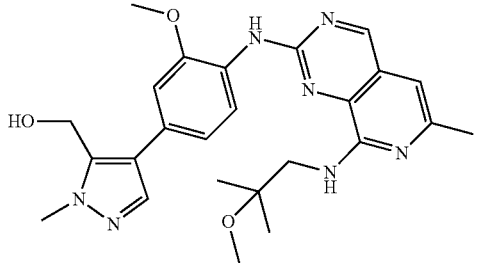 | $^1$H NMR (500 MHz, MeOD): δ 9.00 (s, 1H), 8.56 (d, J = 8.5 Hz, 1H), 7.63 (s, 1H), 7.21 (d, J = 2.0 Hz, 1H), 7.15 (dd, J = 8.5, 2.0 Hz, 1H), 6.71 (d, J = 0.5 Hz, 1H), 4.75 (s, 2H), 4.02 (s, 3H), 4.00 (s, 3H), 3.64 (s, 2H), 3.37 (s, 3H), 2.44 (d, J = 0.5 Hz, 3H), 1.32 (s, 6H).<br>HRMS (ESI) calcd for $C_{25}H_{32}N_7O_3$ [M + H]$^+$ 478.2561, found 478.2546.<br>Using N-(2-methoxy-2-methylpropyl)-6-methyl-2-(methylsulfonyl)pyrido[3,4-d]pyrimidin-8-amine (Preparation 172) and (4-(4-formamido-3-methoxyphenyl)-1-methyl-1H-pyrazol-5-yl)methyl formate (Preparation 145) at 120° C. for 18 hours and purification method B. | 0.009 |
| 199 | N-(2-chloro-4-(methylsulfonyl)phenyl)-8-(2-oxa-6-azaspiro[3.4]octan-6-yl)pyrido[3,4-d]pyrimidin-2-amine 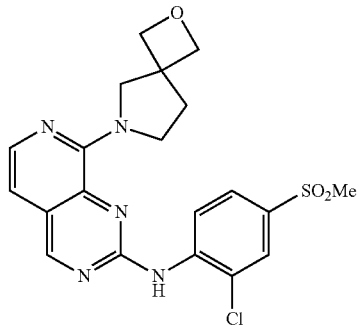 | $^1$H NMR (500 MHz, DMSO-d$_6$): δ 9.52 (s, 1H), 9.27 (s, 1H), 8.10 (d, J = 8.5 Hz, 1H), 8.06 (d, J = 2.2 Hz, 1H), 7.94 (dd, J = 2.2, 8.5 Hz, 1H), 7.91 (d, J = 5.3 Hz, 1H), 6.96 (d, J = 5.5 Hz, 1H), 4.51-4.46 (m, 4H), 4.05 (s, 2H), 3.72 (t, J = 6.7 Hz, 2H), 3.29 (s, 3H), 2.14 (t, J = 6.8 Hz, 2H).<br>HRMS (ESI) calcd for $C_{20}H_{21}ClN_6O_3S$ [M + H]$^+$ 446.1048, found 446.1053.<br>Using 6-(2-(methylsulfonyl)pyrido[3,4-d]pyrimidin-8-yl)-2-oxa-6-azaspiro[3.4]octane (Preparation 220) and 2-chloro-4-(methylsulfonyl)aniline and purification method D. | 0.025 |

-continued

| Example No | Name/Structure | Data | MPS1 IC50 (μM) |
|---|---|---|---|
| 200 | N-(2-Chloro-4-(pyrimidin-5-yl)phenyl)-8-(2-oxa-6-azaspiro[3.4]octan-6-yl)pyrido[3,4-d]pyrimidin-2-amine 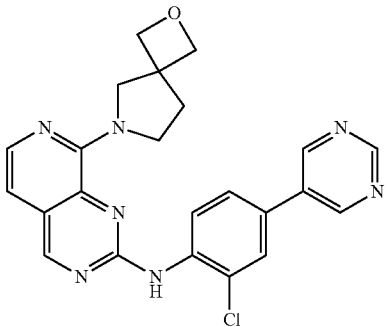 | $^1$H NMR (500 MHz, DMSO-d$_6$): δ 9.39 (s, 1H), 9.21 (br s, 3H), 9.20 (s, 1H), 8.10 (br s, 1H), 7.88 (br s, 2H), 7.85 (d, J = 5.5 Hz, 1H), 6.91 (d, J = 5.5 Hz, 1H), 4.46 (d, J = 5.9 Hz, 2H), 4.39 (d, J = 6.0 Hz, 2H), 4.02 (s, 2H), 3.69 (t, J = 6.7 Hz, 2H), 2.09 (t, J = 6.9 Hz, 2H).<br>HRMS (ESI) calcd for C$_{23}$H$_{21}$ClN$_7$O [M + H]$^+$ 446.1491, found 446.1498.<br>Using 6-(2-(methylsulfonyl)pyrido[3,4-d]pyrimidin-8-yl)-2-oxa-6-azaspiro[3.4]octane (Preparation 220) and 2-chloro-4-(pyrimidin-5-yl)aniline (WO2012123745 A1) and purification method D. | 0.006 |
| 201 | N-(2-Chloro-4-(5-methyl-1,3,4-oxadiazol-2-yl)phenyl)-8-(2-oxa-6-azaspiro[3.4]octan-6-yl)pyrido[3,4-d]pyrimidin-2-amine 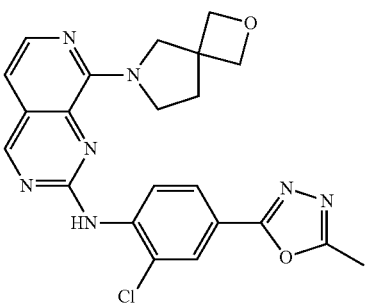 | $^1$H NMR (500 MHz, DMSO-d$_6$): δ 9.46 (s, 1H), 9.25 (s, 1H), 8.08 (d, J = 1.8 Hz), 8.05-7.99 (m, 2H), 7.89 (d, J = 5.6 Hz), 6.94 (d, J = 5.5 Hz), 4.46 (d, J = 6.0 Hz, 2H), 4.42 (d, J = 6.0 Hz, 2H), 4.03 (s, 2H), 3.71 (t, J = 6.9 Hz, 2H), 2.59 (s, 3H), 2.11 (t, J = 7.0 Hz, 2H).<br>HRMS (ESI) calcd for C$_{22}$H$_{21}$ClN$_7$O$_2$ [M + H]$^+$ 450.1440, found 450.1431.<br>Using 6-(2-(methylsulfonyl)pyrido[3,4-d]pyrimidin-8-yl)-2-oxa-6-azaspiro[3.4]octane (Preparation 220) and 2-chloro-4-(5-methyl-1,3,4-oxadiazol-2-yl)aniline (Preparation 157) and purification method D. | 0.040 |
| 202 | N2-(4-Chloro-2-(difluoromethoxy)phenyl)-N8-(2-methoxy-2-methylpropyl)pyrido[3,4-d]pyrimidine-2,8-diamine 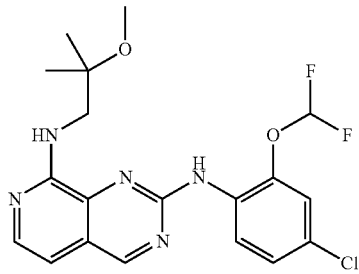 | $^1$H NMR (500 MHz, DMSO-d$_6$): δ 9.29 (s, 1H), 9.19 (s, 1H), 7.99 (d, J = 8.7 Hz, 1H), 7.77 (d, J = 5.7 Hz, 1H), 7.37 (d, J = 2.3 Hz, 1H), 7.33 (dd, J = 8.7, 2.3 Hz, 1H), 7.07 (t, J = 73.3 Hz, 1H), 6.87 (d, J = 5.7 Hz, 1H), 3.51 (d, J = 5.6 Hz, 2H), 3.16 (s, 3H), 1.16 (s, 6H).<br>HRMS (ESI) calcd for C$_{19}$H$_{21}$ClF$_2$N$_5$O$_2$ [M + H]$^+$ 424.1346, found 424.1356.<br>Using N-(2-methoxy-2-methylpropyl)-2-(methylsulfonyl)pyrido[3,4-d]pyrimidin-8-amine (Preparation 173) and N-(4-chloro-2-(difluoromethoxy)phenyl)formamide (Preparation 151) at 120° C. for 1 hour and purification method E. | 0.070 |

| Example No | Name/Structure | Data | MPS1 IC50 (μM) |
|---|---|---|---|
| 203 | N2-(2-(Difluoromethoxy)-4-fluorophenyl)-N8-(2-methoxy-2-methylpropyl)pyrido[3,4-d]pyrimidine-2,8-diamine | $^1$H NMR (500 MHz, CDCl$_3$): δ 8.99 (s, 1H), 8.61 (dd, J = 9.5, 6 Hz, 1H), 7.9 (d, J = 5.8 Hz, 1H), 7.61 (s 1H), 7.02-7 (m, 2H), (d, J = 2.3 Hz, 1H), 6.76 (d, J = 6 Hz, 2H), 1H), 6.62 (t, J = 72.7 Hz, 1H), 3.63 (d, J = 5.3 Hz, 2H), 3.34 (s, 3H), 1.32 (s, 6H). HRMS (ESI) calcd for C$_{19}$H$_{21}$F$_3$N$_5$O$_2$ [M + H]$^+$ 408.1642, found 408.1659. Using N-(2-methoxy-2-methylpropyl)-2-(methylsulfonyl)pyrido[3,4-d]pyrimidin-8-amine (Preparation 173) and N-(2-(difluoromethoxy)-4-fluorophenyl)formamide (Preparation 152) at 120° C. for 1 hour and purification method E. | 0.046 |
| 204 | N2-(2-(Difluoromethoxy)-4-(1-methyl-1H-pyrazol-4-yl)phenyl)-N8-(2-methoxy-2-methylpropyl)pyrido[3,4-d]pyrimidine-2,8-diamine | $^1$H NMR (500 MHz, CDCl$_3$): δ 9.00 (s, 1H), 8.66 (d, J = 8.6 Hz, 1H), 7.9 (d, J = 5.7 Hz, 1H), 7.62 (s 1H), 7.38 (dd, J = 8.6, 1.9 Hz, 1H), 7.29 (d, J = 1.6 Hz, 1H), 6.78 (d, J = 5.8 Hz, 1H), 6.65 (t, J = 73.3 Hz, 1H), 3.97 (s, 3H), 3.66 (d, J = 5.2 Hz, 2H), 3.36 (s, 3H), 1.33 (s, 6H). HRMS (ESI) calcd for C$_{23}$H$_{26}$F$_2$N$_7$O$_2$ [M + H]$^+$ 470.2111, found 470.2118. Using N-(2-methoxy-2-methylpropyl)-2-(methylsulfonyl)pyrido[3,4-d]pyrimidin-8-amine (Preparation 173) and N-(2-(difluoromethoxy)-4-(1-methyl-1H-pyrazol-4-yl)phenyl)formamide (Preparation 149) at 120° C. for 1 hour and purification method A. | 0.002 |
| 205 | 4-(8-(2-Oxa-6-azaspiro[3.4]octan-6-yl)pyrido[3,4-d]pyrimidin-2-ylamino)-3-chlorobenzonitrile | $^1$H NMR (500 MHz, CDCl$_3$): δ 9.10 (s, 1H), 8.61 (d, J = 8.7 Hz, 1H), 8.06 (d, J = 5.5 Hz, 1H), 1H), 7.95 (s, 1H), 7.74 (d, J = 1.9 Hz, 1H), 7.6 (dd, J = 8.7,1.9 Hz, 1H), 6.88 (d, J = 5.5 Hz, 1H), 4.74-4.71 (m, 2H), 4.29 (s, 2H), 4.04 (t, J = 6.7 Hz, 2H), 2.34 (t, J = 7 Hz, 2H). HRMS (ESI) calcd for C$_{20}$H$_{18}$ClN$_6$O [M + H]$^+$ 393.1225, found 393.1219. Using 6-(2-(methylsulfonyl)pyrido[3,4-d]pyrimidin-8-yl)-2-oxa-6-azaspiro[3,4]octane (Preparation 220) and 4-cyano-2-chloroaniline at 120° C. for 1 hour and purification method A. | 0.087 |

| Example No | Name/Structure | Data | MPS1 IC50 (µM) |
|---|---|---|---|
| 206 | 4-(8-(2-Oxa-6-azaspiro[3.4]octan-6-yl)pyrido[3,4-d]pyrimidin-2-ylamino)-3-methoxybenzonitrile | $^1$H NMR (500 MHz, CDCl$_3$): δ 9.05(s, 1H), 8.52 (d, J = 8.4 Hz, 1H), 8.03 (s, 1H), 8.02 (s, 1H), 7.35 (dd, J = 8.4, 1.7 Hz, 1H), 7.15 (d, J = 1.7 Hz, 1H), 6.85 (d, J = 5.5 Hz, 1H), 4.75-4.71 (m, 2H), 4.32 (s, 2H), 4.04 (t, J = 6.8 Hz, 2H), 4.01 (s, 3H), 2.33 (t, J = 6.9 Hz, 2H) HRMS (ESI) calcd for C$_{21}$H$_{21}$N$_6$O$_2$ [M + H]$^+$ 389.1721, found 389.1715. Using 6-(2-(methylsulfonyl)pyrido[3,4-d]pyrimidin-8-yl)-2-oxa-6-azaspiro[3,4]octane (Preparation 220) and N-(4-cyano-2-methoxyphenyl)formamide (Preparation 148) at 120° C. for 1 hour and purification method A. | 0.017 |
| 207 | N-(2,4-Dichlorophenyl)-8-(2-oxa-6-azaspiro[3.4]octan-6-yl)pyrido[3,4-d]pyrimidin-2-amine | $^1$H NMR (500 MHz, CDCl$_3$): δ 9.03 (s, 1H), 8.23 (d, J = 8.8 Hz, 1H), 7.99 (d, J = 5.5 Hz, 1H), 7.56 (s, 1H), 7.47 (d, J = 2.4 Hz, 1H), 7.29 (dd, J = 8.9, 2.4 Hz, 1H), 6.83 (d, J = 5.5 Hz, 1H), 4.71 (d, J = 6.2 Hz, 2H), 4.68 (d, J = 6.1 Hz, 2H), 4.24 (s, 2H), 3.96 (t, J = 6.9 Hz, 2H), 2.3 (t, J = 6.9 Hz, 2H). HRMS (ESI) MS m/z C$_{19}$H$_{18}$Cl$_2$N$_5$O [M + H]$^+$ 398.1378, found 398.1375. Using 6-(2-(methylsulfonyl)pyrido[3,4-d]pyrimidin-8-yl)-2-oxa-6-azaspiro[3,4]octane (Preparation 220) and N-(2,4-dichlorophenyl)formamide (Preparation 153) at 120° C. for 1 hour and purification method A. | 0.094 |

Example 208

N-(2-methoxy-4-(1-methyl-1H-pyrazol-4-yl)phenyl)-8-(pyrimidin-5H)pyrido[3,4-d]pyrimidin-2-amine

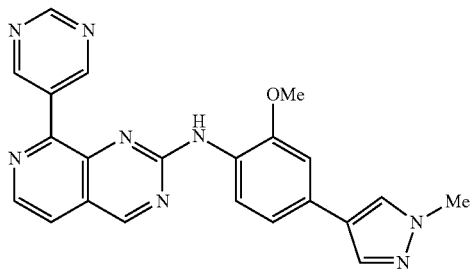 [SMILES: COc1cc(-c2cnn(C)c2)ccc1Nc1ncc2ccnc(-c3cncnc3)c2n1]

8-Chloro-N-(2-methoxy-4-(1-methyl-1H-pyrazol-4-yl)phenyl)pyrido[3,4-d]pyrimidin-2-amine (Example 94, 36 mg 0.1 mmole) and pyrimidine-5-boronic acid (18 mg 0.14 mmole) with potassium carbonate (50 mg, 0.36 mmole) and tetrakis(triphenylphosphine)palladium(O) (6 mg 0.0005 mmole) were dissolved in DMF (0.8 mL) and placed under argon and the mixture was heated under microwave irradiation at 150° C. for 30 minutes. The reaction was diluted with ethyl acetate (20 mL) and washed with water (7 mL). The aqueous layer was backwashed with ethyl acetate (10 mL). The combined organic layers were washed with water (2×10 mL) and with brine, then dried and concentrated in vacuo. The residue was purified using preparative TLC eluting with 2:1 ethyl acetate:ethanol followed by recrystallization from EtOAc to afford the title compound (12 mg, 33%).

$^1$H NMR (500 MHz, CDCl$_3$): δ 9.65 (s, 2H), 9.38 (s, 1H), 9.24 (s, 1H), 8.65 (d, J=5.04 Hz, 1H), 8.52 (d, J=8.51 Hz, 1H), 8.19 (br s, 1H), 7.78 (d, J=0.95 Hz, 1H), 7.64 (s, 1H), 7.62 (d, J=5.04 Hz, 1H), 7.12 (dd, J=1.89, 8.51 Hz, 1H), 7.03 (d, J=1.89 Hz, 1H), 4.00 (s, 3H), 3.98 (s, 3H).

HRMS (ESI) calcd for C$_{22}$H$_{13}$N$_8$O [M+H]$^+$ 411.1676. found 411.1688.

MPS1 IC50 (µM): 0.200

Example 209

N-(2-Methoxy-4-(1-methyl-1H-pyrazol-4-yl)phenyl)-8-(pyridin-4-yl)pyrido[3,4-d]pyrimidin-2-amine pyridin-4-ylboronate

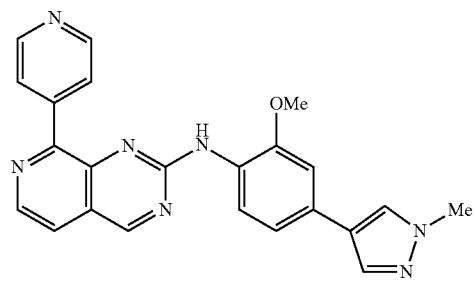 [SMILES: COc1cc(-c2cnn(C)c2)ccc1Nc1ncc2ccnc(-c3ccncc3)c2n1]

The title compound was prepared according to the method described for Example 208 using 8-Chloro-N-(2-methoxy-4-

(1-methyl-1H-pyrazol-4-yl)phenyl)pyrido[3,4-d]pyrimidin-2-amine (Example 94) and pyridine-4-boronic acid for 30 minutes at each of 100° C., 110° C., 120° C. and 130° C.

$^1$H NMR (500 MHz, CDCl$_3$): δ 9.22 (s, 1H), 8.84 (d, J=5.99 Hz, 2H), 8.63 (d, J=5.36 Hz, 1H), 8.19 (d, J=6.31 Hz, 2H), 7.76 (d, J=0.63 Hz, 1H), 7.64 (s, 1H), 7.61 (d, J=5.36 Hz, 1H), 7.03 (dd, 1.89, 6.31 Hz, 1H), 7.02 (s, 1H), 4.00 (s, 3H), 3.98 (s, 3H).

HRMS (ESI) calcd for C$_{23}$H$_{20}$N$_7$O [M+H]$^+$ 410.1724. found 410.1722.

MPS1 IC50 (μM): 0.007

Preparation Methods

Preparation 1: 2-(4-(3-Chloroisoquinolin-5-yl)-1H-pyrazol-1-yl)-N,N-dimethylethanamine

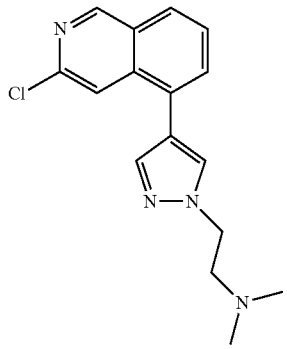 [SMILES: CN(C)CCn1cc(-c2cccc3cnc(Cl)cc23)cn1]

A mixture of 3-chloro-5-(1H-pyrazol-4-yl)isoquinoline (Preparation 3, 28 mg, 0.122 mmol), 2-chloro-N,N-dimethylethanamine hydrochloride (35.1 mg, 0.244 mmol) and K$_2$CO$_3$ (50.5 mg, 0.366 mmol) in DMF (4 mL) was stirred at 190° C. under microwave irradiation for 90 minutes.

The reaction mixture was diluted with EtOAc, purified by SCX-2 column eluting with 2M NH$_3$/MeOH and concentrated in vacuo to afford the title compound as a yellow oil that was used in the next step without further purification.

Preparation 2: 3-Chloro-5-(1-(2-methoxyethyl)-1H-pyrazol-4-yl)isoquinoline

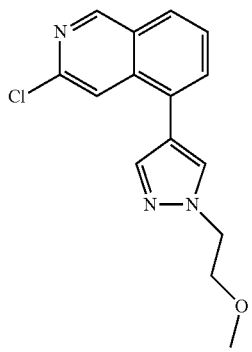 [SMILES: COCCn1cc(-c2cccc3cnc(Cl)cc23)cn1]

To a solution of 3-chloro-5-(1H-pyrazol-4-yl)isoquinoline (Preparation 3, 10 mg, 0.42 mmol) in DMF (3 mL) was added NaH (60%, 28 mg, 0.122 mmol). After stirring at room temperature for 15 minutes, 1-bromo-2-methoxyethane (25.4 mg, 0.183 mmol) was added and the reaction mixture was stirred at 80° C. for 60 minutes. The reaction was diluted with brine and extracted with EtOAc, the organic layers were dried with Na$_2$SO$_4$ and concentrated in vacuo to afford the title compound that was used in the next step without further purification (15 mg).

LCMS (ESI) Rt=2.37 minutes MS m/z 288 [M+H]$^+$

Preparation 3: 3-Chloro-5-(1H-pyrazol-4-yl)isoquinoline

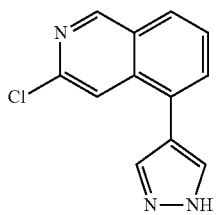 [SMILES: Clc1cc2c(-c3cn[nH]c3)cccc2cn1]

Method 9

A suspension of 5-bromo-3-chloroisoquinoline (522 mg, 2.15 mmol), tert-butyl 4-(4,4,5,5-tetramethyl-1,3,2-dioxaborolan-2-yl)-1H-pyrazole-1-carboxylate (697 mg, 2.37 mmol), Pd(dppf)Cl$_2$.DCM (182 mg, 0.22 mmol) and Na$_2$CO$_3$ (2M, 2.2 mL, 4.30 mmol) in DME (10 mL) was stirred at 130° C. under microwave irradiation for 120 minutes. The reaction mixture was filtered and concentrated in vacuo. The residue was purified using Biotage silica gel column chromatography eluting with between 20-30% EtOAc in cyclohexane to afford the title compound as a yellow solid (182 mg, 37%).

$^1$H NMR (500 MHz, MeOD): δ 9.15 (d, J=0.9 Hz, 1H), 8.09 (dt, J=8.4, 1.1 Hz, 1H), 8.04 (s, broad, 1H), 8.01 (t, J=0.9 Hz, 1H), 7.87 (s, broad, 1H), 7.84 (dd, J=7.1, 1.2 Hz, 1H), 7.72 (dd, J=8.3, 7.2 Hz, 1H).

LCMS (ESI) Rt=2.17 minutes MS m/z 230 [M+H]$^+$

Preparation 4: 3-Chloro-5-(1-methyl-1H-imidazol-5-yl)isoquinoline

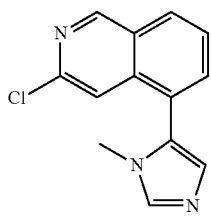 [SMILES: Cn1cncc1-c1cccc2cnc(Cl)cc12]

Method 10

A suspension of 3-chloro-5-(4,4,5,5-tetramethyl-1,3,2-dioxaborolan-2-yl)isoquinoline (Preparation 16 40 mg, 0.14 mmol), 5-iodo-1-methyl-1H-imidazole (43 mg, 0.21 mmol), Pd(PPh$_3$)$_4$ (16 mg, 0.014 mmol), CsF (63 mg, 0.41 mmol) in DME/MeOH (3/1 mL) was stirred at 150° C. under microwave irradiation for 60 minutes. The reaction mixture was filtered and concentrated in vacuo. The residue was purified using Biotage silica gel column chromatography eluting with 0-4% MeOH in EtOAc to afford the title compound (12 mg, 36%).

$^1$H NMR (500 MHz, CDCl$_3$): δ 9.17 (d, J=0.9 Hz, 1H), 8.17-8.03 (m, 1H), 7.80-7.67 (m, 3H), 7.61 (t, J=0.9 Hz, 1H), 7.22 (d, J=1.2 Hz, 1H), 3.49 (s, 3H).

LCMS (ESI) Rt=0.90 minutes MS m/z 244 [M+H]$^+$

The following Preparations were prepared according to Methods 9 or 10 (Preparations 3 or 4) above using the appropriate chloroisoquinoline and the appropriate cross-coupling partner as described.

The Preparations were purified according to the methods described or as described below:

Method A: Biotage silica gel column chromatography eluting with 30-35% EtOAc in cyclohexane.
Method B: Biotage silica gel column chromatography eluting with 50% EtOAc in cyclohexane.

| Preparation No | Name/Structure | Data |
|---|---|---|
| 5 | tert-Butyl 4-(4-(3-chloroisoquinolin-5-yl)-1H-pyrazol-1-yl)piperidine-1-carboxylate 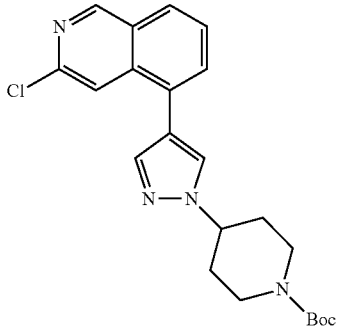 | $^1$H NMR (500 MHz, CDCl$_3$): δ 9.07 (d, J = 0.9 Hz, 1H), 7.94 (t, J = 0.9 Hz, 1H), 7.90 (dt, J = 8.2, 1.1 Hz, 1H), 7.74 (d, J = 0.8 Hz, 1H), 7.69-7.64 (m, 2H), 7.64-7.58 (m, 1H), 4.42-4.18 (m, 3H), 3.00-2.84 (m, 2H), 2.28-2.20 (m, 2H), 2.08-1.97 (m, 2H), 1.52 (s, 9H). LCMS (ESI) Rt = 2.83 minutes MS m/z 413 [M + H]$^+$ Using tert-butyl 4-(4-(4,4,5,5-tetramethyl-1,3,2-dioxaborolan-2-yl)-1H-pyrazol-1-yl)piperidine-1-carboxylate in Method 9. |
| 6 | (4-(3-Chloroisoquinolin-5-yl)-3,5-dimethylisoxazole 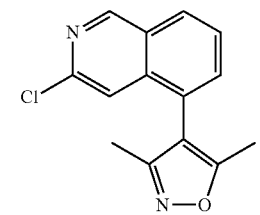 | $^1$H NMR (500 MHz, CDCl$_3$): δ 9.17 (d, J = 0.8 Hz, 1H), 8.07 (dt, J = 8.3, 1.1 Hz, 1H), 7.70 (dd, J = 8.3, 7.0 Hz, 1H), 7.59 (dd, J = 7.0, 1.2 Hz, 1H), 7.45 (t, J = 0.9 Hz, 1H), 2.30 (s, 3H), 2.13 (s, 3H). LCMS (ESI) Rt = 2.42 minutes MS m/z 259 [M + H]$^+$ Using 3,5-dimethyl-4-(4,4,5,5-tetramethyl-1,3,2-dioxaborolan-2-yl)isoxazole in Method 9 at 110° C. for 90 minutes. |
| 7 | 3-Chloro-5-(1-methyl-1H-pyrazol-4-yl)isoquinoline 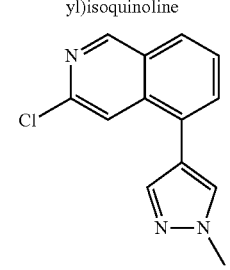 | $^1$H NMR (500 MHz, CDCl$_3$): δ 9.10 (d, J = 0.9 Hz, 1H), 8.02-7.97 (m, 1H), 7.97-7.89 (m, 1H), 7.74 (d, J = 0.8 Hz, 1H), 7.72-7.59 (m, 3H), 4.07 (s, 3H). LCMS (ESI) Rt = 2.30 minutes MS m/z 244 [M + H]$^+$ Using 1-methyl-4-(4,4,5,5-tetramethyl-1,3,2-dioxaborolan-2-yl)-1H-pyrazole in Method 9 at 110° C. for 120 minutes. |
| 8 | 3-Chloro-5-(1-isopropyl-1H-pyrazol-4-yl)isoquinoline 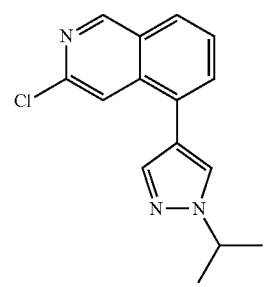 | $^1$H NMR (500 MHz, CDCl$_3$): δ 9.10 (d, J = 0.8 Hz, 1H), 8.00 (t, J = 0.9 Hz, 1H), 7.92 (dt, J = 8.2, 1.1 Hz, 1H), 7.76 (d, J = 0.8 Hz, 1H), 7.72-7.66 (m, 2H), 7.61 (dd, J = 8.2, 7.1 Hz, 1H), 4.64 (hept, J = 6.7 Hz, 1H), 1.64 (d, J = 6.7 Hz, 6H). LCMS (ESI) Rt = 2.56 minutes MS m/z 272 [M + H]$^+$ Using 1-isopropyl-4-(4,4,5,5-tetramethyl-1,3,2-dioxaborolan-2-yl)-1H-pyrazole in Method 9 at 110° C. for 60 minutes. |

| Preparation No | Name/Structure | Data |
|---|---|---|
| 9 | 3-Chloro-5-(1,3-dimethyl-1H-pyrazol-4-yl)isoquinoline | $^1$H NMR (500 MHz, CDCl$_3$): δ 9.10 (d, J = 0.8 Hz, 1H), 7.95 (ddd, J = 7.8, 1.5, 0.9 Hz, 1H), 7.70 (t, J = 0.9 Hz, 1H), 7.66-7.57 (m, 2H), 7.43 (s, 1H), 3.98 (s, 3H), 2.17 (s, 3H).<br>LCMS (ESI) Rt = 2.39 minutes MS m/z 258 [M + H]$^+$<br>Using 1,3-dimethyl-4-(4,4,5,5-tetramethyl-1,3,2-dioxaborolan-2-yl)-1H-pyrazole in Method 9 at 130° C. for 60 minutes. |
| 10 | 3-Chloro-5-(1-methyl-1H-pyrazol-5-yl)isoquinoline | $^1$H NMR (500 MHz, CDCl$_3$): δ 9.17 (d, J = 0.9 Hz, 1H), 8.16-8.09 (m, 1H), 7.72 (s, 1H), 7.71 (d, J = 2.5 Hz, 1H), 7.69 (d, J = 1.9 Hz, 1H), 7.54 (t, J = 1.0 Hz, 1H), 6.43 (d, J = 1.9 Hz, 1H), 3.71 (s, 3H).<br>LCMS (ESI) Rt = 2.34 minutes MS m/z 244 [M + H]$^+$<br>Using 5-bromo-3-chloroisoquinoline and 1-methyl-5-(4,4,5,5-tetramethyl-1,3,2-dioxaborolan-2-yl)-1H-pyrazole in Method 9 and purification method A. |
| 11 | 3-Chloro-5-(1-methyl-1H-pyrazol-3-yl)isoquinoline | $^1$H NMR (500 MHz, CDCl$_3$): δ 9.10 (d, J = 0.9 Hz, 1H), 8.59 (t, J = 0.9 Hz, 1H), 8.01-7.90 (m, 2H), 7.64 (dd, J = 8.2, 7.2 Hz, 1H), 7.53 (d, J = 2.2 Hz, 1H), 6.58 (d, J = 2.2 Hz, 1H), 4.07 (s, 3H).<br>LCMS (ESI) Rt = 2.38 minutes MS m/z 244 [M + H]$^+$<br>Using 3-iodo-1-methyl-1H-pyrazole in Method 10 and purification method A. |
| 12 | 3-Chloro-5-(1,5-dimethyl-1H-pyrazol-4-yl)isoquinoline | $^1$H NMR (500 MHz, CDCl$_3$): δ 9.10 (d, J = 0.8 Hz, 1H), 7.96 (dt, J = 8.2, 1.1 Hz, 1H), 7.72 (t, J = 0.9 Hz, 1H), 7.64 (dd, J = 8.2, 7.1 Hz, 1H), 7.57 (dd, J = 7.1, 1.3 Hz, 1H), 7.55 (s, 1H), 3.94 (s, 3H), 2.20 (s, 3H).<br>LCMS (ESI) Rt = 2.38 minutes MS m/z 258 [M + H]$^+$<br>Using 5-bromo-3-chloroisoquinoline and 1,5-dimethyl-4-(4,4,5,5-tetramethyl-1,3,2-dioxaborolan-2-yl)-1H-pyrazole in Method 9 and purification method A. |
| 13 | 3-Chloro-5-(pyrimidin-5-yl)isoquinoline | $^1$H NMR (500 MHz, CDCl$_3$) δ 9.39 (s, 1H), 9.21 (d, J = 0.9 Hz, 1H), 8.92 (s, 2H), 8.14 (dt, J = 8.2, 1.2 Hz, 1H), 7.79-7.70 (m, 2H), 7.68-7.57 (m, 1H).<br>LCMS (ESI) Rt = 2.03 minutes MS m/z 242 [M + H]$^+$<br>Using 5-(4,4,5,5-tetramethyl-1,3,2-dioxaborolan-2-yl)pyrimidine in Method 9 at 110° C. for 60 minutes. |

-continued

| Preparation No | Name/Structure | Data |
|---|---|---|
| 14 | 3-Chloro-5-(pyridin-3-yl)isoquinoline | $^1$H NMR (500 MHz, CDCl$_3$): δ 9.14 (d, J = 0.9 Hz, 1H), 8.81-8.68 (m, 2H), 8.10-7.99 (m, 1H), 7.80 (ddd, J = 7.7, 2.3, 1.7 Hz, 1H), 7.75-7.62 (m, 3H), 7.49 (ddd, J = 7.8, 4.8, 0.9 Hz, 1H). LCMS (ESI) Rt = 2.04 minutes MS m/z 241 [M + H]$^+$ Using pyridin-3-ylboronic acid in Method 9 at 110° C. for 60 minutes. |
| 15 | 3-Chloro-5-(furan-2-yl)isoquinoline | $^1$H NMR (500 MHz, CDCl$_3$): δ 9.09 (s, 1H), 8.33 (s, 1H), 7.99-7.90 (m, 2H), 7.71-7.55 (m, 2H), 6.79 (dd, J = 3.4, 0.6 Hz, 1H), 6.62 (dd, J = 3.4, 1.8 Hz, 1H). LCMS (ESI) MS m/z 230 [M + H]$^+$ HRMS (ESI) MS m/z calcd for C$_{13}$H$_9$ClNO [M + H]$^+$ 230.0367, found 230.0343. Using furan-2-ylboronic acid in Method 9 at 105° C. for 1 hour. |

Preparation 16: 3-Chloro-5-(4,4,5,5-tetramethyl-1,3,2-dioxaborolan-2-yl)isoquinoline

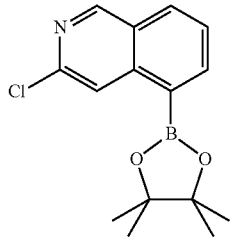 [SMILES: CC1(C)OB(c2cccc3cnc(Cl)cc23)OC1(C)C]

A mixture of 5-bromo-3-chloroisoquinoline (63 mg, 0.41 mmol), KOAc (63 mg, 0.41 mmol), Pd(dppf)Cl$_2$.DCM (22 mg, 0.03 mmol) and bis(pinacolato)diboron (63 mg, 0.41 mmol) in DMF (8 mL) was stirred at 100° C. under microwave irradiation for 60 minutes. The reaction mixture was filtered, diluted with NaCl solution and extracted with EtOAc. The crude was purified by Biotage silica gel column chromatography eluting with 20% EtOAc/cyclohexane to afford the title compound as yellow oil (170 mg, 41%).

$^1$H NMR (500 MHz, CDCl$_3$): δ 9.06 (d, J=0.9 Hz, 1H), 8.66-8.64 (m, 1H), 8.31 (dd, J=6.9, 1.4 Hz, 1H), 8.15-7.96 (m, 1H), 7.60 (dd, J=8.2, 6.9 Hz, 1H), 1.44 (s, 12H).

LCMS (ESI) Rt=3.02 minutes MS m/z 290 [M+H]$^+$

Preparation 17: 2-methoxy-4-(1-methyl-1H-imidazol-5-yl)aniline

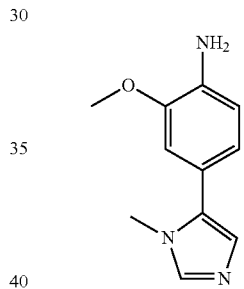

Method 11

A suspension of 5-bromo-1-methyl-1H-imidazole (228 mg, 1.42 mmol), 2-methoxy-4-(4,4,5,5-tetramethyl-1,3,2-dioxaborolan-2-yl)aniline (423 mg, 1.70 mmol), Pd(PPh$_3$)$_4$ (164 mg, 0.142 mmol) and CsF (645 mg, 4.25 mmol) in DME/MeOH (9/3 mL) was stirred at 150° C. under microwave irradiation for 60 minutes. The reaction mixture was filtered and concentrated in vacuo. The residue was purified using Biotage silica gel column chromatography eluting with between 0-4% MeOH in EtOAc to afford the title compound (137 mg, 48%).

$^1$H NMR (500 MHz, CDCl$_3$): δ 7.56 (s, 1H), 7.02 (s, 1H), 6.81-6.76 (m, 3H), 3.95 (s, broad, 2H), 3.88 (s, 3H), 3.64 (s, 3H).

LCMS (ESI) Rt=0.43 minutes MS m/z 204 [M+H]$^+$

The following Preparations were prepared according to Method 11 (Preparation 17) above using the appropriate aniline and heterocyclic cross-coupling partner as described.

The Preparations were purified according to the method described or as described below:

Method A: Biotage silica gel column chromatography eluting with 40% EtOAc in cyclohexane.

Method B: The reaction mixture was diluted with EtOAc and filtered. The organic layer was extracted with 2M HCl. The combined aqueous layers were washed with EtOAc and basified with solid NaHCO₃. The resulting aqueous solution was extracted with EtOAc, dried with Na₂SO₄ and concentrated in vacuo to afford the title compound with no further purification.

Method C: Method B followed by Biotage silica gel column chromatography eluting with between 25-40% EtOAc in cyclohexane.

Method D: Biotage silica gel column chromatography eluting with 1-5% MeOH in DCM.

| Preparation No | Name/Structure | Data |
|---|---|---|
| 18 | 4-(1,2-dimethyl-1H-imidazol-5-yl)-2-methoxyaniline | $^1$H NMR (500 MHz, DMSO-$d_6$): δ 6.77 (s, 1H), 6.65-6.72 (s, 3H), 4.87 (s, 2H), 3.78 (s, 3H), 3.46 (s, 3H), 2.31 (s, 3H). LCMS (ESI) Rt = 0.49 minutes MS m/z 218 [M + H]⁺ Using 5-bromo-1,2-dimethyl-1H-imidazole. |
| 19 | 2-methoxy-4-(1-methyl-1H-pyrazol-4-yl)aniline | $^1$H NMR (500 MHz, CDCl₃): δ 7.70 (s, 1H), 7.52 (s, 1H), 6.92 (dd, J = 7.9, 1.8 Hz, 1H), 6.90 (d, J = 1.8 Hz, 1H), 6.73 (d, J = 7.9 Hz, 1H), 3.94 (s, 3H), 3.91 (s, 3H), 3.80 (s, broad, 2H). LCMS (ESI) Rt = 0.95 minutes MS m/z 204 [M + H]⁺ Using 4-bromo-2-methoxyaniline and 1-methyl-4-(4,4,5,5-tetramethyl-1,3,2-dioxaborolan-2-yl)-1H-pyrazole and purification method A. |
| 20 | 2-chloro-4-(1-methyl-1H-imidazol-5-yl)aniline | $^1$H NMR (500 MHz, CDCl₃): δ 7.52 (d, J = 1.3 Hz, 1H), 7.26 (d, J = 2.0 Hz, 1H), 7.06 (dd, J = 8.2, 2.0 Hz, 1H), 6.99 (d, J = 1.3 Hz, 1H), 6.81 (d, J = 8.2 Hz, 1H), 4.05 (s, broad, 2H), 3.61 (s, 3H). LCMS (ESI) Rt = 0.79 minutes MS m/z 208 [M + H]⁺ Using 5-iodo-1-methyl-1H-imidazole at 140° C. in DME. |
| 21 | 2-chloro-4-(1-methyl-1H-pyrazol-4-yl)aniline | $^1$H NMR (500 MHz, CDCl₃): δ 7.66 (s, 1H), 7.50 (s, 1H), 7.37 (d, J = 2.0 Hz, 1H), 7.18 (dd, J = 8.2, 2.0 Hz, 1H), 6.77 (d, J = 8.2 Hz, 1H), 4.04 (s, 2H), 3.93 (s, 3H). LCMS (ESI) Rt = 1.91 minutes MS m/z 208 [M + H]+ Using 4-bromo-2-chloroaniline and 1-methyl-4-(4,4,5,5-tetramethyl-1,3,2-dioxaborolan-2-yl)-1H-pyrazole at 100° C. in THF and purification method B. |

-continued

| Preparation No | Name/Structure | Data |
|---|---|---|
| 22 | 4-(3,5-dimethylisoxazol-4-yl)-2-methoxyaniline 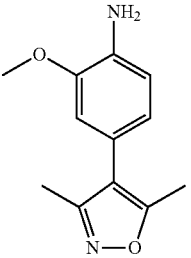 | $^1$H NMR (500 MHz, CDCl$_3$): δ 6.77 (d, J = 7.8 Hz, 1H), 6.71-6.64 (m, 2H), 3.96-3.88 (s, broad, 2H), 3.88 (s, 3H), 2.39 (s, 3H), 2.27 (s, 3H).<br>LCMS (ESI) Rt = 1.48 minutes MS m/z 219 [M + H]$^+$<br>Using 4-bromo-2-methoxyaniline and 3,5-dimethyl-4-(4,4,5,5-tetramethyl-1,3,2-dioxaborolan-2-yl)isoxazole at 120° C. for 60 minutes and purification method C. |
| 23 | 2-Chloro-4-(1,2-dimethyl-1H-imidazol-5-yl)aniline 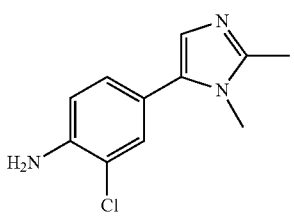 | $^1$H NMR (500 MHz, CDCl$_3$): δ 2.43 (s, 3H), 3.48 (s, 3H), 4.21 (br s, 2H), 6.81 (d, J = 8.2 Hz, 1H), 6.87 (s, 1H), 7.05 (dd, J = 8.2, 2.0 Hz, 1H), 7.24 (d, J = 2.0 Hz, 1H).<br>LCMS (ESI) Rt = 0.96 minutes MS m/z 222 [M + H]$^+$<br>Using 5-bromo-1,2-dimethyl-1H-imidazole for 10 minutes at 150° C. and purification method D. |

Preparation 24:
4-amino-3-methoxy-N,N-dimethylbenzamide

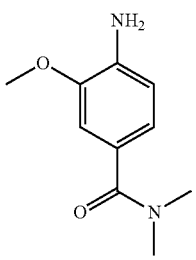

HATU (0.296 g, 0.778 mmol) was added to a solution of 4-amino-3-methoxybenzoic acid (0.1 g, 0.598 mmol), DIPEA (0.156 mL, 0.897 mmol) and dimethylamine (2M in THF, 0.598 mL, 1.196 mmol) in THF (1.617 ml). The reaction mixture was stirred for 18 hours. The reaction was partitioned between EtOAc and water, the organic layers were washed with water, dried over Na$_2$SO$_4$ and concentrated in vacuo. The residue was purified by Biotage silica gel column chromatography eluting with DCM/EtOAc 60/40 to 40/60 followed by filtration through an SCX-2 column eluting with 2M NH$_3$/MeOH to afford the title compound as a colourless oil (69 mg, 59%).

$^1$H NMR (500 MHz, MeOD): δ 6.95 (d, J=1.8 Hz, 1H), 6.89 (dd, J=8.0, 1.8 Hz, 1H), 6.74 (d, J=8.0 Hz, 1H), 3.88 (s, 3H), 3.08 (s, 6H).

LCMS (ESI) Rt=0.96 minutes MS m/z 195 [M+H]$^+$

Preparation 25: 4-amino-3-chloro-N,N-dimethylbenzamide

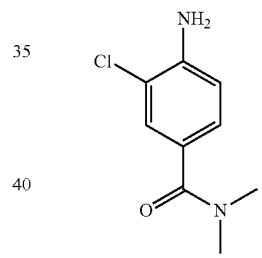

The title compound was prepared according to the method described for Preparation 24 using 4-amino-3-chlorobenzoic acid. Aqueous NaCl solution was added and the precipitate was filtered. The filtrate was extracted with ethyl acetate and the combined organic phases were washed with brine, dried over anhydrous Na$_2$SO$_4$, filtered and evaporated to afford the title compound (265 mg, 99%).

$^1$H NMR (500 MHz, MeOD): δ 7.35 (d, J=2.0 Hz, 1H), 7.17 (dd, J=8.3, 2.0 Hz, 1H), 6.83 (d, J=8.3 Hz, 1H), 3.07 (s, 6H).

LCMS (ESI) Rt=1.55 minutes MS m/z 199 [M+H]$^+$

Preparation 26: 4-amino-N-(1-methylpiperidin-4-yl)-3-(trifluoromethoxy)benzamide

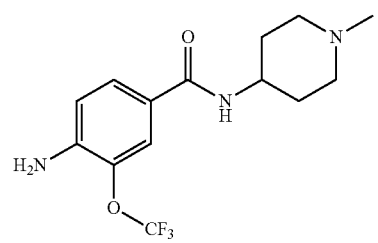 [SMILES: CN1CCC(NC(=O)c2ccc(N)c(OC(F)(F)F)c2)CC1]

The title compound was prepared according to the method described for Preparation 25 using 4-amino-3-(trifluoromethoxy)benzoic acid and 4-amino-1-methylpiperidine.

$^1$H NMR (500 MHz, DMSO-d$_6$): δ 8.01 (d, J=7.6 Hz, 1H), 7.66 (s, broad, 1H), 7.63 (dd, J=8.4, 2.0 Hz, 1H), 6.79 (d, J=8.4 Hz, 1H), 3.85-3.74 (m, 1H), 3.00-2.92 (m, 2H), 2.69 (s, 3H), 2.32-2.23 (m, 2H), 1.86-1.74 (m, 2H), 1.69-1.55 (m, 2H).

LCMS (ESI) Rt=0.95 minutes MS m/z 318 [M+H]$^+$

Preparation 27: (4-amino-3-chlorophenyl)(3-methoxyazetidin-1-yl)methanone

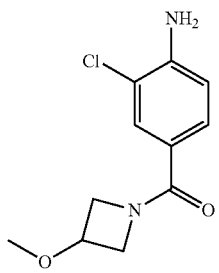 [SMILES: COC1CN(C(=O)c2ccc(N)c(Cl)c2)C1]

The title compound was prepared according to the method described for Preparation 25 using 4-amino-3-chlorobenzoic acid and 3-methoxyazetidine hydrochloride.

$^1$H NMR (500 MHz, CDCl$_3$): δ 7.60 (d, J=2.0 Hz, 1H), 7.39 (dd, J=8.4, 1.9 Hz, 1H), 6.74 (d, J=8.3 Hz, 1H), 4.45-4.35 (m, 4H), 4.28-4.00 (m, 3H), 3.32 (s, 3H).

LCMS (ESI) Rt=1.68 minutes MS m/z 241 [M+H]$^+$

Preparation 28: (4-amino-3-methoxyphenyl)(3-methoxyazetidin-1-yl)methanone

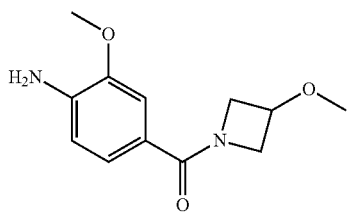 [SMILES: COc1cc(C(=O)N2CC(OC)C2)ccc1N]

HATU (2.70 g, 7.10 mmol) was added to a solution of 4-amino-3-methoxybenzoic acid (880 mg, 5.26 mmol), 3-methoxyazetidine hydrochloride (0.971 g, 7.86 mmol) and DIPEA (2.85 mL, 16.32 mmol) in THF (15 mL) at room temperature. THF was removed under reduced pressure, and the residue partitioned between EtOAc and saturated aqueous NaHCO$_3$. The aqueous layer was extracted with EtOAc and the combined organic layers were washed with brine, dried and concentrated. The residue was purified by silica gel column chromatography eluting with 0 to 100% EtOAc in cyclohexane followed by a second chromatography eluting with 0 to 4% MeOH in DCM to afford the title compound (728 mg, 59%).

$^1$H NMR (500 MHz, CDCl$_3$): δ 7.24 (d, J=1.7 Hz, 1H), 7.06 (dd, J=8.1, 1.8 Hz, 1H), 6.66 (d, J=8.0 Hz, 1H), 4.42 (br s, 2H), 4.31-3.99 (m, 5H), 3.91 (s, 3H), 3.34 (s, 3H).

Preparation 29: (E)-2-(2-ethoxyvinyl)-4,4,5,5-tetramethyl-1,3,2-dioxaborolane

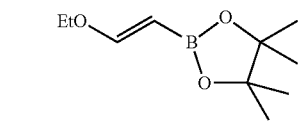

A solution of ethoxyethyne (60% w/w in hexanes, 30 mL, 154 mmol) in DCM (230 mL) was cooled at 0° C. and pinacol borane (27 mL, 186 mmol) was added followed by Cp$_2$Zr(H)Cl (1.96 g, 7.60 mmol). The mixture was allowed to reach room temperature and stirred for 18 hours. The reaction was filtered through a pad of neutral alumina eluting with 10% EtOAc in cyclohexane to afford the title compound (27.66 g, 91%).

$^1$H NMR (500 MHz, CDCl$_3$): δ 7.05 (d, J=14.4 Hz, 1H), 4.45 (d, J=14.4 Hz, 1H), 3.86 (q, J=7.1 Hz, 2H), 1.30 (t, J=7.1 Hz, 3H), 1.27 (s, 12H).

Preparation 30: Methyl 5-bromo-2-(methylthio)pyrimidine-4-carboxylate

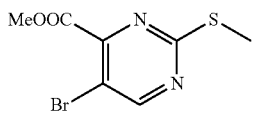

A solution of 5-bromo-2-(methylthio)pyrimidine-4-carboxylic acid (7.64 g, 30.7 mmol) in MeOH (60 mL) was treated with sulfuric acid (2 mL) and boiled for 24 hours. The mixture was poured onto ice water and extracted with DCM. The DCM phase was washed with saturated aqueous sodium hydrogen carbonate solution, dried and evaporated to give the title compound (6.42 g, 80%).

$^1$H NMR (500 MHz, CDCl$_3$): δ 8.72 (s, 1H), 4.01 (s, 3H), 2.58 (s, 3H).

LCMS (ESI) Rt=2.35 minutes 263 [M+H]$^+$

Preparation 31: (E)-methyl 5-(2-ethoxyvinyl)-2-(methylthio)pyrimidine-4-carboxylate

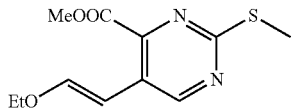 [SMILES: CCO/C=C/c1cnc(SC)nc1C(=O)OC]

A solution of (E)-2-(2-ethoxyvinyl)-4,4,5,5-tetramethyl-1,3,2-dioxaborolane (Preparation 29, 4.34 g, 21.91 mmol), methyl 5-bromo-2-(methylthio)pyrimidine-4-carboxylate (Preparation 30, 3.81 g, 14.48 mmol) and Pd(dppf)Cl$_2$.DCM (505 mg, 0.618 mmol) was dissolved in THF (45 mL) and 2M sodium carbonate in water (15 mL) and heated to 65° C. for 18 hours. The mixture was diluted with EtOAc and quenched with brine. The aqueous layer was extracted with EtOAc three times. The combined organic layers were washed with water and brine, dried and concentrated. The residue was purified by silica gel column chromatography eluting with 0 to 10% EtOAc in cyclohexane to give the title compound (2.30 g, 63%).

$^1$H NMR (500 MHz, CDCl$_3$): δ 8.67 (s, 1H), 6.96 (d, J=13.1 Hz, 1H), 6.26 (d, J=13.1 Hz, 1H), 4.13-3.81 (m, 5H), 2.60 (s, 3H), 1.37 (t, J=7.0 Hz, 3H).

LCMS (ESI) Rt=2.49 minutes MS m/z 255 [M+H]$^+$

Preparation 32:
2-(methylthio)pyrido[3,4-d]pyrimidin-8(7H)-one

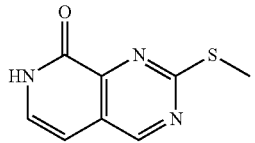

(E)-Methyl 5-(2-ethoxyvinyl)-2-(methylthio)pyrimidine-4-carboxylate (Preparation 31, 2.30 g, 9.04 mmol) was treated with ammonia in methanol 7M (45 mL) and heated to 85° C. for 18 hours in a capped vial. The solvent was removed under reduced pressure, and the resulting solid was treated with TsOH monohydrate (175 mg, 0.92 mmol), suspended in toluene (50 mL) and heated to 90° C. for 2 hours. The mixture was concentrated and the residue was purified by silica gel column chromatography eluting with 0 to 5% MeOH in DCM to give the title compound (1.47 g, 84%).

$^1$H NMR (500 MHz, DMSO): δ 9.21 (s, 1H), 7.28 (d, J=7.0 Hz, 1H), 6.58 (d, J=7.0 Hz, 1H), 2.60 (s, 3H).

LCMS (ESI) Rt=1.38 minutes MS m/z 194 [M+H]$^+$

Preparation 33:
8-Chloro-2-(methylthio)pyrido[3,4-d]pyrimidine

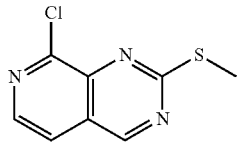

A solution of 2-(methylthio)pyrido[3,4-d]pyrimidin-8 (7H)-one (Preparation 32, 1.47 g, 7.61 mmol) in POCl$_3$ (70 mL) was heated to 70° C. for 18 hours. The reaction was concentrated under reduced pressure and partitioned between EtOAc and saturated aqueous NaHCO$_3$ solution. The aqueous layer was extracted with EtOAc and the combined organic layers were washed with water and brine, dried and concentrated. The residue was purified by silica gel column chromatography eluting with 0 to 20% EtOAc in cyclohexane to give the title compound (1.39 g, 86%).

$^1$H NMR (500 MHz, CDCl$_3$): δ 9.24 (s, 1H), 8.43 (d, J=5.4 Hz, 1H), 7.62 (d, J=5.4 Hz, 1H), 2.77 (s, 3H).

LCMS (ESI) Rt=2.36 minutes MS m/z 212 [M+H]$^+$

Preparation 34: 8-(1-methyl-1H-pyrazol-4-yl)-2-(methylthio)pyrido[3,4-d]pyrimidine

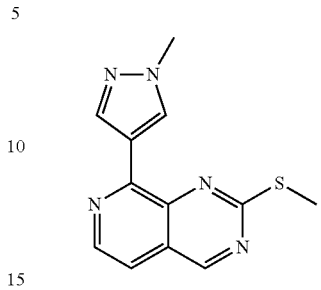

A solution of 8-chloro-2-(methylthio)pyrido[3,4-d]pyrimidine (Preparation 33, 480 mg, 2.268 mmol), 1-methyl-4-(4,4,5,5-tetramethyl-1,3,2-dioxaborolan-2-yl)-1H-pyrazole (940 mg, 4.52 mmol) and Pd(dppf)Cl$_2$.DCM (100 mg, 0.122 mmol) was dissolved in THF (15 mL) and 2M sodium carbonate in water (5 mL) and heated to 65° C. for 18 hours. The mixture was diluted with EtOAc and quenched with brine. The aqueous layer was extracted with EtOAc three times. The combined organic layers were washed with water and brine, dried and concentrated. The residue was purified by silica gel column chromatography eluting with 0 to 4% MeOH in DCM to give the title compound (658 mg, quant).

$^1$H NMR (500 MHz, CDCl$_3$): δ 9.22 (s, 1H), 8.67 (s, 1H), 8.63-8.56 (m, 2H), 7.47 (d, J=5.3 Hz, 1H), 4.05 (s, 3H), 2.78 (s, 3H).

LCMS (ESI) Rt=2.24 minutes MS m/z 258 [M+H]$^+$

Preparation 35: 8-(1-methyl-1H-pyrazol-4-yl)-2-(methylsulfonyl)pyrido[3,4-d]pyrimidine

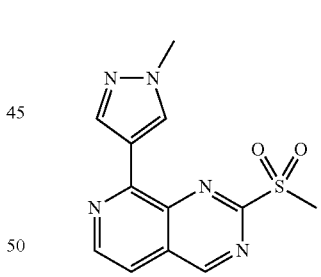

A suspension of 8-(1-methyl-1H-pyrazol-4-yl)-2-(methylthio)pyrido[3,4-d]pyrimidine (Preparation 34, 0.584 g, 2.27 mmol) in DCM (22 mL) was treated with mCPBA (77% w/w, 1.12 g, 4.98 mmol) at 0° C. and then allowed to reach room temperature for 18 hours. The mixture was quenched with water and extracted with DCM. The combined organic layers were washed with water, dried and concentrated. The residue was purified by silica gel column chromatography eluting with 0 to 100% EtOAc in cyclohexane to give the title compound (408 mg, 62%).

$^1$H NMR (500 MHz, DMSO-d$_6$): δ 10.00 (s, 1H), 8.91 (d, J=5.4 Hz, 1H), 8.81 (s, 1H), 8.53 (s, 1H), 7.99 (d, J=5.4 Hz, 1H), 3.99 (s, 3H), 3.59 (s, 3H).

LCMS (ESI) Rt=1.60 minutes MS m/z 290 [M+H]$^+$

Preparation 36:
2-(methylsulfonyl)-8-phenylpyrido[3,4-d]pyrimidine

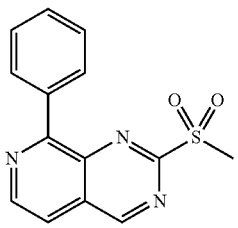 [SMILES: CS(=O)(=O)c1ncc2ccnc(-c3ccccc3)c2n1]

A solution of 8-chloro-2-(methylthio)pyrido[3,4-d]pyrimidine (Preparation 33, 131 mg, 0.619 mmol) phenylboronic acid (150 mg, 1.230 mmol) and Pd(dppf)Cl$_2$.DCM (25 mg, 0.031 mmol) was dissolved in THF (3 mL) and 2M sodium carbonate in water (1 mL) and heated to 60° C. for 18 hours. The mixture was diluted with EtOAc and quenched with brine. The aqueous layer was extracted with EtOAc three times. The combined organic layers were washed with water and brine, dried and concentrated. The residue was purified by silica gel column chromatography eluting with 0 to 20% EtOAc in cyclohexane to give the crude sulfide (ca. 134 mg).

A suspension of crude sulfide (134 mg, ca. 0.53 mmol) in DCM (5 mL) was treated with mCPBA (77% w/w, 260 mg, 1.157 mmol) at 0° C. and then allowed to reach room temperature for 18 hours. The mixture was quenched with water and extracted with DCM. The combined organic layers were washed with water, dried and concentrated. The residue was purified by silica gel column chromatography eluting with 0 to 60% EtOAc in cyclohexane to give the title compound (78 mg, 44% over two steps).

$^1$H NMR (500 MHz, DMSO-d$_6$): δ 10.10 (s, 1H), 9.09 (d, J=5.4 Hz, 1H), 8.27-8.16 (m, 3H), 7.65-7.51 (m, 3H), 3.50 (s, 3H).

LCMS (ESI) Rt=1.89 minutes MS m/z 286 [M+H]$^+$

Preparation 37: 8-cyclopropyl-2-(methylthio)pyrido[3,4-d]pyrimidine

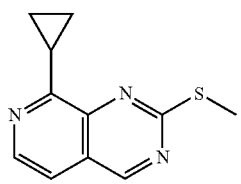

A solution of 8-chloro-2-(methylthio)pyrido[3,4-d]pyrimidine (Preparation 33, 20 mg, 0.094 mmol), cyclopropyl boronic acid (11 mg, 0.128 mmol), PCy$_3$ (3 mg, 10.70 µmol), and Pd(OAc)$_2$ (1 mg, 4.45 µmol) was dissolved in toluene/water 6:1 (1 mL) and heated to 95° C. for 18 hours. The mixture was diluted with EtOAc and quenched with brine. The aqueous layer was extracted with EtOAc three times. The combined organic layers were washed with water and brine, dried and concentrated. The residue was purified by silica gel column chromatography eluting with 0 to 20% EtOAc in cyclohexane to give the title compound (13 mg, 62%).

$^1$H NMR (500 MHz, CDCl$_3$): δ 9.18 (s, 1H), 8.46 (d, J=5.4 Hz, 1H), 7.37 (d, J=5.5 Hz, 1H), 3.46 (tt, J=8.2, 4.8 Hz, 1H), 2.74 (s, 3H), 1.34-1.27 (m, 2H), 1.25-1.17 (m, 2H).

LCMS (ESI) Rt=2.65 minutes MS m/z 218 [M+H]$^+$

Preparation 38: 8-cyclopropyl-2-(methylsulfonyl)pyrido[3,4-d]pyrimidine

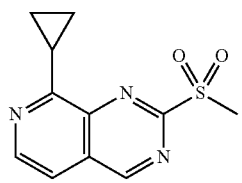 [SMILES: CS(=O)(=O)c1ncc2ccnc(C3CC3)c2n1]

A suspension of 8-cyclopropyl-2-(methylthio)pyrido[3,4-d]pyrimidine (Preparation 37, 127 mg, 0.584 mmol) in DCM (5 mL) was treated with mCPBA (77% w/w, 290 mg, 1.291 mmol) at 0° C. and then allowed to reach room temperature for 18 hours. The mixture was quenched with water and extracted with DCM. The combined organic layers were washed with water, dried and concentrated on silica gel. The residue was purified by silica gel column chromatography eluting with 0 to 70% EtOAc in cyclohexane to give the title compound (128 mg, 88%).

$^1$H NMR (500 MHz, DMSO-d$_6$): δ 9.99 (s, 1H), 8.79 (d, J=5.5 Hz, 1H), 7.94 (d, J=5.5 Hz, 1H), 3.56 (s, 3H), 3.49-3.39 (m, 1H), 1.30-1.25 (m, 2H), 1.24-1.20 (m, 2H).

LCMS (ESI) Rt=1.49 minutes MS m/z 250 [M+H]$^+$

Preparation 39: 4-bromo-2-methoxy-5-methylaniline

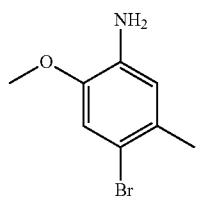

To a cooled (0° C.) solution of 2-methoxy-5-methylaniline (500 mg, 3.64 mmol) in DMF (5 mL) was added slowly, over 10 minutes, a solution of N-bromosuccinimide (662 mg, 3.72 mmol) in DMF (2.5 mL). The reaction mixture was stirred for 18 hours, whilst slowly warming to room temperature. The reaction mixture was diluted with brine (25 mL) and extracted with EtOAc (25 mL). The organic layer was dried (MgSO$_4$) and concentrated in vacuo. The residue was purified by silica gel column chromatography eluting with 0-20% EtOAc in cyclohexane to give the title compound (679 mg, 86%). $^1$H NMR (500 MHz, CDCl$_3$): δ 6.93 (s, 1H), 6.62 (d, J=0.5 Hz, 1H), 3.83 (s, 3H), 3.73 (br s, 2H), 2.26 (s, 3H).

LCMS (ESI) Rt=1.95 minutes MS m/z 216.297 [M+H]$^+$

Preparation 40: 2-methoxy-5-methyl-4-(1-methyl-1H-pyrazol-4-yl)aniline

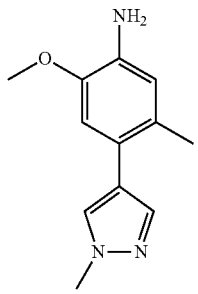

To a solution of 4-bromo-2-methoxy-5-methylaniline (Preparation 39, 350 mg, 1.620 mmol) in EtOH (2.5 mL), toluene (2.5 mL) and water (2.5 mL) was added 1-methylpyrazole-4-boronic acid pinacol ester (404 mg, 1.944 mmol), sodium carbonate (343 mg, 3.24 mmol) and Pd(PPh$_3$)$_4$ (225 mg, 0.194 mmol). The reaction mixture was heated to 80° C. for 2.5 hours, under nitrogen. The reaction mixture was cooled to room temperature and diluted with EtOAc (30 mL), washed with water (30 mL) and brine (30 mL), dried (MgSO$_4$) and concentrated in vacuo. The residue was purified by silica gel column chromatography eluting with 0-5% MeOH in DCM to give the title compound (140 mg, 36%). $^1$H NMR (500 MHz, CDCl$_3$): δ 7.56 (d, J=0.5 Hz, 1H), 7.39 (s, 1H), 6.75 (s, 1H), 6.63 (s, 1H), 3.96 (s, 3H), 3.86 (s, 3H), 3.76 (br s, 2H), 2.27 (s, 3H).

LCMS (ESI) Rt=1.13 minutes MS m/z 218.30 [M+H]$^+$

Preparation 41: 2-(methylsulfonyl)-8-(pyrrolidin-1-yl)pyrido[3,4-d]pyrimidine

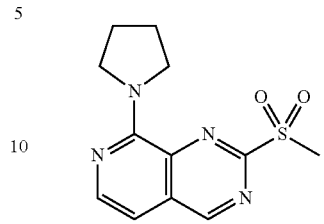

Method 12

A mixture of 8-chloro-2-(methylthio)pyrido[3,4-d]pyrimidine (Preparation 33, 105 mg, 0.496 mmol) and pyrrolidine (425 µL, 5.08 mmol) in N-methyl-2-pyrrolidinone (2.5 mL) was stirred at 135° C. for 3 hours. The reaction was quenched with saturated aqueous NaHCO$_3$ and extracted with EtOAc. The combined organic layers were washed with water and brine, dried and concentrated to afford the crude sulfide.

A suspension of crude sulfide (ca. 0.49 mmol) in DCM (4 mL) was treated with mCPBA (250 mg, 1.113 mmol) at 0° C. and then allowed to reach room temperature for 18 hours. An additional portion of mCPBA (77% w/w, 60 mg, 0.27 mmol) was added at room temperature and the mixture stirred for 2 hours. The mixture was quenched with water and extracted with DCM. The combined organic layers were washed with saturated aqueous NaHCO$_3$, brine, dried and concentrated. The residue was purified by silica gel column chromatography eluting with 0 to 70% EtOAc in cyclohexane to give the title compound (62 mg, 45% over two steps).

$^1$H NMR (500 MHz, DMSO-d$_6$): δ 9.62 (s, 1H), 8.30 (d, J=5.4 Hz, 1H), 7.11 (d, J=5.5 Hz, 1H), 3.97 (br s, 4H), 3.45 (s, 3H), 1.98 (s, 4H).

LCMS (ESI) Rt=0.90 minutes MS m/z 279 [M+H]$^+$

The following Preparations were prepared according to Method 12 using 8-chloro-2-(methylthio)pyrido[3,4-d]pyrimidine (Preparation 33) and the appropriate amine.

| Preparation No | Name/Structure | Data |
|---|---|---|
| 42 | N,N-diethyl-2-(methylsulfonyl)pyrido[3,4-d]pyrimidin-8-amine | $^1$H NMR (500 MHz, DMSO): δ 9.65 (s, 1H), 8.32 (d, J = 5.4 Hz, 1H), 7.16 (d, J = 5.3 Hz, 1H), 3.95 (q, J = 6.9 Hz, 4H), 3.44 (s, 3H), 1.30 (t, J = 6.9 Hz, 6H). LCMS (ESI) Rt = 1.48 minutes MS m/z 281 [M + H]$^+$ Using diethylamine. |
| 43 | N-cyclopentyl-2-(methylsulfonyl)pyrido[3,4-d]pyrimidin-8-amine | $^1$H NMR (500 MHz, DMSO) δ 9.66 (s, 1H), 8.26 (d, J = 5.6 Hz, 1H), 7.64 (d, J = 7.4 Hz, 1H), 7.11 (d, J = 5.6 Hz, 1H), 4.53 (h, J = 7.3 Hz, 1H), 3.62 (s, 3H), 2.12-1.99 (m, 2H), 1.82-1.72 (m, 2H), 1.73-1.57 (m, 4H). LCMS (ESI) Rt 1.50 minutes MS m/z 293 [M + H]$^+$ Using cyclopentylamine. |

-continued

| Preparation No | Name/Structure | Data |
|---|---|---|
| 44 | N-cyclohexyl-2-(methylsulfonyl)pyrido[3,4-d]pyrimidin-8-amine<br><br>![structure] | $^1$H NMR (500 MHz, DMSO): δ 9.65 (s, 1H), 8.25 (d, J = 5.6 Hz, 1H), 7.55 (d, J = 8.3 Hz, 1H), 7.09 (d, J = 5.6 Hz, 1H), 4.21-4.07 (m, 1H), 3.61 (s, 3H), 2.05-1.91 (m, 2H), 1.85-1.73 (m, 2H), 1.70-1.62 (m, 1H), 1.57-1.44 (m, 2H), 1.42-1.33 (m, 2H), 1.27-1.13 (m, 1H). LCMS (ESI) Rt = 2.20 minutes MS m/z 307 [M + H]$^+$<br>Using cyclohexylamine. |
| 45 | 2-(methylsulfonyl)-N-(tetrahydro-2H-pyran-4-yl)pyrido[3,4-d]pyrimidin-8-amine<br><br>![structure] | $^1$H NMR (500 MHz, DMSO): δ 9.67 (s, 1H), 8.26 (d, J = 5.6 Hz, 1H), 7.71 (d, J = 8.1 Hz, 1H), 7.13 (d, J = 5.6 Hz, 1H), 4.44-4.33 (m, 1H), 3.98-3.89 (m, 2H), 3.62 (s, 3H), 3.52-3.39 (m, 2H), 1.95-1.85 (m, 2H), 1.85-1.71 (m, 2H). LCMS (ESI) Rt = 1.36 minutes MS m/z 309 [M + H]$^+$<br>Using aminotetrahydropyrane. |

Preparation 46: 2-(methylthio)-N-neopentylpyrido[3,4-d]pyrimidin-8-amine

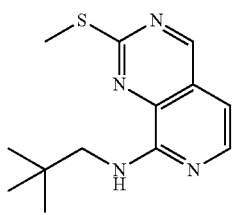 [SMILES: CSc1ncc2ccnc(NCC(C)(C)C)c2n1]

To a solution of 8-chloro-2-(methylthio)pyrido[3,4-d]pyrimidine (Preparation 33, 1 g, 4.72 mmol) in NMP (15 mL) was added neopentylamine (5.5 mL, 4.72 mmol). The reaction mixture was heated to 80° C. for 20 hours. The reaction mixture was diluted with saturated aqueous NaHCO$_3$ (50 mL) and EtOAc (2×50 mL). The combined organic layers were washed with water (50 mL) and brine (50 mL), dried (MgSO$_4$) and concentrated in vacuo. The residue was purified by silica gel column chromatography eluting with 0-100% EtOAc in cyclohexane give the title compound (915 mg, 74%).

$^1$H NMR (500 MHz, CDCl$_3$): δ 9.01 (s, 1H), 8.01 (d, J=6.0 Hz, 1H), 6.76 (d, J=6.0 Hz, 1H), 6.72 (br s, 1H), 3.46 (d, J=6.0 Hz, 2H), 2.67 (s, 3H), 1.06 (s, 9H).

LCMS (ESI) Rt=2.12 minutes MS m/z 263.07 [M+H]$^+$

Preparation 47: 2-(methylsulfonyl)-N-neopentylpyrido[3,4-d]pyrimidin-8-amine

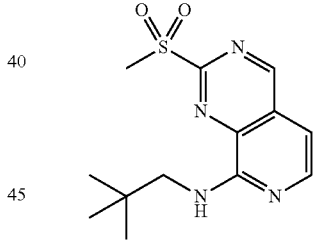

To a cooled (0 C) solution of 2-(methylthio)-N-neopentylpyrido[3,4-d]pyrimidin-8-amine (Preparation 46, 1.0 g, 4.72 mmol) in DCM (40 mL) was added portionwise mCPBA (2.54 g, 11.34 mmol). The reaction mixture was stirred for 18 hours, whilst slowly warming to room temperature. The reaction mixture was quenched with water (40 mL) and diluted with DCM (40 mL). The organic layer was washed with aqueous saturated NaHCO$_3$ (40 mL), brine (40 mL), dried (MgSO$_4$) and concentrated in vacuo. The residue was purified by silica gel column chromatography eluting with 0-100% EtOAc in cyclohexane to give the title compound (700 mg, 68%).

$^1$H NMR (500 MHz, CDCl$_3$): δ 9.35 (s, 1H), 8.28 (d, J=5.5 Hz, 1H), 6.95 (br t, J=6.5 Hz, 1H), 6.92 (d, J=5.5 Hz, 1H), 3.53 (d, J=6.5 Hz, 2H), 3.44 (s, 3H), 1.06 (s, 9H).

LCMS (ESI) Rt=2.00 minutes MS m/z 295.05 [M+H]$^+$

Preparation 48: 4-(1,5-dimethyl-1H-pyrazol-4-yl)-2-methoxyaniline

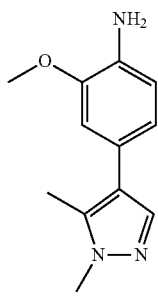 [SMILES: COc1cc(-c2cnn(C)c2C)ccc1N]

To a solution of 2-methoxy-4-bromoaniline (100 mg, 0.495 mmol) in dioxane (2 mL) and water (1 mL) was added boronate ester (143 mg, 0.643 mmol), Pd(PPh$_3$)$_4$ (57 mg, 0.049 mmol) and sodium carbonate (91 mg, 1.089 mmol). The reaction was heated to 120° C. for 30 minutes under microwave irradiation. The reaction mixture was diluted with EtOAc (30 mL) and water (30 mL). The aqueous layer was re-extracted with EtOAc (30 mL). The combined organic layer was washed with water (30 mL) and brine (30 mL), dried (MgSO$_4$) and concentrated in vacuo. The residue was purified by silica gel column chromatography eluting with 0-10% MeOH in EtOAc to give the title compound (35 mg, 33%).

$^1$H NMR (500 MHz, CDCl$_3$): δ 7.63 (s, 1H), 6.91 (dd, J=8.0, 2.0 Hz, 1H), 6.89 (d, J=2.0 Hz, 1H), 6.85 (app s, 1H), 3.97 (s, 6H), 2.41 (s, 3H).

LCMS (ESI,) Rt=1.12 minutes MS m/z 218.20 [M+H]$^+$

Preparation 49: Methyl 2-(methylthio)-5-prop-1-yn-1yl)pyrimidine-4-carboxylate

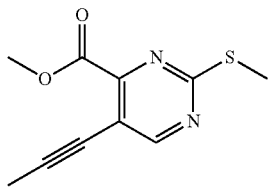

To a solution of methyl 5-bromo-2-(methylthio)pyrimidine-4-carboxylate (Preparation 30, 1.0 g, 3.80 mmol) in DMF (10 mL) was added tributylpropynyl tin (1.4 mL, 4.56 mmol) and Pd(PPh$_3$)$_4$ (132 mg, 0.114 mmol). The reaction mixture was heated to 110° C. under microwave conditions for 30 minutes. The reaction mixture was diluted with EtOAc (30 mL), washed with aqueous saturated NaHCO$_3$ (30 mL) and water (30 mL), dried (MgSO$_4$) and concentrated in vacuo. The residue was purified by silica gel column chromatography eluting with 50-100% DCM in cyclohexane to give the title compound (414 mg, 49%).

$^1$H NMR (500 MHz, CDCl$_3$): δ 8.67 (s, 1H), 4.00 (s, 3H), 2.61 (s, 3H), 2.14 (s, 3H).

LCMS (ESI) Rt=2.42 minutes MS m/z 223.23 [M+H]$^+$

Preparation 50: 2-(methylthio)-5-(prop-1-yn-1yl)pyrimidine-4-carboxamide

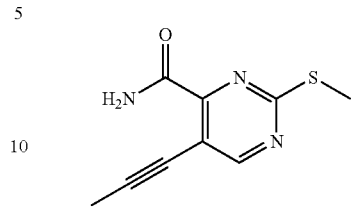

A solution of methyl 2-(methylthio)-5-prop-1-yn-1yl)pyrimidine-4-carboxylate (Preparation 49, 410 mg, 1.845 mmol) in NH$_3$ in MeOH (7M, 12 mL) was heated to 120° C. for 18 hours. The reaction mixture was cooled to room temperature and concentrated in vacuo. The residue was purified by silica gel column chromatography eluting with 0-5% MeOH in DCM to give the title compound (280 mg, 73%).

$^1$H NMR (500 MHz, CDCl$_3$): δ 8.74 (s, 1H), 7.52 (br s, 1H), 5.61 (br s, 1H), 2.61 (s, 3H), 2.19 (s, 3H).

LCMS (ESI) Rt=1.87 minutes MS m/z 208.27 [M+H]$^+$

Preparation 51: 6-methyl-2-(methylthio)pyrido[3,4-d]pyrimidin-8(7H)-one

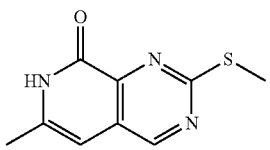

To a solution of 2-(methylthio)-5-(prop-1-yn-1yl)pyrimidine-4-carboxamide (Preparation 50, 270 mg, 1.303 mmol) in toluene (30 mL) was added pTSA (50 mg, 0.261 mmol). The reaction mixture was heated to 90° C. for 18 hours. The reaction mixture was concentrated in vacuo. The residue was dissolved in NH$_3$ in MeOH (7M, 10 mL) and heated to 80° C. for 18 hours. The reaction mixture was concentrated in vacuo. The residue was purified by column chromatography eluting with 0-5% MeOH in DCM to give the title compound (150 mg, 56%).

$^1$H NMR (500 MHz, CDCl$_3$): δ 10.52 (br s, 1H), 8.91 (s, 1H), 6.28 (s, 1H), 2.72 (s, 3H), 2.45 (s, 3H).

LCMS (ESI) Rt=1.66 minutes MS m/z 208.24 [M+H]$^+$

Preparation 52: 8-chloro-6-methyl-2-(methythio)pyrido[3,4-d]pyrimidine

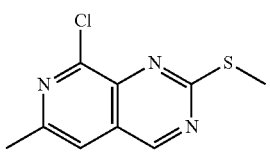

A solution of 6-methyl-2-(methythio)pyrido[3,4-d]pyrimidin-8(7H)-one (Preparation 51, 100 mg, 0.483 mmol) in POCl$_3$ (5 mL) was heated to 70° C. for 1 hour. The reaction mixture was concentrated in vacuo. The residue was partitioned between EtOAc (30 mL) and washed with water (30 mL), dried (MgSO$_4$) and concentrated in vacuo. The residue was purified by silica gel column chromatography eluting with 0-20% EtOAc in cyclohexane to give the title compound (28.4 mg, 52%).

$^1$H NMR (500 MHz, CDCl$_3$): δ 9.16 (s, 1H), 7.43 (s, 1H), 2.75 (s, 3H), 2.71 (s, 3H).

LCMS (ESI) Rt=2.57 minutes MS m/z 226.20 [M+H]$^+$

Preparation 53: 6-methyl-2-(methythio)-N-neopentylpyrido[3,4-d]pyrimidin-8-amine

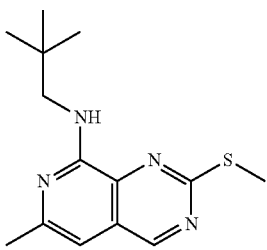

To a solution of 8-chloro-6-methyl-2-(methythio)pyrido[3,4-d]pyrimidine (Preparation 52, 128 mg, 0.567 mmol) in NMP (6 mL) was added neopentylamine (0.66 mL, 5.67 mmol). The reaction mixture was heated to 80° C. for 3 hours. The reaction mixture was diluted with EtOAc (30 mL) and water (30 mL), the organic layer was dried (MgSO$_4$) and concentrated in vacuo. The residue was purified by silica gel column chromatography eluting with 0-50% EtOAc in cyclohexane to give the title compound (38 mg, 24%).

$^1$H NMR (500 MHz, CDCl$_3$): δ 8.93 (s, 1H), 6.70 (br s, 1H), 6.59 (s, 1H), 3.48 (br s, 2H), 2.66 (s, 3H), 2.50 (s, 3H), 1.07 (s, 9H).

LCMS (ESI) Rt=2.37 minutes MS m/z 277.31 [M+H]$^+$

Preparation 54: 6-methyl-2-(methysulfonyl)-N-neopentylpyrido[3,4-d]pyrimidin-8-amine

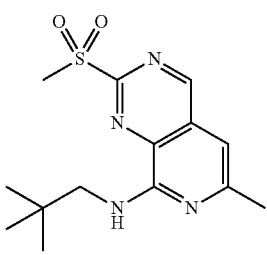 [SMILES: Cc1cc2cnc(S(C)(=O)=O)nc2c(NCC(C)(C)C)n1]

To a cooled (0° C.) solution of 6-methyl-2-(methythio)-N-neopentylpyrido[3,4-d]pyrimidin-8-amine (Preparation 53, 38 mg, 0.137 mmol) in DCM (2 mL) was added portionwise mCPBA (37 mg, 0.165 mmol). The reaction mixture was stirred for 6 hours, whilst slowly warming to room temperature. The reaction mixture was quenched with water (40 mL) and diluted with DCM (40 mL). The organic layer was washed with aqueous saturated NaHCO$_3$ (40 mL), brine (40 mL), dried (MgSO$_4$) and concentrated in vacuo. The residue was purified by silica gel column chromatography eluting with 0-100% EtOAc in cyclohexane to give the title compound (12.5 mg, 30%).

$^1$H NMR (500 MHz, CDCl$_3$): δ 9.23 (s, 1H), 6.90 (br s, 1H), 6.75 (s, 1H), 3.55 (d, J=6.0 Hz, 1H), 3.42 (s, 3H), 2.57 (s, 3H), 1.05 (s, 9H).

LCMS (ESI) Rt=2.44 minutes MS m/z 309.33 [M+H]$^+$

Preparation 55: N-(4-(1,2-dimethyl-1H-imidazol-5-yl)-2-methoxyphenyl)formamide

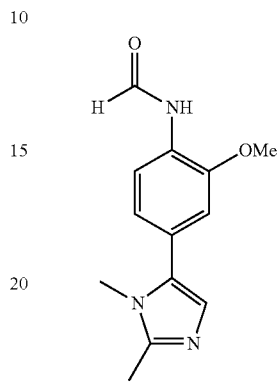

Method 13

A solution of 4-(1,2-dimethyl-1H-imidazol-5-yl)-2-methoxyaniline (Preparation 18, 127 mg, 0.585 mmol) in formic acid (3 mL) was heated to reflux for 1 hour 30 minutes. The solution was concentrated under reduced pressure. The residue was partitioned between saturated aqueous NaHCO$_3$ and EtOAc. The aqueous layer was extracted with EtOAc and the combined organic layers washed with water and brine, dried and concentrated. The residue was purified by silica gel column chromatography eluting with 0 to 10% MeOH in DCM to give the title compound (60 mg, 42%).

$^1$H NMR (500 MHz, DMSO): δ 9.73 (s, 1H), 8.32 (s, 1H), 8.22 (d, J=8.3 Hz, 1H), 7.05 (s, 1H), 6.96 (dd, J=8.2, 1.9 Hz, 1H), 6.86 (s, 1H), 3.89 (s, 3H), 3.53 (s, 3H), 2.34 (s, 3H).

LCMS (ESI) Rt=0.83 minutes MS m/z 246 [M+H]$^+$

Preparation 56: N-(2-methoxy-4-(1-methyl-1H-pyrazol-4-yl)phenyl)formamide

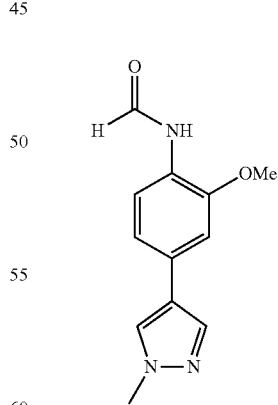

The title compound was prepared according to Method 13 (Preparation 55) using 2-methoxy-4-(1-methyl-1H-pyrazol-4-yl)aniline (Preparation 19). The residue was purified by silica gel column chromatography eluting with 0 to 80% EtOAc in cyclohexane to give the title compound (81 mg, 65%).

$^1$H NMR (500 MHz, DMSO-d$_6$): δ 9.61 (s, 1H), 8.27 (d, J=2.0 Hz, 1H), 8.15-8.05 (m, 2H), 7.85 (s, 1H), 7.22 (d, J=1.8 Hz, 1H), 7.10 (d, J=8.2 Hz, 1H), 3.90 (s, 3H), 3.85 (s, 3H).

LCMS (ESI) Rt=1.75 minutes MS m/z 232 [M+H]$^+$

Preparation 57: 2-(4-iodo-1H-pyrazol-1-yl)ethanol

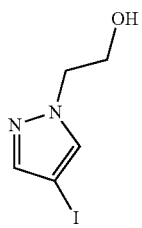

A solution of 4-iodo-1H-pyrazole (4.50 g, 23.20 mmol) in DMF (45 mL) was treated with sodium hydride (60% w/w, 1.42 g, 35.5 mmol) at 0° C. and stirred at room temperature. After 1 hour the resulting mixture was treated with 2-bromoethanol (2.5 mL, 35.2 mmol) at 0° C. The resulting mixture was heated to 65° C. for 3 days. The reaction quenched with brine/EtOAc and the aqueous layer extracted with EtOAc. The combined organic layers were washed with water, brine, dried and concentrated. The residue was purified by silica gel column chromatography eluting with 0 to 50% EtOAc in cyclohexane to give the title compound (3.55 g, 64%).

$^1$H NMR (500 MHz, CDCl$_3$): δ 7.55 (s, 1H), 7.52 (s, 1H), 4.32-4.22 (m, 2H), 4.04-3.95 (m, 2H), 2.79-2.68 (br m, 1H).

LCMS (ESI) Rt=1.50 minutes MS m/z 238 [M+H]$^+$

Preparation 58: 2-(4-iodo-1H-pyrazol-1-yl)ethyl 4-methylbenzenesulfonate

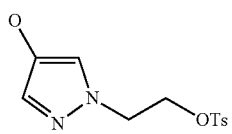 [SMILES: Cc1ccc(S(=O)(=O)OCCn2cc(O)cn2)cc1]

2-(4-Iodo-1H-pyrazol-1-yl)ethanol (Preparation 57, 535 mg, 2.248 mmol) in DCM (11 mL) was treated with triethylamine (1.55 mL, 11.14 mmol) at 0° C. Tosyl chloride (857 mg, 4.50 mmol) was added at 0° C. and the mixture was allowed to warm to room temperature for 18 hours. The organic layer was washed with water, HCl 1M and water (twice). The organic layers were dried, concentrated and purified by silica gel column chromatography eluting with 0 to 30% EtOAc in cyclohexane to give the title compound (817 mg, 93%).

$^1$H NMR (500 MHz, CDCl$_3$): δ 7.64 (d, J=8.4 Hz, 2H), 7.40 (s, 1H), 7.39 (s, 1H), 7.32 (d, J=8.4 Hz, 2H), 4.38-4.34 (m, 4H), 2.47 (s, 3H).

LCMS (ESI) Rt=2.26 minutes MS m/z 393 [M+H]$^+$

Preparation 59: 1-(2-(4-iodo-1H-pyrazol-1-yl)ethyl)-4-methylpiperazine

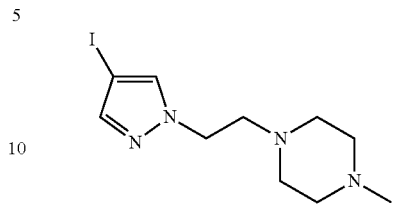

A solution of 2-(4-iodo-1H-pyrazol-1-yl)ethyl 4-methylbenzenesulfonate (Preparation 58, 377 mg, 0.961 mmol) in acetonitrile (6 mL) was treated with 1-methylpiperazine (1.1 mL, 9.88 mmol). The resulting mixture was stirred at room temperature for 3 days. The majority of the solvent was removed under reduced pressure and the residue partitioned between saturated aqueous NaHCO$_3$ and EtOAc. The aqueous layer was extracted with EtOAc twice and the combined organic layers washed with water, brine, dried and concentrated. The residue was purified by silica gel column chromatography eluting with 0 to 15% MeOH in DCM to give the title compound (208 mg, 68%).

$^1$H NMR (500 MHz, CDCl$_3$): δ 7.54 (d, J=0.7 Hz, 1H), 7.50 (d, J=0.7 Hz, 1H), 4.25 (t, J=6.6 Hz, 2H), 2.80 (t, J=6.6 Hz, 2H), 2.54-2.46 (br m, 8H), 2.32 (s, 3H).

LCMS (ESI) Rt=0.97 minutes MS m/z 321 [M+H]$^+$

Preparation 60: 2-methoxy-4-(1-(2-(4-methylpiperazin-1-yl)ethyl)-1H-pyrazol-4-yl)aniline

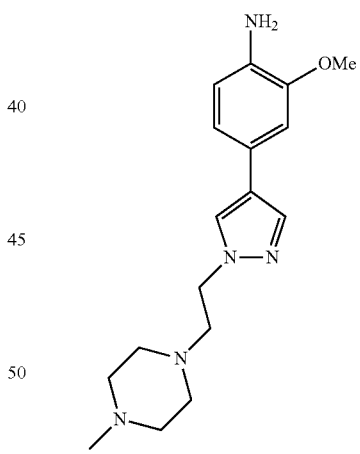

A solution of 2-methoxy-4-(4,4,5,5-tetramethyl-1,3,2-dioxaborolan-2-yl)aniline (210 mg, 0.843 mmol), 1-(2-(4-iodo-1H-pyrazol-1-yl)ethyl)-4-methylpiperazine (Preparation 59, 206 mg, 0.643 mmol) and Pd(dppf)Cl$_2$.DCM (52 mg, 0.064 mmol) was dissolved in THF (4.5 mL) and 2M sodium carbonate in water (1.5 mL) and heated to 60° C. for 18 hours. The mixture was concentrated under reduced pressure. The residue was partitioned between water and DCM. The aqueous layer was extracted with DCM three times and the combined organic layers dried and concentrated. The residue was purified by silica gel column chromatography eluting with 0 to 15% MeOH in DCM to give the title compound (72 mg, 35%).

¹H NMR (500 MHz, CDCl₃): δ 7.69 (d, J=0.9 Hz, 1H), 7.61 (d, J=0.8 Hz, 1H), 6.93 (dd, J=7.9, 1.8 Hz, 1H), 6.90 (d, J=1.8 Hz, 1H), 6.73 (d, J=7.9 Hz, 1H), 4.27 (t, J=6.8 Hz, 2H), 3.91 (s, 3H), 3.80 (br s, 2H), 2.88 (t, J=6.8 Hz, 2H), 2.68-2.40 (m, 8H), 2.32 (s, 3H).
LCMS (ESI) Rt=0.30 minutes MS m/z 316 [M+H]⁺

Preparation 61: N-(2-methoxy-4-(1-(2-(4-methylpiperazin-1-yl)ethyl)-1H-pyrazol-4-yl)phenyl)formamide

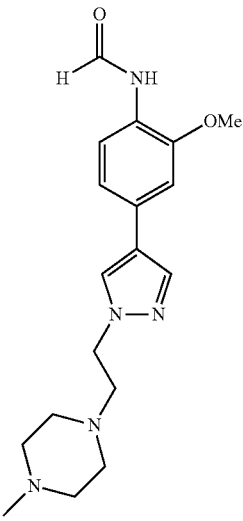 [SMILES: COc1cc(-c2cnn(CCN3CCN(C)CC3)c2)ccc1NC=O]

The title compound was prepared according to Method 13 (Preparation 55) using 2-methoxy-4-(1-(2-(4-methylpiperazin-1-yl)ethyl)-1H-pyrazol-4-yl)aniline (Preparation 60). The residue was purified by silica gel column chromatography eluting with 0 to 17% MeOH in DCM to give the title compound (71 mg, 69%).
¹H NMR (500 MHz, DMSO): δ 9.63 (d, J=2.1 Hz, 1H), 8.28 (d, J=1.9 Hz, 1H), 8.17 (s, 1H), 8.11 (d, J=8.3 Hz, 1H), 7.87 (s, 1H), 7.22 (d, J=1.8 Hz, 1H), 7.11 (dd, J=8.2, 1.8 Hz, 1H), 4.21 (t, J=6.7 Hz, 2H), 3.91 (s, 3H), 2.74 (t, J=6.7 Hz, 2H), 2.48-2.29 (br m, 8H), 2.17 (s, 3H).
LCMS (ESI) Rt=1.16 minutes MS m/z 344 [M+H]⁺

Preparation 62: 2-(4-iodo-1H-pyrazol-1-yl)-N,N-dimethylethanamine

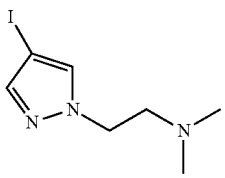

2-(4-Iodo-1H-pyrazol-1-yl)ethyl 4-methylbenzenesulfonate (Preparation 58) (1.03 g, 2.63 mmol) was treated with dimethylamine in THF (2M, 10 mL, 20.00 mmol) and stirred at room temperature for 3 days. Solvents were removed under reduced pressure and the residue partitioned between DCM and saturated aqueous NaHCO₃. The aqueous were extracted with DCM and the combined organic layers dried and concentrated. The residue was purified by silica gel column chromatography eluting with 0 to 10% MeOH in DCM to give the title compound (616 mg, 89%).
¹H NMR (500 MHz, CDCl₃): δ 7.55 (d, J=0.7 Hz, 1H), 7.52 (d, J=0.8 Hz, 1H), 4.24 (t, J=6.5 Hz, 2H), 2.74 (t, J=6.5 Hz, 2H), 2.29 (s, 6H).
LCMS (ESI) Rt=0.59 minutes MS m/z 266 [M+H]⁺

Preparation 63: 4-(1-(2-(dimethylamino)ethyl)-1H-pyrazol-4-yl)-2-methoxyaniline

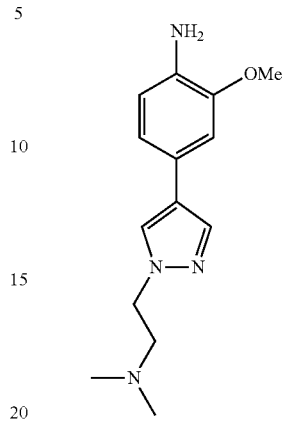

A solution of 2-methoxy-4-(4,4,5,5-tetramethyl-1,3,2-dioxaborolan-2-yl)aniline (313 mg, 1.256 mmol), 2-(4-iodo-1H-pyrazol-1-yl)-N,N-dimethylethanamine (Preparation 62, 270 mg, 1.019 mmol) and Pd(dppf)Cl₂.DCM (80 mg, 0.098 mmol) was dissolved in THF (4.5 mL) and 2M sodium carbonate in water (1.5 mL) and heated to 60° C. for 18 hours. The mixture was concentrated under reduced pressure. The residue was partitioned between water and DCM and the aqueous layer extracted with DCM three times. The combined organic layers were dried and concentrated. The residue was purified by silica gel column chromatography eluting with 0 to 10% MeOH in DCM to give the title compound (74 mg, 28%).
¹H NMR (500 MHz, CDCl₃): δ 7.70 (s, 1H), 7.62 (s, 1H), 6.93 (dd, J=7.9, 1.8 Hz, 1H), 6.90 (d, J=1.8 Hz, 1H), 6.72 (d, J=7.9 Hz, 1H), 4.27 (t, J=6.8 Hz, 2H), 3.91 (s, 3H), 3.79 (br s, 2H), 2.83 (t, J=6.8 Hz, 2H), 2.32 (s, 6H).
LCMS (ESI) Rt=0.29 minutes MS m/z 261 [M+H]⁺

Preparation 64: N-(4-(1-(2-(dimethylamino)ethyl)-1H-pyrazol-4-yl)-2-methoxyphenyl)formamide

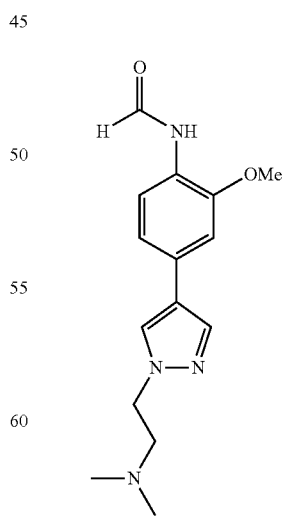

The title compound was prepared according to Method 13 (Preparation 55) using 4-(1-(2-(dimethylamino)ethyl)-1H- pyrazol-4-yl)-2-methoxyaniline (Preparation 63). The residue was purified by silica gel column chromatography eluting with 0 to 15% MeOH in DCM.

$^1$H NMR (500 MHz, DMSO-d$_6$): δ 9.61 (s, 1H), 8.27 (d, J=1.9 Hz, 1H), 8.17 (s, 1H), 8.11 (d, J=8.2 Hz, 1H), 7.86 (d, J=0.9 Hz, 1H), 7.22 (d, J=1.8 Hz, 1H), 7.10 (dd, J=8.2, 1.8 Hz, 1H), 4.20 (t, J=6.5 Hz, 2H), 3.90 (s, 3H), 2.75-2.63 (m, 2H), 2.20 (s, 6H).

Preparation 65: 1-(2-(tert-butyldiphenylsilyloxy) ethyl)-4-iodo-1H-pyrazole

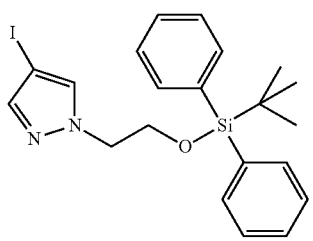 [SMILES: CC(C)(C)[Si](OCCn1cc(I)cn1)(c1ccccc1)c1ccccc1]

A solution of 2-(4-iodo-1H-pyrazol-1-yl)ethanol (Preparation 57) (1.01 g, 4.24 mmol) in DMF (21 mL) was treated with imidazole (410 mg, 6.03 mmol) followed by tert-butylchlorodiphenylsilane (1.321 mL, 5.09 mmol) and the mixture was stirred to room temperature for 18 hours. The mixture was diluted with EtOAc and quenched with brine. The aqueous layer was extracted with EtOAc three times. The combined organic layers were washed with water and brine, dried and concentrated. The residue was purified by silica gel column chromatography eluting with 0 to 10% EtOAc in cyclohexane to give the title compound (2.25 g, quant).

$^1$H NMR (500 MHz, CDCl$_3$): δ 7.56 (s, 1H), 7.54-7.50 (m, 5H), 7.47-7.35 (m, 6H), 4.26 (t, J=5.2 Hz, 2H), 3.96-3.91 (m, 2H), 1.03 (s, 9H).
LCMS (ESI) Rt=1.98 minutes MS m/z 498 [M+Na]$^+$ Preparation 66: 4-(1-(2-(tert-butyldiphenylsilyloxy) ethyl)-1H-pyrazol-4-yl)-2-methoxyaniline

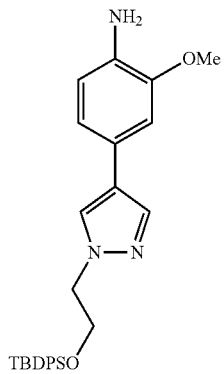

A solution of 2-methoxy-4-(4,4,5,5-tetramethyl-1,3,2-dioxaborolan-2-yl)aniline (383 mg, 1.537 mmol), 1-(2-(tert-butyldiphenylsilyloxy)ethyl)-4-iodo-1H-pyrazole (Preparation 65, 554 mg, 1.163 mmol) and Pd(dppf)Cl$_2$.DCM (90 mg, 0.110 mmol) was dissolved in THF (6 mL) and 2M sodium carbonate in water (2 mL) and heated to 60° C. for 18 hours. The mixture was diluted with EtOAc and quenched with brine. The aqueous layer was extracted with EtOAc three times. The combined organic layers were washed with brine, dried and concentrated. The residue was purified by silica gel column chromatography eluting with 0 to 20% EtOAc in cyclohexane to give the title compound (141 mg, 26%).

$^1$H NMR (500 MHz, CDCl$_3$): δ 7.73 (d, J=0.8 Hz, 1H), 7.71 (d, J=0.8 Hz, 1H), 7.61-7.52 (m, 4H), 7.46-7.40 (m, 2H), 7.39-7.34 (m, 4H), 6.94 (dd, J=7.9, 1.8 Hz, 1H), 6.91 (d, J=1.8 Hz, 1H), 6.74 (d, J=7.9 Hz, 1H), 4.30 (t, J=5.2 Hz, 2H), 4.01 (t, J=5.2 Hz, 2H)), 3.90 (s, 3H), 3.81 (br s, 2H), 1.06 (s, 9H).
LCMS (ESI) Rt=2.83 minutes MS m/z 472 [M+H]$^+$ Preparation 67: N-(4-(1-(2-(tert-butyldiphenylsilyloxy)ethyl)-1H-pyrazol-4-yl)-2-methoxyphenyl)formamide

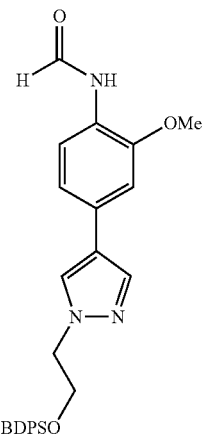

A solution of 4-(1-(2-(tert-butyldiphenylsilyloxy)ethyl)-1H-pyrazol-4-yl)-2-methoxyaniline (Preparation 66, 130 mg, 0.276 mmol) in formic acid (2 mL) was heated to reflux for 3 hours. The solution was concentrated under reduced pressure and azeotroped with toluene twice. The residue was dissolved in MeOH (1 mL) and treated with Et$_3$N (50 at room temperature for 1 hour. The mixture was concentrated under reduced pressure, co-evaporated with DCM twice to afford the crude formylated aniline.

A solution of crude formylated aniline (ca. 0.27 mmol) in DMF (1.5 mL) was treated with imidazole (30 mg, 0.441 mmol) followed by tert-butylchlorodiphenylsilane (100 μul, 0.386 mmol) and the mixture was stirred to room temperature for 18 hours. The mixture was diluted with EtOAc and quenched with brine. The aqueous layer was extracted with EtOAc three times. The combined organic layers were washed with water and brine, dried and concentrated. The residue was purified by silica gel column chromatography eluting with 0 to 40% EtOAc in cyclohexane to give the title compound (126 mg, 91% over two steps).

$^1$H NMR (500 MHz, CDCl$_3$): δ 8.48 (d, J=1.8 Hz, 1H), 8.36 (d, J=8.3 Hz, 1H), 7.81-7.74 (m, 3H), 7.59-7.52 (m, 5H), 7.45-7.40 (m, 2H), 7.38-7.32 (m, 5H), 4.33-4.27 (m, 2H), 4.06-3.99 (m, 2H), 3.93 (s, 3H), 1.04 (s, 9H).
LCMS (ESI) Rt=3.08 minutes MS m/z 500 [M+H]$^+$

Preparation 68: 8-(cyclopropylmethoxy)-2-(methylthio)pyrido[3,4-d]pyrimidine

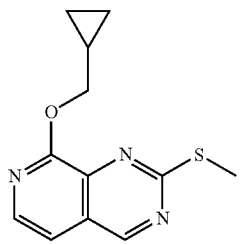 [SMILES: CSc1ncc2ccnc(OCC3CC3)c2n1]

A suspension of 2-(methylthio)pyrido[3,4-d]pyrimidin-8 (7H)-one (Preparation 32, 502 mg, 2.60 mmol) and silver carbonate (988 mg, 3.58 mmol) in CHCl$_3$ (25 mL) was treated with bromomethyl cyclopropane (310 μl, 3.19 mmol) and stirred at room temperature for 18 hours. The mixture was stirred at reflux for 4 hours and additional bromomethyl cyclopropane (310 μl, 3.19 mmol) was added. The reaction was stirred for 18 hours at 6° C. Further bromomethyl cyclopropane (310 μl, 3.19 mmol) was added and heated continued for 2 hours. Et$_3$N was added (6 mL), the mixture filtered through celite washing with DCM and the solvent removed under reduced pressure. The residue was purified by silica gel column chromatography eluting with 0 to 80% EtOAc in cyclohexane to give the title compound (112 mg, 17%).

$^1$H NMR (500 MHz, CDCl$_3$): δ 9.14 (s, 1H), 8.07 (d, J=5.6 Hz, 1H), 7.18 (d, J=5.6 Hz, 1H), 4.43 (d, J=7.0 Hz, 2H), 2.74 (s, 3H), 1.54-1.43 (m, 1H), 0.73-0.61 (m, 2H), 0.54-0.43 (m, 2H).

LCMS (ESI) Rt=2.69 minutes MS m/z 248 [M+H]$^+$

Preparation 69: 8-(cyclopropylmethoxy)-2-(methylsulfonyl)pyrido[3,4-d]pyrimidine

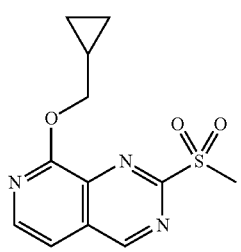 [SMILES: CS(=O)(=O)c1ncc2ccnc(OCC3CC3)c2n1]

A suspension of 8-(cyclopropylmethoxy)-2-(methylthio) pyrido[3,4-d]pyrimidine (Preparation 68, 110 mg, 0.445 mmol) in DCM (4 mL) was treated with mCPBA (77% w/w, 325 mg, 1.353 mmol) at 0° C. and then allowed to reach room temperature for 18 hours. The mixture was quenched with water and extracted with DCM. The combined organic layers were washed with saturated aqueous NaHCO$_3$, dried and concentrated. The residue was purified by silica gel column chromatography eluting with 0 to 55% EtOAc in cyclohexane to give the title compound (95 mg, 77%).

$^1$H NMR (500 MHz, DMSO): δ 9.92 (s, 1H), 8.44 (d, J=5.7 Hz, 1H), 7.72 (d, J=5.7 Hz, 1H), 4.43 (d, J=7.2 Hz, 2H), 3.50 (s, 3H), 1.51-1.32 (m, 1H), 0.69-0.57 (m, 2H), 0.49-0.40 (m, 2H).

LCMS (ESI) Rt=1.95 minutes MS m/z 302 [M+Na]$^+$

Preparation 70: 2-methoxy-6-morpholinopyridin-3-amine

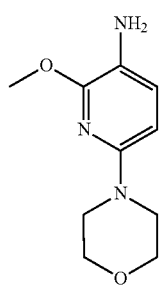

To a solution of 4-(6-methoxy-5-nitropyridin-2-yl)morpholine (Preparation 81, 280 mg, 1.170 mmol) in EtOAc/EtOH (1:1, 10 ml) was added palladium on charcoal (10%, 100 mg). The flask was charged with hydrogen and the reaction mixture was stirred at room temperature for 2 hours. The reaction mixture was filtered through Celite® and concentrated in vacuo to give the title compound (245 mg, 99%).

$^1$H NMR (500 MHz, CDCl$_3$): δ 6.98 (d, J=8.0 Hz, 1H), 6.09 (d, J=8.0 Hz, 1H), 4.05 (br s, 2H), 3.94 (s, 3H), 3.85 (t, J=4.5 Hz, 4H), 3.34 (t, J=4.5 Hz, 4H).

LCMS (ESI) Rt=1.05 minutes MS m/z 210.12 [M+H]$^+$

Preparation 71: N-(2-methoxy-6-morpholinopyridin-3-yl)formamide

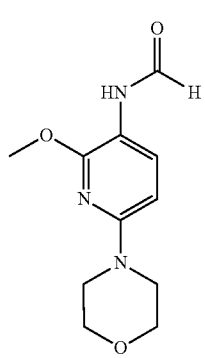 [SMILES: COc1nc(N2CCOCC2)ccc1NC=O]

A solution of 2-methoxy-6-morpholinopyridin-3-amine (Preparation 70, 40 mg, 0.191 mmol) in formic acid (3 mL) was heated to reflux for 3 hours. The reaction mixture was concentrated in vacuo. The residue was partitioned between aqueous saturated NaHCO$_3$ (40 mL) and EtOAc (40 mL). The aqueous layer was re-extracted with EtOAc (40 mL). The combined organic layers were washed with water (40 mL) and brine (40 mL), dried (MgSO$_4$) and concentrated in vacuo, to give the title compound (40 mg, 88%).

LCMS (ESI) Rt=1.84 minutes MS m/z 238.12 [M+H]$^+$

Preparation 72: 2-methoxy-6-(methysulfonyl)pyridine-3-amine

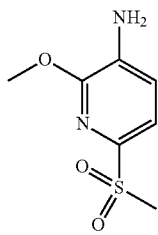

To a solution of 2-methoxy-6-(methylsulfonyl)-3-nitropyridine (Preparation 83, 290 mg, 1.249 mmol) in EtOAc/EtOH (1:1, 10 mL) was added palladium on charcoal (10%, 100 mg). The flask was charged with hydrogen and the reaction mixture was stirred at room temperature for 2 hours. The reaction mixture was filtered through Celite® and concentrated in vacuo to give the title compound (245 mg, 97%).
 $^1$H NMR (500 MHz, CDCl$_3$): δ 7.51 (d, J=8.0 Hz, 1H), 6.90 (d, J=8.0 Hz, 1H), 4.75 (br s, 2H), 4.03 (s, 3H), 3.13 (s, 3H).
 LCMS (ESI) Rt=1.52 minutes MS m/z 203.05 [M+H]$^+$

Preparation 73: N-(2-methoxy-6-(methylsulfonyl)pyridin-3-yl)formamide

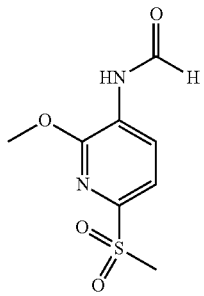

The title compound was prepared according to Method 13 (Preparation 55) using 2-methoxy-6-(methysulfonyl)pyridine-3-amine (Preparation 72) for 3 hours. The crude residue was used directly in the next reaction.
 LCMS (ESI) Rt=1.26 minutes MS m/z 231.06 [M+H]$^+$

Preparation 74: N-(2-methoxy-4-(1-methyl-1H-imidazol-5-yl)phenyl)formamide

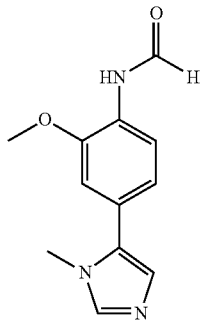 [SMILES: COc1cc(-c2cncn2C)ccc1NC=O]

The title compound was prepared according to Method 13 (Preparation 55) using 2-methoxy-4-(1-methyl-1H-imidazol-5-yl)aniline (Preparation 17). The crude residue was used directly in the next reaction.
 $^1$H NMR (500 MHz, MeOD): δ 8.36 (s, 1H), 8.33 (d, J=8.0 Hz, 1H), 7.69 (s, 1H), 7.10 (d, J=2.0 Hz, 1H), 7.04 (dd, J=8.0, 2.0 Hz, 2H), 3.96 (s, 3H), 3.74 (s, 3H).
 LCMS (ESI) Rt=0.69 minutes MS m/z 232.11 [M+H]$^+$

Preparation 75: 4-(1,3-dimethyl-1H-pyrazol-4-yl)-2-methoxyaniline

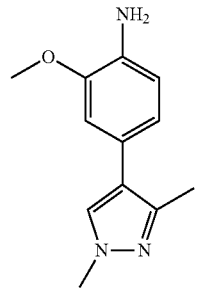

A suspension of 2-methoxy-4-(4,4,5,5-tetramethy-1,3,2-dioxaborolan-2-yl)aniline (50 mg, 0.201 mmol), 4-bromo-1,3-methylpyrazole (35 mg, 0.201 mmol), CsF (91 mg, 0.602 mmol) and Pd(PPh$_3$)$_4$ (12 mg, 10.04 umol) in DME/MeOH (2:1, 1.5 mL) was heated to 150° C. for 10 minutes, under microwave irradiation. The reaction mixture was diluted with EtOAc (30 mL) and water (30 mL). The organic layer was washed with water (30 mL), brine (30 mL), dried (MgSO$_4$) and concentrated in vacuo. The residue was purified by silica gel column chromatography eluting with 0-20% MeOH in EtOAc to give the title compound (10 mg, 23%).
 $^1$H NMR (500 MHz, CDCl$_3$): δ 7.38 (s, 1H), 6.92 (d, J=8.0 Hz, 1H), 6.85-6.83 (m, 2H), 3.90 (s, 3H), 3.89 (s, 3H), 2.39 (s, 3H).
 LCMS (ESI) Rt=1.15 minutes MS m/z 218.14 [M+H]$^+$

Preparation 76: N-(4-(1,3-dimethyl-1H-pyrazol-4-yl)-2-methoxyphenyl)formamide

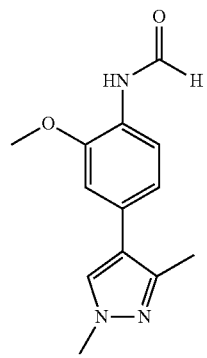 [SMILES: COc1cc(-c2cn(C)nc2C)ccc1NC=O]

The title compound was prepared according to Method 13 (Preparation 55) using 4-(1,3-dimethyl-1H-pyrazol-4-yl)-2-methoxyaniline (Preparation 75). The crude residue was used directly in the next reaction.
 $^1$H NMR (500 MHz, MeOD): δ 8.33 (s, 1H), 8.20 (d, J=8.5 Hz, 1H), 7.72 (s, 1H), 7.05 (d, J=2.0 Hz, 1H), 6.99 (dd, J=8.5, 2.0 Hz, 1H), 3.95 (s, 3H), 3.86 (s, 3H), 2.37 (s, 3H).
 LCMS (ESI) Rt=1.92 minutes MS m/z 246.11 [M+H]$^+$ Preparation 77; N-(4-(1,5-dimethy-1H-pyrazol-4-yl)-2-methoxyphenyl)formamide

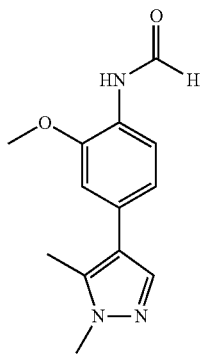 [SMILES: COc1cc(-c2cnn(C)c2C)ccc1NC=O]

The title compound was prepared according to Method 13 (Preparation 55) using 4-(1,5-dimethyl-1H-pyrazol-4-yl)-2-methoxyaniline (Preparation 48). The crude residue was used directly in the next reaction.
LCMS (ESI) Rt=1.90 minutes MS m/z 246.10 [M+H]$^+$ Preparation 78:
4-(3-methoxy-4-nitrophenyl)morpholine

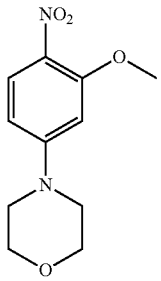 [SMILES: COc1cc(N2CCOCC2)ccc1[N+](=O)[O-]]

To a solution of 4-fluoro-2-methoxy-1-nitrobenzene (750 mg, 4.38 mmol) in MeCN (10 mL) was added morpholine (3.83 mL, 43.8 mmol) and potassium carbonate (606 mg, 4.38 mmol). The reaction mixture was heated at 70° C. for 18 hours. The reaction mixture was concentrated in vacuo. The residue was dissolved in DCM (30 mL) and washed with water (2×30 mL), dried (MgSO$_4$) and concentrated in vacuo, to give the title compound (1.0 g, 96%).
$^1$H NMR (500 MHz, CDCl$_3$): δ 8.03 (d, J=9.0 Hz, 1H), 6.48 (dd, J=9.0, 2.5 Hz, 1H), 6.44 (d, J=2.5 Hz, 1H), 3.98 (s, 3H), 3.90 (app, t, J=5.0 Hz, 4H), 3.38 (app t, J=5.0 Hz, 4H).
LCMS (ESI) Rt=1.95 minutes MS m/z 239.28 [M+H]$^+$ Preparation 79: 2-methoxy-4-morpholinoaniline

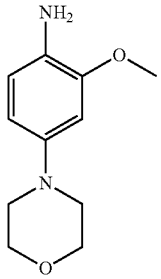

To a solution of 4-(3-methoxy-4-nitrophenyl)morpholine (Preparation 78, 1.00 g, 4.20 mmol) in EtOH (42 mL) was added tin (II) chloride (2.79 g, 14.69 mmol). The reaction mixture was heated to 70° C. for 18 hours. The reaction mixture was diluted with ice-water (10 mL) and concentrated in vacuo. Aqueous Na$_2$CO$_3$ (2M, 20 mL) was added and the reaction mixture was extracted with EtOAc (3×20 mL). The combined organic layers were washed with brine (30 mL), dried (MgSO$_4$) and concentrated in vacuo. The residue was purified by passage through a SCX-2 cartridge eluting with 100% MeOH—1M NH$_3$ in MeOH to give the title compound (418 mg, 48%).
$^1$H NMR (500 MHz, CDCl$_3$): δ 6.71-6.64 (m, 2H), 6.49 (m, 1H), 3.93 (t, J=5.5 Hz, 4H), 3.87 (s, 3H), 3.14-3.08 (m, 4H).
LCMS (ESI) Rt=0.60 minutes MS m/z 209.34 [M+H]$^+$ Preparation 80:
N-(2-methoxy-4-morpholinophenyl)formamide

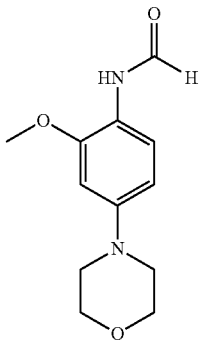 [SMILES: COc1cc(N2CCOCC2)ccc1NC=O]

The title compound was prepared according to Method 13 (Preparation 55) using 2-methoxy-4-morpholinoaniline (Preparation 79). The crude residue was used directly in the next reaction.
$^1$H NMR (500 MHz, MeOD): δ 8.24 (s, 1H), 7.98 (d, J=8.5 Hz, 1H), 6.65 (d, J=2.5 Hz, 1H), 6.52 (dd, J=8.5, 2.5 Hz, 1H), 3.89 (s, 3H), 3.85-3.83 (m, 4H), 3.15-3.13 (m, 4H).
LCMS (ESI) Rt=1.49 minutes MS m/z 237.32 [M+H]$^+$ Preparation 81:
4-(6-methoxy-5-nitropyridin-2-yl)morpholine

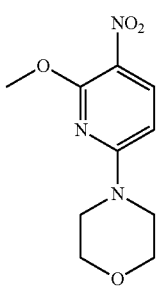 [SMILES: COc1nc(N2CCOCC2)ccc1[N+](=O)[O-]]

To a solution of 6-chloro-2-methoxy-3-nitropyridine (283 mg, 1.5 mmol) in acetonitrile/DMF (2:1, 3 mL) was added morpholine (0.13 mL, 1.5 mmol) and triethylamine (0.21 mL, 1.5 mmol). The reaction mixture was stirred at room temperature for 18 hours. The reaction mixture was concentrated in vacuo and the residue was partitioned between water (30 mL) and EtOAc (30 mL). The organic layer was dried (MgSO$_4$) and concentrated in vacuo. The residue was purified by silica gel column chromatography eluting with 20% cyclohexane in EtOAc to give the title compound (280 mg, 78%). $^1$H NMR (500 MHz, CDCl$_3$): δ 8.28 (d, J=9.0 Hz, 1H), 6.16 (d, J=9.0 Hz, 1H), 4.04 (s, 3H), 3.82 (t, J=4.5 Hz, 4H), 3.71 (t, J=4.5 Hz, 4H).
LCMS (ESI) Rt=1.96 minutes MS m/z 240.11 [M+H]$^+$

Preparation 82: 2-methoxy-6-(methylthio)-3-nitropyridine

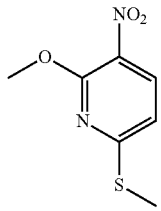

To a solution of 6-chloro-2-methoxy-3-nitropyridine (300 mg, 1.591 mmol) in acetonitrile/DMF (2:1, 3 mL) was added sodium thiomethoxide (133 mg, 1.91 mmol). The reaction mixture was stirred at room temperature for 18 hours and then concentrated in vacuo. The residue was partitioned between water (30 mL) and EtOAc (30 mL). The organic layer was dried (MgSO$_4$) and concentrated in vacuo to give the title compound (290 mg, 91%).

$^1$H NMR (500 MHz, CDCl$_3$): δ 8.17 (d, J=8.5 Hz, 1H), 6.85 (d, J=8.5 Hz, 1H), 4.12 (s, 3H), 2.62 (s, 3H).

LCMS (ESI) Rt=2.42 minutes MS m/z 201.07 [M+H]$^+$

Preparation 83: 2-methoxy-6-(methylsulfonyl)-3-nitropyridine

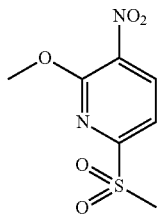

To a solution of 2-methoxy-6-(methylthio)-3-nitropyridine (Preparation 82, 290 mg, 1.45 mmol) in DCM (10 mL) was added mCPBA (650 mg, 3.2 mmol). The reaction mixture was stirred at room temperature for 3 hours. The reaction mixture was diluted with DCM (30 mL) and washed with aqueous saturated NaHCO$_3$ (30 mL), water (30 mL) and brine (30 mL), dried (MgSO$_4$) and concentrated in vacuo to give the title compound (290 mg, 86%).

$^1$H NMR (500 MHz, CDCl$_3$): δ 8.44 (d, J=8.0 Hz), 7.8 (d, J=8.0 Hz, 1H), 4.19 (s, 3H), 3.25 (s, 3H).

LCMS (ESI) Rt=1.48 minutes MS m/z 233.03 [M+H]$^+$

Preparation 84: Methyl 2-(benzyloxy)-5-bromoisonicotinate

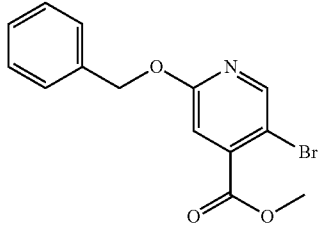 [SMILES: COC(=O)c1cc(OCc2ccccc2)ncc1Br]

To a suspension of methyl 5-bromo-2-oxo-1,2-dihydropyridine-4-carboxylate (2.5 g, 10.77 mmol) in MeCN (35 mL) was added silver carbonate (4.46 g, 16.16 mmol) and benzyl bromide (1.54 mL, 12.93 mmol). The reaction mixture was heated to 65° C. and stirred for 18 hours. The reaction mixture was filtered through a plug of Celite® and concentrated in vacuo. The residue was purified by silica gel column chromatography eluting with 50-100% DCM in cyclohexane to give the title compound (3.31 g, 95%).

$^1$H NMR (500 MHz, CDCl$_3$): δ 8.38 (s, 1H), 7.45 (dd, J=8.0, 2.0 Hz, 2H), 7.41-7.38 (m, 2H), 7.34 (m, 1H), 7.17 (m, 1H), 5.39 (s, 2H), 3.96 (s, 3H).

LCMS (ESI) Rt=3.04 minutes MS m/z 321.97 [M+H]$^+$

Preparation 85: (E)-methyl 2-(benzyloxy)-5-(2-ethoxyvinyl)isonicotinate

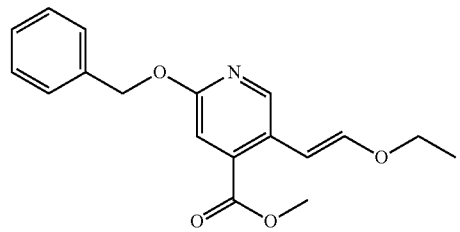 [SMILES: CCO/C=C/c1cnc(OCc2ccccc2)cc1C(=O)OC]

To a suspension of methyl 2-(benzyloxy)-5-bromoisonicotinate (Preparation 84, 1.5 g, 4.66 mmol), (E)-2-(2-ethoxyvinyl)-4,4,5,5-tetramethyl-1,3,2-dioxaborolane (Preparation 29, 1.844 g, 9.31 mmol) and Na$_2$CO$_3$ (0.99 g, 9.31 mmol) in toluene (5 mL), EtOH (5 mL) and water (5 mL) was added Pd(PPh$_3$)$_4$ (377 mg, 0.326 mmol). The reaction mixture was heated to 70° C. for 18 hours, under nitrogen. The reaction mixture was diluted with EtOAc (75 mL) and water (75 mL). The organic layer was dried (MgSO$_4$) and concentrated in vacuo. The residue was purified by silica gel column chromatography eluting with 0-10% EtOAc in cyclohexane to give the title compound (1.2 g, 82%). 1H NMR (500 MHz, CDCl$_3$): δ 8.23 (s, 1H), 7.47 (d, J=7.5, 1.5 Hz, 2H), 7.39 (td, J=8.5, 2.5 Hz, 2H), 7.33 (m, 1H), 7.24 (s, 1H), 6.80 (d, J=13.0 Hz, 1H), 6.39 (d, J=13.0 Hz, 1H), 5.40 (s, 2H), 3.95 (q, J=7.5 Hz, 2H), 3.92 (s, 3H), 1.37 (t, J=7.5 Hz, 3H).

LCMS (ESI) Rt=3.09 minutes MS m/z 314.27 [M+H]$^+$

Preparation 86: 7-(benzyloxy)-2,6-naphthyridin-1-ol

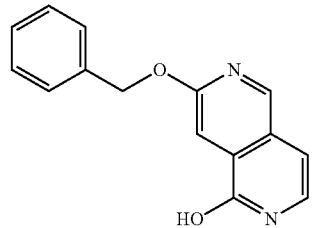 [SMILES: Oc1nccc2cnc(OCc3ccccc3)cc12]

(E)-methyl 2-(benzyloxy)-5-(2-ethoxyvinyl)isonicotinate (Preparation 85, 1.2 g, 3.83 mmol) was dissolved in methanolic ammonia (7M, 28 mL) in 3 microwave tubes. The reaction mixture was sealed and heated to 80° C. for 3 days. The reaction mixture was concentrated in vacuo. The residue was dissolved in toluene (30 mL) and pTsOH.H$_2$O (150 mg, 0.789 mmol) was added. The reaction mixture was heated at 90° C. for 2 hours. The reaction mixture was filtered and dried under vacuum, to give the title compound (937 mg, 97%).

$^1$H NMR (500 MHz, CDCl$_3$): δ 10.20 (br s, 1H), 8.68 (s, 1H), 7.70 (s, 1H), 7.50 (d, J=7.5 Hz, 2H), 7.40 (t, J=7.5 Hz, 2H), 7.34 (m, 1H), 7.03 (m, 1H), 6.61 (d, J=7.0 Hz, 1H), 5.50 (s, 2H).

LCMS (ESI) Rt=2.47 minutes MS m/z 253.33 [M+H]$^+$

Preparation 87: 7-(benzyloxy)-2,6-naphthyridin-1-yl trifluoromethanesulfonate

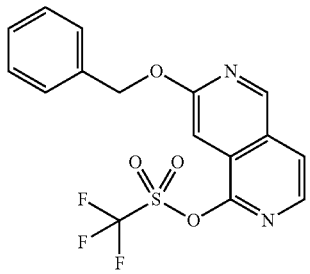 [SMILES: O=S(=O)(Oc1nccc2cnc(OCc3ccccc3)cc12)C(F)(F)F]

To a suspension of 7-(benzyloxy)-2,6-naphthyridin-1-ol (Preparation 86, 450 mg, 1.784 mmol) in DCM (20 mL) was added Et$_3$N (0.50 mL, 3.57 mmol) and trifluoromethanesulfonic anhydride (0.36 mL, 2.141 mmol). The reaction mixture was stirred at room temperature under for 2.5 hours. The reaction mixture was concentrated in vacuo. The residue was purified by silica gel column chromatography eluting with 50-80% DCM to give the title compound (415 mg, 58%).

$^1$H NMR (500 MHz, CDCl$_3$): δ 9.13 (s, 1H), 8.14 (d, J=6.0 Hz, 1H), 7.76 (dd, J=6.0, 1.0 Hz, 1H), 7.52 (d, J=7.5 Hz, 2H), 7.43-7.39 (m, 2H), 7.37 (m, 1H), 7.31 (s, 1H), 5.56 (s, 2H).

LCMS (ESI) Rt=3.15 minutes MS m/z 385.28 [M+H]$^+$

Preparation 88: 7-(benzyloxy)-1-(1-methyl-1H-pyrazol-4-yl)-2,6-naphthyridine

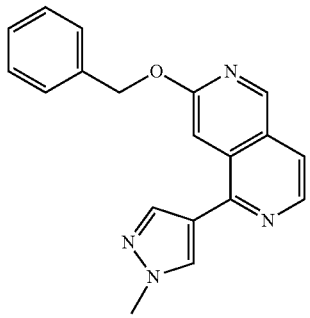 [SMILES: Cn1cc(-c2nccc3cnc(OCc4ccccc4)cc23)cn1]

To a suspension of 7-(benzyloxy)-2,6-naphthyridin-1-yl trifluoromethanesulfonate (Preparation 87, 350 mg, 0.911 mmol) in 1,4-dioxane (6 mL) and water (3 mL) was added 1-Methylpyrazole-4-boronic acid pinacol ester (379 mg, 1.821 mmol), cesium carbonate (460 mg, 1.412 mmol) and Pd(PPh$_3$)$_4$ (220 mg, 0.190 mmol). The reaction mixture was heated to 100° C. for 30 minutes under microwave conditions. The reaction mixture was diluted with EtOAc (25 mL) and water (25 mL). The organic layer was dried (MgSO$_4$) and concentrated in vacuo. The residue was purified by silica gel column chromatography eluting with 0-15% MeOH in DCM followed by a second chromatography eluting with 0-10% MeOH in DCM to give the title compound (249 mg, 86%).

$^1$H NMR (500 MHz, CDCl$_3$): δ 9.04 (d, J=1.0 Hz, 1H), 8.47 (d, J=6.0 Hz, 1H), 8.02 (s, 1H), 7.93 (s, 1H), 7.58-7.54 (m, 2H), 7.53-7.51 (m, 2H), 7.44-7.40 (m, 2H), 7.36 (m, 1H), 5.53 (s, 2H), 4.04 (s, 3H).

LCMS (ESI) Rt=2.60 minutes MS m/z 317.28 [M+H]$^+$

Preparation 89: 5-(1-methyl-1H-pyrazol-4-yl)-2,6-naphthyridin-3-ol

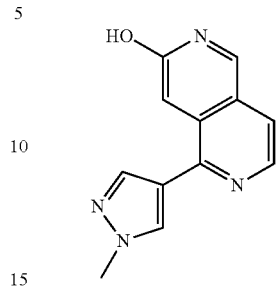

A solution of Pd(OAc)$_2$ (4 mg, 0.019 mmol), Et$_3$N (7.5 uL, 0.053 mmol), triethylsilane (0.085 mL, 0.531 mmol) in DCM (8 mL) was stirred at room temperature for 10 minutes. A solution of 7-(benzyloxy)-1-(1-methyl-1H-pyrazol-4-yl)-2,6-naphthyridine (Preparation 88, 120 mg, 0.379 mmol) in DCM (1 mL) was added. The reaction mixture was stirred at room temperature for 18 hours. The reaction mixture was quenched with aqueous saturated ammonium chloride (20 mL) and extracted with ether (2×30 mL). The combined organic layers were dried (MgSO$_4$) and concentrated in vacuo. The residue was purified by silica gel column chromatography eluting with 0-10% MeOH in DCM to give the title compound (13 mg, 15%).

$^1$H NMR (500 MHz, CDCl$_3$): δ 8.91 (s, 1H), 8.46 (d, J=5.5 Hz, 1H), 8.09 (s, 1H), 8.00 (s, 1H), 7.57-7.55 (m, 2H), 4.06 (s, 3H).

LCMS (ESI) Rt=1.10 minutes MS m/z 227.12 [M+H]$^+$

Preparation 90: 5-(1-methyl-1H-pyrazol-4-yl)-2,6-naphthyridin-3-yl trifluoromethanesulfonate

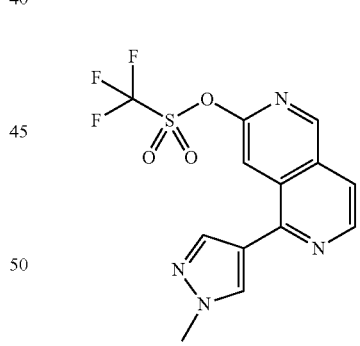

To a solution of 5-(1-methyl-1H-pyrazol-4-yl)-2,6-naphthyridin-3-ol (Preparation 89, 15 mg, 0.066 mmol) in DCM (0.5 mL) was added Tf$_2$O (0.013 mL, 0.080 mmol) and triethylamine (9.3 uL, 0.066 mmol). The reaction mixture was stirred at room temperature under 1 hour. The reaction mixture was concentrated in vacuo. The residue was passed through a SCX-2 cartridge eluting with 100% MeOH—1M NH$_3$ in MeOH to give the title compound (14 mg, 59%).

1H NMR (500 MHz, CDCl$_3$): δ 9.18 (s, 1H), 8.78 (d, J=5.5 Hz, 1H), 8.06 (s, 1H), 7.75 (dd, J=5.5, 1.0 Hz, 1H), 7.48 (s, 1H), 7.07 (s, 1H), 4.09 (s, 3H).

LCMS (ESI) Rt=2.52 minutes MS m/z 358.96 [M+H]$^+$

Preparation 91: 7-(benzyloxy)-N-cyclohexyl-2,6-naphthyridin-1-amine

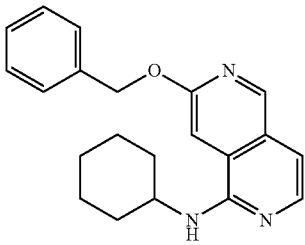 [SMILES: c1ccc(COc2cc3c(NC4CCCCC4)nccc3cn2)cc1]

To a solution of 7-(benzyloxy)-2,6-naphthyridin-1-yl trifluoromethanesulfonate (Preparation 87, 130 mg, 0.338 mmol) in NMP (6 mL) was added cyclohexylamine (0.39 mL, 3.38 mmol). The reaction mixture was heated to 120° C. for 30 minutes. The reaction was quenched with aq. sat. NaHCO$_3$ (30 mL) and extracted with EtOAc (2×30 mL). The combined organic layers were washed with water (40 mL) and brine (30 mL), dried (MgSO$_4$) and concentrated in vacuo. The residue was purified by silica gel column chromatography eluting with 0-10% MeOH in DCM to give the title compound (70 mg, 62%).

$^1$H NMR (500 MHz, CDCl$_3$): δ 8.78 (s, 1H), 7.90 (d, J=6.0 Hz, 1H), 7.51-7.48 (m, 2H), 7.41-7.38 (m, 2H), 7.34 (m, 1H), 6.97 (s, 1H), 6.91 (d, J=6.0 Hz, 1H), 5.51 (s, 2H), 4.99 (br d, J=7.0 Hz, 1H), 4.16 (m, 1H), 2.16-2.14 (m, 2H), 1.81-1.76 (m, 2H), 1.54-1.47 (m, 2H), 1.32-1.25 (m, 4H).

LCMS (ESI) Rt=2.11 minutes MS m/z 334.11 [M+H]$^+$

Preparation 92: 5-(cyclohexylamino)-2,6-naphthyridin-3-ol

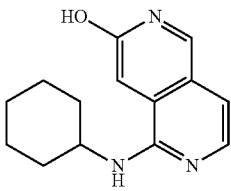 [SMILES: Oc1cc2c(NC3CCCCC3)nccc2cn1]

The title compound was prepared according to the method described for Preparation 89 using 7-(benzyloxy)-N-cyclohexyl-2,6-naphthyridin-1-amine (Preparation 91).

$^1$H NMR (500 MHz, CDCl$_3$): δ 8.46 (s, 1H), 7.79 (d, J=6.0 Hz, 1H), 6.87 (s, 1H), 6.79 (d, J=6.0 Hz, 1H), 5.03 (d, J=7.5 Hz, 1H), 4.16 (m, 1H), 2.18-2.14 (m, 2H), 1.83-1.78 (m, 2H), 1.70 (m, 2H), 1.64-1.48 (m, 2H), 1.35-1.28 (m, 2H).

LCMS (ESI) Rt=1.18 minutes MS m/z 244.14 [M+H]$^+$

Preparation 93: 5-(cyclohexylamino)-2,6-naphthyridin-3-yl trifluoromethanesulfonate

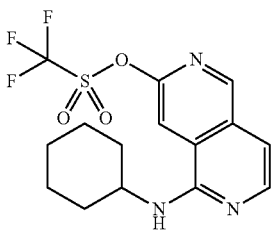

The title compound was prepared according to the method described for Preparation 90 using 5-(cyclohexylamino)-2,6-naphthyridin-3-ol (Preparation 92).

$^1$H NMR (500 MHz, CDCl$_3$): δ 8.88 (d, J=0.5 Hz, 1H), 8.18 (d, J=5.5 Hz, 1H), 7.40 (s, 1H), 7.03 (dd, J=5.5, 1.0 Hz, 1H), 5.11 (br d, J=7.5 Hz, 1H), 4.19 (m, 1H), 2.20-2.16 (m, 2H), 1.84 (dt, J=13.0, 3.5 Hz, 2H), 1.73 (dt, J=13.0, 3.5 Hz, 2H), 1.51 (m, 2H), 1.37-1.30 (m, 2H).

LCMS (ESI) Rt=2.50 minutes MS m/z 375.99 [M+H]$^+$

Preparation 94: 7-(benzyloxy)-N-(cyclopropylmethyl)-2,6-naphthyridin-1-amine

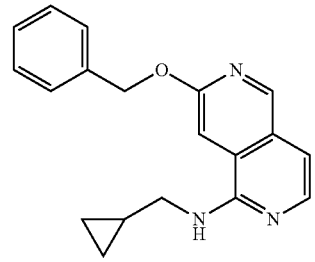 [SMILES: c1ccc(COc2cc3c(NCC4CC4)nccc3cn2)cc1]

The title compound was prepared according to the method described for Preparation 91 using cyclopropanemethylamine.

$^1$H NMR (500 MHz, CDCl$_3$): δ 8.80 (d, J=0.5 Hz, 1H), 7.90 (d, J=6.0 Hz, 1H), 7.52-7.50 (m, 2H), 7.42-7.39 (m, 2H), 7.35 (m, 1H), 7.05 (s, 1H), 6.94 (dd, J=6.0, 0.5 Hz, 1H), 5.52 (s, 2H), 5.23 (br s, 1H), 3.43 (dd, J=7.0, 5.0 Hz, 2H), 1.19 (m, 1H), 0.63-0.59 (m, 2H), 0.35-0.31 (m, 2H).

LCMS (ESI) Rt=1.96 minutes MS m/z 306.11 [M+H]$^+$

Preparation 95: 5-((cyclopropylmethyl)amino)-2,6-naphthyridin-3-ol

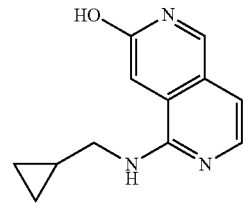 [SMILES: Oc1cc2c(NCC3CC3)nccc2cn1]

The title compound was prepared according to the method described for Preparation 89 using 7-(benzyloxy)-N-(cyclopropylmethyl)-2,6-naphthyridin-1-amine (Preparation 94).

$^1$H NMR (500 MHz, CDCl$_3$): δ 8.46 (s, 1H), 7.81 (d, J=7.5 Hz, 1H), 6.96 (s, 1H), 6.83 (d, J=6.5 Hz, 1H), 5.29 (br s, 1H), 3.44 (dd, J=7.0, 5.0 Hz, 2H), 1.22 (m, 1H), 0.63 (q, J=5.5 Hz, 2H), 0.35 (q, J=5.5 Hz, 2H).

LCMS (ESI) Rt=0.84 minutes MS m/z 216.14 [M+H]$^+$

Preparation 96: 5-((cyclopropylmethyl)amino)-2,6-naphthyridin-3-yl trifluoromethanesulfonate

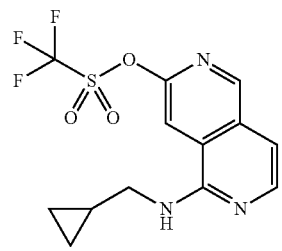 [SMILES: O=S(=O)(Oc1cc2c(NCC3CC3)nccc2cn1)C(F)(F)F]

The title compound was prepared according to the method described for Preparation 90 using 5-((cyclopropylmethyl)amino)-2,6-naphthyridin-3-ol (Preparation 95).

$^1$H NMR (500 MHz, CDCl$_3$): δ 8.91 (d, J=0.5 Hz, 1H), 8.18 (d, J=6.0 Hz, 1H), 7.51 (s, 1H), 7.06 (dd, J=6.0, 0.5 Hz, 1H), 5.46 (br t, J=5.0 Hz, 1H), 3.47 (dd, J=7.0, 5.0 Hz, 2H), 1.22 (m, 1H), 0.67-0.63 (m, 2H), 0.38-0.34 (m, 2H).

LCMS (ESI) Rt=2.22 minutes MS m/z 347.99 [M+H]$^+$

Preparation 97:
8-chloro-2-(methylsulfonyl)pyrido[3,4-d]pyrimidine

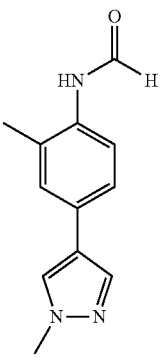

A suspension of 8-chloro-2-(methylthio)pyrido[3,4-d]pyrimidine (Preparation 33, 71 mg, 0.335 mmol) in DCM (3 mL) was treated with mCPBA (77% w/w, 180 mg, 0.801 mmol) at 0° C. and then allowed to reach room temperature for 18 hours. The mixture was quenched with water and extracted with DCM. The combined organic layers were washed with water, dried and concentrated. The residue was purified by silica gel column chromatography eluting with 0 to 80% EtOAc in cyclohexane to give the title compound (55 mg, 67%).

$^1$H NMR (500 MHz, CDCl$_3$) δ 9.76 (s, 1H), 8.77 (d, J=5.5 Hz, 1H), 7.89 (d, J=5.5 Hz, 1H), 3.59 (s, 3H).

LCMS (ESI) Rt=1.31 minutes MS m/z 266 [M+Na]$^+$

Preparation 98:
2-methyl-4-(1-methyl-1H-pyrazol-4-yl)aniline

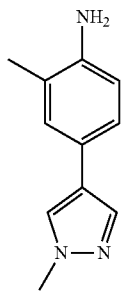

To a solution of 4-bromo-2-methylaniline (500 mg, 2.69 mmol) in EtOH (10 mL), toluene (10 mL) and water (10 mL) was added 1-methylpyrazole-4-boronic acid pinacol ester (671 mg, 3.22 mmol), sodium carbonate (570 mg, 5.37 mmol) and Pd(PPh$_3$)$_4$ (373 mg, 0.322 mmol). The reaction mixture was heated to 80° C. for 2.5 hours. The reaction mixture was cooled to room temperature and diluted with EtOAc (30 mL), washed with water (30 mL) and brine (30 mL), dried (MgSO$_4$) and concentrated in vacuo. The residue was purified by passage through a SCX-2 cartridge eluting with 100% MeOH—1M NH$_3$ in MeOH. The residue was purified by silica gel column chromatography eluting with 0-10% MeOH in DCM to give the title compound (106 mg, 21%).

$^1$H NMR (500 MHz, CDCl$_3$) 7.68 (s, 1H), 7.51 (s, 1H), 7.19 (m, 1H), 7.16 (dd, J=8.0, 2.0 Hz, 1H), 6.69 (d, J=8.0 Hz, 1H), 3.93 (s, 3H), 3.62 (br s, 2H), 2.22 (s, 3H).

LCMS (ESI) Rt=0.98 minutes MS m/z 188.17 [M+H]$^+$

Preparation 99:N-(2-methyl-4-(1-methyl-1H-pyrazol-4-yl)phenyl)formamide

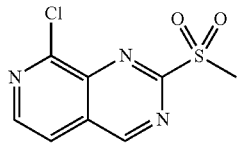

A solution of 2-methyl-4-(1-methyl-1H-pyrazol-4-yl)aniline (Preparation 98, 100 mg, 0.534 mmol) in formic acid (3 mL) was heated to reflux for 3 hours. The reaction mixture was concentrated in vacuo. The residue was partitioned between aqueous saturated NaHCO$_3$ solution (30 mL) and EtOAc (30 mL). The aqueous layer was re-extracted with EtOAc (30 mL).

The combined organic layers were washed with water (30 mL) and brine (30 mL)), dried (MgSO$_4$) and concentrated in vacuo. The residue was purified by silica gel column chromatography eluting with 0-10% MeOH in EtOAc to give the title compound (160 mg, 34%).

$^1$H NMR (500 MHz, MeOD): δ 8.31 (s, 1H), 7.93 (s, 1H), 7.80 (s, 1H), 7.67 (d, J=8.0 Hz, 1H), 7.44 (d, J=2.0 Hz, 1H), 7.38 (dd, J=8.0, 2.0, Hz, 1H), 3.92 (s, 3H), 2.31 (s, 3H).

LCMS (ESI) Rt=1.72 minutes MS m/z 216.13 [M+H]$^+$

Preparation 100: 4-bromo-2-ethoxy-1-nitrobenzene

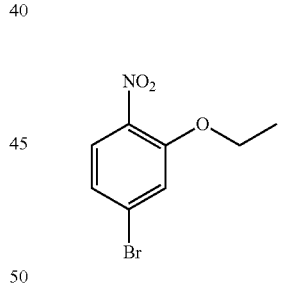

To a cooled (0° C.) solution of EtOH (0.07 mL, 1.193 mmol) in THF (5 mL) was added NaH (60% suspension in mineral oil, 68 mg, 1.705 mmol). The reaction mixture was stirred under nitrogen at 0° C. for 15 minutes. 2-fluoro-4-bromo-nitrobenzene (250 mg, 1.136 mmol) was added and the reaction mixture stirred for a further 18 hours, whilst warming slowly to room temperature. The reaction mixture was concentrated in vacuo. Ether (20 mL) and HCl (0.5 M, 20 mL) were added. The aqueous layer was basified with aqueous saturated NaHCO$_3$ solution and extracted with EtOAc (3×20 mL). The combined organic layers were washed with brine (20 mL), dried (MgSO$_4$) and concentrated in vacuo, to give the title compound (270 mg, 97%).

$^1$H NMR (500 MHz, CDCl$_3$): δ 7.74 (d, J=8.5 Hz, 1H), 7.24 (d, J=2.0 Hz, 1H), 7.17 (dd, J=8.5, 2.0 Hz, 1H), 4.19 (q, J=7.0 Hz, 2H), 1.50 (t, J=7.0 Hz, 3H).

Preparation 101: 1 4-bromo-2-ethoxyaniline

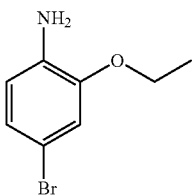

To a solution of 4-bromo-2-ethoxy-1-nitrobenzene (Preparation 100, 250 mg, 1.016 mmol) in EtOH (15 mL) was added tin (II) chloride (963 mg, 5.08 mmol). The reaction mixture was heated to 70° C. for 2 hours. The reaction mixture was diluted with ice-water (10 mL) and concentrated in vacuo. Aqueous $Na_2CO_3$ (2M, 20 mL) was added and the reaction mixture was extracted with EtOAc (3×20 mL). The combined organic layers were washed with brine (30 mL), dried ($MgSO_4$) and concentrated in vacuo. The residue was purified by passage through a SCX-2 cartridge eluting with 100% MeOH—1M $NH_3$ in MeOH to give the title compound (179 mg, 82%).

1H NMR (500 MHz, $CDCl_3$): δ 6.91-6.88 (m, 2H), 6.60 (dd, J=8.0, 0.5 Hz, 1H), 4.05 (q, J=7.0 Hz, 2H), 1.45 (t, J=7.0 Hz, 3H).

LCMS (ESI) Rt=1.96 minutes MS m/z 216.01 [M+H]+

Preparation 102:
2-ethoxy-4-(1-methyl-1H-pyrazol-4-yl)aniline

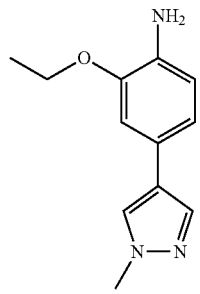 [SMILES: CCOc1cc(-c2cnn(C)c2)ccc1N]

The title compound was prepared according to Preparation 98 using 4-bromo-2-ethoxyaniline (Preparation 101).

$^1$H NMR (500 MHz, $CDCl_3$): δ 7.67 (d, J=0.5 Hz, 1H), 7.51 (s, 1H), 6.92 (d, J=2.0 Hz, 1H), 6.90 (dd, J=7.5, 2.0 Hz, 1H), 6.73 (d, J=7.5 Hz, 1H), 4.12 (q, J=7.0 Hz, 2H), 3.94 (s, 3H), 3.81 (br s, 2H), 1.47 (t, J=7.0 Hz, 3H).

LCMS (ESI) Rt=1.18 minutes MS m/z 218.16 [M+H]+

Preparation 103: N-(2-ethoxy-4-(1-methyl-1H-pyrazol-4-yl)phenyl)formamide

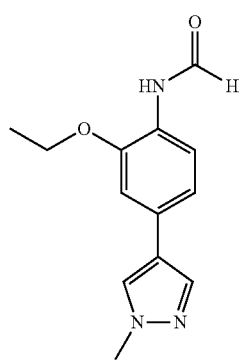 [SMILES: CCOc1cc(-c2cnn(C)c2)ccc1NC=O]

The title compound was prepared according to Preparation 99 using 2-ethoxy-4-(1-methyl-1H-pyrazol-4-yl)aniline (Preparation 102).

$^1$H NMR (500 MHz, $CDCl_3$): δ 8.49 (d, J=2.0 Hz, 1H), 8.37 (d, J=8.5 Hz, 1H), 7.81 (br s, 1H), 7.72 (s, 1H), 7.59 (s, 1H), 7.07 (dd, J=8.5, 2.0 Hz, 1H), 6.97 (d, J=2.0 Hz, 1H), 4.18 (q, J=7.0 Hz, 2H), 3.96 (s, 3H), 1.51 (t, J=7.0 Hz, 3H).

LCMS (ESI) Rt=1.96 minutes MS m/z 246.12 [M+H]+

Preparation 104:
4-bromo-2-isopropoxy-1-nitrobenzene

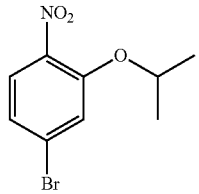

The title compound was prepared according to Preparation 100 using 2-propanol.

$^1$H NMR (500 MHz, $CDCl_3$): δ 7.69 (d, J=8.5 Hz, 1H), 7.23 (d, J=2.0 Hz, 1H), 7.14 (dd, J=8.5, 2.0 Hz, 1H), 4.67 (quin, J=6 Hz, 1H), 1.43 (s, 3H), 1.42 (s, 3H).

Preparation 105: 4-bromo-2-isopropoxyaniline

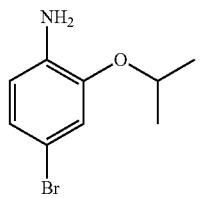

The title compound was prepared according to Preparation 101 using 4-bromo-2-isopropoxy-1-nitrobenzene (Preparation 104).

$^1$H NMR (500 MHz, MeOD): δ 7.03 (d, J=2.0 Hz, 1H), 6.91 (dd, J=8.5, 2.0 Hz, 1H), 6.77 (d, J=8.5 Hz, 1H), 4.60 (quin, J=6.0 Hz, 1H), 1.36 (s, 3H), 1.35 (s, 3H).

LCMS (ESI) Rt=2.22 minutes MS m/z 230.03 [M+H]+

Preparation 106:
2-isopropoxy-4-(1-methyl-1H-pyrazol-4-yl)aniline

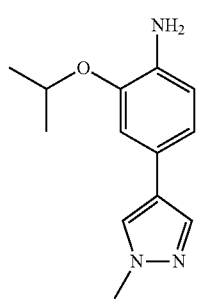 [SMILES: CC(C)Oc1cc(-c2cnn(C)c2)ccc1N]

The title compound was prepared according to Preparation 98 using 4-bromo-2-isopropoxyaniline (Preparation 105).

$^1$H NMR (500 MHz, $CDCl_3$): δ 7.66 (d, J=0.5 Hz, 1H), 7.50 (s, 1H), 6.92 (s, 1H), 6.91 (dd, J=7.5, 2.0 Hz, 1H), 6.73 (d, J=7.5 Hz, 1H), 4.59 (quin, J=6.0 Hz, 1H), 3.94 (s, 3H), 3.80 (br s, 2H), 1.40 (s, 3H), 1.39 (s, 3H).

LCMS (ESI) Rt=1.36 minutes MS m/z 232.18 [M+H]+

Preparation 107: N-(2-isopropoxy-4-(1-methyl-1H-pyrazol-4-yl)phenyl)formamide

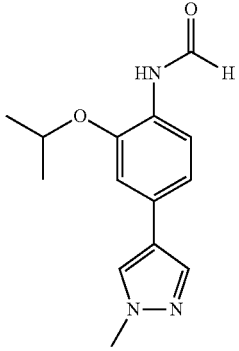 [SMILES: CC(C)Oc1cc(-c2cnn(C)c2)ccc1NC=O]

The title compound was prepared according to Preparation 99 using 2-isopropoxy-4-(1-methyl-1H-pyrazol-4-yl)aniline (Preparation 106).

$^1$H NMR (500 MHz, CDCl$_3$): δ 8.48 (d, J=2.0 Hz, 1H), 8.38 (d, J=8.5 Hz, 1H), 7.81 (br s, 1H), 7.71 (s, 1H), 7.59 (s, 1H), 7.05 (dd, J=8.5, 2.0 Hz, 1H), 4.69 (quin, J=6.0 Hz, 1H), 3.96 (s, 3H), 1.42 (d, J=6.0 Hz, 3H), 1.40 (d, J=6.0 Hz, 3H).

LCMS (ESI) Rt=2.03 minutes MS m/z 260.14 [M+H]$^+$

Preparation 108: 4-bromo-2-(2-methoxyethoxy)-1-nitrobenzene

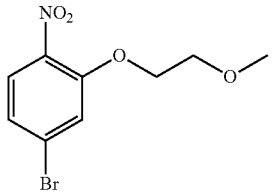

The title compound was prepared according to Preparation 100 using 2-methoxyethanol.

$^1$H NMR (500 MHz, CDCl$_3$): δ 7.76 (d, J=8.5 Hz, 1H), 7.30 (d, J=2.0 Hz, 1H), 7.20 (dd, J=8.5, 2.0 Hz, 1H), 4.26 (dd, J=5.0, 4.0 Hz, 2H), 3.82 (dd, J=5.0, 4.0 Hz, 2H), 3.47 (s, 3H).

Preparation 109: 4-bromo-2-(2-methoxyethoxy)aniline

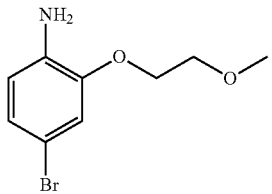

The title compound was prepared according to Preparation 101 using 4-bromo-2-(2-methoxyethoxy)-1-nitrobenzene (Preparation 108).

$^1$H NMR (500 MHz, MeOD): δ 6.99 (d, J=2.0 Hz, 1H), 6.89 (dd, J=8.5, 2.0 Hz, 1H), 6.68 (d, J=8.5 Hz, 1H), 4.14-4.12 (m, 2H), 3.78-3.76 (m, 2H), 3.45 (s, 3H).

LCMS (ESI) Rt=1.73 minutes MS m/z 246.02 [M+H]$^+$

Preparation 110: 2-(2-methoxyethoxy)-4-(1-methyl-1H-pyrazol-4-yl)aniline

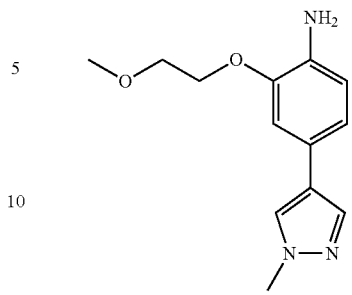

The title compound was prepared according to Preparation 98 using 4-bromo-2-(2-methoxyethoxy)aniline (Preparation 109).

$^1$H NMR (500 MHz, CDCl$_3$): δ 7.67 (d, J=0.5 Hz, 1H), 7.50 (s, 1H), 6.95 (dd, J=7.5, 2.0 Hz, 1H), 6.94 (s, 1H), 6.73 (dd, J=7.5, 1.5 Hz, 1H), 4.21-4.19 (m, 2H), 3.94 (s, 3H), 3.87 (br s, 2H), 3.80-3.78 (m, 2H), 3.47 (s, 3H).

LCMS (ESI) Rt=1.15 minutes MS m/z 248.16 [M+H]$^+$

Preparation 111: N-(2-(2-methoxyethoxy)-4-(1-methyl-1H-pyrazol-4-yl)phenyl)formamide

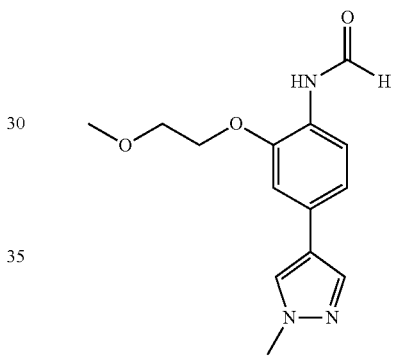

The title compound was prepared according to Preparation 99 using 2-(2-methoxyethoxy)-4-(1-methyl-1H-pyrazol-4-yl)aniline (Preparation 110).

$^1$H NMR (500 MHz, CDCl$_3$): δ 8.47 (d, J=2.0 Hz, 1H), 8.38 (d, J=8.5 Hz, 1H), 8.08 (br s, 1H), 7.72 (s, 1H), 7.59 (s, 1H), 7.12 (dd, J=8.5, 2.0 Hz, 1H), 7.05 (m, 1H), 4.26-4.23 (m, 2H), 3.96 (s, 3H), 3.79-3.77 (m, 2H), 3.48 (s, 3H).

Preparation 112: 1-(2,2-difluoroethyl)-4-(4,4,5,5-tetramethyl-1,3,2-dioxaborolan-2-yl)-1H-pyrazole

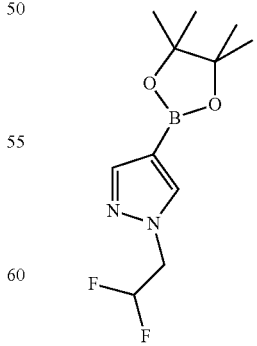

NaH (60%, 128 mg) was added to a solution of 4-(4,4,5,5-tetramethyl-1,3,2-dioxaborolan-2-yl)-1H-pyrazole (313 mg, 1.61 mmol) in DMF (4 mL). After stirring for 15 minutes, 1,1-difluoro-2-iodoethane (372 mg, 1.94 mmol) in DMF (1 mL) was added. The resulting solution was stirred at 80° C. under microwave irradiation for 60 minutes. The reaction mixture was diluted with brine and extracted with EtOAc. The combined organic layers were washed with water, dried with Na₂SO₄, and concentrated in vacuo to afford the title compound as a yellow oil that was used directly in the next step (210 mg, 50%).

¹H NMR (500 MHz, CDCl₃): δ 7.84 (d, J=0.7 Hz, 1H), 7.77 (d, J=0.7 Hz, 1H), 6.25-5.93 (m, 1H), 4.57-4.39 (m, 2H), 1.33 (s, 12H).

LCMS (ESI) Rt=2.64 minutes MS m/z 259 [M+H]⁺

Preparation 113: 8-chloro-N-(2-methyl-4-(1-methyl-1H-pyrazol-4-yl)phenyl)pyrido[3,4-d]pyrimidin-2-amine

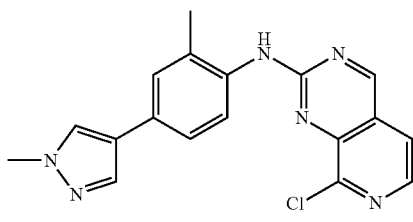 [SMILES: Cc1cc(-c2cnn(C)c2)ccc1Nc1ncc2ccnc(Cl)c2n1]

To a cooled (0° C.) suspension of N-(2-methyl-4-(1-methyl-1H-pyrazol-4-yl)phenyl)formamide (Preparation 99, 40 mg, 0.186 mmol) in THF (4 mL) was added NaH (60% dispersion in oil, 12 mg, 0.297 mmol). The reaction mixture was stirred at room temperature for 10 minutes. The reaction mixture was cooled to 0° C. and 8-chloro-2-(methylsulfonyl)pyrido[3,4-d]pyrimidine (Preparation 97, 59 mg, 0.242 mmol) was added. The reaction mixture was stirred for 18 hours, whilst slowly warming to room temperature. The reaction mixture was concentrated in vacuo. The residue was partitioned between EtOAc (30 mL) and water (30 mL). The aqueous layer was extracted with EtOAc (30 mL) and DCM (30 mL). The combined organic layers were washed with water (30 mL) and brine (30 mL), dried (MgSO₄) and concentrated in vacuo. The residue was purified by silica gel column chromatography eluting with 0-5% MeOH in EtOAc to give the title compound (79 mg, 97%).

¹H NMR (500 MHz, CDCl₃): δ 9.17 (s, 1H), 8.26 (d, J=5.0 Hz, 1H), 7.79 (s, 1H), 7.63 (s, 1H), 7.52 (d, J=5.0 Hz, 1H), 7.47 (dd, J=8.0, 2.0 Hz, 1H), 7.42 (m, 1H), 7.39 (d, J=2.0 Hz, 1H), 3.98 (s, 3H), 2.44 (s, 3H).

LCMS (ESI) Rt=2.56 minutes MS m/z 351.02 [M+H]⁺

Preparation 114: 8-chloro-N-(2-ethoxy-4-(1-methyl-1H-pyrazol-4-yl)phenyl)pyrido[3,4-d]pyrimidin-2-amine

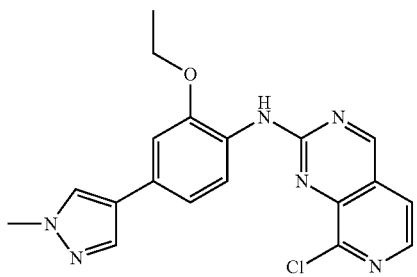 [SMILES: CCOc1cc(-c2cnn(C)c2)ccc1Nc1ncc2ccnc(Cl)c2n1]

The title compound was prepared according to the method described for Preparation 113 using N-(2-ethoxy-4-(1-methyl-1H-pyrazol-4-yl)phenyl)formamide (Preparation 103). The residue was purified by silica gel column chromatography eluting with 50-100% EtOAc in cyclohexane to give the title compound (27 mg, 44%).

¹H NMR (500 MHz, CDCl₃): δ 9.17 (s, 1H), 9.07 (br s, 1H), 8.33 (br s, 1H), 8.26 (d, J=5.0 Hz, 1H), 7.78 (d, J=0.5 Hz, 1H), 7.63 (s, 1H), 7.52 (d, J=5.0 Hz, 1H), 7.25 (dd, J=8.5, 2.0 Hz, 1H), 7.05 (d, J=2.0 Hz, 1H), 4.25 (q, J=7.0 Hz, 2H), 3.98 (s, 3H), 1.56 (t, J=7.0 Hz, 3H).

LCMS (ESI) Rt=2.88 minutes MS m/z 381.01 [M+H]⁺

Preparation 115: 8-chloro-N-(2-isopropoxy-4-(1-methyl-1H-pyrazol-4-yl)phenyl)pyrido[3,4-d]pyrimidin-2-amine

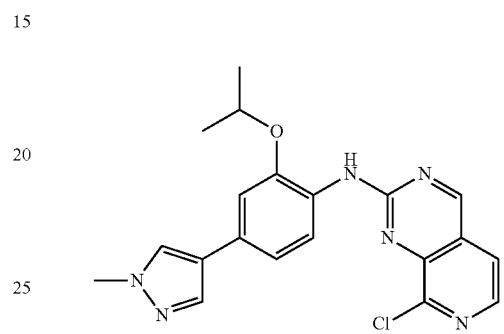

The title compound was prepared according to the method described for Preparation 113 using N-(2-isopropoxy-4-(1-methyl-1H-pyrazol-4-yl)phenyl)formamide (Preparation 107). The residue was purified by silica gel column chromatography eluting with 50-80% EtOAc in cyclohexane to give the title compound (37.7 mg, 62%).

¹H NMR (500 MHz, CDCl₃): δ 9.16 (s, 1H), 9.07 (br s, 1H), 8.34 (br s, 1H), 8.26 (d, J=5.5 Hz, 1H), 7.77 (s, 1H), 7.62 (s, 1H), 7.52 (d, J=5.5 Hz, 1H), 7.52 (m, 1H), 7.24 (dd, J=8.0, 2.0 Hz, 1H), 7.07 (d, J=2.0 Hz, 1H), 4.76 (quin, J=6.0 Hz, 1H), 3.98 (s, 3H), 1.48 (s, 3H), 1.47 (s, 3H).

LCMS (ESI) Rt=2.93 minutes MS m/z 395.02 [M+H]⁺

Preparation 116: 8-chloro-N-(2-(2-methoxyethoxy)-4-(1-methyl-1H-pyrazol-4-yl)phenyl)pyrido[3,4-d]pyrimidin-2-amine

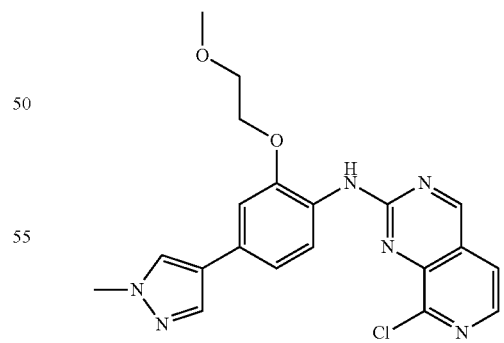

The title compound was prepared according to the method described for Preparation 113 using N-(2-(2-methoxyethoxy)-4-(1-methyl-1H-pyrazol-4-yl)phenyl)formamide (Preparation 1H). The residue was purified by silica gel column chromatography eluting with 50-100% EtOAc in cyclohexane—5% MeOH in EtOAc to give the title compound (18 mg, 30%).

¹H NMR (500 MHz, CDCl₃): δ 9.17 (s, 1H), 9.08 (br s, 1H), 8.56 (s, 1H), 8.26 (d, 1H), 7.78 (s, 1H), 7.63 (s, 1H), 7.52 (d, J=5.5 Hz, 1H), 7.29 (dd, J=8.5, 2.0 Hz, 1H), 7.12 (d, J=2.0 Hz, 1H), 4.33-4.31 (m, 2H), 3.98 (s, 3H), 3.86-3.84 (m, 2H), 3.53 (s, 3H).

LCMS (ESI,) Rt=2.68 minutes MS m/z 410.97 [M+H]⁺

MPS1 IC50 (uM):

Preparation 117

8-chloro-N-(4-(1,5-dimethyl-1H-pyrazol-4-yl)-2-methoxyphenyl)pyrido[3,4-d]pyrimidin-2-amine

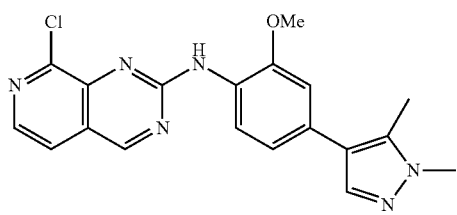

Method 14

A solution of N-(4-(1,5-dimethyl-1H-pyrazol-4-yl)-2-methoxyphenyl)formamide (Preparation 77, 240 mg, 0.978 mmol) in THF (8 mL) was treated with sodium hydride (60% w/w, 65 mg, 1.625 mmol) at 0° C. After stirring for 20 minutes at room temperature the mixture was cooled to 0° C. and 8-chloro-2-(methylsulfonyl)pyrido[3,4-d]pyrimidine (Preparation 97, 325 mg, 1.334 mmol) was added. The reaction was allowed to reach room temperature and stirred for 18 hours. A solution of aqueous 2M NaOH (4 mL) and MeOH (4 mL) were added and the resulting mixture stirred at room temperature for 1 hour before concentrating in vacuo. The residue was partitioned between DCM and water. The aqueous layer was extracted with DCM and the combined organic layers were dried and concentrated in vacuo. The residue was purified by silica gel column chromatography eluting with 0-100% EtOAc in cyclohexanes to give the title compound (362 mg, 97%).

¹H NMR (500 MHz, DMSO-d₆): δ 9.47 (s, 1H), 8.85 (br. s, 1H), 8.54 (br. s, 1H), 8.25 (d, J=5.2 Hz, 1H), 7.86 (d, J=5.2 Hz, 1H), 7.63 (s, 1H), 7.09 (d, J=1.8 Hz, 1H), 7.06 (dd, J=8.2, 1.9 Hz, 1H), 3.93 (s, 3H), 3.79 (s, 3H), 2.42 (s, 3H).

LCMS (ESI) Rt=3.10 minutes MS m/z 381 [M+H]⁺

The following Preparations were prepared according to Method 14 using the appropriate formamide and pyrido[3,4-d]pyrimidine as described below. The crude reaction residues were purified as described or according to one of the following methods:

Method A: Silica gel column chromatography eluting with 0-10% MeOH in DCM or EtOAc.

Method B: Silica gel column chromatography eluting with 0 to 40% EtOAc in cyclohexanes followed by preparative HPLC eluting with 40% to 100% MeOH in H₂O (0.1% formic acid).

| Preparation No | Name/Structure | Data |
|---|---|---|
| 118 | 8-chloro-N-(2-methoxy-4-(4-methyl-4H-1,2,4-triazol-3-yl)phenyl)-5-methylpyrido[3,4-d]pyrimidin-2-amine | ¹H NMR (500 MHz, DMSO-d₆): δ 9.63 (s, 1H), 8.96 (s, 1H), 8.83 (br. d, J = 8.2 Hz, 1H), 8.57 (s, 1H), 8.12 (d, J = 1.2 Hz, 1H), 7.46 (d, J = 1.9 Hz, 1H), 7.43 (dd, J = 8.3, 1.9 Hz, 1H), 3.99 (s, 3H), 3.81 (s, 3H), 2.64 (d, J = 1.0 Hz, 3H). LCMS (ESI) Rt = 2.57 minutes MS m/z 382 [M + H]⁺ Using N-(2-methoxy-4-(4-methyl-4H-1,2,4-triazol-3-yl)phenyl)formamide (Preparation 221) and 8-chloro-5-methyl-2-(methylsulfonyl)pyrido[3,4-d]pyrimidine (Preparation 184) and purification method A. |
| 119 | 8-chloro-N-(4-(1-ethyl-1H-pyrazol-4-yl)-2-methoxy)phenyl)pyrido[3,4-d]pyrimidin-2-amine | ¹H NMR (500 MHz, DMSO-d₆): δ 9.47 (s, 1H), 8.83 (s, 1H), 8.53 (s, 1H), 8.31-8.20 (m, 2H), 7.93 (d, J = 0.8 Hz, 1H), 7.87 (d, J = 5.2 Hz, 1H), 7.31 (d, J = 1.8 Hz, 1H), 7.28 (dd, J = 8.4, 1.8 Hz, 1H), 4.16 (q, J = 7.3 Hz, 2H), 3.96 (s, 3H), 1.43 (t, J = 7.3 Hz, 3H). LCMS (ESI) Rt = 3.07 minutes MS m/z 381 [M + H]⁺ Using N-(4-(1-ethyl-1H-pyrazol-4-yl)-2-methoxyphenyl)formamide (Preparation 128) and 8-chloro-2-(methylsulfonyl)pyrido[3,4-d]pyrimidine (Preparation 97). |

| Preparation No | Name/Structure | Data |
|---|---|---|
| 120 | (4-((8-chloropyrido[3,4-d]pyrimidin-2-yl)amino)-3-methoxyphenyl)(3-methoxyazetidin-1-yl)methanone 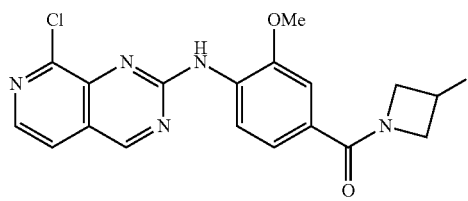 | $^1$H NMR (500 MHz, DMSO-d$_6$): δ 9.55 (s, 1H), 8.94 (s, 1H), 8.74 (br. d, J = 8.4 Hz, 1H), 8.31 (d, J = 5.2 Hz, 1H), 7.92 (d, J = 5.2 Hz, 1H), 7.36 (dd, J = 8.3, 1.8 Hz, 1H), 7.33 (d, J = 1.7 Hz, 1H), 4.54 (br.s, 1H), 4.26 (br.s, 3H), 3.96 (s, 3H), 3.87 (br.s, 1H), 3.25 (s, 3H). LCMS (ESI) Rt = 2.71 minutes MS m/z 400 [M + H]$^+$ Using N-(2-methoxy-4-(3-methoxyazetidine-1-carbonyl)phenyl)formamide (Preparation 129) and 8-chloro-2-(methylsulfonyl)pyrido[3,4-d]pyrimidine (Preparation 97). |
| 121 | 8-chloro-N-(4-(1,2-dimethyl-1H-imidazol-5-yl)-2-methoxyphenyl)-6-methylpyrido[3,4-d]pyrimidin-2-amine 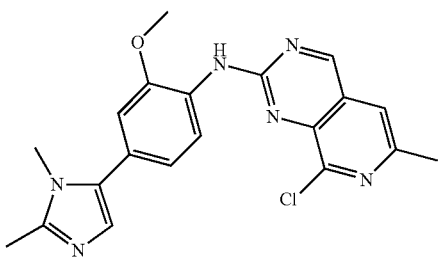 | $^1$H NMR (500 MHz, CDCl$_3$): δ 8.38 (s, 1H), 7.41 (s, 1H), 7.48 (s, 1H), 7.12 (dd, J = 8.0, 2.0 Hz, 1H), 7.07 (d, J = 8.0 Hz, 1H), 6.88 (d, J = 2.0 Hz, 1H), 4.03 (s, 3H), 3.71 (s, 3H), 2.90 (s, 3H), 2.70 (s, 3H). LCMS (ESI) Rt = 2.20 minutes MS m/z 395 [M + H]$^+$ Using N-(4-(1,2-dimethyl-1H-imidazol-5-yl)-2-methoxyphenyl)formamide (Preparation 55) and 8-chloro-6-methyl-2-(methylsulfonyl)pyrido[3,4-d]pyrimidine (Preparation 178) and purification method A. |
| 122 | 8-chloro-N-(2-ethoxy-4-(1-methyl-1H-pyrazol-4-yl)phenyl)pyrido[3,4-d]pyrimidin-2-amine 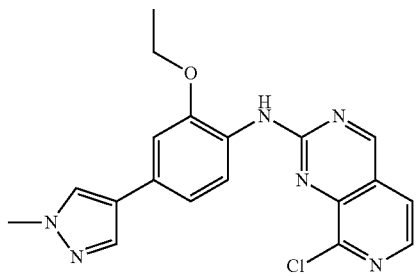 | $^1$H NMR (500 MHz, CDCl$_3$): δ 9.36 (s, 1H), 8.40 (d, J = 5.5 Hz, 1H), 7.78 (s, 1H), 7.64 (s, 1H), 7.51 (d, J = 5.5 Hz, 1H), 7.46 (m, 1H), 7.25 (dd, J = 8.5, 1.5 Hz, 1H), 7.04 (d, J = 1.5 Hz, 1H), 3.97 (s, 3H), 4.25 (q, J = 6.5 Hz, 2H), 1.56 (t, J = 6.5 Hz, 3H). LCMS (ESI) Rt = 2.93 minutes MS m/z 381[M + H]$^+$ Using N-(2-ethoxy-4-(1-methyl-1H-pyrazol-4-yl)phenyl)formamide (Preparation 103) and 8-chloro-2-(methylsulfonyl)pyrido[3,4-d]pyrimidine (Preparation 97) and purification method A. |
| 123 | 8-chloro-N-(2-methoxy-4-(tetrahydro-2H-pyran-4-yl)phenyl)pyrido[3,4-d]pyrimidin-2-amine 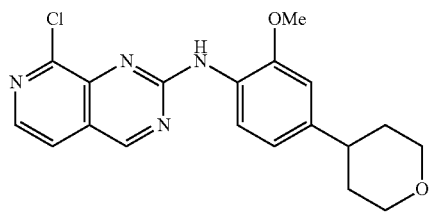 | $^1$H NMR (500 MHz, DMSO): δ 9.46 (s, 1H), 8.81 (br.s, 1H), 8.40 (br.s, 1H), 8.24 (d, J = 5.2 Hz, 1H), 7.86 (d, J = 5.3 Hz, 1H), 7.01 (d, J = 1.8 Hz, 1H), 6.92 (dd, J = 8.2, 1.8 Hz, 1H), 4.02-3.92 (m, 2H), 3.90 (s, 3H), 3.53-3.39 (m, 2H), 2.85-2.73 (m, 1H), 1.89-1.63 (m, 4H). LCMS (ESI) Rt = 3.17 minutes MS m/z 371 [M + H]$^+$ Using N-(2-methoxy-4-(tetrahydro-2H-pyran-4-yl)phenyl)formamide (Preparation 154) and 8-chloro-2-(methylsulfonyl)pyrido[3,4-d]pyrimidine (Preparation 97) and purification method A. |

Preparation 124: 8-chloro-N-(2-ethoxy-4-(4-methyl-4H-1,2,4-triazol-3-yl)phenyl)-6-methylpyrido[3,4-d]pyrimidin-2-amine

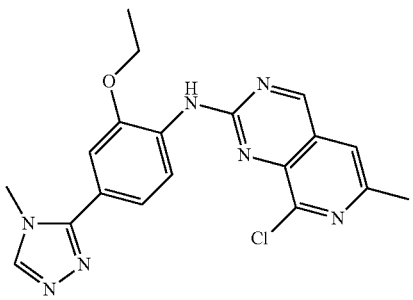

To a solution of 8-chloro-6-methyl-2-(methylsulfonyl)pyrido[3,4-d]pyrimidine (Preparation 178, 31 mg, 0.120 mmol) in DMSO (5 mL) was added N-(2-ethoxy-4-(4-methyl-4H-1,2,4-triazol-3-yl)phenyl)formamide (Preparation 150, 35.5 mg, 0.144 mmol) and $Cs_2CO_3$ (78 mg, 0.241 mmol). The reaction mixture was heated to 120° C. for 18 hours. The reaction mixture was cooled to room temperature and diluted with EtOAc (30 mL) and water (30 mL). The organic layer was washed with brine (30 mL), dried ($MgSO_4$) and concentrated in vacuo. The residue was purified by silica gel column chromatography eluting with 50-100% EtOAc in cyclohexanes followed by elution through an SCX-2 column using MeOH—1M $NH_3$ in MeOH to afford the title compound (12.9 mg, 27%).

$^1$H NMR (500 MHz, acetone-d6): δ 9.41 (s, 1H), 9.25 (d, J=8.0 Hz, 1H), 8.50 (br s, 1H), 8.38 (s, 1H), 7.71 (d, J=1.0 Hz, 1H), 7.50 (s, 1H), 7.49 (dd, J=8.0, 2.0 Hz, 1H), 4.38 (q, J=7.0 HZ, 2H), 3.93 (s, 3H), 2.62 (d, J=1.0 Hz, 3H), 1.57 (t, J=7.0 Hz, 3H).

LCMS (ESI) Rt=2.91 minutes MS m/z 396 [M+H]$^+$

Preparation 125: 8-Chloro-6-cyclopropyl-N-(2-methoxy-4-(1-methyl-1H-pyrazol-4-yl)phenyl)pyrido[3,4-d]pyrimidin-2-amine

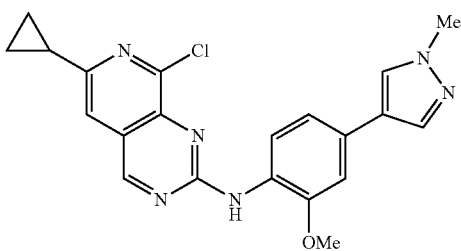 [SMILES: COc1cc(-c2cnn(C)c2)ccc1Nc1ncc2cc(C3CC3)nc(Cl)c2n1]

N-(2-Methoxy-4-(1-methyl-1H-pyrazol-4-yl)phenyl)formamide (Preparation 56, 50 mg 0.21 mmole) was stirred in THF (1 mL). Sodium hexamethyldisilazide (0.25 mL of 1M solution in THF) was added and the reaction stirred at room temperature for 20 minutes. 8-Chloro-6-cyclopropyl-2-(methylsulfonyl)pyrido[3,4-d]pyrimidine (Preparation 179, 80 mg, 0.28 mmole) was added as a suspension in THF (1.5 mL) and the reaction was stirred at room temperature for 80 minutes. Methanol (1 mL) and 1M sodium hydroxide solution (1 mL) were added to the reaction and stirred for 55 minutes. The solvents were then concentrated in vacuo. The residue was partitioned between chloroform (10 mL) and water (10 mL). The layers were separated and the aqueous was again extracted with chloroform. The combined organic layers were dried and concentrated in vacuo. The residue was purified using preparative TLC eluting with 1:1 acetone:cyclohexane to afford the title compound (41 mg 44%).

$^1$H NMR (500 MHz, $CDCl_3$): δ 9.08 (s, 1H), 9.03 (br d, J=8.20 Hz, 1H), 8.24 (br s, 1H), 7.79 (s, 1H), 7.65 (s, 1H), 7.32 (s, 1H), 7.24 (dd, J=1.89, 8.51 Hz, 1H), 7.03 (d, J=1.58 Hz, 1H), 4.01 (s, 3H), 3.99 (s, 3H), 2.14 (m, 1H), 1.04-1.13 (m, 4H).

Preparation 126: N-(2-methoxy-6-(1-methyl-1H-tetrazol-5-yl)pyridin-3-yl)formamide

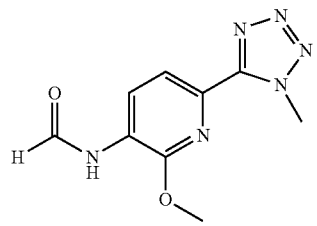 [SMILES: COc1nc(-c2nnnn2C)ccc1NC=O]

Method 15

Formic acid (59.3 µL, 1.571 mmol) was added to acetic anhydride (99 µL, 1.048 mmol) while stirring and cooling at 0° C. Stirring was continued for 1 hour at room temperature. The reaction was cooled to 0° C. and added to a solution of 2-methoxy-6-(1-methyl-1H-tetrazol-5-yl)pyridin-3-amine (Preparation 158, 18 mg, 0.087 mmol) in THF (100 µL) at 0° C. The reaction mixture was stirred at room temperature for 30 hours. The residue was dissolved in DCM and the solution was washed with saturated aqueous $NaHCO_3$ solution. The organic layer was dried ($Na_2SO_4$), filtered and concentrated in vacuo to afford the title compound as a white solid (20 mg, 98%).

$^1$H NMR (500 MHz, $CD_3OD$): δ 8.80 (d, J=8.1 Hz, 1H), 8.46 (s, 1H), 7.91 (d, J=8.1 Hz, 1H), 4.53 (s, 4H), 4.17 (s, 3H).

LCMS (ESI) Rt=2.02 minutes MS m/z 235 [M+H]$^+$

The following Preparations were prepared according to Method 13 (Preparation 55) or Method 15 (Preparation 126) using the appropriate aniline as described below. The crude reaction residues were purified as described or according to one of the following methods:

Method A: Silica gel column chromatography eluting with 0-15% MeOH in EtOAc.

Method B: Silica gel column chromatography eluting with 0-60% EtOAc in cyclohexanes.

| Preparation No | Name/Structure | Data |
|---|---|---|
| 127 | N-(2-methoxy-4-(1-methyl-1H-1,2,4-triazol-5-yl)phenyl)formamide 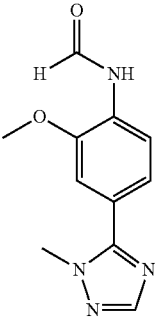 | $^1$H NMR (500 MHz, MeOD): δ 8.47 (d, J = 8.5 Hz, 1H), 8.41 (s, 1H), 7.99 (s, 1H), 7.39 (d, J = 2.0 Hz, 1H), 7.31 (dd, J = 8.5, 2.0 Hz, 1H), 4.03 (s, 3H), 4.00 (s, 3H). LCMS (ESI) Rt = 1.61 minutes MS m/z 233 [M + H]+ Using 2-methoxy-4-(1-methyl-1H-1,2,4-triazol-5-yl)aniline (Preparation 166). Method 13. |
| 128 | N-(4-(1-ethyl-1H-pyrazol-4-yl)-2-methoxyphenyl)formamide 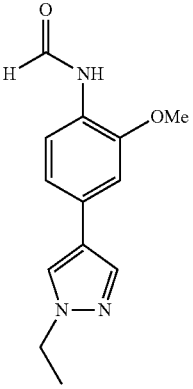 | $^1$H NMR (500 MHz, DMSO-$d_6$): δ 9.63 (s, 1H), 8.28 (d, J = 1.9 Hz, 1H), 8.19 (s, 1H), 8.11 (d, J = 8.3 Hz, 1H), 7.87 (d, J = 0.9 Hz, 1H), 7.24 (d, J = 1.8 Hz, 1H), 7.12 (dd, J = 8.2, 1.9 Hz, 1H), 4.14 (q, J = 7.3 Hz, 2H), 3.91 (s, 3H), 1.41 (t, J = 7.3 Hz, 3H). LCMS (ESI) Rt = 1.99 minutes MS m/z 246 [M + H]$^+$ Using 4-(1-ethyl-1H-pyrazol-4-yl)-2-methoxyaniline (Preparation 155) and purification method B. Method 13. |
| 129 | N-(2-methoxy-4-(3-methoxyazetidine-1-carbonyl)phenyl)formamide 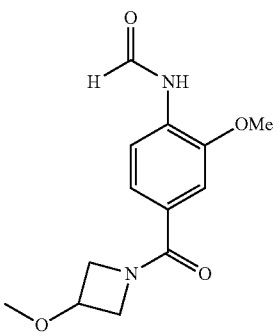 | $^1$H NMR (500 MHz, DMSO-$d^6$): δ 9.86 (s, 1H), 8.34 (s, 1H), 8.25 (d, J = 8.3 Hz, 1H), 7.25 (d, J = 1.8 Hz, 1H), 7.21 (dd, J = 8.4, 1.8 Hz, 1H), 4.46 (br.s, 1H), 4.22 (br.s, 2H), 4.15 (s, 1H), 3.90 (s, 3H), 3.84 (br.s, 1H), 3.22 (s, 3H). LCMS (ESI) Rt = 1.66 minutes MS m/z 265 [M + H]$^+$ Using (4-amino-3-methoxyphenyl)(3-methoxyazetidin-1-yl)methanone (Preparation 28) and purification method A. Method 13. |
| 130 | N-(6-(1,2-Dimethyl-1H-imidazol-5-yl)-2-methoxypyridin-3-yl)formamide 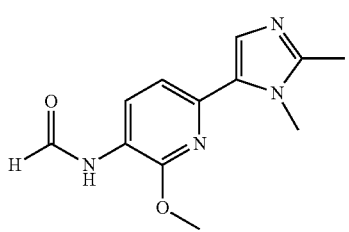 | $^1$H NMR (500 MHz, CD$_3$OD): δ 8.54 (d, J = 8.1 Hz, 1H), 8.38 (s, 1H), 7.23-7.25 (m, 2H), 4.08 (s, 3H), 3.95 (s, 3H), 2.44 (s, 3H). LCMS Rt = 1.32 minutes MS m/z 247 [M + H]$^+$ Using 6-(1,2-dimethyl-1H-imidazol-5-yl)-2-methoxypyridin-3-amine (Preparation 191). Method 15. |

-continued

| Preparation No | Name/Structure | Data |
|---|---|---|
| 131 | N-(2-Methoxy-4-(1-methyl-1H-tetrazol-5-yl)phenyl)formamide 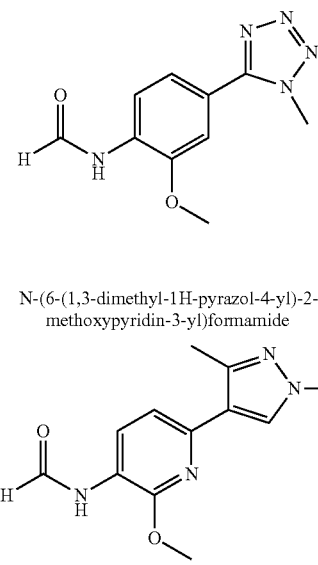 | ¹H NMR (500 MHz, CD₃OD): δ 8.53 (d, J = 8.4 Hz, 1H), 8.42 (s, 1H), 7.48 (d, J = 1.9 Hz, 1H), 7.40 (dd, J = 8.4, 1.9 Hz, 1H), 4.23 (s, 4H), 4.02 (s, 3H). LCMS (ESI) Rt = 1.72 minutes MS m/z 234 [M + H]⁺ Using 2-methoxy-4-(1-methyl-1H-tetrazol-5-yl)aniline (Preparation 192). Method 15. |
| 132 | N-(6-(1,3-dimethyl-1H-pyrazol-4-yl)-2-methoxypyridin-3-yl)formamide | ¹H NMR (500 MHz, CDCl₃): δ 8.56 (d, J = 8.1 Hz, 1H), 8.48 (d, J = 1.7 Hz, 1H), 7.70-7.73 (m, 2H), 7.02 (d, J = 8.1 Hz, 1H), 4.06 (s, 3H), 3.88 (s, 3H), 2.57 (s, 3H). LCMS (ESI) Rt = 2.36 minutes [M + H]⁺ Using 6-(1,3-dimethyl-1H-pyrazol-4-yl)-2-methoxypyridin-3-amine (Preparation 163). Method 15. |
| 133 | N-(6-(1,5-Dimethyl-1H-pyrazol-4-yl)-2-methoxypyridin-3-yl)formamide 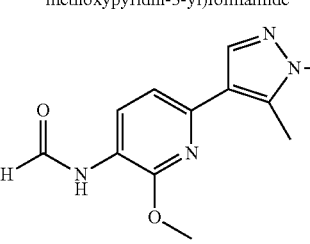 | ¹H NMR (500 MHz, CDCl₃): δ 8.57 (d, J = 8.1 Hz, 1H), 8.49 (s, 1H), 7.79 (s, 1H), 7.67 (br s, 1H), 7.07 (d, J = 8.1 Hz, 1H), 4.07 (s, 3H), 3.85 (s, 3H), 2.65 (s, 3H). LCMS (ESI) Rt = 2.36 minutes MS m/z 247 [M + H]⁺ Using 6-(1,5-dimethyl-1H-pyrazol-4-yl)-2-methoxypyridin-3-amine (Preparation 167). Method 15. |
| 134 | N-(2-Methoxy-6-(1-methyl-1H-1,2,3-triazol-5-yl)pyridin-3-yl)formamide 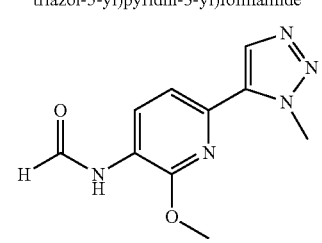 | ¹H NMR (500 MHz, CDCl₃): δ 8.73 (d, J = 8.1 Hz, 1H), 8.55 (s, 1H), 7.96 (s, 1H), 7.82 (br s, 1H), 7.29 (d, J = 8.1 Hz, 1H), 4.43 (s, 3H), 4.10 (s, 3H). LCMS (ESI) Rt = 1.80 minutes MS m/z 234 [M + H]⁺ Using 2-methoxy-6-(1-methyl-1H-1,2,3-triazol-5-yl)pyridin-3-amine (Preparation 193). Method 15. |
| 135 | N-(2-Methoxy-6-(2-methyl-2H-1,2,3-triazol-4-yl)pyridin-3-yl)formamide 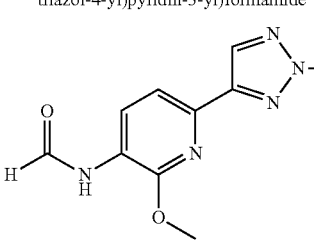 | ¹H NMR (500 MHz, CDCl₃): δ 8.67 (d, J = 8.1 Hz, 1H), 8.52 (s, 1H), 8.04 (s, 1H), 7.77 (br s, 1H), 7.53 (d, J = 8.1 Hz, 1H), 4.26 (s, 3H), 4.11 (s, 3H). LCMS (ESI) Rt = 2.06 minutes MS m/z 234 [M + H]⁺ Using 2-methoxy-6-(2-methyl-2H-1,2,3-triazol-4-yl)pyridin-3-amine (Preparation 194). Method 15. |

| Preparation No | Name/Structure | Data |
|---|---|---|
| 136 | N-(2-ethyl-4-(1-methyl-1H-pyrazol-4-yl)phenyl)formamide 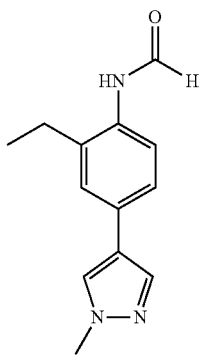 | $^1$H NMR (500 MHz, MeOD): δ 8.31 (s, 1H), 7.95 (s, 1H), 7.81 (s, 1H), 7.65 (d, J = 8.5 Hz, 1H), 7.45 (d, J = 2.0 Hz, 1H), 7.38 (dd, J = 8.5, 2.0 Hz, 1H), 3.98 (s, 3H), 2.68 (q, J = 7.5 Hz, 2H), 1.25 (t, J = 7.5 Hz, 3H).<br>LCMS (ESI) Rt = 1.87 minutes MS m/z 230 [M + H]$^+$<br>Using 2-ethyl-4-(1-methyl-1H-pyrazol-4-yl)aniline (Preparation 168) for 3 hours.<br>Method 13. |
| 137 | N-(4-(1-methyl-1H-pyrazol-4-yl)-2-(trifluoromethoxy)phenyl)formamide 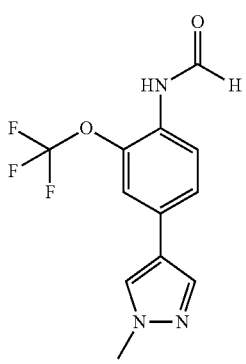 | $^1$H NMR (500 MHz, MeOD): δ 8.35 (s, 1H), 8.25 (d, J = 8.5 Hz, 1H), 8.01 (s, 1H), 7.84 (d, J = 0.5 Hz, 1H), 7.54 (dd, J = 8.5, 2.0 Hz, 1H), 3.94 (s, 3H).<br>LCMS (ESI) Rt = 2.09 minutes MS m/z 286 [M + H]$^+$<br>Using 4-(1-methyl-1H-pyrazol-4-yl)-2-(trifluoromethoxy)aniline (Preparation 169) for 1 hour.<br>Method 13. |
| 138 | N-(2-methoxy-4-(4-morpholinopiperidin-1-yl)phenyl)formamide 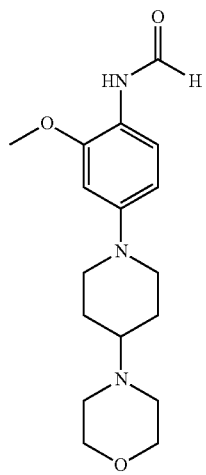 | $^1$H NMR (500 MHz, MeOD): δ 8.23 (s, 1H), 7.96 (d, J = 9.0 Hz, 1H), 6.61 (d, J = 2.5 Hz, 1H), 6.54 (dd, J = 9.0, 2.5 Hz, 1H), 3.89 (s, 3H), 3.76-3.72 (m, 6H), 2.71 (dt, J = 12.5, 2.0 Hz, 2H), 2.63 (app t, J = 5.0 Hz, 4H), 2.33 (m, 1H), 2.04 (br d, J = 12.5 Hz, 2H), 1.63 (qd, J = 12.5, 3.5 Hz, 2H).<br>LCMS (ESI) Rt = 0.64 minutes MS m/z 320 [M + H]$^+$<br>Using 2-methoxy-4-(4-morpholinopiperidin-1-yl)aniline (Preparation 170) for 3 hours.<br>Method 13. |

| Preparation No | Name/Structure | Data |
|---|---|---|
| 139 | N-(2-methoxy-4-(piperidin-1-yl)phenyl)formamide 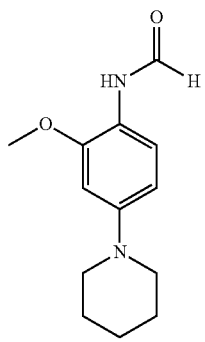 | $^1$H NMR (500 MHz, MeOD): δ 8.23 (s, 1H), 7.95 (d, J = 9.0 Hz, 1H), 6.65 (d, J = 3.0 Hz, 1H), 6.54 (dd, J = 9.0, 3.0 Hz, 1H), 3.89 (s, 3H), 3.15-3.12 (m, 4H), 1.73 (quin, J = 6.0 Hz, 4H), 1.63-1.58 (m, 2H). LCMS (ESI) Rt = 0.86 minutes MS m/z 235 [M + H]$^+$<br>Using 2-methoxy-4-(piperidin-1-yl)aniline (Preparation 171) for 3 hours.<br>Method 13. |
| 140 | N-(2-methoxy-4-(4-(morpholine-4-carbonyl)piperidin-1-yl)phenyl)formamide 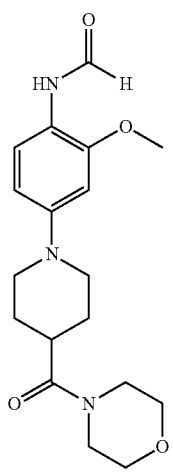 | $^1$H NMR (500 MHz, MeOD): δ 8.23 (s, 1H), 7.96 (d, J = 9.0 Hz, 1H), 6.67 (d, J = 2.5 Hz, 1H), 6.54 (dd, J = 9.0, 2.5 Hz, 1H), 3.89 (s, 3H), 3.73-3.69 (m, 4H), 3.68-3.64 (m, 4H), 3.62-3.59 (m, 2H), 2.81 (m, 1H), 2.77 (dd, J = 12.0, 2.5 Hz, 2H), 1.91-1.86 (m, 2H), 1.85-1.81 (m, 2H).<br>LCMS (ESI) Rt = 1.09 minutes MS m/z 348 [M + H]$^+$<br>Using (1-(4-amino-3-methoxyphenyl)piperidin-4-yl)(morpholino)methanone (Preparation 159) for 2 hours.<br>Method 13. |
| 141 | N-(2-methoxy-4-(4-methylpiperazin-1-yl)phenyl)formamide 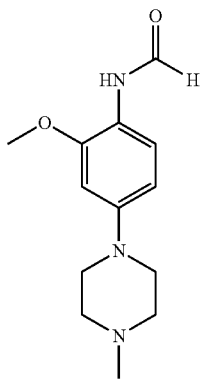 | $^1$H NMR (500 MHz, MeOD): δ 8.24 (s, 1H), 7.98 (d, J = 9.0 Hz, 1H), 6.66 (d, J = 2.5 Hz, 1H), 6.53 (dd, J = 9.0, 2.5 Hz, 1H), 3.89 (s, 3H), 3.22 (t, J = 5.5 Hz, 4H), 2.68 (app t, J = 5.5 Hz, 4H), 2.40 (s, 3H). LCMS (ESI) Rt = 0.50 minutes MS m/z 250 [M + H]$^+$<br>Using 2-methoxy-4-(4-methylpiperazin-1-yl)aniline (Preparation 160) for 2 hours.<br>Method 13. |

-continued

| Preparation No | Name/Structure | Data |
|---|---|---|
| 142 | N-(2-chloro-4-morpholinophenyl)formamide 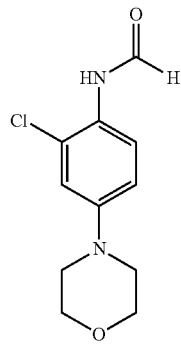 | $^1$H NMR (500 MHz, MeOD): δ 8.29 (s, 1H), 7.87 (d, J = 9.0 Hz, 1H), 7.03 (d, J = 3.0 Hz, 1H), 6.93 (dd, J = 9.0, 3.0 Hz, 1H), 3.84-3.81 (m, 4H), 3.15-3.13 (m, 4H). LCMS (ESI) Rt = 1.74 minutes MS m/z 241 [M + H]$^+$ Using 2-chloro-4-morpholinoaniline (Preparation 161). Method 13. |
| 143 | N-(2-methoxy-4-(4-(methylsulfonyl)piperazin-1-yl)phenyl)formamide 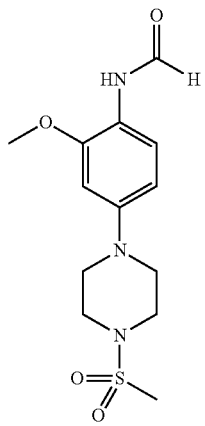 | $^1$H NMR (500 MHz, MeOD): δ 8.23 (s, 1H), 8.00 (d, J = 9.0 Hz, 1H), 6.69 (d, J = 2.5 Hz, 1H), 6.56 (dd, J = 9.0, 2.5 Hz, 1H), 3.90 (s, 3H), 3.38-3.36 (m, 4H), 3.28-3.26 (m, 4H), 2.90 (s, 3H). LCMS (ESI) Rt = 1.57 minutes MS m/z 314 [M + H]$^+$ Using 2-methoxy-4-(4-(methylsulfonyl)piperazin-1-yl)aniline (Preparation 162). Method 13. |
| 144 | N-(2-methoxy-4-(1-(2-methoxyethyl)-2-methyl-1H-pyrazol-5-yl)phenyl)formamide 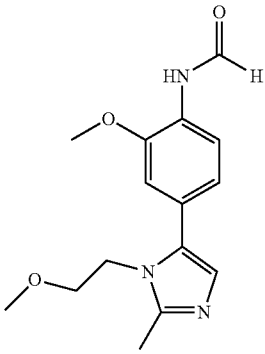 | $^1$H NMR (500 MHz, MeOD): δ 8.37 (s, 1H), 8.30 (d, J = 8.5 Hz, 1H), 7.14 (d, J = 1.5 Hz, 1H), 7.00 (dd, J = 8.5, 1.5 Hz, 1H), 6.86 (s, 1H), 4.19 (t, J = 5.5 Hz, 2H), 3.95 (s, 3H), 3.48 (t, J = 5.5 Hz, 2H), 3.23 (s, 3H), 2.46 (s, 3H). LCMS (ESI) Rt = 1.16 minutes MS m/z 290 [M + H]$^+$ Using 2-methoxy-4-(1-(2-methoxyethyl)-2-methyl-1H-imidazol-5-yl)aniline (Preparation 164) for 1 hour. Method 13. |

| Preparation No | Name/Structure | Data |
|---|---|---|
| 145 | (4-(4-formamido-3-methoxyphenyl)-1-methyl-1H-pyrazol-5-yl)methyl formate 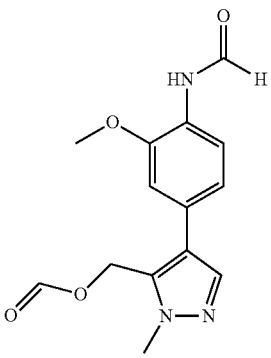 | $^1$H NMR (500 MHz, MeOD): δ 8.34 (s, 1H), 8.25 (d, J = 8.0 Hz, 1H), 7.66 (s, 1H), 7.10 (d, J = 2.0 Hz, 1H), 7.00 (dd, J = 8.0, 2.0 Hz, 1H), 3.98 (s, 3H), 3.95 (s, 3H). LCMS (ESI) Rt = 1.95 minutes MS m/z 290 [M + H]$^+$ Using (4-(4-amino-3-methoxyphenyl)-1-methyl-1H-pyrazol-5-yl)methanol (Preparation 165). Method 13. |
| 146 | 4-formamido-3-methoxy-N,N-dimethylbenzamide 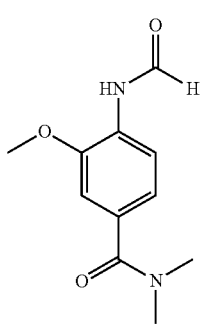 | $^1$H NMR (500 MHz, MeOD): δ 8.37 (s, 1H), 8.32 (d, J = 8.0 Hz, 1H), 7.11 (d, J = 2.0 Hz, 1H), 7.02 (dd, J = 8.0, 2.0 Hz, 1H), 3.95 (s, 3H), 3.08 (s, 6H). LCMS (ESI) Rt = 1.50 minutes MS m/z 223 [M + H]$^+$ Using 4-amino-3-methoxy-N,N-dimethylbenzamide (Preparation 24) for 3 hours. Method 13. |
| 147 | N-(2-methoxy-4-(4-methylpiperazine-1-carbonyl)phenyl)formamide 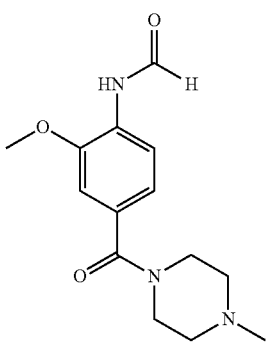 | $^1$H NMR (500 MHz, MeOD): δ 8.37 (s, 1H), 8.34 (d, J = 8.5 Hz, 1H), 7.10 (d, J = 1.5 Hz, 1H), 7.01 (dd, J = 8.5, 1.5 Hz, 1H), 3.96 (s, 3H), 3.70-3.67 (m, 2H), 2.51-2.48 (m, 2H), 2.35 (s, 3H). LCMS (ESI) Rt = 0.51 minutes MS m/z 278 [M + H]$^+$ Using (4-amino-3-methoxyphenyl)(4-methylpiperazin-1-yl)methanone (Preparation 211) for 3 hours. Method 13. |
| 148 | N-(4-Cyano-2-methoxyphenyl)formamide 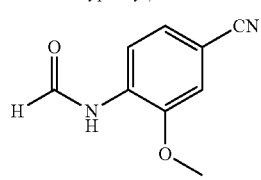 | $^1$H NMR (500 MHz, DMSO-d$_6$): δ 10.07 (s, 1H), 8.39 (s, 1H), 8.37 (s, 1H), 7.52 (d, J = 1.7 Hz, 1H), 7.4 (dd, J = 8.4, 1.8 Hz, 1H), 3.92 (s, 3H). LCMS (ESI) Rt = 1.76 minutes MS m/z 177 [M + H]$^+$ Using 4-amino-3-methoxybenzonitrile. Method 15. |

| Preparation No | Name/Structure | Data |
|---|---|---|
| 149 | N-(2-(difluoromethoxy)-4-(1-methyl-1H-pyrazol-4-yl)phenyl)formamide 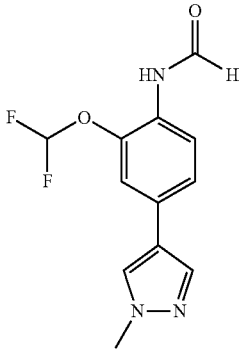 | ¹H NMR (500 MHz, MeOD): 8.34 (s, 1H), 8.24 (d, J = 8.0 Hz, 1H), 7.99 (s, 1H), 7.83 (s, 1H), 7.43-7.40 (m, 2H), 3.96 (d, J = 3.5 Hz, 1H), 3.94 (s, 3H).<br>LCMS (ESI) Rt = 1.99 minutes MS m/z 268 [M + H]⁺<br>Using 2-(difluoromethoxy)-4-(1-methyl-1H-pyrazol-4-yl)aniline (Preparation 213). Method 13. |
| 150 | N-(2-ethoxy-4-(4-methyl-4H-1,2,4-triazol-3-yl)phenyl)formamide 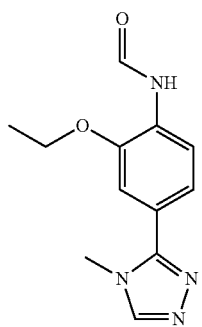 | ¹H NMR (500 MHz, Acetone-d6): δ 9.22 (br s, 1H), 8.55 (d, J = 8.5 Hz, 1H), 8.52 (s, 1H), 8.36 (s, 1H), 7.41 (d, J = 1.5 Hz, 1H), 7.31 (dd, J = 8.5, 1.5 Hz, 1H), 4.25 (q, J = 7.0 Hz, 2H), 3.88 (s, 3H), 1.45 (t, J = 7.0 Hz, 3H).<br>LCMS (ESI) Rt = 1.29 minutes MS m/z 247 [M + H]⁺<br>Using 2-ethoxy-4-(4-methyl-4H-1,2,4-triazol-3-yl)aniline (Preparation 216) for 30 minutes.<br>Method 13. |
| 151 | N-(4-chloro-2-(difluoromethoxy)phenyl)formamide 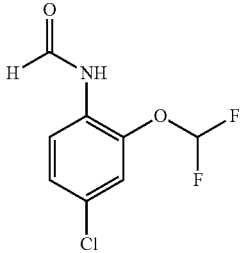 | ¹H NMR (500 MHz, d6-DMSO): δ 10.01(s, 1H), 8.32 (d, J = 1.5 Hz, 1H), 8.24 (d, J = 8.8 Hz, 1H), 7.37 (d, J = 2 Hz, 1H), 7.31 (dd, J = 8.8, 2.2 Hz, 1H), 7.14 (t, J = 73 Hz, 1H).<br>LCMS (ESI) Rt = 2.12 minutes MS m/z 222 [M + H]⁺<br>Using 4-chloro-2-(difluoromethoxy)aniline. Method 13. |
| 152 | N-(2-(difluoromethoxy)-4-fluorophenyl)formamide 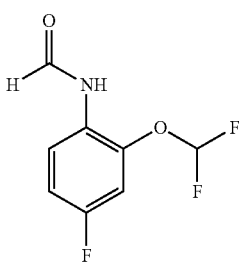 | ¹H NMR (500 MHz, d6-DMSO): δ 9.91(s, 1H), 8.29 (d, J = 1.7 Hz, 1H), 8.14 (dd, J = 9.1, 6.2 Hz, 1H), 7.27 (t, J = 70 Hz, 1H), 7.21 (dd, J = 9.6, 2.8 Hz, 1H), 7.12 (m, 1H).<br>LCMS (ESI) Rt = 2.04 minutes MS m/z 206 [M + H]⁺<br>Using 2-(difluoromethoxy)-4-fluoroaniline. Method 13. |

| Preparation No | Name/Structure | Data |
|---|---|---|
| 153 | N-(2,4-Dichlorophenyl)formamide | $^1$H NMR (500 MHz, CDCl$_3$): δ 8.51 (s, 1H), 8.39 (d, J = 8.9 Hz, 1H), 7.67 (s, 1H), 7.42 (s, 1H), 7.24 (d, J = 8.9 Hz, 1H). LCMS (ESI) Rt = 1.84 minutes MS m/z 190 [M + H]$^+$ Using 2,4-dichloroaniline. Method 13. |

Preparation 154: N-(2-methoxy-4-(tetrahydro-2H-pyran-4-yl)phenyl)formamide

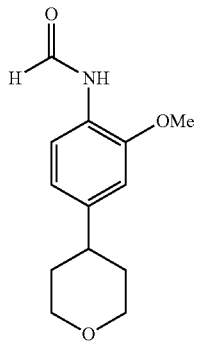 [SMILES: COc1cc(C2CCOCC2)ccc1NC=O]

A solution of 4-(3,6-dihydro-2H-pyran-4-yl)-2-methoxyaniline (Preparation 156, 206 mg, 1.004 mmol) in EtOH (10 mL) was treated with Pd/C (10% w/w, 50 mg, 0.047 mmol) and stirred in an atmosphere of hydrogen for 36 hours. The suspension was filtered over celite and concentrated in vacuo. The residue was dissolved in formic acid (6 mL) and heated to reflux for 2 hours. The solution was concentrated in vacuo and azeotroped with toluene twice. The residue was purified by silica gel column chromatography eluting with 0 to 30% EtOAc in cyclohexanes to give the title compound (165 mg, 70%).

$^1$H NMR (500 MHz, DMSO-d$_6$): δ 9.56 (s, 1H), 8.27 (d, J=1.9 Hz, 1H), 8.04 (d, J=8.2 Hz, 1H), 6.94 (d, J=1.8 Hz, 1H), 6.79 (dd, J=8.2, 1.8 Hz, 1H), 3.95 (dt, J=11.1, 3.1 Hz, 2H), 3.86 (s, 3H), 3.42 (ddd, J=11.3, 8.6, 5.5 Hz, 2H), 2.80-2.67 (m, 1H), 1.78-1.57 (m, 4H).

LCMS (ESI) Rt=2.09 minutes MS m/z 236 [M+H]$^+$

The following Preparations were prepared according to Preparation 66 using the appropriate halo aniline and boronic acid or ester as described below. The crude reaction residues were purified as described or according to one of the following methods:
Method A: Silica gel column chromatography eluting with
Method B: Silica gel column chromatography eluting with

| Preparation No | Name/Structure | Data |
|---|---|---|
| 155 | 4-(1-ethyl-1H-pyrazol-4-yl)-2-methoxyaniline | $^1$H NMR (500 MHz, CDCl$_3$): δ 7.71 (d, J = 0.9 Hz, 1H), 7.57 (d, J = 0.8 Hz, 1H), 6.94 (dd, J = 7.9, 1.8 Hz, 1H), 6.92 (d, J = 1.8 Hz, 1H), 6.74 (d, J = 7.9 Hz, 1H), 4.22 (q, J = 7.3 Hz, 2H), 3.92 (s, 3H), 3.80 (br.s, 2H), 1.55 (t, J = 7.3 Hz, 3H). LCMS (ESI) Rt = 1.28 minutes MS m/z 218 [M + H]$^+$ Using 4-bromo-2-methoxyaniline and 1-ethyl-4-(4,4,5,5-tetramethyl-1,3,2-dioxaborolan-2-yl)-1H-pyrazole. |
| 156 | 4-(3,6-dihydro-2H-pyran-4-yl)-2-methoxyaniline | $^1$H NMR (500 MHz, DMSO-d6): δ 6.89 (d, J = 1.9 Hz, 1H), 6.78 (dd, J = 8.1, 1.9 Hz, 1H), 6.59 (d, J = 8.1 Hz, 1H), 6.03 (p, J = 1.6 Hz, 1H), 4.77 (s, 2H), 4.19 (q, J = 2.7 Hz, 2H), 3.85-3.73 (m, 5H), 2.42-2.33 (m, 2H). LCMS (ESI) Rt = 1.28 minutes MS m/z 206 [M + H]$^+$ Using 2-(3,6-dihydro-2H-pyran-4-yl)-4,4,5,5-tetramethyl-1,3,2-dioxaborolane and 4-bromo-2-methoxyaniline. |

Preparation 157: 2-Chloro-4-(5-methyl-1,3,4-oxadiazol-2-yl)aniline

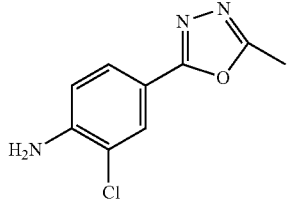

To a mixture of 4-(5-methyl-1,3,4-oxadiazol-2-yl)aniline (0.220 g, 1.26 mmol) and anhydrous DMF (1.9 mL) was added N-chlorosuccinimide (0.168 g, 1.26 mmol). The reaction mixture was heated at 40° C. for 1.5 hours under argon before cooling to room temperature and partitioning between EtOAc (90 mL) and saturated aqueous NaHCO$_3$ (15 mL). The organic layer was washed with saturated aqueous NaHCO$_3$ (15 mL), dried (Na$_2$SO$_4$) and concentrated in vacuo. The residue was absorbed on silica gel (1.4 g) and purified using silica gel column chromatography eluting with 0-30% EtOAc in DCM to afford the title compound (0.130 g, 49%).

$^1$H NMR (500 MHz, DMSO-d$_6$): δ 7.72 (d, J=2.0 Hz, 1H), 7.61 (dd, J=2.0, 8.5 Hz, 1H), 6.90 (d, J=8.2 Hz, 1H), 6.14 (s, 2H), 2.53 (s, 3H).

LCMS (ESI) Rt=2.06 minutes MS m/z 210 [M$^{35}$Cl+H]$^+$

Preparation 158: 2-Methoxy-6-(1-methyl-1H-tetrazol-5H)pyridin-3-amine

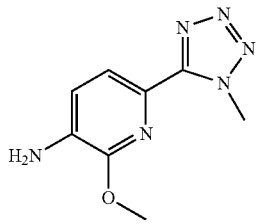

10% Pd on carbon (10 mg, 0.411 mmol) was added to a solution of 2-methoxy-6-(1-methyl-1H-tetrazol-5-yl)-3-nitropyridine (Preparation 189, 97 mg, 0.411 mmol) in EtOH/DCM 2/1 (2.7 mL). The reaction mixture was stirred at room temperature under a hydrogen atmosphere for 2 hours. The reaction was filtered and the filtrate was concentrated under reduced pressure to afford the title product as a white solid (84 mg, 99%).

$^1$H NMR (500 MHz, CD$_3$OD): δ 7.67 (d, J=8.0 Hz, 1H); 7.03 (d, J=8.0 Hz, 1H), 4.48 (s, 3H), 4.07 (s, 3H).

LCMS (ESI) Rt=2.08 minutes MS m/z 207 [M+H]$^+$

Preparation 159: (1-(4-amino-3-methoxyphenyl)piperidin-4-yl)(morpholino)methanone

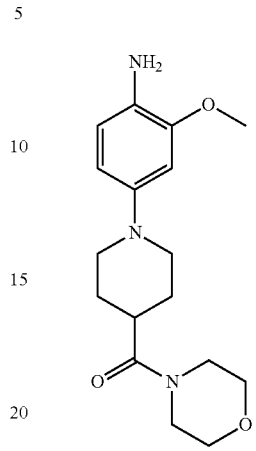

The title compound was prepared according to the method described for Preparation 158 using (1-(3-methoxy-4-nitrophenyl)piperidin-4-yl)(morpholino)methanone (Preparation 204) at 30° C.

$^1$H NMR (500 MHz, MeOD): 6.71 (d, J=9.0 Hz, 1H), 6.63 (d, J=2.5 Hz, 1H), 6.48 (dd, J=9.0, 2.5 Hz, 1H), 3.85 (s, 3H), 3.71-3.59 (m, 8H), 3.50 (br d, J=12.5 Hz, 2H), 2.76 (m, 1H), 2.70 (dt, J=12.5, 2.5 Hz, 2H), 1.92 (dq, J=12.5, 2.5 Hz, 2H), 1.82 (br d, J=12.5 Hz, 2H).

LCMS (ESI) Rt=0.81 minutes MS m/z 320 [M+H]$^+$

Preparation 160: 2-methoxy-4-(4-methylpiperazin-1-yl)aniline

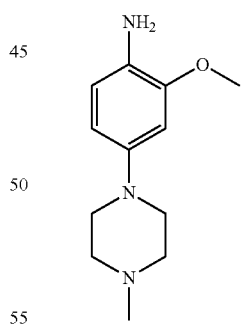

The title compound was prepared according to the method described for Preparation 158 using 1-(3-methoxy-4-nitrophenyl)-4-methylpiperazine (Preparation 206).

$^1$H NMR (500 MHz, MeOD): δ 6.72 (d, J=8.5 Hz, 1H), 6.61 (d, J=2.5 Hz, 1H), 6.46 (dd, J=8.5, 2.5 Hz, 1H), 3.85 (s, 3H), 3.08 (br t, J=5.0 Hz, 4H), 2.63 (br t, J=5.0 Hz, 4H), 2.36 (s, 3H).

LCMS (ESI) Rt=0.24 minutes MS m/z 222 [M+H]$^+$

Preparation 161: 2-chloro-4-morpholinoaniline

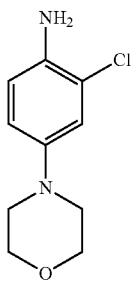

The title compound was prepared according to the method described for Preparation 158 using 4-(3-chloro-4-nitrophenyl)morpholine (Preparation 207). The residue was purified using reverse phase chromatography eluting with 0-20% MeCN in water.

$^1$H NMR (500 MHz, MeOD): δ 6.90 (dd, J=2.5, 0.5 Hz, 1H), 6.83-6.79 (m, 2H), 3.82-3.80 (m, 4H), 3.00-2.98 (m, 4H).

LCMS (ESI) Rt=1.13 minutes MS m/z 213 [M+H]$^+$

Preparation 162: 2-methoxy-4-(4-(methylsulfonyl)piperazin-1-yl)aniline

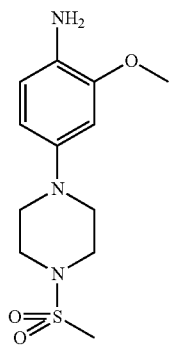

The title compound was prepared according to the method described for Preparation 158 using 1-(3-methoxy-4-nitrophenyl)-4-(methylsulfonyl)piperazine (Preparation 208).

$^1$H NMR (500 MHz, MeOD): δ 6.72 (d, J=8.0 Hz, 1H), 6.63 (d, J=2.0 Hz, 1H), 6.47 (dd, J=8.0, 2.0 Hz, 1H), 3.86 (s, 3H), 3.37-3.35 (m, 4H), 3.14-3.12 (m, 4H), 2.89 (s, 3H).

LCMS (ESI) Rt=0.67 minutes MS m/z 286.31 [M+H]$^+$

Preparation 163: 6-(1,3-Dimethyl-1H-pyrazol-4-yl)-2-methoxypyridin-3-amine

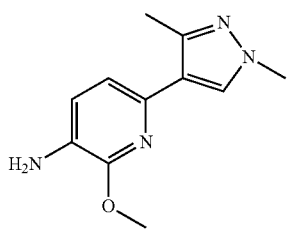 [SMILES: COc1nc(-c2cn(C)nc2C)ccc1N]

Tetrakis(triphenylphosphine)palladium (0.085 g, 0.074 mmol) was added to a solution of 6-bromo-2-methoxypyridin-3-amine (0.15 g, 0.739 mmol), 1,3-dimethyl-4-(4,4,5,5-tetramethyl-1,3,2-dioxaborolan-2-yl)-1H-pyrazole (0.180 g, 0.813 mmol) and cesium fluoride (0.337 g, 2.216 mmol) in DME/MeOH 2/1 (4.6 mL). The reaction mixture was heated under microwave irradiation at 150° C. for 10 minutes. The reaction was concentrated in vacuo. The residue was purified via Biotage silica gel column chromatography eluting with DCM/EtOH (99/1 to 90/10, 12 g column) and then eluted through an SCX-2 column to afford the title product as a yellow solid (120 mg, 74%).

$^1$H NMR (500 MHz, CD$_3$OD): δ 7.79 (s, 1H), 6.97 (d, J=7.7 Hz, 1H), 6.90 (d, J=7.7 Hz, 1H), 4.00 (s, 3H), 3.82 (s, 3H), 1.50 (s, 3H).

LCMS (ESI) Rt=2.19 minutes MS m/z 219 [M+H]$^+$

Preparation 164: 2-methoxy-4-(1-(2-methoxyethyl)-2-methyl-1H-imidazol-5-yl)aniline

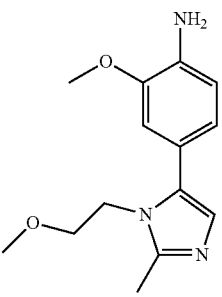 [SMILES: COCCn1c(-c2ccc(N)c(OC)c2)cnc1C]

The title compound was prepared according to the method described for Preparation 158 using 2-methoxy-4-(4,4,5,5-tetramethyl-1,3,2-dioxaborolan-2-yl)aniline and 5-bromo-1-(2-methoxyethyl)-2-methyl-1H-imidazole (Preparation 209).

$^1$H NMR (500 MHz, MeOD): δ 6.90 (d, J=1.5 Hz, 1H), 6.81 (d, J=8.0 Hz, 1H), 6.78 (dd, J=8.0, 1.5 Hz, 1H), 6.75 (s, 1H), 4.13 (t, J=5.5 Hz, 2H), 3.88 (s, 3H), 3.45 (t, J=5.5 Hz, 2H), 3.22 (s, 3H), 2.44 (s, 3H).

LCMS (ESI) Rt=1.02 minutes MS m/z 262.27 [M+H]$^+$

Preparation 165: (4-(4-Amino-3-methoxyphenyl)-1-methyl-1H-pyrazol-5-yl)methanol

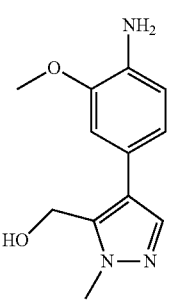

The title compound was prepared according to the method described for Preparation 158 using (4-bromo-1-methyl-1H-pyrazol-5-yl)methanol (Preparation 222) and 2-methoxy-4-(4,4,5,5-tetramethyl-1,3,2-dioxaborolan-2-yl)aniline. The residue was purified using Biotage silica gel column chromatography eluting with EtOAc followed by elution through an SCX-2 cartridge.

Preparation 166: 2-methoxy-4-(1-methyl-1H-1,2,4-triazol-5-yl)aniline

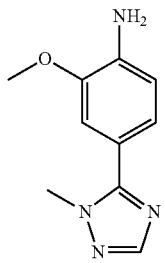

The title compound was prepared according to the method described for Preparation 158 using 5-bromo-1-methyl-1H-1,2,4-triazole and 2-methoxy-4-(4,4,5,5-tetramethyl-1,3,2-dioxaborolan-2-yl)aniline. The residue was purified using Biotage silica gel column chromatography eluting with EtOAc.

¹H NMR (500 MHz, CDCl₃): δ 7.88 (s, 1H), 7.18 (d, J=1.86 Hz, 1H), 7.04 (dd, J=1.86, 8.02 Hz, 1H), 6.76 (d, J=8.02 Hz, 1H), 3.98 (s, 3H), 3.90 (s, 3H).
LCMS (ESI) Rt=1.25 minutes MS m/z 205 [M+H]⁺

Preparation 167: 6-(1,5-Dimethyl-1H-pyrazol-4-yl)-2-methoxypyridin-3-amine

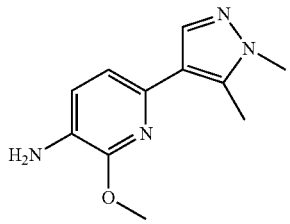 [SMILES: COc1nc(-c2cnn(C)c2C)ccc1N]

The title compound was prepared according to the method described for Preparation 158 using 6-bromo-2-methoxypyridin-3-amine and 1,5-dimethyl-4-(4,4,5,5-tetramethyl-1,3,2-dioxaborolan-2-yl)-1H-pyrazole. The crude residue was purified using silica gel column chromatography eluting with 1-10% MeOH/aqueous ammonia (10/1) in DCM.

¹H NMR (500 MHz, CD₃OD): δ 7.69 (s, 1H), 7.00 (d, J=7.7 Hz, 1H), 6.95 (d, J=7.7 Hz, 1H), 4.01 (s, 3H), 3.81 (s, 3H), 2.64 (s, 3H).
LCMS (ESI) Rt=2.24 minutes MS m/z 219 [M+H]⁺

Preparation 168: 2-ethyl-4-(1-methyl-1H-pyrazol-4-yl)aniline

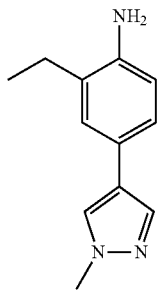

The title compound was prepared according to the method described for Preparation 98 using 4-bromo-2-ethylaniline and 1-methylpyrazole-4-boronic acid pinacol ester.

¹H NMR (500 MHz, MeOD): δ 7.76 (s, 1H), 7.66 (s, 1H), 7.20 (d, J=2.0 Hz, 1H), 7.15 (dd, J=8.0, 2.0 Hz, 1H), 6.73 (d, J=8.0 Hz, 1H), 3.89 (s, 3H), 2.57 (q, J=7.5 Hz, 2H), 1.25 (t, J=7.5 Hz, 3H).
LCMS (ESI) Rt=1.24 minutes MS m/z 202 [M+H]⁺

Preparation 169: 4-(1-methyl-1H-pyrazol-4-yl)-2-(trifluoromethoxy)aniline

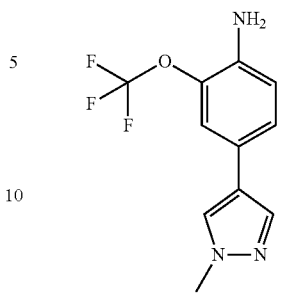

The title compound was prepared according to the method described for Preparation 98 using 2-trifluoromethoxy-4-bromoaniline and 1-methylpyrazole-4-boronic acid pinacol ester.

¹H NMR (500 MHz, MeOD): δ 7.82 (s, 1H), 7.69 (s, 1H), 7.28-7.26 (m, 2H), 6.87 (d, J=9.0 Hz, 1H), 3.90 (s, 3H).
LCMS (ESI) Rt=2.16 minutes MS m/z 258 [M+H]⁺

Preparation 170: 2-methoxy-4-(4-morpholinopiperidin-1-yl)aniline

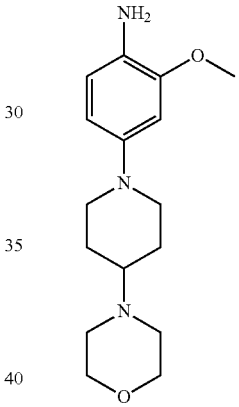

The title compound was prepared according to the method described for Preparation 79 using 4-(1-(3-methoxy-4-nitrophenyl)piperidin-4-yl)morpholine (Preparation 202). The residue was purified using reverse phase chromatography eluting with 100% water.

¹H NMR (500 MHz, MeOD): δ 6.71 (d, J=8.5 Hz, 1H), 6.63 (d, J=2.5 Hz, 1H), 6.48 (dd, J=8.5, 2.5 Hz, 1H), 3.85 (3H, s), 3.73 (t, J=5.0 Hz, 4H), 3.53 (br d, J=12.5 Hz, 2H), 2.67-2.62 (m, 6H), 2.31 (m, 1H), 2.03 (br d, J=12.5 Hz, 2H), 1.67 (qd, J=12.5, 4.0 Hz, 2H).
LCMS (ESI) Rt=0.25 minutes MS m/z not observed.

Preparation 171: 2-methoxy-4-(piperidin-1-yl)aniline

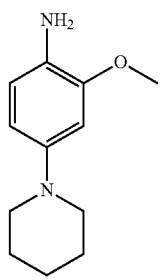

The title compound was prepared according to the method described for Preparation 79 using 1-(3-methoxy-4-nitrophenyl)piperidine (Preparation 203). The residue was purified using reverse phase chromatography eluting with 100% water.

$^{1}$H NMR (500 MHz, MeOD): δ 6.71 (d, J=8.5 Hz, 1H), 6.63 (s, 1H), 6.49 (d, J=8.5 Hz, 1H), 3.85 (s, 3H), 2.99 (app br s, 4H), 1.75 (quin, J=5.5 Hz, 4H), 1.60-1.54 (m, 2H).

LCMS (ESI) Rt=0.55 minutes MS m/z 207 [M+H]$^{+}$

Preparation 172: N-(2-methoxy-2-methylpropyl)-6-methyl-2-(methylsulfonyl)pyrido[3,4-d]pyrimidin-8-amine

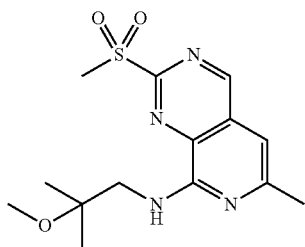

To a cooled (0° C.) solution of N-(2-methoxy-2-methylpropyl)-6-methyl-2-(methylthio)pyrido[3,4-d]pyrimidin-8-amine (Preparation 175, 63 mg, 0.215 mmol) in DCM (10 mL) was added mCPBA (116 mg, 0.517 mmol). The reaction mixture was stirred for 18 hours, whilst slowly warming to room temperature. Further mCPBA (50 mg, 0.223 mmol) was added and the reaction mixture stirred at room temperature for a further 2 hours. The reaction mixture was diluted with DCM (30 mL), washed with saturated aqueous NaHCO$_3$ (30 mL), brine (30 mL), dried (MgSO$_4$) and concentrated in vacuo. The residue was purified by silica gel column chromatography eluting with 50-100% EtOAc in cyclohexanes to afford the title compound (29 mg, 41%).

$^{1}$H NMR (500 MHz, MeOD): δ 9.41 (s, 1H), 6.94 (d, J=0.5 Hz, 1H), 3.76 (s, 2H), 3.46 (s, 3H), 3.33 (s, 3H), 2.53 (d, J=0.5 Hz, 3H), 1.29 (s, 6H).

LCMS (ESI) Rt=1.94 minutes MS m/z 325 [M+H]$^{+}$

Preparation 173: N-(2-Methoxy-2-methylpropyl)-2-(methylsulfonyl)pyrido[3,4-d]pyrimidin-8-amine

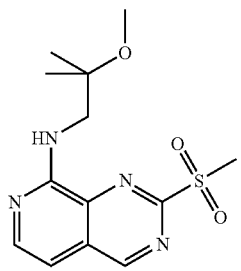 [SMILES: COC(C)(C)CNc1nccc2cnc(S(C)(=O)=O)nc12]

N-(2-Methoxy-2-methylpropyl)-2-(methylthio)pyrido[3,4-d]pyrimidin-8-amine (Preparation 176, 220 mg, 0.79 mmol) was dissolved in dichloromethane (10 mL). To the stirred solution was added portionwise 3-chlorobenzoperoxoic acid (75%, 370 mg, 1.58 mmol). After 1 hour, ethyl acetate was added (50 mL) and the organic solution was washed with saturated sodium bicarbonate (20 mL), brine (20 mL), dried and concentrated in vacuo. The crude was purified by silica gel column chromatography eluting with 20% hexane in ethyl acetate to afford the title compound as a yellow powder (180 mg, 73%).

$^{1}$H NMR (500 MHz, CDCl$_3$): δ 9.37 (s, 1H), 8.25 (d, J=5.8 Hz, 1H), 7.15 (br s, 1H), 6.93 (d, J=5.8 Hz, 1H), 3.71 (d, J=5.7 Hz, 2H), 3.44 (s, 3H), 3.29 (s, 3H), 1.28 (s, 6H).

LCMS (ESI) Rt=1.68 minutes MS m/z 311 [M+H]$^{+}$

Preparation 174: 2-(methylsulfonyl)-N-((3-methyltetrahydrofuran-3-yl)methyl)pyrido[3,4-d]pyrimidin-8-amine

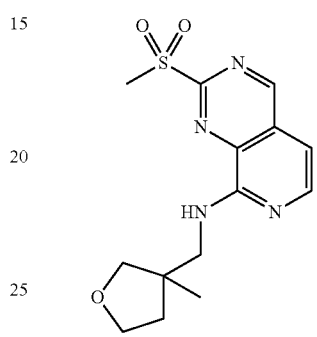

The title compound was prepared according to the method described for Preparation 172 using N-((3-methyltetrahydrofuran-3-yl)methyl)-2-(methylthio)pyrido[3,4-d]pyrimidin-8-amine (Preparation 177). The residue was purified using silica gel column chromatography eluting with 0-3% MeOH in EtOAc.

$^{1}$H NMR (500 MHz, MeOD): δ 9.54 (s, 1H), 8.23 (d, J=5.5 Hz, 1H), 7.09 (d, J=5.5 Hz, 1H), 3.99 (td, J=8.5, 6.5 Hz, 1H), 3.90 (td, J=8.5, 6.5 Hz, 1H), 3.84 (d, J=8.5 Hz, 1H), 3.77 (d, J=13.5 Hz, 1H), 3.71 (d, J=13.5 Hz, 1H), 3.49 (s, 3H), 3.47 (d, J=8.5 Hz, 1H), 2.06 (m, 1H), 1.75 (m, 1H), 1.24 (s, 3H).

LCMS (ESI) Rt=1.75 minutes MS m/z 323 [M+H]$^{+}$

Preparation 175: N-(2-methoxy-2-methylpropyl)-6-methyl-2-(methylthio)pyrido[3,4-d]pyrimidin-8-amine

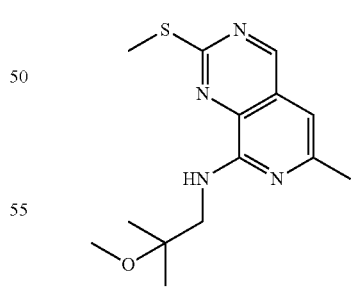

To a solution of 8-chloro-6-methyl-2-(methylthio)pyrido[3,4-d]pyrimidine (Preparation 52, 80 mg, 0.354 mmol) in NMP (7 mL) was added 2-methoxy-2-methylpropan-1-amine (0.086 ml, 0.709 mmol) and triethylamine (0.249 mL, 1.772 mmol). The reaction mixture was heated to 120° C. for 18 hours. The reaction mixture was diluted with EtOAc (30 mL), washed with water (30 mL), dried (MgSO$_4$) and concentrated in vacuo. The residue was purified by silica gel column chromatography eluting with 0-50% EtOAc in cyclohexane to afford the title compound (63 mg, 61%).

$^1$H NMR (500 MHz, MeOD): δ 9.03 (s, 1H), 6.75 (d, J=0.5 Hz, 1H), 3.66 (s, 2H), 3.32 (s, 3H), 2.65 (s, 3H), 2.45 (d, J=0.5 Hz, 3H), 1.29 (s, 6H).

LCMS (ESI) Rt=2.10 minutes MS m/z 293 [M+H]$^+$

Preparation 176: N-(2-Methoxy-2-methylpropyl)-2-(methylthio)pyrido[3,4-d]pyrimidin-8-amine

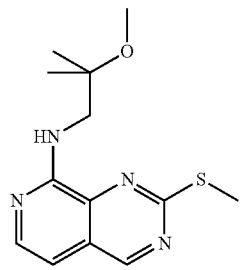 [SMILES: COC(C)(C)CNc1nccc2cnc(SC)nc12]

The title compound was prepared according to the method described for Preparation 175 using 2-methoxy-2-methylpropan-1-amine and 8-chloro-2-(methylthio)pyrido[3,4-d]pyrimidine (Preparation 33). The residue was purified by elution through an SCX-2 column using 50% methanol in chloroform followed by 50% chloroform in 7N NH$_3$/MeOH followed by silica gel column chromatography eluting with EtOAc.

$^1$H NMR (500 MHz, CDCl$_3$): δ 8.99 (s, 1H), 7.97 (d, J=5.8 Hz, 1H), 6.95 (br s, 1H), 6.75 (d, J=5.8 Hz, 1H), 3.63 (d, J=5.5 Hz, 1H), 3.29 (s, 3H), 2.64 (s, 3H), 1.28 (s, 6H).

LCMS (ESI) Rt=2.01 minutes MS m/z 279 [M+H]$^+$

Preparation 177: N-((3-methyltetrahydrofuran-3-yl)methyl)-2-(methylthio)pyrido[3,4-d]pyrimidin-8-amine

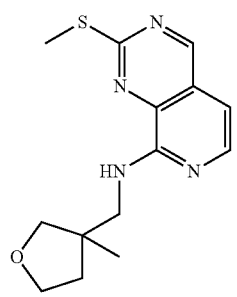 [SMILES: CSc1ncc2ccnc(NCC3(C)CCOC3)c2n1]

The title compound was prepared according to the method described for Preparation 175 using of 8-chloro-2-(methylthio)pyrido[3,4-d]pyrimidine (Preparation 33) and (3-methyltetrahydrofuran-3-yl)methanamine at 130° C.

$^1$H NMR (500 MHz, MeOD): δ 9.13 (s, 1H), 7.92 (d, J=6.0 Hz, 1H), 6.93 (d, J=6.0 Hz, 1H), 4.01 (dt, J=8.5, 5.5 Hz, 1H), 3.89 (dt, J=8.5, 7.0 Hz, 1H), 3.84 (d, J=8.5 Hz, 1H), 3.65 (q, J=13.0 Hz, 2H), 3.48 (d, J=8.5 Hz, 1H), 2.68 (s, 3H), 2.04 (m, 1H), 1.78 (m, 1H), 1.25 (s, 3H).

LCMS (ESI) Rt=1.89 minutes MS m/z 291 [M+H]$^+$

Preparation 178: 8-chloro-6-methyl-2-(methylsulfonyl)pyrido[3,4-d]pyrimidine

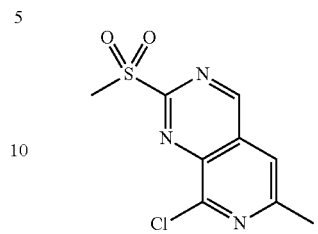

The title compound was prepared according to the method described for Preparation 172 using 8-chloro-6-methyl-2-(methylthio)pyrido[3,4-d]pyrimidine (Preparation 52). The residue was purified using silica gel column chromatography eluting with 0-100% EtOAc in cyclohexanes.

$^1$H NMR (500 MHz, acetone-d6): δ 9.91 (s, 1H), 8.07 (d, J=1.0 Hz, 1H), 3.52 (s, 3H), 2.77 (d, J=1.0 Hz, 3H).

LCMS (ESI) Rt=1.52 minutes MS m/z 258 [M+H]$^+$

Preparation 179: 8-Chloro-6-cyclopropyl-2-(methylsulfonyl)pyrido[3,4-d]pyrimidine

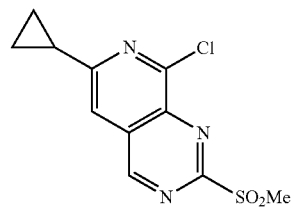 [SMILES: CS(=O)(=O)c1ncc2cc(C3CC3)nc(Cl)c2n1]

The title compound was prepared according to the method described for Preparation 172 using 8-Chloro-6-cyclopropyl-2-(methylthio)pyrido[3,4-d]pyrimidine (Preparation 180). The residue was purified using preparative TLC eluting with 2:3 EtOAc:DCM.

$^1$H NMR (500 MHz, acetone-d$_6$): δ 8.10 (s, 1H), 3.50 (s, 3H), 2.42 (m, 1H), 1.13-1.22 (m, 4H).

Preparation 180: 8-Chloro-6-cyclopropyl-2-(methylthio)pyrido[3,4-d]pyrimidine

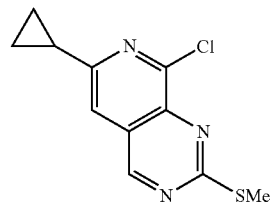 [SMILES: CSc1ncc2cc(C3CC3)nc(Cl)c2n1]

6-Cyclopropyl-2-(methylthio)pyrido[3,4-d]pyrimidin-8 (7H)-one (Preparation 181, 180 mg 0.77 mmole) was stirred with phosphorus oxychloride (6 mL) and the reaction was heated at 70° C. for 2 hours before concentrating in vacuo. Ethyl acetate (20 mL) was added to the residue and the solution was cooled in ice. A little ice and then sodium bicarbonate solution (10 mL) was added. The mixture was shaken thoroughly and the aqueous layer separated. The organic layer was washed with sodium bicarbonate solution (10 mL), brine (5 mL), dried and concentrated in vacuo. The residue was purified using preparative TLC eluting with 1:3 ethyl acetate:cyclohexane to afford the title compound (171 mg 88%).

$^1$H NMR (500 MHz, CDCl$_3$): δ 9.13 (s, 1H), 7.40 (s, 1H), 2.73 (s, 3H), 2.17 (m, 1H), 1.14 (m, 2H), 1.09 (m, 2H).

Preparation 181: 6-Cyclopropyl-2-(methylthio)pyrido[3,4-d]pyrimidin-8(7H)-one

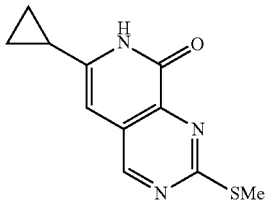 [SMILES: CSc1ncc2cc(C3CC3)[nH]c(=O)c2n1]

5-(Cyclopropylethynyl)-2-(methylthio)pyrimidine-4-carboxylic acid (Preparation 182, 215 mg 0.92 mmole) was dissolved in deuteriochloroform (4.3 mL) and camphor-10-sulphonic acid (22 mg 0.092 mmole) was added. The reaction was heated at 60° C. for 18 hours. The solution was concentrated in vacuo and the residue dissolved in 7M ammonia in methanol (4.5 mL). The reaction was heated to 80° C. under microwave irradiation for 7.5 hours. The reaction was cooled and concentrated in vacuo. The residue was taken up in chloroform (20 mL) and the solution was washed with 10% sodium carbonate solution (5 mL) and with water (5 mL). The solution was filtered and concentrated in vacuo. The residue was purified by preparative TLC eluting with EtOAc to afford the title compound (95 mg, 44%).

$^1$H NMR (500 MHz, CDCl$_3$): δ 8.78 (s, 1H), 6.27 (s, 1H), 2.68 (s, 3H), 1.82-1.89 (m, 1H), 0.96-1.05 (m, 4H).

Preparation 182: 5-(Cyclopropylethynyl)-2-(methylthio)pyrimidine-4-carboxylic acid

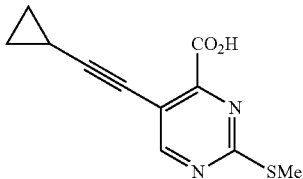 [SMILES: CSc1ncc(C#CC2CC2)c(C(=O)O)n1]

Methyl 5-(cyclopropylethynyl)-2-(methylthio)pyrimidine-4-carboxylate (Preparation 183, 520 mg 2.1 mmole) was dissolved in methanol (8 mL) and 2M sodium hydroxide (1.6 mL, 3.2 mmole) was added. The reaction was stirred at room temperature for 3 hours. The reaction was cooled in ice and 2M hydrochloric acid (1.6 mL) was added. The deposited solid was filtered, washed with water and dried to afford the title compound (387 mg, 78%).

$^1$H NMR (500 MHz, CDCl$_3$): δ 8.75 (s, 1H), 2.63 (s, 3H), 1.55-1.61 (m, 1H), 0.95-1.02 (m, 4H).

Preparation 183: Methyl 5-(cyclopropylethynyl)-2-(methylthio)pyrimidine-4-carboxylate

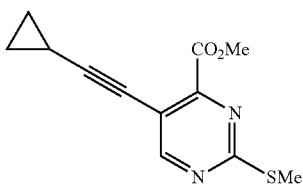 [SMILES: COC(=O)c1nc(SC)ncc1C#CC1CC1]

Methyl 5-bromo-2-(methylthio)pyrimidine-4-carboxylate (639 mg, 2.43 mmole) was dissolved in DMF (6 mL) and triethylamine (1.37 mL) was added. To the solution was added ethynylcyclopropane (287 uL, 3.40 mmole), followed by copper (I) iodide (22.4 mg 0.115 mmole) and bis(triphenylphosphine)palladium dichloride (85.4 mg 0.115 mmole). The reaction was placed under nitrogen at heated at 80° C. for 3.25 hours. The reaction was diluted with ethyl acetate (75 mL) and the solution was washed with water (25 mL). The organic layer was washed again with water (2×25 mL), brine, dried and concentrated in vacuo. The residue was purified by silica gel column chromatography eluting with 5-10% ethyl acetate in cyclohexanes to afford the title compound (520 mg, 86%). Taken on directly to the next step.

Preparation 184: 8-chloro-5-methyl-2-(methylsulfonyl)pyrido[3,4-d]pyrimidine

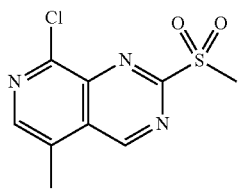 [SMILES: Cc1cnc(Cl)c2nc(S(C)(=O)=O)ncc12]

A suspension of 8-chloro-5-methyl-2-(methylthio)pyrido[3,4-d]pyrimidine (Preparation 185, 53 mg, 0.235 mmol) in DCM (2.5 mL) was treated with mCPBA (77% w/w, 150 mg, 0.668 mmol) at 0° C. and then allowed to reach room temperature for 18 hours. The mixture was quenched with water and extracted with DCM. The combined organic layers were washed with water and saturated aqueous NaHCO$_3$, dried and concentrated in vacuo. The residue was purified by silica gel column chromatography eluting with 60% EtOAc in cyclohexanes to give the title compound (44 mg, 72%).

$^1$H NMR (500 MHz, DMSO-d$_6$): δ 10.19 (s, 1H), 8.63 (d, J=1.0 Hz, 1H), 3.56 (s, 3H), 2.78 (d, J=1.1 Hz, 3H).

LCMS (ESI) Rt=1.60 minutes MS m/z 258 [M+H]$^+$

Preparation 185: 8-chloro-5-methyl-2-(methylthio)pyrido[3,4-d]pyrimidine

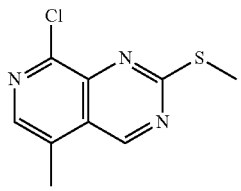

A solution of 5-methyl-2-(methylthio)pyrido[3,4-d]pyrimidin-8(7H)-one (Preparation 186, 48 mg, 0.232 mmol) in POCl$_3$ (1.5 mL) was heated to 70° C. for 2 hours. The reaction was concentrated in vacuo and partitioned between EtOAc and saturated aqueous NaHCO$_3$. The aqueous layer was extracted with EtOAc and the combined organic layers were washed with water and brine, dried and adsorbed on silica. The residue was purified by silica gel column chromatography eluting with 0 to 15% EtOAc in cyclohexanes to give the title compound (27 mg, 52%).

$^1$H NMR (500 MHz, CDCl$_3$): δ 9.38 (s, 1H), 8.23 (d, J=1.1 Hz, 1H), 2.77 (s, 3H), 2.68 (d, J=1.0 Hz, 3H).

LCMS (ESI) Rt=2.70 minutes MS m/z 226 [M+H]$^+$

Preparation 186: 5-methyl-2-(methylthio)pyrido[3,4-d]pyrimidin-8(7H)-one

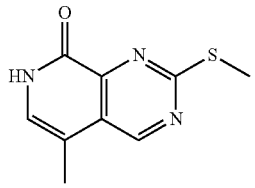

A solution of N-allyl-5-bromo-2-(methylthio)pyrimidine-4-carboxamide (Preparation 187, 24 mg, 0.083 mmol), diisopropylethyl amine (60 µl, 0.344 mmol) and PdCl$_2$dppf.DCM (7 mg, 8.57 µmol) was dissolved in DMA (0.8 mL) and heated to 120° C. for 18 hours. Additional batches of base (60 uL) and catalyst (7 mg) were added and the mixture stirred at 150° C. for 8 hours. The mixture was diluted with DCM and quenched with brine. The aqueous layer was extracted with DCM and the combined organic layers washed with water, dried and concentrated in vacuo. The residue was purified by silica gel column chromatography eluting with 0 to 5% MeOH in DCM to give the title compound (8 mg, 47%).

$^1$H NMR (500 MHz, DMSO-d$_6$): δ 11.68 (br. s, 1H), 9.21 (s, 1H), 7.07 (dd, J=5.7, 1.2 Hz, 1H), 2.61 (s, 3H), 2.25 (d, J=1.2 Hz, 3H).

LCMS (ESI) Rt=1.74 minutes MS m/z 208 [M+H]$^+$

Preparation 187: N-allyl-5-bromo-2-(methylthio)pyrimidine-4-carboxamide

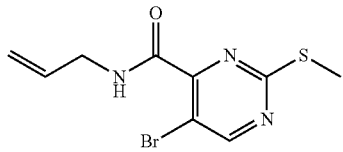

A solution of methyl 5-bromo-2-(methylthio)pyrimidine-4-carboxylate (Preparation 30, 1.00 g, 3.80 mmol) was dissolved in methanol (16 mL), treated with allylamine (3.00 mL, 40.0 mmol) and heated to 90° C. for 18 hours. The mixture was concentrated in vacuo and the residue purified by silica gel column chromatography eluting with 0 to 5% EtOAc in cyclohexanes to give the title compound (981 mg, 90%).

$^1$H NMR (500 MHz, CDCl$_3$) δ 8.79 (s, 1H), 7.73 (br. s, 1H), 5.94 (ddt, J=17.2, 10.2, 5.6 Hz, 1H), 5.31 (dq, J=17.1, 1.6 Hz, 1H), 5.23 (dq, J=10.3, 1.4 Hz, 1H), 4.09 (tt, J=5.9, 1.6 Hz, 2H), 2.60 (s, 3H).

LCMS (ESI) Rt=2.18 minutes MS m/z 289 [M+H]$^+$

Preparation 188: 6-Methoxy-N-methyl-5-nitropicolinamide

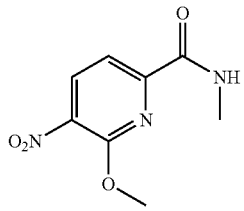

HATU (0.606 g, 1.594 mmol) was added to a solution of 6-methoxy-5-nitropicolinic acid (Preparation 190, 0.243 g, 1.226 mmol), DIPEA (0.320 mL, 1.840 mmol) and 2M methylamine solution in THF (1.2 mL, 2.453 mmol) in THF (3.3 mL). The reaction mixture was stirred at room temperature for 3 hours. Further methylamine (0.6 mL) was added and the mixture was stirred for 18 hours. The reaction was quenched with water and concentrated in vacuo. The aqueous phase was extracted with EtOAc (×2) and the combined organic layers were washed twice with water, dried (Na$_2$SO$_4$), filtered and concentrated in vacuo. The residue was purified by Biotage silica gel column chromatography eluting with DCM/EtOAc 99/1 to 90/10 to afford the title compound as a yellow solid (182 mg, 70%).

$^1$H NMR (500 MHz, CDCl$_3$): δ 8.40 (d, J=8.0 Hz, 1H), 7.96 (d, J=8.0 Hz, 1H), 7.64 (br s, 1H), 4.18 (s, 3H), 3.09 (d, J=5.1 Hz, 3H).

LCMS (ESI) Rt=2.06 minutes MS m/z 212 [M+H]$^+$

Preparation 189: 2-Methoxy-6-(1-methyl-1H-tetrazol-5-yl)-3-nitropyridine

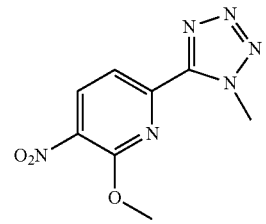 [SMILES: COc1nc(-c2nnnn2C)ccc1[N+](=O)[O-]]

Triflic anhydride (0.29 mL, 1.724 mmol) was added dropwise to a solution of 6-methoxy-N-methyl-5-nitropicolinamide (Preparation 188, 0.182 g, 0.862 mmol) and sodium azide (0.224 g, 3.45 mmol) in MeCN (4.3 mL) at −10° C. The reaction mixture was warmed to room temperature over 3 hours. The reaction mixture was neutralised with saturated aqueous NaHCO$_3$. The mixture was extracted with EtOAc and the organic layer washed with saturated aqueous NaHCO$_3$ and then with brine, dried (Na$_2$SO$_4$), filtered and concentrated in vacuo. The residue was purified by Biotage silica gel column chromatography eluting with cyclohexane/EtOAc 70/30 to 50/50 to afford the title compound as a white solid (99 mg, 49%).

$^1$H NMR (500 MHz, CDCl$_3$): δ 8.48 (d, J=8.2 Hz, 1H), 8.15 (d, J=8.2 Hz, 1H), 4.56 (s, 3H), 4.22 (s, 3H).

LCMS (ESI) Rt=2.15 minutes MS m/z 237 [M+H]$^+$

Preparation 190: 6-Methoxy-5-nitropicolinic acid

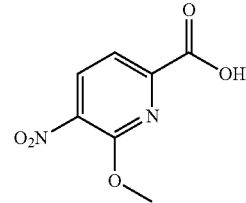

Chromium trioxide (519 mg, 5.19 mmol) was added to a solution of 2-methoxy-6-methyl-3-nitropyridine (300 mg, 1.731 mmol) in sulfuric acid (1.7 mL). The reaction mixture was stirred at room temperature for 20 hours. The mixture was poured onto ice/water (15 mL). The solid was collected and washed with cold water. The aqueous layer was then extracted with EtOAc. The combined organic layers were dried (Na$_2$SO$_4$), filtered and concentrated in vacuo. The solids obtained were combined and purified by Biotage silica gel column chromatography eluting with 1% formic acid in DCM/EtOAc, 90/10 to 70/30 to afford the title product as a white solid (254 mg, 74%).

$^1$H NMR (500 MHz, Acetone-d$_6$): δ 8.56 (d, J=8.0 Hz, 1H), 7.95 (d, J=8.0 Hz, 1H), 4.19 (s, 3H).

LCMS (ESI) Rt=1.96 minutes MS m/z 199 [M+H]$^+$

Preparation 191: 6-(1,2-Dimethyl-1H-imidazol-5-yl)-2-methoxypyridin-3-amine

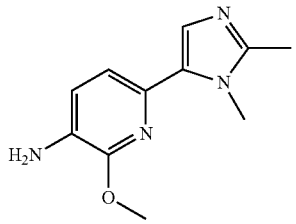 [SMILES: COc1nc(-c2cnc(C)n2C)ccc1N]

Palladium acetate (5.5 mg, 0.025 mmol) was added to a solution of 6-bromo-2-methoxypyridin-3-amine (25 mg, 0.123 mmol), 1,2-dimethyl-1H-imidazole (35.5 mg, 0.369 mmol), pivalic acid (3.8 mg, 0.037 mmol), tricyclohexylphosphine tetrafluoroborate salt (18.1 mg, 0.049 mmol) and potassium carbonate (25.5 mg, 0.185 mmol) in DMA (410 µL). The reaction mixture was heated under microwave irradiation at 120° C. for 1 hour. The reaction was diluted with EtOAc and quenched with water. The layers were separated and the aqueous layer was extracted with EtOAc. The combined organic layers were dried ($Na_2SO_4$), filtered and concentrated in vacuo. The crude mixture was purified by Biotage silica gel column chromatography eluting with 1 to 5% MeOH/aq. $NH_3$ (10/1) in DCM to afford the title compound as a white solid (9 mg, 35%).

$^1$H NMR (500 MHz, $CDCl_3$): δ 7.12 (s, 1H), 6.99 (d, J=7.7 Hz, 1H), 6.92 (d, J=7.7 Hz, 1H), 4.02 (s, 3H), 3.86 (s, 3H), 3.82 (br s, 2H), 2.44 (s, 3H).

LCMS (ESI) Rt=1.09 minutes MS m/z 219 [M+H]$^+$

Preparation 192: 2-Methoxy-4-(1-methyl-1H-tetrazol-5-yl)aniline

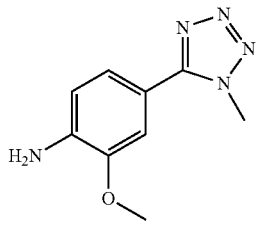

10% Pd on carbon (7 mg, 0.268 mmol) was added to a solution of 5-(3-methoxy-4-nitrophenyl)-1-methyl-1H-tetrazole (Preparation 195, 63 mg, 0.268 mmol) in EtOAc (1.2 mL). The reaction mixture was stirred at room temperature under a hydrogen atmosphere for 1 hour. EtOH (0.5 mL) was added and the reaction mixture was stirred for 1.5 hours. The reaction was filtered and the filtrate concentrated in vacuo to afford the title product as a white solid (52 mg, 95%).

$^1$H NMR (500 MHz, $CD_3OD$): δ 7.25-7.26 (m, 1H), 7.20-7.22 (m, 1H), 6.86-6.88 (m, 1H), 4.19 (s, 3H), 3.93 (s, 3H).

LCMS (ESI) Rt=1.54 minutes MS m/z 206 [M+H]$^+$

Preparation 193: 2-Methoxy-6-(1-methyl-1H-1,2,3-triazol-5-yl)pyridin-3-amine

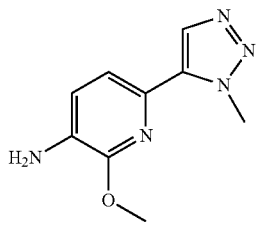

The title compound was prepared according to the method described for Preparation 192 using 2-methoxy-6-(1-methyl-1H-1,2,3-triazol-5-yl)-3-nitropyridine (Preparation 197) at 35° C. for 18 hours. The residue was purified using silica gel column chromatography eluting with 0-5% EtOAc in DCM.

$^1$H NMR (500 MHz, $CDCl_3$): δ 7.84 (s, 1H), 7.11 (d, J=7.8 Hz, 1H), 6.96 (d, J=7.8 Hz, 1H), 4.40 (s, 3H), 4.05 (s, 5H).

LCMS (ESI) Rt=1.98 minutes MS m/z 206 [M+H]$^+$

Preparation 194: 2-Methoxy-6-(2-methyl-2H-1,2,3-triazol-4-yl)pyridin-3-amine

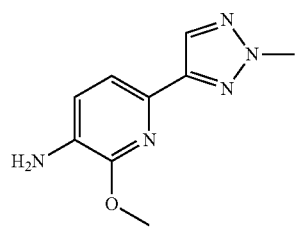

The title compound was prepared according to the method described for Preparation 192 using 2-methoxy-6-(2-methyl-2H-1,2,3-triazol-4-yl)-3-nitropyridine (Preparation 198) for 36 hours.

$^1$H NMR (500 MHz, $CDCl_3$): δ 7.97 (s, 1H), 7.34 (d, J=7.7 Hz, 1H), 6.93 (d, J=7.7 Hz, 1H), 4.23 (s, 3H), 4.07 (s, 3H), 3.89 (br s, 3H).

LCMS (ESI) Rt=2.11 minutes MS m/z 206 [M+H]$^+$

Preparation 195: 5-(3-Methoxy-4-nitrophenyl)-1-methyl-1H-tetrazole

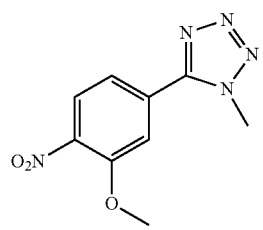

Triflic anhydride (0.27 mL, 1.580 mmol) was added dropwise to a solution of 3-methoxy-N-methyl-4-nitrobenzamide (Preparation 196, 0.166 g, 0.790 mmol) and sodium azide (0.205 g, 3.16 mmol) in MeCN (4.0 mL) at −10° C. The reaction mixture was warmed up to room temperature over 3 hours. The reaction was neutralised with saturated aqueous $NaHCO_3$. The mixture was extracted with EtOAc and the organic layer washed with saturated aqueous $NaHCO_3$, brine, dried ($Na_2SO_4$), filtered and concentrated in vacuo. The residue was purified by Biotage silica gel column chromatography eluting with cyclohexane/EtOAc 70/30 to 50/50 to afford the title compound as a white solid (129 mg, 69%).

$^1$H NMR (500 MHz, $CDCl_3$): δ 8.04 (d, J=8.3 Hz, 1H), 7.64 (d, J=1.7 Hz, 1H), 7.35 (dd, J=8.3, 1.7 Hz, 1H), 4.27 (s, 3H), 4.08 (s, 3H).

LCMS (ESI) Rt=1.98 minutes MS m/z 236 [M+H]$^+$

Preparation 196: 3-Methoxy-N-methyl-4-nitrobenzamide

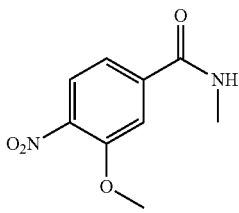

HATU (0.501 g, 1.319 mmol) was added to a solution of 3-methoxy-4-nitrobenzoic acid (0.2 g, 1.014 mmol), DIPEA (0.265 mL, 1.522 mmol) and 2M methylamine solution in THF (1.0 mL, 2.029 mmol) in THF (2.7 mL). The reaction mixture was stirred at room temperature for 18 hours. The reaction was concentrated in vacuo and purified by Biotage silica gel column chromatography eluting with DCM/EtOAc 80/20 to 60/40 followed by a second chromatography eluting with cyclohexane/EtOAc 50/50 to 40/60 to afford the title compound as a white solid (166 mg, 78%).

$^1$H NMR (500 MHz, CDCl$_3$): δ 7.88 (d, J=8.3 Hz, 1H), 7.64 (d, J=1.6 Hz, 1H), 7.28 (dd, J=8.3, 1.6 Hz, 1H), 6.27 (s, 1H), 4.04 (s, 3H), 3.07 (d, J=4.9 Hz, 3H).

LCMS (ESI) Rt=2.04 minutes MS m/z 211 [M+H]$^+$

Preparation 197: 2-Methoxy-6-(1-methyl-1H-1,2,3-triazol-5-yl)-3-nitropyridine

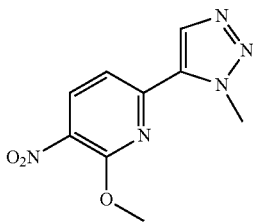 [SMILES: COc1nc(-c2cnnn2C)ccc1[N+](=O)[O-]]

1-Methyl-1H-1,2,3-triazole (0.044 g, 0.530 mmol) was dissolved in THF (5.3 mL) and cooled to −78° C. n-Butyllithium solution in hexanes (0.25 mL, 0.636 mmol) was added dropwise and the solution was stirred for further 5 minutes before zinc chloride (3.18 mL, 1.591 mmol) was added. After 30 minutes at −78° C., the reaction mixture was diluted with DMF (2.1 mL), tetrakis(triphenylphosphine)palladium(O) (0.031 g, 0.027 mmol) and a solution of 6-chloro-2-methoxy-3-nitropyridine (0.1 g, 0.530 mmol) in DMF (0.53 mL) were added. The solution was stirred at 80° C. for 4 hours. After the mixture was cooled to room temperature, H$_2$O and EtOAc were added and the phases were separated. The organic phase was washed with H$_2$O, brine, dried (Na$_2$SO$_4$), filtered and the solvent was removed in vacuo. The residue was purified via Biotage silica gel column chromatography eluting with cyclohexane/EtOAc (99/1 to 50/50) to afford the title compound as a light yellow solid (51 mg, 41%).

$^1$H NMR (500 MHz, CDCl$_3$): δ 8.44 (d, J=8.2 Hz, 1H), 8.15 (s, 1H), 7.43 (d, J=8.2 Hz, 1H), 4.50 (s, 3H), 4.21 (s, 3H).

LCMS Rt=2.26 minutes MS m/z 236 [M+H]$^+$

Preparation 198: 2-Methoxy-6-(2-methyl-2H-1,2,3-triazol-4-yl)-3-nitropyridine

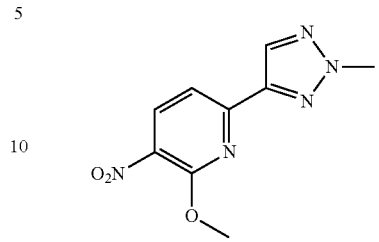

Iodomethane (330 μL, 5.31 mmol) was added to a solution of 2-methoxy-3-nitro-6-(2H-1,2,3-triazol-4-yl)pyridine (Preparation 199, 235 mg, 1.063 mmol) and potassium carbonate (294 mg, 2.125 mmol) in THF (5.1 mL). The reaction mixture was stirred at room temperature for 72 hours. The solid was filtered and the filtrate concentrated in vacuo. The residue was purified using Biotage silica gel column chromatography eluting with cyclohexane/EtOAc 80/20 to 40/60 to afford the title compound as a beige solid (48 mg, 19%).

$^1$H NMR (500 MHz, CDCl$_3$): δ 8.40 (d, J=8.2 Hz, 1H), 8.17 (s, 1H), 7.66 (d, J=8.2 Hz, 1H), 4.31 (s, 3H), 4.22 (s, 3H).

LCMS (ESI) Rt=2.97 minutes MS m/z 236 [M+H]$^+$

Preparation 199: 2-Methoxy-3-nitro-6-(2H-1,2,3-triazol-4-yl)pyridine

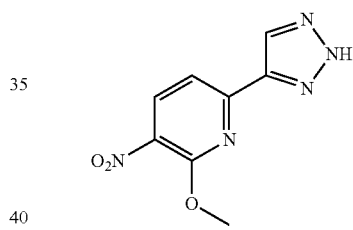

Trimethylsilylazide (1.2 mL, 9.21 mmol) was added to a solution of 6-ethynyl-2-methoxy-3-nitropyridine (Preparation 200, 0.082 g, 0.460 mmol) in toluene (10.2 mL). The reaction mixture was stirred at 130° C. for 48 hours. The reaction was diluted with water and concentrated in vacuo. The residue was purified using Biotage silica gel column chromatography eluting with cyclohexane/EtOAc 70/30 to 50/50 to afford the title compound as a beige solid (235 mg, 77%).

$^1$H NMR (500 MHz, CD$_3$OD): δ 8.44-8.46 (m, 2H), 7.77 (d, J=8.2 Hz, 1H), 4.19 (s, 3H).

LCMS (ESI) Rt=2.47 minutes MS m/z 222 [M+H]$^+$

Preparation 200: 6-Ethynyl-2-methoxy-3-nitropyridine

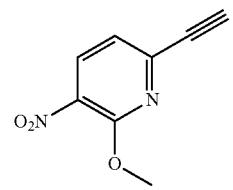

Potassium carbonate (0.020 g, 0.148 mmol) was added to a solution of 2-methoxy-3-nitro-6-((trimethylsilyl)ethynyl)pyridine (Preparation 201, 0.37 g, 1.478 mmol) in MeOH (3 mL). The reaction mixture was stirred at room temperature for 1 hour. The reaction was concentrated in vacuo and diluted with EtOAc. The solution was washed with water and the organic layer was dried (Na$_2$SO$_4$) and concentrated in vacuo to afford the title compound as a brown solid (248 mg, 94%).

$^1$H NMR (500 MHz, CDCl$_3$): δ 8.24 (d, J=8.1 Hz, 1H), 7.20 (d, J=8.1 Hz, 1H), 4.12 (s, 3H), 3.37 (s, 1H).

LCMS (ESI) Rt=2.56 minutes MS m/z 179 [M+H]$^+$

Preparation 201: 2-Methoxy-3-nitro-6-((trimethylsilyl)ethynyl)pyridine

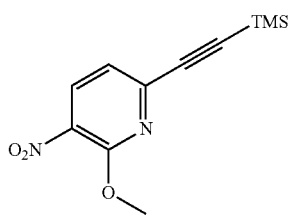 [SMILES: COc1nc(C#C[Si](C)(C)C)ccc1[N+](=O)[O-]]

Bis(triphenylphosphine)palladiumdichloride (0.082 g, 0.118 mmol) was added to a solution of 6-chloro-2-methoxy-3-nitropyridine (0.554 g, 2.94 mmol), trimethylsilylacetylene (0.623 mL, 4.41 mmol), triethylamine (1.843 mL, 13.22 mmol) and copper iodide (0.022 g, 0.118 mmol) in DMF (10.1 mL). The reaction mixture was heated at 80° C. for 1 hour. The reaction mixture was diluted with water and the aqueous layer was extracted with EtOAc. The combined organic layers were dried over Na$_2$SO$_4$, filtered and concentrated in vacuo. The crude residue was purified by Biotage silica gel column chromatography eluting with cyclohexane/EtOAc (99/1) to afford the title compound as a yellow oil (370 mg, 50%).

$^1$H NMR (500 MHz, CDCl$_3$): δ 8.24 (d, J=8.1 Hz, 1H), 7.17 (d, J=8.1 Hz, 1H), 4.15 (s, 3H), 0.31 (s, 9H).

LCMS (ESI) Rt=3.25 minutes MS m/z 251 [M+H]$^+$

Preparation 202: 4-(1-(3-methoxy-4-nitrophenyl)piperidin-4-yl)morpholine

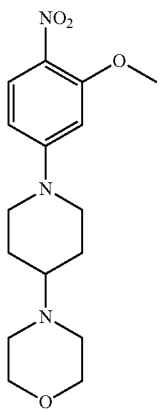

The title compound was prepared according to the method described for Preparation 78 using 4-fluoro-2-methoxy-1-nitrobenzene and 4-(piperidin-4-yl)morpholine. The residue was purified using silica gel column chromatography eluting with 80-100% DCM in cyclohexanes.

$^1$H NMR (500 MHz, MeOD): δ 7.95 (d, J=9.5 Hz, 1H), 6.57 (dd, J=9.5, 2.5 Hz, 1H), 6.52 (d, J=2.5 Hz, 1H), 4.10 (br d, J=13.0 Hz, 2H), 3.95 (s, 3H), 3.72 (t, J=5.0 Hz, 4H), 2.99 (td, J=13.0, 2.5 Hz, 2H), 2.62 (t, J=5.0 Hz, 4H), 2.49 (m, 1H), 2.04 (d, J=13.0 Hz, 2H), 1.58 (dd, J=13.0, 5.0 Hz, 1H), 1.53 (dd, J=13.0, 5.0 Hz, 1H).

LCMS (ESI) Rt=1.03 minutes MS m/z 322 [M+H]$^+$

Preparation 203: 1-(3-methoxy-4-nitrophenyl)piperidine

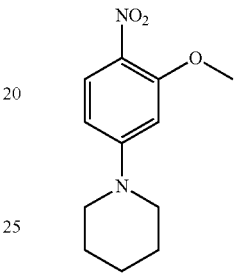

The title compound was prepared according to the method described for Preparation 78 using 4-fluoro-2-methoxy-1-nitrobenzene and piperidine. The residue was purified using silica gel column chromatography eluting with 50-80% DCM in cyclohexanes.

$^1$H NMR (500 MHz, CDCl$_3$): 8.02 (d, J=9.5 Hz, 1H), 6.46 (dd, J=9.5, 3.0 Hz, 1H), 6.41 (m, 1H), 3.97 (s, 3H), 3.45-3.42 (m, 4H), 1.76-1.70 (m, 6H).

LCMS (ESI) Rt=2.46 minutes MS m/z 237 [M+H]$^+$

Preparation 204: (1-(3-methoxy-4-nitrophenyl)piperidin-4-yl)(morpholino)methanone

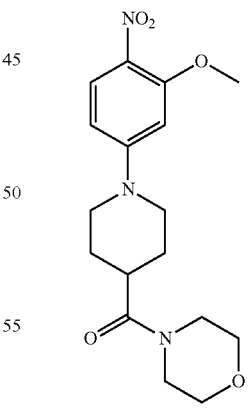

To a solution of 1-(3-methoxy-4-nitrophenyl)piperidine-4-carboxylic acid (Preparation 205, 150 mg, 0.535 mmol) in DMF (5 mL) was added morpholine (0.07 mL, 0.803 mmol), DIPEA (0.19 mL, 1.070 mmol) and HATU (244 mg, 0.642 mmol). The reaction mixture was stirred at room temperature for 18 hours. The reaction mixture was diluted with water (30 mL) and EtOAc (30 ml), dried (MgSO$_4$) and concentrated in vacuo. The residue was purified by silica gel column chromatography eluting with 0-10% MeOH in EtOAc to afford the title compound (166 mg, 89%).

¹H NMR (500 MHz, MeOD): δ 7.96 (d, J=9.5 Hz, 1H), 6.58 (dd, J=9.5, 2.5 Hz, 1H), 6.52 (d, J=2.5 Hz, 1H), 4.11-4.06 (m, 2H), 3.95 (s, 3H), 3.72-3.69 (m, 2H), 3.68-3.65 (m, 4H), 3.61-3.58 (m, 2H), 3.11-3.05 (m, 2H), 3.01 (m, 1H), 1.85-1.78 (m, 4H).

LCMS (ESI) Rt=1.90 minutes MS m/z 350 [M+H]⁺

Preparation 205:
1-(3-methoxy-4-nitrophenyl)piperidine-4-carboxylic acid

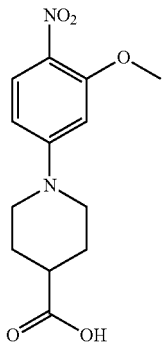 [SMILES: COc1cc(N2CCC(C(=O)O)CC2)ccc1[N+](=O)[O-]]

The title compound was prepared according to the method described for Preparation 78 using 4-fluoro-2-methoxy-1-nitrobenzene and piperidine-4-carboxylic acid.

¹H NMR (500 MHz, MeOD): δ 7.95 (d, J=9.5 Hz, 1H), 6.57 (dd, J=9.5, 2.5 Hz, 1H), 6.52 (d, J=2.5 Hz, 1H), 3.98 (dt, J=13.5, 3.5 Hz, 2H), 3.95 (s, 3H), 3.11 (ddd, J=13.5, 12.0, 3.5 Hz, 2H), 2.62 (m, 1H), 2.06-2.01 (m, 2H), 1.81-1.73 (m, 2H).

LCMS (ESI) Rt=2.04 minutes MS m/z 281 [M+H]⁺

Preparation 206:
1-(3-methoxy-4-nitrophenyl)-4-methylpiperazine

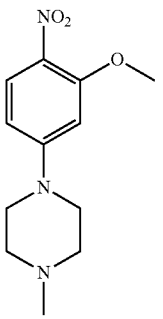

The title compound was prepared according to the method described for Preparations 78 and 79 using 4-fluoro-2-methoxy-1-nitrobenzene and 1-methylpiperazine. The residue was purified by silica gel column chromatography eluting with 0-20% MeOH in EtOAc.

¹H NMR (500 MHz, MeOD): δ 7.95 (d, J=9.5 Hz, 1H), 6.58 (dd, J=9.5, 2.5 Hz, 1H), 6.55 (d, J=2.5 Hz, 1H), 3.95 (s, 3H), 3.49-3.47 (m, 4H), 2.61-2.59 (m, 4H), 2.37 (s, 3H).

LCMS (ESI) Rt=0.82 minutes MS m/z 252 [M+H]⁺

Preparation 207:
4-(3-chloro-4-nitrophenyl)morpholine

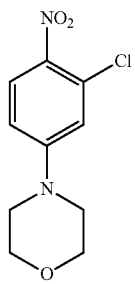 [SMILES: O=[N+]([O-])c1ccc(N2CCOCC2)cc1Cl]

The title compound was prepared according to the method described for Preparation 78 using 2-chloro-4-fluoro-1-nitrobenzene. The residue was purified by silica gel column chromatography eluting with 0-50% EtOAc in cyclohexane.

¹H NMR (500 MHz, CDCl₃): δ 8.05 (d, J=9.5 Hz, 1H), 6.89 (d, J=2.5 Hz, 1H), 6.77 (dd, J=9.5, 2.5 Hz, 1H), 3.88-3.87 (m, 4H), 3.37-3.35 (m, 4H).

LCMS (ESI) Rt=2.31 minutes MS m/z 243 [M+H]⁺

Preparation 208: 1-(3-methoxy-4-nitrophenyl)-4-(methylsulfonyl)piperazine

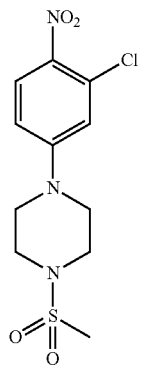 [SMILES: CS(=O)(=O)N1CCN(c2ccc([N+](=O)[O-])c(Cl)c2)CC1]

The title compound was prepared according to the method described for Preparation 78 using 4-fluoro-2-methoxy-1-nitrobenzene and 1-(methylsulfonyl)piperazine for 96 hours. The residue was purified by silica gel column chromatography eluting with 50-100% DCM in cyclohexanes.

¹H NMR (500 MHz, CDCl₃): δ 8.02 (d, J=9.0 Hz, 1H), 6.54-6.50 (m, 2H), 3.99 (s, 3H), 3.55-3.53 (m, 4H), 3.47-3.45 (m, 4H), 2.87 (s, 3H).

LCMS (ESI) Rt=1.82 minutes MS m/z 316 [M+H]⁺

Preparation 209:
5-bromo-1-(2-methoxyethyl)-2-methyl-1H-imidazole

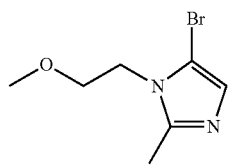

To a solution of 1-(2-methoxyethyl)-2-methyl-1H-imidazole (Preparation 210, 0.5 g, 3.57 mmol) in THF (6.5 ml) was added potassium carbonate (0.1 g, 0.713 mmol) and NBS (0.6 g, 3.39 mmol). The reaction mixture was stirred at r.t for 18 hrs. The reaction mixture was diluted with EtOAc (30 ml) and water (30 ml). The aqueous layer was re-extracted with EtOAc (30 ml). The combined organic layers were washed with brine (30 ml), dried (MgSO$_4$) and concentrated in vacuo to afford the title compound (500 mg, 64%).

1H NMR (500 MHz, MeOD) 6.86 (s, 1H), 4.16 (t, J=5.0 Hz, 2H), 3.63 (t, J=5.0 Hz, 2H), 3.31 (s, 3H), 2.42 (s, 3H).

LCMS (ESI) Rt=0.67 mins, MS m/z 219.13 [M+H]$^+$;

Preparation 210:
1-(2-methoxyethyl)-2-methyl-1H-imidazole

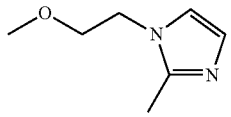

To a solution of 2-methyl-1H-imidazole (1.0 g, 12.2 mmol) and 1-chloro-2-methoxyethane (1.34 ml, 14.62 mmol) in DMF (15 ml) was added sodium hydride (0.49 g, 12.2 mmol). The reaction mixture was heated to 80° C. for 18 hrs. The reaction mixture was transferred to a microwave vial and heated to 80° C. under microwave conditions for 1 hr. The reaction mixture was diluted with DCM (40 ml) and aq. 2M Na2CO3 (30 ml) and water (40 ml). The aqueous layer was re-extracted with DCM several times. The residue was purified by reverse phase chromatography (C18, 100% water) to afford the title compound (1.13 g, 66%).

1H NMR (500 MHz, MeOD) 7.02 (d, J=1.5 Hz, 1H), 6.80 (d, J=1.5 Hz, 1H), 4.09 (t, J=5.0 Hz, 2H), 3.64 (t, J=5.0 Hz, 2H), 3.31 (s, 3H), 2.36 (s, 3H).

LCMS (ESI) Rt=0.47 mins, MS m/z 141.26 [M+H]$^+$

Preparation 211: (4-Amino-3-methoxyphenyl)(4-methylpiperazin-1-yl)methanone

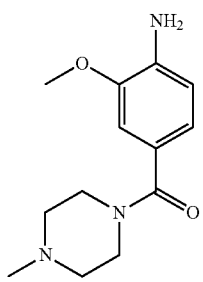 [SMILES: COc1cc(C(=O)N2CCN(C)CC2)ccc1N]

HATU (1179 mg, 3.10 mmol) was added to a solution of 4-amino-3-methoxybenzoic acid (461 mg, 2.76 mmol), DIPEA (1.24 mL, 7.12 mmol) and 1-methylpiperazine (230 mg, 2.30 mmol) in DMF (12 mL) and the reaction mixture was stirred for 18 hours. The reaction was partitioned between EtOAc and water. The organic phase was washed with saturated aqueous NaHCO$_3$ solution, water, dried over Na$_2$SO$_4$ and concentrated in vacuo. The residue was purified by elution through an SCX-2 column to afford the title compound as brown oil (179 mg, 31%).

$^1$H NMR (500 MHz, MeOD): δ 6.94 (dd, J=1.78, 8.62 Hz, 1H), 6.88 (ddd, J=1.78, 8.00, 8.62 Hz, 1H), 6.73 (dd, J=0.87, 8.00 Hz, 1H), 3.87 (s, 3H), 3.72-3.60 (m, 4H), 3.08 (s, 3H), 2.50-2.42 (m, 4H).

LCMS (ESI) Rt=0.43 minutes MS m/z 250 [M+H]$^+$

Preparation 212: 6-(2-(Methylthio)pyrido[3,4-d]pyrimidin-8-yl)-2-oxa-6-azaspiro[3.4]octane

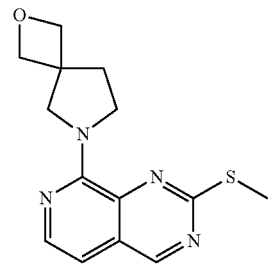 [SMILES: CSc1ncc2ccnc(N3CCC4(COC4)C3)c2n1]

The title compound was prepared according to the method described for Preparation 175 using 8-chloro-2-(methylthio)pyrido[3,4-d]pyrimidine (Preparation 33) and 2-oxa-6-azaspiro[3.4]octane hemioxalate salt. The residue was purified using silica gel column chromatography eluting with 0-2% MeOH in EtOAc.

$^1$H NMR (500 MHz, CDCl$_3$): δ 8.98 (s, 1H), 8.05 (d, J=5.5 Hz, 1H), 6.78 (d, J=5.5 Hz, 1H), 4.75 (d, J=6.1 Hz, 2H), 4.68 (d, J=6.1 Hz, 2H), 4.29 (br, s, 2H), 4.1 (br s, 2H), 2.66 (s, 3H), 2.32 (t, J=6.9 Hz, 2H).

LCMS (ESI) Rt=1.32 minutes MS m/z 289 [M+H]$^+$

Preparation 213: 2-(Difluoromethoxy)-4-(1-methyl-1H-pyrazol-4-yl)aniline

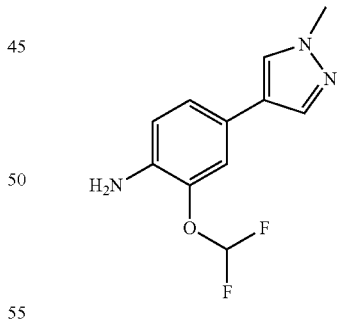

The title compound was prepared according to the method described for Preparation 158 using 4-(3-(difluoromethoxy)-4-nitrophenyl)-1-methyl-1H-pyrazole (Preparation 214) in EtOH for 40 minutes. The residue was purified by elution through an SCX-2 column using 50% methanol in chloroform followed by 50% chloroform in 7N NH$_3$/MeOH.

$^1$H NMR (500 MHz, CDCl$_3$): δ 7.66 (s, 1H), 7.5 (s, 1H), 7.15-7.13 (m, 2H), 6.77 (d, J=8, Hz, 1H), 6.5 (t, J=74.3 Hz, 1H), 3.92 (s, 3H), 3.88 (br s, 2H).

LCMS (ESI) R$_t$=2.07 minutes MS m/z 240 [M+H]$^+$

Preparation 214: 4-(3-(Difluoromethoxy)-4-nitrophenyl)-1-methyl-1H-pyrazole

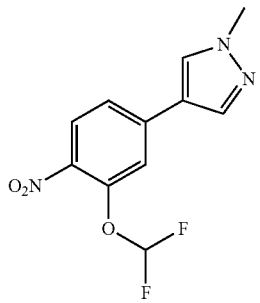 [SMILES: Cn1cc(-c2ccc([N+](=O)[O-])c(OC(F)F)c2)cn1]

A suspension of 4-bromo-2-(difluoromethoxy)-1-nitrobenzene (Preparation 215, 174 mg, 0.65 mmol), 1-methyl-4-(4,4,5,5-tetramethyl-1,3,2-dioxaborolan-2-yl)-1H-pyrazole (150 mg, 0.72 mmol), Pd(dppf)Cl$_2$.DCM (55 mg, 0.068 mmol), Na$_2$CO$_3$ (2M, 0.65 mL, 1.3 mmol) in THF (4 mL) was stirred at 65° C. for 18 hours.

The reaction mixture was diluted with EtOAc and washed with water (10 mL), brine (10 mL) dried over sodium sulphate and concentrated in vacuo. The crude product was purified by silica gel column chromatography eluting with 2% methanol in ethyl acetate to afford the title compound as a white powder (140 mg, 80%).

$^1$H NMR (500 MHz, CDCl$_3$): δ 7.98 (d, J=8.5 Hz, 1H), 7.82 (s, 1H), 7.76 (s, 1H), 7.44 (dd, J=8.5, 1.8 Hz, 1H), 7.41 (s, 1H), 6.67 (t, J=73.3 Hz, 1H), 3.98 (s, 3H).

LCMS (ESI) Rt=2.38 minutes MS m/z 270 [M+H]$^+$

Preparation 215: 2-(Difluoromethoxy)-4-bromo-1-nitrobenzene

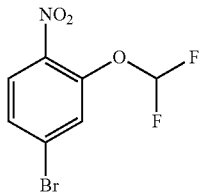 [SMILES: O=[N+]([O-])c1ccc(Br)cc1OC(F)F]

5-Bromo-2-nitrophenol (1 g, 4.59 mmol) and methyl 2-chloro-2,2-difluoroacetate (991 mg, 6.9 mmol) were dissolved in dry DMF (3 mL). Potassium carbonate (1.27 g, 9.18 mmol) was added and the reaction was stirred at 120° C. for 1 hour. The reaction was cooled to room temperature and diluted with ethyl acetate (20 mL). The organic solution was washed with water (20 mL), brine (20 mL), dried over sodium sulphate and concentrated in vacuo. The residue was purified by silica gel column chromatography eluting with 20% dichloromethane in hexanes to afford the title compound as a dark brown oil (375 mg, 30%).

$^1$H NMR (500 MHz, CDCl$_3$): δ 7.84 (d, J=8.7 Hz, 1H), 7.59-7.55 (m, 1H), 7.54 (dd, J=8.7, 2 Hz, 1H), 6.65 (t, J=72.5 Hz, 1H).

LCMS (ESI) Rt=2.58 minutes

Preparation 216: 2-Ethoxy-4-(4-methyl-4H-1,2,4-triazol-3-yl)aniline

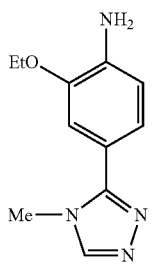 [SMILES: CCOc1cc(-c2nncn2C)ccc1N]

The title compound was prepared according to the method described for Preparation 158 using 3-(3-Ethoxy-4-nitrophenyl)-4-methyl-4H-1,2,4-triazole (Preparation 217) in EtOAc and EtOH (1:8 v:v).

$^1$H NMR (500 MHz, DMSO-d$_6$): δ 8.44 (s, 1H), 7.11 (d, J=1.89 Hz, 1H), 7.04 (dd, J=1.89, 7.88 Hz, 1H), 6.73 d, J=7.88 Hz, 1H), 5.12 (s, 2H), 4.06 (q, J=6.94 Hz, 2H), 3.69 (s, 3H), 1.36 (t, J=6.94 Hz, 3H).

Preparation 217: 3-(3-Ethoxy-4-nitrophenyl)-4-methyl-4H-1,2,4-triazole

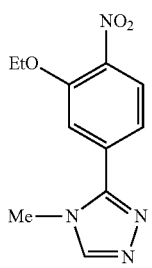 [SMILES: CCOc1cc(-c2nncn2C)ccc1[N+](=O)[O-]]

5-(3-Ethoxy-4-nitrophenyl)-4-methyl-4H-1,2,4-triazole-3-thiol (Preparation 218, 1.16 g 4.14 mmole) was stirred with dichloromethane (11.8 mL) and the suspension cooled in ice. A solution of 35% hydrogen peroxide (0.91 mL, 12.2 mmole) in acetic acid (6 mL) was added dropwise and the reaction was stirred at room temperature for 70 minutes. Dichloromethane (50 mL) was added followed by 2M aqueous sodium hydroxide (48 mL) to pH=7. The layers were separated, the aqueous extracted with more dichloromethane, the organic layers combined, dried over sodium sulphate and concentrated in vacuo. The residue was purified by silica gel column chromatography eluting with 5-10% EtOH in DCM to afford the title compound (607 mg, 60%).

$^1$H NMR (500 MHz, DMSO-d$_6$): δ 8.66 (s, 1H), 8.03 (d, J=8.51 Hz, 1H), 7.65 (d, J=1.58 Hz, 1H), 7.47 (dd, J=1.58, 8.51 Hz, 1H), 4.31 (q, J=7.25 Hz, 2H), 3.81 (s, 3H), 1.36 (t, J=6.94 Hz, 3H).

Preparation 218: 5-(3-Ethoxy-4-nitrophenyl)-4-methyl-4H-1,2,4-triazole-3-thiol

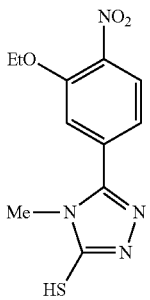 [SMILES: CCOc1cc(-c2nnc(S)n2C)ccc1[N+](=O)[O-]]

3-Ethoxy-4-nitrobenzohydrazide (Preparation 219, 1287 mg 5.72 mmole) was stirred in THF (26 mL) and a solution of methyl isothiocyanate (422 mg 5.78 mmole) in THF (5 mL) was added. Triethylamine (102 uL, 0.71 mmole) was added and the reaction was stirred at 20° C. for 22 hours. The solvent was evaporated and replaced with 1M sodium hydroxide solution (85 mL) and the reaction was stirred at 45° C. for 2.5 hours. The reaction was filtered through Celite and the filtrate extracted with ether (2×45 mL). The aqueous was acidified using conc. hydrochloric acid and extracted with ethyl acetate (2×50 mL). The combined ethyl acetate extracts were washed with water and with brine, dried over sodium sulfate and concentrated in vacuo to afford the title compound (1.16 g, 72%).

$^1$H NMR (500 MHz, DMSO-d$_6$): δ 14.11 (br s, 1H), 8.03 (d, J=8.51 Hz, 1H), 7.66 (d, J=1.58 Hz, 1H), 7.44 (dd, J=1.89, 8.51 Hz, 1H), 4.29 (q, J=6.94 Hz, 2H), 3.56 (s, 3H), 1.35 (t, J=6.94 Hz, 3H).

Preparation 219: 3-Ethoxy-4-nitrobenzohydrazide

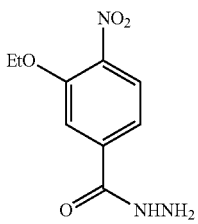 [SMILES: CCOc1cc(C(=O)NN)ccc1[N+](=O)[O-]]

3-Ethoxy-4-nitrobenzoic acid (PCT Int Appl. 2008003958, 1.06 g 5.02 mmole) was stirred with dry THF (10 mL) and triethylamine (0.86 mL, 6.1 mmol) and the solution was cooled in an ice bath. Ethyl chloroformate (0.56 mL, 5.85 mmol) was added dropwise and the reaction was stirred in the ice bath for 15 minutes. Hydrazine hydrate (1.27 mL, 26 mmol) was added in one portion and the reaction stirred in the ice bath for 5 minutes and then at 20° C. for 1 hour. The reaction was concentrated in vacuo, partitioned between EtOAc (100 mL) and saturated aqueous sodium bicarbonate (15 mL). The organic layer was collected, washed with brine, dried over sodium sulfate and concentrated in vacuo to afford the title compound (1.07 g, 95%).

$^1$H NMR (500 MHz, DMSO-d$_6$): δ 10.05 (br s, 1H, NH), 7.92 (d, J=8.20 Hz, 1H), 7.69 (d, J=1.89 Hz, 1H), 7.51 (dd, J=1.58, 8.51 Hz, 1H), 4.70 (br s, 2H, NH$_2$), 4.27 (q, J=6.94 Hz, 2H), 1.35 (t, J=6.94 Hz, 3H).

Preparation 220: 6-(2-(Methylsulfonyl)pyrido[3,4-d]pyrimidin-8-yl)-2-oxa-6-azaspiro[3.4]octane

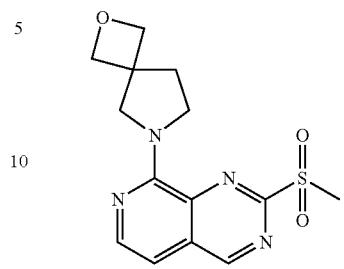

The title compound was prepared according to the method described for Preparation 172 using 6-(2-(Methylthio)pyrido[3,4-d]pyrimidin-8-yl)-2-oxa-6-azaspiro[3.4]octane (Preparation 212). The residue was purified using silica gel column chromatography eluting with 0-5% MeOH in EtOAc.

$^1$H NMR (500 MHz, CDCl$_3$): δ 9.34 (s, 1H), 8.34 (d, J=5.4 Hz, 1H), 6.96 (d, J=5.4 Hz, 1H), 4.78 (d, J=6.2 Hz, 2H), 4.69 (d, J=6.2 Hz, 2H), 4.25 (br s, 4H), 3.4 (s, 3H), 2.39 (t, J=6.8 Hz, 2H)

LCMS (ESI) R$_t$=1.25 minutes MS m/z 321 [M+H]$^+$

Preparation 221: N-(2-methoxy-4-(4-methyl-4H-1,2,4-triazol-3-yl)phenyl)formamide

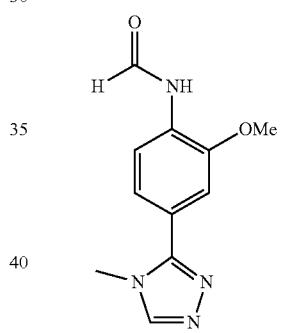

The title compound was prepared according to the methods described for Preparations 150, 216, 217, 218 and 219 using 3-methoxy-4-nitrobenzoic acid.

$^1$H NMR (500 MHz, DMSO-d$_6$): δ 9.89 (br. s, 1H), 8.56 (s, 1H), 8.37 (d, J=1.9 Hz, 1H), 8.35 (d, J=8.3 Hz, 1H), 7.39 (d, J=1.9 Hz, 1H), 7.30 (dd, J=8.3, 1.9 Hz, 1H), 3.94 (s, 3H), 3.76 (s, 3H).

LCMS (ESI) Rt=1.27 minutes MS m/z 233 [M+H]$^+$

Preparation 222: (4-Bromo-1-methyl-1H-pyrazol-5-yl)methanol

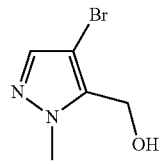

To a solution of 4-bromo-1-methyl-1H-pyrazole-5-carbaldehyde (677 mg, 3.58 mmol) in MeOH (8 mL) at 0° C., NaBH$_4$ (136 mg, 0.86 mmol) was added. The solution was stirred at room temperature for 2 hours. The reaction was concentrated in vacuo and diluted with water. The solution was extracted with EtOAc, the organic layer collected, dried over sodium sulphate and concentrated in vacuo to afford the title compound as a white solid (614 mg, 90%).

$^1$H NMR (500 MHz, CDCl$_3$): δ 7.43 (s, 1H), 4.72 (s, 2H), 3.97 (s, 3H), 2.09 (s, 1H).

LCMS (ESI) Rt=1.29 minutes MS m/z 191 [M$^{79}$Br+H]$^+$

The invention claimed is:

1. The compound N2-(2-ethoxy-4-(4-methyl-4H-1,2,4-triazol-3-yl)phenyl)-6-methyl-N8-neopentylpyrido[3,4-d]pyrimidine-2,8-diamine;

or a pharmaceutically acceptable salt or solvate thereof.

2. A pharmaceutical composition comprising a compound according to claim 1, or a pharmaceutically acceptable salt or solvate thereof, in admixture with a pharmaceutically acceptable diluent or carrier.

* * * * *